(12) United States Patent
Sanz Molinero et al.

(10) Patent No.: US 8,350,119 B2
(45) Date of Patent: Jan. 8, 2013

(54) TRANSGENIC PLANTS COMPRISING AS TRANSGENE A CLASS I TCP OR CLAVATA 1 (CLV1) OR CAH3 POLYPEPTIDE HAVING INCREASED SEED YIELD AND A METHOD FOR MAKING THE SAME

(75) Inventors: Ana Isabel Sanz Molinero, Gentbrugge (BE); Valerie Frankard, Waterloo (BE)

(73) Assignee: CropDesign N.V., Zwijnaarde (BE)

( * ) Notice: Subject to any disclaimer, the term of this patent is extended or adjusted under 35 U.S.C. 154(b) by 290 days.

(21) Appl. No.: 12/515,852

(22) PCT Filed: Nov. 22, 2007

(86) PCT No.: PCT/EP2007/062720
§ 371 (c)(1),
(2), (4) Date: Jun. 15, 2009

(87) PCT Pub. No.: WO2008/062049
PCT Pub. Date: May 29, 2008

(65) Prior Publication Data
US 2011/0016586 A1    Jan. 20, 2011

Related U.S. Application Data

(60) Provisional application No. 60/868,381, filed on Dec. 4, 2006, provisional application No. 60/883,166, filed on Jan. 3, 2007, provisional application No. 60/883,170, filed on Jan. 3, 2007.

(30) Foreign Application Priority Data

Nov. 24, 2006  (EP) .................................. 06124785
Nov. 30, 2006  (EP) .................................. 06125156
Dec. 13, 2006  (EP) .................................. 06126018

(51) Int. Cl.
*C12N 15/82*    (2006.01)
(52) U.S. Cl. ........................................ 800/278; 800/287
(58) Field of Classification Search .................. None
See application file for complete search history.

(56) References Cited

U.S. PATENT DOCUMENTS 7,235,710 B2 *  6/2007  Hatzfeld et al. .............. 800/278

FOREIGN PATENT DOCUMENTS

| WO | WO-01/79517 A2 | 10/2001 |
| WO | 2004/031349 A2 * | 4/2004 |
| WO | WO 2004/031349 A2 * | 4/2004 |

OTHER PUBLICATIONS

Merriam Webster Online Dictionary. 2008, www.m-w.com/home.html.*
Viola et al (2011, Biochemical Journal 435(part 1):143-155).*
Bowie et al, Science 247:1306-1310, 1990.*
McConnell et al, Nature 411 (6838):709-713, 2001.*
Brucker et al (Planta (2005) 220:864-874).*
Smidansky, E.D., et al., "Enhanced ADP-Glucose Pyrophosphorylase Activity in Wheat Endosperm Increases Seed Yield", PNAS, vol. 99, No. 3, 2002 , pp. 1724-1729.
Ingram, G.C., et al., "Keeping it Together: Co-Ordinating Plant Growth", Current Opinion in Plant Biology, vol. 9, (2006), pp. 12-20.
Welchen, E., et al., "Differential Expression of the *Arabidopsis* Cytochrome *c* Genes *Cytc-1* and *Cytc-2*. Evidence for the Involvement of TCP-Domain Protein-Binding Elements in Anther- and Meristem-Specific Expression of the *Cytc-1* Gene", Plant Physiology, vol. 139, (2005), pp. 757-766.
Tatematsu, K., et al., "Identification of cis-Elements That Regulate Gene Expression During Initiation of Axillary Bud Outgrowth in *Arabidopsis*", Plant Physiology, vol. 138, (2005), pp. 757-766.
Li, C., et al., "*Arabidopsis* TCP20 Links Regulation of Growth and Cell Division Control Pathways", PNAS, vol. 102, No. 36, (2005), pp. 12978-12983.
Cubas, P., et al., "The TCP Domain: a Motif Found in Proteins Regulating Plant Growth and Development", The Plant Journal, vol. 18, No. 2, (1999), pp. 215-222.
Kosugi, S., et al., "DNA Binding and Dimerization Specificity and Potential Targets for the TCP Protein Family", The Plant Journal, vol. 30, No. 3, (2002), pp. 337-348.
Toledo-Ortiz, G., et al., "The *Arabidopsis* Basic/Helix-Loop-Helix Transcription Factor Family", The Plant Cell, vol. 15, (2003), pp. 1749-1770.
Gegas, V.C., et al., "Expression of Cell Cycle Genes in Shoot Apical Meristems", Plant Molecular Biology, vol. 60, (2006), pp. 947-961.

* cited by examiner

Primary Examiner — Stuart F. Baum
(74) Attorney, Agent, or Firm — Connolly Bove Lodge & Hutz LLP

(57) ABSTRACT

The present invention relates generally to the field of molecular biology and concerns a method for enhancing various economically important yield-related traits in plants. More specifically, the present invention concerns a method for enhancing various economically important yield-related traits in plants relative to control plants, by increasing expression in a plant of a nucleic acid sequence encoding a Yield-Enhancing Polypeptide (YEP). The YEP may be a Class I TCP or a CAH3 or a Clayata 1 (CLV1) polypeptide with a non-functional C-terminal domain. The present invention also concerns plants having increased expression of a nucleic acid sequence encoding a YEP, which plants have enhanced yield-related traits in plants relative to control plants. The invention also provides constructs useful in the methods of the invention.

12 Claims, 96 Drawing Sheets

TCP phylogenetic tree according to the Arabidopsis Database for Transcription factors, available at the Center for Bioinformatics(CBI), Peking University, China

| | | 1 | | | | 50 |
|---|---|---|---|---|---|---|
| Arath_TCP20 | (1) | --DPKNLNRHQVPNFLNPPPPPRNQG--------------------- | | | | |
| Arath_TCP6 | (1) | MVPPKKNQN--------LPSFLNPSRQNQ-------------------- | | | | |
| Aqufo_CL I TCP | (1) | --DDLKNSSKQPQE--VVTSFLRHSSQ------------QEMGG--- | | | | |
| Glyma_CL I TCP | (1) | --DPKGSKQQPQQSQEVVPNFLSLP-------------QQQQGNTNNN- | | | | |
| Goshi_CL I TCP | (1) | --DPKGAKQPP----EEVANLLSLPPQPQ-----Q---QQPQ------ | | | | |
| Lyces_CL I TCP | (1) | --DPKQA---------------------------------------- | | | | |
| Maldo_CL I TCP | (1) | --DPKGSKQT-----QDIPSFLSLPPQSQPQPEQQ---QQPQQQPQPNN | | | | |
| Medtr_CL I TCP | (1) | --DPKNSKQQSQ----------LSN----------------MG---- | | | | |
| Nicbe_CL I TCP | (1) | --DPKQPPAQSN---------AI------------------------ | | | | |
| Ociba_CL I TCP | (1) | --DPKSSK---Q-----------P-------------QEVSNHSNTN- | | | | |
| Poptr_CL I TCP | (1) | --DPKGSNSKNP---HELPTFLTHTHPSPPHPPPQPHLQQPQQLHSQNQ | | | | |
| Vitvi_CL I TCP | (1) | --DPKGSKQP-----QEVPNFLSLP-------------QP-------- | | | | |
| Soltu_CL I TCP | (1) | --DPKQP---------------------------------------- | | | | |
| Orysa_PCF1 | (1) | --DPKFPPPPPLNKTEPTTTTTNQQHHHDE---------Q-QQ----- | | | | |
| Sacof_CL I TCP | (1) | --DPKFPTPPPLNKTEPTTATTTTTST---AQQLDPKDYQQQ-PA-- | | | | |
| Sorbi_CL I TCP | (1) | --DPKFPTPPPLNKTEPTTATTTTSTAQQQQQQLDPKDYQQP--AQ-- | | | | |
| Zeama_CL I TCP_1 | (1) | --DPKFPTPLALNKTEPTTATTTTSTAQ--HHQLDPKDYQQQTAQHQE | | | | |
| Zeama_CL I TCP_2 | (1) | --DPKFPPPPPLNKTEPTTATTTTSTAQQQQQQLDPKDYQQQQQQP-- | | | | |
| Consensus | (1) | MDPK T Q | | | | |

| | | 51 | | | | 100 |
|---|---|---|---|---|---|---|
| Arath_TCP20 | (26) | -------------LVDDDAASAVVSDENRKPTTEIKDFQIVVSASDKEPN | | | | |
| Arath_TCP6 | (23) | ----------------------DNDKKRKQTEVKGFDIVVGEKRKKE | | | | |
| Aqufo_CL I TCP | (30) | -----------------------GGGENKQTEIRDFQIST-VVADKDG | | | | |
| Glyma_CL I TCP | (35) | -----------------------NMGENKPAEVKDFQIVVAENKEESK | | | | |
| Goshi_CL I TCP | (30) | -----------------------NMGENKAAEIKDFQIVVADKGEGKK | | | | |
| Lyces_CL I TCP | (7) | -----------------------NHNNIKPTHDQIKELQILKNDETN- | | | | |
| Maldo_CL I TCP | (41) | -----------------------NMSDNKPAEIKDFQIVIADKDESGK | | | | |
| Medtr_CL I TCP | (17) | ---------------------------ENKESETKNLQIVLSETTTKDE | | | | |
| Nicbe_CL I TCP | (14) | -----------------------NINNNIMVEYNKPVHDQIKDDETKK | | | | |
| Ociba_CL I TCP | (20) | -----------------------SLGENKAAEIKDFQIVVAEKDDSKK | | | | |
| Poptr_CL I TCP | (46) | Q---------------------QPNMGDNKPAEIKDFQIVVADKEE-QK | | | | |
| Vitvi_CL I TCP | (22) | -----------------------NMGENKPAEVKDFQIVIADKEE-GK | | | | |
| Soltu_CL I TCP | (7) | -----------------------NKNIKPTHDQIKDLQILKNDETKK | | | | |
| Orysa_PCF1 | (33) | ------QHRLQIQVHPQQQEQQDGGGGGGKDQQQQQQMQVVVAAAGERR | | | | |
| Sacof_CL I TCP | (43) | ------QHHLQIQIHQPP--QQDGGGG-GKEQQQ----QLQVVAQPGERR | | | | |
| Sorbi_CL I TCP | (45) | ------QHHLQIQIHQPPQQQQQQDG-GKEQ------QLQVVAQPGERR | | | | |
| Zeama_CL I TCP_1 | (47) | QQQHHHHPHLQIQIHQPPPPPQDGGGG-VKEQQQ----LLQVVAQPGDRR | | | | |
| Zeama_CL I TCP_2 | (47) | ------AQHLQIQIHQSQ---QDGGGG-GKEQQ-----QLQVVAQPGERR | | | | |
| Consensus | (51) | N NK EIK FQIVVA E KK | | | | |

| | | 101 | | | | 150 |
|---|---|---|---|---|---|---|
| Arath_TCP20 | (63) | KKS--QNQNQLGPRSS--NKDRHTKVEGRGRRIRMPALQAARIFQLTRE | | | | |
| Arath_TCP6 | (49) | NEEEDQEIQILYEEKKKP...L D VL P Y K | | | | |
| Aqufo_CL I TCP | (54) | GK------KQLAPRTS-- T E I A F R | | | | |
| Glyma_CL I TCP | (60) | KQQ-----QQLAPRSS-- T E I A F R | | | | |
| Goshi_CL I TCP | (55) | --------QQLAPRSS-- T E I A F R | | | | |
| Lyces_CL I TCP | (31) | --------KVAAPR---- T E I A F R | | | | |
| Maldo_CL I TCP | (66) | --------KQLAPRSS-- T E I A F R | | | | |
| Medtr_CL I TCP | (39) | TK------KQLAPRTS-- T E I A F R | | | | |
| Nicbe_CL I TCP | (39) | R-------QQLVPR---- T E I A F R | | | | |
| Ociba_CL I TCP | (45) | --------LALAPRSS-- T E I A F R | | | | |
| Poptr_CL I TCP | (73) | --------KQLAPRSS-- T E I A F R | | | | |
| Vitvi_CL I TCP | (46) | --------KQLAPRSS-- T E I A F R | | | | |
| Soltu_CL I TCP | (32) | QQ------QVAAPR---- T E I A F R | | | | |
| Orysa_PCF1 | (77) | M-------QGLGPRSS-- T D I A F R | | | | |
| Sacof_CL I TCP | (80) | Q-------QPLAPRSS-- T D I A F R | | | | |
| Sorbi_CL I TCP | (82) | Q-------QALAPRSS-- T D I A F R | | | | |
| Zeama_CL I TCP_1 | (92) | Q-------QALAPRSS-- T D I A F R | | | | |
| Zeama_CL I TCP_2 | (82) | Q-------QALAPRSS-- T D I A F R | | | | |
| Consensus | (101) | QQLAPKRSS NKDRHTKVEGRGRRIR MPALQ AARIFQLTRE | | | | |

Basic residues
     Helix 1
CONSERVED TCP DOMAIN

FIGURE 2

```
                            301                                                              350
        Arath_TCP20  (222) KIGFPGFDFP-------------GVGHMSFASILGGNHN----QM
         Arath_TCP6  (168) GQTIGGFDLNYG-----------IGFDFNGVPEIGFGDN-----QT
       Aqufo_CL I TCP (211) KFGIHGFEMP-GSN---------LGTMNLNSFMGVG-NN----QQL
       Glyma_CL I TCP (242) KIAFPGFDLPTSAT---------NMMGHMSFTSILGGGGGGGAQHM
       Goshi_CL I TCP (215) KLGFPGFDLPAS-----------NMMGQISFTSILGGANQ----QL
       Lyces_CL I TCP (194) KIGFPGFDLPAA-----------TSMNPMCFTSILGGSN----QQL
       Maldo_CL I TCP (225) KIGFPGFDLPVS-----------NMMGPMSFTSILGGGNQQQQQQL
       Medtr_CL I TCP (197) KIGFSGFDMPTGTN---------LGVGGMSFTSILGGAN----QQM
       Nicbe_CL I TCP (212) KIGFPGFDLPAA-----------TNMS---FTSILGSSNN---QQL
       Ociba_CL I TCP (206) KMGFAGFELPG------------NIGQMSFTSILSGGG----QQL
       Poptr_CL I TCP (238) KLGFPGFDLPGN-----------NMMGPMSFTSILGGGTQ----QL
       Vitvi_CL I TCP (205) KIAFPGFDLPAT-----------NLGPMSFTSILGGSNQ----QL
       Soltu_CL I TCP (197) KIGFPGFDLPAA-----------TNMNPMSFTSILGGSN----QQL
         Orysa_PCF1  (207) RMGIPAGIELQGGGAGGLGGGGGGGGHIGFAPMFASHAAA-AAAM
       Sacof_CL I TCP (216) RMGIPAGLELPGG----------GAAGAXGFAPMFAEH----PAAT
       Sorbi_CL I TCP (218) RMGIPAGLELPGGGAAGGTL---GAGGHIGFAPMFAGH----AAAM
     Zeama_CL I TCP_1 (222) RMGVPAGLELPGGG---------AAGGHIGFAPMFAGH----AAAM
     Zeama_CL I TCP_2 (207) RMGIPAGFELPGASAAGATL---GAGGHIGFAPMFAGH----AAAM
          Consensus  (301) KIGFPGFDLP G          GMG MSFTSILGG N    QL PGLE
C-terminal motif                                                              XXXX 351                                                              400
        Arath_TCP20  (254) .....-GNV.V..PQSFTQIYQQMGQAQAQAGRVLHHMHHNEEHQQE
         Arath_TCP6  (202) ...-----V.V..P----QVFQQMGKE-------QFRVLHHHSHEDQQ
       Aqufo_CL I TCP (246) .G...-VHT.V..PQALQFYQQMVQSRGVVMHQQQHQQQQQQQQQQ
       Glyma_CL I TCP (283) .G...-GHI.V..QQALNQIYQQMNQAGRVHHHQHQHHHQHHQQQHHQ
       Goshi_CL I TCP (249) .G...-GHI.V..PHALNQIYQQMEQARM--------- PQHQHQHQQ
       Lyces_CL I TCP (229) .G...-GHI.V..N-----QIYQQARM-----------QHPQQQHQQQ
       Maldo_CL I TCP (263) .G...-GHI.V..SQALSQIYQQMGHVRV---HQQPPQHHHQQHHHQQ
       Medtr_CL I TCP (234) .G...-GHI.V..QQALTQIYQQIG---------QNQTRVQHQNQ
       Nicbe_CL I TCP (245) .G...DRGHI.V..SQGLSQIYQARIHN---------QQQHQQNQHE
       Ociba_CL I TCP (239) .G...-GNI.V..PQAFGQIYQQINPAARVVNA----HHQNHHQQHHQQ
       Poptr_CL I TCP (272) .G...-GHI.V..PQALNQIYQQMGHARV---------HQQQHQQQN
       Vitvi_CL I TCP (239) .G...-GHI.V..SQALSQIYQQMGQARV---HQQQQHQHQHQHQHQQ
       Soltu_CL I TCP (232) .G...-GHI.V..N----QIYQQERMQ-------HPQQQQQDQHQHQ
         Orysa_PCF1  (256) .G...-GHI.V..AAQSLSQFYHQVGAAG----QLQHQHHHHQ-QQQQQ
       Sacof_CL I TCP (252) .A...-GHI.L..AAQSITQFXHQVGAAGGSG-QMQHPHGHQ-------Q
       Sorbi_CL I TCP (261) .G...-GHI.V..AAQSTSQFYHQVGAAGGSG-QMQHPHGHQHH-HHQQQ
     Zeama_CL I TCP_1 (259) .G...-GHI.V..AAQSISQFYHQVGAAAGGSGQMQHPHGHQHH-HHQQQ
     Zeama_CL I TCP_2 (250) .G...-GHI.V..AAQSISQFYHQVGAAAGGGGQMHHAHGHHHH-HHQQQ
          Consensus  (351) LGLSQD GHIGVLN QALSQIYQQMG A      QQ   H H    QQQ
C-terminal motif 1         XXXXXXXXXXXX
HQ rich region                                                  XXXXXXXXXXXXXXXXXXXXXXXXXX 401         418
        Arath_TCP20  (303) SG---EKDD---SQGS-GR
         Arath_TCP6  (236) QS---AEEN-----GS--
       Aqufo_CL I TCP (295) QPHDDDEDD---SQGS-RH
       Glyma_CL I TCP (332) QT--PAKDD--SQGSGGQ
       Goshi_CL I TCP (288) QP--PAKDD---SQGS-GQ
       Lyces_CL I TCP (260) QQ--SPEED---SQGS-GH
       Maldo_CL I TCP (309) QP--PSKDD---SQGS-GQ
       Medtr_CL I TCP (270) QNNNTTKDD---SHSS-EQ
       Nicbe_CL I TCP (283) HL--SPEDD---SHGS-GH
       Ociba_CL I TCP (284) PL--SSKDDD--SQES-GQ
       Poptr_CL I TCP (310) ----PSKDD---SQGS-GQ
       Vitvi_CL I TCP (284) QP--PAKDD---SQGS-GQ
       Soltu_CL I TCP (269) QQ--SPEDD---SQGS-GH
         Orysa_PCF1  (300) QDGEDNRDDGESDEES-GQ
       Sacof_CL I TCP (293) EDGEDDREDGESDDES-GQ
       Sorbi_CL I TCP (308) EDGEDDREDGESDDES-GQ
     Zeama_CL I TCP_1 (307) EDGEDDREDGESDDES-GQ
     Zeama_CL I TCP_2 (298) EDGEDDREDGESDDES-GQ
          Consensus  (401)   Q   KDD   SQGS GQ
```

FIGURE 2 (continued)

(A)
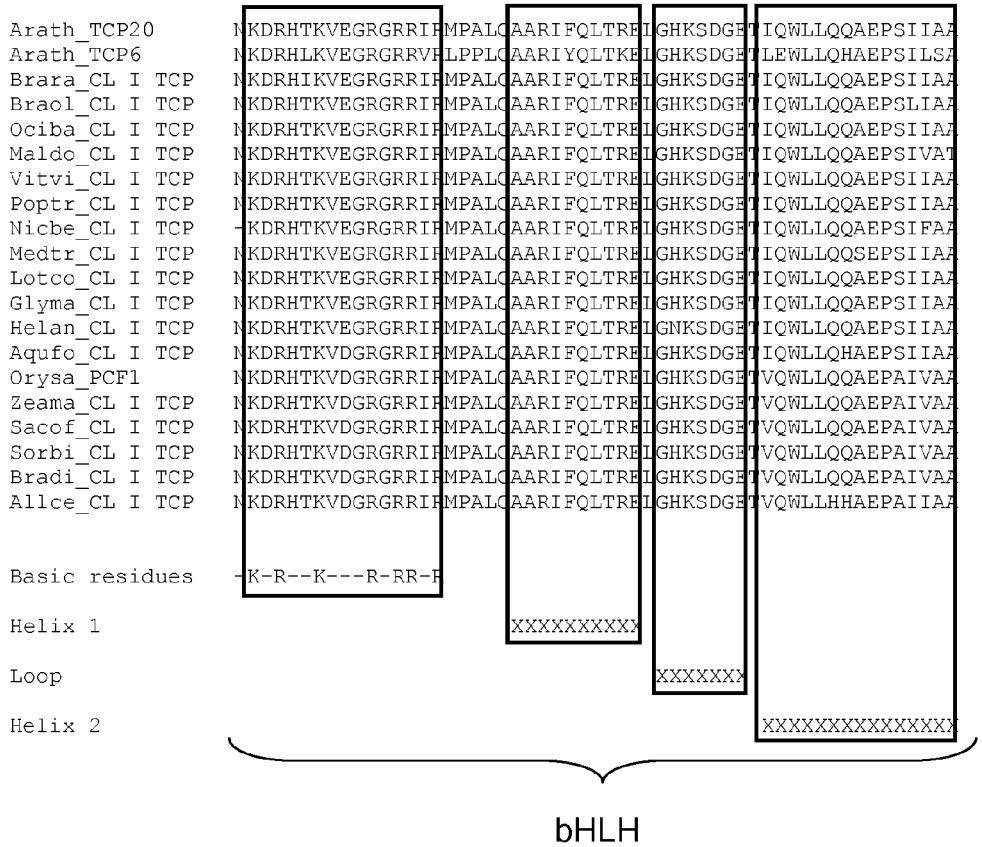
(B)
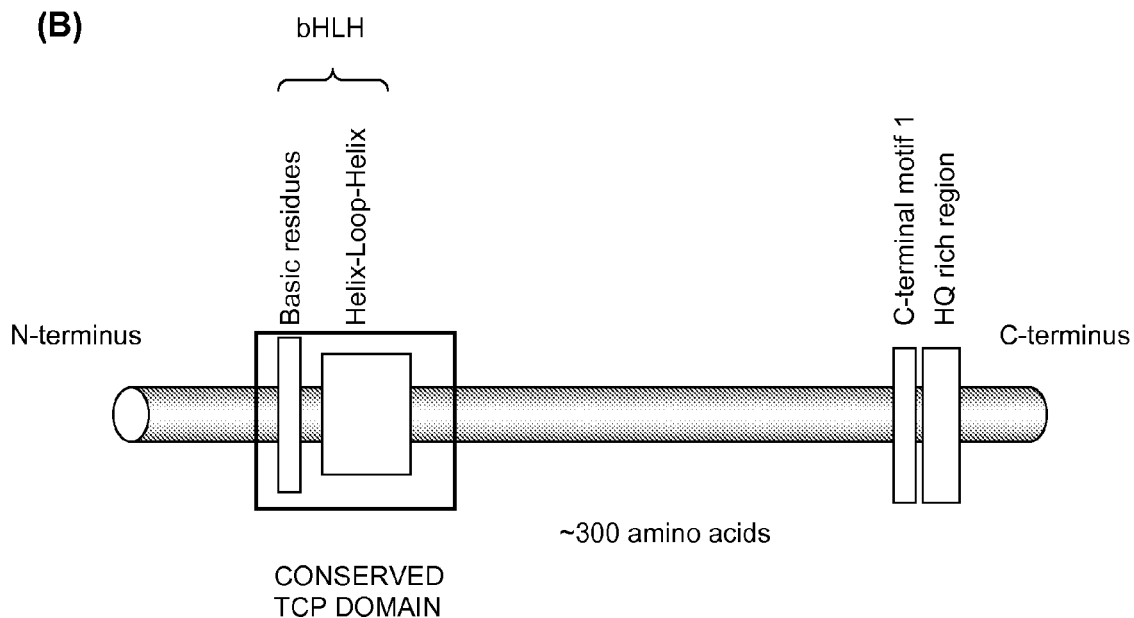
FIGURE 3

SEQ ID NO : 1 Arabidopsis thaliana Arath_TCP20 nucleic acid sequence AK118178 At3g27010
ATGGATCCCAAGAACCTAAATCGTCACCAAGTACCAAATTTCTTGAACCCACCACCACCACCGCGA
AATCAGGGTTTGGTAGATGATGATGCTGCTTCTGCTGTTGTTTCCGACGAGAATCGCAAACCAACA
ACTGAGATTAAAGATTTCCAGATCGTGGTCTCTGCTTCCGACAAAGAACCAAACAAGAAGAGTCAG
AATCAGAACCAGCTTGGTCCTAAGAGAAGCTCTAACAAAGACAGACACACTAAAGTCGAAGGTAGA
GGTCGACGAATTCGGATGCCTGCTCTTTGTGCTGCTAGGATTTTTCAATTGACTAGAGAATTGGGT
CATAAATCTGATGGTGAAACTATCCAGTGGCTGCTTCAACAAGCTGAGCCATCGATTATTGCAGCT
ACTGGTTCAGGAACTATACCGGCCTCTGCTTTAGCTTCTTCAGCTGCAACCTCTAACCATCATCAA
GGTGGGTCTCTTACTGCTGGTTTAATGATCAGTCATGACTTAGATGGTGGGTCTAGTAGTAGTGGT
AGACCATTAAATTGGGGGATTGGTGGCGGTGAAGGAGTTTCTAGGTCAAGTTTACCAACTGGGTTA
TGGCCAAATGTAGCTGGGTTTGGTTCTGGTGTGCCAACCACTGGTTTAATGAGTGAAGGAGCTGGT
TATAGAATTGGGTTTCCTGGTTTTGATTTTCCTGGTGTTGGTCATATGAGTTTTGCATCTATTTTG
GGTGGGAATCATAATCAGATGCCTGGACTTGAGTTAGGCTTGTCTCAAGAAGGGAATGTTGGTGTT
TTGAATCCTCAGTCTTTTACTCAGATTTATCAACAGATGGGTCAGGCTCAGGCTCAAGCTCAAGGT
AGGGTTCTTCACCATATGCATCATAACCATGAAGAACATCAGCAAGAGAGTGGTGAGAAAGATGAT
TCTCAAGGCTCAGGTCGTTAA

SEQ ID NO : 2 Arabidopsis thaliana Arath_TCP20 translated polypeptide sequence
MDPKNLNRHQVPNFLNPPPPPRNQGLVDDDAASAVVSDENRKPTTEIKDFQIVVSASDKEPNKKSQ
NQNQLGPKRSSNKDRHTKVEGRGRRIRMPALCAARIFQLTRELGHKSDGETIQWLLQQAEPSIIAA
TGSGTIPASALASSAATSNHHQGGSLTAGLMISHDLDGGSSSSGRPLNWGIGGGEGVSRSSLPTGL
WPNVAGFGSGVPTTGLMSEGAGYRIGFPGFDFPGVGHMSFASILGGNHNQMPGLELGLSQEGNVGV
LNPQSFTQIYQQMGQAQAQAQGRVLHHMHHNHEEHQQESGEKDDSQGSGR

SEQ ID NO : 3 Arabidopsis thaliana Arath_TCP6 nucleic acid sequence At5g41030
ATGGTCATGGAGCCCAAGAAGAACCAAAATCTACCAAGTTTCTTAAACCCATCACGACAGAATCAG
GACAACGACAAGAAGAGGAAACAAACAGAGGTTAAAGGTTTCGACATTGTGGTCGGCGAAAAGAGG
AAGAAGAAGGAGAATGAAGAGGAAGACCAAGAAATTCAGATTCTTTATGAGAAGGAGAAGAAGAAA
CCAAACAAAGATCGTCACCTTAAAGTTGAAGGAAGAGGTCGTAGAGTTAGGTTACCTCCACTCTGT
GCAGCAAGGATTTATCAATTGACTAAAGAATTAGGTCACAAATCAGATGGTGAGACTCTTGAATGG
TTGCTTCAACATGCTGAGCCATCGATACTCTCTGCTACTGTAAATGGTATCAAACCCACTGAGTCT
GTTGTTTCTCAACCTCCTCTCACGGCTGATTTGATGATTTGTCATAGCGTTGAAGAAGCTTCAAGG
ACTCAAATGGAGGCAAATGGGTTGTGGAGAAATGAAACAGGACAGACCATTGGAGGGTTTGATCTG
AATTACGGAATTGGGTTTGATTTCAATGGTGTTCCAGAGATTGGTTTTGGAGATAATCAAACGCCT
GGACTTGAATTAAGGCTGTCTCAAGTTGGGGTTTTGAATCCACAGGTTTTTCAACAAATGGGTAAA
GAACAGTTCAGGGTTCTTCATCATCATTCACATGAAGATCAGCAGCAGAGTGCAGAGGAAAATGGT
TCATAA

SEQ ID NO : 4 Arabidopsis thaliana Arath_TCP6 translated polypeptide sequence
MVMEPKKNQNLPSFLNPSRQNQDNDKKRKQTEVKGFDIVVGEKRKKKENEEEDQEIQILYEKEKKK
PNKDRHLKVEGRGRRVRLPPLCAARIYQLTKELGHKSDGETLEWLLQHAEPSILSATVNGIKPTES
VVSQPPLTADLMICHSVEEASRTQMEANGLWRNETGQTIGGFDLNYGIGFDFNGVPEIGFGDNQTP
GLELRLSQVGVLNPQVFQQMGKEQFRVLHHHSHEDQQQSAEENGS

FIGURE 5

SEQ ID NO : 5 Aquilegia formosa x Aquilegia pubescens Aqufo_CLASS I TCP nucleic acid sequence contig of DR951658, DT754291
ATGGATGATCTTAAGAATTCATCAAAGCAACCACAAGAAGTAGTAACAAGTTTCTTGAGACATTCT
TCACAACAAGAGATGGGAGGAGGAGGAGGAGAGAATAAACAAACAGAAATCAGAGATTTTCAAATC
TCAACAGTTGTTGCAGATAAAGATGGTGGTAAGAAGCAGTTAGCACCAAAAAGAACTTCAAATAAA
GATAGACATACTAAGGTAGATGGAAGAGGTAGAAGGATAAGGATGCCAGCTTTATGTGCAGCTAGA
ATTTTTCAGTTAACAAGAGAATTGGGTCATAAATCTGATGGAGAAACTATACAATGGTTATTACAA
CATGCTGAACCATCAATAATTGCCGCTACAGGTACTGGAACTATACCAGCTTCAGCTTTAGTTCAA
TCTAGTAGCTCAGTTTCACAACAGGGGAATTCTGTTTCAGTTGGTTTACAAACAAAGATCAGTGAA
TTGGGACATGAAATTGGGTCCAGTAGTAGTAGGACCAATTGGAATTTGGTTAGATCCCCAGTAACA
ACAAGTTTATGGCCCTCTGTCAGTGGTTATGTACCAGGGTTTCATCCTTCTTCAGGCCAACCGACA
TCGAATCTGAGTAGTGATGGTTTGAATTATTTGCCTAAATTCGGTATTCATGGTTTCGAAATGCCT
GGATCAAATTTAGGTACAATGAATTTAAATTCATTCATGGGGGTTGGTAATAATCAACAACTTCCT
GGATTGGAATTAGGATTATCTCAAGATGTGCATACCGGGGTATTGAATCCTCAAGCTTTACAGTTT
TATCAGCAGATGGTTCAATCAAGAGGAGTTGTCATGCATCAACAACAGCAGCACCAGCAACAACAA
CAACAACAACAGCAGCAGCAGCAGCAACCACATGATGATGATGAGGATGATTCTCAAGGTTCAAGA
CATTAA

SEQ ID NO : 6 Aquilegia formosa x Aquilegia pubescens Aqufo_CLASS I TCP translated polypeptide sequence
MDDLKNSSKQPQEVVTSFLRHSSQQEMGGGGGENKQTEIRDFQISTVVADKDGGKKQLAPKRTSNK
DRHTKVDGRGRRIRMPALCAARIFQLTRELGHKSDGETIQWLLQHAEPSIIAATGTGTIPASALVQ
SSSSVSQQGNSVSVGLQTKISELGHEIGSSSSRTNWNLVRSPVTTSLWPSVSGYVPGFHPSSGQPT
SNLSSDGLNYLPKFGIHGFEMPGSNLGTMNLNSFMGVGNNQQLPGLELGLSQDVHTGVLNPQALQF
YQQMVQSRGVVMHQQQQHQQQQQQQQQQQQQPHDDDEDDSQGSRH

SEQ ID NO : 7 Glycine max Glyma_CLASS I TCP nucleic acid sequence contig of AI736626.1, BI470329.1, BG044313.1, CA784744.1, BF424472.1
ATGGATCCCAAGGGCTCAAAGCAGCAGCCACAGCAATCACAGGAGGTGGTACCAAACTTCCTCAGC
CTCCCCCAACAGCAACAAGGGAATACCAACAACAACAACATGGGAGAGAACAAACCTGCAGAGGTG
AAGGATTTCCAGATAGTGGTAGCTGAGAACAAGGAAGAGAGCAAGAAACAGCAGCAACAGTTGGCA
CCAAAGAGGAGTTCCAACAAGGACAGGCACACCAAGGTTGAAGGCAGGGGAAGGAGGATAAGGATG
CCTGCTCTCTGCGCAGCCAGAATCTTCCAGTTGACCAGGGAATTGGGTCACAAATCTGATGGGGAA
ACCATCCAGTGGCTCCTCCAGCAGGCTGAGCCATCCATCATAGCTGCCACTGGGACTGGCACAATA
CCAGCATCTGCTCTTGCTGCTGCTGGAAACTCACTCTCACCACAAGCTGCTTCTCTTTCATCATCC
TTGCACCAACATCAACAAAAGATTGATGAATTGGGTGGGTCAGGGGGAGTAGTAGTAGGGCCAGC
TGGCAAATGGTTGGGGGGAATTTGGGGAGACCCCATTTGGGTGTGGGTGTGGCCACAGCAGCAGGC
CTATGGCCCCCTCATGTCAGTGGATTTGGATTTCAAACACCACCAACAACAACAACACCAACAACA
ACAACATCATCATCTGGTCCATCTAATGCCACCTTAGCCACTGAGAGCTCCAATTACCTTCAGAAA
ATTGCATTCCCTGGCTTTGACTTGCCTACTTCTGCCACTAACATGATGGGTCACATGAGTTTCACC
TCAATTTTGGGTGGAGGTGGGGGTGGTGGGCCCAGCATATGCCTGGCTTGGAGCTTGGTCTTTCC
CAGGATGGCCATATTGGGGTGTTGAATCAACAGGCCTTGAACCAGATTTATCAGCAGATGAATCAG
GCTGGTAGAGTGCATCATCATCAGCATCAGCATCATCATCAGCATCATCAGCAGCAACAACACCAT
CAGCAAACTCCTGCTAAGGATGATTCTCAAGGCTCAGGAGGACAGTAG FIGURE 5 (continued)

SEQ ID NO : 8 Glycine max Glyma_CLASS I TCP translated polypeptide sequence
MDPKGSKQQPQQSQEVVPNFLSLPQQQQGNTNNNMGENKPAEVKDFQIVVAENKEESKKQQQQLA
PKRSSNKDRHTKVEGRGRRIRMPALCAARIFQLTRELGHKSDGETIQWLLQQAEPSIIAATGTGTI
PASALAAAGNSLSPQAASLSSSLHQHQQKIDELGGSGGSSRASWQMVGGNLGRPHLGVGVATAAG
LWPPHVSGFGFQTPPTTTTPTTTTSSSGPSNATLATESSNYLQKIAFPGFDLPTSATNMMGHMSFT
SILGGGGGGAQHMPGLELGLSQDGHIGVLNQQALNQIYQQMNQAGRVHHHQHQHHHQHHQQQQHH
QQTPAKDDSQGSGGQ

SEQ ID NO : 9 Gossypium hirsutum Goshi_CLASS I TCP nucleic acid sequence contig of DT574583, DW499958
ATGGATCCCAAGGGCGCCAAGCAGCCTCCAGAGGAAGTAGCCAACTTGTTGAGCCTGCCACCCCAA
CCCCAACAGCAACAGCCTCAAAACATGGGAGAGAATAAAGCAGCAGAAATCAAGGATTTCCAGATT
GTGGTTGCAGATAAAGGAGAAGGGAAGAAGCAACAGTTGGCCCCAAAGAGAAGTTCTAACAAAGAC
AGGCACACCAAAGTTGAAGGAAGAGGTAGAAGGATAAGGATGCCTGCTTTATGTGCTGCTAGAATC
TTTCAGTTGACCAGGGAATTGGGTCACAAGTCTGATGGGGAAACCATACAGTGGCTGTTACAACAA
GCTGAACCATCCATAATTGCCGCCACTGGGAGCGGAACAATTCCAGCATCAGCTTTGGCTGCAGCT
GGAGGCTCAGTTTCACAGCCAGGGGCCTCTCTATCAGCAGGGTTGCACCAAAAGATGGAAGATTTA
GGGGGGTCCAGTATAGGGTCAGGGAGCAGTAGGACCAGTTGGACAATGGTTGGTGGCAATTTGGGA
AGACCCCATCATGTGGCGACCGGGTTATGGCCACCAGTCAGTGGTTTTGGGTTTCAGTCATCATCT
GGTCCGTCTACAACAAATTTAGGCAGTGATAGTTCCAATTATCTGCAAAAGCTTGGGTTTCCAGGT
TTTGATTTGCCAGCTAGTAACATGGGTCAGATAAGTTTCACCTCAATCTTGGGCGGAGCTAATCAG
CAGCTCCCGGGTTTGGAACTTGGGTTATCTCAAGATGGTCATATTGGGGTCTTAAATCCTCATGCT
TTGAACCAGATTTATCAGCAGATGGAGCAAGCTCGGATGCAACCCCAACATCAGCATCAGCACCAG
CAACAACCCCTGCTAAGGATGACTCCCAAGGATCGGGCCAGTAA

SEQ ID NO : 10 Gossypium hirsutum Goshi_CLASS I TCP translated polypeptide sequence
MDPKGAKQPPEEVANLLSLPPQPQQQQPQNMGENKAAEIKDFQIVVADKGEGKKQQLAPKRSSNKD
RHTKVEGRGRRIRMPALCAARIFQLTRELGHKSDGETIQWLLQQAEPSIIAATGSGTIPASALAAA
GGSVSQPGASLSAGLHQKMEDLGGSSIGSGSSRTSWTMVGGNLGRPHHVATGLWPPVSGFGFQSSS
GPSTTNLGSDSSNYLQKLGFPGFDLPASNMGQISFTSILGGANQQLPGLELGLSQDGHIGVLNPHA
LNQIYQQMEQARMQPQHQHQHQQQPPAKDDSQGSGQ

SEQ ID NO : 11 Lycopersicon esculentum Lyces_CLASS I TCP nucleic acid sequence contig of BW688913, BP878035.1, BI931745.1
ATGGATCCCAAACAGGCTAACCACAACAATATTAAGCCTACTCATGATCAGATAAAAGAGTTGCAG
ATTTTGAAAATGATGAAACGAACAAGGTGGCTGCTCCCAAAAGAAAAGATAGGCATACAAAAGTT
GAAGGTAGAGGGAGGAGAATACGTATGCCGGCGCTCTGTGCAGCAAGAATCTTCCAGCTTACGCGC
GAATTGGGTCATAAATCTGATGGTGAGACAATTCAGTGGCTGCTGCAGCAAGCCGAGCCTTCGATT
ATTGCTGCTACTGGCACAGGGACAATACCTGCCTCGGCTTTAGCTGCAGCAGCCTCTGTTTCTCAA
CAGGGGATCTCTGTATCAGCTGGTTTAATGATTGAATCGGGGCGAATATCGCGGGTCTGGTAGC
AGTAGAAGTAGTAATAGTAGGACCAATTGGCCAATGATCTGTGGGAATTTTGGAAGACCCCATTTG
GCTACAGCAGGAATGTGGCCTGCCCCTGCCCCTGTTGTCACTAGTTTTGGGTTTCAATCCTCATCT
GCTCCATCAAGCGCGAGTTTAGGTAGTGATAGTTCAAATTATTACTTACAGAAAATTGGGTTTCCT
GGATTTGATCTGCCTGCAGCTACAAGTATGAATCCGATGTGTTTTACTTCAATTCTTGGTGGAAGT
AATCAGCAACTGCCAGGATTGGAACTGGGATTATCTCAAGAGGGTCATTTAGGGGTTTTGAACCAG
ATATACCAGCAGGCAAGAATGCAACATCCGCAGCAGCAACATCAACAACAACAACAATCTCCGGAG
GAGGATTCTCAAGGATCAGGACATTAA

SEQ ID NO : 12 Lycopersicon esculentum Lyces_CLASS I TCP translated polypeptide sequence
MDPKQANHNNIKPTHDQIKELQILKNDETNKVAAPKRKDRHTKVEGRGRRIRMPALCAARIFQLTR
ELGHKSDGETIQWLLQQAEPSIIAATGTGTIPASALAAAASVSQQGISVSAGLMIESGANIAGSGS
SRSSNSRTNWPMICGNFGRPHLATAGMWPAPAPVVTSFGFQSSSAPSSASLGSDSSNYYLQKIGFP
GFDLPAATSMNPMCFTSILGGSNQQLPGLELGLSQEGHLGVLNQIYQQARMQHPQQQHQQQQQSPE
EDSQGSGH

SEQ ID NO : 13 Malus domestica Maldo_CLASS I TCP nucleic acid sequence contig of EB153444, CN895103
ATGGATCCCAAGGGCTCAAAGCAGACACAAGACATACCCAGCTTCTTGAGCCTTCCCCCACAATCA
CAACCACAACCTGAGCAGCAGCAGCAACCACAACAACAACCTCAACCCAACAACAACATGAGCGAC
AACAAACCTGCTGAAATCAAAGACTTCCAGATTGTAATCGCCGACAAAGATGAGTCGGGAAAGAAG
CAGTTGGCGCCCAAGAGAAGCTCCAACAAAGACAGACACACTAAAGTCGAAGGCAGGGGAAGGAGG
ATACGGATGCCGGCCCTCTGCGCCGCCAGAATCTTTCAATTGACCAGAGAGTTGGGTCACAAATCC
GATGGGGAAACAATCCAGTGGCTCCTCCAGCAGGCCGAGCCGTCGATTGTTGCCACCACCGGGACC
GGGACGATTCCGGCGTCGGCTTTGGCGGCGGCAGGTGGCTCTGTTTCGCAACAGGGGACTTCTTTA
TCAGCTGGATTGCACCAAAAGATCGATGAATTGGGGGGGTCCAGTGGGGGTAGGACCAGTTGGGCA
ATGGTGGGCGGGAATTTGGGGAGACCCCATGTGGCAGGGGTGGGCGGGCTATGGCCCCCTGTCAGT
AGCTTTGGGTTCCAGTCATCATCTGGTCCTCCATCGGCCACCACAAATCTGGGCACTGAGAGTTCA
AATTACCTGCAAAAAATTGGGTTTCCTGGCTTTGACTTGCCTGTCTCTAACATGGGTCCGATGAGT
TTTACTTCAATTTTGGGTGGGGGCAATCAGCAGCAGCAGCAGCAGCTTCCTGGGTTGGAACTTGGG
TTGTCACAGGATGGACATATTGGGGTTCTGAACTCTCAGGCTTTGAGCCAGATTTACCAGCAGATG
GGGCATGTTAGAGTGCACCAGCAGCCGCCGCAGCACCACCACCAGCAACACCACCACCACCAGCAG
CAACCGCCTTCCAAGGACGATTCTCAAGGATCCGGACAGTAG

SEQ ID NO : 14 Malus domestica Maldo_CLASS I TCP translated polypeptide sequence
MDPKGSKQTQDIPSFLSLPPQSQPQPEQQQQPQQQPQPNNNMSDNKPAEIKDFQIVIADKDESGKK
QLAPKRSSNKDRHTKVEGRGRRIRMPALCAARIFQLTRELGHKSDGETIQWLLQQAEPSIVATTGT
GTIPASALAAAGGSVSQQGTSLSAGLHQKIDELGGSSGGRTSWAMVGGNLGRPHVAGVGGLWPPVS
SFGFQSSSGPPSATTNLGTESSNYLQKIGFPGFDLPVSNMGPMSFTSILGGGNQQQQQQLPGLELG
LSQDGHIGVLNSQALSQIYQQMGHVRVHQQPPQHHHQQHHHHQQQPPSKDDSQGSGQ

SEQ ID NO : 15 Medicago truncatula Medtr_CLASS I TCP nucleic acid sequence contig of CG926048.1 CA921765.1
ATGGATCCCAAAAACTCAAAGCAACAATCACAACTCTCAAACATGGGAGAGAACAAAGAATCAGAG
ACAAAAAATCTTCAAATTGTGTTATCTGAAACAACAACAAAAGATGAAACAAAGAAACAACTAGCA
CCAAAAAGAACATCAAACAAAGACAGACACACAAAAGTTGAAGGAAGAGGAAGAAGAATAAGGATG
CCAGCTTTATGTGCAGCAAGAATCTTTCAGCTAACAAGAGAGTTAGGTCATAAATCAGATGGTGAA
ACAATTCAATGGCTTTTACAACAATCTGAACCATCAATCATAGCTGCAACAGGAACAGGAACAATA
CCAGCTTCAGCTTTAGCTTCTTCTGGTAATACTTTGACACCACAAGGTTCATCTTTGTCTTCTGGT
TTACAGTTGAATGATAGGAATACTTGGGCTCAGACCCATCAAGCCCATCAGGCCCATCAGGGCCAT
CATGTTAGTTCTACAAGTTTATGGCCACATCATCATGTTGGTGGATTTGGATTTCATCAATCATCA
TCATCTGGTGGTTTAGTAGCTACTACTGTTGGTGAAAATAATAGTGGAAATTATTTTCAGAAAATT
GGGTTTTCTGGATTTGATATGCCAACAGGAACAAATTTGGGAGTGGGAGGGATGAGTTTTACTTCA
ATTTTGGGGGGTGCAAATCAGCAGATGCCTGGTTTGGAATTAGGGTTGTCACAAGATGGACATATT
GGTGTGTTAATCAACAAGCTTTAACTCAGATTTATCAGCAGATTGGTCAAATCAAACTAGGGTT
CAGCACCAGAATCAGCAGAATAATAATACTACTAAGGATGATTCTCACAGTTCAGAACAGTAG

FIGURE 5 (continued)

SEQ ID NO : 16 Medicago truncatula Medtr_CLASS I TCP translated polypeptide sequence
MDPKNSKQQSQLSNMGENKESETKNLQIVLSETTTKDETKKQLAPKRTSNKDRHTKVEGRGRRIRM
PALCAARIFQLTRELGHKSDGETIQWLLQQSEPSIIAATGTGTIPASALASSGNTLTPQGSSLSSG
LQLNDRNTWAQTHQAHQAHQGHHVSSTSLWPHHHVGGFGFHQSSSSGGLVATTVGENNSGNYFQKI
GFSGFDMPTGTNLGVGGMSFTSILGGANQQMPGLELGLSQDGHIGVLNQQALTQIYQQIGQNQTRV
QHQNQQNNNTTKDDSHSSEQ

SEQ ID NO : 17 Nicotiana benthamiana Nicbe_CLASS I TCP nucleic acid sequence CK296978
ATGGATCCCAAGCAGCCGCCAGCGCAGTCTAACGCTATCAACATTAACAACAATATTATGGTTGAG
TACAATAAGCCTGTTCATGATCAAATAAAAGATGATGAAACCAAGAAGCGGCAGCAATTGGTTCCT
AAAAGAAAAGATAGGCACACAAAAGTTGAAGGCAGAGGGAGGAGGATACGTATGCCTGCTCTTTGC
GCTGCTAGGATTTTCCAACTCACCCGCGAATTAGGTCATAAATCTGATGGAGAGACAATCCAGTGG
CTGCTGCAGCAAGCCGAGCCCTCCATATTTGCGGCCACCGGGACAGGGACCATCCCTGCCTCGGCT
TTAGCTGTAGCAGCCGCTGGCCCCTCTGTTTCCCAACAGAGGACCTCTGTATCTGCTGGTTTGCAT
AAAAAAATGGATGAATTGGGAGCGAATATAGTCGGGTCCGCTAGTATATGTAGTAGTAGTAGTACT
AGTAGGGCCAGTTGGCCAATGATGATTGGGAATTTTGGAAGACCCCATTTGGCCACAGCAGGAATA
TGGCCCGGACCTACTCCTGTTGTCAATAGTTTCGCGTTACAGACAGCACTGACTCCTGGATCAAGC
ACCAATTTGGGTAGTGAAAGTTCCAATTATTACCTACAAAAGATTGGCTTTCCTGGATTTGATCTG
CCTGCAGCCACCAATATGAGTTTTACTTCAATTCTAGGTTCCAGTAATAACCAGCAATTGCCAGGT
TTGGAGCTTGGATTATCTCAAGACAGGGGTCATATAGGGGTTTTAAACTCTCAAGGCTTGAGCCAG
ATATACCAGGCTAGAATTCATAATCAACAGCAGCACCAGCAAAATCAGCATGAGCATCTATCTCCC
GAGGATGATTCTCACGGATCAGGACACTAA

SEQ ID NO : 18 Nicotiana benthamiana Nicbe_CLASS I TCP translated polypeptide sequence
MDPKQPPAQSNAININNNIMVEYNKPVHDQIKDDETKKRQQLVPKRKDRHTKVEGRGRRIRMPALC
AARIFQLTRELGHKSDGETIQWLLQQAEPSIFAATGTGTIPASALAVAAAGPSVSQQRTSVSAGLH
KKMDELGANIVGSASICSSSSTSRASWPMMIGNFGRPHLATAGIWPGPTPVVNSFALQTALTPGSS
TNLGSESSNYYLQKIGFPGFDLPAATNMSFTSILGSSNNQQLPGLELGLSQDRGHIGVLNSQGLSQ
IYQARIHNQQQHQQNQHEHLSPEDDSHGSGH

SEQ ID NO : 19 Ocimum basilicum Ociba_CLASS I TCP nucleic acid sequence DY322462
ATGGATCCGAAGAGCTCGAAGCAGCCGCAGGAGGTTTCGAATCACAGCAACACCAACAGCTTAGGC
GAAAACAAAGCAGCGGAAATCAAGGATTTTCAGATTGTAGTTGCGGAGAAGGATGATTCGAAGAAG
CTAGCCCTAGCTCCGAAGCGAAGCTCCAACAAGGACCGCCACACCAAGGTGGAAGGCCGCGGCCGG
CGAATTCGGATGCCGGCGCTCTGCGCCGCCAGAATCTTCCAATTGACCCGAGAATTAGGGCACAAA
TCCGATGGCGAGACCATCCAGTGGCTCCTCCAGCAAGCCGAGCCGTCGATCATCGCCGCCACGGGG
AGCGGCACCATCCCCGCCTCCGCCCTCGCCGCAGCCGCCGGCTCGATTTCTCAGCAAGGTAGCTCG
ATTCGTCTGGACTCCATCAGAAAATCGAGGATTTAGGCGCTTCTATGGGTGGTGGTGGGGGCAGG
AATCCCTGGCCTATGATTGGTGGGAATCTGAGTAGACCACATGTGGGCGCAAGCACAGGATTATGG
CCTCCCACTGGATTCGGCTTCCAGACGGCGTCGTCTTCTTCCTCGTCTGGTCCGTCAATCGCGGCG
GAGAATCCTAATTATCTCCAGAAAATGGGGTTTGCTGGATTTGAGCTGCCCGGGAATATCGGGCAG
ATGAGTTTCACCTCCATCTTAAGCGGCGGCGGCAGCAGCTGCCCGGATTGGAGCTCGGCCTTTCA
CAAGATGGAAATATTGGGGTTTTGAATCCGCAAGCTTTTGGGCAGATTTATCAGCAGATTAATCCG
GCGGCGCGTGTGGTTAACGCACATCAAAATCACCACCAACAACACCACCATCAGCAGCCATTGTCG
TCGAAAGATGATGATTCTCAAGAATCAGGACAGTAG

FIGURE 5 (continued)

SEQ ID NO : 20 Ocimum basilicum Ociba_CLASS I TCP translated polypeptide sequence
MDPKSSKQPQEVSNHSNTNSLGENKAAEIKDFQIVVAEKDDSKKLALAPKRSSNKDRHTKVEGRGR
RIRMPALCAARIFQLTRELGHKSDGETIQWLLQQAEPSIIAATGSGTIPASALAAAAGSISQQGSS
ISSGLHQKIEDLGASMGGGGGRNPWPMIGGNLSRPHVGASTGLWPPTGFGFQTASSSSSGPSIAA
ENPNYLQKMGFAGFELPGNIGQMSFTSILSGGGQQLPGLELGLSQDGNIGVLNPQAFGQIYQQINP
AARVVNAHQNHHQQHHHQQPLSSKDDDSQESGQ

SEQ ID NO : 21 Oryza sativa Orysa_PCF1 nucleic acid sequence Os01g0924400 NM_001051782
ATGGACCCCAAATTCCCCCCACCCCCACCGCTAAACAAAACGGAGCCCACCACCACCACCACCAAC
CAGCAGCATCACCACGATGAGCAGCAGCAGCAGCATCGCCTCCAGATTCAAGTTCATCCTCAGCAG
CAGGAGCAGCAGGATGGAGGTGGAGGAGGAGGGAAGGATCAGCAGCAGCAGCAGCAGATGCAGGTG
GTGGTTGCGGCGGCGGCGGGGGAGAGGAGGATGCAGGGCTAGGGCCGAAGCGGAGCTCGAACAAG
GACCGCCACACCAAGGTGGACGGGCGGGGGCGGCGGATCCGGATGCCGGCGCTGTGCGCCGCCCGG
ATCTTCCAGCTCACGCGGGAGCTCGGCCACAAGTCCGACGGCGAGACCGTCCAGTGGCTGCTCCAG
CAGGCGGAGCCGGCCATCGTCGCCGCCACGGGGACCGGGACCATCCCGGCGTCCGCGCTCGCCTCC
GTCGCCCCCTCCCTCCCTTCCCCCAACTCCGCCCTCTCCAGGTCGCACCACCACCACCACCACATG
TGGGCGGCAGCGCCGCCCACGGCGTCCGCCGGGTTCGCCGGTGCAGGGTTCTCCGGCGCCGACTCC
GGGGTGATCGGCGGGATCATGCAGCGGATGGGGATCCCCGCCGGGATCGAGCTCCAGGGCGGGGGA
GCGGGGGGGTTGGGGGGTGGGGGTGGCGGCGGCGGTGGCCACATCGGGTTCGCGCCCATGTTCGCC
AGCCACGCGGCGGCGGCGGCGGCCATGCCGGGGCTAGAGCTAGGGCTCTCGCAGGACGGCCACATC
GGCGTGCTCGCCGCGCAGTCGCTCAGCCAGTTCTACCACCAGGTCGGCGCCGCCGGTCAGCTGCAG
CACCAGCACCAGCATCACCATCAGCAGCAGCAGCAGCAGCAGGACGGGGAGGACAACCGCGACGAC
GGCGAGTCCGATGAGGAGTCCGGGCAGTAG

SEQ ID NO : 22 Oryza sativa Orysa_PCF1 translated polypeptide sequence
MDPKFPPPPPLNKTEPTTTTTNQQHHHDEQQQQHRLQIQVHPQQQEQQDGGGGGKDQQQQQQMQV
VVAAAAGERRMQGLGPKRSSNKDRHTKVDGRGRRIRMPALCAARIFQLTRELGHKSDGETVQWLLQ
QAEPAIVAATGTGTIPASALASVAPSLPSPNSALSRSHHHHHHMWAAAPPTASAGFAGAGFSGADS
GVIGGIMQRMGIPAGIELQGGGAGGLGGGGGGGGGHIGFAPMFASHAAAAAAMPGLELGLSQDGHI
GVLAAQSLSQFYHQVGAAGQLQHQHQHHHQQQQQQQDGEDNRDDGESDEESGQ

SEQ ID NO : 23 Populus tremuloides Poptr_CLASS I TCP nucleic acid sequence contig of CX169560.1, DT515387.1
ATGGATCCCAAGGGCTCTAACTCAAAAAACCCACATGAGTTACCCACTTTCTTGACCCACACCCAC
CCTTCTCCTCCTCATCCTCCTCCACAACCTCATCTTCAACAACCACAACAACTCCATAGCCAAAAC
CAACAACAACCCAACATGGGAGACAACAAACCAGCAGAAATCAAAGACTTTCAGATTGTAGTAGCT
GACAAAGAAGAGCAAAAGAAACAGTTAGCACCAAAGAGAAGCTCAAACAAAGACAGACACACAAAA
GTTGAAGGTAGAGGTAGAAGGATAAGGATGCCAGCTCTTTGTGCAGCGAGAATCTTTCAATTGACA
AGAGAATTGGGTCACAAATCTGATGGAGAGACAATACAGTGGCTTCTACAACAAGCTGAACCATCT
ATAATTGCAGCAACTGGACTGGTACTATACCTGCATCAGCTTTAGCAGCTGCTGGCGGTGCAATT
TCACAACAAGGAGCTTCTCTTTCTGCTGGTTTGCATCAAAAGATTGATGATTTAGGTGGGTCCAGT
AGTAGTAGGGCCAGTTGGGCAATGTTAGGTGGCAATTTAGGGAGACCCCATCATGTTACTACTGCA
GGATTATGGCCCCCAGTTGGAGGTTATGGGTTCCAGTCATCATCTAATTCCACTGGTCCATCAACA
ACAAATATAGGGACTGAAGCTGCTGCTGCTGGTGGTTCTAGTTATTTGCAAAAACTCGGGTTTCCA

```
GGGTTTGACTTGCCGGGTAACAACATGGGGCCTATGAGTTTTACTTCAATTTTAGGTGGGGGTACC
CAGCAGTTACCAGGATTGGAACTTGGGTTGTCACAGGACGGGCATATTGGGGTTTTGAGTCCACAA
GCTTTGAATCAGATTTATCAGCAGATGGGGCATGCTAGAGTGCACCAGCAGCAGCATCAGCAACAA
AATCCTTCTAAAGATGATTCACAAGGATCAGGCCAGTGA
```

SEQ ID NO : 24 Populus tremuloides Poptr_CLASS I TCP translated polypeptide sequence
```
MDPKGSNSKNPHELPTFLTHTHPSPPHPPPQPHLQQPQQLHSQNQQQPNMGDNKPAEIKDFQIVVA
DKEEQKKQLAPKRSSNKDRHTKVEGRGRRIRMPALCAARIFQLTRELGHKSDGETIQWLLQQAEPS
IIAATGTGTIPASALAAAGGAISQQGASLSAGLHQKIDDLGGSSSSRASWAMLGGNLGRPHHVTTA
GLWPPVGGYGFQSSSNSTGPSTTNIGTEAAAAGGSSYLQKLGFPGFDLPGNNMGPMSFTSILGGGT
QQLPGLELGLSQDGHIGVLSPQALNQIYQQMGHARVHQQQHQQQNPSKDDSQGSGQ
```

SEQ ID NO : 25 Saccharum officinarum Sacof_CLASS I TCP nucleic acid sequence SCJLRT1023A09.g
```
ATGGACCCCAAGTTCCCCACACCCCCACCGCTAAACAAAACGGAGCCCACCACCGCGACGACCACC
ACCACCACCTCGACCGCGCAGCAGCTGGATCCTAAGGACTACCAGCAGCAGCAGCCGGCGCAGCAC
CACCTGCAAATCCAAATCCACCAGCCGCCGCAGCAGGACGGGGGCGGCGGAGGGAAGGAGCAACAG
CAGCAGCTGCAGGTGGTGGCGCAGCCCGGGGAGCGGAGGCAGCAGCCGCTCGCGCCCAAGCGGAGC
TCCAACAAGGACCGCCACACCAAGGTCGATGGCAGGGGCCGCCGGATCCGGATGCCCGCGCTGTGC
GCCGCGCGGATCTTCCAGCTCACGCGGGAGCTCGGCCACAAGTCCGACGGCGAGACCGTGCAGTGG
CTGCTGCAGCAGGCCGAGCCGGCCATCGTCGCCGCCACCGGCACGGGCACCATACCGGCGTCCGCG
CTCGCATCCGTCGCGCCCTCGCTCCCGTCGCCCACCTCCGGGCTCGCCAGGCCGCACCACCACCAC
CATCCGCACCACATGTGGGCGCCTTCCGCCGCGTCCGCGGGTTTCTCCTCGCCCTCCTTCCTCAAT
TCCGCCGCCGCAGGCACGGGAGACGCCGCTGGTATCGGCGGCATCATGCAGCGGATGGGGATCCCC
GCGGGCCTCGAGCTGCCGGGAGGGGCGCCGCTGGGGCNNNCGGCTTTGCGCCCATGTTCGCTGAA
CACCCCGCGGCCATTCCGGGGCTCGAGCTTGCCCTCTCGCAGGACGGCCACATCGGGTTGCTCGCC
GCGCAGTCGATCACCCAGTTCTACCACCAGGTGGGTGCTGCCGGCGGCAGCGGCCAGATGCAGCAC
CCTCACGGCCACCAGCAGGAGGACGGGGAGGACGACCGCGAGGACGGCGAGTCCGATGATGAGTCT
GGGCAGTAG
```

SEQ ID NO : 26 Saccharum officinarum Sacof_CLASS I TCP translated polypeptide sequence
```
MDPKFPTPPPLNKTEPTTATTTTTTSTAQQLDPKDYQQQQPAQHHLQIQIHQPPQQDGGGGKEQQ
QQLQVVAQPGERRQQPLAPKRSSNKDRHTKVDGRGRRIRMPALCAARIFQLTRELGHKSDGETVQW
LLQQAEPAIVAATGTGTIPASALASVAPSLPSPTSGLARPHHHHHPHHMWAPSAASAGFSSPSFLN
SAAAGTGDAAGIGGIMQRMGIPAGLELPGGGAAGAXGFAPMFAEHPAAIPGLELALSQDGHIGLLA
AQSITQFYHQVGAAGGSGQMQHPHGHQQEDGEDDREDGESDDESGQ
```

SEQ ID NO : 27 Solanum tuberosum Soltu_CLASS I TCP nucleic acid sequence contig of CK271473.1, BQ507674.2
```
ATGGATCCCAAGCAGCCTAACAACAAAAATATTAAGCCTACTCATGATCAGATAAAAGACTTGCAG
ATTTTGAAAAATGATGAAACCAAGAAACAGCAGCAGGTGGCTGCTCCTAAAAGAAAAGATAGGCAT
ACCAAAGTTGAAGGTAGAGGGAGGAGGATACGTATGCCTGCTCTATGTGCAGCAAGAATCTTTCAA
CTTACGCGCGAATTGGGTCATAAATCTGATGGTGAGACAATTCAGTGGCTGCTGCAGCAAGCCGAG
CCTTCGATTATTGCTGCTACTGGCACAGGGACAATTCCTGCATCGGCTTTAGCTGCAGCAGCATCT
GTTTCTCAACAGGGGATCTCTGTATCAGCTGGTTTAATGATTGAATCGGGGGCGAATATCGCGGGG
```

FIGURE 5 (continued)

```
TCAGGTAGCAGTAGAAGTAGTAATAGTAGGACCAATTGGCCAATGATCTGTGGGAATTTTGGAAGA
CCCCATTTGGCTACAGTAGGAATATGGCCTGCCCCTGCCCCTGTTGTCACTAGTTTTGGGTTTCAG
TCCTCATCTGCTCCATCAAGCGCCAGTTTAGACAGTGAAAGTTCAAACTATTACTTACAGAAAATT
GGGTTTCCTGGATTTGATCTGCCTGCAGCTACAAATATGAATCCTATGAGTTTTACTTCAATTCTT
GGTGGAAGTAACCAGCAACTGCCAGGATTGGAGCTTGGATTATCTCAAGAGGGTCATTTAGGGGTT
TTGAACCAGATATACCAGCAGGAAAGAATGCAACATCCGCAGCAGCAACAACAAGATCAGCATCAG
CATCAGCATCAACAACAATCTCCGGAGGATGATTCTCAAGGATCAGGACATTAA
```

SEQ ID NO : 28 Solanum tuberosum Soltu_CLASS I TCP translated polypeptide sequence
```
MDPKQPNNKNIKPTHDQIKDLQILKNDETKKQQQVAAPKRKDRHTKVEGRGRRIRMPALCAARIFQ
LTRELGHKSDGETIQWLLQQAEPSIIAATGTGTIPASALAAAASVSQQGISVSAGLMIESGANIAG
SGSSRSSNSRTNWPMICGNFGRPHLATVGIWPAPAPVVTSFGFQSSSAPSSASLDSESSNYYLQKI
GFPGFDLPAATNMNPMSFTSILGGSNQQLPGLELGLSQEGHLGVLNQIYQQERMQHPQQQQQDQHQ
HQHQQQSPEDDSQGSGH
```

SEQ ID NO : 29 Sorghum bicolor Sorbi_CLASS I TCP nucleic acid sequence contig of CL162154.1, ED507285.1, CW333599.1
```
ATGGACCCCAAGTTCCCCACACCCCCACCGCTAAACAAAACGGAGCCCACCACCGCGACGACCACC
ACCACCTCGACCGCGCAGCAGCAGCAGCAGCTGGATCCTAAGGACTACCAGCAGCCGGCGCAG
CAGCACCACCTGCAAATCCAAATCCACCAGCCGCCGCCGCAGCAGCAGCAGCAGCAGGACGGAGGC
AAGGAGCAGCAGCTGCAGGTGGTGGCGCAGCCCGGGGAGCGGAGGCAGCAGGCGCTCGCGCCCAAG
CGGAGCTCCAACAAGGACCGCCACACCAAGGTCGACGGCAGGGGCCGCCGGATCCGGATGCCCGCG
CTGTGCGCCGCGCGGATCTTCCAGCTCACGCGGGAACTCGGCCACAAGTCCGACGGCGAGACCGTG
CAGTGGCTGCTGCAGCAGGCCGAGCCGGCCATCGTCGCCGCCACCGGCACCGGCACCATACCGGCG
TCCGCGCTCGCATCCGTCGCGCCCTCGCTCCCGTCGCCCACCTCCGGGCTCGCCAGGCCGCACCAC
CACCACCACCCGCACCACATGTGGGCGCCGTCCGCCGCGTCCGCGGGTTTCTCCTCGCCCTCCTTC
CTCAATTCCGCCGCCGCGGGCACGGGAGACGCCGCTGGTATCGGCGGACTCATGCAGCGGATGGGG
ATCCCCGCGGGTCTCGAGCTGCCGGGAGGCGGCGCCGCTGGAGGCACCCTCGGCGCTGGCGGCCAC
ATCGGCTTTGCGCCCATGTTCGCTGGACACGCCGCGGCCATGCCGGGGCTCGAGCTCGGCCTCTCG
CAGGACGGCCACATCGGCGTGCTCGCAGCGCAGTCGATCAGCCAGTTCTACCACCAAGTGGGTGCT
GCTGGCGGCAGCGGCCAGATGCAGCACCCGCACGGCCACCAGCATCACCATCATCAGCAGCAGGAG
GACGGGGAGGACGACCGCGAGGACGGCGAGTCCGATGACGAGTCTGGGCAGTAG
```

SEQ ID NO : 30 Sorghum bicolor Sorbi_CLASS I TCP translated polypeptide sequence
```
MDPKFPTPPPLNKTEPTTATTTTTSTAQQQQQQLDPKDYQQPAQQHHLQIQIHQPPPQQQQQQDGG
KEQQLQVVAQPGERRQQALAPKRSSNKDRHTKVDGRGRRIRMPALCAARIFQLTRELGHKSDGETV
QWLLQQAEPAIVAATGTGTIPASALASVAPSLPSPTSGLARPHHHHPHHMWAPSAASAGFSSPSF
LNSAAAGTGDAAGIGGLMQRMGIPAGLELPGGGAAGGTLGAGGHIGFAPMFAGHAAAMPGLELGLS
QDGHIGVLAAQSISQFYHQVGAAGGSGQMQHPGHQHHHHQQQEDGEDDREDGESDDESGQ
```

SEQ ID NO : 31 Vitis vinifera Vitvi_CLASS I TCP nucleic acid sequence contig of CB972449, EC971921
```
ATGGATCCCAAGGGCTCAAAGCAGCCGCAGGAGGTACCAAACTTCTTGAGCCTACCTCAGCCAAAC
ATGGGAGAGAACAAGCCAGCTGAAGTGAAGGACTTTCAGATTGTGATTGCAGATAAGGAAGAGGGT
AAGAAGCAGTTGGCCCCCAAGAGGAGCTCAAACAAGGACAGGCACACCAAGGTTGAAGGCAGAGGG
AGGAGAATAAGGATGCCGGCTCTTTGTGCAGCCAGAATTTTTCAGTTGACTAGGGAATTGGGTCAC
```

```
AAATCTGACGGGGAAACCATACAGTGGTTGTTGCAGCAGGCCGAGCCGTCCATAATAGCGGCCACT
GGTACTGGGACAATACCGGCGTCGGCTTTAGCGGCGGCAGGAGGCTCTGTGTCGCAACAGGGAACT
TCTATATCAGCAGGATTGCATCAAAAGATTGATGAATTGGGGGGGTCCAGTATTGGGTCAGGGAGT
AGTAGGACCAGTTGGGCAATGGTAGGTGCAAATTTGGGGAGACCCCATGTGGCCACAGGGCTATGG
CCCCCAGTCAGTGGTTTTGGGTTTCAGTCATCATCTGGACCATCAACCACCAATTTGGGGAATGAA
AGTTCCAATTATCTGCAAAAAATTGCCTTCCCTGGGTTTGACTTGCCTGCAACAAATCTGGGTCCT
ATGAGTTTTACTTCAATTTTGGGTGGGAGTAACCAGCAGCTTCCTGGTTTGGAGCTGGGCCTATCA
CAGGATGGTCATATTGGGGTTTTGAACTCACAAGCCTTAAGCCAGATTTACCAGCAGATGGGGCAG
GCCAGGGTGCACCAGCAACAGCAGCATCAACATCAGCATCAGCATCAGCATCAACAGCAACCTCCT
GCTAAGGATGATTCTCAAGGTTCAGGGCAGTAG
```

SEQ ID NO : 32 Vitis vinifera Vitvi_CLASS I TCP translated polypeptide sequence
```
MDPKGSKQPQEVPNFLSLPQPNMGENKPAEVKDFQIVIADKEEGKKQLAPKRSSNKDRHTKVEGRG
RRIRMPALCAARIFQLTRELGHKSDGETIQWLLQQAEPSIIAATGTGTIPASALAAAGGSVSQQGT
SISAGLHQKIDELGGSSIGSGSSRTSWAMVGANLGRPHVATGLWPPVSGFGFQSSSGPSTTNLGNE
SSNYLQKIAFPGFDLPATNLGPMSFTSILGGSNQQLPGLELGLSQDGHIGVLNSQALSQIYQQMGQ
ARVHQQQQHQHQHQHQQQPPAKDDSQGSGQ
```

SEQ ID NO : 33 Zea mays Zeama_CLASS I TCP_1 nucleic acid sequence contig of DR826915.1, DR794438.1
```
ATGGACCCCAAGTTCCCCACACCCCTAGCGCTAAACAAAACGGAGCCCACCACCGCGACGACCACC
ACCACCTCGACCGCGCAGCATCATCAGCTGGATCCTAAGGACTACCAGCAGCAGACGGCGCAGCAC
CAGGAGCAGCAGCAGCACCACCATCACCCCCACCTGCAAATCCAAATCCACCAGCCGCCGCCGCCG
CCGCAGGACGGGGGCGGCGGAGTGAAGGAGCAGCAGCAGCTGCTGCAGGTGGTGGCGCAGCCCGGG
GATCGGAGGCAGCAGGCGCTCGCCCCAAGCGGAGCTCCAACAAGGACCGCCACACCAAGGTCGAC
GGCAGGGGCCGCCGGATCCGGATGCCGGCGCTCTGCGCCGCGCGGATCTTCCAGCTCACGCGGGAG
CTCGGCCACAAGTCCGACGGCGAGACTGTGCAGTGGCTGCTGCAGCAGGCCGAGCCGGCCATCGTC
GCCGCCACCGGCACGGGCACCATACCGGCGTCCGCGCTCGCCTCCGTCGCGCCCTCGCTCCCGTCG
CCTACCTCCGGGCTCGCCAGGCCGCACCACCACCACCCGCACCACATGTGGGCGCCGTCCGCCGGC
TTCTCCTCGCCCTCCTTCCTGAATTCCGCGGGCGCGGGCGACGGCACCGGTATCGGCGGCATCATG
CAGCGGATGGGGGTCCCCGCGGGCCTGGAGCTGCCGGGAGGCGGCGCCGCCGGCGGCCACATCGGC
TTTGCGCCCATGTTCGCTGGACACGCCGCGGCCATGCCGGGGCTCGAGCTCGGCCTCTCGCAGGAC
GGTCACATCGGCGTGCTCGCCGCGCAGTCGATCAGCCAGTTCTACCACCAGGTGGGTGCCGCTGCC
GGCGGCAGTGGCCAGATGCAGCACCCGCACGGGCACCAGCATCACCATCATCAGCAGCAGGAGGAC
GGGGAGGACGACCGCGAGGACGGCGAGTCTGATGACGAGTCTGGGCAGTAG
```

SEQ ID NO : 34 Zea mays Zeama_CLASS I TCP_1 translated polypeptide sequence
```
MDPKFPTPLALNKTEPTTATTTTSTAQHHQLDPKDYQQQTAQHQEQQQHHHHPHLQIQIHQPPPP
PQDGGGGVKEQQQLLQVVAQPGDRRQQALAPKRSSNKDRHTKVDGRGRRIRMPALCAARIFQLTRE
LGHKSDGETVQWLLQQAEPAIVAATGTGTIPASALASVAPSLPSPTSGLARPHHHHPHHMWAPSAG
FSSPSFLNSAGAGDGTGIGGIMQRMGVPAGLELPGGGAAGGHIGFAPMFAGHAAAMPGLELGLSQD
GHIGVLAAQSISQFYHQVGAAAGGSGQMQHPHGHQHHHQQQEDGEDDREDGESDDESGQ
```

SEQ ID NO : 35 Zea mays Zeama_CLASS I TCP_2 nucleic acid sequence contig of DR963477.1, EE022629.1
ATGGACCCCAAGTTCCCCCCACCCCCACCGCTAAACAAAACGGAGCCCACCACCGCGACGACCACC
ACCACCTCGACCGCGCAGCAGCAGCAGCAGCAGCTGGATCCTAAGGACTACCAGCAGCAGCAGCAG
CAGCCGGCGCAGCACCTGCAAATCCAAATCCACCAGTCGCAGCAGGACGGAGGCGGCGGAGGGAAG
GAGCAGCAGCAGCTGCAGGTGGTGGCGCAGCCCGGGGAGAGGAGGCAGCAGGCGCTCGCGCCCAAG
CGGAGCTCCAACAAGGACCGACACACCAAGGTCGACGGCAGGGGCCGGCGGATCCGGATGCCCGCG
CTCTGCGCCGCGCGGATCTTCCAGCTCACGCGGGAACTCGGCCACAAGTCCGACGGCGAGACCGTC
CAGTGGCTGCTGCAGCAGGCCGAGCCGGCCATCGTCGCCGCCACCGGCACGGGCACCATACCGGCG
TCCGCGCTCGCCTCCGTCGCGCCCTCGCTCCCGTCGCCCACCTCCGGGCTCGCCAGGCCGCACCAC
CACATGTGGGCGCCGTCCGCCGGCTTCTCCTCGCCCTCCTTCCTGAACTCTGCCGCCGCGGGCACG
GGCGATGCCGCCGGTATCATGCAGCGGATGGGGATCCCCGCGGGCTTCGAGCTGCCGGGAGCCTCC
GCCGCCGGAGCCACCCTCGGCGCCGGCGGCCACATCGGCTTTGCGCCCATGTTCGCTGGACACGCC
GCCGCCATGCCGGGGCTCGAGCTCGGGCTATCGCAGGACGGCCACATCGGCGTGCTCGCCGCGCAG
TCGATCAGCCAGTTCTACCACCAGGTGGGTGCTGCCGCCGGCGGCGGCGGCCAGATGCATCACGCG
CACGGGCACCATCATCACCATCACCAGCAGCAGGAGGACGGGGAGGACGACCGCGAGGACGGCGAG
TCCGATGACGAGTCTGGGCAGTAG

SEQ ID NO : 36 Zea mays Zeama_CLASS I TCP_2 translated polypeptide sequence
MDPKFPPPPPLNKTEPTTATTTTTSTAQQQQQQLDPKDYQQQQQQPAQHLQIQIHQSQQDGGGGGK
EQQQLQVVAQPGERRQQALAPKRSSNKDRHTKVDGRGRRIRMPALCAARIFQLTRELGHKSDGETV
QWLLQQAEPAIVAATGTGTIPASALASVAPSLPSPTSGLARPHHHMWAPSAGFSSPSFLNSAAAGT
GDAAGIMQRMGIPAGFELPGASAAGATLGAGGHIGFAPMFAGHAAAMPGLELGLSQDGHIGVLAAQ
SISQFYHQVGAAAGGGGQMHHAHGHHHHHHQQQEDGEDDREDGESDDESGQ

SEQ ID NO : 37 Allium cepa Allce_CLASS I TCP partial 5' nucleic acid sequence CF439613
ATGGATCCAAAAGAATCCCAACCCAACTCGGATCGTCAATTGATGACCCAAACCGAATCCATTCAA
GACCCGCAAAAAAGAGCCCTTCTTGCCCCAAAACGGACCTCCAACAAAGACCGCCACACCAAAGTT
GACGGCCGCGGCCGGAGGATTCGCATGCCCGCTCTCTGCGCCGCCAGAATCTTCCAGCTGACCCGA
GAACTCGGCCATAAATCCGACGGCGAGACCGTTCAGTGGCTTCTGCATCATGCAGAACCTGCCATC
ATCGCCGCTACCGGGTCGGGTACCATACCCGCATCCGCTTTAGCTTCTTCTCAGGCGATGCCGAAC
TCTAAGCCCGACAACAGTTGGGCTGTTGGGTTATGGGGAGGTTTTAATTCCGGATTTATGAATTCC
AATAATAGCAGTAACAACAACAATAATAATGGAGTCGGCCCTAGCTCGAGCAATTTAGGGTTTGTG
GGGATGGAGATGACAGGGATGAGTGGGCACATGAGCTTTACTTCAATGCTGGGAGGGCAGCCTGGG
CCACAAATGCCCGGGCTTCAGTTAGGGCTGTCTCAAGATGGGCATATTGGGGTTTTGAATACACAA
GGGTTGAACCATTTTTATCAACAGATGGGTCATAATGTTAGGGTTGGAAATGGG

SEQ ID NO : 38 Allium cepa Allce_CLASS I TCP partial 5' translated polypeptide sequence
MDPKESQPNSDRQLMTQTESIQDPQKRALLAPKRTSNKDRHTKVDGRGRRIRMPALCAARIFQLTR
ELGHKSDGETVQWLLHHAEPAIIAATGSGTIPASALASSQAMPNSKPDNSWAVGLWGGFNSGFMNS
NNSSNNNNNNGVGPSSNLGFVGMEMTGMSGHMSFTSMLGGQPGPQMPGLQLGLSQDGHIGVLNTQ
GLNHFYQQMGHNVRVGNG

FIGURE 5 (continued)

SEQ ID NO : 39 Brachypodium distachyon Bradi_CLASS I TCP partial 5' nucleic acid sequence DV480032
ATGGACCCCAAGTTTCCTCCTCCCCCACCGCTAAACAAAACGGAGCCCACCACCGGCGTGACGACC
ACCACCACCACGACCTCCCAGCAGCAGCTGGATCACGAGCAGTATCACCAGCCGCAGCAGCACCTG
CAAATCCAAGTGCACCAGCAGCAGCAGGAGGAAGATGGCGGCGGGGGAAAGGAGCAGCAGCAGCAG
GTGGTGGCGGCGGCGGGGGCGGGGGAGAGGAGGGTGCAGGGGCTGGGGCCGAAGCGGAGCTCCAAC
AAGGACCGGCACACCAAGGTGGACGGGCGGGGCGGCGGATCCGGATGCCGGCGCTGTGCGCGGCG
CGGATCTTCCAGCTGACGCGGGAGCTGGGGCACAAGTCGGACGGGGAGACGGTCCAGTGGCTGCTG
CAGCAGGCGGAGCCGGCCATCGTCGCCGCCACAGGGTCCGGCACCATACCGGCGTCCGCGCTCGCC
TCCGTCGCGCCCTCGCTGCCTTCGCCCACCTCCGCGCTCGCCAGGCCGCACCACCACCACCACCTC
TGGGGGCCCTCGGCGGCGGGGTTCTCCCCGGCCGGGTTCATGAACTCGGCCCCAGCCGGCGCTGAC
TCTGGGGGCGGCCTCGGCGGGCTTATGCAGAGGATAGGGCTTCCCGCCGGGATGGAGCTCCCTGGC
GGCGGTGGTGGGGGGCACATCGGGTTCGCGCCCATGTTCGCCAGCCACGCGGCGGCGGCGGCGGCC
ATGCC

SEQ ID NO : 40 Brachypodium distachyon Bradi_CLASS I TCP partial 5' translated polypeptide sequence
MDPKFPPPPPLNKTEPTTGVTTTTTTTSQQQLDHEQYHQPQQHLQIQVHQQQQEEDGGGGKEQQQQ
VVAAAGAGERRVQGLGPKRSSNKDRHTKVDGRGRRIRMPALCAARIFQLTRELGHKSDGETVQWLL
QQAEPAIVAATGSGTIPASALASVAPSLPSPTSALARPHHHHHLWGPSAAGFSPAGFMNSAPAGAD
SGGGLGGLMQRIGLPAGMELPGGGGGHIGFAPMFASHAAAAAAM

SEQ ID NO : 41 Brassica oleracea Braol partial 5' nucleic acid sequence contig of BZ446639.1, BH464032.1, BZ445385.1
ATGGATCCCAAGAACCCAAATCCACACCAAGTACCAAACTTCTTGATACCACCACCACAACCGAGA
GATGCTTCCGATGACAACAAAGAAGTAAATGATTTTCAGATCGTGGTCGCTTCCGACAAAGAACCG
AACAGTAACGGTAAGAAGCAGCTTGCCCCCAAGAGAAGCTCAAACAAAGACAGACACACCAAAGTG
GAAGGTCGCGGTCGGAGAATCAGGATGCCTGCTCTCTGCGCGGCAAGGATTTTTCAACTGACCAGA
GAATTGGGTCACAAATCAGACGGTGAAACAATCCAGTGGCTGCTTCAACAAGCCGAACCGTCGCTT
ATCGCAGCCACCGGTTCAGGAACTGTACCGGCCTCTGCTTTAGCCTCAGCTGCTTCTGCTGTAGTC
TCTAACCAAGGCGGGTCTCTCACTGCTGGTTTGATGATCAGTCATCATGACTTAGACTGTGGTGGT
GGGTCTAGTAGTGGTAGACCAAGTTGGGGAGAAGGAGGAGGAGAAGTATGGCCAAATGGAGCTGGT
TACAGAATTGGGTTTCCCGGATTTGATTTTCCTGGTGGAGCTATGAGTTTTGCTTCCATTTTTGGT
GCTAGTGGTGGTGGTAATGGTAATCAGATGCTTGGACTTGAGTTAGGGTTGTCTCAGGTAGGGAAT
GTTGGGGTCTTGAATCAACAGATTTATCAACAGATGGCTCAAGCTCAGGCTCAGGCTCAGGGTAGG
GTTCTTCACCATACTCTTCATCATAATCCAGGACATGAAGAG

SEQ ID NO : 42 Brassica oleracea Braol partial 5' translated polypeptide sequence
MDPKNPNPHQVPNFLIPPPQPRDASDDNKEVNDFQIVVASDKEPNSNGKKQLAPKRSSNKDRHTKV
EGRGRRIRMPALCAARIFQLTRELGHKSDGETIQWLLQQAEPSLIAATGSGTVPASALASAASAVV
SNQGGSLTAGLMISHHDLDCGGGSSSGRPSWGEGGGEVWPNGAGYRIGFPGFDFPGGAMSFASIFG
ASGGGNGNQMLGLELGLSQVGNVGVLNQQIYQQMAQAQAQAQGRVLHHTLHHNPGHEE

SEQ ID NO : 43 Brassica rapa Brara_CLASS I TCP partial 3' nucleic acid sequence Contig of DX909657.1, DU115108.1
AGAAGCTCAAACAAAGACAGACACATCAAAGTGGAAGGCAGGGGTCGGAGAATCAGGATGCCTGCT
CTCTGCGCCGCTAGGATCTTCCAGTTGACTAGAGAATTGGGTCACAAATCCGACGGCGAGACAATC
CAGTGGCTGCTTCAGCAGGCTGAGCCGTCGATTATCGCAGCCACCGGTTCAGGAACTATACCGGCC FIGURE 5 (continued)

```
TCTGCTTTAGCCTCAGCCGCTGCTGCTGTATCGAGCCACCATCTTCAGGGTGGTGGGTCTCTCACT
GCTGGTTTGATGATCAGTCATGAGTTGGATGGTGGGTCTAGTAGTGGGAGACCAAATTGGGGTGTT
GGCGGGGGAGATGGAGGGTCTAGGTCGAGTTTACCAACTGGGCTGTGGCCAAATGTAGCTGGGTTT
GGAGCTGGGGTGCAGACCATGAGTGATGGAGGTGGTTACAGGATTGGGTTCCTGGGTTTGATTAT
CCTGGTGGAGCTATGAGTTTTGCGTCCATTCTTGGTGGTGGTAGTAACAATCAGATGCCTGGACTT
GAGTTAGGGTTGGCTCAGGAAGGGAATGTTGGTGTCTTGAATCCTCAGTCTTTTGCACAGATTTAT
CAGCAGCAGATGAGTCAGGCTCAAGCTCAGGGTAGGGTTCTTCACCATACTCTTCAGCATAACCCA
TCACATGAGGAGCATCAGCAAGAGAGTGGTGAGAAAGATGATTCTCAAGGGTCAGGGCGTTAA
```

SEQ ID NO : 44 Brassica rapa Brara_CLASS I TCP partial 3′ translated polypeptide sequence
```
RSSNKDRHIKVEGRGRRIRMPALCAARIFQLTRELGHKSDGETIQWLLQQAEPSIIAATGSGTIPA
SALASAAAAVSSHHLQGGGSLTAGLMISHELDGGSSSGRPNWGVGGGDGGSRSSLPTGLWPNVAGF
GAGVQTMSDGGGYRIGFPGFDYPGGAMSFASILGGGSNNQMPGLELGLAQEGNVGVLNPQSFAQIY
QQQMSQAQAQGRVLHHTLQHNPSHEEHQQESGEKDDSQGSGR
```

SEQ ID NO : 45 Coffea canephora Cofca_CLASS I TCP partial middle nucleic acid sequence DV701323
```
ATTTTCCAGCTCACCAGAGAATTGGGTCACAAATCCGATGGAGAAACCATCCAATGGCTGTTACAG
CAGGCTGAACCATCCATTATAGCCGCCACGGGGACGGGGACCATACCGGCCTCCGCTCTAGCCGCT
GCGGCCGCTGGAGCAGGGGGCTCTGTTTCCATGTCAGCTGGGCTGCATCCTCCAAAGATCAGTGCT
GAATTGGGTGCACACCACCCCCCACACATGGATATTGCCGGGTCAGGTCAAGGAGCGGGTAGCACC
GGTGCTAGTAGGACCAATTGGCCAATGGTCGGCGGGAGTTTGTTACGAGCCCCCCATATGGGAATG
CCCACTACAACTGCAGGGATATGGCCCCCTACTTCTGCTTCTGGTGCTGTCAGTGGTTTCGGGTTC
CAGTCATCATCCTCCCCTGCTCCAGCAGCCACCAGTTTGGGCACTGAAAGTTCAAATTACCTACAC
AAGCTTGGGTTTCCTGGTTTTGACTTGCCAGCTGCAACTAACAACTTGGGTCCTATGAGTTTCACC
TCCATCGTGGGGGCTGCTACTGACCAGCAGCANCACCTTCCTGGATTGGAGCTGGGGCTATCACAA
GATGGTCATGTTGGGGTTTTGAACCCTNCAACCTTGAGCCAGATTTATCAGCATATGGGGCAGGCT
CGAGCGCACCAGCACAACACAGCACGAGACCACAGC
```

SEQ ID NO : 46 Coffea canephora Cofca_CLASS I TCP partial middle translated polypeptide sequence
```
IFQLTRELGHKSDGETIQWLLQQAEPSIIAATGTGTIPASALAAAAAGAGGSVSMSAGLHPPKISA
ELGAHHPPHMDIAGSGQGAGSTGASRTNWPMVGGSLLRAPHMGMPTTTAGIWPPTSASGAVSGFGF
QSSSSPAPAATSLGTESSNYLHKLGFPGFDLPAATNNLGPMSFTSIVGAATDQQXHLPGLELGLSQ
DGHVGVLNPXTLSQIYQHMGQARAHQHNTARDHS
```

SEQ ID NO : 47 Helianthus annuus & petiolaris Helan_CLASS I TCP partial 3′ nucleic acid sequence contig of DY906028, DY940311.1
```
TCGGCCGGGGGACCCAAAGGCTCAAACCTACATCATCCTCAACAGCAGCCACATGAGGCCTCAAGT
TCAACCTTCTTAGCCCACCCAAACCCCACCACAACAGACAACATGGGAGATCACAACAACAATAAC
ATCAACACCAACAACCTCAACAAACTTTCTGAAATCAAAGATTTCCAGATTACAGTTTCTGACAAA
CAAGAGTCTGCTACCAAGAAACAACAGTTAGCCCCCAAAAGAACCTCCAATAAAGACAGGCACACC
AAGGTTGAAGGAAGAGGTAGGAGGATAAGGATGCCTGCTTTATGTGCTGCAAGAATCTTTCAGCTC
ACTAGAGAGTTAGGTAACAAATCTGATGGTGAAACTATTCAATGGCTGCTACAGCAAGCTGAGCCT
TCCATTATAGCCGCCACCGGAACCGGGACAATCCCGGCTTCTGTGTTAGCCGCCACTGGGCGGCT
TCACACGGGGTCTCGATTTCGGTTGGCTTGCAACAAAAGATTGATGAATTAAGCGGGAGTAATAAT
```

```
AACAGTAATAGTAATATTAATACTGGTGTCAACTGTAGGACCAGTTGGCCAATGGTTGGTCCAGCT
TTGGGTGTGGGTAGACCCACTACCCATATGGCTACGCCTACGGCTATCTGGCCCGCTGCTGGATTC
GGGTTCCAGTCCTCTTCTTCGTCCCCAGGTCCATCGGGCAACAATTTGGGCGTCGAAAGTTCGAAT
TACTTGCAAAAGATGGCGTTTTCCGGGTTTGATTTGCCCGGTTCTAATATGGGTCAGATGAGTTTT
TCTTCGATTTTGGGTAATCATAATCATAATCATAATCATCATCAGCAGCAGCTTCCTGGGCTGGAG
CTTGGACTGTCCCAGGATGGTCATTTAGGGGTTTTGAATCAACAGGCTTTGAATCAGATATACCAA
ATGGACCAGACCAGAATGCAACAACAGCAGACTTCAAATGATAATTCTCAAGGTTCAGAGGGGCAG
TAG
```

SEQ ID NO : 48 Helianthus annuus & petiolaris Helan_CLASS I TCP partial 3' translated polypeptide sequence
```
SAGGPKGSNLHHPQQQPHEASSSTFLAHPNPTTTDNMGDHNNNNINTNNLNKLSEIKDFQITVSDK
QESATKKQQLAPKRTSNKDRHTKVEGRGRRIRMPALCAARIFQLTRELGNKSDGETIQWLLQQAEP
SIIAATGTGTIPASVLAATGAASHGVSISVGLQQKIDELSGSNNNSNSNINTGVNCRTSWPMVGPA
LGVGRPTTHMATPTAIWPAAGFGFQSSSSSPGPSGNNLGVESSNYLQKMAFSGFDLPGSNMGQMSF
SSILGNHNHNHNHHQQQLPGLELGLSQDGHLGVLNQQALNQIYQMDTRMQQQQTSNDNSQGSEGQ
```

SEQ ID NO : 49 Horduem vulgare Horvu_CLASS I TCP partial 3' nucleic acid sequence DN181323
```
ATCGGCGGCCTCATGCAGCGGATCGGCCTCCCCGCCGGGATCGAGCTGCCGGGCGGCGGCGCGGGG
GGCATGGGCGGGCACATCGGGTTCGCGCCCATGTTCGCCAGCCACGCGGCGGCCGCAATACCGGGG
CTGGAGCTCGGCCTGTCGCAGGAGGGCCACATCGGGGTGCTCAGCCAGTTCTACCACCAGGTCGGC
GGCGCCGGGGCCAGCGGGCAGCTGCAGCACCCGCACCCTCATCAGCACCACCACCACGAACAGCAC
CACCATCACCAGCAGCAGCAGCAGGAGGAGGACGGGGAGGAGGAGCGCGAGGACGGCGACTCCGAG
GAGGAGTCCGGCCAG
```

SEQ ID NO : 50 Horduem vulgare Horvu_CLASS I TCP partial 3' translated polypeptide sequence
```
IGGLMQRIGLPAGIELPGGGAGGMGGHIGFAPMFASHAAAAIPGLELGLSQEGHIGVLSQFYHQVG
GAGASGQLQHPHPQHHHHEQHHHHQQQQQEEDGEEEREDGDSEEESGQ
```

SEQ ID NO : 51 Linum usitatissimum Linus_CLASS I TCP partial middle nucleic acid sequence Contig LU04MC03342_61667197
```
ATCATCATCACCCATCTATTCTCTTGTCTATCCTCTCTCCCCTGCAGCTCTTCTTATCTTGTGCTT
ATGAACAACAACAACAACAACCAAAGGTCCCAAACCACCTTGATGATCCACACCAAAACAGCAAC
AACCCTCTTTCGGCAATGAAAGACGTTCAAATCACATCACTTGTTCCAAACAGCAGTACAAAGAAG
CAGCAGAGTTTAGGTCCGAAGAGGAGTTCGAACAAGGACAGGCACAAGAAAGTGGACGGAAGAGGG
AGAAGGATCAGGATGCCAGCTTTATGCGCCGCTAGCATCTTCCAGCTGACTCGAGAATTGGGTCAC
AAATCCGACGGCGAGACCATCCAGTGGCTTCTGAACCAATCTGAGCCGTCCATCATTGCAGCCACC
GGCACCGGGACAATTCCGGCCTCTGCTCTTGCCGCTGCAGGGTCCTCTGTTTCTAATTCGGAGATG
CAGGGGAGCTCTGTTTCTTTCTCTGCTGGGAACAATTGGGCAGCCTTGATGAATGCCAA
```

SEQ ID NO : 52 Linum usitatissimum Linus_CLASS I TCP partial middle translated polypeptide sequence
```
IIITHLFSCLSSLPCSSSYLVLMEQQQQQPKVPNHLDDPHQNSNNPLSAMKDVQITSLVPNSSTKK
QQSLGPKRSSNKDRHKKVDGRGRRIRMPALCAASIFQLTRELGHKSDGETIQWLLNQSEPSIIAAT
GTGTIPASALAAAGSSVSNSEMQGSSVSFSAGNNWAALMNA
```

SEQ ID NO : 53 Lotus corniculatus Lotco_CLASS I TCP partial 5′ nucleic acid sequence
ATGGATCCCAAGGGCTCAAAGCAGCAGAACCAGGAGGTTGTTCCAAACTTCCTTCAACAACAACAA
CAAGGGAACAACAACAACAACATGGGAGAGAACAAACCATCCGAGGTTAAGGATTTCCAGATTGTG
ATTGCTGAGAAAGATGAGAGCAAGAAGCAGTTGGCACCAAAGAGGACCTCCAACAAGGACAGACAC
ACAAAAGTTGAAGGCAGGGGAAGGAGGATAAGGATGCCAGCTCTGTGTGCAGCAAGAATCTTCCAG
TTGACCAGAGAATTAGGTCACAAATCTGATGGTGAAACCATCCAGTGGCTTCTGCAGCAGGCTGAG
CCATCAATCATAGCAGCCACTGGAACTGGAACAATCCCAGCATCTGCTTTAGCTTCTGCTGCTGGT
AACTCTGTTTCACAACAGGGGACCTCTTTATCTGCTGGTTTGCAC

SEQ ID NO : 54 Lotus corniculatus Lotco_CLASS I TCP partial 5′ translated polypeptide sequence
MDPKGSKQQNQEVVPNFLQQQQQGNNNNNMGENKPSEVKDFQIVIAEKDESKKQLAPKRTSNKDRH
TKVEGRGRRIRMPALCAARIFQLTRELGHKSDGETIQWLLQQAEPSIIAATGTGTIPASALASAAG
NSVSQQGTSLSAGLH

SEQ ID NO : 55 Petunia hybrida Pethy_CLASS I TCP partial middle nucleic acid sequence contig of CV296461, CV297628
GCGGCGTCTAAATATGGATCCCCGGGCTGCAGGAATCGGCACGAGAGAGAAAGTAGCAAGAAACAA
TTAGCTCCAAAAAGAAGTTCAAACAAAGATAGGCATAAAAAAGTAGATGGTAGAGGTAGAAGAATT
CGTATGCCAGCTTTATGTGCTGCAAGAATTTTCCAATTGACTCGTGAATTGGGTCATAAAACTGAT
GGTGAAACAATTCAATGGCTGTTACAACAAGCTGAGCCTTCAATTATTGCTGCTACTGGGACTGGT
ACTATTCCTGCTTCAGTTCTTGCAGCTGCTACTTCCTCTGTTTCTGAACAGGGGAACTCTGTTTCT
GCTACTTCTTTACATTCAAGAATTGATGATTATGGTTTGTTTAGAGCTAATTGGGCTAATTTAAGT
AGACCCCAGATGCCTGTTTCTGGTTCTTGGCCTAGTTTTGGATCAGGATTTGTGCAAAATTCAAGT
AATTTGAGTACTCAAATGTTGAGTTCTGTTCCAAGATTTGGCTTTGAGTTTACTCAAAATTCATTG
GGATTTAATCAGAATCAAAATGTTCCTGGTTTAGAACTTGGATTATCTCAAGAGGGTCGAATTGGG
AACTTGAATTTTCAATCTTTACAACAGTTTTATCAGCAAATAGCTACACAAAGTGGAGATGCTGCT
GCTCGAGG

SEQ ID NO : 56 Petunia hybrida Pethy_CLASS I TCP partial middle translated polypeptide sequence
AASKYGSPGCRNRHERESSKKQLAPKRSSNKDRHKKVDGRGRRIRMPALCAARIFQLTRELGHKTD
GETIQWLLQQAEPSIIAATGTGTIPASVLAAATSSVSEQGNSVSATSLHSRIDDYGLFRANWANLS
RPQMPVSGSWPSFGSGFVQNSSNLSTQMLSSVPRFGFEFTQNSLGFNQNQNVPGLELGLSQEGRIG
NLNFQSLQQFYQQIATQSGDAAAR

SEQ ID NO : 57 Prunus persica Prupe_CLASS I TCP partial 3′ nucleic acid sequence BU044166
GAGTTCAAATTACATGCAAAAGATGGCTTTCCTGGCTTTGACTTGCCTGTCTCCAACATGGGTCCT
ATGAGTTTCACCTCAATTTTGGGTGGTGGGAGTAACCAACAGCTTCCTGGCTTGGAGCTTGGGTTG
TCTCAGGATGGTCATATTGGGGTTTTGAACTCACAAGCCTTGAGCCAGATTTACCAGCAGATGGGG
CATGCTAGAGTACACCAGCACCAGCACCAGCACCAGCACCAGCACCAGCAACCCCCTGCT
AAGGATGACTCTCAAGGCTCAGGACAGTAG

SEQ ID NO : 58 Prunus persica Prupe_CLASS I TCP partial 3′ translated polypeptide sequence
EFKLHAKDGFPGFDLPVSNMGPMSFTSILGGGSNQQLPGLELGLSQDGHIGVLNSQALSQIYQQMG
HARVHQHQHQHQHQHQQPPAKDDSQGSGQ

SEQ ID NO : 59 Ricinus communis Ricco_CLASS I TCP partial 3' nucleic acid sequence contig of EG685326.1, EG671551
AACCCACATGAATTACCTAACTTCTTGACTCACCCTCCTCAACCAGCCCTACAGCAACAACAACAA
CCACAACAAGAACAACAACATCAAAACCAGAAACAACAGACAAACATGGGAGAGAATAAACCAGCA
GAAATCAAAGATTTCCAGATTGTTATTGCAGATAAAGAAGAGCAGAAGAAACAGTTAGCACCAAAA
AGAAGCTCAAACAAAGACAGACATACGAAAGTTGAAGGAAGAGGGAGGAGGATAAGGATGCCAGCA
CTTTGTGCAGCAAGAATCTTTCAATTGACAAGAGAATTGGGTCATAAATCTGATGGGGAAACAATA
CAGTGGTTATTACAACAAGCTGAACCATCTATAATTGCTGCAACTGGGACAGGAACGATACCAGCA
TCAGCTTTGGTAGCTGCTGGTGGATCAGTTTCACAGCAAGGGACTTCTCTATCAGCTGGATTACAC
CAAAAGATTGATGATTTAGGTGGGTCCAGTAGTATTACTAGTAGTAATAGTAGGACAAGTTGGGCA
ATGGTAGGTGGCAATTTAGGGAGACCCCATCATGTGGCAACAACAGGGTTATGGCCCCAGTTGGT
GGTTTTGGATTCCAGTCATCATCTACTACTACTGGTCCAGTAACATCAAATTTGGGAAATGAAAGT
TCTAGTTATTTGCAAAAAATTGGGTTTCCTGGGTTTGATTTGCCAGGGAATAATATGGGACCTATG
AGTTTTACCTCAATCTTGGGTGGGACTAGCAACCAGCAGATACCTGGTTTGGAGCTTGGGTTGTCA
CAAGATGGTCATATTGGGGTTTTGAATTCACAAGCTTTTAGTCAGATTTATCAGCAGATGGGGCAG
GCCAGAGTGCAGCACCAGCACCAGCACCAGCACCAGCAAAATCCTGCTAAGGATGATTCTCAAGGG
TCAGGACAGTAA

SEQ ID NO : 60 Ricinus communis Ricco_CLASS I TCP partial 3' translated polypeptide sequence
NPHELPNFLTHPPQPALQQQQQPQQEQQHQNQKQQTNMGENKPAEIKDFQIVIADKEEQKKQLAPK
RSSNKDRHTKVEGRGRRIRMPALCAARIFQLTRELGHKSDGETIQWLLQQAEPSIIAATGTGTIPA
SALVAAGGSVSQQGTSLSAGLHQKIDDLGGSSSITSSNSRTSWAMVGGNLGRPHHVATTGLWPPVG
GFGFQSSSTTTGPVTSNLGNESSSYLQKIGFPGFDLPGNNMGPMSFTSILGGTSNQQIPGLELGLS
QDGHIGVLNSQAFSQIYQQMGQARVQHQHQHQHQQNPAKDDSQGSGQ

SEQ ID NO : 61 Salvia miltiorrhiza Salmi_CLASS I TCP partial 3' nucleic acid sequence CV163534
AGTTTCACCTCAATTTTGAGCGGCGGCGCTCAGCAGCTGCCCGGATTGGAGCTTGGCCTATCACAA
GATGGAAATATTGGCGTGCTCAATCCTCAAGCATTCGGGCAGTTTTATCAGCAGATGGCACCGGCG
GCGCGTGTTGCCCACCACCATCAGCAGCAACACCACCACCACCATCAGCAGCAGCCTTTGTCGCCC
AAGGATGATGATTCTCAAGAATCAGGACAGTAG

SEQ ID NO : 62 Salvia miltiorrhiza Salmi_CLASS I TCP partial 3' translated polypeptide sequence
SFTSILSGGAQQLPGLELGLSQDGNIGVLNPQAFGQFYQQMAPAARVAHHHQQQHHHHHQQQPLSP
KDDDSQESGQ

SEQ ID NO : 63 Zinnia elegans Zinel_CLASS I TCP partial middle nucleic acid sequence AU307217
CACACAAAGGTTAAAGGAAGAGGTAGAAGAATTAGGATGCCAGCTTTATGTGCTGCAAGAATCTTT
CAACTCACTAGGGAGTTAGGTAACAAATCTGATGGGGAAACAATCCAGTGGCTGCTACAGCAGGCC
GAGCCATCTATCATAGCAGCCACTGGCACCGGGACTATCCCGGCTTCCGTGTTAGCCACCACCGGA
GCGGCTTCACACGGAGTCTCGATTTCGGTAGGATTGCAACATAAGATTGATGTATTAGGTAGTGGG
AATAGTAACACTAGTATTAGTAATAGTAACAGTAATAGTAATATCTGTGGCAACAACTGTAGGACC
AGTTGGCCTATGGGTAGACCCACAACCCATATGGCCACGCCTACTACAGGTATATGGCCCGCAATG
GGATACGGGTCTTCGGGTCCCTCGGGCAACAATTTAGGGGTTGAAAGCTCGAATTACCTGCAAAAG
ATGGCGTTTTCCGGGTTTGAATTGCCTGGGTCTAATATGGGTCAGATGAGTTTTTCGTCGATTTTA
GGTAATCATAATCATGATCATCATCAGCAGCAGCAGCTTCCTGGGTTGGAACTTGGGTTGTCCCAA
GATG

SEQ ID NO : 64 Zinnia elegans Zine1_CLASS I TCP partial middle translated polypeptide sequence
HTKVKGRGRRIRMPALCAARIFQLTRELGNKSDGETIQWLLQQAEPSIIAATGTGTIPASVLATTG
AASHGVSISVGLQHKIDVLGSGNSNTSISNSNSNSNICGNNCRTSWPMGRPTTHMATPTTGIWPAM
GYGSSGPSGNNLGVESSNYLQKMAFSGFELPGSNMGQMSFSSILGNHNHDHHQQQQLPGLELGLSQ
D

SEQ ID NO : 65 Consensus C-terminal motif 1
PGLEL(G/R/A)LSQX$_{1-5}$G(V/L)L where X is any amino acid

SEQ ID NO : 66 Conserved TCP domain of SEQ ID NO : 2
KDRHTKVEGRGRRIRMPALCAARIFQLTRELGHKSDGETIQWLLQQAEPSIIAATGSGTIPASALA
SSA

SEQ ID NO : 67 Oryza sativa GOS 2 promoter
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTCCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTTCGATCCATATCTTCCGGTCGAGTTCTTGG
TCGATCTCTTCCCTCCTCCACCTCCTCCTCACAGGGTATGTGCCCTTCGGTTGTTCTTGGATTTAT
TGTTCTAGGTTGTGTAGTACGGGCGTTGATGTTAGGAAAGGGGATCTGTATCTGTGATGATTCCTG
TTCTTGGATTTGGGATAGAGGGGTTCTTGATGTTGCATGTTATCGGTTCGGTTTGATTAGTAGTAT
GGTTTTCAATCGTCTGGAGAGCTCTATGGAAATGAAATGGTTTAGGGTACGGAATCTTGCGATTTT
GTGAGTACCTTTTGTTTGAGGTAAAATCAGAGCACCGGTGATTTTGCTTGGTGTAATAAAAGTACG
GTTGTTTGGTCCTCGATTCTGGTAGTGATGCTTCTCGATTTGACGAAGCTATCCTTTGTTTATTCC
CTATTGAACAAAAATAATCCAACTTTGAAGACGGTCCCGTTGATGAGATTGAATGATTGATTCTTA
AGCCTGTCCAAAATTTCGCAGCTGGCTTGTTTAGATACAGTAGTCCCCATCACGAAATTCATGGAA
ACAGTTATAATCCTCAGGAACAGGGGATTCCCTGTTCTTCCGATTTGCTTTAGTCCCAGAATTTTT
TTTCCCAAATATCTTAAAAAGTCACTTTCTGGTTCAGTTCAATGAATTGATTGCTACAAATAATGC
TTTTATAGCGTTATCCTAGCTGTAGTTCAGTTAATAGGTAATACCCCTATAGTTTAGTCAGGAGAA
GAACTTATCCGATTTCTGATCTCCATTTTTAATTATATGAAATGAACTGTAGCATAAGCAGTATTC
ATTTGGATTATTTTTTTATTAGCTCTCACCCCTTCATTATTCTGAGCTGAAAGTCTGGCATGAAC

FIGURE 5 (continued)

```
TGTCCTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAATCGG
GATAGTTATACTGCTTGTTCTTATGATTCATTTCCTTTGTGCAGTTCTTGGTGTAGCTTGCCACTT
TCACCAGCAAAGTTC
```

SEQ ID NO : 68 prm01501
```
GGGGACAAGTTTGTACAAAAAAGCAGGCTTCACAATGGATCCCAAGAACCTAA
```

SEQ ID NO : 69 prm01502
```
GGGGACCACTTTGTACAAGAAAGCTGGGTTTTTAACGACCTGAGCCTT
```

SEQ ID NO : 70 Cichorium endivia Cicen_Class I TCP partial 3' nucleic acid sequence EL361878; Cichorium intybus EH709336
```
CGGGGGGATCCAGAGTTCAAGCAACAACATCCTCAACAGCAGCCATATGAGGTTTCAAGCTTCTTA
AGCATCCCGCAACCCACCAGCAACAACATGGGAGATAACGACAACAGCAAGCCTTCTGAAATCAAA
GATTTACAGATTGTAATTCCCGACAAGGAAACCAGCAAGAAGCAACAACAATTAGCACCCAAACGC
ACATCCAACAAAGACAGGCATACAAAGGTTGAAGGCCGAGGTCGCAGGATTAGGATGCCCGCTCTC
TGTGCTGCAAGAATCTTTCAGCTGACTCGAGAATTAGGTCATAAATCCGATGGGGAAACAATCCAG
TGGCTCCTACAGCAGGCCGAGCCTTCCATTATCGCCGCCACCGGAACTGGAACTATCCCGGCTTCG
GTGTTAGCCACAGCCGGCGCAGTTTCACATGGGGTTTCGACTTCGGCGGGATTACAACAGAAACTT
GACGAATTAGTTGGTGTGGGAAATACTAGTGACAGCTGTAGGACCAGTTGGCCGATTGTTGGTCCG
GGGGTGGGTAGACCCGCAACCCACATGGCCACTCCTTTAGGTATGTGGCCAACCACAACCGGATTT
GGGTTTCAGTCGCCTCCGTCGTCCTCTGGTCCATCATCGGCCAACAATTTGGGCATCGAAAGCTCC
AATTACTTGCAAAAGATTGCATTTTCTGGGTTTGATCTGCCCGGTTCTAATCTGGGCCCGATGAGT
TTTTCTTCGATTTTGGGTAATCATCATCAACAGCAACTTCCCGGGTTGGAGCTGGGACTGTCACAA
GATGGTCACATAGGGGTCTTGAATCAACAAGCGCTGAACCAGATTTACCAGATGGGTCAGGCCAGA
ATGCACCATCAACAACAACAACATCAAACTTCTAAGGATGATTCTCAAGGTTCAGGGGGACAATAG
```

SEQ ID NO : 71 Cichorium endivia Cicen_Class I TCP partial translated polypeptide sequence EL361878; Cichorium intybus EH709336
```
RGDPEFKQQHPQQQPYEVSSFLSIPQPTSNNMGDNDNSKPSEIKDLQIVIPDKETSKKQQQLAPKR
TSNKDRHTKVEGRGRRIRMPALCAARIFQLTRELGHKSDGETIQWLLQQAEPSIIAATGTGTIPAS
VLATAGAVSHGVSTSAGLQQKLDELVGVGNTSDSCRTSWPIVGPGVGRPATHMATPLGMWPTTTGF
GFQSPPSSSGPSSANNLGIESSNYLQKIAFSGFDLPGSNLGPMSFSSILGNHHQQQLPGLELGLSQ
DGHIGVLNQQALNQIYQMGQARMHHQQQQHQTSKDDSQGSGGQ
```

SEQ ID NO : 72 Fragaria vesca Frave_Class I TCP partial nucleic acid sequence EX657224
```
ACCACCGGCACCGGGACGATCCCGGCGTCGGCTCTAGCGGCGGCAGGAGGGTCTGTATCGCAGCAG
GGGAGTTCAATATCAGCTGGCTTGTATCAAAAGACAGATGATTTAGGGTCCAGTGGAGGTAGGACC
AGTTGGGCTATGGTGGAGGGAATTTAGGGAGGCCCCATGTGGCTGCAGCAACTGGGCTATGGCCC
CCTGCTGGGTTTGGTTTTTCTTCACAGTCATCTTCATCTGGTCCATCTACTACAAATCTGGGAGGG
ACTGAGAGCAGCTCCAATTACCTCCAAAAGATTGGCCTTCCTGGGTTTGACTTGCCAGTCACCAAC
ATGGGACCTATGAGCTTCACTTCAATTCTGGGTGGGGAAGTCAACAGCTGCCTGGTTTGGAACTT
GGGTTGTCTCAAGATGGCCATCTTGGGGTTTTGAATTCTCAGGCTTACCAGATTTACCAGCAGATG
GGCCATGCTAGAGTGCACCACCATCAACAGCAGCAACAGCAACACCACCAGCAGCAGCACCAACAC
CAGCAACAGCAGCAAGCTCCGTCTTCTAAGGATGATTCTCAAGGCTCAGGACAGTAG
```

FIGURE 5 (continued)

SEQ ID NO : 73 Fragaria vesca Frave_Class I TCP partial translated polypeptide
TTGTGTIPASALAAAGGSVSQQGSSISAGLYQKTDDLGSSGGRTSWAMVGGNLGRPHVAAATGLWP
PAGFGFSSQSSSSGPSTTNLGGTESSSNYLQKIGLPGFDLPVTNMGPMSFTSILGGGSQQLPGLEL
GLSQDGHLGVLNSQAYQIYQQMGHARVHHHQQQQQQHHQQQHQHQQQQQAPSSKDDSQGSGQ

SEQ ID NO : 74 Juglans hindsii x Juglans regia (walnut) Jugsp_Class I TCP partial nucleic acid sequence middle EL896093
CCAAGGGCTCAACAACAGCAAAGCAGCCACAACAAGTACCAAACTTCTTGAGCCTCCCACAACCAC
AACAACAACCTAACATGGGTGAGAACAAGCCTGCTGAAATCAAAGACTTCCAGATTGTGATTGCTG
ACAAAGAAGAGGGCAAGAAGCAGTTGGCCCCCAAGAGAAGCTCAAACAAAGACCGGCACACCAAAG
TTGAAGGCAGGGGAAGGAGAATAAGGATGCCAGCTCTTTGTGCAGCGAGGATTTTTCAATTGACCA
GAGAATTGGGCCACAAATCTGATGGAGAAACCATACAGTGGCTGTTACAGCAGGCTGAGCCATCGA
TAATAGCAGCCACTGGGACTGGAACCATACCGGCTTCAGCTTTAGCAGCGGCAGGGGTTCTGTAT
CACAGCAGGGGGCCTCTCTATCAGCTGGATTGCACCAAAAGATTGATGATTTGGGGGGGTCCAGTA
TCGGGTTAGGGAGTAGGACCAGTTGGGCAATGGTAGGTGGGAATTTAGGGAGACCCCATGTGGCCA
CAGGGCTATGGCCCCCGGTCAGTGGGTTTGGGTTTCAGTCATCATCTGGTCCATCGACTGCGAATT
TGGGAAGTGAGAGTTCAAATTACCTGCAAAAGATTGGCTTCCCTGGCTTTGACTTGCCAGCCACCC
CTATGAGTTTCACCTCAATATTGGGTGGGAATAATCAGCAGCTACCGGGATTGGAGCTCGGCTTAT
CCCAAGATGGTCATATCGGGGTTTTGAACCCACAAGCCTTGAGTCAGATTTATCAACAGATGGGGC
AGGCTAGAGTGCAGCAGCAACAGCAA

SEQ ID NO : 75 Juglans hindsii x Juglans regia Jugsp_Class I TCP partial translated polypeptide sequence
KGSTTAKQPQQVPNFLSLPQPQQQPNMGENKPAEIKDFQIVIADKEEGKKQLAPKRSSNKDRHTKV
EGRGRRIRMPALCAARIFQLTRELGHKSDGETIQWLLQQAEPSIIAATGTGTIPASALAAAGGSVS
QQGASLSAGLHQKIDDLGGSSIGLGSRTSWAMVGGNLGRPHVATGLWPPVSGFGFQSSSGPSTANL
GSESSNYLQKIGFPGFDLPATPMSFTSILGGNNQQLPGLELGLSQDGHIGVLNPQALSQIYQQMGQ
ARVQQQQQ

SEQ ID NO : 76 Panax ginseng Pangi_Class I tCP partial 3' nulceic acid sequence CN846083
TCAGCAGGGCTGTATCAGAAAATTGATGAATTGGGCGGGTCTAGTAGTAGGAGCAGTTGGCCAATG
GTTGGTGGGAATTTGGGAAGACCCCATATGGCCACAGCAGGATTATGGCCCGCTGCTGCAGTCGGT
GGCTATGGGTTTCAGTCATCATCATCTGGTCCATCGACAACCAATTTGGGACATGAAAGTTCAAAT
TACTTGCAAAAAATTGGGTTTTCTGGGTTTGACTTGCCAGCCACCAATTTGGGTCCTATGAGTTTT
GCCTCAATTTTGGGTGCAAGTAATCAGCAGCTCCCTGGTTTGGAGCTTGGCCTCTCACAAGATGGA
CATATTGGGGTTTTGTGCCCTCAAGCCTTGACCCAGATTTACCAGCAGATGGGAAATGATAGAATG
CACCAGCAACAGCAACAACAGCACCGGAATCACCAGCAGGCATCTCCCAAGGATGAATCTCAAGGG
TCAGGAGAGTAG

SEQ ID NO : 77 Panax ginseng Pangi_Class I tCP partial translated polypeptide sequence
SAGLYQKIDELGGSSSRSSWPMVGGNLGRPHMATAGLWPAAAVGGYGFQSSSSGPSTTNLGHESSN
YLQKIGFSGFDLPATNLGPMSFASILGASNQQLPGLELGLSQDGHIGVLCPQALTQIYQQMGNDRM
HQQQQQQHRNHQQASPKDESQGSGE

FIGURE 5 (continued)

SEQ ID NO : 78 Poncirus trifoliata Pontr_Class I TCP partial 3' nucleic acid sequence CX644761
GAACCATCTATCATCGCTGCTACAGGAACTGGGACTATTCCAGCCTCTATGCTTGCAGCTGCAGGG
GCCTCTGTTTCTGAACAGGGGAACTCTGTTTCAGCAGGCTTGCATACAAAAATAGAAGGGTTGGGA
CCAGGTGTTGGGTCCATTAATAGGGCCAACTGGACAATGATGAGTGCAAATTTTGGAAGGTCTCAA
ATTCCAAGTGGAGTTTGGCCAAATATAAATGGAACTGGGTCTGGGTTTATTCAAAATTCTGGCCAG
TTGACTTCAAATTTTGGAAGTGAAAATTTGAGTGCAAATCCAAAATTTGGGTTCCACGGGATTGAA
TTTCCAAATATGAATATGGGTTTGATGAGTTTCTCCTCTATGTTGAGCGGTGCTAGCCATCAAATT
CCTGGCTTGGAGCTTGGTCTCTCACAGGATGCGCATGTGGGGGTGATGAATTCTCAAGCTATAAGC
CAGTTCTATCAACAGATGGGGCATCACAGAAGCGCTTCAGGATCCTTGAATCAGCAGCATCAGCAT
CAGCAACAAATTTCTGATAAGGATGATTCTCAGGGATCAGGATCAAAGCAGTAG

SEQ ID NO : 79 Poncirus trifoliata Pontr_Class I TCP partial translated polypeptide sequence
EPSIIAATGTGTIPASMLAAAGASVSEQGNSVSAGLHTKIEGLPGVGSINRANWTMMSANFGRSQ
IPSGVWPNINGTGSGFIQNSGQLTSNFGSENLSANPKFGFHGIEFPNMNMGLMSFSSMLSGASHQI
PGLELGLSQDAHVGVMNSQAISQFYQQMGHHRSASGSLNQQHQHQQQISDKDDSQGSGSKQ FIGURE 5 (continued)

MRSAVLQRGQARRVSCRVRADGSGVDSLPSTSASSSARPLIDRRQLLTGAAASVITFVGCPCPLCK
PGEAKAAAWNYGEVAGPPTWKGVCATGKRQSPINIPLNTSAPKVDAEMGEFDFAYGSFEKCDVLNT
GHSTMQVNFPAGNLAFIGNMELELLQFHFHAPSEHAMDGRRYAMEAHLVHKNKSTGNLAVLGIMLE
PGGLIKNPALSTALEVAPEVPLAKKPSPKGINPVMLLPKKSKAGTRPFVHYPGSLTTPPCSEGVDW
FVFMQPIKVPDSQILDFMRFVGDNKTYATNTRPLQLLNSRLVEYEL

FIGURE 6

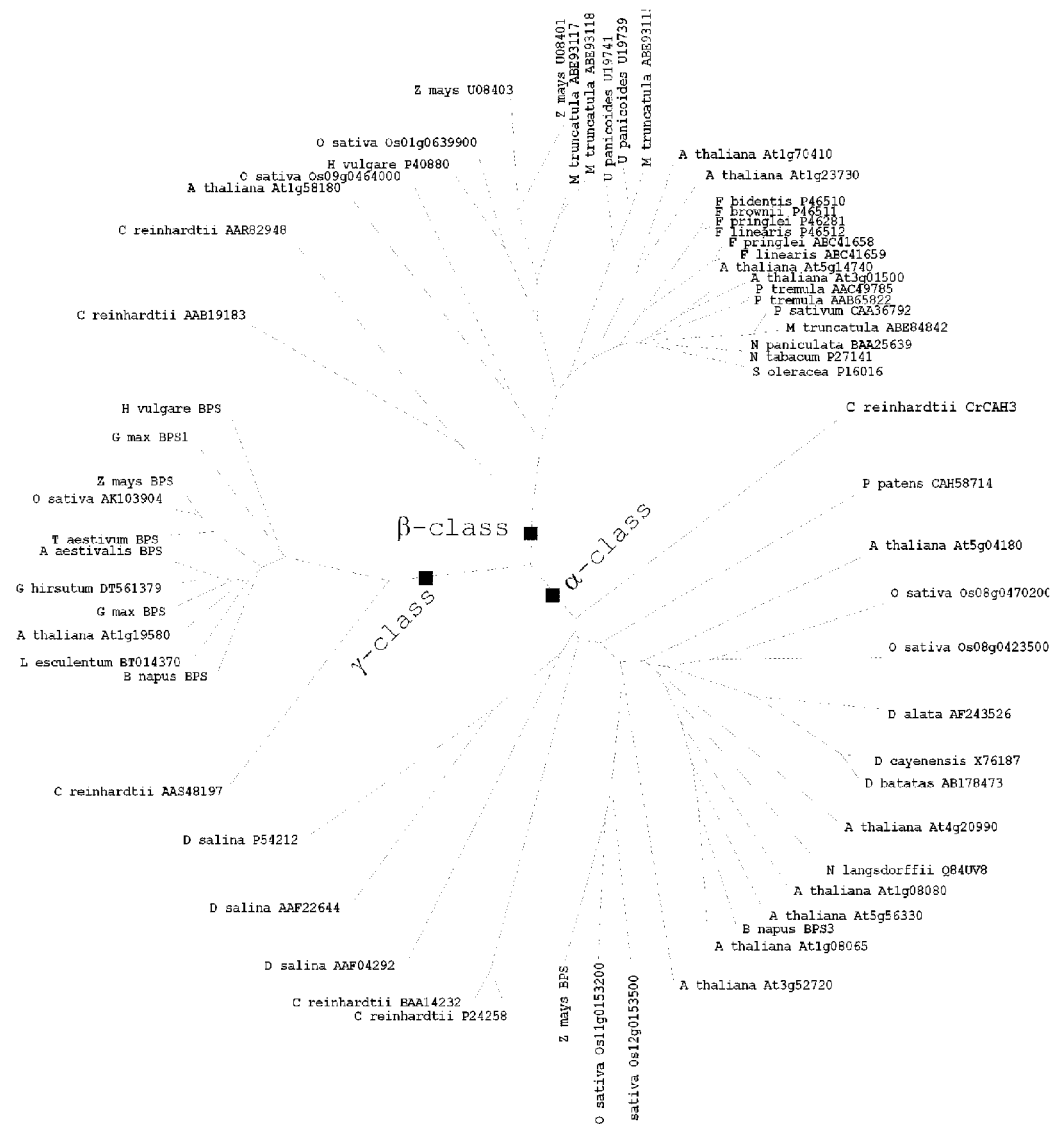

FIGURE 7 A

```
CLUSTAL W (1.83) multiple sequence alignment

SEQID179        -----------MG-STRLLVLLAAASLLLATAVPAAR---------------------
SEQID187        -----------MSTSARRLLLLAGAAAAIALLLSAT----------------------
SEQID181        -----------MS-SSTLLHLLLLSSLLFSCLPNAK----------------------
SEQID183        -----------MS-SSTLLHLLLLSSLLFSCLAN------------------------
SEQID185        -----------MS-SSTLFHLFLLSSLLFSCFSNAR----------------------
SEQID115        ---------------MKTIILFVTFLALSSSSLAD-----------------------
SEQID117        -----------MRMAAITKMLFISFLFLSSVFLARS----------------------
SEQID113        -----------MKISSLGWVLVLIFISITIVSSAPAPKPPKPKPAPAPTPPKPKPTPAPT
SEQID193        -------------------MKHIFFNSCITKKN-------------------------
SEQID153        ----------MVNYSSISCIFFVALFSIFTIVSISS----------------------
SEQID191        ----------MDTNAKTIFFMAMCFIYLSFPNISH-----------------------
SEQID189        ----------MVSLRAAIVLVVAASSVAVAFSHAEG----------------------
SEQID95         ----------------------------------------------------------
SEQID111        -----------MKIMMMIKLCFFSMSLICIAPADAQ----------------------
SEQID109        ------------MGSRRITLLGALF-AVLAVAIEGRT---------------------
SEQID99         --------------MARLVLLGALLGALCATAVQG----------------------
SEQID101        -----------MARTGALLLAALALAGCAQACIYKFG---------------------
SEQID103        -----------MARTGALLLVALALAGCAQACIYKFG---------------------
SEQID105        -----------MASQLVQAVAAVVVLQCISASWVGAWAG-------------------
SEQID81         MRSAVLQRGQARRVSCRVRADGSGVDSLPSTSASSSARPLIDRRQLLTG----------
SEQID97         ---------------MARLALLGAALLCALAVSTQGSPEGHG---------------

SEQID179        ----------------------------------------------------------
SEQID187        ----------------------------------------------------------
SEQID181        ----------------------------------------------------------
SEQID183        ----------------------------------------------------------
SEQID185        ----------------------------------------------------------
SEQID115        ----------------------------------------------------------
SEQID117        ----------------------------------------------------------
SEQID113        PPKPKPKPAPTPPKPKPAPAPTPPKPKPAPAPTPPKPKPKPAPTPPNPKPTPAPTPPKPK
SEQID193        ----------------------------------------------------------
SEQID153        ----------------------------------------------------------
SEQID191        ----------------------------------------------------------
SEQID189        ----------------------------------------------------------
SEQID95         ----------------------------------------------------------
SEQID111        ----------------------------------------------------------
SEQID109        ----------------------------------------------------------
SEQID99         ----------------------------------------------------------
SEQID101        ----------------------------------------------------------
SEQID103        ----------------------------------------------------------
SEQID105        ----------------------------------------------------------
SEQID81         ----------------------------------------------------------
SEQID97         ----------------------------------------------------------
```

Figure 7 B

```
SEQID179         ------------------AQEETDHEKEFTYISGDEKGPEHWGKLK--PEW-------
SEQID187         ------------------APVAGAEDDGYSYIPGSPRGPQNWGSLK--PEW-------
SEQID181         -----------------------PQQAEDEFSYIEGSPNGPENWGNLK--KEW-------
SEQID183         --------------------------VEDEFSYIEGNPNGPENWGNLK--PEW-------
SEQID185         ----------------------LDGDDDFSYIEGSPNGPENWGNLR--PEW-------
SEQID115         ------------------------ETETEFHYKPGEIADPSKWSSIK--AEW-------
SEQID117         --------------------GEVDDESEFSYDEKSENGPANWGNIR--PDW-------
SEQID113         PAPAPAPTPAPKPKPAPKPAPGGEVEDETEFSYETKGNKGPAKWGTLD--AEW-------
SEQID193         -----------------------IEDETQFNYEKKGEKGPENWGRLK--PEW-------
SEQID153         -----------------AASSHGEVEDEREFNYKKNDEKGPERWGELK--PEW-------
SEQID191         -------------------AHSEVDDETPFTYEQKTEKGPEGWGKIN--PHW-------
SEQID189         ------------------------NEGPDFTYIEGAMDGPSNWGKLS--PEY-------
SEQID95          ----------------------------------------------------------
SEQID111         ----------------------TEGVVFGYKG--KNGPNQWGHLN--PHF-------
SEQID109         -----LLTHNLKAEAAETVDAVSSVVAGSAGRQLLVSEPHDYNYEKVG--FDWTGG----
SEQID99          ---------------SLDG-SQVEAG-LGRQLTQDKPHEYNYNRHG--IDWRDE----
SEQID101         ------------------TSPDSKATHTGDHWDHSLNGENWEGKDG--AGN-------
SEQID103         ------------------TSPDSKATVSGDHWDHGLNGENWEGKDG--AGN-------
SEQID105         ------------------SAQAEGGDEVHWDYSGGSHGPGGWGDLK--AEWG------
SEQID81          ----------------AAASVITFVGCPCPLCKPGEAKAAAWNYGEVAGPPTWKG-----
SEQID97          ------------------TKTEMMGAGRLLQQGPHTNSDPPYNYNCHGFDWAASSSSA

SEQID179         --------------AQCGAGEMQSPIDLSHERVKL------------VRD-LGYLDDSYR
SEQID187         ------------ATCSSGKMQSPINLGLLDLTL------------APG-LGNLNYTYQ
SEQID181         --------------ETCGKGMEQSPIQLRDNRVIF------------DQT-LGELRRNYR
SEQID183         --------------ETCGKGMEQSPIQLRDNRVIF------------DQT-LGRLRRNYR
SEQID185         --------------KTCGYGMEQSPINLCDDRVIR------------TPT-LGKLRTSYQ
SEQID115         --------------KICGTGKRQSPINLTPKIARI------------VHNSTEILQTYYK
SEQID117         --------------KEC-SGKLQSPIDIFDLRAEV------------VSN-LRILQKDYK
SEQID113         --------------KMCGIGKMQSPIDLRDKNVVV------------SNK-FGLLRSQYL
SEQID193         --------------AMCGKGNMQSPIDLTDKRVLI------------DHN-LGYLRSQYL
SEQID153         --------------EMCGKGEMQSPIDLMNERVNI------------VSH-LGRLNRDYN
SEQID191         --------------KVCNTGRYQSPIDLTNERVSL------------IHD-QAWTR-QYK
SEQID189         --------------RMCGEGRSQSPIDINTKTVVP------------RSD-LDTLDRNYN
SEQID95          ----------------------------------------------------------
SEQID111         --------------TTCAVGKLQSPIDIQRRQIFY------------NHK-LNSIHREYY
SEQID109         ------------VCVNTGTSKQSPINIETDSLAEESERLGTADDTSRLALKGLLSSSYQ
SEQID99          ------------GLDNCAGSMQSPINIDMATLNRGEERS----DVSGLYLNGLASPAYD
SEQID101         --------------PWVCKTGRKQSPINVPQYHVLDGKGSK---IATGLQTQWSYPDLMSN
SEQID103         --------------AWVCKTGRKQSPINVPQYQVLDGKGSK---IANGLQTQWSYPDLMSN
SEQID105         --------------VCKSGSRQSPIAITALDLVT------------DRSLGKLDAKYRK
SEQID81          --------------VCATGKRQSPINIPLNTSAP-----------KVDAEMGEFDFAYG
SEQID97          EITELCDSPASSFPVADCDGDMQSPINIVTSELADPTDRS----GVSGINLRGMGSSDFV
```

Figure 7 B (continued)

```
SEQID179    AAE-ASIVNRGH-DIMVRFDGD--AGSVVING----------------------TAYYL
SEQID187    NAN-ASVVNRGH-DIMVRFDGD--AGSLKING----------------------TAYQL
SEQID181    AAE-ATLRNSGH-DVLVEFEGN--AGSLSINR----------------------VAYQL
SEQID183    AVD-ARLRNSGH-DVLVEFKGN--AGSLSINR----------------------VAYQL
SEQID185    AAR-ATVKNNGH-DIMVYFKSD--AGTQFINQ----------------------VEYQL
SEQID115    PVE-AILKNRGF-DMKVKWEDD--AGKIVIND----------------------TDYKL
SEQID117    PSN-ATLLNRGH-DIMLRLDD---GGYLKINE----------------------TQYQL
SEQID113    PSN-TTIKNRGH-DIMLKFKGNKGIGVTIRG-----------------------TRYQL
SEQID193    PSN-ATIKNRGH-DIMMKFEGGNAGLGITING----------------------TEYKL
SEQID153    PSN-ATLKNRGH-DIMLKFEDG-AGT-IKING----------------------FEYEL
SEQID191    PAP-AVITNRGH-DIMVSWKGD-AGK-MTIRK----------------------TDFNL
SEQID189    AVN-ATIVNNGK-DITMKFHG--EVGQVIIAG----------------------KPYRF
SEQID95     -------------MAQMEFEPD-KVGTVTVNG----------------------KVYSF
SEQID111    FTN-ATLVNHVC-NVAMFFGE--GAGDVIIEN----------------------KNYTL
SEQID109    LTS-EVAINLEQ-DMQFSFN-APDEDLPQLTIGGVV------------------HTFKP
SEQID99     VAA-DVTVNAEQ-DMKITFKDVAQNNMPAIKIDGSD------------------MLFKP
SEQID101    GSS-VQVINNGH-TIQVQWTYDYAGHATIAIPAMRNQSNRIVDVLEMRPNDASDRVTAVP
SEQID103    GTS-VQVINNGH-TIQVQWTYNYAGHATIAIPAMHNQTNRIVDVLEMRPNDAADRVTAVP
SEQID105    RVH-ATLYNSGH-GAEVSMPAG--SGRLRIGG----------------------ETYRP
SEQID81     SFEKCDVLNTGHSTMQVNFPAG---NLAFIGN----------------------MELEL
SEQID97     LRS-NVKLNIEQ-DMKISWDAPTSGNLPTIMIDG--------------------TEQRFQP
                        .

SEQID179    RQLHWHS-PTEHSVDGRRYDMELHMVH-------ESAEKKAAVIGLLYEVGR--PDRFLQ
SEQID187    RQMHWHT-PSEHTIDGRRYDMELHMVH-------LNAQNQAAVIGILYTIGT--RDEFLQ
SEQID181    KRIHFHS-PSEHEMNGERFDLEAQLVH-------ESQDQKRAVVSILFRFGR--ADTFLS
SEQID183    KRIHFHS-PSEHEMNGERFDLEAQLVH-------ESQDQKRAVVSILFIFGR--ADPFLS
SEQID185    KRIHFHS-PSEHALSGERYDLEVQMVH-------ESQDQRRAVIAIMFRFGR--SDPFLP
SEQID115    VQSHWHA-PSEHFLDGQRLAMELHMVH-------KSVEGHLAVIGVLFREGE--PNAFIS
SEQID117    KQLHWHT-PSEHTINGERFNLEAHLVH-------ESNNGKFVVIGIVYEIGLW-PDPFLS
SEQID113    QQLHWHS-PSEHTINGKRFALEEHLVH-------ESKDKRYAVVAFLYNLGA--SDPFLF
SEQID193    QQIHWHS-PSEHTLNGKRFVLEEHMVH-------QSKDGRNAVVAFFYKLGK--PDYFLL
SEQID153    QQLHWHS-PSEHTINGRRFALELHMVH-------EGRNRRMAVVTVLYKIGR--ADTFIR
SEQID191    VQCHWHS-PSEHTVNGTRYDLELHMVH-------TSARGRTAVIGVLYKLGE--PNEFLT
SEQID189    QAIHWHA-PSEHTINGRRFPLELHLVHK------SDADGGLAVISVLYKLGA--PDSFYL
SEQID95     RRVHWHA-PSEHTINGEKHPLELQMVH-------AAADGSLAVIAILYKYGA--PDSFYF
SEQID111    LQMHWHT-PSEHHLHGVQYAAELHMVH------QAKDGSFAVVASLFKIGT--EEPFLS
SEQID109    VQIHFHHFASEHAIDGQLYPLEAHMVMAS----QNDGSDQLAVIGIMYKYGEE--DPFLK
SEQID99     VQLHFHHFLSEHAINGAHYPLEAHLVMGD----ASGNTNQLAVLGIMYQYGEQ-PDDFVR
SEQID101    TQFHFS-TSEHLLAGKIFPLELHIVHKVTDKLEACGGCFSVTGILFQLDNGPDNELLE
SEQID103    TQFHFS-TSEHLLAGKIYPLELHIVHQVTEKLEACGGCFSVTGILFQLDNGPDNELLE
SEQID105    VQFHIHM-PSEHTIMNQSFPLELHLVH-------KSDDGKLAVIGFLFEEGG--ESEFLA
SEQID81     LQFHFHA-PSEHAMDGRRYAMEAHLVHK------NKSTGNLAVLGIMLEPGGLIKNPALS
SEQID97     IQLYFHHFASEHTINGQLYPLDAHLVMAS-----LDDPNQLAVIGTMYKYGN--GDDFLA
              : *    : **  : .       : ::*               *    .   .
```

Figure 7 B (continued)

```
SEQID179    KMEPYLK-MIAD------KEDRE-EKVGMIDPRG-ARGRASVYYRYMGSLTTPPCTQGVV
SEQID187    KLEPYII-EISK------QEGKERVIIGGADPNV-AKGQDTVYYRYMGSFTTPPCTEGVI
SEQID181    DLEDFIK-QFSS------SQKNE-INAGVVDPNQ-LQFDDCAYFRYMGSFTAPPCTEGIS
SEQID183    DLEDFIK-QFSS------SQKNE-INAGVVDPNQ-LQIDDSAYYRYMGSFTAPPCTEGIS
SEQID185    DLEDFIS-QISR------RETNE-VDAGVVDPRQLLQFDDPAYYRYMGSYTAPPCTEDIT
SEQID115    RIMDKIH-KIAD------VQDGE-VSIGKIDPRE-FGWDLTKFYEYRGSLTTPPCTEDVM
SEQID117    MIENDLK-VPAN------KKGIE-RGIGIIDPNQ-IKLDGKKYFRYIGSLTTPPCTEGVV
SEQID113    SLEKQLK-KITD------THAS--------------------------------------
SEQID193    TLERYLK-RITD------THESQ-EFVEMVHPRT-FGFESKHYYRFIGSLTTPPCSENVI
SEQID153    SLEKELE-GIAE------MEEAE-KNVGMIDPTK-IKIGSRKYYRYTGSLTTPPCTQNVT
SEQID191    KLLNGIK-AVGN------KEIN----LGMIDPRE-IRFQTRKFYRYIGSLTVPPCTEGVI
SEQID189    QFKDHLA-ELGADE-CDFSKEEAHVAAGLVQMRS-LQKRTGSYFRYGGSLTTPPCGENVV
SEQID95     QLKRKLA-ELAADG-CSFGEENAQVALGLVHLRS-LQKRTGSYFRYAGSLTAPPCTEDVF
SEQID111    QMKEKLV-KLKEER-LK-GNHTAQVEVGRIDTRH-IERKTRKYYRYIGSLTTPPCSENVS
SEQID109    RLQETAQ----SNG-EAGDKNVELNSFSINVARDLLPESDLTYYGYDGSLTTPGCDERVK
SEQID99     RLQTKTIDEIATNG-AGYGETVNVTDLSVNIMKDVLPPTHHNYVGYDGSLTTPPCDERVK
SEQID101    PIFANMPTR--------EGTFTNLPAGTTIKLGELLPSDRDYVTYEGSLTTPPCSEGLL
SEQID103    PIFANMPSR--------EGTFSNLPAGTTIKLGELLPSDRDYVTYEGSLTTPPCSEGLL
SEQID105    QFAHEVP----------SSNSPGVKVDLGHIKMMKPERNYGTYMGSLTTPPCAEGVT
SEQID81     TALEVAPEVPLAK-----KPSPKGINPVMLLPKK-SKAGTRPFVHYPGSLTTPPCSEGVD
SEQID97     RLFGKVEDALEERDDVSYGSKEVPIDMEISPKDHVLPQSSLEYAGYDGSLTTPPCSEVVK

SEQID179    WTI-VKRVRTVSRYQLDLLREAVHDEM---------ENNARPLQAVNNRDISIFRPYPHK
SEQID187    WTV-VRKVRTVSLSQITLLKAAVLTGN---------ENNARPLQGVNNREIDLFLPLPLI
SEQID181    WTV-MRKVATVSPRQVLLLKQAVNENA---------INNARPLQPTNYRSVFYFEQLKSK
SEQID183    WTV-MRKVATVSPRQVLLLKQAVNENA---------INNARPLQPTNFRSVFYFEQLKSK
SEQID185    WTV-IKKLGTVSPKQVLMLKQAVNENS---------MNNARPLQPLKFRTVFFYPRQKSD
SEQID115    WTI-INKVGTVSREQIDVLTDARRGGY---------EKNARPAQPLNGRLVYLNEQSSPS
SEQID117    WII-DRKVKTVTRRQIKLLQEAVHDGF---------ETNARPTQPENER--YIN-----S
SEQID113    ----EEHIRTVSSKQVKLLRVAVHDAS---------DSNARPLQAVNKRKVYLYKPKVKL
SEQID193    WTI-SKEMRTVTLKQLIMLRVTVHDQS---------NSNARPLQRKNERPVALYIP-TWH
SEQID153    WSV-VRKVRTVTRKQVKLLRVAVHDDA---------NSNARPVQPTNKRIVHLYRPIV--
SEQID191    WTV-VKRVNTISMEQITALRQAVDDGF---------ETNSRPVQDSKGRSVWFYDPNV--
SEQID189    WSV-LGKVREISQEQLHLLMSPLPT-----------KDARPAQPLNGRAVFYYNPPGSA
SEQID95     WSV-LGKIRQISQEQVALITALLPA-----------GGARPTQPLNGRTVQFYNPPNST
SEQID111    WTI-LGKVRSMSKEQVELLRSPLDTSF---------KNNSRPCQPLNGRRVEMFHDHERV
SEQID109    WHV-FKEARTVSVAQLKVFSEVTLAAHP-----EATVTNNRVIQPLNGRKVYEYKGEPND
SEQID99     WHV-FTEPRTITTGQLEKFLMITKRGHT-----DAIVTNNRIVQPIG-RPLYHYKPTP-A
SEQID101    WHV-MTQPQRISFGQWNRYRLAVGEKECNSTETDAAHADAGHHHHHHRRLLHNHAHLEEV
SEQID103    WHV-MTQPQRISFGQWNRYRLAVGLKECNSTET---AADAG-HHHHHRRLLHNHAHLEEV
SEQID105    WILSLFNFQTASAEQLAKLRASVPKGH----------NNRPTFGSAGRGFRMRTNA---
SEQID81     WFVFMQPIKVPDSQILDFMRFVGDNKT--------YATNTRPLQLLNSRLVEYEL-----
SEQID97     WHV-FTSPRTISIDQLKTFERVSFNAHPN----EAIPTNNRVIQPLGTRAVYRYEATAMD
                                                    .               *
```

Figure 7 B (continued)

```
SEQID179    RY----------------------------------------------------------
SEQID187    NN----------------------------------------------------------
SEQID181    LGVI--------------------------------------------------------
SEQID183    VCAI--------------------------------------------------------
SEQID185    HVAI--------------------------------------------------------
SEQID115    PTPRLRIPRVGPV-----------------------------------------------
SEQID117    TYHSFGIEKQQ-------------------------------------------------
SEQID113    MKKYCNISSY--------------------------------------------------
SEQID193    SKLY--------------------------------------------------------
SEQID153    ------------------------------------------------------------
SEQID191    ------------------------------------------------------------
SEQID189    VSFQEFAK----------------------------------------------------
SEQID95     ISFKV-------------------------------------------------------
SEQID111    DKKETGNKKKKPN-----------------------------------------------
SEQID109    KYNYVQHGFDWRDNGLDSCAGDVQSPIDIVTSTLQAGSSRSDVSSVNLMTLNTDAFTLTG
SEQID99     SYNYARKGIDWREAGLDNCAGDRQSPINIDTTDLQPG----AVSGISLNGLESQSFTFTD
SEQID101    PAATSEPKHYFRRVM-EETENPDAYTCTTVAFGQNFRNAQYANGRTIKLARYE-------
SEQID103    PAATSEPKHYFRRVMLAESANPDAYTCKAVAFGQNFRNPQYANGRTIKLARYH-------
SEQID105    ------------------------------------------------------------
SEQID81     ------------------------------------------------------------
SEQID97     DSGDGTGNADELSSPTTVTATYDIMVSGTASSLADMFNNGARLDNGGFGPDDQAEADLLR

SEQID179    ------------------------------------------------------------
SEQID187    ------------------------------------------------------------
SEQID181    ------------------------------------------------------------
SEQID183    ------------------------------------------------------------
SEQID185    ------------------------------------------------------------
SEQID115    ------------------------------------------------------------
SEQID117    ------------------------------------------------------------
SEQID113    ------------------------------------------------------------
SEQID193    ------------------------------------------------------------
SEQID153    ------------------------------------------------------------
SEQID191    ------------------------------------------------------------
SEQID189    ------------------------------------------------------------
SEQID95     ------------------------------------------------------------
SEQID111    ------------------------------------------------------------
SEQID109    NTVNIGQGMQINFGDPPAGDLPVIRIGTRDVTFRPLQVHWHFFLSEHTVDGVHYPLEAHI
SEQID99     AYVNLEQDMKVSFTAPTN-NLPTVNIDGNDESFRPIQLHFHHFSSEHTVDGMIYPLEAHL
SEQID101    ------------------------------------------------------------
SEQID103    ------------------------------------------------------------
SEQID105    ------------------------------------------------------------
SEQID81     ------------------------------------------------------------
SEQID97     QIQRRARANSG-----------------------------AEGAEVVRMMKF
```

Figure 7 B (continued)

```
SEQID179        ------------------------------------------------------------
SEQID187        ------------------------------------------------------------
SEQID181        ------------------------------------------------------------
SEQID183        ------------------------------------------------------------
SEQID185        ------------------------------------------------------------
SEQID115        ------------------------------------------------------------
SEQID117        ------------------------------------------------------------
SEQID113        ------------------------------------------------------------
SEQID193        ------------------------------------------------------------
SEQID153        ------------------------------------------------------------
SEQID191        ------------------------------------------------------------
SEQID189        ------------------------------------------------------------
SEQID95         ------------------------------------------------------------
SEQID111        ------------------------------------------------------------
SEQID109        VMKDNDNLGDSAGQLAVIGIMYKYG-DADPFITDMQKRVSDKIASGAITYGQSGVSLNNP
SEQID99         VMAS---QAENSNQLAVIAIFYQYGSEADDFLTRLHTEAISAQQ-GNANWGDNNVPINLP
SEQID101        ------------------------------------------------------------
SEQID103        ------------------------------------------------------------
SEQID105        ------------------------------------------------------------
SEQID81         ------------------------------------------------------------
SEQID97         TAALGRRRLNQQGAAAEMDIRYYFEGSTDQEEATSAVNGMNPSSLGSSSSGLTDVQQTEV

SEQID179        ------------------------------------------------------------
SEQID187        ------------------------------------------------------------
SEQID181        ------------------------------------------------------------
SEQID183        ------------------------------------------------------------
SEQID185        ------------------------------------------------------------
SEQID115        ------------------------------------------------------------
SEQID117        ------------------------------------------------------------
SEQID113        ------------------------------------------------------------
SEQID193        ------------------------------------------------------------
SEQID153        ------------------------------------------------------------
SEQID191        ------------------------------------------------------------
SEQID189        ------------------------------------------------------------
SEQID95         ------------------------------------------------------------
SEQID111        ------------------------------------------------------------
SEQID109        DDPFNVNIKNNFLPSELGYAGYDGSLTTPPCSEIVKWHVFLEPRTVSVEQMEVFADVTLN
SEQID99         ------ITFATDLMPSSTEHWAYEGSLTTPPCDERVRWIVMKEPRTTTAEQMETFKTATVN
SEQID101        ------------------------------------------------------------
SEQID103        ------------------------------------------------------------
SEQID105        ------------------------------------------------------------
SEQID81         ------------------------------------------------------------
SEQID97         TSSASSLRAGLGLVVAAFFGAALAL-----------------------------------
```

Figure 7 B (continued)

```
SEQID179         ------------------------------
SEQID187         ------------------------------
SEQID181         ------------------------------
SEQID183         ------------------------------
SEQID185         ------------------------------
SEQID115         ------------------------------
SEQID117         ------------------------------
SEQID113         ------------------------------
SEQID193         ------------------------------
SEQID153         ------------------------------
SEQID191         ------------------------------
SEQID189         ------------------------------
SEQID95          ------------------------------
SEQID111         ------------------------------
SEQID109         SNPGATVTTNRMIQPLEGRTVYGYNGAAA
SEQID99          AHYAAEIVNNRAIQERNSRPISSIP----
SEQID101         ------------------------------
SEQID103         ------------------------------
SEQID105         ------------------------------
SEQID81          ------------------------------
SEQID97          ------------------------------
```

SEQ ID NO: 80 Chlamydomonas reinhardtii CAH3 encoding sequence
ATGCGCTCAGCCGTTCTACAACGCGGCCAGGCGCGGCGAGTGTCTTGCCGGGTTCGGGCGGATGGT
TCGGGCGTGGATTCGCTGCCCTCGACCAGCGCCAGCAGCAGCGCACGCCCTCTCATTGATCGCCGT
CAGCTCCTGACCGGTGCTGCTGCGTCGGTCATAACCTTCGTTGGCTGCCCTTGCCCCTGTGCAAG
CCTGGGGAGGCAAAGGCCGCAGCTTGGAACTATGGCGAAGTTGCGGGTCCGCCAACCTGGAAGGGT
GTGTGTGCGACGGGCAAGCGCCAGTCGCCCATCAACATCCCGTTGAACACATCGGCGCCGAAGGTC
GACGCGGAGATGGGCGAATTCGATTTCGCCTACGGCAGCTTCGAGAAGTGCGACGTGCTGAACACG
GGACACAGCACCATGCAGGTGAACTTCCCCGCTGGCAACCTGGCGTTCATTGGCAACATGGAGCTG
GAGCTGCTGCAGTTCCACTTCCACGCGCCCTCGGAGCACGCCATGGATGGCCGCCGTTACGCCATG
GAGGCGCATCTGGTGCACAAGAATAAAAGCACCGGCAACCTAGCTGTGCTGGGCATTATGCTGGAG
CCCGGCGGCCTGATCAAGAACCCGGCGCTGTCCACTGCTCTGGAGGTGGCGCCCGAGGTGCCCCTG
GCCAAGAAGCCCTCGCCCAAGGGCATCAACCCCGTCATGCTGCTGCCCAAGAAGAGCAAGGCCGGG
ACACGGCCGTTCGTGCACTACCCTGGCTCGCTTACCACGCCCCGTGTTCGGAGGGGTGGACTGG
TTTGTGTTCATGCAGCCCATCAAGGTGCCCGACAGCCAGATCCTGGACTTCATGCGCTTCGTGGGC
GACAACAAGACATACGCCACCAACACGCGGCCACTGCAGCTGCTCAACAGCCGCCTGGTCGAATAC
GAGCTGTGA

SEQ ID NO: 81 Chlamydomonas reinhardtii CAH3 deduced protein sequence
MRSAVLQRGQARRVSCRVRADGSGVDSLPSTSASSSARPLIDRRQLLTGAAASVITFVGCPCPLCK
PGEAKAAAWNYGEVAGPPTWKGVCATGKRQSPINIPLNTSAPKVDAEMGEFDFAYGSFEKCDVLNT
GHSTMQVNFPAGNLAFIGNMELELLQFHFHAPSEHAMDGRRYAMEAHLVHKNKSTGNLAVLGIMLE
PGGLIKNPALSTALEVAPEVPLAKKPSPKGINPVMLLPKKSKAGTRPFVHYPGSLTTPPCSEGVDW
FVFMQPIKVPDSQILDFMRFVGDNKTYATNTRPLQLLNSRLVEYEL

SEQ ID NO: 82 Chlamydomonas reinhardtii CAH3 isoform (U40871), mRNA sequence
CTTTTGTAGACCCACTTGTCAGTGGGCACTGCCCCTAGAAGCGGCTTCTTGACCAGAGAAGATGCG
CTCAGCCGTTCTACAACGCGGCCAGGCGCGGCGAGTGTCTTGCCGGGTTCGGGCGGATGGTTCGGG
CGTGGATTCGCTGCCCTCGACCAGCGCCAGCAGCAGCGCACGCCCTCTCATTGATCGCCGTCAGCT
CCTGACCGGTGCTGCTGCGTCGGTCATAACCTTCGTTGGCTGCCCTTGCCCCTGTGCAAGCCTGG
GGAGGCAAAGGCCGCAGCTTGGAACTATGGCGAAGTTGCGGGTCCGCCAACCTGGAAGGGTGTGTG
TGCGACGGGCAAGCGCCAGTCGCCCATCAACATCCCGTTGAACACATCGGCGCCGAAGGTCGACGC
GGAGATGGGCGAATTCGATTTCGCCTACGGCAGCTTCGAGAAGTGCGACGTGCTGAACACGGGACA
CGGCACCATGCAGGTGAACTTCCCCGCTGGCAACCTGGCGTTCATTGGCAACATGGAGCTGGAGCT
GCTGCAGTTCCACTTCCACGCGCCCTCGGAGCACGCCATGGATGGCCGCCGTTACGCCATGGAGGC
GCATCTGGTGCACAAGAATAAAAGCACCGGCAACCTAGCTGTGCTGGGCATTATGCTGGAGCCCGG
CGGCCTGATCAAGAACCCGGCGCTGTCCACTGCTCTGGAGGTGGCGCCCGAGGTGCCCCTGGCCAA
GAAGCCCTCGCCCAAGGGCATCAACCCCGTCATGCTGCTGCCCAAGAAGAGCAAGGCCGGGACACG
GCCGTTCGTGCACTACCCTGGCTCGCTTACCACGCCCCGTGTTCGGAGGGGTGGACTGGTTTGT
GTTCATGCAGCCCATCAAGGTGCCCGACAGCCAGATCCTGGACTTCATGCGCTTCGTGGGCGACAA
CAAGACATACGCCACCAACACGCGGCCACTGCAGCTGCTCAACAGCCGCCTGGTCGAATACGAGCT
GTGAGCGGACACGAGTGTGCTAGGGTCAGTGAGCAGCGTGTGAACATGAAGATTACAAGTTTGCTG
ACAGAGAGCGGGCGGAGTGCCCATGCATCGCATCGTAACAGCCCGCGAAGTACGACTTAACATGAC
ATAAAAGTGCAATGCGCATATTGACTGGTTTGGCCCACGGTGGGAAGGCGTACGCGCGGTTCCAT
CAAGCAGCCTTTGGGGAGGCATCGCCTTGCACGCACTTGCCGTATGTAGGCGTGCTGGTGAATGAG
GTATGGGGCGAGAGACCCGCGAACTAAACTTAAGTAGATTACCCATGTATCCTTTATTTGGCTTGC
GTGCCCTCTCAATTGGGGCACCGATGCAGGGGCTGGAAGGCCCCGTGTAACACATGACACTCA FIGURE 9 (continued)

SEQ ID NO: 83 Chlamydomonas reinhardtii CAH3 isoform (AAC49983), deduced protein sequence
MRSAVLQRGQARRVSCRVRADGSGVDSLPSTSASSSARPLIDRRQLLTGAAASVITFVGCPCPLCK
PGEAKAAAWNYGEVAGPPTWKGVCATGKRQSPINIPLNTSAPKVDAEMGEFDFAYGSFEKCDVLNT
GHGTMQVNFPAGNLAFIGNMELELLQFHFHAPSEHAMDGRRYAMEAHLVHKNKSTGNLAVLGIMLE
PGGLIKNPALSTALEVAPEVPLAKKPSPKGINPVMLLPKKSKAGTRPFVHYPGSLTTPPCSEGVDW
FVFMQPIKVPDSQILDFMRFVGDNKTYATNTRPLQLLNSRLVEYEL SEQ ID NO: 84 Arabidopsis thaliana carbonate dehydratase/ zinc ion binding (AT1G58180) mRNA, complete cds
CAAAATTCATGTGTTAGTTCTTCTTCTTTACAAAATTGAGTTTAAACTGTTTTATTACTAATCCAA
ATGAGGAATCACTTTGCACTATTAATAGAAATAATACACAACCAAACATCTAAAAGATACTATAA
TAGTAGAGATCAAAGACCTGAGCAAAAACTGAAAGAAAAAAAAAAAAAAAAAAAAAAGACTTCTCCT
CAAAAATGGCGTTTACACTAGGTGGAAGAGCTCGTCGTCTAGTCTCTGCAACATCAGTTCATCAAA
ATGGTTGCTTACACAAACTGCAACAAATTGGATCGGATCGGTTTCAGCTTGGTGAAGCAAAAGCAA
TAAGATTACTACCCAGGTGATAAGATAAAGTTTGGTCTTTATAGTTCTTTAAAAAAAAAGTGAAT
CAAAGAATAAAGACAGAGATTACTCTGTTTTTTGTATCATAGGAGAACAAACATGGTTCAAGAAT
TAGGAATCAGGGAAGAATTTATGGATCTAAACAGAGAAACAGAGACAAGTTATGATTTCTGGATG
AAATGAGACACAGATTTCTGAAATTCAAGAGACAAAAGTATCTACCGGAGATAGAAAAGTTTAAAG
CTTTGGCCATAGCTCAATCACCAAAGGTAATGGTGATAGGATGTGCAGATTCAAGGGTATGTCCAT
CTTATGTACTAGGATTTCAACCTGGTGAAGCTTTTACTATCCGAAATGTCGCCAATCTCGTTACCC
CGGTTCAGAATGGACCAACAGAAACCAACTCGGCTCTTGAGTTTGCGGTCACCACTCTTCAGGTTG
AGAACATTATAGTTATGGGTCATAGCAATTGTGGAGGAATTGCAGCACTTATGAGTCATCAAAACC
ACCAAGGGCAACACTCTAGTTTAGTAGAAAGGTGGGTTATGAATGGGAAGCCGCTAAGTTAAGAA
CACAATTAGCTTCATCACATTTATCCTTTGATGAACAATGCAGAAACTGTGAGAAGGAATCTATAA
AGGATTCTGTGATGAATTTGATAACTTATTCATGGATAAGAGATAGAGTAAAGAGAGGTGAAGTCA
AGATTCATGGATGTTATTACAATTTGTCAGATTGTAGTCTTGAAGAGTGGAGATTAAGTTCAGACA
AGACTAACTATGGATTCTATATTTCAGACAGAGAGATATGGAGTTGAGTAAATATTGAACAATCCT
CAGTTCTAATATTCAGATGTATCTTTGTACATACGAAATGATATTTACACAATTGG SEQ ID NO: 85 A. thaliana, carbonate dehydratase (NP_001031206, At1g58180)
MAFTLGGRARRLVSATSVHQNGCLHKLQQIGSDRFQLGEAKAIRLLPRRTNMVQELGIREEFMDLN
RETETSYDFLDEMRHRFLKFKRQKYLPEIEKFKALAIAQSPKVMVIGCADSRVCPSYVLGFQPGEA
FTIRNVANLVTPVQNGPTETNSALEFAVTTLQVENIIVMGHSNCGGIAALMSHQNHQGQHSRWVMN
GKAAKLRTQLASSHLSFDEQCRNCEKESIKDSVMNLITYSWIRDRVKRGEVKIHGCYYNLSDCSLE
KWRLSSDKTNYGFYISDREIWS SEQ ID NO: 86 M. truncatula. ABE93115 encoding sequence
ATGGCAAATCAATCATCTGAGCTAGCCATTGAACAACTGAAGAAGCTTCTCAGAGAGAAGGAGGAA
CTTAATGGGGTGGCCACAGCAAAAATTGAGCAGCTTATAGTTGAATTACAGGGATGTCATCCAAAT
CCAATTGAACCTGCTGATCAGAGAATCATTGATGGTTTTACGTACTTCAAGCTCAACAATTTCAAC
AAGAACCCGGAACTGTATGATCGACTTGCTAAAGGCCAGTCTCCCAAGTTTATGGTATTTGCTTGT
TCCGACTCTCGAGTGAGTCCCTCTGTTATCCTGAACTTTCAACCTGGTGAAGCTTTCATGGTTCGA
AACATTGCTAACATGGTCCCTCCATTTAATCAGTTAAGATACAGTGGAGTTGGTGCAACCCTTGAG
TATGCTATTACAGCTCTAAAGGTGGAGAACATCTTGGTTATTGGACATAGTCGCTGCGGCGGAATC
TCAAGGCTTATGAATCATCCAGAGGATGGTTCTGCTCCATATGACTTCATAGATGATTGGGTGAAA
ATTGGTTTATCTTCCAAAGTCAAGGTTTTGAAAGAACATGAACGCTGTGATTTCAAGAACAATGC

```
AAATTCTGTGAAATGGAATCAGTGAATAACTCATTAGTGAACCTGAAGACATATCCATATGTTGAT
AGAGAAATAAGGAACAAGAACTTAGCTCTGTTGGGAGGTTACTATGATTTTGTGAGTGGAGAATTC
AAGCTTTGGAAGTATAAGAATCATGTCACTGAACCTGTTACCATCCCTCTAAAAGGCCTTGACATG
ACCATCTAA
```

SEQ ID NO: 87 M. truncatula. ABE93115
```
MANQSSELAIEQLKKLLREKEELNGVATAKIEQLIVELQGCHPNPIEPADQRIIDGFTYFKLNNFN
KNPELYDRLAKGQSPKFMVFACSDSRVSPSVILNFQPGEAFMVRNIANMVPPFNQLRYSGVGATLE
YAITALKVENILVIGHSRCGGISRLMNHPEDGSAPYDFIDDWVKIGLSSKVKVLKEHERCDFKEQC
KFCEMESVNNSLVNLKTYPYVDREIRNKNLALLGGYYDFVSGEFKLWKYKNHVTEPVTIPLKGLDM
TI
```

SEQ ID NO: 88 M. truncatula. ABE93118 encoding sequence
```
ATGGCAAATCAATCATCTGAGCTAGCCATTGAACAACTGAAGAAGCTTCTCAGAGAGAAAGAGGAA
CTTAATGAGGTGGCCACTGCAAAAATTGAGGAAATTATAGTTGAGTTGCAGGGATGTCATCCACAA
CCAATTGATCCTGCTGAGCAGAGAATCATTGATGGTTTTACTTACTTCAAGCTCAACAATTTCGAC
AAGGACCGGAAATTGTATGATCGACTTGCTAAAGGACAATCCCCCAAGTTTATGGTATTTGCTTGT
TCTGACTCTAGAGTGAGTCCCTCTATTATCCTGAACTTTCAACCTGGAGAAGCTTTCATGGTCCGA
AACATTGCTAACATGGTCCCTCCATTTAATCAGTTAAGATACAGTGGAGTTGGTGCAACCCTTGAG
TATGCTATTACAGCTCTAAAGGTGGAGAACATCTTGGTTATTGGACATAGTCGCTGCGGCGGTATA
TCAAGGCTTATGAGTCATCCAGAGGATGGTTCTGCTCCATATGACTTCATAGATGATTGGGTGAAA
ATTGGTTTACCTTCTAAAGTCAAGGTCCTGAAAGAACATAAATTCTGTGATTTCGAGCAACAATGT
GAATTTTGTGAAATGGAATCAGTGAATAACTCATTAGTGAACCTTCAGACATATCCATATGTTGAT
GCAGAAATAAGGAACAAGAACTTAGCACTATTGGGGGGTTACTATGACTTTGTGAGTGGAGAATTC
AAGTTTTGGAAGTATAAGACTCATATTACTGAACCCATTACAATCTGA
```

SEQ ID NO: 89 M. truncatula. ABE93118
```
MANQSSELAIEQLKKLLREKEELNEVATAKIEEIIVELQGCHPQPIDPAEQRIIDGFTYFKLNNFD
KDRKLYDRLAKGQSPKFMVFACSDSRVSPSIILNFQPGEAFMVRNIANMVPPFNQLRYSGVGATLE
YAITALKVENILVIGHSRCGGISRLMSHPEDGSAPYDFIDDWVKIGLPSKVKVLKEHKFCDFEQQC
EFCEMESVNNSLVNLQTYPYVDAEIRNKNLALLGGYYDFVSGEFKFWKYKTHITEPITI
```

SEQ ID NO: 90 Arabidopsis thaliana carbonate dehydratase/ zinc ion binding (AT1G70410) mRNA, complete cds
```
TTCTTCGATAAGGATTTTACTCTCCAGAGAAAGAAAAAAAAAACCTCCTCTGCTTTTGTGATCCTT
TAAGGAAAAAGACGAAATGGCAACGGAATCGTACGAAGCCGCCATTAAAGGACTCAATGATCTTCT
CAGTACGAAAGCGGATCTCGGAAACGTCGCCGCCGCGAAGATCAAAGCGTTGACGGCGGAGCTAAA
GGAGCTTGACTCAAGCAATTCAGACGCAATTGAACGAATCAAGACCGGTTTTACTCAATTCAAAAC
CGAGAAATATTTGAAGAATAGTACTTTGTTCAATCATCTTGCCAAGACTCAGACCCCAAAGTTTCT
GGTGTTTGCTTGCTCTGATTCTCGAGTTTGTCCATCTCACATCTTGAATTTCCAACCTGGTGAGGC
TTTTGTTGTCAGAAACATAGCCAATATGGTTCCACCTTTTGACCAGAAGAGACACTCTGGAGTTGG
CGCCGCCGTTGAATACGCAGTTGTACATCTCAAGGTGGAGAACATTTTGGTGATAGGCCATAGCTG
CTGTGGTGGTATTAAGGGACTCATGTCCATTGAAGATGATGCTGCCCCAACTCAAAGTGACTTCAT
TGAAAATTGGGTGAAGATAGGCGCATCAGCGAGGAACAAGATCAAGGAGGAACATAAAGACTTGAG
CTACGATGATCAATGCAACAAGTGTGAGAAGGAAGCTGTGAACGTATCGCTTGGAAACTTGCTTTC
GTACCCATTCGTGAGAGCTGAGGTGGTGAAGAACACACTTGCAATAAGAGGAGGTCACTACAATTT
CGTCAAAGGAACGTTTGATCTCTGGGAGCTCGATTTCAAGACCACTCCTGCTTTTGCCTTCTCTTA
```

AGAAAGAAAGCTACCGGAACATATAAAACTCTTTTGAGATAAAAAAAGACACTTTGACTCATCTTT
CTTCATTCTCTCATGTTGATGATTCCTCTCCAACTTCTTTGATTTCTTTTTGTTAATTCAAAACTT
CAACTTTGCTGCTTCTATTTCAAAAGCTCAAACAATAAAGCTGTAACCAACGTTTGAAACTTCTAT
ATTTGTCTAATTGATGTTTGAACGAAGATTTGAACTTTCCTTCT

SEQ ID NO: 91 A. thaliana, carbonate dehydratase At1g70410
MAPAFGKCFMFCCAKTSPEKDEMATESYEAAIKGLNDLLSTKADLGNVAAAKIKALTAELKELDSS
NSDAIERIKTGFTQFKTEKYLKNSTLFNHLAKTQTPKFLVFACSDSRVCPSHILNFQPGEAFVVRN
IANMVPPFDQKRHSGVGAAVEYAVVHLKVENILVIGHSCCGGIKGLMSIEDDAAPTQSDFIENWVK
IGASARNKIKEEHKDLSYDDQCNKCEKEAVNVSLGNLLSYPFVRAEVVKNTLAIRGGHYNFVKGTF
DLWELDFKTTPAFAFS

SEQ ID NO: 92 Oryza sativa (japonica cultivar-group) Os09g0464000 (Os09g0464000) mRNA, complete cds
ATCATTTTTCTAAAAAAGAAAATCGCTGCCTCGACCTCGGTTTCTCCGTCGCATCGCCGTCGTGCT
CGCTGCCTCGCTCTACCCCGTAAAATCCCCCCGGCCGTTGCCGCGCGAAGCTTTTCCCTCCCACA
AATGCCCGAGACCCCGACCACGACGACCACCACCCGCGCGAGCACCGGGACATCCTCACATGGCTC
CTAGTCTGCTCCGCCCCGCCTCCCCGTGCCTCAACCTCGCGCCCCCACCGCCGACGGCCCCGGCC
GGAGCCGCTCCGCTGTGACGATCGGTGGTTCGAGGCCGCTCAGCGTTTCCCTGCGTGTGGGAGGAT
CTAGCCGGAGGGACTTTCCGTGTACCACAATGGCCTCAAGAGATCATTCTGGTTTGACTCGACAGC
TTTTAGATTTTCAACATGGTACAGTAGATGAGATAGATGGGGAACATGATCCATTCATGGAGTTGA
AAGCAAGGTTCATGGACTTCAAGCACAGGAATTGTGTGGATAATATTTCTAACTATCAAATCTTG
CTCAGCAGCAAACACCAAAGTTCATGGTGGTTGCTTGTGCTGATTCTAGGGTATGTCCTTCAAGTG
TTTTGGGGTTTCAGCCCGGGGAAGCATTTACTGTCCGTAATATAGCAAATTTGGTACCACCATATC
AGCATGGTGCTTCAGAGACTAGCGCTGCACTGGAGTTCGCTGTCAACACACTAGAGGTAGAGAATG
TATTAGTGGTAGGTCACAGCCGTTGTGGTGGTATCCAAGCACTAATGAGTATGAAAAGTAAGCAAG
ATGATTCGCAATCTAGAAGCTTTATCAGAGATTGGGTGTCAATTGCAAAGAGTGCAAGGTTAAGTA
CGGAAGCAGCAGCTGGAAATTTGAATTTTGAATTACAGTGCAAACATTGTGAAAAGGAATCAATTA
ATAGCTCACTGTTGAACTTGTTAACATACCCTTGGATAGAGAAAAGGGTGAATGAAGGAACTTTGA
GCCTTCATGGGGGCTATTACAATTTTATTGATTGCACATTCGAGAAGTGGAAATTAGTATACCGCC
AAGGGTTGGAAGGTGGAAGCAAGTATGCCATAAAGAATAGGACTACCTGGTCTTGATCAAGAGGCA
TTGCTTACCTGGGTAAATTTCACTCTGCCCCCTGCAGTTTAGCATGGTTTTGCTTTGCCACTGTGC
TGTCCATTTTCATTGCACTTTGCTCCATTGTGGTATTGACATTCTGCAAGAACGAGTCCCAGTATC
AAGTCACTGTTACGGTGTTGTTGGTACCATTGATTAACATAACACTTGACGGCCATACTTGGTCAT
GTTGTATGTTATCAGCTTCACAGAGGTACATGTGGCACTTTAACAGTTATTTGATACAGTGACTAG
GCTGCAGTTGAGCGAAACCACAATGGAGTGAAGTGCAACAGAAATGAACATTATGGCAGCAAAGTG
AAAGTTTGTCAAACTGCCGGGGACAAAGTGAATTTTGTCCAAATATCCCTGTATTATTTTCTGCTT
AGAAGCATCATATTAATTCAATAAGCTGCAAACTCATATTCATACCAAAAACATGTACGATCTTGC
CACATTTGGCAAATTATTGTGTTGTATCATTTATCGTGTAATTGCAAAAATAAGATAGAGCTTTGT
AATCTGGTGTGCCGGGCAGCTGCTGTATCAATATAATAATTCTCAAATAGTTGAAACAATGTTGTG
TTTAAAGTTCAATCTTTACTGTTCTTTTGTCG

SEQ ID NO: 93 Oryza sativa. Os09g0464000
MAPSLLRPASPCLNLAPPTADGPGRSRSAVTIGGSRPLSVSLRVGGSSRRDFPCTTMASRDHSGLT
RQLLDFQHGTVDEIDGEHDPFMELKARFMDFKHRNCVDNISNYQNLAQQQTPKFMVVACADSRVCP
SSVLGFQPGEAFTVRNIANLVPPYQHGASETSAALEFAVNTLEVENVLVVGHSRCGGIQALMSMKS
KQDDSQSRSFIRDWVSIAKSARLSTEAAAGNLNFELQCKHCEKESINSSLLNLLTYPWIEKRVNEG
TLSLHGGYYNFIDCTFEKWKLVYRQGLEGGSKYAIKNRTTWS

FIGURE 9 (continued)

SEQ ID NO: 94 Oryza sativa (japonica cultivar-group) Os11g0153200 (Os11g0153200) mRNA, complete cds

```
AGCAGCAATGGTGTCCTCCCATGCAGCCATCGTCTTCTTCCTCGTCGCCGCGTCGTCGCTCCTCTC
ATACGGTGAGGCGGCGCCGAAGATGACGGCGGTGGCGGCGGACTACGGGTACCCGGCGGACTACGG
GTACGCGGCGGGGAGCAAGCTGGGGCCGGAGAACTGGGGGAAGCTGAGCCCGGCGTACAAGCTGTG
CGGCGACGGCAAGAAGCAGTCGCCCATCGACATCGTCACCAAGCAGGCCATCTCCAACCCCAACCT
CGACTCACTCAACCGCACCTACACCGCCTCCGACGGCACCCTCGTCAACAACGGCAAGGACATCTT
GGCAAGCCATCTAACCTAACTAGCTAGACCTACCTACATTGGATTTTTTTTGAATTTGTTTTTAT
TTTTAATTCTAAAAACAAACATTTCTCATTCATATTTTCAATATCTGAACCTTTTGACCACGGGTT
GGCGTGGCAAAATAATACTGCCATGTCAGTCTGAATACACGGTGTGGTAGAAATAAATTTTCATGC
TGGTTTTAGGTGACGTGATATGTTATTTTACCATGGTAGGCAGGTTGGCGTGGCCAAAAGATTCAG
ATTTTGGAAATAAATTTAAGAAAGGTTTGTTTTTGAAATAAAAAAATTTAGAAAAGTTCAAGAAAA
AAATAAAAAAAAATTCTCCATTGGGAAAACTCTATTCATCCCTTCAAGAGATATCCCCTTATTTTT
GCATGTCACTTAAAAAGTCATTAAAAATTTTGAAAAAATTTAGTAGCATATGTAATATGTCACTTC
ACAATACATATTCAAATTCAACTTGTACATATAGAAACAAAAATAACAAATTTGACTATGAATAGA
ACGCATAATTCACGGTTAAATTTATTATTTTTGTTTCGAATTGTATAAGAATTTTAACTTGCGTGT
CTGTGAAAAGATATATCATATATTGATCTATCTTGATGATTTTTTTTTAATTTTTCGATAACGTT
TTGAACGTCATGCACAAAACGAGAGGATGTCCCCCGAGGGACAAAAATCCACTTCCCCTGCATTGT
TGCATTATCCAATGGAGCTAGCTAGCAGAGATTTGATTGATTGGCATATCGAACCATGGCGCAGAT
GGAGTTCGAGCCAGACAAGGTGGGGACGGTGACGGTGAACGGCAAGGTGTACAGCTTCAGGCGGGT
GCACTGGCACGCGCCGTCGGAGCACACCATCAACGGGGAGAAGCACCCGCTGGAGCTCCAGATGGT
GCACGCTGCCGCCGACGGCAGCCTCGCCGTCATCGCCATCCTCTACAAGTACGGCGCCCCGGACTC
CTTCTACTTCCAGCTCAAGAGGAAGCTCGCCGAGCTCGCCGCCGACGGCTGCAGCTTCGGCGAGGA
GAACGCCCAGGTCGCCCTCGGCCTCGTCCACCTCCGCTCGCTGCAGAAGCGGACGGGGAGCTACTT
CCGCTACGCCGGCTCGCTGACGGCGCCGCCGTGCACCGAGGACGTCTTCTGGAGCGTGCTCGGCAA
GATCAGGCAGATCAGCCAGGAGCAGGTCGCCCTCATCACCGCGCTGCTCCCCGCCGGCGGCGCGAG
GCCGACGCAGCCGCTCAACGGCCGCACCGTGCAGTTCTACAACCCGCCCAACAGCACCATCTCCTT
CAAGGTCTAGTAGCCCCAGGCCCAATGGGCTTTGGCCCATTTATATATACTATATGGGTTGCATTG
GGCTGCACAGGCCCTGAAATTGATTGAAGGATCTCAATTTTTGAGATTTTCTTGTTTCTGGAGAA
AAAAAATTCATGTACTGTTGCTTAGATAGGCCCTTATCTATAGTATAGTAACATATGTATATGAAT
TTAATTTTAGGATTTGGAAACATGGTTGCTTATCCTCACTTGGAATTAGGCTTTTAAAAGTCGAGC
ACATGTGCACTTGTTTTTCATTCAAACATTAGCCTGTCGCATAGATAGTCTTTTTCTTAATAATTA
GAGCTGATTTGAATTTT
```

SEQ ID NO: 95 NP_001065776.1, Os11g0153200 [Oryza sativa (japonica cultivar-group)]

```
MAQMEFEPDKVGTVTVNGKVYSFRRVHWHAPSEHTINGEKHPLELQMVHAAADGSLAVIAILYKYG
APDSFYFQLKRKLAELAADGCSFGEENAQVALGLVHLRSLQKRTGSYFRYAGSLTAPPCTEDVFWS
VLGKIRQISQEQVALITALLPAGGARPTQPLNGRTVQFYNPPNSTISFKV
```

SEQ ID NO: 96 Dunaliella salina carbonic anhydrase (CA) mRNA, complete cds

```
ATGGCGCGCCTCGCGCTGTTAGGCGCCGCGCTACTATGCGCCCTGGCGGTCTCGACGCAAGGGTCA
CCTGAGGGGCATGGCACTAAGACTGAGATGATGGGCGCTGGAAGGCTGCTCCAGCAAGGGCCTCAT
ACCAACAGCGACCCCCCTACAACTACAACTGCCATGGCTTTGACTGGGCGGCTTCCAGTTCAAGT
GCCGAAATTACTGAGCTGTGCGACAGCCCAGCATCAAGTTTTCCAGTGGCCGACTGTGATGGGGAC
ATGCAGAGCCCAATCAACATCGTGACGAGCGAGCTTGCAGACCCGACTGACCGCAGCGGCGTGTCT
GGCATCAACCTGAGAGGCATGGGCTCCTCGGATTTTGTGCTGCGAAGCAACGTCAAGTTGAACATC
```

FIGURE 9 (continued)

```
GAGCAAGACATGAAGATCAGCTGGGACGCGCCCACGTCCGGCAACCTGCCCACCATCATGATCGAC
GGCACAGAGCAGCGATTCCAGCCCATCCAGCTTTACTTCCACCACTTTGCCAGTGAGCACACCATC
AATGGGCAGCTCTACCCTCTTGATGCCCACCTTGTCATGGCTTCCCTTGATGACCCCAACCAGCTG
GCTGTCATCGGCACCATGTATAAGTATGGCAATGGCGATGACTTCCTGGCGCGCCTGTTCGGCAAG
GTTGAGGATGCACTTGAGGAGCGTGATGATGTGTCTTACGGCAGCAAAGAAGTGCCAATTGACATG
GAGATCAGCCCGAAAGACCATGTCCTGCCCCAGTCCTCCCTGGAGTACGCTGGCTACGACGGCAGC
CTGACCACCCCTCCCTGCAGTGAGGTGGTGAAGTGGCACGTGTTCACCAGCCCCAGGACCATCTCC
ATCGACCAGCTGAAGACATTTGAGAGGGTCTCCTTCAACGCGCACCCCAATGAAGCCATCCCCACC
AACAACCGCGTGATCCAGCCTCTCGGCACCAGGGCTGTCTACCGCTACGAGGCTACAGCCATGGAT
GACTCCGGCGATGGCACCGGCAACGCTGACGAGCTGTCTTCTCCCACGACCGTCACAGCAACCTAC
GACATCATGGTCTCAGGCACCGCTAGCAGCCTGGCGGACATGTTCAACAATGGAGCTCGTCTGGAC
AATGGCGGTTTTGGTCCTGATGACCAGGCAGAGGCTGACCTGCTGCGCCAGATCCAGCGGCGTGCA
CGTGCAAACTCTGGTGCTGAAGGCGCTGAGGTGGTCCGCATGATGAAGTTCACAGCTGCCCTTGGC
CGTCGCAGGCTCAACCAGCAGGGCGCGGCAGCAGAGATGGACATCAGGTACTACTTTGAGGGTAGC
ACCGATCAAGAAGAGGCTACATCAGCTGTGAATGGCATGAACCCCTCTTCGCTGGGCAGCTCCAGC
AGTGGCCTGACTGATGTGCAGCAGACTGAGGTAACCTCTTCTGCCAGCAGCCTGCGTGCTGGCCTG
GGCTTGGTTGTGGCAGCCTTCTTCGGTGCTGCATTGGCACTGTGA
```

SEQ ID NO: 97 AF190735_1 carbonic anhydrase [Dunaliella salina]
MARLALLGAALLCALAVSTQGSPEGHGTKTEMMGAGRLLQQGPHTNSDPPYNYNCHGFDWAASSSS
AEITELCDSPASSFPVADCDGDMQSPINIVTSELADPTDRSGVSGINLRGMGSSDFVLRSNVKLNI
EQDMKISWDAPTSGNLPTIMIDGTEQRFQPIQLYFHHFASEHTINGQLYPLDAHLVMASLDDPNQL
AVIGTMYKYGNGDDFLARLFGKVEDALEERDDVSYGSKEVPIDMEISPKDHVLPQSSLEYAGYDGS
LTTPPCSEVVKWHVFTSPRTISIDQLKTFERVSFNAHPNEAIPTNNRVIQPLGTRAVYRYEATAMD
DSGDGTGNADELSSPTTVTATYDIMVSGTASSLADMFNNGARLDNGGFGPDDQAEADLLRQIQRRA
RANSGAEGAEVVRMMKFTAALGRRRLNQQGAAAEMDIRYYFEGSTDQEEATSAVNGMNPSSLGSSS
SGLTDVQQTEVTSSASSLRAGLGLVVAAFFGAALAL

SEQ ID NO: 98 Dunaliella salina duplicated carbonic anhydrase (DCA1) mRNA, complete cds
```
ATGGCGAGGCTCGTCCTGCTAGGGGCGTTGCTCGGCGCGCTGTGTGCCACGGCTGTTCAAGGCTCC
CTGGATGGCTCTCAGGTTGAGGCGGGTCTAGGAAGGCAGCTCACACAGGACAAGCCCCATGAGTAC
AACTACAACAGACATGGCATCGACTGGAGGGACGAGGGCCTGGACAACTGCGCTGGCTCCATGCAG
AGCCCCATCAACATCGACATGGCCACTTTGAACCGTGGCGAGGAGCGCAGCGATGTGAGCGGCCTC
TACCTCAATGGCCTCGCCTCGCCCGCCTACGATGTCGCCGCCGACGTGACAGTGAACGCGGAGCAG
GACATGAAGATCACCTTCAAGGACGTCGCGCAGAACAACATGCCTGCCATCAAGATCGACGGCAGC
GACATGCTCTTCAAGCCCGTGCAGCTGCACTTCCACCACTTCCTCAGCGAGCACGCCATCAACGGC
GCGCACTACCTCTGGAGGCGCACCTTGTGATGGGGACGCAAGCGGCAACACCAACCAGCTGGCG
GTGCTGGGCATCATGTACCAGTACGGCGAGCAGCCTGACGACTTCGTCCGGCGCTTGCAGACGAAG
ACCATTGATGAGATCGCGACCAACGGTGCTGGGTACGGAGAGACTGTGAACGTCACCGACTTGTCT
GTGAACATCATGAAGGATGTGCTGCCCCCCACCCACCACAACTACGTGGGCTACGACGGGAGCCTG
ACCACGCCCCGTGCGATGAGAGGGTGAAGTGGCACGTGTTCACCGAGCCCAGGACCATCACAACT
GGGCAGCTGGAGAAGTTCCTGATGATCACAAAGCGCGGCCACACTGATGCGATCGTCACCAACAAC
CGCATCGTGCAGCCCATTGGCAGGCCTCTGTACCACTACAAGCCCACACCCGCCAGCTACAACTAC
GCGCGCAAGGGCATTGACTGGAGGGAGGCTGGCCTGGACAACTGTGCTGGTGACAGGCAGAGCCCC
ATCAACATTGACACAACCGATCTCCAACCTGGCGCTGTCTCTGGCATCAGCCTGAACGGCCTGGAG
TCACAGAGCTTCACATTCACCGACGCCTACGTGAACCTGGAGCAGGACATGAAGGTCAGCTTCACC
GCCCCCACAAACAACCTGCCCACTGTCAACATCGATGGGAACGACGAGTCGTTCAGGCCCATCCAG
```

FIGURE 9 (continued)

CTGCACTTCCACCACTTCTCCAGCGAGCACACCGTGGATGGCATGATCTACCCCCTGGAGGCCCAC
CTTGTGATGGCATCCCAGGCCGAGAACAGCAACCAGCTGGCAGTCATTGCCATCTTCTACCAGTAC
GGCAGTGAGGCTGATGACTTCCTGACCAGGCTGCACACCGAGGCCATCAGCGCTCAGCAAGGCAAC
GCCAACTGGGGCGACAACAACGTGCCCATCAACCTGCCCATCACCTTCGCCACGGATTTGATGCCC
AGCAGTACTGAGCACTGGGCCTATGAGGGCAGCTTGACCACCCCACCTTGCGATGAGAGGGTGAGG
TGGATTGTGATGAAGGAGCCCAGGACCACCACTGCTGAGCAGATGGAGACCTTCAAGACTGCCACC
GTGAACGCCCACTACGCTGCCGAGATTGTCAACAACCGCGCGATTCAGGAGCGCAACAGCAGGCCT
ATTAGCAGTATCCCTTAA

SEQ ID NO: 99 Dunaliella salina, DCA1, AAF22644
MARLVLLGALLGALCATAVQGSLDGSQVEAGLGRQLTQDKPHEYNYNRHGIDWRDEGLDNCAGSMQ
SPINIDMATLNRGEERSDVSGLYLNGLASPAYDVAADVTVNAEQDMKITFKDVAQNNMPAIKIDGS
DMLFKPVQLHFHHFLSEHAINGAHYPLEAHLVMGDASGNTNQLAVLGIMYQYGEQPDDFVRRLQTK
TIDEIATNGAGYGETVNVTDLSVNIMKDVLPPTHHNYVGYDGSLTTPPCDERVKWHVFTEPRTITT
GQLEKFLMITKRGHTDAIVTNNRIVQPIGRPLYHYKPTPASYNYARKGIDWREAGLDNCAGDRQSP
INIDTTDLQPGAVSGISLNGLESQSFTFTDAYVNLEQDMKVSFTAPTNNLPTVNIDGNDESFRPIQ
LHFHHFSSEHTVDGMIYPLEAHLVMASQAENSNQLAVIAIFYQYGSEADDFLTRLHTEAISAQQGN
ANWGDNNVPINLPITFATDLMPSSTEHWAYEGSLTTPPCDERVRWIVMKEPRTTTAEQMETFKTAT
VNAHYAAEIVNNRAIQERNSRPISSIP

SEQ ID NO: 100 Chlamydomonas reinhardtii CAH2 gene for carbonic dehydratase, ORF derived from X54488
ATGGCGCGTACTGGCGCTCTACTCCTGGCCGCGCTGGCGCTTGCGGGCTGCGCGCAGGCTTGCATC
TACAAGTTCGGCACGTCGCCGGACTCCAAGGCCACTCACACAGGCGACCACTGGGATCATAGTCTC
AATGGCGAGAACTGGGAGGGCAAGGACGGCGCGGGCAACCCCTGGGTCTGCAAGACTGGCCGCAAG
CAGTCGCCCATCAACGTGCCCCAGTACCATGTCCTGGACGGGAAGGGTTCCAAGATTGCCACCGGC
CTGCAGACCCAGTGGTCGTACCCTGACCTGATGTCCAACGGCAGCTCGGTTCAAGTCATCAACAAC
GGCCACACCATCCAGGTGCAGTGGACCTACGACTACGCCGGCCATGCCACCATCGCCATCCCTGCC
ATGCGCAACCAGAGCAACCGCATCGTGGACGTGCTGGAGATGCGCCCCAACGACGCCTCCGACCGC
GTGACTGCCGTGCCCACCCAGTTCCACTTCCACTCCACCTCGGAGCACCTGCTGGCGGGCAAGATC
TTTCCTCTTGAGTTGCACATTGTGCACAAGGTGACTGACAAGCTAGAGGCCTGCAAGGGCGGCTGC
TTCAGCGTCACCGGCATCCTGTTCCAGCTCGACAACGGCCCCGATAACGAGCTGCTTGAGCCCACG
CGCGAGGGCACCTTCACCAACCTGCCGGCGGGCACCACCATCAAGCTGGGTGAGCTGCTGCCCAGC
GACCGCGACTACGTCACCTACGAGGGCAGCCTCACCACCCCGCCCTGCAGCGAGGGCCTGCTGTGG
CACGTCATGACCCAGCCGCAGCGCATCAGCTTCGGCCAGTGGAACCGCTACCGCCTGGCTGTGGGC
GAGAAGGAGTGCAACTCCACGGAGACCGATGCTGCCCACGCGGACGCCGGCCATCATCACCACCAC
CACCGCCGCCTGCTGCACAACCACGCGCACCTGGAGGAGGTGCCTGCCGCCACCTCCGAGCCCAAG
CACTACTTCCGCCGCGTGATGGAGGAGACCGAGAACCCCGATGCTTACACCTGCACGACCGTTGCC
TTTGGCCAGAACTTCCGCAACGCCCAGTACGCCAACGGCCGCACCATCAAGCTGGCCCGCTACGAG
TAA

SEQ ID NO: 101 C. reinhardtii, P24258
MARTGALLLAALALAGCAQACIYKFGTSPDSKATHTGDHWDHSLNGENWEGKDGAGNPWVCKTGRK
QSPINVPQYHVLDGKGSKIATGLQTQWSYPDLMSNGSSVQVINNGHTIQVQWTYDYAGHATIAIPA
MRNQSNRIVDVLEMRPNDASDRVTAVPTQFHFHSTSEHLLAGKIFPLELHIVHKVTDKLEACKGGC
FSVTGILFQLDNGPDNELLEPIFANMPTREGTFTNLPAGTTIKLGELLPSDRDYVTYEGSLTTPPC
SEGLLWHVMTQPQRISFGQWNRYRLAVGEKECNSTETDAAHADAGHHHHHHRRLLHNHAHLEEVPA
ATSEPKHYFRRVMEETENPDAYTCTTVAFGQNFRNAQYANGRTIKLARYE

SEQ ID NO: 102 Chlamydomonas reinhardtii CAH1 gene for carbonic anhydrase, ORF derived from D90206.
ATGGCGCGTACTGGCGCTCTACTCCTGGTCGCGCTGGCGCTTGCGGGCTGCGCGCAGGCTTGCATC
TACAAGTTCGGCACGTCGCCGGACTCCAAGGCCACCGTTTCGGGTGATCACTGGGACCATGGCCTC
AACGGCGAGAACTGGGAGGGCAAGGACGGCGCAGGCAACGCCTGGGTTTGCAAGACTGGCCGCAAG
CAGTCGCCCATCAACGTGCCCCAGTACCAGGTCCTGGACGGGAAGGGTTCCAAGATTGCCAACGGC
CTGCAGACCCAGTGGTCGTACCCTGACCTGATGTCCAACGGCACCTCGGTCCAAGTCATCAACAAC
GGCCACACCATCCAGGTGCAGTGGACTTACAACTACGCCGGCCATGCCACCATCGCCATCCTGCC
ATGCACAACCAGACCAACCGCATCGTGGACGTGCTGGAGATGCGCCCCAACGACGCCGCCGACCGC
GTGACTGCCGTGCCCACCCAGTTCCACTTCCACTCCACCTCGGAGCACCTGCTGGCGGGCAAGATC
TATCCCCTTGAGTTGCACATTGTGCACCAGGTGACTGAGAAGCTGGAGGCCTGCAAGGGCGGCTGC
TTCAGCGTCACCGGCATCCTGTTCCAGCTCGACAACGGCCCCGATAACGAGCTGCTTGAGCCCATC
TTTGCGAACATGCCCTCGCGCGAGGGCACCTTCAGCAACCTGCCGGCGGGCACCACCATCAAGCTG
GGTGAGCTGCTGCCCAGCGACCGCGACTACGTAACGTACGAGGGCAGCCTCACCACCCCGCCCTGC
AGCGAGGGCCTGCTGTGGCACGTCATGACCCAGCCGCAGCGCATCAGCTTCGGCCAGTGGAACCGC
TACCGCCTGGCTGTGGGCCTGAAGGAGTGCAACTCCACGGAGACCGCCGCGGACGCCGGCCACCAC
CACCACCACCGCCGCCTGCTGCACAACCACGCGCACCTGGAGGAGGTGCCTGCCGCCACCTCCGAG
CCCAAGCACTACTTCCGCCGCGTGATGCTGGCCGAGTCCGCGAACCCCGATGCCTACACCTGCAAG
GCCGTTGCCTTTGGCCAGAACTTCCGCAACCCCAGTACGCCAACGGCCGCACCATCAAGCTGGCC
CGCTATCACTAA

SEQ ID NO: 103 C. reinhardtii. BAA14232
MARTGALLLVALALAGCAQACIYKFGTSPDSKATVSGDHWDHGLNGENWEGKDGAGNAWVCKTGRK
QSPINVPQYQVLDGKGSKIANGLQTQWSYPDLMSNGTSVQVINNGHTIQVQWTYNYAGHATIAIPA
MHNQTNRIVDVLEMRPNDAADRVTAVPTQFHFHSTSEHLLAGKIYPLELHIVHQVTEKLEACKGGC
FSVTGILFQLDNGPDNELLEPIFANMPSREGTFSNLPAGTTIKLGELLPSDRDYVTYEGSLTTPPC
SEGLLWHVMTQPQRISFGQWNRYRLAVGLKECNSTETAADAGHHHHHRRLLHNHAHLEEVPAATSE
PKHYFRRVMLAESANPDAYTCKAVAFGQNFRNPQYANGRTIKLARYH

SEQ ID NO: 104 Physcomitrella patens mRNA for carbonic anhydrase-like protein precursor (calp gene)
ATGGCGAGCCAACTTGTGCAGGCAGTGGCCGCTGTTGTGGTTCTGCAATGCATCTCCGCAAGCTGG
GTTGGCGCGTGGGCAGGATCGGCTCAGGCTGAGGGAGGTGACGAGGTGCACTGGGACTACAGCGGT
GGGTCGCATGGGCCAGGTGGCTGGGGTGACCTGAAGGCCGAGTGGGGTGTGTGCAAGTCGGGCAGC
CGGCAGTCCCCGATCGCCATCACGGCGCTCGACCTGGTCACAGACCGCAGTCTGGGGAAGCTGGAT
GCCAAGTACCGGAAGAGAGTTCATGCCACTCTTTACAACAGCGGGCATGGGGCTGAGGTGAGCATG
CCAGCCGGCTCGGGACGCTTGAGGATCGGTGGCGAGACGTACCGACCCGTCCAGTTCCACATCCAC
ATGCCCAGCGAGCACACAATCATGAACCAGAGTTTCCCGCTGGAGCTCCACTTGGTGCACAAGTCC
GATGATGGGAAGCTTGCGGTGATCGGGTTCCTGTTTGAGGAAGGAGGCGAGAGCGAATTCCTGGCC
CAGTTCGCACATGAGGTGCCATCGTCAAATAGCCCAGGCGTGAAGGTCGACTTGGGGCACATCAAG
ATGATGAAGCCGGAGAGGAACTACGGCACTTACATGGGATCCCTCACCACCCCACCATGCGCGGAG
GGTGTCACCTGGATTCTGTCGTTGTTCAACTTTCAAACGGCGTCCGCGGAACAGCTGGCTAAGCTC
CGGGCTTCTGTGCCGAAGGGACACAACAACCGTCCAACCTTCGGCAGCGCCGGAAGGGGTTTCCGC
ATGCGCACCAACGCTTGA

FIGURE 9 (continued)

SEQ ID NO: 105 P. patens. CAH58714
MASQLVQAVAAVVVLQCISASWVGAWAGSAQAEGGDEVHWDYSGGSHGPGGWGDLKAEWGVCKSGS
RQSPIAITALDLVTDRSLGKLDAKYRKRVHATLYNSGHGAEVSMPAGSGRLRIGGETYRPVQFHIH
MPSEHTIMNQSFPLELHLVHKSDDGKLAVIGFLFEEGGESEFLAQFAHEVPSSNSPGVKVDLGHIK
MMKPERNYGTYMGSLTTPPCAEGVTWILSLFNFQTASAEQLAKLRASVPKGHNNRPTFGSAGRGFR
MRTNA

SEQ ID NO: 106 Arabidopsis thaliana At5g14740, CA2 (CARBONIC ANHYDRASE 2); carbonate dehydratase/ zinc ion binding (CA2) mRNA, complete cds
AAATAGAGAAGCTCTTCAAGTATCCGATGTTTTTGTTTAATCAACAAGAGGCGGAGATACGGGAGA
AATTGCATGTGTAATCATAAAATGTAGATGTTAGCTTCGTCGTTTTTACTATAGTTTAGTTCTCTT
CTTCTTCTTTTTTCGTCATTACAATCTCTTTCTTAATTTACTTCTTCTTGATAGTATAATTAAGTT
GTTTGTAATAATCTGTACAAAGATGTTGTGTTCTCATAAAAAATTCAATTTTGTAAAGAAGCTCTA
CATGTTCCTTGCTCTGTAAACATGGTCCCCTTTTGGACTACAGTTTCTCGAAATGGCTCATCAGAC
TCAGAGACGACTCTCCAATCTGCTTCAAAAGCCACAAAACAGTATAAATATCCTTCTCTTCGTCCC
TCTCATCGCCTGTCTCTCCTCTTCCTCTTCCCGTTCCATTTATCCGCAAACGGAGCTTGTTTTCGG
TGCACCTGCTTCAGCCACTTCAAACTTGGTATAAACTGAGAAGGATGGGAAACGAATCATATGAAG
ACGCCATCGAAGCTCTCAAGAAGCTTCTCATTGAGAAGGATGATCTGAAGGATGTAGCTGCGGCCA
AGGTGAAGAAGATCACGGCGGAGCTTCAGGCAGCCTCGTCATCGGACAGCAAATCTTTTGATCCCG
TCGAACGAATTAAGGAAGGCTTCGTCACCTTCAAGAAGGAGAAATACGAGACCAATCCTGCTTTGT
ATGGTGAGCTCGCCAAAGGTCAAAGCCCAAAGTACATGGTGTTTGCTTGTCGGACTCACGAGTGT
GCCCATCACACGTACTAGACTTCCATCCTGGAGATGCCTTCGTGGTTCGTAATATCGCCAATATGG
TTCCTCCTTTTGACAAGGTCAAATATGCAGGAGTTGGAGCCGCCATTGAATACGCTGTCTTGCACC
TTAAGGTGGAAAACATTGTGGTGATAGGGCACAGTGCATGTGGTGGCATCAAGGGGCTTATGTCAT
TTCCTCTTGACGGAAACAACTCTACTGACTTCATAGAGGATTGGGTCAAAATCTGTTTACCAGCAA
AGTCAAAAGTTTTGGCAGAAAGTGAAAGTTCAGCATTTGAAGACCAATGTGGCCGATGCGAAAGGG
AGGCAGTGAATGTGTCACTAGCAAACCTATTGACATATCCATTTGTGAGAGAAGGAGTTGTGAAAG
GAACACTTGCTTTGAAGGGAGGCTACTATGACTTTGTTAATGGCTCCTTTGAGCTTTGGGAGCTCC
AGTTTGGAATTTCCCCCGTTCATTCTATATGAACTAACACATCACCATCACCATCGCTACCACCAC
CATCACAAACATCATCATCGTCGTCATCATCATGATCAGCATCTTCATATATAAATGTTTTACTCT
TATTTAATTGCTACTTGTAATGGTATACATTTACTTGCGATGAGCTTCTTTTCCTTCATTATCCAG
TTATAAAATAAATAAATAAATCATGTTTACTTTCACAGATATCGTTTTGCTGAAGTTGCTTTGATT
T

SEQ ID NO: 107 A. thaliana. At5g14740
MGNESYEDAIEALKKLLIEKDDLKDVAAAKVKKITAELQAASSSDSKSFDPVERIKEGFVTFKKEK
YETNPALYGELAKGQSPKYMVFACSDSRVCPSHVLDFHPGDAFVVRNIANMVPPFDKVKYAGVGAA
IEYAVLHLKVENIVVIGHSACGGIKGLMSFPLDGNNSTDFIEDWVKICLPAKSKVLAESESSAFED
QCGRCEREAVNVSLANLLTYPFVREGVVKGTLALKGGYYDFVNGSFELWELQFGISPVHSI

SEQ ID NO: 108 Dunaliella salina carbonic anhydrase (dca) mRNA, complete cds
ATGGGATCCCGCCGCATCACCCTCTTGGGGGCTCTGTTCGCTGTCCTGGCGGTCGCAATCGAAGGG
CGTACCCTGCTTACACACAACCTGAAGGCCGAGGCTGCTGAGACAGTGGATGCAGTGAGCTCTGTG
GTAGCTGGTTCTGCAGGCAGGCAGTTGCTGGTGAGTGAGCCTCACGACTACAACTATGAGAAAGTT
GGCTTTGATTGGACGGGGGGGGTCTGCGTCAATACCGGGACCAGCAAGCAGAGCCCAATCAACATT
GAGACTGACAGCCTGGCTGAGGAATCAGAGAGGCTGGGGACCGCGGATGACACTTCACGCCTGGCC FIGURE 9 (continued)

```
TTGAAGGGCCTACTGTCTTCATCCTACCAGCTGACCAGCGAAGTGGCAATCAACCTGGAGCAGGAT
ATGCAGTTTTCTTTTAATGCGCCTGATGAAGACTTGCCTCAACTTACTATTGGTGGGGTTGTCCAC
ACCTTCAAGCCTGTGCAAATCCACTTTCACCACTTTGCCAGCGAGCACGCTATTGACGGCCAGCTT
TATCCTCTTGAGGCCCACATGGTGATGGCATCCCAGAATGACGGCTCTGACCAGCTTGCTGTCATT
GGCATCATGTACAAGTACGGGGAAGAAGATCCTTTCCTCAAAAGGCTGCAAGAAACTGCACAGAGC
AATGGCGAAGCTGCCGACAAAAATGTGGAGCTGAACTCGTTTTCCATCAATGTGGCCAGGGATTTG
CTGCCTGAGTCAGACCTGACCTACTATGGATATGATGGTAGCTTGACTACCCCCGGTTGTGATGAG
CGAGTGAAGTGGCATGTGTTCAAGGAGGCAAGGACTGTCTCAGTGGCGCAGCTCAAGGTGTTTTCA
GAGGTCACGCTGGCTGCCCACCCTGAAGCTACGGTTACCAACAACCGTGTCATTCAGCCGCTCAAT
GGCAGGAAGGTCTACGAGTACAAGGGTGAACCCAACGACAAGTACAACTATGTCCAGCATGGCTTT
GACTGGCGCGATAATGGCTTGGATAGCTGTGCTGGCGACGTCCAGAGCCCTATTGACATCGTGACC
AGCACTTTGCAAGCTGGATCTTCTCGGAGTGATGTTTCTAGTGTCAACCTGAATGACTTGAACACC
GACGCGTTCACGCTGACCGGCAACACTGTGAATATTGGGCAAGGCATGCAAATCAATTTTGGTGAC
CCCCCTGCGGGTGACCTGCCCGTCATCAGAATTGGTACTAGGGACGTCACTTTCAGGCCCCTCCAG
GTGCACTGGCACTTCTTTTTGAGTGAGCACACTGTGGATGGAGTGCACTACCCCCTGGAAGCTCAT
ATTGTTATGAAGGACAATGACAACCTTGGTGATTCTGCCGGCCAGCTTGCTGTCATCGGTATTATG
TACAAGTACGGCGATGCAGACCCCTTCATTACTGATATGCAGAAGAGGGTGTCAGATAAAATTGCA
TCAGGTGCCATCACCTATGGACAATCAGGAGTGTCTCTGAACAATCCTGATGATCCCTTCAATGTC
AACATCAAGAATAATTTCCTGCCCTCTGAGCTTGGATATGCTGGCTACGATGGCAGCCTGACCACC
CCTCCTTGCTCTGAGATTGTGAAGTGGCATGTGTTCCTGGAGCCTAGGACTGTTTCAGTGGAGCAG
ATGGAGGTCTTTGCAGATGTGACTCTGAACTCTAATCCAGGTGCGACCGTGACAACCAACCGAATG
ATCCAGCCACTGGAGGGTAGGACTGTGTACGGATATAACGGTGCTGCTGCTTAA
```

SEQ ID NO: 109 D. salina carbonic anhydrase (dca), P54212

MGSRRITLLGALFAVLAVAIEGRTLLTHNLKAEAAETVDAVSSVVAGSAGRQLLVSEPHDYNYEKV
GFDWTGGVCVNTGTSKQSPINIETDSLAEESERLGTADDTSRLALKGLLSSSYQLTSEVAINLEQD
MQFSFNAPDEDLPQLTIGGVVHTFKPVQIHFHHFASEHAIDGQLYPLEAHMVMASQNDGSDQLAVI
GIMYKYGEEDPFLKRLQETAQSNGEAGDKNVELNSFSINVARDLLPESDLTYYGYDGSLTTPGCDE
RVKWHVFKEARTVSVAQLKVFSEVTLAAHPEATVTNNRVIQPLNGRKVYEYKGEPNDKYNYVQHGF
DWRDNGLDSCAGDVQSPIDIVTSTLQAGSSRSDVSSVNLMTLNTDAFTLTGNTVNIGQGMQINFGD
PPAGDLPVIRIGTRDVTFRPLQVHWHFFLSEHTVDGVHYPLEAHIVMKDNDNLGDSAGQLAVIGIM
YKYGDADPFITDMQKRVSDKIASGAITYGQSGVSLNNPDDPFNVNIKNNFLPSELGYAGYDGSLTT
PPCSEIVKWHVFLEPRTVSVEQMEVFADVTLNSNPGATVTTNRMIQPLEGRTVYGYNGAAA

SEQ ID NO: 110 Arabidopsis thaliana carbonate dehydratase/ zinc ion binding (AT3G52720) mRNA, ORF

```
ATGAAGATTATGATGATGATTAAGCTCTGCTTCTTCTCCATGTCCCTCATCTGCATTGCACCTGCA
GATGCTCAGACAGAAGGAGTAGTGTTTGGATATAAAGGCAAAATGGACCAAACCAATGGGGACAC
TTAAACCCTCACTTCACCACATGCGCGGTCGGTAAATTGCAATCTCCAATTGATATTCAAAGGAGG
CAAATATTTTACAACCACAAATTGAATTCAATACACCGTGAATACTACTTCACAAACGCAACACTA
GTGAACCACGTCTGTAATGTTGCCATGTTCTTCGGGGAGGGAGCAGGAGATGTGATAATAGAAAAC
AAGAACTATACCTTACTGCAAATGCATTGGCACACTCCTTCTGAACATCACCTCCATGGAGTCCAA
TATGCAGCTGAGCTGCACATGGTACACCAAGCAAAGATGGAAGCTTTGCTGTGGTGGCAAGTCTC
TTCAAAATCGGCACTGAAGAGCCTTTCCTCTCAGATGAAGGAGAAATTGGTGAAGCTAAAGGAA
GAGAGACTCAAAGGGAACCACACAGCACAAGTGGAAGTAGGAAGAATCGACACAAGACACATTGAA
CGTAAGACTCGAAAGTACTACAGATACATTGGTTCACTCACTACTCCTCCTTGCTCCGAGAACGTT
TCTTGGACCATCCTTGGCAAGGTAATCTTTTAA
```

SEQ ID NO: 111 A. thaliana. At3g52720 protein sequence
MKIMMMIKLCFFSMSLICIAPADAQTEGVVFGYKGKNGPNQWGHLNPHFTTCAVGKLQSPIDIQRR
QIFYNHKLNSIHREYYFTNATLVNHVCNVAMFFGEGAGDVIIENKNYTLLQMHWHTPSEHHLHGVQ
YAAELHMVHQAKDGSFAVVASLFKIGTEEPFLSQMKEKLVKLKEERLKGNHTAQVEVGRIDTRHIE
RKTRKYYRYIGSLTTPPCSENVSWTILGKVRSMSKEQVELLRSPLDTSFKNNSRPCQPLNGRRVEM
FHDHERVDKKETGNKKKKPN

SEQ ID NO: 112 Arabidopsis thaliana carbonate dehydratase/ zinc ion binding (AT5G56330) mRNA, complete cds
ATGAAGATATCATCACTAGGATGGGTCTTAGTCCTTATCTTCATCTCTATTACCATTGTTTCGAGT
GCACCAGCACCTAAACCTCCTAAACCTAAGCCTGCACCAGCACCTACACCTCCTAAACCTAAGCCC
ACACCAGCACCTACACCTCCTAAACCTAAGCCCAAACCAGCACCTACACCTCCTAAACCTAAGCCT
GCACCAGCACCTACACCTCCTAAACCTAAGCCCGCACCAGCACCTACACCTCCTAAACCTAAGCCC
AAACCAGCACCTACACCTCCTAATCCTAAGCCCACACCAGCACCTACACCTCCTAAACCTAAGCCT
GCACCAGCACCAGCACCAACACCAGCACCGAAACCTAAACCTGCACCTAAACCAGCACCAGGTGGA
GAAGTTGAGGACGAAACCGAGTTTAGCTACGAGACGAAAGGAAACAAGGGGCCAGCGAAATGGGGA
ACACTAGATGCAGAGTGGAAAATGTGTGGAATAGGCAAAATGCAATCTCCTATTGATCTTCGGGAC
AAAAATGTGGTAGTTAGTAATAAATTTGGATTGCTTCGTAGCCAGTATCTGCCTTCTAATACCACC
ATTAAGAACAGAGGTCATGATATCATGTTGAAATTCAAAGGAGGAAATAAAGGTATTGGTGTCACT
ATCCGTGGTACTAGATATCAACTTCAACAACTTCATTGGCACTCTCCTTCCGAACATACAATCAAT
GGCAAAAGGTTTGCGCTAGAGGAACACTTGGTTCATGAGAGCAAAGATAAACGCTACGCTGTTGTC
GCATTCTTATACAATCTCGGAGCATCTGACCCTTTTCTCTTTTCGTTGGAAAAACAATTGAAGAAG
ATAACTGATACACATGCGTCCGAGGAACATATTCGCACTGTGTCAAGTAAACAAGTGAAGCTTCTC
CGTGTGGCTGTACACGATGCTTCAGATTCAAATGCCAGGCCGCTTCAAGCAGTCAATAAGCGCAAG
GTATATTTATACAAACCAAAGGTTAAGTTAATGAAGAAATACTGTAATATAAGTTCTTACTAG

SEQ ID NO: 113 A. thaliana. At5g56330 protein sequence
MKISSLGWVLVLIFISITIVSSAPAPKPPKPKPAPAPTPPKPKPTPAPTPPKPKPKPAPTPPKPKP
APAPTPPKPKPAPAPTPPKPKPKPAPTPPNPKPTPAPTPPKPKPAPAPAPTPAPKPKPAPKPAPGG
EVEDETEFSYETKGNKGPAKWGTLDAEWKMCGIGKMQSPIDLRDKNVVVSNKFGLLRSQYLPSNTT
IKNRGHDIMLKFKGGNKGIGVTIRGTRYQLQQLHWHSPSEHTINGKRFALEEHLVHESKDKRYAVV
AFLYNLGASDPFLFSLEKQLKKITDTHASEEHIRTVSSKQVKLLRVAVHDASDSNARPLQAVNKRK
VYLYKPKVKLMKKYCNISSY

SEQ ID NO: 114 Arabidopsis thaliana carbonate dehydratase/ zinc ion binding (AT5G04180) mRNA, complete cds
ATGAAAACCATTATCCTTTTTGTAACATTTCTTGCTCTTTCTTCTTCATCTCTAGCCGATGAGACA
GAGACTGAATTTCATTACAAACCCGGTGAGATAGCCGATCCCTCGAAATGGAGCAGTATCAAGGCT
GAATGGAAAATTTGCGGGACAGGGAAGAGGCAATCGCCAATCAATCTTACTCCAAAAATAGCTCGC
ATTGTTCACAATTCTACAGAGATTCTTCAGACATATTACAAACCTGTAGAGGCTATTCTTAAGAAC
CGTGGATTCGACATGAAGGTTAAGTGGGAAGACGATGCAGGGAAGATCGTGATCAATGATACCGAC
TATAAATTGGTTCAAAGCCACTGGCACGCACCTTCAGAGCATTTTCTCGATGGACAGAGGTTGGCA
ATGGAACTTCACATGGTACACAAAAGTGTAGAAGGGCACTTGGCAGTGATTGGAGTTCTCTTCAGA
GAAGGAGAACCAAATGCTTTCATTTCGCGGATCATGGACAAGATCCATAAGATCGCAGACGTACAA
GATGGAGAGGTCAGCATCGGAAAGATAGATCCAAGAGAATTGGATGGGATCTTACAAAGTTTTAT
GAATACAGAGGTTCTCTCACGACTCCTCCTTGCACGGAAGATGTCATGTGGACCATCATCAACAAG
GTGGGGACTGTTTCACGTGAGCAAATTGATGTATTGACAGATGCTCGTCGCGGTGGTTATGAGAAG
AACGCGAGACCAGCTCAACCTCTGAACGGACGTCTGGTTTATTTAAACGAGCAGTCCAGTCCAAGT
CCAACTCCACGGCTAAGAATACCACGAGTTGGTCCGGTCTAA

SEQ ID NO: 115 A. thaliana. At5g04180 protein sequence
MKTIILFVTFLALSSSSLADETETEFHYKPGEIADPSKWSSIKAEWKICGTGKRQSPINLTPKIAR
IVHNSTEILQTYYKPVEAILKNRGFDMKVKWEDDAGKIVINDTDYKLVQSHWHAPSEHFLDGQRLA
MELHMVHKSVEGHLAVIGVLFREGEPNAFISRIMDKIHKIADVQDGEVSIGKIDPREFGWDLTKFY
EYRGSLTTPPCTEDVMWTIINKVGTVSREQIDVLTDARRGGYEKNARPAQPLNGRLVYLNEQSSPS
PTPRLRIPRVGPV

SEQ ID NO: 116 Nicotiana langsdorffii x Nicotiana sanderae nectarin III (NEC3) mRNA, complete cds
ATGAGGATGGCAGCAATAACCAAAATGTTGTTCATTTCGTTTCTTTTCCTTTCAAGTGTATTTCTT
GCAAGGTCCGGAGAAGTTGATGATGAGAGTGAATTTAGTTACGATGAAAAAAGTGAGAATGGACCA
GCTAATTGGGGCAATATTCGTCCAGATTGGAAAGAATGTAGTGGCAAATTGCAGTCTCCTATTGAT
ATTTTTGACTTGAGGGCTGAAGTAGTTTCAAACTTGAGAATACTTCAAAAGGACTACAAACCATCG
AATGCCACTCTCTTGAACAGAGGTCATGATATAATGTTGAGATTGGATGATGGAGGATACTTGAAG
ATAAATGAAACTCAATATCAACTCAAGCAATTGCATTGGCACACACCTTCTGAACACACTATCAAT
GGAGAAAGGTTTAATTTGGAGGCTCATTTGGTACATGAAAGTAATAATGGAAAGTTTGTTGTCATT
GGAATAGTCTACGAGATCGGATTATGGCCTGATCCCTTCTTATCTATGATAGAGAACGATTTGAAA
GTTCCTGCTAATAAAAAAGGTATAGAGAGAGGCATTGGAATTATTGATCCAAATCAAATAAAATTG
GATGGCAAAAAATATTTTAGGTATATTGGCTCACTTACAACACCTCCTTGCACCGAAGGTGTTGTC
TGGATAATTGATAGAAAGGTAAAAACTGTAACCAGAAGACAAATAAAACTACTCCAAGAAGCTGTT
CATGATGGATTTGAAACCAACGCTAGACCAACTCAACCAGAAAACGAACGTTATATCAACTCAACA
TACCATTCCTTTGGTATTGAAAAGCAGCAGTGA

SEQ ID NO: 117 Nicotiana langsdorffii x Nicotiana sanderae Q84UV8 protein sequence
MRMAAITKMLFISFLFLSSVFLARSGEVDDESEFSYDEKSENGPANWGNIRPDWKECSGKLQSPID
IFDLRAEVVSNLRILQKDYKPSNATLLNRGHDIMLRLDDGGYLKINETQYQLKQLHWHTPSEHTIN
GERFNLEAHLVHESNNGKFVVIGIVYEIGLWPDPFLSMIENDLKVPANKKGIERGIGIIDPNQIKL
DGKKYFRYIGSLTTPPCTEGVVWIIDRKVKTVTRRQIKLLQEAVHDGFETNARPTQPENERYINST
YHSFGIEKQQ

SEQ ID NO: 118 Flaveria bidentis carbonic anhydrase mRNA, complete cds
ATGTCGGCCGCCTCTGCTTTCGCCATGAATGCGCCTTCGTTCGTCAACGCTTCGTCGCTGAAGAAA
GCGTCTACTTCAGCTAGATCTGGTGTGTTGTCCGCCAGATTTACGTGCAATTCGTCGTCGTCGTCG
TCTTCGTCTGCAACTCCTCCGAGTCTCATTCGTAACGAGCCTGTTTTCGCTGCTCCCGCGCCCATC
ATCACACCGAATTGGACCGAAGACGGAAATGAATCATACGAAGAAGCCATTGACGCGCTCAAGAAA
ACGCTCATTGAAAAGGGTGAGTTAGAACCAGTTGCCGCTACAAGAATCGACCAAATCACAGCTCAA
GCCGCAGCACCCGACACCAAAGCTCCATTTGACCCTGTTGAGAGGATCAAATCCGGCTTCGTGAAG
TTCAAGACAGAGAAATTCGTCACAAACCCAGCCTTGTACGATGAGCTTGCTAAAGGCCAAAGCCCA
AAGTTCATGGTGTTTGCATGCTCAGACTCGCGTGTTTGCCCGTCACACGTTCTTGATTTCCAGCCC
GGTGAGGCGTTTGTTGTTCGTAACGTTGCCAACATGGTCCCTCCCTTTGACAAGACCAAATATTCT
GGAGTAGGAGCTGCTGTTGAGTATGCAGTTTTGCATCTAAAGGTACAAGAAATCTTTGTAATTGGG
CATAGCCGTTGTGGAGGAATCAAGGGTCTCATGACTTTCCCAGACGAAGGACCTCACTCAACCGAT
TTCATCGAAGATTGGGTGAAAGTGTGTCTCCCCGCGAAGTCAAAAGTGGTAGCAGAACACAACGGC
ACACATCTTGATGATCAATGTGTACTATGTGAAAAGGAAGCTGTGAACGTGTCGCTTGGAAACCTG
TTGACATACCCATTTGTAAGGGATGGATTGAGGAACAAGACACTCGCGCTCAAGGGTGGTCACTAT
GACTTTGTTAACGGGACCTTTGAGCTGTGGGCACTTGACTTTGGGCTTTCGTCTCCTACCTCTGTA
TGA

SEQ ID NO: 119 F. bidentis. P46510 protein sequence
MSAASAFAMNAPSFVNASSLKKASTSARSGVLSARFTCNSSSSSSSSATPPSLIRNEPVFAAPAPI
ITPNWTEDGNESYEEAIDALKKTLIEKGELEPVAATRIDQITAQAAAPDTKAPFDPVERIKSGFVK
FKTEKFVTNPALYDELAKGQSPKFMVFACSDSRVCPSHVLDFQPGEAFVVRNVANMVPPFDKTKYS
GVGAAVEYAVLHLKVQEIFVIGHSRCGGIKGLMTFPDEGPHSTDFIEDWVKVCLPAKSKVVAEHNG
THLDDQCVLCEKEAVNVSLGNLLTYPFVRDGLRNKTLALKGGHYDFVNGTFELWALDFGLSSPTSV

SEQ ID NO: 120 Hordeum vulgare carbonic anhydrase mRNA, complete cds
ATGTCGTTGCAGATTGGGCGGACAGAGAGGGCCCGGTCCCCGGTCTTTGTCTTTGCACACAAGCGG
CAACTGCTCCATGGACGGTGTAGTACCATCGACAATGCAAATTGCAGCACCTGCAGCATGAAAATC
AATAGCACTTGTACATTGACGGCCCTGCCGATTGCCGCACTGCCTGGGCCACGTACTACCTCACAC
TACTCGACCGCCGCGGCTAACTGGTGCTACGAACCGTCGCGCCCCGTGCCCGCTCCTCCACCATC
GCCGCCAGCCTCGGCACCCCCGCGCCCTCCTCCTCCGCCTCCTTCCGCCCCAAGCTCATCAGGACC
ACCCCCGTCCAGGCCGCGCCCGTCGCACCTGCATTGATGGACGCCGCCGTGGAGCGCCTCAAGACC
GGGTTCGAGAAGTTCAAGACCGAGGTCTACGACAAGAAGCCCGATTTCTTCGAGCCGCTCAAGGCC
GGCCAGGCGCCCAAGTACATGGTGTTCGCGTGCGCCGACTCGCGTGTGTGCCCGTCGGTCACCCTG
GGCCTTGAGCCCGGTGAGGCCTTCACCATCCGCAACATCGCCAACATGGTCCCGGCCTACTGCAAG
AACAAGTACGCCGGTGTTGGATCGGCCATCGAATACGCCGTCTGCGCGCTCAAGGTTGAGGTCATC
GTGGTGATTGGCCACAGCCGCTGCGGTGGAATCAAGGCTCTGCTCTCGCTCAAGGATGGCGCAGAC
GACTCCTTCCACTTCGTTGAGGACTGGGTCAGGATCGGGTTCCCGGCCAAGAAGAAGGTGCAGACT
GAGTGCGCCTCCATGCCTTTCGATGACCAGTGCACCGTCCTGGAGAAGGAGGCCGTCAACGTGTCC
CTCCAGAACCTCTTGACCTACCCGTTCGTCAAGGAGGGTGTGACCAACGGAACCCTCAAGCTCGTC
GGCGGCCACTACGACTTCGTCTCCGGCAAGTTCGAAACATGGGAGCAGTAA

SEQ ID NO: 121 H. vulgare. P40880 protein sequence
MSLQIGRTERARSPVFVFAHKRQLLHGRCSTIDNANCSTCSMKINSTCTLTALPIAALPGPRTTSH
YSTAAANWCYATVAPRARSSTIAASLGTPAPSSSASFRPKLIRTTPVQAAPVAPALMDAAVERLKT
GFEKFKTEVYDKKPDFFEPLKAGQAPKYMVFACADSRVCPSVTLGLEPGEAFTIRNIANMVPAYCK
NKYAGVGSAIEYAVCALKVEVIVVIGHSRCGGIKALLSLKDGADDSFHFVEDWVRIGFPAKKKVQT
ECASMPFDDQCTVLEKEAVNVSLQNLLTYPFVKEGVTNGTLKLVGGHYDFVSGKFETWEQ

SEQ ID NO: 122 Chlamydomonas reinhardtii carbonic anhydrase precursor (beta-CA1) mRNA, nuclear gene encoding mitochondrial protein, complete cds
ATGTCGTCGCGGAATGTCGCTACCGCTCTGCGCATGTTCGCGACCCTCGGTCCGAGCCAGGCTGGC
GAGGCCTCGGCCATGATGGGCACCGGCTCGGCGCTGCTCGCGCAGCGCGCGGCCGCCCTGGGCGGC
GCCTCGGCTGTTAACAAGGGCTGCAGCTGCCGCTGCGGCCGCGTGGCGTGCATGGGCGCGTGCATG
CCGATGCGCCACCTCCACGCCCACCCCAACCCGCCCTCGGACCCCGACCAGGCCCTGGAGTACCTT
CGCGAGGGCAACAAGCGCTTCGTGAACAACAAGCCGCACGACTCGCACCCCACGCGCAACCTGGAC
CGCGTCAAGGCCACCGCCGCGGGCCAGAAGCCCTTCGCCGCCTTCCTGTCCTGCGCCGACTCGCGC
GTGCCTGTCGAGATCATCTTCGACCAGGGCTTCGGTGACGTGTTCGTGACGCGCGTGGCCGGCAAC
ATCGTGACCAACGAGATCACGGCGTCGCTGGAGTTCGGCACGGCCGTCCTGGGCTCCAAGGTGCTC
ATGGTGCTGGGCCACAGCGCTTGCGGCGCCGTGGCGGCCACCATGAACGGCGCCGCCGTGCCTGGC
GTCATCTCCTCTCTACTACAGCATCAGCCCGGCCTGCAAGAAGGCTCAGGCTGGCGACGTTGAC
GGTGCCATTGCCGAGAACGTCAAGGTCCAGATGGAGCAGCTCAAGGTGTCGCCCGTGCTGCAGGGG
CTCGTGAAGGAGGGCAAGCTCAAGATCGTGGGCGGCGTGTACGACCTGGCCACCGGCAAGGTGACC
GAGATCGCCTAA FIGURE 9 (continued)

SEQ ID NO: 123 C. reinhardtii beta-CA1 AAB19183
MSSRNVATALRMFATLGPSQAGEASAMMGTGSALLAQRAAALGGASAVNKGCSCRCGRVACMGACM
PMRHLHAHPNPPSDPDQALEYLREGNKRFVNNKPHDSHPTRNLDRVKATAAGQKPFAAFLSCADSR
VPVEIIFDQGFGDVFVTRVAGNIVTNEITASLEFGTAVLGSKVLMVLGHSACGAVAATMNGAAVPG
VISSLYYSISPACKKAQAGDVDGAIAENVKVQMEQLKVSPVLQGLVKEGKLKIVGGVYDLATGKVT
EIA

SEQ ID NO: 124 Oryza sativa (japonica cultivar-group) Os01g0639900 (Os01g0639900) mRNA, partial cds
GGAGCGCGCCGTGCACCGCCTCTCACAATGTCGACCGCCGCCGCCGCCGCCGCTGCCCAGAGCTGG
TGCTTCGCCACTGTCACCCCGCGCTCCCGCGCCACAGTCGTCGCCAGCCTCGCCTCCCCATCACCG
TCCTCCTCCTCCTCCTCCAACAGCAGCAACCTCCCGGCCCCCTTCCGCCCCCGCCTCATCCGC
AACACCCCCGTCTTCGCCGCCCCCGTCGCCCCCGCCGCGATGGACGCCGCCGTCGACCGCCTCAAG
GATGGGTTCGCCAAGTTCAAGACCGAGTTCTATGACAAGAAGCCGGAGCTCTTCGAGCCGCTCAAG
GCCGGCCAGGCACCCAAGTACATGGTGTTCTCGTGCGCCGACTCTCGCGTGTGCCCGTCGGTGACC
ATGGGCCTGGAGCCCGGCGAGGCCTTCACCGTCCGCAACATCGCCAACATGGTCCCAGCTTACTGC
AAGATCAAGCACGCTGGCGTCGGGTCGGCCATCGAGTACGCCGTCTGCGCCCTCAAGGTCGAACTC
ATCGTGGTGATTGGCCACAGCCGCTGCGGTGGAATCAAGGCCCTCCTCTCACTCAAGGATGGAGCA
CCAGACTCCTTCCACTTCGTCGAGGACTGGGTCAGGACCGGTTTCCCCGCCAAGAAGAAGGTTCAG
ACCGAGCACGCCTCGCTGCCTTTCGATGACCAATGCGCCATCTTGGAGAAGGAGGCCGTGAACCAA
TCCCTGGAGAACCTCAAGACCTACCCGTTCGTCAAGGAGGGGATCGCCAACGGCACCCTCAAGCTC
GTCGGCGGCCACTACGACTTCGTCTCCGGCAACTTGGACTTATGGGAGCCCTAA

SEQ ID NO: 125 O. sativa Os01g0639900
MSTAAAAAAAQSWCFATVTPRSRATVVASLASPSPSSSSSSSSNSSNLPAPFRPRLIRNTPVFAAP
VAPAAMDAAVDRLKDGFAKFKTEFYDKKPELFEPLKAGQAPKYMVFSCADSRVCPSVTMGLEPGEA
FTVRNIANMVPAYCKIKHAGVGSAIEYAVCALKVELIVVIGHSRCGGIKALLSLKDGAPDSFHFVE
DWVRTGFPAKKKVQTEHASLPFDDQCAILEKEAVNQSLENLKTYPFVKEGIANGTLKLVGGHYDFV
SGNLDLWEP

SEQ ID NO: 126 Arabidopsis thaliana CA2 (CARBONIC ANHYDRASE 2); carbonate dehydratase/ zinc ion binding (CA2) mRNA, complete cds
ATGGTCCCCTTTTGGACTACAGTTTCTCGAAATGGCTCATCAGACTCAGAGACGACTCTCCAATCT
GCTTCAAAAGCCACAAAACAGTATAAATATCCTTCTCTTCGTCCCTCTCATCGCCTGTCTCTCCTC
TTCCTCTTCCCGTTCCATTTATCCGCAAACGGAGCTTGTTTTCGGTGCACCTGCTTCAGCCACTTC
AAACTTGAACTGAGAAGGATGGGAAACGAATCATATGAAGACGCCATCGAAGCTCTCAAGAAGCTT
CTCATTGAGAAGGATGATCTGAAGGATGTAGCTGCGGCCAAGGTGAAGAAGATCACGGCGGAGCTT
CAGGCAGCCTCGTCATCGGACAGCAAATCTTTTGATCCCGTCGAACGAATTAAGGAAGGCTTCGTC
ACCTTCAAGAAGGAGAAATACGAGACCAATCCTGCTTTGTATGGTGAGCTCGCCAAAGGTCAAAGC
CCAAAGTACATGGTGTTTGCTTGTTCGGACTCACGAGTGTGCCCATCACACGTACTAGACTTCCAT
CCTGGAGATGCCTTCGTGGTTCGTAATATCGCCAATATGGTTCCTCCTTTTGACAAGGTCAAATAT
GCAGGAGTTGGAGCCGCCATTGAATACGCTGTCTTGCACCTTAAGGTGGAAACATTGTGGTGATA
GGGCACAGTGCATGTGGTGGCATCAAGGGGCTTATGTCATTTCCTCTTGACGGAAACAACTCTACT
GACTTCATAGAGGATTGGGTCAAAATCTGTTTACCAGCAAAGTCAAAAGTTTTGGCAGAAAGTGAA
AGTTCAGCATTTGAAGACCAATGTGGCCGATGCGAAAGGGCAGTGAATGTGTCACTAGCAAACCTA
TTGACATATCCATTTGTGAGAGAAGGAGTTGTGAAAGGAACACTTGCTTTGAAGGGAGGCTACTAT
GACTTTGTTAATGGCTCCTTTGAGCTTTGGGAGCTCCAGTTTGGAATTTCCCCCGTTCATTCTATA
TGA FIGURE 9 (continued)

SEQ ID NO: 127 A. thaliana. At3g01500
MSTAPLSGFFLTSLSPSQSSLQKLSLRTSSTVACLPPASSSSSSSSSSSSRSVPTLIRNEPVFAAP
APIIAPYWSEEMGTEAYDEAIEALKKLLIEKEELKTVAAAKVEQITAALQTGTSSDKKAFDPVETI
KQGFIKFKKEKYETNPALYGELAKGQSPKYMVFACSDSRVCPSHVLDFQPGDAFVVRNIANMVPPF
DKVKYGGVGAAIEYAVLHLKVENIVVIGHSACGGIKGLMSFPLDGNNSTDFIEDWVKICLPAKSKV
ISELGDSAFEDQCGRCEREAVNVSLANLLTYPFVREGLVKGTLALKGGYYDFVKGAFELWGLEFGL
SETSSVKDVATILHWKL

SEQ ID NO: 128 Flaveria pringlei carbonic anhydrase mRNA, complete cds
ATGTCGACCGCCTCTGCTTTCGCCATTAATGCGCCTTCGTTCGTCAACGCTTCGTCGCTGAAGAAG
TCGTCTTCTTCAGCCAGATCTGGTGTGTTGTCCGCCAGATTTACGTGCAATTCGTCGTCGTCTTCT
TCGTCTGCTACTCCTCCGAGTCTCATTCGTAACGAGCCTGTTTTCGCTGCTCCGGCTCCTATCATC
ACACCGAATTGGACCGAAGATGGAAATGAATCATACGAGGAAGCCATTGACGCACTCAAGAAAATG
CTCATTGAAAAGGGTGAGTTAGAACCAGTTGCCGCTGCAAGAATCGACCAAATCACAGCTCAAGCC
GCAGCACCCGACACCAAAGCTCCATTTGACCCTGTTGAGAGGATCAAATCCGGCTTCGTGAAGTTC
AAGACAGAGAAATTCGTCACAAACCCGGTCTTGTACGATGAGCTTGCTAAAGGCCAAAGCCCAAAG
TTCATGGTGTTTGCATGCTCAGACTCGCGTGTTTGCCCATCACACGTTCTTGATTTCCAGCCCGGT
GAGGCGTTTGTTGTCCGTAACGTTGCCAACATGGTCCCTCCCTTTGACAAGACCAAATATTCTGGA
GTAGGAGCTGCTGTTGAGTATGCAGTTTTGCATCTAAAGGTACAAGAAATATTTGTAATTGGGCAT
AGCCGTTGTGGAGGGATCAAGGGTCTCATGACTTTCCCAGACGAAGGACCTCACTCAACCGATTTC
ATCGAAGATTGGGTGAAAGTATGTCTCCCCGCGAAGTCAAAAGTGGTAGCAGAACACAACGGCACA
CATCTTGATGATCAATGTGTACTATGTGAAAAGGAAGCTGTGAACGTGTCGCTTGGAAACCTGTTG
ACATACCCATTTGTAAGGGATGGATTGAGGAACAATACACTCGCGCTCAAGGGTGGTCACTATGAC
TTTGTTAACGGGACCTTTGAGCTGTGGGCACTTGACTTTGGCCTTTCGTCTCCTACCTCTGTATGA

SEQ ID NO: 129 F. pringlei. P46281
MSTASAFAINAPSFVNASSLKKSSSSARSGVLSARFTCNSSSSSSSATPPSLIRNEPVFAAPAPII
TPNWTEDGNESYEEAIDALKKMLIEKGELEPVAAARIDQITAQAAAPDTKAPFDPVERIKSGFVKF
KTEKFVTNPVLYDELAKGQSPKFMVFACSDSRVCPSHVLDFQPGEAFVVRNVANMVPPFDKTKYSG
VGAAVEYAVLHLKVQEIFVIGHSRCGGIKGLMTFPDEGPHSTDFIEDWVKVCLPAKSKVVAEHNGT
HLDDQCVLCEKEAVNVSLGNLLTYPFVRDGLRNNTLALKGGHYDFVNGTFELWALDFGLSSPTSV

SEQ ID NO: 130 Flaveria linearis carbonic anhydrase 1 mRNA, complete cds
ATGTCGACCGCCTCTGCTTTCGCCATTAACGCGCCTTCGTTCGTCAACGCTTCATCGCTGAAGAAG
TCGTCGACTTCTTCAGCCAGATCTGGTGTGTTGTCCGCCAGATTTACGTGCAATTCGTCGTCGTCT
TCTTCGTCTGCAACTCCTCCGAGTCTCATTCGTAACGAGCCTGTTTTCGCTGCCCCGGCGCCCATC
ATAACACCGAATTGGACCGAAGACGGAAATGAATCATACGAGGAAGCCATTGACGCACTCAAGAAA
ATGCTCATTGAAAAGGGTGAGTTAGAACCCGTTGCCGCTGCAAGAATCGACCAAATCACAGCTCAA
GCCGCAGCACCCGACACCAAAGCTCCATTCGACCCTGTTGAGAGGATCAAATCCGGCTTCGTGAAG
TTCAAGACAGAGAAATTCGTAACAAACCCAGCCTGTACGATGAGCTTGCTAAAGGCCAAAGCCCA
AAGTTCATGGTGTTTGCATGCTCAGACTCGCGTGTTTGCCCATCACACGTTCTTGATTTCCAGCCC
GGTGAGGCGTTTGTTGTCCGTAACGTTGCCAACATGGTCCCTCCCTTTGACAAGACCAAATATTCT
GGAGTAGGAGCTGCTGTTGAGTATGCAGTTTTGCATCTAAAGGTACAAGAAATATTTGTAATTGGG
CATAGCCGTTGCGGAGGGATCAAGGGTCTCATGACTTTCCCAGACGAAGGACCTCACTCAACTGAT
TTCATCGAAGATTGGGTGAAAGTATGCCTCCCCGCAAAGTCAAAAGTGGTAGCAGAACACAACGGC FIGURE 9 (continued)

ACACATCTTGATGATCAATGTGTACAATGTGAAAAGGAAGCTGTGAACGTGTCGCTTGGAAACCTG
TTGACATACCCATTTGTAAGGGATGGTTTGAGGAACAATACACTCGCGCTCAAGGGTGGTCACTAT
GATTTTGTTAACGGGACCTTTGAGCTGTGGGCACTTGACTTTGGGCTTTCGTCTCCTACCTCTGTA
TGA

SEQ ID NO: 131 F. linearis. P46512
MSTASAFAINAPSFVNASSLKKSSTSSARSGVLSARFTCNSSSSSSSATPPSLIRNEPVFAAPAPI
ITPNWTEDGNESYEEAIDALKKMLIEKGELEPVAAARIDQITAQAAAPDTKAPFDPVERIKSGFVK
FKTEKFVTNPALYDELAKGQSPKFMVFACSDSRVCPSHVLDFQPGEAFVVRNVANMVPPFDKTKYS
GVGAAVEYAVLHLKVQEIFVIGHSRCGGIKGLMTFPDEGPHSTDFIEDWVKVCLPAKSKVVAEHNG
THLDDQCVQCEKEAVNVSLGNLLTYPFVRDGLRNNTLALKGGHYDFVNGTFELWALDFGLSSPTSV

SEQ ID NO: 132 Flaveria brownii carbonic anhydrase mRNA, complete cds
ATGTCGACCGCCTCTGCTTTCGCCACTAACGTGCCTTCGTTCGTCAACGCTTCATCGCTGAAGAAG
TCGTCCACTTCTTCAGCCAGATCTGGTGTGTTGTCCGCCAAATTTACGTGCAATTCGTCGTCGTCT
TCTTCGTCTGCAACTCCTCCGAGTCTCATTCGTAACGAGCCTGTTTTCGCTGCTCCGGCGCCCATC
ATCACACCGAATTGGACCGAAGACGGAAATGAATCATACGAGGAAGCCATTGACGCACTCAAGAAA
ATGCTCATTGAAAAGGGTGAGTTAGAACCAGTTGCGGCTGCAAGAATCGACCAAATCACAGCTCAA
GCCGCGGCACCCGACACCAAAGCTCCATTCGACCCTGTTGAGAGGATCAAATCCGGCTTCGTGAAG
TTCAAGACTGAGAAATTCGTAACAAACCCAGCCCTGTACGATGAGCTTGCTAAAGGCAAAGCCCA
AAGTTCATGGTGTTTGCATGCTCAGACTCGCGTGTTTGCCCATCACACGTTCTTGATTTCCAGCCC
GGTGAGGCGTTTGTTGTCCGTAACGTTGCCAACATGGTCCCTCCCTTTGACAAGACCAAATATTCT
GGAGTAGGAGCTGCTGTTGAGTATGCAGTTTTGCATCTGAAGGTACAAGAAATATTTGTAATTGGG
CATAGCCGTTGCGGAGGGATCAAGGGTCTCATGACTTTCCCAGACGAAGGACCTCACTCAACCGAT
TTCATCGAAGATTGGGTGAAAGTATGCCTCCCCGCGAAGTCAAAAGTGGTAGCAGAACACAACGGC
ACACATCTTGATGATCAATGTGTACTATGTGAAAAGGAAGCTGTGAACGTGTCGCTTGGAAACCTG
TTGACATACCCATTTGTAAGGGATGGTTTGAGGAACAATACACTCGCGCTCAAGGGTGGTCACTAT
GATTTTGTTAACGGGACCTTTGAGCTGTGGGCACTTGACTTTGGGCTTTCGTCTCCTACCTCTGTA
TGA

SEQ ID NO: 133 F. brownii. P46511
MSTASAFATNVPSFVNASSLKKSSTSSARSGVLSAKFTCNSSSSSSSATPPSLIRNEPVFAAPAPI
ITPNWTEDGNESYEEAIDALKKMLIEKGELEPVAAARIDQITAQAAAPDTKAPFDPVERIKSGFVK
FKTEKFVTNPALYDELAKGQSPKFMVFACSDSRVCPSHVLDFQPGEAFVVRNVANMVPPFDKTKYS
GVGAAVEYAVLHLKVQEIFVIGHSRCGGIKGLMTFPDEGPHSTDFIEDWVKVCLPAKSKVVAEHNG
THLDDQCVLCEKEAVNVSLGNLLTYPFVRDGLRNNTLALKGGHYDFVNGTFELWALDFGLSSPTSV

SEQ ID NO: 134 Nicotiana paniculata mRNA for NPCA1, complete cds
ATGTCAACTGCTTCCATTAACAGTTGCCTTACTATCTCCCAGCTCAAGCTTCCCTTAAGAAACCA
ATTCGTCCTGTTGCTTTTGCTAGGCTTAGCAACACCTCTTCTTCTTCTTCCGTTCCCAGTCTC
ATCAGAAACGAGCCCGTCTTCGCCGCCCCAACTCCCATCATCAACCCCATTTTGAGAGAAGAAATG
GCAAAGGAATCCTATGAGCAGGCCATTGCTGCACTCGAGAAACTCCTCAGCGAAAAGGAGAACTT
GGACCAATTGCTGCAGCAAGAGTTGACCAGATTACAGCTGAATTGCAATCATCAGATGGCAGCAAA
CCATTCGACCCTGTTGAGCACATGAAAGCTGGCTTTATTCACTTCAAAACTGAGAAATACGAGAAG
AACCCAGCCTTATATGGGGAACTATCAAAAGGCCAGAGCCCCAAGTTCATGGTCTTTGCCTGCTCT
GACTCTCGAGTGTGCCCATCACATGTTCTGAACTTCCAACCTGGTGAGGCTTTCGTGGTCCGAAAC
ATCGCCAACATGGTCCCCGCTTATGACAAGACCAGATACTCTGGTGTCGGAGCAGCTATCGAATAC GCTGTTCTCCACCTTAAGGTAGAGAACATTGTTGTCATTGGCCACAGCGCATGTGGAGGTATCAAA
GGTCTCATGTCTCTATCTGCAGATGGTTCTGAATCAACTGCCTTTATTGAGGATTGGGTGAAAATT
GGTTTACCTGCCAAGGCCAAGGTGGAGGGTGAACACGCGGATAAATGTTTTGCAGATCAATGCACA
GCTTGTGAGAAGGAAGCTGTGAATGTGTCACTTGGAAATTTGCTGACCTATCCATTTGTGAGAGAA
GGTTTGGTGAAGAAAACACTAGCATTGAAGGGAGGTCACTATGATTTTGTGAATGGAGGATTTGAG
CTGTGGGGACTTGAGTTCGGTCTTTCTCCTTCTCTTTCCGTATGA

SEQ ID NO: 135 N. paniculata. BAA25639
MSTASINSCLTISPAQASLKKPIRPVAFARLSNTSSSSSSVPSLIRNEPVFAAPTPIINPILREEM
AKESYEQAIAALEKLLSEKGELGPIAAARVDQITAELQSSDGSKPFDPVEHMKAGFIHFKTEKYEK
NPALYGELSKGQSPKFMVFACSDSRVCPSHVLNFQPGEAFVVRNIANMVPAYDKTRYSGVGAAIEY
AVLHLKVENIVVIGHSACGGIKGLMSLSADGSESTAFIEDWVKIGLPAKAKVEGEHADKCFADQCT
ACEKEAVNVSLGNLLTYPFVREGLVKKTLALKGGHYDFVNGGFELWGLEFGLSPSLSV

SEQ ID NO: 136 Nicotiana tabacum chloroplast carbonic anhydrase gene, complete cds
ATGTCAACTGCTTCCATTAACAGTTGCCTTACTATCTCCCCTGCTCAAGCTTCCCTTAAGAAACCA
ACTCGTCCTGTTGCTTTTGCAAGGCTTAGCAACTCTTCTTCTTCTACTTCTGTTCCCAGTCTCATC
AGAAACGAGCCCGTCTTCGCCGCCCCTACTCCCATCATCAACCCTATTTTGAGAGAAGAAATGGCA
AAGGAATCCTATGAGCAGGCCATTGCTGCACTCGAGAAACTCCTCAGCGAAAAGGAGAACTTGGA
CCAATTGCTGCAGCAAGAGTTGACCAGATTACAGCTGAATTGCAATCATCAGATGGCAGCAAACCA
TTCGACCCTGTTGAGCACATGAAAGCTGGCTTTATTCACTTCAAAACTGAGAAATACGAGAAGAAC
CCAGCCTTATATGGGGAACTATCAAAAGGCCAGAGCCCCAAGTTCATGGTCTTTGCCTGCTCTGAC
TCTCGAGTGTGCCCATCACATGTCCTGAACTTCCAACCTGGTGAGGCTTTCGTGGTCCGAAACATC
GCCAACATGGTCCCTGCTTATGACAAGACCAGATACTCCGGAGTCGGAGCAGCTATCGAATACGCT
GTTCTTCACCTTAAGGTAGAGAACATTGTTGTCATTGGCCATAGCGCATGTGGAGGTATCAAAGGT
CTCATGTCTTTACCTGCAGATGGTTCTGAATCAACTGCCTTCATTGAGGATTGGGTGAAAATTGGT
TTACCTGCCAAGGCGAAGGTGCAGGGTGAACACGTGGATAAATGTTTTGCAGATCAATGCACAGCT
TGTGAGAAGGAAGCTGTGAATGTGTCACTTGGAAATTTGCTGACCTATCCATTTGTGAGAGAAGGT
TTGGTGAAGAAAACACTAGCATTGAAGGGAGGTCACTATGATTTCGTGAATGGAGGATTTGAGCTG
TGGGGACTTGAGTTCGGTCTTTCTCCTTCTCTTTCCGTATGA

SEQ ID NO: 137 N. tabacum. P27141
MSTASINSCLTISPAQASLKKPTRPVAFARLSNSSSSTSVPSLIRNEPVFAAPTPIINPILREEMA
KESYEQAIAALEKLLSEKGELGPIAAARVDQITAELQSSDGSKPFDPVEHMKAGFIHFKTEKYEKN
PALYGELSKGQSPKFMVFACSDSRVCPSHVLNFQPGEAFVVRNIANMVPAYDKTRYSGVGAAIEYA
VLHLKVENIVVIGHSACGGIKGLMSLPADGSESTAFIEDWVKIGLPAKAKVQGEHVDKCFADQCTA
CEKEAVNVSLGNLLTYPFVREGLVKKTLALKGGHYDFVNGGFELWGLEFGLSPSLSV

SEQ ID NO: 138 Populus tremula x Populus tremuloides carbonic anhydrase (CA1a) mRNA, nuclear gene encoding chloroplast protein, complete cds
ATGTCGACTGCTTCGATTAACAGCTGGTGTCTCACCTCTGTCTCTGCCTCTAAGAAATCACTACCC
GCATTACGTCCTTCAGTCTTTGCAAGCCTCAACTCCTCTGTTTCTCCTCCTACCCTTATCAGAAAC
CAGCCTGTTTTCGCAGCCCCTGCTCCTATTCTCTATCCACGGAGAGGCGAAGAAATGGGAAACGAC
TACAACGAGGCCATTGAATCTCTCAAGAAACTCCTCAGTGACAAGGAAGAGCTGAAAACTGTAGCA
GCTGCGAAAGTGGAGCAGATAACAGCTGAATTACAAACCGTCTCATCTTCTGACCCCAAGGCATTC
GATCCTGTTGAGAAGATTAAATCCGGATTCATTCACTTCAAGAAGGAGAAATATGACAAGAATCCG FIGURE 9 (continued)

```
GGACTGTACTCCGAGCTTGCCAAAGGCCAAAGCCCCAAGTTTATGGTGTTTGCATGCTCGGATTCC
CGGGTTTGCCCGTCCCATGTGCTTGATTTCCAACCAGGGGAAGCTTTTGTGGTCCGCAATGTTGCG
AATATGGTCCCGCCATACGATAAGACTAAGTACGCTGGAGTTGGGGCAGCGATAGAGTACGCAGTT
TTGCATCTGAAGGTGGAATACATTGTGGTCATCGGACACAGCGCCTGTGGTGGAATTAAGGGCCTC
ATGTCCTTCCCGTATGATGGAACAACATCAACTGATTTCATAGAAGACTGGGTCAAAGTCTGCTAC
AATGCCAAGACCAAGATTTTAGCAGAACATGCCAACTCACCTTTCCCAGACATGTGTACACAATGT
GAAAAGGAGGCAGTGAACGTGTCCATCGGACACTTGCTCACCTACCCGTTTGTGAGAGATGGCTTG
GTGAACAAAACTCTAGGACTGAAGGGTGGTTATTATGATTTTGTCAAAGGCAGTTTTGAGCTCTGG
GGGCTTGAGTACAGCCTCTCCCCCTCTCTCTCCGTATGA
```

SEQ ID NO: 139 Populus tremula x Populus tremuloides CA1a, AAC49785
```
MSTASINSWCLTSVSASKKSLPALRPSVFASLNSSVSPPTLIRNQPVFAAPAPILYPRRGEEMGND
YNEAIESLKKLLSDKEELKTVAAAKVEQITAELQTVSSSDPKAFDPVEKIKSGFIHFKKEKYDKNP
GLYSELAKGQSPKFMVFACSDSRVCPSHVLDFQPGEAFVVRNVANMVPPYDKTKYAGVGAAIEYAV
LHLKVEYIVVIGHSACGGIKGLMSFPYDGTTSTDFIEDWVKVCYNAKTKILAEHANSPFPDMCTQC
EKEAVNVSIGHLLTYPFVRDGLVNKTLGLKGGYYDFVKGSFELWGLEYSLSPSLSV
```

SEQ ID NO: 140 Populus tremula x Populus tremuloides carbonic anhydrase (CA1b) mRNA, nuclear gene encoding chloroplast protein, complete cds
```
ATGTCGACTGCTTCGATTAACAGCTGGTGTCTCACCTCTGTCTCTCCCTCTAAGAAATCACTACCC
GCATTACGTCCTTCAGTCTTTGCAAGCCTCAACTCCTCTGTTTCTCCTCCTACCCTTATCAGAAAC
CAGCCTGTTTTCGCAGCCCCTGCTCCTATTCTCTATCCACGGAGAGGCGAAGAAATGGGAAACGAC
TACAACGAGGCCATTGAATCTCTCAAGAAACTCCTCAGTGATAAGGAGGAGCTGAAAACTGTAGCA
GCTGCGAAAGTGGAGCAGATAACAGCTGAATTACAAACCGTCTCATCTTCTGACCCCAAGGCATTC
GATCCTGTTGAGAAGATTAAATCCGGATTCATTCACTTCAAGAAGGAGAAATATGACAAGAATCCG
GGACTGTACTCCGAGCTTGCCAAAGGCCAAAGCCCCAAGTTTATGGTGTTTGCATGCTCGGATTCC
CGGGTTTGCCCGTCCCATGTGCTTGATTTCCAACCGGGGGAAGCTTTTGTGGTCCGCAATGTTGCG
AATATGGTCCCGCCATACGATAAGACTAAGTACGCTGGAGTTGGGGCAGCGATAGAGTACGCAGTT
TTGCATCTGAAGGTGGAATACATTGTGGTCATCGGACACAGCGCCTGTGGTGGAATTAAGGGCCTC
ATGTCCTTCCCGTATGATGGAACAACATCAACTGATTTCATAGAAGACTGGGTCAAAGTCTGCTAC
AATGCCAAGACCAAGATTTTAGCAGAACATGCCAACTCACCTTTCCCAGACATGTGTACACAATGT
GAAAAGGAGGCAGTGAACGTGTCCCTCGGACACTTGCTCACCTACCCGTTTGTGAGAGATGGCTTG
GTGAACAAAACTCTAGGCCTTAAGGGTGGTTATTATGATTTTGTCAAAGGAAGTTTTGAGCTCTGG
GGCCTTGAGTACAGCCTCTCTCCCTCTCTCTCCGTATGA
```

SEQ ID NO: 141 P. tremula. AAB65822
```
MSTASINSWCLTSVSPSKKSLPALRPSVFASLNSSVSPPTLIRNQPVFAAPAPILYPRRGEEMGND
YNEAIESLKKLLSDKEELKTVAAAKVEQITAELQTVSSSDPKAFDPVEKIKSGFIHFKKEKYDKNP
GLYSELAKGQSPKFMVFACSDSRVCPSHVLDFQPGEAFVVRNVANMVPPYDKTKYAGVGAAIEYAV
LHLKVEYIVVIGHSACGGIKGLMSFPYDGTTSTDFIEDWVKVCYNAKTKILAEHANSPFPDMCTQC
EKEAVNVSLGHLLTYPFVRDGLVNKTLGLKGGYYDFVKGSFELWGLEYSLSPSLSV
```

FIGURE 9 (continued)

SEQ ID NO: 142 Arabidopsis thaliana carbonate dehydratase/ zinc ion binding (AT1G23730) mRNA, complete cds
ATGTCGACAGAGTCGTACGAAGACGCCATTAAAAGACTCGGAGAGCTTCTCAGTAAGAAATCGGAT
CTCGGGAACGTGGCAGCCGCAAAGATCAAGAAGTTAACGGATGAGTTAGAGGAACTTGATTCCAAC
AAGTTAGATGCCGTAGAACGAATCAAATCCGGATTTCTCCATTTCAAGACTAATAATTATGAGAAG
AATCCTACTTTGTACAATTCACTTGCCAAGAGCCAGACCCCCAAGTTTTTGGTGTTTGCTTGTGCG
GATTCACGAGTTAGTCCATCTCACATCTTGAATTTCCAACTTGGGGAAGCCTTCATCGTTAGAAAC
ATTGCAAACATGGTGCCACCTTATGACAAGACAAAGCACTCTAATGTTGGTGCGGCCCTTGAATAT
CCAATTACAGTCCTCAACGTGGAGAACATTCTTGTTATTGGACACAGCTGTTGTGGTGGAATAAAG
GGACTCATGGCCATTGAAGATAATACAGCTCCCACTAAGACCGAGTTCATAGAAAACTGGATCCAG
ATCTGTGCACCGGCCAAGAACAGGATCAAGCAGGATTGTAAAGACCTAAGCTTTGAAGATCAGTGC
ACCAACTGTGAGAAGGAAGCCGTGAACGTGTCCTTGGGGAATCTTTTGTCTTACCCATTCGTGAGA
GAAAGAGTGGTGAAGAACAAGCTTGCCATAAGAGGAGCTCACTATGATTTCGTAAAAGGAACGTTT
GATCTTTGGGAACTTGACTTCAAGACTACCCCTGCCTTTGCCTTGTCTTAA

SEQ ID NO: 143 A. thaliana. At1g23730
MSTESYEDAIKRLGELLSKKSDLGNVAAAKIKKLTDELEELDSNKLDAVERIKSGFLHFKTNNYEK
NPTLYNSLAKSQTPKFLVFACADSRVSPSHILNFQLGEAFIVRNIANMVPPYDKTKHSNVGAALEY
PITVLNVENILVIGHSCCGGIKGLMAIEDNTAPTKTEFIENWIQICAPAKNRIKQDCKDLSFEDQC
TNCEKEAVNVSLGNLLSYPFVRERVVKNKLAIRGAHYDFVKGTFDLWELDFKTTPAFALS

SEQ ID NO: 144 Spinacia oleracea chloroplast carbonic anhydrase mRNA, complete cds
ATGTCTACTATTAACGGCTGCCTCACCTCTATCTCTCCTTCCCGTACTCAATTGAAAAATACCTCC
ACTTTAAGGCCAACTTTCATTGCTAACAGCAGGGTTAACCCTTCTTCTTCTGTTCCTCCTTCCCTT
ATTAGAAACCAGCCCGTTTTCGCCGCCCCCGCCCCTATCATCACCCCTACTTTGAAAGAAGATATG
GCATACGAAGAAGCCATCGCTGCCCTTAAGAAGCTTCTAAGCGAGAAGGGAGAACTTGAAAATGAA
GCCGCATCAAAGGTGGCACAGATAACATCTGAGTTAGCCGACGGTGGCACACCATCCGCCAGTTAC
CCGGTTCAGAGAATTAAGGAAGGGTTTATCAAATTCAAGAAGGAGAAATACGAGAAAATCCAGCA
TTGTATGGTGAGCTTTCTAAGGGCCAAGCTCCCAAGTTTATGGTGTTTGCGTGCTCAGACTCCCGT
GTGTGTCCCTCGCACGTACTAGATTTCCAGCCCGGTGAGGCTTTCATGGTTCGCAACATCGCCAAC
ATGGTGCCAGTGTTTGACAAGGACAAATACGCTGGAGTCGGAGCAGCCATTGAATACGCAGTGTTG
CACCTTAAGGTGGAGAACATTGTCGTGATTGGACACAGTGCTTGTGGTGGAATCAAGGGGCTTATG
TCTTTCCCAGATGCAGGACCAACCACAACTGATTTATTGAGGATTGGGTCAAAATCTGCTTGCCT
GCCAAGCACAAGGTGTTAGCCGAGCATGGTAATGCAACTTTCGCTGAACAATGCACCCATTGTGAA
AAGGAAGCTGTGAATGTATCTCTCGGAAACTTGTTGACTTACCCATTTGTAAGAGATGGTTTGGTG
AAGAAGACTCTAGCTTTGCAGGGTGGTTACTACGATTTTGTCAATGGATCATTCGAGCTATGGGGA
CTCGAATACGGCCTCTCTCCTTCCCAATCTGTATGA

SEQ ID NO: 145 S. oleracea. P16016
MSTINGCLTSISPSRTQLKNTSTLRPTFIANSRVNPSSSVPPSLIRNQPVFAAPAPIITPTLKEDM
AYEEAIAALKKLLSEKGELENEAASKVAQITSELADGGTPSASYPVQRIKEGFIKFKKEYEKNPA
LYGELSKGQAPKFMVFACSDSRVCPSHVLDFQPGEAFMVRNIANMVPVFDKDKYAGVGAAIEYAVL
HLKVENIVVIGHSACGGIKGLMSFPDAGPTTTDFIEDWVKICLPAKHKVLAEHGNATFAEQCTHCE
KEAVNVSLGNLLTYPFVRDGLVKKTLALQGGYYDFVNGSFELWGLEYGLSPSQSV

FIGURE 9 (continued)

SEQ ID NO: 146 Pisum sativum cap mRNA for carbonic anhydrase (EC 4.2.1.1)
ATGTCTACCTCTTCAATAAACGGCTTTAGTCTTTCTTCTTTGTCCCCTGCCAAAACTTCTACCAAA
AGAACTACATTGAGACCCTTTGTTTCTGCATCTCTTAACACTTCTTCTTCATCTTCTTCCTCGACT
TTCCCTTCTCTTATTCAAGACAAGCCGGTTTTCGCTTCTTCTTCTCCTATCATCACCCCAGTTTTG
AGAGAAGAAATGGGAAAGGGCTATGATGAAGCTATTGAAGAACTCCAAAAGTTGTTGAGGGAGAAG
ACTGAACTGAAAGCCACAGCTGCTGAGAAGGTTGAGCAAATCACAGCTCAGCTAGGAACAACATCA
TCATCTGATGGCATTCCAAAATCTGAAGCCTCTGAAAGGATCAAAACTGGTTTCCTTCACTTCAAG
AAAGAGAAATATGACAAGAATCCAGCTTTGTATGGTGAACTTGCCAAAGGCCAAAGCCCTCCGTTT
ATGGTGTTTGCATGTTCAGACTCAAGAGTCTGCCCATCTCATGTGCTAGATTTCCAGCCAGGTGAA
GCCTTTGTGGTCAGAAATGTTGCTAACTTGGTTCCACCATATGACCAGGCAAAATATGCCGGAACT
GGTGCTGCAATTGAGTACGCAGTTCTGCATCTCAAGGTTTCCAACATTGTTGTCATTGGACACAGT
GCTTGTGGTGGTATTAAGGGACTTTTGTCCTTTCCATTTGATGGAACCTACTCCACTGATTTCATT
GAGGAGTGGGTCAAAATTGGTTTACCTGCAAAGGCGAAGGTGAAAGCACAACATGGAGATGCACCT
TTTGCAGAGCTATGCACACACTGTGAGAAGGAAGCTGTGAATGCTTCCCTTGGAAACCTTCTCACC
TACCCATTTGTGAGAGAGGGATTGGTGAACAAGACATTGGCACTCAAAGGAGGATACTATGACTTT
GTGAAAGGATCCTTTGAGCTTTGGGGACTTGAATTTGGCCTTTCGTCCACTTTCTCCGTATGA

SEQ ID NO: 147 P. sativum. CAA36792
MSTSSINGFSLSSLSPAKTSTKRTTLRPFVSASLNTSSSSSSSTFPSLIQDKPVFASSSPIITPVL
REEMGKGYDEAIEELQKLLREKTELKATAAEKVEQITAQLGTTSSSDGIPKSEASERIKTGFLHFK
KEKYDKNPALYGELAKGQSPPFMVFACSDSRVCPSHVLDFQPGEAFVVRNVANLVPPYDQAKYAGT
GAAIEYAVLHLKVSNIVVIGHSACGGIKGLLSFPFDGTYSTDFIEEWVKIGLPAKAKVKAQHGDAP
FAELCTHCEKEAVNASLGNLLTYPFVREGLVNKTLALKGGYYDFVKGSFELWGLEFGLSSTFSV

SEQ ID NO: 148 Medicago truncatula carbonic anhydrase coding sequence, derived from AC124951
ATGTCTACCTCTTCCATAAACGGCTTTAGTCTCTCTTCTTTGTCCCCTACAAAAACTTCTATTAAA
AAAGTTACATTGAGACCTATTGTTTCTGCATCTCTTAACTCTTCTTCTTCTTCCTCTTCCACTTCT
AACTTCCCTTCTCTTATTCAAGACAAGCCTGTTTTTGCTTCATCTTCTTCTCCTATCATCACCCCA
GTTTTGAGAGAAGAAATGGGAAAGGGCTATGATGAAGCTATTGAAGAACTCCAAAAATTGTTGAGG
GAGAAGACTGAATTGAAAGCCACAGCAGCTGAAAAGGTTGAGCAAATTACAGCTCAGCTAGGAACA
ACAGCATCAGCTGATGGTGTTCCAACATCTGATCAAGCCTCAGAGAGGATCAAAACTGGTTTCCTT
CACTTCAAGAAAGAGAAATATGACACAAAACCAGCTTTGTATGGTGAACTTGCCAAAGGCCAAGCC
CCCCCGTTTATGGTGTTTGCATGCTCAGACTCAAGAGTCTGCCCATCTCATGTGCTAGACTTCCAG
CCAGGAGAAGCTTTTGTGGTCAGAAATGTTGCTAACATGGTTCCACCATATGACCAGGCAAAATAT
GCTGGAACTGGATCTGCAATTGAGTATGCTGTTCTGCATCTCAAGGTTTCCAACATTGTGGTCATT
GGACACAGTGCTTGTGGTGGTATTAAGGGCTTTTGTCTTTTCCATTTGATGGAGCCTACTCCACT
GATTTCATTGAGGAGTGGGTCAAAATTGGTTTACCTGCAAAGGCAAAGGTGAAGGCAAAGCATGGA
GATGCACCTTTTGGAGAGCTATGCACACACTGTGAGAAGGAAGCTGTGAATGTTTCTCTTGGAAAC
CTTCTAACCTACCCATTTGTGAGAGAGGGATTGGTGAACAAAACATTGGCACTAAAAGGAGGATAC
TATGACTTTGTGAAAGGATCTTTTGAGCTTTGGGGACTTGAATTTGGCCTTTCTTCAACTTTCTCC
GTATGA

SEQ ID NO: 149 M. truncatula. ABE84842
MSTSSINGFSLSSLSPTKTSIKKVTLRPIVSASLNSSSSSSSTSNFPSLIQDKPVFASSSSPIITP
VLREEMGKYDEAIEELQKLLREKTELKATAAEKVEQITAQLGTTASADGVPTSDQASERIKTGFL
HFKKEKYDTKPALYGELAKGQAPPFMVFACSDSRVCPSHVLDFQPGEAFVVRNVANMVPPYDQAKY
AGTGSAIEYAVLHLKVSNIVVIGHSACGGIKGLLSFPFDGAYSTDFIEEWVKIGLPAKAVKAKHG
DAPFGELCTHCEKEAVNVSLGNLLTYPFVREGLVNKTLALKGGYYDFVKGSFELWGLEFGLSSTFS
V

SEQ ID NO: 150 Medicago truncatula clone mth2-27e7, carbonic anhydrase coding sequence, derived from AC122172
ATGGTATTTGCTTGCTCTGACTCTAGAGTGAGTCCCTCTATTATCCTGAACTTTCAACATGGAGAA
GCTTTCATGGTCCGAAACATTGCTAACATGGTCCCTACATTTAATCAGGTGGAGAACATCTTGGTT
ATTGGACATAGTCGCTGCGGTGGAATCTCAAGGCTTATGCCTTCCAGAGGATGGCTGCTCCATAAT
GATTGGGTGAAAATTGGTTTATCTTTCAAAGTCAAGGTTCTGAAAGAACATGAATGCTGTGATTTC
AAAGAACAATGCAAATTTTGTGAAATGGAATCAGTGAATAATTCATTAGTGAACCTGAAGACATAT
CTATATGTTGATAGAGAAGTAAGGAACAAGAACTTAGCACTATTGGGAGGTTACTATGATTTTGTG
AATGGAGAATTCAAGCTCTGGAAGTATAAGACCCATGTCACTAAACCCATTACAATCCCCTCTAAA
AGACCTTGA

SEQ ID NO: 151 M. truncatula. ABE93117
MVFACSDSRVSPSIILNFQHGEAFMVRNIANMVPTFNQVENILVIGHSRCGGISRLMPSRGWLLHN
DWVKIGLSFKVKVLKEHECCDFKEQCKFCEMESVNNSLVNLKTYLYVDREVRNKNLALLGGYYDFV
NGEFKLWKYKTHVTKPITIPSKRP

SEQ ID NO: 152 Arabidopsis thaliana carbonate dehydratase/ zinc ion binding (AT1G08080) mRNA, complete cds
ATGGTGAACTACTCATCAATCAGTTGCATCTTCTTTGTGGCTCTGTTTAGTATTTTCACAATTGTT
TCGATTTCGAGTGCTGCCTTCAAGTCACGGAGAAGTTGAGGACGAACGCGAGTTTAACTACAAGAAG
AACGATGAGAAGGGGCCAGAGAGATGGGGAGAACTTAAACCGGAATGGGAAATGTGTGGAAAAGGA
GAGATGCAATCTCCCATAGATCTTATGAACGAGAGAGTTAACATTGTTTCTCATCTTGGAAGGCTT
AATAGAGACTATAATCCTTCAAATGCAACTCTTAAGAACAGAGGCCATGACATCATGTTAAAATTT
GAAGATGGAGCAGGAACTATTAAGATCAATGGTTTTGAATATGAACTTCAACAGCTTCACTGGCAC
TCTCCGTCTGAACATACTATTAATGGAAGAAGGTTTGCACTTGAGCTGCATATGGTTCACGAAGGC
AGGAATAGAAGAATGGCTGTTGTGACTGTGTTGTACAAGATCGGAAGAGCAGATACTTTTATCAGA
TCGTTGGAGAAAGAATTAGAGGGCATTGCTGAAATGGAGGAGGCTGAGAAAAATGTAGGAATGATT
GATCCCACCAAAATTAAGATCGGAAGCAGAAAATATTACAGATACACTGGTTCACTTACCACTCCT
CCTTGCACTCAAAACGTTACTTGGAGCGTCGTTAGAAAGGTTAGGACCGTGACAAGAAAACAAGTG
AAGCTCCTCCGCGTGGCAGTGCACGATGATGCTAATTCGAATGCGAGGCCGGTTCAACCAACCAAC
AAGCGCATAGTGCACTTATACAGACCAATAGTTTAA

SEQ ID NO: 153 A. thaliana. At1g08080
MVNYSSISCIFFVALFSIFTIVSISSAASSHGEVEDEREFNYKKNDEKGPERWGELKPEWEMCGKG
EMQSPIDLMNERVNIVSHLGRLNRDYNPSNATLKNRGHDIMLKFEDGAGTIKINGFEYELQQLHWH
SPSEHTINGRRFALELHMVHEGRNRRMAVVTVLYKIGRADTFIRSLEKELEGIAEMEEAEKNVGMI
DPTKIKIGSRKYYRYTGSLTTPPCTQNVTWSVVRKVRTVTRKQVKLLRVAVHDDANSNARPVQPTN
KRIVHLYRPIV

FIGURE 9 (continued)

SEQ ID NO: 154 Flaveria pringlei carbonic anhydrase 3 mRNA, complete cds
ATGTATGCTACAGCTGCCGCATTTGCACCCTCCTTCACCACCTCCCGCCGCAAACCGTCATCGTCG
TCTTCCACCGTATCCACTTGCTTTGCAAGGCTTAGCAACAGCGCTCAGTCGTCGTCGTCGTCTGCC
ACTCCACCACCCAGCCTCATCCGTAATCAGCCCGTTTTTGCCGCCCCGACTCCCATCATCACCCCC
ACTGTGAGAGGAGACATGGAAGTGAATCATATGATGAGGCAATTGCTGCACTCAAGAAGCTTTTA
AGTGAAAAGGAGGAGTTGGCACCTGTGGCTGCTGCCAAAATCGACGAAATCACGGCCCAACTTCAA
ACTCTCGACACCAAACCTGCATTTGACGCGGTCGAGAGGATCAAAACCGGGTTTGCCAAGTTCAAG
ACCGAGAAATACCTGACAAATCCAGCTTTGTACGATGAACTTTCCAAAGGCCAGAGCCCAAAATTT
ATGGTTTTTGCATGCTCTGACTCTCGAGTTTGCCCGTCACACGTGCTGGATTTCCAACCCGGTGAG
GCGTTTGTGGTCCGTAACGTAGCCAACATTGTCCCCCCCTTTGATAAGCTTAAATACGCTGGAGTA
GGATCCGCAGTCGAGTATGCAGTTCTGCATCTCAAGGTGGAGCAGATAGTCGTAATTGGGCATAGT
AAATGTGGTGGATCAAGGGTCTGATGACTTTCCCGATGAGGGACCGACCAGCACCGACTTCATT
GAGGACTGGGTCAGAGTTGGTCTCCCTGCAAAGTCAAAGGTGAAAGCGGAGCATGGAAGTGCATCA
CTTGATGATCAATGTGTATCCTGCGAGAAGGAGGCGGTGAATGTGTCTCTTGCAAACCTGTTGACT
TACCCGTTTGTGAGAAACGGATTGATGAACAAAACATTGGCGCTCAAGGGTGCACACTATGACTTT
GTTAACGGGGCCTTTGAGTTGTGGGGCTTGATTTCAGCCTTTCGCCTCCTACCTCGGCATAA

SEQ ID NO: 155 F. pringlei. ABC41658
MYATAAAFAPSFTTSRRKPSSSSSTVSTCFARLSNSAQSSSSSATPPPSLIRNQPVFAAPTPIITP
TVRGDMGSESYDEAIAALKKLLSEKEELAPVAAAKIDEITAQLQTLDTKPAFDAVERIKTGFAKFK
TEKYLTNPALYDELSKGQSPKFMVFACSDSRVCPSHVLDFQPGEAFVVRNVANIVPPFDKLKYAGV
GSAVEYAVLHLKVEQIVVIGHSKCGGIKGLMTFPDEGPTSTDFIEDWVRVGLPAKSKVKAEHGSAS
LDDQCVSCEKEAVNVSLANLLTYPFVRNGLMNKTLALKGAHYDFVNGAFELWGLDFSLSPPTSA

SEQ ID NO: 156 Flaveria linearis carbonic anhydrase 3 mRNA, complete cds, DQ273588
ATGTATGCCACAGCTGCCGCATTAATTGCACCCTCCTTCACCACCTCTCTCCGCAAACCGTCATCG
TCGTCTTCCACCGTATCCGCTCCCTTCGCAAGGCTAATTACCAACAACTCGCTGGCGTCGTCGTCG
TTGTCTGCCACTCCACCACCGAGCCTCATCCGTAACCAGCCCGTTTTTGCCGCCCCGACTCCCATC
ATCACCCCCACTGTGAGAGGAGACATGGAAGTGAATCATATGACGAGGCAATTGCTGCACTGAAG
AAGCTTTTAAGTGAAAGGGAGGATTTGGCACCTGTGGCTGCTGCAAAAATCGACGAAATCACCTCC
CAACTTCAAACGCTCGACACCAAACCCGCATTTGACGCGGTCGAGAGGATCAAAACCGGCTTTGCC
AAGTTCAAGACCGAGAAATACTTGACAAATCCAGCTTTGTACGATGAACTTTCCAAAGGCCAGAGC
CCAAAATTTATGGTTTTTGCATGCTCTGACTCTCGAGTTTGCCCGTCACACGTGCTCGATTTCCAA
CCTGGTGAGGCGTTTGTGGTCCGTAACGTAGCCAACATTGTCCCCCCCTTTGATAAGCTTAAATAT
GCTGGAGTAGGATCCGCTGTCGAGTATGCAGTTTTGCATCTCAAGGTGGAGCAGATAGTTGTAATT
GGGCATAGTAAATGTGGTGGATCAAGGGTCTGATGACTTTCCCGGACGAAGGACCGACAAGCACC
GACTTCATTGAGGACTGGGTCAGAGTTGGTCTCCCTGCAAAGTCAAAGGTGAAAGCGGAGCATGGA
AGTGCATCAATTGATGATCAATGTGTATCCTGCGAGAAGGAGGCGGTGAATGTGTCTCTTGCAAAC
CTGTTGACTTACCCGTTTGTGAGAAACGGATTGATAAACAAAACATTGGCGCTCAAGGGTGCACAC
TATGACTTTGTTAACGGGACCTTTGAGTTGTGGGGCTTGATTTCTGCCTTTCGCCTCCTACCTCG
GCATAA

FIGURE 9 (continued)

SEQ ID NO: 157 F. linearis. ABC41659
MYATAAALIAPSFTTSLRKPSSSSSTVSAPFARLITNNSLASSSLSATPPPSLIRNQPVFAAPTPI
ITPTVRGDMGSESYDEAIAALKKLLSEREDLAPVAAAKIDEITSQLQTLDTKPAFDAVERIKTGFA
KFKTEKYLTNPALYDELSKGQSPKFMVFACSDSRVCPSHVLDFQPGEAFVVRNVANIVPPFDKLKY
AGVGSAVEYAVLHLKVEQIVVIGHSKCGGIKGLMTFPDEGPTSTDFIEDWVRVGLPAKSKVKAEHG
SASIDDQCVSCEKEAVNVSLANLLTYPFVRNGLINKTLALKGAHYDFVNGTFELWGLDFCLSPPTS
A

SEQ ID NO: 158 Arabidopsis thaliana unknown protein (AT1G19580) mRNA, complete cds
ATGGGAACCCTAGGCAGAGCATTTTACTCGGTCGGTTTTTGGATCCGTGAGACTGGTCAAGCTCTT
GATCGCCTCGGTTGTCGCCTTCAAGGCAAAAATTACTTCCGAGAACAACTGTCAAGGCATCGGACA
CTGATGAATGTATTTGATAAGGCTCCGATTGTGGACAAGGAAGCTTTTGTGGCACCAAGCGCCTCA
GTTATTGGGGACGTTCACATTGGAAGAGGATCGTCCATTTGGTATGGATGCGTATTACGAGGCGAT
GTGAACACCGTAAGTGTTGGGTCAGGAACTAATATTCAGGACAACTCACTTGTGCATGTGGCAAAA
TCAAACTTAAGCGGGAAGGTGCACCCAACCATAATTGGAGACAATGTAACCATTGGTCATAGTGCT
GTTTTACATGGATGTACTGTTGAGGATGAGACCTTTATTGGGATGGGTGCGACACTTCTTGATGGG
GTCGTTGTTGAAAAGCATGGGATGGTTGCTGCTGGTGCACTTGTACGACAAAACACCAGAATTCCT
TCTGGAGAGGTATGGGGAGGAAACCCAGCAAGGTTCCTCAGGAAGCTCACTGATGAGGAAATTGCT
TTTATCTCTCAGTCAGCAACAAACTACTCAAACCTCGCACAGGCTCACGCTGCAGAGAATGCAAAG
CCATTAAATGTGATTGAGTTCGAGAAGGTTCTACGCAAGAAGCATGCTCTAAAGGACGAGGAGTAT
GACTCAATGCTCGGAATAGTGAGAGAAACTCCACCAGAGCTTAACCTCCCTAACAACATACTGCCT
GATAAAGAAACCAAGCGTCCTTCTAATGTGAACTGA

SEQ ID NO: 159 A. thaliana. At1g19580
MGTLGRAFYSVGFWIRETGQALDRLGCRLQGKNYFREQLSRHRTLMNVFDKAPIVDKDAFVAPSAS
VIGDVHIGRGSSIWYGCVLRGDVNTVSVGSGTNIQDNSLVHVAKSNLSGKVHPTIIGDNVTIGHSA
VLHGCTVEDETFIGMGATLLDGVVVEKHGMVAAGALVRQNTRIPSGEVWGGNPARFLRKLTDEEIA
FISQSATNYSNLAQAHAAENAKPLNVIEFEKVLRKKHALKDEEYDSMLGIVRETPPELNLPNNILP
DKETKRPSNLN

SEQ ID NO: 160 DT561379 EST1072019 GH_TMO Gossypium hirsutum cDNA, mRNA sequence
CATTTCGAGCTTTGTTTCCTAATCACTCGCCCGCTGCGCAATCACCGATCAAAGCTGAAGATGGGA
AGCCTTGGAAAAGCAATATACACCGTCGGATTCTGGATTCGGGAGACCGGTCAGGCTCTCGATCGC
CTAGGCTGCCGCCTACAAGGCAACTATTTTTTCCAGGAGCAACTTTCTAGGCATCGGACTCTGATG
AACGTATTTGATAAATCTCCTCTGGTGGACAAGGATGCATTTGTAGCCCCTAGCGCATCTGTCATT
GGCGATGTTCAGGTGGGAAGAGGATCATCTATTTGGTATGGATGTGTTTTAAGGGGGGATGTCAAC
AGCATTAGTGTTGGATCTGGAACTAATATACAAGACAACTCCCTTGTGCATGTTGCAAAGTCTAAT
CTAAGTGGGAAAGTGCTACCAACTAACATTGGAAACAATGTTACTGTAGGTCATAGTGCTGTTTTA
CATGGCTGTACCGTTGAGGATGAAGCATTTGTTGGCATGGGAGCCACACTTCTTGATGGTGTAGTT
GTGGAAAAACATGCTATGGTTGCTGCTGGAGCCCTTGTAAGACAGAATACAAGGATCCCTGCTGGA
GAGGTGTGGGGAGGCAATCCTGCTAAATTCCTGAGGAAGCTAACTGAGAAGAGATAGCGTTTATT
TCCCAGTCAGCCACCAATTATACCAACCTTGCACAGGTACATGCTGCTGAGAATGCAAAACCCTTT
GATGAAATTGAATTTGAGAAAATTCTTCGCAAGAAGTTTGCGAAGAGGGATGAAGAGTATGACTCA
ATGCTGGGTGTTGTCCGTGAAACTCCACCAGAACTAATTCTTCCAGACAATGTCCTACCAGATAAA
GAGCAAAAGTCCTCTC FIGURE 9 (continued)

SEQ ID NO: 161 G. hirsutum. DT561379, derived protein sequence
MGSLGKAIYTVGFWIRETGQALDRLGCRLQGNYFFQEQLSRHRTLMNVFDKSPLVDKDAFVAPSAS
VIGDVQVGRGSSIWYGCVLRGDVNSISVGSGTNIQDNSLVHVAKSNLSGKVLPTNIGNNVTVGHSA
VLHGCTVEDEAFVGMGATLLDGVVVEKHAMVAAGALVRQNTRIPAGEVWGGNPAKFLRKLTEEEIA
FISQSATNYTNLAQVHAAENAKPFDEIEFEKVLRKKFAKRDEEYDSMLGVVRETPPELILPDNVLP
DKEQKSSQK

SEQ ID NO: 162 BT014370, Lycopersicon esculentum clone 133658F, mRNA sequence
AGGCATGTGGTATTCACTATTCTGCCCTACCAATTACTCTGTGGAAAGCCTTCATTTCTCACTCAA
TCGTCCCTTTTGCTACACAAACACCTTGACTGCACAGCTCTACTGATCAGAAAGAGGGCTAAACCG
AAAGAAGAAGAAGGAGGAGGTCAAACATGGGAACCCTCGGGAAAGCAATTTACTCCCTGGGATCCA
TCGTTCGAGCGACCGGCAAAGCTCTTGATCGCGTCGGAAATCGCCTACAAGGCAGCTCCCACATAG
AGGAACACCTGTCCAGGCATCGGACTCTTATGAACGTATTCGATAAAGCTCCGGTGGTGGATAAGG
ATGTATTTGTAGCTCCAGGTGCCTCAGTCATTGGAGATGTCCATGTGGGACGCAATTCATCTATTT
GGTATGGATGTGTACTAAGAGGTGATGTTAACAGCATCAGTGTCGGATCTGGTACCAATATACAGG
ACAACTCCCTTGTTCATGTGGCCAAATCAAATATAAGTCAAAAGGTGCTGCCCACCATCATAGGGA
ACAATGTTACTGTTGGTCATAGTGCTGTTGTACATGGCTGCACCATTGAGGATGAGGCCTTCATTG
GTATGGGGGCCACACTGCTTGATGGTGTTCATGTAGAGAAACATGCCATGGTTGCTGCAGGAGCCC
TTGTGAAACAGAACACAAGGATTCCCTCCGGAGAGGTATGGGCAGGCAATCCCGCTAAGTTTCTGA
GGAAGCTAACTGATGAAGAGATAGCCTTCATTGCTCAGTCAGCAACCAACTACTGTAACCTTGCTC
GTGTCCATGCAGCTGAGAACTCCAAGTCCTTTGACGAAATTGAATTTGAAAAGATGCTTCGTAAGA
AGTATGCCAAACGTGATGAGGAATATGATTCTATGATTGGTGTTGTCCGTGAAACACCTCCCGAGC
TTGTACTTCCTGATAATATCCTCCCCGAAAAAGCTGCTAAGAGCATCGCCCAATGAGATCAGTGCC
CAAGCAACTCTCTCTTTTTTTGCTTTCCAGAGATTTATTTTACACCGTGAGCATCTGTATGGAGAA
CAGTCATGGATATTGGCTGTTACCCTTCCAAATAATATCAAACTTATTGGATAGCATCGGTACGTC
ACTGCTTTGTAGTTAAGACTTTTGCCCCTTATTTCCCAGAAATTCTTCAGCTTGGAAAAGGAAGTT
ACGCCCGAAAAAAAAAAAAAAAAAAAAAA

SEQ ID NO: 163 L. esculentum. BT014370, derived protein sequence
MGTLGKAIYSLGSIVRATGKALDRVGNRLQGSSHIEEHLSRHRTLMNVFDKAPVVDKDVFVAPGAS
VIGDVHVGRNSSIWYGCVLRGDVNSISVGSGTNIQDNSLVHVAKSNISQKVLPTIIGNNVTVGHSA
VVHGCTIEDEAFIGMGATLLDGVHVEKHAMVAAGALVKQNTRIPSGEVWAGNPAKFLRKLTDEEIA
FIAQSATNYCNLARVHAAENSKSFDEIEFEKMLRKKYAKRDEEYDSMIGVVRETPPELVLPDNILP
EKAAKSIAQ

SEQ ID NO: 164 Zea mays Golden Bantam carbonic anhydrase mRNA, complete cds, U08403
ATGTACACATTGCCCGTCCGTGCCACCACATCCAGCATCGTGCCAGCCTGCCACCCCCGCGCCGTC
CTCCTCCTCCGGCTCCGGCCCCAGGCTCAGGCTCATCCGGAACGCCCCGTCTTCGCCGCCCCGCC
ACCGTCGTGGGCATGGACCCCACCGTCGAGCGCTTGAAGAGCGGGTTCCAGAAGTTCAAGACCGAG
GTCTATGACAAGAAGCCGGAGCTGTTCGAGCCTCTCAAGTCCGGCCAGAGCCCCAGGTACATGGTG
TTCGCCTGCTCCGACTCCCGCGTGTGCCCGTCGGTGACACTGGGACTGCAGCCCGGCGAGGCATTC
ACCGTCCGCAACATCGCTTCCATGGTCCCACCCTACGACAAGATCAAGTACGCCGGCACAGGGTCC
GCCATCGAGTACGCCGTGTGCGCGCTCAAGGTGCAGGTCATCGTGGTCATTGGCCACAGCTGCTGC
GGTGGCATCAGGGCGCTCCTCTCCCTCAAGGACGGCGCGCCCGACAACTTCACCTTCGTGGAGGAC
TGGGTCAGGATCGGCAGCCCTGCCAAGAACAAGGTGAAGAAGAGCACGCGTCCGTGCCGTTCGAT
GACCAGTGCTCCATCCTGGAGAAGGAGGCCGTGAACGTGTCGCTCCAGAACCTCAAGAGCTACCCC

```
TTCGTCAAGGAAGGGCTGGCCGGCGGGACGCTCAAGCTGGTTGGCGCCCACTACAGCTTCGTCAAA
GGGCAGTTCGTCACATGGGAGCCTCCCCAGGACGCCATCGAGCGCTTGACGAGCGGCTTCCAGCAG
TTCAAGGTCAATGTCTATGACAAGAAGCCGGAGCTTTTCGGGCCTCTCAAGTCCGGCCAGGCCCCC
AAGTACATGGTGTTCGCCTGCTCCGACTCCGTGTGTGCCCGTCGGTGACCCTGGGCCTGCAGCCC
GCGAAGGCCTTCACCGTTCGCAACATCGCCGCCATGGTCCCAGGCTACGACAAGACCAAGTACACC
GGCATCGGGTCCGCCATCGAGTACGCTGTGTGCGCCCTCAAGGTGGAGGTCCTCGTGGTCATTGGC
CATAGCTGCTGCGGTGGCATCAGGGCGCTCCTCTCCCTCAAGGACGGCGCGCCCGACAACTTCCAC
TTCGTGGAGGACTGGGTCAGGATCGGCAGCCCTGCCAAGAACAAGGTGAAGAAAGAGCACGCGTCC
GTGCCGTTCGATGACCAGTGCTCCATCCTGGAGAAGGAGGCCGTGAACGTGTCGCTCCAGAACCTC
AAGAGCTACCCCTTGGTCAAGGAAGGGCTGGCCGGCGGGACGTCAAGTGGTTGGCCCCACTACGAC
TTCGTTAAAGGGCAGTTCGTCACATGGGAGCCTCCCCAGGACGCCATCGAGCGCTTGACGAGCGGC
TTCCAGCAGTTCAAGGTCAATGTCTATGACAAGAAGCCGGAGCTTTTCGGGCCTCTCAAGTCCGGC
CAGGCCCCCAAGTACATGGTGTTCGCCTGCTCCGACTCCGTGTGTCCCCGTCGGTGACCCTGGGC
CTGCAGCCCGGCGAGGCCTTCACCGTTCGCAACATCGCCGCCATGGTCCCCGGCTACGACAAGACC
AAGTACACCGGCATCGGGTCCGCCATCGAGTACGCTGTGTGCGCCCTCAAGGTGGAGGTCCTCGTG
GTCATTGGCCATAGCTGCTGCGGTGGCATCAGGGCGCTCCTCTCACTCCAGGACGGCGCACCTGAC
ACCTTCCACTTCGTCGAGGACTGGGTTAAGATCGCCTTCATTGCCAAGATGAAGGTAAAGAAAGAG
CACGCCTCGGTGCCGTTCGATGACCAGTGGTCCATTCTCGAGAAGGAGGCCGTGAACGTGTCCCTG
GAGAACCTCAAGACCTACCCCTTCGTCAAGGAAGGGCTTGCAAATGGGACCCTCAAGCTGATCGGC
GCCCACTACGACTTTGTCTCAGGAGAGTTCCTCACATGGAAAAAGTGA
```

SEQ ID NO: 165 Z. mays. U08403, derived protein sequence
```
MYTLPVRATTSSIVPACHPRAVLLLRLRPPGSGSSGTPRLRRPATVVGMDPTVERLKSGFQKFKTE
VYDKKPELFEPLKSGQSPRYMVFACSDSRVCPSVTLGLQPGEAFTVRNIASMVPPYDKIKYAGTGS
AIEYAVCALKVQVIVVIGHSCCGGIRALLSLKDGAPDNFTFVEDWVRIGSPAKNKVKKEHASVPFD
DQCSILEKEAVNVSLQNLKSYPFVKEGLAGGTLKLVGAHYSFVKGQFVTWEPPQDAIERLTSGFQQ
FKVNVYDKKPELFGPLKSGQAPKYMVFACSDSRVCPSVTLGLPAKAFTVRNIAAMVPGYDKTKYT
GIGSAIEYAVCALKVEVLVVIGHSCCGGIRALLSLKDGAPDNFHFVEDWVRIGSPAKNKVKKEHAS
VPFDDQCSILEKEAVNVSLQNLKSYPLVKEGLAGGTSSGWPHYDFVKGQFVTWEPPQDAIERLTSG
FQQFKVNVYDKKPELFGPLKSGQAPKYMVFACSDSRVSPSVTLGLQPGEAFTVRNIAAMVPGYDKT
KYTGIGSAIEYAVCALKVEVLVVIGHSCCGGIRALLSLQDGAPDTFHFVEDWVKIAFIAKMKVKKE
HASVPFDDQWSILEKEAVNVSLENLKTYPFVKEGLANGTLKLIGAHYDFVSGEFLTWKK
```

SEQ ID NO: 166 ZMU08401 Zea mays carbonic anhydrase mRNA, complete cds
```
ATGTACACATTGCCCGTCCGTGCCACCACATCCAGCATCGTCGCCAGCCTCGCCACCCCCGCGCCG
TCCTCCTCCTCCGGCTCCGGCCGCCCCAGGCTCAGGCTCATCCGGAACGCCCCCGTCTTCGCCGCC
CCCGCCACCGTCTGTAAACGGGACGGCGGGCAGCTGAGGAGTCAAACGAGAGAGATCGAGAGAGAA
AGAAAGGGAGGGCATCCACCAGCCGGCGGGCATAAGAGGGGAGGAGAGAGAGGCCAGAGAAGAGGA
GGAGAAGAAGAAGAAGATGAGCAGCTGCCTCTGCCTTCCGAAAAAAAGGAGGGGCCAGCGAAGGA
GAAGCCGTCCACAGATACCCCCACCTCGTCACTCCTTCAGAACCAGAAGCCCTCCAACCTCCACCT
CCTCCCTCCAAGGCTTCCTCCAAGGGCATGGACCCCACCGTCGAGCGCTTGAAGAGCGGGTTCCAG
AAGTTCAAGACCGAGGTCTATGACAAGAAGCCGGAGCTGTTCGAGCCTCTCAAGTCCGGCCAGAGC
CCCAGGTACATGGTGTTCGCCTGCTCCGACTCCGCGTGTGCCCGTCGGTGACACTGGGACTGCAG
CCCGGCGAGGCATTCACCGTCCGCAACATCGCTTCCATGGTCCCACCCTACGACAAGATCAAGTAC
GCCGGCACAGGGTCCGCCATCGAGTACGCCGTGTGCGCGCTCAAGGTGCAGGTCATCGTGGTCATT
GGCCACAGCTGCTGCGGTGGCATCAGGGCGCTCCTCTCCCTCAAGGACGGCGCGCCCGACAACTTC
ACCTTCGTGGAGGACTGGGTCAGGATCGGCAGCCCTGCCAAGAACAAGGTGAAGAAAGAGCACGCG
```

TCCGTGCCGTTCGATGACCAGTGCTCCATCCTGGAGAAGGAGGCCGTGAACGTGTCGCTCCAGAAC
CTCAAGAGCTACCCCTTCGTCAAGGAAGGGCTGGCCGGCGGGACGCTCAAGCTGGTTGGCGCCCAC
TCACACTTCGTCAAAGGGCAGTTCGTCACATGGGAGCCTCCCCAGGACGCCATCGAGCGCTTGACG
AGCGGCTTCCAGCAGTTCAAGGTCAATGTCTATGACAAGAAGCCGGAGCTTTTCGGGCCTCTCAAG
TCCGGCCAGGCCCCCAAGTACATGGTGTTCGCCTGCTCCGACTCCCGTGTGTGCCCGTCGGTGACC
CTGGGCCTGCAGCCGGGCGAGGCCTTCACCGTTCGCAACATCGCCGCCATGGTCCCAGGCTACGAC
AAGACCAAGTACACCGGCATCGGGTCCGCCATCGAGTACGCTGTGTGCGCCCTCAAGGTGGAGGTC
CTCGTGGTCATTGGCCATAGCTGCTGCGGTGGCATCAGGGCGCTCCTCTCACTCCAGGACGGCGCA
GCCTACACCTTCCACTTCGTCGAGGACTGGGTTAAGATCGGCTTCATTGCCAAGATGAAGGTAAAG
AAAGAGCACGCCTCGGTGCCGTTCGATGACCAGTGCTCCATTCTCGAGAAGGAGGCCGTGAACGTG
TCCCTGGAGAACCTCAAGACCTACCCCTTCGTCAAGGAAGGGCTTGCAAATGGGACCCTCAAGCTG
ATCGGCGCCCACTACGACTTTGTCTCAGGAGAGTTCCTCACATGGAAAAAGTGAAAAACTAGGGCT
AAGGCAATTCTACCGGCCCGCCGACTCTGCATCATCATAATATATATACTATAACTATACTACTAG
CTACCTACCGATAGTCACCCGAGCAATGTGAATGCGTCAGTACTATCTGTTTTCTGCATCTACAT
ATATATACCGGATCAACAATCGCCCAATGTGAATGTAATAAGCAATATCATTTTCTACCACTTTTC
ATTCCTAACGCTGAGGCTTTTTATGTACTATATCTTATATGATGAATAATAATATGACCGCCTTGT
GATCTA

SEQ ID NO: 167 Z. mays. U08401, derived protein sequence
MYTLPVRATTSSIVASLATPAPSSSSGSGRPRLRLIRNAPVFAAPATVCKRDGGQLRSQTREIERE
RKGGHPPAGGHKRGGERGQRRGGEEEEDEQLPLPSEKKGGASEGEAVHRYPHLVTPSEPEALQPPP
PPSKASSKGMDPTVERLKSGFQKFKTEVYDKKPELFEPLKSGQSPRYMVFACSDSRVCPSVTLGLQ
PGEAFTVRNIASMVPPYDKIKYAGTGSAIEYAVCALKVQVIVVIGHSCCGGIRALLSLKDGAPDNF
TFVEDWVRIGSPAKNKVKKEHASVPFDDQCSILEKEAVNVSLQNLKSYPFVKEGLAGGTLKLVGAH
SHFVKGQFVIWEPPQDAIERLTSGFQQFKVNVYDKKPELFGPLKSGQAPKYMVFACSDSRVCPSVT
LGLQPGEAFTVRNIAAMVPGYDKTKYTGIGSAIEYAVCALKVEVLVVIGHSCCGGIRALLSLQDGA
AYTFHFVEDWVKIGFIAKMKVKKEHASVPFDDQCSILEKEAVNVSLENLKTYPFVKEGLANGTLKL
IGAHYDFVSGEFLTWKK

SEQ ID NO: 168 UPU19741 Urochloa panicoides carbonic anhydrase 1 mRNA, complete cds
GGGCAGCCCGCACTTTAATGTCGGCATTGGCCATCCGTGCAGCCCCGTCCAGCATCATCGCCAGCG
TCCGCACCCCCGCGCTCTCCGCCCGCCGCCGCCCCAGGCTCGTCGGCAACGCCGCCGCCGCCAACG
CCGTCGTGTAAACCGGCCGGCGCACGGGGAGCTCGAAAGTCAAACGAGAGACTAGAGAGAGGGGGG
CGAGAAGTACTAGTAGGTCGAAGCCGGCTGTGATAAAAAGAGGAGAAGATGAGCGGGTGCCTCTGC
CTCCCCGGCTACAAAAAGAAGACCATGGACCCCGTCGAGCGCTTGCAGAGCGGGTTCAAGCAGTTC
AAGAGCGAGGTCTACGACAAGAAGCCGGAGCTGTTCGAGCCACTCAAGGAAGGCCAGGCCCCCACG
TACATGGTGTTCGCCTGCTCCGACTCCCGTTGCTGCCCGTCGGTGACCCTCGGCCTGAAGCCCGGC
GAGGCCTTCACCGTCCGCAACATCGCCGCCATGGTCCCACCCTACGACAAGAATCGGTACACCGGC
ATCGGGTCCGCCATCGAGTACGCCGTCTGCGCCCTCAAGGTCAAGGTCCTCACCGTCATCGGCCAC
AGCCGCTGCGGTGGCATCAAGGCGCTCCTCTCAATGCAGGACGGCGCAGCCGACAACTTCCACTTC
GTCGAGGACTGGGTCAGGATCGGCTTCCTCGCCAAGAAGAAGGTTCTCACCGACCACCCCATGGCT
CCCTTCGACGACCAGTGCTCCATCTTGGAGAAGGAGGCCGTCAACGTCTCCCTGTACAACCTCCTG
ACCTACCCCTGGGTGAAGGAAGGTGTGTCCAACGGCTCCCTCAAGCTGGTCGGCGGCCACTACGAC
TTCGTCAAGGGCGCGTTCGTCACATGGGAGAAATAAGCCACCCGATTTACAACTCCTACACCATCA
TACATATATACATACGTACATCGTCTCCCGATATGCACCCCATCCGACGTGAATGGGTGGAGTGCT
CACTACCTATTTTCGGCCGCTACATACGGGATCGTCGTCCTTCTATGTGAATGTAATAAGCAATAG
CATCCTCTACCGCTTTAATTTCTATAAGGCCGAGCTTTTTATTTTACCATATGATGCATAATTTGA
CCGCCTTGTGGTCAAAAGACATCACCAATATATGTATAAGCCTTCTTCATAATAATATATAATCAT
CAAGTGTTTACCTTTTTATT

FIGURE 9 (continued)

SEQ ID NO: 169 U. panicoides. U19741, derived protein sequence
MSGCLCLPGYKKKTMDPVERLQSGFKQFKSEVYDKKPELFEPLKEGQAPTYMVFACSDSRCCPSVT
LGLKPGEAFTVRNIAAMVPPYDKNRYTGIGSAIEYAVCALKVKVLTVIGHSRCGGIKALLSMQDGA
ADNFHFVEDWVRIGFLAKKKVLTDH

SEQ ID NO: 170 UPU19739 Urochloa panicoides carbonic anhydrase 2 mRNA, complete cds
CCGCACTGGAATGTCGGCATTGGCCATCCGCTCAGCCCCGTCCAGCATCATCGCCAGCGTCCGCAC
CCCCGCGCACCGCCGCCCCGGGCTCGTCAGGAACGCCGCCGCCACCACCGCCGAGTTGACCATGGA
CCCCGTCGAGCGCTTGCAGAGCGGCTTCAAGCAGTTCAAGAGCGAGGTCTATGACAAGAAGCCGGA
GCTGTTCGAGCCACTCAAGGAAGGCCAGGCCCCCACGTACATGGTGTTCGCCTGCTCCGACTCTCG
TTGCTGCCCGTCGGTGACCCTCGGCCTGAAGCCCGGCGAGGCCTTCACCGTCCGCAACATCGCCGC
CATGGTCCCACCCTACGACAAGAACCGGTACACCGGCATCGGTCCGCCATCGAGTACGCCGTCTG
CGCCCTCAAGGTCAAGGTCCTCACCGTCATCGGCCACAGCCGCTGCGGTGGCATCAAGGCGCTCCT
CTCCATGCAGGATGGCGCAGCCGACAACTTCCACTTCGTCGAGGATTGGGTCAGGATCGGCTTCCT
CGCGAAGAAGAAGGTTCTGACCGACCACCCCATGGCTCCGTTCGATGACCAGTGCTCCATCTTGGA
GAAGGAGGCAGTCAACGTCTCCCTCTACAACCTCCTGACCTACCCCTGGGTGAAGGAAGGCGTGTC
CAACGGGTCCCTCAAGCTGGTCGGCGGCCACTACGACTTCGTCAAGGGGGCGTTCGTCACATGGGA
GAAATAAGCCACCCGATTTACAGCTCCTACACCACCGTACATACATACGTACATCCCGATATGTAC
CCCATCCGACGTGAACGGGTGGAGTACTTACTACTACCTATTTTCGGCCGCTACGTACCGGGTCGT
CGTTCTATGTGAATGTAATAAGCAATAGCATTCTCTACCGCTTTAATTTCTAAGGCCGAGCTTTTT
ATTTATGTACCGTATGATGCATAATTTGACCTCCTTGTGGTCAAAAGACATCAGCTATATATGTAT
AAGTCTTCTTCATAATATAATCATAAAGTGTTTACCTTTTTACT

SEQ ID NO: 171 U. panicoides. U19739, derived protein sequence
MSALAIRSAPSSIIASVRTPAHRRPGLVRNAAATTAELTMDPVERLQSGFKQFKSEVYDKKPELFE
PLKEGQAPTYMVFACSDSRCCPSVTLGLKPGEAFTVRNIAAMVPPYDKNRYTGIGSAIEYAVCALK
VKVLTVIGHSRCGGIKALLSMQDGAADNFHFVEDWVRIGFLAKKKVLTDHPMAPFDDQCSILEKEA
VNVSLYNLLTYPWVKEGVSNGSLKLVGGHYDFVKGAFVTWEK

SEQ ID NO: 172 AY463239, Chlamydomonas reinhardtii chloroplast beta carbonic anhydrase (Cah6) mRNA, complete cds; nuclear gene for chloroplast product
ATGGGATGCGGTGCCAGCGTGCCTCAGAATGGTGGAGGAGCTCCCGTTACGCGGGTTATGCCCGCG
CCAGCACAACCAGTGTCTGAGGCGCAATCGGCAATCAGCTTCCAACCATCGCGCAGCAACCGCAGC
AGCCTTGAAAAGATCAATTCGCTCACGGATAGGGCATCGCCTGAGCAGGTGCTGCAGAACCTGCTG
GACGGCAACATGCGCTTCCTGGATGGCGCCGTCGCGCATCCCCACCAGGACTTCAGCCGCGTGCAG
GCCATTAAGGCCAAGCAAAAGCCCCTCGCGGCCATCCTGGGCTGCGCCGACTCTCGCGTGCCTGCG
GAAATTGTGTTCGACCAAGGCTTTGGCGACGTGTTCGTGTGCCGTGTCGCCGGCAACATTGCTACG
CCAGAGGAGATCGCCAGTCTGGAGTATGCCGTGCTTGACCTCGGAGTTAAGGTGGTGATGGTCCTC
GGACACACACGCTGCGGAGCCGTGAAGGCTGCACTTTCAGGCAAGGCGTTCCCCGGCTTCATCGAC
ACGCTGGTGGACCACCTGGACGTCGCCATCAGCCGCGTCAACAGCATGAGCGCCAAGGCGCACCAG
GCCATCAAGGACGGCGACGTGGACATGCTGGACCGCGTGGTGAAGGAGAACGTCAAGTACCAGGTG
CAGCGGTGCCAGCGCTCCGTCATCATCCAGGAGGGGTTGCAGAAGGGGAACCTGCTGCTGGCGGGC
GCCGTGTACGACCTGGACACGGGCAAGGTGCACGTCAGCGTCACCAAGGGCGGCAGCAGCGCCGAG
TAG FIGURE 9 (continued)

SEQ ID NO: 173 C. reinhardtii. AAR82948
MGCGASVPQNGGGAPVTRVMPAPAQPVSEAQSAISFQPSRSNRSSLEKINSLTDRASPEQVLQNLL
DGNMRFLDGAVAHPHQDFSRVQAIKAKQKPLAAILGCADSRVPAEIVFDQGFGDVFVCRVAGNIAT
PEEIASLEYAVLDLGVKVVMVLGHTRCGAVKAALSGKAFPGFIDTLVDHLDVAISRVNSMSAKAHQ
AIKDGDVDMLDRVVKENVKYQVQRCQRSVIIQEGLQKGNLLLAGAVYDLDTGKVHVSVTKGGSSAE

SEQ ID NO: 174 Chlamydomonas reinhardtii mitochondrial NADH:ubiquinone oxidoreductase 32 kDa subunit mRNA, complete cds; nuclear gene for mitochondrial product, AY538681
ATGTCGCTATTCAAGTCTAGCCTGCCTGCGGGCTTCCTATTCCCCTATCGGCACCCCAAGGCCAAG
GGGCTTGTTGAGGGCACGCTTTATGGACTGGGCTCCCTGTTTCGCGGCGTGGGCGCCGCGCTGGAT
GAGCTGGGCTCTATGGTTCAGGGCCCTCAGGGTAGTGTCAAGGACCACGTCCAGCCTAACCTGGCG
TTTGCACCAGTGCACCGCAAGCCGGATGTGCCCGTTAACGCGGGCCAGGTGGTGCCCGCTCCACCC
GCTGCTGCTCGCACGCTGAAAATCAAGGAGGTGGTTGTGCCCAACAAGCACAGCACCGCGTTCGTG
GCTGCCAACGCCAATGTGCTCGGGAACGTTAAGCTGGGGGCGGGCTCATCGGTGTGGTATGGCGCC
GTGCTGCGCGGTGACGTGAACGGCATTGAGGTGGGCGCCAACAGCAACATCCAGGACAACGCCATC
GTGCACGTGTCCAAGTACAGCATGGACGGCACGGCACGGCCCACCGTCATCGGCAACAATGTGACC
ATTGGCCACGCCGCCACGGTGCACGCCTGCACCATTGAGGACAACTGCCTGGTGGGCATGGGCGCC
ACCGTGCTCGACGGAGCGACGGTCAAGAGCGGCTCCATCGTGGCTGCCGGCGCCGTGGTGCCGCCC
AACACCACCATCCCCTCGGGCCAGGTGTGGGCCGGCTCGCCCGCCAAGTTCCTGCGCCACCTGGAG
CCGGAGGAGGCCAGCTTCATCGGCAAGTCTGCCAGCTGCTACGCCGAGCTGTCCGCCATCCACAAG
TTCGAGCAGAGCAAGACGTTTGAGGAGCAGTACACGGAGAGCTGCATCATCAAGGACCGCGCCGCT
CTGGCCGACCCGTCAAACTCAGTGCACCAGATGTGGGAGTACGACAGCCAGACGGCGTTGGTGGCC
CGCGCCAAGAGGTAG

SEQ ID NO: 175 C. reinhardtii. AAS48197
MSLFKSSLPAGFLFPYRHPKAKGLVEGTLYGLGSLFRGVGAALDELGSMVQGPQGSVKDHVQPNLA
FAPVHRKPDVPVNAGQVVPAPPAAARTLKIKEVVVPNKHSTAFVAANANVLGNVKLGAGSSVWYGA
VLRGDVNGIEVGANSNIQDNAIVHVSKYSMDGTARPTVIGNNVTIGHAATVHACTIEDNCLVGMGA
TVLDGATVKSGSIVAAGAVVPPNTTIPSGQVWAGSPAKFLRHLEPEEASFIGKSASCYAELSAIHK
FEQSKTFEEQYTESCIIKDRAALADPSNSVHQMWEYDSQTALVARAKR

SEQ ID NO: 176 AK103904, Oryza sativa (japonica cultivar-group) cDNA clone:J033150M03, full insert sequence
GGGGCTCATCTCTCTCTCTCACTCTTCTCCCTCTTCTCACCACCAGACGCCATCAAACCCCTAC
CTCCCGCGGCGGCGGCGGCGGCGGCCGGCGGCGAGCTCCGGACAGACAGAGGAGGGCGCGAGC
GGAGAGGGCGAGGAGGGAAGGAGGGAGGGAGGCGACAGGCATGGGGACCCTCGGGCGCGCGATCTA
CACGGTGGGGAAGTGGATCCGCGGCACGGGCAGGCCATGGACCGCCTCGGATCCACCATCCAGGG
CGGCCTCCGCGTCGAGGAGCAGCTTTCAAGGCATCGCACGATCATGAACATATTTGAGAAAGAGCC
CAGAGTCCACAAGGATGTTTTTGTTGCTCCCAGTGCAGCTGTGATTGGCGATGTTGAGATCGGACA
TGGATCCTCAATCTGGTACGGCTCCATTTTAAGAGGTGATGTCAACAGCATTCATATTGGATCTGG
ATCAAATATACAAGACAATTCCCTTGTACATGTTGCAAAAGCTAACATCAGCGGGAAGGTTCTCCC
AACCATAATTGGAAACAATGTTACAATAGGTCATAGTGCTGTTCTGCACGCATGCACCGTCGAGGA
TGAAGCTTTTGTTGGTATGGGTGCCACTCTGCTTGATGGAGTGGTCGTTGAAAAGCACAGCATGGT
TGGTGCAGGATCGCTTGTTAAGCAGAACACAAGGATTCCTTCTGGAGAGGTCTGGGTCGGTAATCC
TGCCAAGTTCCTAAGAAAGCTTACTGAAGAGGAGATAGCGTTCATTGCTCAGTCAGCAACGAACTA
CATCAATCTGGCCCAAGTCCATGCTGCCGAGAATTCCAAGACCTTCGACGAGATCGAGCTCGAGAA
GATGCTGAGGAAAAAGTATGCCCACAAAGACGAGGAGTATGATTCGATGCTCGGCGTGGTCCGTGA FIGURE 9 (continued)

```
GATCCCGCCGGAGCTCATCCTCCCGGACAACATCCTCCCAAACAAGGCTCAGAAGGCTGTTGCTCA
CTGAATGTTTTGTCAAGCTCCCGCTTGGGAAAAGCTTGGTTTTTTGTTACGTGTTTTGACCTGGA
ACAACATTTGACACATGTCTTTTGATCTCATTGTCTGTTTTTCAAGCCCAATAAGAATTTGGGTCG
AGCATTGTTTTAGGATCGACCATATACAGTACCTCTCTTTGCATTACAATGAAGAGCAGTTAATTT
GGGTCACTTTTTACATCTTTACTGAAGTAGAAACGCGTCCTCTGTCTGTG
```

SEQ ID NO: 177 O. sativa. AK103904, derived protein sequence
```
MGTLGRAIYTVGKWIRGTGQAMDRLGSTIQGGLRVDEQLSRHRTIMNIFEKEPRVHKDVFVAPSAA
VIGDIEIGHGSSIWYGSILRGDVNSIHIGVGTNIQDNSLVHVSKANISGKVLPTIIGNNVTIGHSA
VLHACIVEDEAFVGMGATLLDGVVVEKHSMVGAGSLVKQNTRIPSGEVWVGNPAKFLRKLTEEEIA
FIAQSATNYINLAQVHAAENSKTFDEIELEKMLRKKYAHKDEEYDSMLGVVREIPPELILPDNILP
NKAQKAVAH
```

SEQ ID NO: 178 Oryza sativa (japonica cultivar-group) Os08g0470200 (Os08g0470200) mRNA, complete cds
```
ATGGGTTCGACTCGCCTCCTCGTACTGCTCGCCGCCGCTTCCCTCCTCCTCGCCACCGCCGTCCCG
GCAGCCAGAGCACAGGAAGAAACTGATCACGAGGAGGAGTTCACGTACATCAGCGGGGACGAGAAG
GGGCCGGAGCACTGGGGCAAGCTGAAGCCGGAGTGGGCGCAGTGCGGCGCCGGCGAGATGCAGTCG
CCGATCGACCTCTCCCACGAGCGGGTCAAGCTGGTGCGCGACCTCGGCTACCTCGACGACTCCTAC
CGCGCCGCCGAGGCCTCCATCGTCAACCGCGGCCACGACATCATGGTCAGGTTCGACGGCGACGCC
GGCAGCGTCGTCATCAACGGCACCGCCTACTACCTCCGCCAGCTCCACTGGCACTCCCCCACCGAG
CACAGCGTCGACGGCCGCAGGTACGACATGGAGCTGCACATGGTCCACGAGAGCGCCGAGAAGAAG
GCCGCCGTGATCGGCCTCCTCTACGAGGTCGGCCGCCCCGACCGCTTCCTCCAAAAGATGGAGCCA
TATCTCAAGATGATTGCGGACAAGGAGGACAGGGCCGCCTTGCACGCAGGGGTGGTCTGGACGAT
TGTCAAGAGGGTTCGCACCGTGTCGAGGTATCAGCTCGACCTTCTCAGGGAAGCTGTGCATGA
```

SEQ ID NO: 179 O. sativa. Os08g0470200, derived protein sequence
```
MGSTRLLVLLAAASLLLATAVPAARAQEETDHEKEFTYISGDEKGPEHWGKLKPEWAQCGAGEMQS
PIDLSHERVKLVRDLGYLDDSYRAAEASIVNRGHDIMVRFDGDAGSVVINGTAYYLRQLHWHSPTE
HSVDGRRYDMELHMVHESAEKKAAVIGLLYEVGRPDRFLQKMEPYLKMIADKEDREEKVGMIDPRG
ARGRASVYYRYMGSLTTPPCTQGVVWTIVKRVRTVSRYQLDLLREAVHDEMENNARPLQAVNNRDI
SIFRPYPHKRY
```

SEQ ID NO: 180 Dioscorea cayenensis mRNA for storage protein, X76187
```
ATGAGTTCATCCACCCTTCTCCATCTCCTCCTCCTCCTCCCTCCTCTTCTCTTGCCTTCCAAAT
GCAAAACCTCAGCAAGCTGAGGATGAGTTTAGCTACATTGAAGGAAGTCCTAATGGTCCTGAAAAC
TGGGGAAATCTTAAAAAGGAGTGGGAGACTTGTGGCAAAGGCATGGAGCAGTCACCCATTCAATTG
CGTGATAACAGAGTGATATTCGATCAAACTTTGGGGGAGCTGAGAAGAAATTATAGAGCCGCTGAA
GCAACATTAAGGAACAGTGGACATGATGTATTGGTGGAATTTGAGGGTAATGCTGGTTCACTATCC
ATCAATCGAGTTGCATACCAACTCAAGCGAATTCATTTTCACTCCCCTTCAGAGCATGAAATGAAT
GGCGAAAGGTTTGACCTTGAGGCACAGCTGGTCCATGAGAGCCAAGACCAAAAGAGAGCAGTGGTT
TCTATTCTTTTCAGATTTGGACGTGCTGATACATTCCTCTCAGATCTTGAAGACTTTATCAAGCAG
TTTAGCAGTAGCCAGAAGAATGAAATAAATGCAGGAGTTGTGGATCCAAATCAATTACAGTTTGAT
GACTGTGCATATTTTAGATACATGGCTCATTCACAGCTCCACCTTGCACTGAAGGTATTTCATGG
ACCGTCATGAGGAAGGTTGCAACTGTTTCACCAAGGCAAGTACTTCTGTTGAAGCAGGCAGTGAAT
GAAAATGCTATAAACAATGCGAGACCACTTCAACCAACCAATTACCGCTCCGTTTTTTACTTTGAA
CAGCTGAAATCGAAGCTTGGTGTCATATAA
```

SEQ ID NO: 181 D. cayenensis. X76187, derived protein sequence
MSSSTLLHLLLLSSLLFSCLPNAKPQQAEDEFSYIEGSPNGPENWGNLKKEWETCGKGMEQSPIQL
RDNRVIFDQTLGELRRNYRAAEATLRNSGHDVLVEFEGNAGSLSINRVAYQLKRIHFHSPSEHEMN
GERFDLEAQLVHESQDQKRAVVSILFRFGRADTFLSDLEDFIKQFSSSQKNEINAGVVDPNQLQFD
DCAYFRYMGSFTAPPCTEGISWTVMRKVATVSPRQVLLLKQAVNENAINNARPLQPTNYRSVFYFE
QLKSKLGVI

SEQ ID NO: 182 Dioscorea batatas DB3S mRNA for tuber storage protein, complete cds, AB178473
ATGAGTTCATCCACCCTTCTCCATCTCCTCCTCCTCTCCTCCCTCCTCTTCTCTTGCCTTGCAAAT
GTAGAGGATGAGTTTAGCTACATTGAAGGAAATCCTAATGGTCCTGAAAACTGGGGAAATCTTAAA
CCGGAGTGGGAGACTTGTGGCAAAGGCATGGAGCAGTCACCCATTCAGTTGCGTGATAACAGAGTG
ATATTCGATCAAACTTTGGGGAGGTTGAGAAGAAATTACAGAGCCGTTGATGCAAGATTAAGGAAC
AGTGGACATGATGTATTGGTGGAATTTAAGGGTAATGCTGGTTCACTATCAATCAATCGAGTTGCA
TACCAACTCAAGCGAATTCATTTTCACTCCCCTTCAGAGCATGAAATGAATGGCGAAAGGTTTGAC
CTTGAGGCACAGCTGGTTCATGAGAGCCAAGATCAAAGAGAGCAGTGGTTTCTATTCTTTTCATA
TTTTGGACGTGCTGACCCATTCCTCTCAGATCTTGAAGACTTTATCAAGCAGTTTAGCAGTAGCCAG
AAGAATGAAATAAATGCAGGAGTTGTGGATCCAAATCAATTACAGATTGATGACTCTGCATATTAT
AGATACATGGGCTCATTCACAGCTCCACCTTGCACTGAAGGTATTTCATGGACCGTCATGAGGAAG
GTTGCAACTGTTTCACCAAGACAAGTACTGCTGTTGAAGCAGGCAGTGAATGAAAATGCTATAAAC
AATGCAAGACCACTTCAACCAACCAATTTCCGCTCCGTTTTTTACTTTGAACAGCTGAAATCGAAG
GTTTGTGCCATATAA

SEQ ID NO: 183 D. batatas, AB178473, derived protein sequence
MSSSTLLHLLLLSSLLFSCLANVEDEFSYIEGNPNGPENWGNLKPEWETCGKGMEQSPIQLRDNRV
IFDQTLGRLRRNYRAVDARLRNSGHDVLVEFKGNAGSLSINRVAYQLKRIHFHSPSEHEMNGERFD
LEAQLVHESQDQKRAVVSILFIFGRADPFLSDLEDFIKQFSSSQKNEINAGVVDPNQLQIDDSAYY
RYMGSFTAPPCTEGISWTVMRKVATVSPRQVLLLKQAVNENAINNARPLQPTNFRSVFYFEQLKSK
VCAI

SEQ ID NO: 184 AF243526, Dioscorea alata dioscorin B (dioB-1) mRNA, complete cds
ATGAGTTCATCCACCCTTTTCCATCTCTTCCTCCTCTCCTCCCTCCTCTTCTCTTGCTTTTCAAAT
GCAAGGCTTGATGGCGATGATGACTTTAGCTACATTGAAGGAAGTCCTAATGGTCCTGAAACTGG
GGAAATCTTAGACCGGAGTGGAAGACTTGTGGCTATGGCATGGAGCAGTCACCCATTAATTTGTGT
GATGATAGAGTGATACGGACTCCAACTTTGGGGAAGCTGAGAACAAGTTATCAGGCTGCTCGTGCA
ACAGTGAAGAACAATGGACATGATATAATGGTGTACTTTAAAAGTGATGCTGGTACACAATTCATC
AATCAAGTAGAGTACCAACTCAAACGAATTCATTTTCACTCCCCATCAGAACATGCACTCAGTGGT
GAAAGGTATGACCTTGAGGTTCAGATGGTCCATGAGAGCCAAGATCAAAGGAGAGCAGTAATTGCT
ATTATGTTCAGATTTGGACGTTCTGACCCATTCCTCCCAGACCTTGAAGACTTTATCAGCCAGATA
AGCAGACGTGAGACCAATGAAGTAGATGCAGGAGTTGTGGATCCAAGGCAATTATTACAGTTTGAT
GACCCTGCATATTATAGATACATGGGCTCATACACAGCTCCACCTTGCACTGAAGATATTACATGG
ACCGTTATTAAGAAGCTTGGAACTGTTTCACCAAAGCAAGTACTGATGTTGAAGCAAGCAGTGAAT
GAAAATTCTATGAACAATGCAAGGCCACTTCAACCACTGAAATTTCGCACCGTTTTTTTCTATCCG
CGTCAGAAATCTGATCATGTTGCCATATAA

FIGURE 9 (continued)

SEQ ID NO: 185 D. alata. AF243526, derived protein sequence
MSSSTLFHLFLLSSLLFSCFSNARLDGDDDFSYIEGSPNGPENWGNLRPEWKTCGYGMEQSPINLC
DDRVIRTPTLGKLRTSYQAARATVKNNGHDIMVYFKSDAGTQFINQVEYQLKRIHFHSPSEHALSG
ERYDLEVQMVHESQDQRRAVIAIMFRFGRSDPFLPDLEDFISQISRRETNEVDAGVVDPRQLLQFD
DPAYYRYMGSYTAPPCTEDITWTVIKKLGTVSPKQVLMLKQAVNENSMNNARPLQPLKFRTVFFYP
RQKSDHVAI

SEQ ID NO: 186 Oryza sativa (japonica cultivar-group) Os08g0423500 (Os08g0423500) mRNA, complete cds
ATGAGTACTTCAGCTCGCCGCCTCCTCCTCCTCGCCGGCGCCGCTGCCGCCATCGCACTCCTGCTC
TCGGCCACTGCCCCGGTGGCCGGAGCCGAGGACGACGGCTACAGCTACATCCCTGGCTCACCCAGG
GGGCCGCAGAACTGGGGCAGCCTGAAGCCGGAATGGGCCACCTGCAGCAGCGGCAAGATGCAGTCG
CCGATCAACCTCGGCCTCCTCGACCTCACCTTGGCTCCCGGCCTCGGCAACCTCAACTACACCTAC
CAGAACGCCAACGCCTCCGTCGTCAACCGTGGCCACGACATCATGGTCAGGTTTGACGGCGACGCC
GGTAGCCTAAAGATAAATGGCACGGCGTACCAGCTCCGGCAGATGCACTGGCACACGCCGTCGGAG
CACACCATCGATGGCCGGAGGTACGACATGGAGCTGCACATGGTGCACCTCAACGCCCAGAACCAG
GCCGCCGTCATTGGCATCCTCTACACCATCGGCACCCGGGACGAGTTTCTGCAAAAGCTAGAGCCT
TATATAATTGAGATATCAAAGCAAGAAGGCAAAGAGAGAGTGATCATTGGTGGGGCGGATCCAAAT
GTAGCCAAGGGACAGGATACCGTGTACTACCGCTACATGGGCTCCTTTACCACACCACCTTGCACT
GAGGGAGTCATCTGGACCGTTGTCAGGAAGGTGCGCACCGTGTCACTGTCCCAAATCACACTTCTC
AAGGCAGCTGTGCTCACGGGTAACGAGAACAACGCGAGACCCCTTCAGGGCGTGAACAACAGGGAG
ATTGACCTGTTCCTTCCTCTCCCTCTCATCAACAACTGA

SEQ ID NO: 187 O. sativa. Os08g0423500, derived protein sequence
MSTSARRLLLLAGAAAAIALLLSATAPVAGAEDDGYSYIPGSPRGPQNWGSLKPEWATCSSGKMQS
PINLGLLDLTLAPGLGNLNYTYQNANASVVNRGHDIMVRFDGDAGSLKINGTAYQLRQMHWHTPSE
HTIDGRRYDMELHMVHLNAQNQAAVIGILYTIGTRDEFLQKLEPYIIEISKQEGKERVIIGGADPN
VAKGQDTVYYRYMGSFTTPPCTEGVIWTVVRKVRTVSLSQITLLKAAVLTGNENNARPLQGVNNRE
IDLFLPLPLINN

SEQ ID NO: 188 Oryza sativa (japonica cultivar-group) Os12g0153500 (Os12g0153500) mRNA, complete cds
ATGGTGTCTCTCCGCGCGGCCATCGTCCTCGTCGTCGCCGCCCTCGTCGGTCGCCGTCGCCTTCTCT
CATGCGGAAGGGAACGAGGGGCCGGACTTCACCTACATCGAAGGCGCCATGGACGGGCCGTCGAAC
TGGGGGAAGCTGAGCCCGGAGTACAGGATGTGCGGCGAGGGGAGGTCGCAGTCGCCGATCGACATC
AACACCAAGACCGTCGTCCCGCGCTCGGACCTCGACACGCTGGACCGCAACTACAACGCCGTGAAC
GCCACCATCGTCAACAACGGCAAGGACATCACCATGAAGTTCCACGGCGAGGTCGGCCAGGTGATC
ATCGCCGGGAAGCCGTACAGGTTCCAGGCGATCCACTGGCACGCGCCGTCGGAGCACACCATCAAC
GGCAGGCGCTTCCCGCTCGAGCTCCACCTCGTCCACAAGTCCGACGCCGACGGCGGCCTCGCCGTC
ATCTCCGTCCTCTACAAGCTCGGCGCCCCGGACTCCTTCTACCTCCAGTTCAAGGACCACCTCGCC
GAGCTCGGCGCCGACGAGTGCGACTTCAGCAAGGAGGAGGCCCACGTCGCCGCCGGGCTGGTGCAG
ATGAGGTCGCTGCAGAAGCGCACGGGGAGCTACTTCCGGTACGGCGGCTCGCTGACGACGCCGCCG
TGCGGCGAGAACGTGGTGTGGAGCGTGCTCGGGAAGGTGAGGGAGATCAGCCAGGAGCAGCTGCAC
CTGCTCATGTCGCCATTGCCGACCAAGGACGCCAGGCCGGCGCAGCCGCTCAATGGCAGGGCCGTC
TTCTACTACAACCCGCCGGGCAGCGCCGTCTCCTTCCAGGAATTCGCCAAGTGA FIGURE 9 (continued)

SEQ ID NO: 189 O. sativa. Os12g0153500, derived protein sequence
MVSLRAAIVLVVAASSVAVAFSHAEGNEGPDFTYIEGAMDGPSNWGKLSPEYRMCGEGRSQSPIDI
NTKTVVPRSDLDTLDRNYNAVNATIVNNGKDITMKFHGEVGQVIIAGKPYRFQAIHWHAPSEHTIN
GRRFPLELHLVHKSDADGGLAVISVLYKLGAPDSFYLQFKDHLAELGADECDFSKEEAHVAAGLVQ
MRSLQKRTGSYFRYGGSLTTPPCGENVVWSVLGKVREISQEQLHLLMSPLPTKDARPAQPLNGRAV
FYYNPPGSAVSFQEFAK SEQ ID NO: 190 Arabidopsis thaliana carbonate dehydratase/ zinc
ion binding (AT4G20990) mRNA, complete cds
ATGGATACCAACGCAAAAACAATTTTCTTCATGGCTATGTGTTTCATCTATCTATCTTTCCCTAAT
ATTTCACACGCTCATTCTGAAGTCGACGACGAAACTCCATTTACTTACGAACAAAAAACGGAAAAG
GGACCAGAGGGATGGGGCAAAATAAATCCGCACTGGAAAGTTTGTAACACCGGAAGATATCAATCC
CCGATCGATCTTACTAACGAAAGAGTCAGTCTTATTCATGATCAAGCATGGACAAGACAATATAAA
CCAGCTCCGGCTGTAATTACAAACAGAGGCCATGACATTATGGTATCATGGAAAGGAGATGCTGGG
AAGATGACAATACGGAAAACGGATTTTAATTTGGTGCAATGCCATTGGCATTCACCTTCTGAGCAT
ACCGTTAACGGAACTAGGTACGACCTAGAGCTTCACATGGTTCACACGAGTGCACGAGGCAGAACT
GCGGTTATCGGAGTTCTTTACAAATTAGGCGAACCTAATGAATTCCTCACCAAGCTACTAAATGGA
ATAAAAGCAGTGGGAAATAAAGAGATAAATCTAGGGATGATTGATCCACGAGAGATTAGGTTTCAA
ACAAGAAAATTCTATAGATACATTGGCTCTCTCACTGTTCCTCCTTGCACTGAAGGCGTCATTTGG
ACTGTCGTCAAAAGGGTGAACACAATATCAATGGAGCAAATTACAGCTCTTAGGCAAGCCGTTGAC
GATGGATTTGAGACAAATTCAAGACCGGTTCAAGACTCAAAGGGAAGATCAGTTTGGTTCTATGAT
CCAAATGTTTGA SEQ ID NO: 191 A. thaliana. At4g20990
MDTNAKTIFFMAMCFIYLSFPNISHAHSEVDDETPFTYEQKTEKGPEGWGKINPHWKVCNTGRYQS
PIDLTNERVSLIHDQAWTRQYKPAPAVITNRGHDIMVSWKGDAGKMTIRKTDFNLVQCHWHSPSEH
TVNGTRYDLELHMVHTSARGRTAVIGVLYKLGEPNEFLTKLLNGIKAVGNKEINLGMIDPREIRFQ
TRKFYRYIGSLTVPPCTEGVIWTVVKRVNTISMEQITALRQAVDDGFETNSRPVQDSKGRSVWFYD
PNV SEQ ID NO: 192 Arabidopsis thaliana carbonate dehydratase/ zinc
ion binding (AT1G08065) mRNA, complete cds
ATGAAACACATTTTTTTTAACTCGTGTATAACCAAAAAAAATATAGAGGACGAAACGCAGTTTAAC
TACGAGAAGAAAGGAGAGAAGGGGCCAGAGAACTGGGGAAGACTAAAGCCAGAGTGGGCAATGTGT
GGAAAAGGCAACATGCAGTCTCCGATTGATCTTACGGACAAAAGAGTCTTGATTGATCATAATCTT
GGATACCTTCGTAGCCAGTATTTACCTTCAAATGCCACCATTAAGAACAGAGGCCATGATATCATG
ATGAAATTTGAAGGAGGAAATGCAGGTTTAGGTATCACTATTAATGGTACTGAATATAAACTTCAA
CAGATTCATTGGCACTCTCCTTCCGAACACACACTCAATGGCAAAAGGTTTGTTCTTGAGGAACAC
ATGGTTCATCAGAGCAAAGATGGACGCAACGCTGTTGTCGCTTTCTTTTACAAATTGGGAAAACCT
GACTATTTTCTCCTCACGTTGGAAAGATACTTGAAGAGGATAACTGATACACACGAATCCCAGGAA
TTTGTCGAGATGGTTCATCCTAGAACATTCGGTTTTGAATCAAAACACTATTATAGATTATCGGA
TCACTTACAACTCCACCGTGTTCTGAAAATGTGATTTGGACGATTTCCAAAGAGATGAGGACTGTG
ACATTAAAACAATTGATCATGCTTCGAGTGACTGTACACGATCAATCTAACTCAAATGCTAGACCG
CTTCAGCGTAAAAATGAGCGTCCGGTGGCACTTTACATACCAACATGGCATAGTAAACTATATTAA SEQ ID NO: 193 A. thaliana. At1g08065
MKHIFFNSCITKKNIEDETQFNYEKKGEKGPENWGRLKPEWAMCGKGNMQSPIDLTDKRVLIDHNL
GYLRSQYLPSNATIKNRGHDIMMKFEGGNAGLGITINGTEYKLQQIHWHSPSEHTLNGKRFVLEEH
MVHQSKDGRNAVVAFFYKLGKPDYFLLTLERYLKRITDTHESQEFVEMVHPRTFGFESKHYYRFIG
SLTTPPCSENVIWTISKEMRTVTLKQLIMLRVTVHDQSNSNARPLQRKNERPVALYIPTWHSKLY

SEQ ID NO: 194 Adonis aestivalis BPS
MGTLGKAIYTVGFWIRETGQAIDRLGSRLQGNYYFHEQLSRHRTLMNIFDKAPVVDKDAFIAPSAS
VIGDVQVGRSSSIWYGCVLRGDVNSISVGSGTNIQDNSLVHVAKSNLSGKVLPTIIGNNVTVGHSA
VLHGCTVQDSAFVGMGATLLDGVVVENHAMVAAGALVRQNTRIPKGEVWGGNPAKFLRKLTEEEIA
FISQSATNYTNLAQVHAAENAKTFEEIEFEKLLRKKFARKDEEYDSMLGVVRETPQELILPDNILA
DKQSPKAVSSS

SEQ ID NO: 195 Glycine max BPS
MGTLGRAIYSVGNWIRGTGQAIDRLGSLLQGGYYVQEQLSRHRTLMDIFDKAPVVDEDVFVAPSAS
VIGDVQLGRGSSIWYGVVLRGDVNSIRVGNGTNIQDNSLVHVAKSNLSGKVLPTIIGDNVTVGHSA
VIHGCTVEDEAFVGMGAILLDGVVVEKNAMVAAGALVRQNTRIPSGEVWAGNPAKFLRKLTDEEIA
FISQSATNYTNLAQVHAAENSKSFDEIEFEKVLRKKFARKDEEYDSMLGVVREIPPELILPDNVLP
DKAEKALKKSGI

SEQ ID NO: 196 Brassica napus BPS
MGTLGRVIYTVGKWIRGSGQALDRVGSILQGSHRLEEHLSRHRTLMNVFDKSPLVDKDVFVAPSAS
VIGDVQIGKGSSIWYGCVLRGDVNNISVGSGTNIQDNSLVHVAKTNLGGKVLPTTIGDNVTVGHSA
VIHGCTVEDEAFVGMGATLLDGVVVEKHAMVAAGSLVRENTRIPSGEVWGGNPAKFMRKLTDEEIA
YISKSAENYINLAHIHAAENSKSFEEIEVERALRKKYARKDEDYDSMLGIVRETPAELILPDNVLP
EKTTTRVPTTHY

SEQ ID NO: 197 Zea mays BPS
MGTLGRAIFTVGKWIRGTGQAMDRLGSTIQGGLRVEEQVSRHRTIMNIFEKEPRIHRDVFVAPSAA
VIGDVEIGHGSSIWYGSILRGDVNSIHIGSGTNIQDNSLVHVSKANISGKVLPTIIGSNVTVGHSA
VLHACTIEDEAFVGMGATLLDGVVVEKHSMVGAGSLVKQNTRIPSGEVWVGNPAKFLRKLTEEEIA
FIAQSATNYINLAQVHAAENAKSFDEIELEKMLRKKYAHKDEEYDSMLGVVREIPPQLILPDNILP
HNAQKAVAR

SEQ ID NO: 198 Triticum aestivum BPS
MGTLGRAIYTVGKWIRGTGQAMDRLGSTIQGGLRTEEQVSRHRTVMSIFDKEPRINKDVFVAPSAS
VIGDVEIGHGSSIWYGSVLRGDVNSIRIGSGSNIQDNSLVHVAKTNISGKVLPTIIGSNVTVGHSA
VLHACTIEDEAFVGMGATLLDGVVVEKHSMVGAGSLVKQNTRIPSGEVWVGNPAKFLRKLTEEEIT
FIAQSAANYINLAHVHATENSKSFDEIELEKKLRKKFAHKDEEYDSMLGVVREIPPQLILPDNILP
DKAPKAAVAH

SEQ ID NO: 199 Glycine max BPS1
MGTLGRVFYAVGFWIRETGQAIDRLGSRLQGNYLFQEQLSRHRPLMNLFDKAPSVHRDAFVAPSAS
LLGDVHVGPASSIWYGCVLRGDVNSITIGSGTNIQDNSLVHVAKSNLSGKVLPTIIGDNVTVGHSA
VLQGCTVEDEAFIGMGATLLDGVYVEKHAMVAAGALVRQNTRIPYGEVWGGNPARFLRKLTEDEMT
FFSQSALNYSNLAQAHSAENAKGLDETEFVKVLHKKFARHGDEYHSVLGGVQETPTELKSSDNVLL
DKVPKA

SEQ ID NO: 200 Hordeum vulgare BPS
MAKASYAVGFWIRETGQALDRLGCRLQGNYFFHEQISRHRTLMNIFDKAPHVHKEAFVAPSASLIG
DVEVGKGSSIWYGCVLRGDANNVQVGSGTNIQDNSVVHVAKSNLSGKVFPTIIGDNVTVGHSAVLQ
GCTVEDEAFVGMGATLLDGVVVEKHGMVAAGALVRQNTRIPCGEVWGGNPAKFLRKLTDEEIAFIA
ESAANYSNLAKAHAVENAKPVEKIDFEKVLRKKVAHQDEEHGSMLGATRKSLQSWRRPVLLLRPNK
LCLSVFLSFFGAFTIFSLNSYILSVHLVWQFKIISIILGRAMF

FIGURE 9 (continued)

SEQ ID NO: 201 Zea mays X2
MVSSSRAVVVVVGLLVAASSLAVAASDGGGPTYGYTAGSPDGPENWGKLSPAYKLCGQGKQQSPID
IVTKQAVPTATDTLNRTYGATNATLINDGHDITMALEGKVGTVTVNGKAYSFEKLHWHSPSDHTI
NGQRFPLELHLVHRSADGALAVIGILYQLGAPDSFYYQLKRQLGEMAQDRCDFAEEEESRVEAGLI
HLRSLQKRTGSYFRYTGSLTVPPCTENVVWSVLGKVRQISQDQLQLLKAPLPGSDARPTQPLNGRT
VQFYNPPNSTISFQI

SEQ ID NO: 202 Brassica napus BPS3
MKRPSIVRVIFLIVISITTASGSPDHGEVEDETEFNYEKGGEKGPEKWGTLKPEWKMCGNGTMQSP
IDLTDKRVFIDHNLGPLRSHYLPSNATIKNRGHDIMLEFEGGNAGMGIIINGTVYQLQQLHWHSPS
EHTINGKRFVLEQHMLHQSKDGRLAVVAFLYSLGRPDSFLLSLERQLKRITDAHGSEDFVSWIDPR
AVNFKTRLYYRYLGSLTTPPCSENVTWSISREMRTVTLKQLDLLRVSVHDQSNTNARPLQRQNGRP
VKFYLPAWHI

SEQ ID NO: 203 motif 1
(S/T)E(H/N)X(L/I/V/M)XXXX(F/Y/L/H)XX(E/D)X(H/Q)(L/I/V/M/F/A)(L/I/V
/M/F/A)

SEQ ID NO: 204 motif 2
(L/N/Y/M/T/F/A/R)(A/V/S)V(V/I/L/T)(A/T/G/S)(F/V/I/L/S/T)(L/F/V/M)

SEQ ID NO: 205 motif 3
(Y/F)(Y/F/V/G/A)(R/E/G/T/H)(Y/F)XGS(L/F/Y)T(T/V/A)PPC(S/T/G/D/A)(E
/Q)(N/G/D/R)

SEQ ID NO: 206 protochlorophylid reductase promoter
CCCACGCGTCCGCCCACGCGTCCGGGACACCAGAAACATAGTACACTTGAGCTCACTCCAAACTCA
AACACTCACACCAATGGCTCTCCAAGTTCAGGCCGCACTCCTGCCCTCTGCTCTCTCTGTCCCCAA
GAAGGGTAACTTGAGCGCGGTGGTGAAGGAGCCGGGGTTCCTTAGCGTGAGCAGAAGGCCAAGAAG
CCGTCGCTGGTGGTGAGGCGGTGGCGACGCGGCGGGCCGGTGGCGAGCCCCGGCGCGGGCACGTC
GAAGGCGGACGGGAAGAAGACGCTGCGGCAGGGGTGGTGGTGATCACCGGCGCGTCGTCGGGGCT
CGGGCTCGCGGCGGCGAAGGCGCTTGGCGGAGACGGGGAAGTGGCACGTGGTGATGGCGTTCCGCG
ACTTTCCTGAAGGCGGCGACGGCGGCGAAGGCGGCGGGGATGGCGGCGGGGAGCTACACCGTCATG
CACCTGGACCTCGCCTCCCTCGACAGCGTCCGCCAGTTCGTGGACAACTTCCGGCGCTCCGGCATG
CCGCTCGACGCGCTGGTGTGCAACGCCGCACATCTACCGGCCGACGGCGCGGCAACCGACGTTCAA
CGCCGACGGGTACGAGATGAGCGTCGGGGTGAACCACCTGGGCCACTTCCTCCTCGCCCGCCTCAT
GCTCGACGACCTCAAGAAATCCGACTACCCGTCGCGGCGGCTCATCATCCTCGGCTCCATCACCGG
CAACACCAACACCTTCGCCGGCAACGTCCCTCCCAAGGCCGGGCTAGCCGACCTCCGGGGGCTCGC
CGGCGGGCTCCGCGGGCAGAACGGGTCGGCGATGATCGACGGCGCGGAGAGCTTCGACGGCGCCAA
GGCGTACAAGGACAGCAAGATCTGTAACATGCTGACGATGCAGGAGTTCCACCGGAGATTCCACGA
GGAGACCGGGATCACGTTCGCGTCGCTGTACCCGGGGTGCATCGCGACGACGGGCTTGTTCCGCGA
GCACATCCCGCTGTTCCGGCTGCTGTTCCCGCCGTTCCAGCGGTTCGTGACGAAGGGGTTCGTGTC
GGAGGCGGAGTCCGGGAAGCGGCTGGCGCAGGTGGTGGGCGACCCGAGCCTGACCAAGTCCGGCGT
GTACTGGAGCTGGAACAAGGACTCGGCGTCGTTCGAGAACCAGCTCTCGCAGGAGGCCAGCGACCC
GGAGAAGGCCAGGAAGCTCTGGGACCTCAGCGAGAAGCTCGTCGGCCTCGTCTGAGTTTATTATTT
ACCCATTCGTTTCAACTGTTAATTTCTTCGGGGTTTAGGGGGTTTCAGCTTTCAGTGAGAGAGGCC
TGTCAAGTGATGTACAATTAGTAATTTTTTTTACCCGACAAATCATGCAATAAAACCACAGGCTT
ACATTATCGATTTGTCCACCTAAATTAAGT

FIGURE 9 (continued)

SEQ ID NO: 207 primer prm8571
GGGGACAAGTTTGTACAAAAAAGCAGGCTTAAACAATGCGCTCAGCCGTTC

SEQ ID NO: 208 primer prm8572
GGGGACCACTTTGTACAAGAAAGCTGGGTCTCACTGACCCTAGCACACTC FIGURE 9 (continued)

According to Bommert *et al.* (2005) Development 132 (6): 1235

FIGURE 11

```
                         151                                                200
Arath_CLAVAT1 FL  (126)  N GNL T  E LKA-----VDLE DTYNN    KLPP MSE  -
      Brana_RLK  (133)  N VNIN T  E LTP-----VDLE DAYNN    LPP  PG  -
   Eucgr_LRR-RLK (135)  LT--------------------ELE DYDN    AQLPP VG  -
      Glyma_CLV1A (129)  H -VF Y  K ILP-----TELE DYDN    SLEE FK E-
Glyma_NARK_CLV1B (129)  H -VF H  Q ILP-----TKLE DYDN    LEV  K E-
       Lotja_HAR1 (130)  H -LF Q  N VG-----TELE ADAYDNS S LPE   KE-
      Medtr_SUNN (125)  H -LF N  N FG-----KKLE ADAYDN E LPE  SM -
      Orysa_FON1 (126)  N -NL H  VPDGGGASPYFPSLELIDAYNN LS LLPPFSASHAR-
      Pissa_SYM29 (126)  H -TF N  N LR-----TKLE DAYDNS  HLPE   S E-
    Poptr_LRR-RLK II (124)  G -AIG N S K PG-----TQLE DYNN CS  LPI  AN  -
    Poptr_LRR-RLK I  (123)  N -VIA N  K LG-----ALLE DYNN    ALPT  K N-
       Zeama_KIN5 (136)  N -NI P  PPPPAAY----FPALE IVDYNN LS  LPPLGAPHA S
         Consensus (151)  S N  LSG FPG IT       M  LEVLDVYNNNFTGPLP EIV LKK 201                                                250
Arath_CLAVAT1 FL  (170)  L SF GNF  GE IP  GDIQ LE L    AGL G SPAFL  L N
      Brana_RLK  (177)  L H S  GNFLTGE IP  GDIQ LE L    AGL GESPAFL  L N
   Eucgr_LRR-RLK (162)  L W N AGN  TFGE IP V  ME LE L   QA QI G  A  A N Q
      Glyma_CLV1A (172)  L  K DGN   G IP   FK LE LS ST SL GN IPK LL IT
Glyma_NARK_CLV1B (172)  L  K DGN   G IP   FK LE LS ST SL G  IPK LL IT
       Lotja_HAR1 (173)  L  H AGN   G TIP   FQ LE LS  A SL GR  E A  T
      Medtr_SUNN (168)  L  SF  AGNF  G IP   FQK LE IL  Y ST G IPK L  ML
      Orysa_FON1 (174)  LA H GN  TG AIPD GDLAALE  L   TL GH  V L  T R
      Pissa_SYM29 (169)  LTI C AGN  TG IP   FQK LE ILSI A SL G IPK L  TL
    Poptr_LRR-RLK II (167)  L H H GN   GK IPSE  IMILE L   DL G  PS  L L NL
    Poptr_LRR-RLK I  (166)  L HVH GN   G TIPE   IL LE L   AL G  PS  L L NL
       Zeama_KIN5 (181)  L H H GN   NG SIPDTFGD AALE L   AL GR P L L  SR L
         Consensus (201)  LKYL LGGNYFSGTIPESYSEI SLEYLGLNGNSLSGKVP SLSKLK LK 251                                                300
Arath_CLAVAT1 FL  (220)  M I GY NS TG  VPR  GG TKLEI L A  T G  PT S  KHLH
      Brana_RLK  (227)  M  VGYFNS TG  VP   GE TNLEVL  A  T G  PT T S KHLH
   Eucgr_LRR-RLK (212)  W   GYFNT  GE  PA  G  NKE RRL LA  GL SG  PV  SE KK S
      Glyma_CLV1A (222)  I K GYNNAYEG  P   GTNES LKYL L   SG  P  A MRNL T
Glyma_NARK_CLV1B (222)  Y K GYNNAYE   P   G  MKS LRYL L   SG  P  A  TNL T
       Lotja_HAR1 (223)  H  GYSNAYEG  P A G MENL  LLE AN  G  P  G  TKLHS
      Medtr_SUNN (218)  Q  GYFN YSG  P SLG  IKS  RYLEINNA  L  G  P  G  ENL
      Orysa_FON1 (224)  M  GYYNQYDG  VP   GD GA LRL    L  GPV E GR QRL T
      Pissa_SYM29 (219)  R  GYNN  YG   P   G KS RYLEVN  L  G  P   FG ENL
    Poptr_LRR-RLK II (217)  S C GY NH EG  P  G  SNLE LL  G   LNG  PST GQ THLHS
    Poptr_LRR-RLK I  (216)  S CV GY NR EGS P  G  SNLE LL  A   LDG  PSA SQ THLHS
       Zeama_KIN5 (231)  M  GYYNQYSG  VPR  GA  QSLVRL    T L GP E  AR SRL T
         Consensus (251)  ELYLGYYNAYEGGIPPEFGSL SLR LDMSSCNLTGEIPPSLGNL LDS
```

FIGURE 11 (continued)

```
                        301                                                350
Arath_CLAVAT1 FL (270)  LFHINLGHIP LGLVSIKSLDLS NQL G IPQ INLG  LIN
      Brana_RLK (277)  LFHINLGNIP LGLISIKSLDLS NQL G IPQ ISLW  LN
   Eucgr_LRR-RLK (262)  LFWNLMGVIP LKMLSISLDLSNNYL GVIPAT AEL  LLN
     Glyma_CLV1A (272)  LFMNLGTIPS LDMVSISLDLSFNG  IPTR QL    MN
 Glyma_NARK_CLV1B (272) LFINLGTIPS LAMVSISLDLSND G IPM QLF    LN
       Lotja_HAR1 (273) LFMNLGTIP  LSMSISLDLSND G IPE  K    MN
      Medtr_SUNN (268)  LFMNLGTIP  LSMRSISLDLSNGLSG IPET K    IN
       Orysa_FON1 (274) LFWNRLSGEIP QLGDLSSIASLDLSNDLAG IPP LANIS KLN
      Pissa_SYM29 (269) LFMNLGIP   LSMKSISLDLSNNALSG IPE  N SI  LN
   Poptr_LRR-RLK II (267) LFFNLGYIPS LGLISKSLDLSNNL G IPE  AL    LN
   Poptr_LRR-RLK I  (266) LFYNLGHIP  LGLISKSLDLSNNL G IPE  DL  IELN
      Zeama_KIN5 (281)  LFALNGLGEIP LGALTSIRSLDLSNDAG IPA AALT KLN
       Consensus (301)  LFQMNNLTG IPPELSGLISLMSLDLSIN LTGEIP SFS LKNLTLLN 351                                                400
Arath_CLAVAT1 FL (320)  FRNNYGQ PEAI  KL FE WNN LQ PA LG NGN IK L
      Brana_RLK (327)  FRNNHGP PEN  SM LQV WNN LES PA LG NGN KK L
   Eucgr_LRR-RLK (312)  FANHEGQ PE V E  LT  WNN MM PAG LG NGR LYVL
     Glyma_CLV1A (322)  FFHN G YPS VE  LT  LWNN SE PQ LGQNG FKFD
 Glyma_NARK_CLV1B (322) FFHN G YPS VE  LT  LWNN SVV PP LGQNG KFFD I
       Lotja_HAR1 (323) FFN  F G LPS I  LT  WNN SVV PH LGGNGRFL FD
      Medtr_SUNN (318)  FFN  G PA  I  LT  WNN SVV PQ LGSNG FI FD
       Orysa_FON1 (324) FRNH G  PD VAGFAQL VL LWNN L GN PAG LGKNGR KT LA
      Pissa_SYM29 (319) FFN  F G PA  I  LT  WNN SVV PQ LGSNG FIFFD
   Poptr_LRR-RLK II (317) FN  HGP PD V F  LV  WGNN E PKQ LG NG MM LS
   Poptr_LRR-RLK I  (316) FN  HGP PE F F  LV  WGNN E PQ LG NG MM LS
      Zeama_KIN5 (331)  FRN  GE PA L F FL V  WDNNLGP PPA LG NGR KT D
       Consensus (351)  LFQNKLRGSIPEFIGDLPNLEVLQVWENNFTF LP NLGRNGKLIYLDVT 401                                                450
Arath_CLAVAT1 FL (370)  DNH  G PK LCR E LEM SNN  FG PE LKC L  RIVKN
      Brana_RLK (377)  DNH  G PM LCR  LE V NN  FGS PKL RC IN RIVKN
   Eucgr_LRR-RLK (362)  QNHFGT PREL CR RLK  NNS FG PD FEC L  VRYGKN
     Glyma_CLV1A (372)  KNHFSG PRL CS RLQ FLI NT HG PN ANC L  RASN
 Glyma_NARK_CLV1B (372) KNHFCG PRL CS RLQ IMI N RC PN  NC L  RASN
       Lotja_HAR1 (373) KNH  G PP LCS RLK FI N RG PKG ECP L  RVAN
      Medtr_SUNN (368)  KNH  G PPELCS KIK FV N RG PNG PC  LE RVAN
       Orysa_FON1 (374) TNH  GP PAL LCA RRLEM V MENGLG  POSL DC  LR RVRLAKN
      Pissa_SYM29 (369) KNH  G PP LCS KL QFV NN HG PKG AC LL RVAN
   Poptr_LRR-RLK II (367) YNH  G VPR LCR  LK  SMNN IGSIPE  QC LL REICN
   Poptr_LRR-RLK I  (366) INH  G VPR LCR  LT  SMNN LGSIPD  QC LL RIMN
      Zeama_KIN5 (381)  SNH  GT PPL LCA RNLQL V MNGFGS PESL DC  LR VRLGKN
       Consensus (401)  NHLTGLIPRDLCKGGKL TLILTDNFF GPIPEEIG CKSLTKIRIANN
```

FIGURE 11 (continued)

```
                          451                                                500
Arath_CLAVAT1 FL  (420)   L NGT P G FN PL    ELTDNF SG LPVTM G V DQIY   NW S
      Brana_RLK  (427)   L NGT P G FT PL    ELTDNF SG LPGSM G L DHIY   NW
   Eucgr_LRR-RLK (412)   F DGT PPG FN PQA   ELNDNL SG LPAQM GEN VI S   NRIS
      Glyma_CLV1A (422)  Y NGA PSG FK PS    ELA NR NG LPP  G S IT T   NL
 Glyma_NARK_CLV1B (422)  Y NGV PSG FK PS    ELA NR NG LPP  G ES IT T   NL S
       Lotja_HAR1 (423)  F DGP PPG FQ PS    TELS NRLNG LPSV G S T T   NL
      Medtr_SUNN  (418)  Y DGP PPG FQ PS Q  ELG NR NG LPT   CNS N A   NL
      Orysa_FON1  (424)  F TGP PYG LFN PQANM ELTDNLLTG LPDV G G KIS ML G  NGIG
      Pissa_SYM29 (419)  Y DGP PQG FQMPS    ELG NR NG LPS V G VN I T   NL
   Poptr_LRR-RLK II (417) LFTGT PG FN PL  Q ELSHNY SG LPP  G A S SV D NRIS
   Poptr_LRR-RLK I  (416) MFSGT PG FN PLA  IVELS NL SG LPP  G AL L SV  NRI
       Zeama_KIN5 (431)  F TGP PYG LFD PQANM LEL TDNMLTG LPDV AG KI MM G  NRIG
         Consensus (451) FL G VPAGIFNLP VTIIELTNN FSGELP EISGDSLGILTLSNN FT 501                                                550
Arath_CLAVAT1 FL  (470)   GE IP   NFPNL LFL RNR RGN PR  E KHLSR T  AN I GG
      Brana_RLK  (477)   GL IE   NFKNL DFL RNR GN PR  E KHL T SAN  CD
   Eucgr_LRR-RLK (462)   GE IP   NFSGL R LL ANR GK PS I SPRF LRV   NSISGR
      Glyma_CLV1A (472)  GK IP   LKN RAL LL TNE LG PG  DPML VV  N  CP
 Glyma_NARK_CLV1B (472)  GK IP   LKN RAL LL ANE VG PG  DPML VV  N  CP
       Lotja_HAR1 (473)  GR IPA MKN RAL S LL ANE IG PGG EIPML XV  N  CP
      Medtr_SUNN  (468)  GR IPAS KN RSL LLL ANQ LG PA  A PYL    N  GG
      Orysa_FON1  (474)  G IP    N PAL  L LESNN GALPP GN KN SRL V  NA  GA
      Pissa_SYM29 (469)  GR IPAS MKN ISL LWL ANQ VG PK   PYL KF   N  GV
   Poptr_LRR-RLK II (467) GR IPR   N KSL FL TEMNRL G PD  S EIL SKIS RAN ISGE
   Poptr_LRR-RLK I  (466) GK IP   N KNL  L LTNRL G PF  WG KSL K SRAN IRGE
       Zeama_KIN5 (481)  GR IPA   N PAL  L LESNN GSIPP GR RN RLAS  NA  GG
         Consensus (501) GRIPPAIGNLRALQTLSLDAN FSGEIP EVFDLKMLTKINISGNNLTG 551                                                600
Arath_CLAVAT1 FL  (520)   IPDSISR  ST LIS D S NRING  P  NMV NLGT   SGN  TGSIP
      Brana_RLK  (527)   IPDSISR  T LIS D S NRIGGD  P D HDVINLGT   SGN  IGSIP
   Eucgr_LRR-RLK (512)   IPGSYTG T LA LD S NN AG  PN LSS  VLAV   SSNR TGPVP
      Glyma_CLV1A (522)  IPT FTR  V LA  D S NM DG  P  MK  TDL  F  SIN ISGS P
 Glyma_NARK_CLV1B (522)  IPT T R  V L   D S NM EGK P   K  TDL  F  SIN ISGPVP
       Lotja_HAR1 (523)  IPT T HRA L   D S NN AG VP  MK  MDL   SRNEISGPVP
      Medtr_SUNN  (518)  IPK PY TQ S L   DFS NM TG VP  MK  VI  F  SHNSISGKIP
      Orysa_FON1  (524)  IPDEL IR  A LA  D S NGFSG  PES TS  IICT  SRNR TGEIP
      Pissa_SYM29 (519)  IPT TYSQ R L   DFS NMITG VP E MK  VI  F  SHNNISGLIP
   Poptr_LRR-RLK II (517) IPASMFH  T L S DFSQNSISG  P ESTK  DL   DSRN TGQLP
   Poptr_LRR-RLK I  (516) IPASISH  T L S DFSQNS SG  P K AK  NDL F D SRNS TGQLP
       Zeama_KIN5 (531)  IPRE LMG A LG  D S NG TG  PDTVTS  ILCT  SRNR SGEIP
         Consensus (551) IP SIT CTSLTAVDLSRN LSGEIPKGI NLK LSILNLS NQLSG IP
```

```
                          751                                              800
Arath_CLAVAT1 FL    (711) .NV.-AIKRLG.G-.G.SDHGFTAE.QT.G.IRHRHIVRLLG..AN
       Brana_RLK    (718) .NV.-AIKRLG.G-.G.SDHGFTAE.QT.G.IRHRHIVRLLG..AN
    Eucgr_LRR-RLK   (695) ..T.-AIKQLAG.GGNGLSDHGFSAE.QT.G.IRHRIVRLLG..LN
      Glyma_CLV1A   (709) R.S.-AIKRLGAG-.G.DYGFKAE.ET.GKIRHRIVRLLG..AN
   Glyma_NARK_CLV1B (715) ..T.-AIKRLGAG-.G.DYGFKAE.ET.GKIRHRIVRLLG..AN
        Lotja_HAR1  (714) ...-.AIKRLGQG-.G..DYGFRAE.ET.GKIRHRIVRLLG..AN
       Medtr_SUNN   (704) .A.T.-AIKRLGQG-.G.DYGFKAE.ET.GKIRHRIVRLLG..AN
        Orysa_FON1  (723) TRG--AELAIKRLG.G-GGEHDRGFSAEVTT.G.IRHRIVRLLG..AN
       Pissa_SYM29  (705) ..T.-AIKRLGQG-.G..DYGFKAE.ET.GKIRHRIVRLLG..AN
   Poptr_LRR-RLK II (703) .TE.IH.AIKRLG.G-.G.DHGFSAE.QT.G.IRHRIVRLLG..AN
    Poptr_LRR-RLK I (703) .REVH.AIKRLG.G-.G.SDHGFSAE.QT.G.IRHRIVRLLG..AN
       Zeama_KIN5   (722) TRG.-AELAIKRLG.G-CGDHDRGFTAEVTT.G.IRHRIVRLLG..AN
         Consensus  (751) MPNGTD VAIKRLVGRG SGRNDHGFSAEI TLGRIRHRNIVRLLGYVSN
                                 SDII          SDIII            SDIV 801                                              850
Arath_CLAVAT1 FL    (759) .NLLLYEYMPNGSLGE.LHG.KG.HLQWETRH..A.EA..GLCY.HHD
       Brana_RLK    (766) R.NLLLYEYMPNGSLGE.LHG.KG.HLQWETRH..A.EA..GLCY.HHD
    Eucgr_LRR-RLK   (744) ..NLLLYEYMPNGSLGE.LHG.KG.HLQWETR..A.EA..GLCY.HHD
      Glyma_CLV1A   (757) .E.NLLLYEYMPNGSLGEWLHG.KG.HLKWEMR..K.A.EA..GLCY.HHD
   Glyma_NARK_CLV1B (763) .E.NLLLYEYMPNGSLGEWLHG.KG.HLKWEMR..K.A.EA..GLCY.HHD
        Lotja_HAR1  (762) ..NLLLYEYMPNGSLGEWLHG.AKG.HLRWEMR..K.A.EA.RGLCY.HHD
       Medtr_SUNN   (752) ..NLLLYEYMPNGSLGEWLHG.AKG.CHLSWEMR..K.A.EA..GLCY.HHD
        Orysa_FON1  (770) RE.NLLLYEYMPNGSLGE.LHG.KG.HLGWEARA..VAAEA..CGLCY.HHD
       Pissa_SYM29  (753) ..NLLLYEYMPNGSLGEwLHG.AKG.CHLSWEMR..K.A.EAG.GLCY.HHD
   Poptr_LRR-RLK II (752) ..NLLLYEYMPNGSLGE.LHG.KG.HLQWETR..A.EA..GLCY.HHD
    Poptr_LRR-RLK I (752) ..NLLLYEYMPNGSLGE.LHG.KG.HLQWETR..A.EA..GLCY.HHD
       Zeama_KIN5   (770) RE.ANLLLYEYMPNGSLGE.LHG.GKG.HLGWEARA..VAAEA.RGLCY.HHD
         Consensus  (801) KDTNLLLYEYMPNGSLGELLHGAKGGHL WE RYRIAVEAAKGLCYLHHD
                             SDV                                      SDVIa Predicted kinase active site
                          851                                              900
Arath_CLAVAT1 FL    (809) C.P.II.HRDVKSNNILLD..EAHVADFGLAKFLV.G-A..S..MS..AGS
       Brana_RLK    (816) C.P.II.HRDVKSNNILLD..EAHVADFGLAKFLL.G-A..S..MS..AGS
    Eucgr_LRR-RLK   (794) CLP.II.HRDVKSNNILLD..EAHVADFGLAKFLQ.A-..S..MS.VAGS
      Glyma_CLV1A   (807) C.P.II.HRDVKSNNILLDH..EAHVADFGLAKFLY.L-.SSQSMS..AGS
   Glyma_NARK_CLV1B (813) C.P.II.HRDVKSNNILLDG..EAHVADFGLAKFLY.P-.SSQSMS..AGS
        Lotja_HAR1  (812) C.P.II.HRDVKSNNILLDA..EAHVADFGLAKFLY.P-.SSQSMS..AGS
       Medtr_SUNN   (802) C.P.II.HRDVKSNNILLDA..EAHVADFGLAKFLY.P-.SSQSMS..AGS
        Orysa_FON1  (820) CAP.RI.HRDVKSNNILLD.A.EAHVADFGLAKFLGG--ATS..MS..AGS
       Pissa_SYM29  (803) C.P.II.HRDVKSNNILLDA..EAHVADFGLAKFLY.P-.SSQSMS..AGS
   Poptr_LRR-RLK II (802) C.P.II.HRDVKSNNILLD..EAHVADFGLAKFLQ.A-.SS..MS..AGS
    Poptr_LRR-RLK I (802) C.P.II.HRDVKSNNILLD..EAHVADFGLAKFLQ.A-.SS..MS.VAGS
       Zeama_KIN5   (820) CAP.RI.HRDVKSNNILLD.A.EAHVADFGLAKFLGGGGATS..MS..AGS
         Consensus  (851) CSPLIIHRDVKSNNILLDSDFEAHVADFGLAKFL DA GASECMSSIAGS
                                SDVIb              SDVII
```

FIGURE 11 (continued)

```
                           901                   □                        950
Arath_CLAVAT1 FL   (858)  YGYIAPEYAYTLVDEKSDVYSGVVLLELIAG  PVG FG GVDIVRW
       Brana_RLK   (865)  YGYIAPEYAYTLVDEKSDVYSGVVLLELIAG  PVG FG GVDIVRW
   Eucgr_LRR-RLK   (843)  YGYIAPEYAYTLVDEKSDVYSGVVLLELIAG  PVG FG GVDIVRW
      Glyma_CLV1A  (856)  YGYIAPEYAYTLVDEKSDVYSGVVLLELIG   PVG FG GVDIVGW
  Glyma_NARK_CLV1B (862)  YGYIAPEYAYTLVDEKSDVYSGVVLLELIIG  PVG FG GVDIVGW
       Lotja_HAR1  (861)  YGYIAPEYAYTLVDEKSDVYSGVVLLELII   PVG FG GVDIVGW
       Medtr_SUNN  (851)  YGYIAPEYAYTLVDEKSDVYSGVVLLELITG  PVG FG GVDIVGWI
       Orysa_FON1  (868)  YGYIAPEYAYTLVDEKSDVYSGVVLLELIT  PVG G GVDIVHW
       Pissa_SYM29 (852)  YGYIAPEYAYTLVDEKSDVYSGVVLLELIIG  PVG FG GVDIVGW
   Poptr_LRR-RLK II(851)  YGYIAPEYAYTLVDEKSDVYSCGVVLLELIAG PVG FG GVDIVRW
   Poptr_LRR-RLK I (851)  YGYIAPEYAYTLVDEKSDVYSGVVLLELIAG  PVG FG GVDIVRW
       Zeama_KIN5  (870)  YGYIAPEYAYTLVDEKSDVYSCVVLLELITG  PVGSFG GVDIVHW
        Consensus  (901)  YGYIAPEYAYTLVDEKSDVYSFGVVLLELI GRKPVGEFGDGVDIV WV
                          SDVIII             SDIX                   SDX
```

```
                           951                                           1000
Arath_CLAVAT1 FL   (908)  N EE  T   -      VV  DRL  P     V A  CVE  EA
       Brana_RLK   (915)  N EG  P   -      TV  DRL  P     A A  CVEDEATT
   Eucgr_LRR-RLK   (893)  KTASDP P   P     IV  DRL G  IA  L A  CRCVE ESE
      Glyma_CLV1A  (906)  N RL  S   -      VV   D R  P I YM N A CV  VGPT
  Glyma_NARK_CLV1B (912)  N RL  A   -       V   D RL  P   YM N A CV  MGP
       Lotja_HAR1  (911)  N MS  S   -      TV   D RL  P   YM N A CV  MGP
       Medtr_SUNN  (901)  N EL  Y   -    K LV   D RL N P   YM N A CV  MGP
       Orysa_FON1  (918)   VTA  PDN -    T A V  ADRL TPE VALM NLY A ACVE AST
       Pissa_SYM29 (902)  N EL  Y   -    K LV   D RL   MA YM N A CV  MGP
   Poptr_LRR-RLK II(901)   TS  S   -       SV   DRL  P  GA L A  CV  DESSN
   Poptr_LRR-RLK I (901)   TS  S   -       TV   DRL  P  AG L A  CV  DESS
       Zeama_KIN5  (920)   VTADAAAA-EEP---V L  ADRR APE PVPL ADLYRVA ACVE AST
        Consensus  (951)  RKT  ELSQP SDAALVLAVVDPRLSGYPLTSVIHLFKIAMMCVKE SSA
```

```
                                      End of              End of C-
                                      kinase              terminal
                                      domain              domain 1001                                    1040
Arath_CLAVAT1 FL   (957)  RPTMREVVHML   K-------VAN  AF-------
       Brana_RLK   (964)  RPTMREVVHML   K-------VTN  AF-------
   Eucgr_LRR-RLK   (943)  RPTMREVVHML   L A TFAVGATPD  K -------
      Glyma_CLV1A  (955)  RPTMREVVHML   HFT-----HTHN  N -------
  Glyma_NARK_CLV1B (961)  RPTMREVVHML  E H A-----HTHN  N -------
       Lotja_HAR1  (960)  RPTMREVVHML   Q N-----STQD  N -------
       Medtr_SUNN  (950)  RPTMREVVHML    H -------SHN- N -------
       Orysa_FON1  (967)  RPTMREVVHML   NS QPN----SGDL  TF-------
       Pissa_SYM29 (951)  RPTMREVVHML   Q -------THNN  N -------
   Poptr_LRR-RLK II(950)  RPTMREVVHML   Q --------ASS  T -------
   Poptr_LRR-RLK I (950)  RPTMREVVHML   Q --------APS  A -------
       Zeama_KIN5  (967)  RPTMREVVHML  TSAA QPD----VPHAL CK VD
        Consensus (1001)  RPTMREVVHML TNPP S T         LI L
                          SDXI
```

FIGURE 11 (continued)

SEQ ID NO: 209 Arabidopsis thaliana truncated Clavatal LRR-RLK
nucleic acid sequence comprised in ATU96879
ATGGCGATGAGACTTTTGAAGACTCATCTTCTGTTTCTGCATCTGTATCTATTTTTCTCACCATGT
TTCGCTTACACTGACATGGAAGTTCTTCTCAATCTCAAATCCTCCATGATTGGTCCTAAAGGACAC
GGTCTCCACGACTGGATTCACTCATCTTCTCCGGATGCTCACTGTTCTTTCTCCGGCGTCTCATGT
GACGACGATGCTCGTGTTATCTCTCTCAACGTCTCCTTCACTCCTTTGTTTGGTACAATCTCACCA
GAGATTGGGATGTTGACTCATTTGGTGAATCTAACTTTAGCTGCCAACAACTTCACCGGTGAATTA
CCATTGGAGATGAAGAGTCTAACTTCTCTCAAGGTTTTGAATATCTCCAACAATGGTAACCTTACT
GGAACATTCCCTGGAGAGATTTTAAAAGCTATGGTTGATCTTGAAGTTCTTGACACTTATAACAAC
AATTTCAACGGTAAGTTACCACCGGAGATGTCAGAGCTTAAGAAGCTTAAATACCTCTCTTTCGGT
GGAAATTTCTTCAGCGGAGAGATTCCAGAGAGTTATGGAGATATTCAAAGCTTAGAGTATCTTGGT
CTCAACGGAGCTGGACTCTCCGGTAAATCTCCGGCGTTTCTTTCCCGCCTCAAGAACTTAAGAGAA
ATGTATATTGGCTACTACAACAGCTACACCGGTGGTGTTCCACCGGAGTTCGGTGGTTTAACAAAG
CTTGAGATCCTCGACATGGCGAGCTGTACACTCACCGGAGAGATTCCGACGAGTTTAAGTAACCTG
AAACATCTACATACTCTGTTTCTTCACATCAACAACTTAACCGGTCATATACCACCGGAGCTTTCC
GGTTTAGTCAGCTTGAAATCTCTCGATTTATCAATCAATCAGTTAACCGGAGAAATCCCTCAAAGC
TTCATCAATCTCGGAAACATTACTCTAATCAATCTCTTCAGAAACAATCTCTACGGACAAATACCA
GAGGCCATCGGAGAATTACCAAAACTCGAAGTCTTCGAAGTATGGGAGAACAATTTCACGTTACAA
TTACCGGCGAATCTTGGCCGGAACGGGAATCTAATAAAGCTTGATGTCTCTGATAATCATCTCACC
GGACTTATCCCCAAGGACTTATGCAGAGGTGAGAAATTAGAGATGTTAATTCTCTCTAACAACTTC
TTCTTTGGTCCAATTCCAGAAGAGCTTGGTAAATGCAAATCCTTAACCAAAATCAGAATCGTTAAG
AATCTTCTCAACGGCACTGTTCCGGCGGGGCTTTTCAATCTACCGTTAGTTACGATTATCGAACTC
ACTGATAATTTCTTCTCCGGTGAACTTCCGGTAACGATGTCCGGCGATGTTCTGATCAGATTTAC
CTCTCTAACAACTGGTTTTCCGGCGAGATTCCACCTGCGATTGGTAATTTCCCCAATCTACAGACT
CTATTCTTAGATCGGAACCGATTTCGCGGCAACATTCCGAGAGAAATCTTCGAATTGAAGCATTTA
TCGAGGATCAACACAAGTGCGAACAACATCACCGGCGGTATTCCAGATTCAATCTCTCGCTGCTCA
ACTTTAATCTCCGTCGATCTCAGCCGTAACCGAATCAACGGAGAAATCCCTAAAGGGATCAACAAC
GTGAAAAACTTAGGAACTCTAAATATCTCCGGTAATCAATTAACCGGTTCAATCCCTACCGGAATC
GGAAACATGACGAGTTTAACAACTCTCGATCTCTCTTTCAACGATCTCTCCGGTAGAGTACCACTC
GGTGGTCAATTCTTGGTGTTCAACGAAACTTCCTTCGCCGGAAACACTTACCTCTGTCTCCCTCAC
CGTGTCTCTTGCCCAACACGGCCAGGACAAACCTCCGATCACAATCACACGGCGTTGTTCTCACCG
TCAAGGATCGTAATCACGGTTATCGCAGCGATCACCGGTTTGATCCTAATCAGTGTAGCGATTCGT
CAGATGAATAAGAAGAAGAACCAGAAATCTCTCGCCTGGAAACTAATCGCCTTCCAGAAACTAGAT
TTCAAATCTGAAGACGTTCTCGAGTGTCTTAAAGAAGAGAACATAATCGGTAAAGGCGGAGCTGGA
ATTGTCTACCGTGGATCAATGCCAAACAACGTAGACGTCGCGATTAAACGACTCGTTGGCCGTGGG
ACCGGGAGGAGCGATCATGGATTCACGGCGGAGATTCAAACTTTGGGGAGAATCCGCCACCGTCAC
ATAGTGTGA SEQ ID NO: 210 Arabidopsis thaliana truncated Clavatal LRR-RLK
translated amino acid sequence
MAMRLLKTHLLFLHLYLFFSPCFAYTDMEVLLNLKSSMIGPKGHGLHDWIHSSSPDAHCSFSGVSC
DDDARVISLNVSFTPLFGTISPEIGMLTHLVNLTLAANNFTGELPLEMKSLTSLKVLNISNNGNLT
GTFPGEILKAMVDLEVLDTYNNNFNGKLPPEMSELKKLKYLSFGGNFFSGEIPESYGDIQSLEYLG
LNGAGLSGKSPAFLSRLKNLREMYIGYYNSYTGGVPPEFGGLTKLEILDMASCTLTGEIPTSLSNL
KHLHTLFLHINNLTGHIPPELSGLVSLKSLDLSINQLTGEIPQSFINLGNITLINLFRNNLYGQIP
EAIGELPKLEVFEVWENNFTLQLPANLGRNGNLIKLDVSDNHLTGLIPKDLCRGEKLEMLILSNNF
FFGPIPEELGKCKSLTKIRIVKNLLNGTVPAGLFNLPLVTIIELTDNFFSGELPVTMSGDVLDQIY LSNNWFSGEIPPAIGNFPNLQTLFLDRNRFRGNIPREIFELKHLSRINTSANNITGGIPDSISRCS
TLISVDLSRNRINGEIPKGINNVKNLGTLNISGNQLTGSIPTGIGNMTSLTTLDLSFNDLSGRVPL
GGQFLVFNETSFAGNTYLCLPHRVSCPTRPGQTSDHNHTALFSPSRIVITVIAAITGLILISVAIR
QMNKKKNQKSLAWKLIAFQKLDFKSEDVLECLKEENIIGKGGAGIVYRGSMPNNVDVAIKRLVGRG
TGRSDHGFTAEIQTLGRIRHRHIV SEQ ID NO: 211 Arabidopsis thaliana Clavata1 Arath_CLV1 LRR-RLK
nucleic acid sequence ATU96879
ATGGCGATGAGACTTTTGAAGACTCATCTTCTGTTTCTGCATCTGTATCTATTTTTCTCACCATGT
TTCGCTTACACTGACATGGAAGTTCTTCTCAATCTCAAATCCTCCATGATTGGTCCTAAAGGACAC
GGTCTCCACGACTGGATTCACTCATCTTCTCCGGATGCTCACTGTTCTTTCTCCGGCGTCTCATGT
GACGACGATGCTCGTGTTATCTCTCTCAACGTCTCCTTCACTCCTTTGTTTGGTACAATCTCACCA
GAGATTGGGATGTTGACTCATTTGGTGAATCTAACTTTAGCTGCCAACAACTTCACCGGTGAATTA
CCATTGGAGATGAAGAGTCTAACTTCTCTCAAGGTTTTGAATATCTCCAACAATGGTAACCTTACT
GGAACATTCCCTGGAGAGATTTTAAAAGCTATGGTTGATCTTGAAGTTCTTGACACTTATAACAAC
AATTTCAACGGTAAGTTACCACCGGAGATGTCAGAGCTTAAGAAGCTTAAATACCTCTCTTTCGGT
GGAAATTTCTTCAGCGGAGAGATTCCAGAGAGTTATGGAGATATTCAAAGCTTAGAGTATCTTGGT
CTCAACGGAGCTGGACTCTCCGGTAAATCTCCGGCGTTTCTTTCCCGCCTCAAGAACTTAAGAGAA
ATGTATATTGGCTACTACAACAGCTACACCGGTGGTGTTCCACGCGAGTTCGGTGGTTTAACAAAG
CTTGAGATCCTCGACATGGCGAGCTGTACACTCACCGGAGAGATTCCGACGAGTTTAAGTAACCTG
AAACATCTACATACTCTGTTTCTTCACATCAACAACTTAACCGGTCATATACCACCGGAGCTTTCC
GGTTTAGTCAGCTTGAAATCTCTCGATTTATCAATCAATCAGTTAACCGGAGAAATCCCTCAAAGC
TTCATCAATCTCGGAAACATTACTCTAATCAATCTCTTCAGAAACAATCTCTACGGACAAATACCA
GAGGCCATCGGAGAATTACCAAAACTCGAAGTCTTCGAAGTATGGGAGAACAATTTCACGTTACAA
TTACCGGCGAATCTTGGCCGGAACGGGAATCTAATAAAGCTTGATGTCTCTGATAATCATCTCACC
GGACTTATCCCCAAGGACTTATGCAGAGGTGAGAAATTAGAGATGTTAATTCTCTCTAACAACTTC
TTCTTTGGTCCAATTCCAGAAGAGCTTGGTAAATGCAAATCCTTAACCAAAATCAGAATCGTTAAG
AATCTTCTCAACGGCACTGTTCCGGCGGGGCTTTTCAATCTACCGTTAGTTACGATTATCGAACTC
ACTGATAATTTCTTCTCCGGTGAACTTCCGGTAACGATGTCCGGCGATGTTCTCGATCAGATTTAC
CTCTCTAACAACTGGTTTTCCGGCGAGATTCCACCTGCGATTGGTAATTTCCCCAATCTACAGACT
CTATTCTTAGATCGGAACCGATTTCGCGGCAACATTCCGAGAGAAATCTTCGAATTGAAGCATTTA
TCGAGGATCAACACAAGTGCGAACAACATCACCGGCGGTATTCCAGATTCAATCTCTCGCTGCTCA
ACTTTAATCTCCGTCGATCTCAGCCGTAACCGAATCAACGGAGAAATCCCTAAAGGGATCAACAAC
GTGAAAAACTTAGGAACTCTAAATATCTCCGGTAATCAATTAACCGGTTCAATCCCTACCGGAATC
GGAAACATGACGAGTTTAACAACTCTCGATCTCTCTTTCAACGATCTCTCCGGTAGAGTACCACTC
GGTGGTCAATTCTTGGTGTTCAACGAAACTTCCTTCGCCGGAAACACTTACCTCTGTCTCCCTCAC
CGTGTCTCTTGTCCAACACGGCCAGGACAAACCTCCGATCACAATCACACGGCGTTGTTCTCACCG
TCAAGGATCGTAATCACGGTTATCGCAGCGATCACCGGTTTGATCCTAATCAGTGTAGCGATTCGT
CAGATGAATAAGAAGAAGAACCAGAAATCTCTCGCCTGGAAACTAACCGCCTTCCAGAAACTAGAT
TTCAAATCTGAAGACGTTCTCGAGTGTCTTAAAGAAGAGAACATAATCGGTAAAGGCGGAGCTGGA
ATTGTCTACCGTGGATCAATGCCAAACAACGTAGACGTCGCGATTAAACGACTCGTTGGCCGTGGG
ACCGGGAGGAGCGATCATGGATTCACGGCGGAGATTCAAACTTTGGGGAGAATCCGCCACCGTCAC
ATAGTGAGACTTCTTGGTTACGTAGCGAACAAGGATACGAATCTCCTTCTTTATGAGTACATGCCT
AATGGAAGCCTTGGAGAGCTTTTGCATGGATCTAAAGGTGGTCATCTTCAATGGGAGACGAGACAT
AGAGTAGCCGTGGAAGCTGCAAAGGGCTTGTGTTATCTTCACCATGATTGTTCACCATTGATCTTG
CATAGAGATGTTAAGTCCAATAACATTCTTTTGGACTCTGATTTTGAAGCCCATGTTGCTGATTTT
GGGCTTGCTAAGTTCTTAGTTGATGGTGCTGCTTCTGAGTGTATGTCTTCAATTGCTGGCTCTTAT
GGATACATCGCCCCAGAGTATGCATATACCTTGAAAGTGGACGAGAAGAGTGATGTGTATAGTTTC FIGURE 13 (continued)

```
GGAGTGGTTTTGTTGGAGTTAATAGCTGGGAAGAAACCTGTTGGTGAATTTGGAGAAGGAGTGGAT
ATAGTTAGGTGGGTGAGGAACACGGAAGAGGAGATAACTCAGCCATCGGATGCTGCTATTGTTGTT
GCGATTGTTGACCCGAGGTTGACTGGTTACCCGTTGACAAGTGTGATTCATGTGTTCAAGATCGCA
ATGATGTGTGTGGAGGAAGAAGCCGCGGCAAGGCCTACGATGAGGGAAGTTGTGCACATGCTCACT
AACCCTCCTAAATCCGTGGCGAACTTGATCGCGTTCTGA
```

SEQ ID NO: 212 Arabidopsis thaliana Clavata1 Arath_CLV1 LRR-RLK translated amino acid sequence
```
MAMRLLKTHLLFLHLYLFFSPCFAYTDMEVLLNLKSSMIGPKGHGLHDWIHSSSPDAHCSFSGVSC
DDDARVISLNVSFTPLFGTISPEIGMLTHLVNLTLAANNFTGELPLEMKSLTSLKVLNISNNGNLT
GTFPGEILKAMVDLEVLDTYNNNFNGKLPPEMSELKKLKYLSFGGNFFSGEIPESYGDIQSLEYLG
LNGAGLSGKSPAFLSRLKNLREMYIGYYNSYTGGVPREFGGLTKLEILDMASCTLTGEIPTSLSNL
KHLHTLFLHINNLTGHIPPELSGLVSLKSLDLSINQLTGEIPQSFINLGNITLINLFRNNLYGQIP
EAIGELPKLEVFEVWENNFTLQLPANLGRNGNLIKLDVSDNHLTGLIPKDLCRGEKLEMLILSNNF
FFGPIPEELGKCKSLTKIRIVKNLLNGTVPAGLFNLPLVTIIELTDNFFSGELPVTMSGDVLDQIY
LSNNWFSGEIPPAIGNFPNLQTLFLDRNRFRGNIPREIFELKHLSRINTSANNITGGIPDSISRCS
TLISVDLSRNRINGEIPKGINNVKNLGTLNISGNQLTGSIPTGIGNMTSLTTLDLSFNDLSGRVPL
GGQFLVFNETSFAGNTYLCLPHRVSCPTRPGQTSDHNHTALFSPSRIVITVIAAITGLILISVAIR
QMNKKKNQKSLAWKLTAFQKLDFKSEDVLECLKEENIIGKGGAGIVYRGSMPNNVDVAIKRLVGRG
TGRSDHGFTAEIQTLGRIRHRHIVRLLGYVANKDTNLLLYEYMPNGSLGELLHGSKGGHLQWETRH
RVAVEAAKGLCYLHHDCSPLILHRDVKSNNILLDSDFEAHVADFGLAKFLVDGAASECMSSIAGSY
GYIAPEYAYTLKVDEKSDVYSFGVVLLELIAGKKPVGEFGEGVDIVRWVRNTEEEITQPSDAAIVV
AIVDPRLTGYPLTSVIHVFKIAMMCVEEEAAARPTMREVVHMLTNPPKSVANLIAF
```

SEQ ID NO: 213 Brassica napus Brana_LRR-RLK nucleic acid sequence AY283519
```
ATGGCGATGAGACTTTTGAAGACTCACCTTCTGTTTCTCCATCTTCACTACGTTATCTCGATTTTG
CTTCTATCTTTCTCACCATGCTTCGCTTCCACTGACATGGACCATCTCCTCACCCTCAAATCGTCC
ATGGTCGGCCCCAACGGCCACGGCCTCCACGACTGGGTTCGCTCCCCTTCTCCCTCAGCTCACTGT
TCTTTCTCCGGCGTTTCCTGCGACGGCGACGCTCGTGTCATCTCCCTCAACGTCTCTTTCACTCCT
CTCTTCGGAACCATCTCCCCGGAGATTGGGATGCTGGACCGTCTCGTGAATCTGACGTTAGCTGCT
AATAATTTCTCCGGTATGCTCCCGTTGGAGATGAAGAGTCTCACTTCTCTAAAGGTTCTCAACATC
TCCAACAACGTGAACCTCAACGGAACCTTCCCCGGAGAGATTCTCACTCCCATGGTCGACCTCGAA
GTCCTCGACGCGTACAACAACAACTTCACAGGCCCACTACCGCCGGAGATCCCCGGGCTCAAGAAG
CTGAGACACCTCTCTCTCGGAGGAAACTTCTTAACCGGAGAAATCCCAGAGAGTTACGGAGATATC
CAGAGCTTGGAGTATCTTGGCCTCAACGGAGCCGGACTCTCCGGCGAATCTCCGGCGTTCTTGTCT
CGCCTCAAGAATCTTAAAGAAATGTACGTCGGCTACTTCAACAGCTACACCGGCGGCGTACCGCCG
GAGTTCGGTGAATTGACAAACCTAGAGGTTCTCGACATGGCGAGCTGTACACTCACGGGAGAGATT
CCGACGACTCTGAGTAATCTAAAACATTTGCACACTTTGTTTCTCCACATCAACAACTTAACCGGA
AACATCCCTCCGGAACTCTCCGGTTTAATCAGCTTAAAATCTCTAGACCTCTCAATAAACCAGCTA
ACCGGAGAGATTCCTCAGAGCTTCATCTCCCTCTGGAACATCACTCTCGTCAACCTCTTCAGAAAC
AATCTCCACGGGCCCATACCTGAGTTCATCGGAGACATGCCGAACCTCCAAGTCCTCCAGGTGTGG
GAGAACAACTTCACGCTAGAGCTACCGGCGAATCTCGGCCGGAACGGGAATCTGAAAAAGCTCGAC
GTCTCTGATAACCATCTCACCGGACTCATCCCCATGGATTTGTGCAGAGGCGGGAAGCTGGAGACG
CTGGTGCTCTCCGACAACTTCTTCTTCGGCTCGATCCCTGAGAAGCTAGGTCGATGCAAATCGCTA
AACAAGATCAGAATCGTCAAGAATCTCCTCAACGGTACGGTTCCGGCGGGACTATTCACTCTACCG
CTCGTTACCATCATCGAGCTCACCGATAACTTCTTCTCCGGGGAGCTTCCGGGGAGATGTCAGGC
GACCTTCTCGATCATATCTACTTATCTAACAATTGGTTTACCGGTTTAATCCCCCCGGCTATCGGT
```

```
AATTTTAAAAATCTACAGGATTTATTCTTAGACCGGAACCGGTTTAGCGGGAATATTCCGAGAGAA
GTTTTCGAGTTAAAGCATCTCACTAAGATCAACACGAGTGCTAACAACCTCACCGGCGACATCCCT
GACTCGATCTCGCGATGCACTTCCTTAATCTCCGTCGATCTCAGCCGTAACCGAATCGGCGGAGAT
ATCCCGAAAGACATCCACGACGTGATTAACTTAGGAACTCTCAATCTCTCCGGGAATCAACTCACC
GGCTCGATCCCGATCGGAATCGGGAAGATGACGAGCTTAACCACTCTCGATCTCTCCTTCAACGAC
CTCTCGGGGCGAGTCCCACTCGGCGGCCAGTTCCTAGTCTTCAACGACACTTCCTTCGCCGGAAAC
CCTTACCTCTGCCTCCCTCGCCACGTCTCGTGCCTCACGCGTCCCGGCCAAACCTCCGATCGCATC
CACACGGCGCTGTTCTCGCCGTCGAGGATCGCCATCACGATAATCGCAGCGGTCACGGCGCTGATC
CTCATCAGCGTCGCGATTCGTCAGATGAACAAGAAGAAGCACGAGAGATCCCTCTCCTGGAAGCTA
ACCGCCTTCCAGCGGCTCGATTTCAAGGCGGAAGACGTCCTCGAGTGCCTCCAAGAGGAGAACATA
ATCGGCAAAGGCGGAGCGGGGATCGTCTACCGCGGATCCATGCCGAACAACGTAGACGTCGCGATC
AAACGCCTCGTGGGACGCGGAACAGGGAGGAGCGATCACGGATTCACGGCGGAGATTCAGACGCTA
GGGAGGATCCGCCACCGTCACATCGTGAGACTCCTCGGATACGTGGCGAACAGGGACACGAACCTG
CTTCTCTACGAGTACATGCCTAACGGGAGCCTCGGCGAGCTTTTGCACGGGTCTAAAGGAGGTCAT
CTTCAGTGGGAGACGAGGCACAGAGTAGCCGTTGAAGCGGCGAAAGGACTGTGTTATCTTCACCAT
GACTGTTCGCCGTTGATCTTGCATAGAGACGTTAAGTCCAATAACATTTTACTGGACTCTGATTTT
GAGGCCCATGTTGCTGATTTTGGGCTTGCTAAGTTCTTACTGGACGGTGCTGCTTCCGAGTGTATG
TCTTCGATAGCTGGATCCTATGGATACATCGCTCCAGAGTATGCTTACACTCTCAAAGTGGATGAG
AAGAGTGATGTTTATAGTTTTGGAGTGGTGTTATTGGAGCTGATAGCTGGGAAGAAACCGGTTGGT
GAGTTTGGGGAAGGAGTGGATATAGTGAGGTGGGTGAGGAACACGGAGGGTGAGATACCTCAGCCG
TCGGATGCAGCTACTGTTGTTGCGATCGTCGACCAGAGGTTGACTGGTTACCCGTTGACTAGTGTG
ATTCACGTGTTCAAGATAGCGATGATGTGTGTGGAGGATGAGGCAACGACAAGGCCGACGATGAGG
GAAGTTGTGCACATGCTCACTAACCCTCCCAAGTCCGTGACTAACTTGATCGCCTTCTGA

SEQ ID NO: 214 Brassica napus Brana_LRR-RLK translated amino acid
sequence
MAMRLLKTHLLFLHLHYVISILLLSFSPCFASTDMDHLLTLKSSMVGPNGHGLHDWVRSPSPSAHC
SFSGVSCDGDARVISLNVSFTPLFGTISPEIGMLDRLVNLTLAANNFSGMLPLEMKSLTSLKVLNI
SNNVNLNGTFPGEILTPMVDLEVLDAYNNNFTGPLPPEIPGLKKLRHLSLGGNFLTGEIPESYGDI
QSLEYLGLNGAGLSGESPAFLSRLKNLKEMYVGYFNSYTGGVPPEFGELTNLEVLDMASCTLTGEI
PTTLSNLKHLHTLFLHINNLTGNIPPELSGLISLKSLDLSINQLTGEIPQSFISLWNITLVNLFRN
NLHGPIPEFIGDMPNLQVLQVWENNFTLELPANLGRNGNLKKLDVSDNHLTGLIPMDLCRGGKLET
LVLSDNFFFGSIPEKLGRCKSLNKIRIVKNLLNGTVPAGLFTLPLVTIIELTDNFFSGELPGEMSG
DLLDHIYLSNNWFTGLIPPAIGNFKNLQDLFLDRNRFSGNIPREVFELKHLTKINTSANNLTGDIP
DSISRCTSLISVDLSRNRIGGDIPKDIHDVINLGTLNLSGNQLTGSIPIGIGKMTSLTTLDLSFND
LSGRVPLGGQFLVFNDTSFAGNPYLCLPRHVSCLTRPGQTSDRIHTALFSPSRIAITIIAAVTALI
LISVAIRQMNKKKHERSLSWKLTAFQRLDFKAEDVLECLQEENIIGKGGAGIVYRGSMPNNVDVAI
KRLVGRGTGRSDHGFTAEIQTLGRIRHRHIVRLLGYVANRDTNLLLYEYMPNGSLGELLHGSKGGH
LQWETRHRVAVEAAKGLCYLHHDCSPLILHRDVKSNNILLDSDFEAHVADFGLAKFLLDGAASECM
SSIAGSYGYIAPEYAYTLKVDEKSDVYSFGVVLLELIAGKKPVGEFGEGVDIVRWVRNTEGEIPQP
SDAATVVAIVDQRLTGYPLTSVIHVFKIAMMCVEDEATTRPTMREVVHMLTNPPKSVTNLIAF SEQ ID NO: 215 Eucalyptus grandis Eucgr_LRR-RLK nucleic acid
sequence AAA79716
ATGGCGGCGACGGCGGCGAAACCGCCCTGCAAGCCCGCTTCCTACTTCTGCTTCTCCTCCTCCTTC
TGCCTCCTCCTCTTCGTCTCGGCTTCCCTCGCGCAGAGCGACCTCGACGTGCTCCTGCAGCTCAGG
GCCGCCCTGGCCGCGCCCAACTCGACCGCCCTCCACGACTGGGTCGGCCCCTCCTCCTCCTCCTCA
TCCTCCTCGTCGCCGCCGCCCTTTCCGCATTGCTCCTTCACCGGGGTCACGTGCGACGCCGGCTCC
```

FIGURE 13 (continued)

```
CGGGTCGTGTCTCTCAACCTCACTGACGTCCGCCTCTTCGGCCGCGTCCCCCGCGAAATCGGCCTC
CTCCGCGACCTCGTCAACCTCACGCTCACCAGCTGCAACCTCTCGGGGACCCTCCCGCCGGAGCTC
GGCAACCTGACCGAGCTCGAAGTCCTCGACGTGTACGACAACAACTTCACGGCCCAGCTGCCGCCG
GAGGTGGTGGGGCTGAAGAAGCTGAAGTGGCTCAACCTCGCCGGCAATTACTTCTTCGGCGAGATA
CCGGAGGTTTACTCGGAGATGGAGAGCCTGGAGTACCTGGGCCTGCAGGCGAACCAGCTGAGCGGC
AGAGTCCCGGCGAGCCTCGCGAAGCTGAAGAACCTCCAGTGGCTCTACCTGGGCTACTTCAACACG
TACGATGGCGAGATTCCGGCGGAGTTCGGGTCTATGAAAGAGCTCAGACGCCTCGACTTGGCGAGC
TGCCGGCCTCTCCGGCGAGATTCCGGTGAGCCTGAGCGAGCTAAAGAAGTTAGACTCTCTGTTCCTC
CAGTGGAACAACCTCATGGGCGTTATCCCCCCGAGCTCTCGAAGATGTTGAGCCTCATGTCCCTC
GACCTCTCCAACAATTACCTCACTGGAGTGATTCCGGCGACCTTCGCCGAACTCAAGAACCTGACT
CTGCTCAACCTGTTCGCGAACCACCTGGAAGGCCAGATCCCCGAGTTCGTGGGCGAGCTTCCGAAC
CTGGAGACCCTCCAGGTTTGGGGCAACAACTTCACGATGATGTTGCCAGCGGGCCTAGGGAGGAAC
GGGAGGCTGCTATACGTCGACGTCACGCAGAACCACTTCACCGGCACGATCCCTCGGGAATTGTGC
CGGGGAGGGAGGCTCAAGACTCTGATCCTGACCAACAACTCGTTCTTTGGGCCCATCCCTGATGAA
TTCGGGGAGTGCAAGTCGCTGACCAAAGTCCGAGTCGGCAAGAACTTTCTCGACGGGACGATTCCT
CGGGGGATCTTCAACCTGCCGCAAGCAACTATAATCGAGCTTAACGACAATCTCTTCTCCGGCGAG
CTCCCGGCGCAGATGTCCGGCGAGAACTTGGTCATCCTGTCGCTCTCGAACAACCGGATTTCCGGT
GAGATCCCTCCGGCGATTGGCAACTTCAGCGGCCTGCGTACTCTGTTACTGGACGCGAACAGGTTC
TCCGGCAAGATTCCCAGCGAGCTTTTCTCGCCGAGGTTCCTACTGAGGGTGAACATCAGCGGGAAC
AGCATCAGCGGCAGGATTCCTGGTTCGGTCACTGGGTGCACTTCTCTGGCAGCCCTTGATTTGAGC
AGGAACAATCTCGCTGGCGAGATTCCGAACGGCTTGTCTAGCCTGAAAGTGTTGGCCGTCCTCAAT
CTGTCGAGCAACAGATTGACCGGTCCAGTTCCAAAGGAAATTGGCATCATGACCAGCCTCAATACG
CTCGATTTGTCCTTCAACGATCTCTCCGGCGAAGTCCCCCACGAAGGCCAGTTCCTCGTCTTCAAG
AACTCCTCCTTCGCCGGAAACCAGAAACTCTGCTCGCCAGGCCGCTTCTCTTGCCCTTCGCGGTCA
AGTGCCTCGCGCACTTCCTCGAGGGTTGTGATCACGGCAATCTCACTCGTGACCGCGGCGCTGCTC
ATCACCGTCACGGTCTACCAGGTCCTGAAGAGGAGGCGGCAGGGCTCGAGAGCCTGGAAGCTCACT
GCCTTCCAGAAGCTCGGCTTCAAGGCCGAGGACGTGCTCAAGTGCCTGGAGGAGGAGAATATCATC
GGCAAAGGTGGCGCGGGGATCGTCTACCGCGGGTCGATGCCCAACGGGACGGACGTCGCCATCAAG
CAGCTGGCGGGACGGGCGGCAACGGGCTCAGCGACCACGGCTTCTCCGCGGAGATTCAGACCCTC
GGTCGGATCCGGCACCGGAACATCGTGAGGCTCCTCGGATACCTCTCCAACAAGGACACCAACCTG
TTGCTGTACGAGTACATGCCCAATGGGAGCTTAGGGGAGCTGTTGCATGGTTCGAAAGGCGGCCAC
TTGCAGTGGGAGACGCGGTATCGGATCGCCGTGGAGGCCGCGAAGGGGCTGTGCTACCTCCACCAC
GATTGCTTGCCGCTGATAATTCATCGAGACGTGAAGTCGAACAACATTCTGCTGGATTCGGACTTC
GAGGCGCACGTCGCTGATTTCGGGCTGGCCAAGTTCTTGCAGGACGCCGGCGCATCGGAGTGCATG
TCGTCCGTGGCCGGTTCCTACGGCTACATAGCCCCAGAATACGCCTACACGCTGAAAGTGGACGAG
AAGAGCGACGTGTACAGCTTCGGGGTCGTGCTGCTGGAGCTGATAGCCGGGAGGAAGCCGGTGGGG
GAGTTTGGCGACGGCGTGGACATCGTGAGGTGGGTGAAGACCGCGTCGGACCCCCTCCCGCAGCCG
CCGTCGGACGCGGCCTTGGTGCTGGCCGTGATCGACCGCAGGCTGGGCGGGTACCCCATCGCGAGC
GTGATCCACCTCTTCAAGATCGCGTGCCGGTGCGTCGAGGAGGAGAGTTCCGAGAGGCCCACCATG
AGAGAAGTCGTCCACATGCTGACAAACCCGCCTCTGTCCGCCACCACCTTCGCCGTCGGCGCCACC
CCGGACCTCATCAAACTGTAG
```

SEQ ID NO: 216 Eucalyptus grandis Eucgr_LRR-RLK translated amino
acid sequence
MAATAAKPPCKPASYFCFSSSFCLLLFVSASLAQSDLDVLLQLRAALAAPNSTALHDWVGPSSSSS
SSSSPPPFPHCSFTGVTCDAGSRVVSLNLTDVRLFGRVPREIGLLRDLVNLTLTSCNLSGTLPPEL
GNLTELEVLDVYDNNFTAQLPPEVVGLKKLKWLNLAGNYFFGEIPEVYSEMESLEYLGLQANQLSG
RVPASLAKLKNLQWLYLGYFNTYDGEIPAEFGSMKELRRLDLASCGLSGEIPVSLSELKKLDSLFL FIGURE 13 (continued)

QWNNLMGVIPPELSKMLSLMSLDLSNNYLTGVIPATFAELKNLTLLNLFANHLEGQIPEFVGELPN
LETLQVWGNNFTMMLPAGLGRNGRLLYVDVTQNHFTGTIPRELCRGGRLKTLILTNNSFFGPIPDE
FGECKSLTKVRVGKNFLDGTIPRGIFNLPQATIIELNDNLFSGELPAQMSGENLVILSLSNNRISG
EIPPAIGNFSGLRTLLLDANRFSGKIPSELFSPRFLLRVNISGNSISGRIPGSVTGCTSLAALDLS
RNNLAGEIPNGLSSLKVLAVLNLSSNRLTGPVPKEIGIMTSLNTLDLSFNDLSGEVPHEGQFLVFK
NSSFAGNQKLCSPGRFSCPSRSSASRTSSRVVITAISLVTAALLITVTVYQVLKRRRQGSRAWKLT
AFQKLGFKAEDVLKCLEEENIIGKGGAGIVYRGSMPNGTDVAIKQLAGRGGNGLSDHGFSAEIQTL
GRIRHRNIVRLLGYLSNKDTNLLLYEYMPNGSLGELLHGSKGGHLQWETRYRIAVEAAKGLCYLHH
DCLPLIIHRDVKSNNILLDSDFEAHVADFGLAKFLQDAGASECMSSVAGSYGYIAPEYAYTLKVDE
KSDVYSFGVVLLELIAGRKPVGEFGDGVDIVRWVKTASDPLPQPPSDAALVLAVIDRRLGGYPIAS
VIHLFKIACRCVEEESSERPTMREVVHMLTNPPLSATTFAVGATPDLIKL

SEQ ID NO: 217 Glycine max Glyma_CLV1A LRR-RLK nucleic acid sequence AF197946
ATGAGAAGCTGTGTGTGTTACACGCTTTTATTGTTTGTTTTCTTCATATGGCTACACGTGGCAACG
TGTTCTTCGTTCAGTGACATGGATGCGCTGCTGAAGCTGAAGGAGTCCATGAAGGGAGACAGAGCC
AAAGACGACGCGCTCCATGACTGGAAGTTTTCCACGTCGCTTTCTGCACACTGTTTCTTTTCAGGT
GTATCTTGCGACCAAGAACTTCGAGTTGTTGCTATCAACGTCTCCTTTGTTCCTCTCTTCGGCCAC
GTTCCGCCGGAGATCGGAGAATTGGACAAACTTGAAAACCTCACCATCTCGCAGAACAACCTCACC
GGCGAACTTCCCAAGGAGCTCGCCGCCCTCACTTCCCTCAAGCACCTCAACATCTCTCACAACGTC
TTCTCCGGCTATTTTCCCGGCAAAATAATTCTTCCGATGACCGAACTCGAGGTCCTCGACGTCTAC
GACAACAACTTCACCGGATCGCTTCCGGAAGAGTTCGTGAAACTGGAGAAATTGAAATACCTGAAG
CTCGACGGAAACTATTTCTCCGGAAGCATACCGGAGAGTTACTCGGAGTTTAAGAGCTTGGAGTTT
TTAAGCTTAAGCACCAATAGCTTATCGGGGAATATTCCGAAGAGTTTGTCTAAGTTGAAGACGCTG
AGGATTCTCAAGCTCGGATACAACAACGCTTACGAAGGCGGAATTCCACCGGAGTTCGGCACCATG
GAATCTCTGAAATACCTTGACCTCTCAAGCTGCAACCTCAGCGGCGAGATTCCACCGAGTCTAGCA
AATATGAGAAACCTCGACACGTTGTTCTTGCAAATGAATAACCTCACCGGAACCATTCCGTCTGAG
CTCTCCGACATGGTGAGCCTCATGTCACTGGATCTCTCCTTCAACGGCCTCACCGGGGAGATACCG
ACGCGCTTCTCTCAGCTGAAAAACCTCACTCTGATGAACTTCTTCCACAACAATCTCCGAGGCTCA
GTTCCCTCCTTCGTCGGCGAGCTTCCTAATCTGGAAACGCTGCAGCTCTGGGAGAACAATTTCTCC
TCTGAGCTCCCGCAGAACCTGGGGCAAAACGGGAAGTTCAAGTTCTTCGACGTCACGAAGAATCAC
TTCAGCGGGTTGATCCCTCGGGATTTGTGCAAGAGTGGGAGGTTACAAACGTTCTTGATCACAGAT
AACTTCTTCCATGGTCCAATCCCTAACGAGATTGCTAACTGCAAGTCTCTAACCAAGATCCGAGCC
TCCAATAACTACCTTAACGGCGCAGTTCCGTCAGGGATTTTCAAGCTACCTTCCGTCACGATAATC
GAGTTGGCCAATAACCGTTTTAACGGAGAACTGCCTCCCGAAATTTCCGGCGATTCACTCGGGATT
CTCACTCTTTCCAACAACTTATTCACTGGGAAAATTCCCCCAGCGTTGAAGAACTTAAGGGCACTG
CAGACTCTGTCACTTGACACGAACGAATTCCTTGGAGAAATCCCGGGGGAGGTTTTTGACCTACCA
ATGCTGACTGTGGTCAACATAAGCGGCAACAATCTCACCGGACCAATCCCAACGACGTTTACTCGC
TGCGTTTCACTCGCCGCCGTTGATCTTAGCCGGAACATGCTTGACGGGGAGATTCCCAAGGGGATG
AAAAACCTAACGGATTTAAGCATTTTCAATGTGTCGATAAACCAAATCTCAGGGTCAGTCCCAGAC
GAGATTCGCTTCATGTTGAGTCTCACCACGCTGGATCTCTCCTACAACAATTTCATCGGCAAGGTC
CCTACCGGTGGTCAGTTTTTGGTCTTCAGCGACAAATCCTTTGCAGGGAACCCGAATCTCTGTAGT
TCCCACTCTTGCCCTAATTCCTCGTTGAAGAAGAGACGCGGCCCTTGGAGTTTGAAATCGACGAGG
GTGATCGTCATGGTGATTGCACTGGCCACTGCGGCGATTCTCGTGGCGGGGACGGAGTACATGAGG
AGGAGGAGGAAGCTGAAGCTTGCGATGACGTGGAAGCTGACGGGGTTCCAGCGGCTGAACTTGAAA
GCCGAGGAGGTGGTGGAGTGTCTAAAAGAAGAGAACATAATAGGAAAAGGAGGAGCAGGGATCGTG
TACCGCGGGTCCATGAGAAACGGAAGCGACGTGGCAATAAAGCGGTTGGTTGGAGCGGGGAGTGGA
AGGAACGATTACGGGTTCAAAGCGGAGATAGAGACGGTGGGGAAGATAAGGCACAGGAACATAATG

```
AGGCTTTTGGGTTACGTGTCGAACAAGGAGACGAACTTGCTTCTGTATGAGTACATGCCGAATGGG
AGCTTAGGGGAGTGGCTGCATGGTGCCAAGGGAGGTCATTTAAAGTGGGAAATGAGGTACAAGATT
GCGGTGGAAGCTGCAAAGGGACTATGCTATTTGCACCATGATTGTTCCCCTCTTATCATTCACAGG
GATGTCAAGTCTAATAATATATTGCTCGATGCTCACTTTGAGGCTCATGTTGCTGATTTTGGCCTT
GCCAAGTTCTTGTACGACCTTGGCTCCTCTCAGTCCATGTCCTCCATTGCTGGCTCCTACGGCTAC
ATTGCTCCAGAGTATGCTTACACTTTGAAAGTGGACGAGAAAGTGATGTGTACAGCTTTGGCGTG
GTGCTGTTGGAACTGATAATAGGGAGGAAGCCAGTTGGTGAGTTTGGAGACGGGGTGGACATCGTT
GGATGGGTCAACAAAACGAGATTGGAGCTCTCTCAGCCGTCGGATGCAGCAGTAGTGTTGGCAGTG
GTGGACCCAAGGCTTAGTGGGTATCCATTGATAAGTGTCATTTACATGTTCAACATAGCTATGATG
TGTGTTAAAGAAGTGGGGCCCACTAGGCCTACCATGAGGGAAGTAGTTCATATGCTCTCAAATCCT
CCTCACTTTACCACTCACACTCACAACCTAATTAATCTCTAG
```

SEQ ID NO: 218 Glycine max Glyma_CLV1A LRR-RLK translated amino acid sequence

```
MRSCVCYTLLLFVFFIWLHVATCSSFSDMDALLKLKESMKGDRAKDDALHDWKFSTSLSAHCFFSG
VSCDQELRVVAINVSFVPLFGHVPPEIGELDKLENLTISQNNLTGELPKELAALTSLKHLNISHNV
FSGYFPGKIILPMTELEVLDVYDNNFTGSLPEEFVKLEKLKYLKLDGNYFSGSIPESYSEFKSLEF
LSLSTNSLSGNIPKSLSKLKTLRILKLGYNNAYEGGIPPEFGTMESLKYLDLSSCNLSGEIPPSLA
NMRNLDTLFLQMNNLTGTIPSELSDMVSLMSLDLSFNGLTGEIPTRFSQLKNLTLMNFFHNNLRGS
VPSFVGELPNLETLQLWENNFSSELPQNLGQNGKFKFFDVTKNHFSGLIPRDLCKSGRLQTFLITD
NFFHGPIPNEIANCKSLTKIRASNNYLNGAVPSGIFKLPSVTIIELANNRFNGELPPEISGDSLGI
LTLSNNLFTGKIPPALKNLRALQTLSLDTNEFLGEIPGEVFDLPMLTVVNISGNNLTGPIPTTFTR
CVSLAAVDLSRNMLDGEIPKGMKNLTDLSIFNVSINQISGSVPDEIRFMLSLTTLDLSYNNFIGKV
PTGGQFLVFSDKSFAGNPNLCSSHSCPNSSLKKRRGPWSLKSTRVIVMVIALATAAILVAGTEYMR
RRRKLKLAMTWKLTGFQRLNLKAEEVVECLKEENIIGKGGAGIVYRGSMRNGSDVAIKRLVGAGSG
RNDYGFKAEIETVGKIRHRNIMRLLGYVSNKETNLLLYEYMPNGSLGEWLHGAKGGHLKWEMRYKI
AVEEAKGLCYLHHDCSPLIIHRDVKSNNILLDAHFEAHVADFGLAKFLYDLGSSQSMSSIAGSYGY
IAPEYAYTLKVDEKSDVYSFGVVLLELIIGRKPVGEFGDGVDIVGWVNKTRLELSQPSDAAVVLAV
VDPRLSGYPLISVIYMFNIAMMCVKEVGPTRPTMREVVHMLSNPPHFTTHTHNLINL
```

SEQ ID NO: 219 Glycine max Glyma_NARK_CLV1B LRR-RLK nucleic acid sequence AF197947

```
ATGAGAAGCTGTGTGTGCTACACGCTATTATTGTTTATTTTCTTCATATGGCTGCGCGTGGCAACG
TGCTCTTCGTTCACTGACATGGAATCGCTTCTGAAGCTGAAGGACTCCATGAAAGGAGATAAAGCC
AAAGACGACGCTCTCCATGACTGGAAGTTTTTCCCCTCGCTTTCTGCACACTGTTTCTTTTCAGGC
GTAAAATGCGACCGAGAACTTCGAGTCGTTGCTATCAACGTCTCGTTTGTTCCTCTCTTCGGTCAC
CTTCCGCCGGAGATCGGACAATTGGACAAACTCGAGAACCTCACCGTCTCGCAGAACAACCTCACC
GGCGTACTTCCCAAGGAGCTCGCCGCCCTCACTTCCCTCAAGCACCTCAACATCTCTCACAACGTC
TTCTCCGGCCATTTCCCCGGCCAAATTATCCTTCCGATGACGAAACTGGAGGTCCTCGACGTCTAC
GACAACAACTTCACCGGACCGCTTCCCGTAGAGTTGGTGAAACTGGAGAAATTAAAATACCTGAAG
CTCGACGGAAACTATTTCTCCGGCAGCATACCGGAGAGTTACTCGGAGTTTAAGAGCTTGGAGTTT
TTAAGCTTAAGCACCAATAGCTTATCGGGGAAGATTCCCAAGAGTTTGTCGAAGTTGAAGACGCTG
AGGTACCTAAAACTCGGATACAACAACGCTTACGAAGGTGGAATTCCACCGGAGTTTGGCAGCATG
AAATCTCTGAGATACCTTGACCTCTCTAGCTGCAACCTCAGCGGCGAGATTCCACCGAGCCTTGCA
AATCTGACAAACCTTGACACGTTGTTCCTGCAAATTAACAACCTCACCGGAACCATTCCGTCGGAG
CTCTCCGCTATGGTGAGCCTCATGTCACTTGATCTCTCCATCAACGACCTCACCGGTGAGATACCG
ATGAGCTTCTCACAGCTTAGAAACCTCACTCTCATGAACTTCTTCCAAAACAATCTTCGCGGCTCA
GTTCCGTCCTTCGTCGGCGAGCTTCCGAATCTGGAAACGCTGCAGCTCTGGGATAACAACTTCTCC
```

```
TTCGTGCTACCTCCGAACCTTGGGCAAAACGGCAAGTTAAAGTTCTTCGACGTCATCAAGAATCAC
TTCACCGGGTTGATCCCTCGAGATTTGTGTAAGAGTGGGAGGTTACAAACGATCATGATCACAGAT
AACTTCTTCCGCGGTCCAATCCCTAACGAGATTGGTAACTGCAAGTCTCTCACCAAGATCCGAGCC
TCCAATAACTACCTTAACGGCGTGGTTCCGTCAGGGATTTTCAAACTACCTTCTGTCACGATAATC
GAGCTGGCCAATAACCGTTTTAACGGCGAACTGCCTCCTGAGATTTCCGGCGAATCCCTGGGGATT
CTCACTCTTTCCAACAACTTATTCAGTGGGAAAATTCCCCAGCGTTGAAGAACTTGAGGGCACTG
CAGACTCTCTCACTTGACGCAAACGAGTTCGTTGGAGAAATACCGGGAGAGGTTTTGACCTACCG
ATGCTGACTGTGGTCAACATAAGCGGCAACAATCTAACCGGACCAATCCCAACGACGTTGACTCGC
TGCGTTTCACTCACCGCCGTGGACCTCAGCCGGAACATGCTTGAAGGGAAGATTCCGAAGGGAATC
AAAAACCTCACGGACTTGAGCATTTTCAATGTGTCGATAAACCAAATTTCAGGGCCAGTCCCTGAG
GAGATTCGCTTCATGTTGAGTCTCACCACATTGGATCTATCCAACAACAATTTCATCGGCAAGGTC
CCAACCGGGGGTCAGTTCGCGGTCTTCAGCGAGAAATCCTTTGCAGGGAACCCCAACCTCTGTACC
TCCCACTCTTGCCCGAATTCCTCGTTGTACCCTGACGACGCCTTGAAGAAGAGGCGCGGCCCTTGG
AGTTTGAAATCCACGAGGGTGATAGTCATCGTGATTGCACTGGGCACAGCCGCGCTGCTGGTGGCG
GTGACGGTGTACATGATGAGGAGGAGGAAGATGAACCTTGCAAAGACGTGGAAGCTGACGGCGTTC
CAGCGGCTGAACTTCAAAGCCGAGGACGTGGTGGAGTGTCTGAAGGAGGAGAACATAATAGGAAAA
GGAGGGGCAGGGATCGTGTACCGCGGGTCCATGCCAAACGGAACAGACGTGGCGATAAAGCGGTTG
GTTGGGGCGGGGAGTGGAAGGAACGATTACGGATTCAAAGCGGAGATAGAAACGCTGGGGAAGATA
AGGCACAGGAACATAATGAGGCTTTTAGGTTACGTGTCGAACAAGGAGACGAACTTGCTGCTGTAT
GAGTACATGCCAAATGGGAGCTTAGGGGAATGGCTGCATGGTGCCAAAGGAGGGCACTTGAAGTGG
GAAATGAGGTACAAGATTGCGGTGGAAGCTGCTAAGGGACTGTGCTATTTGCACCATGATTGTTCC
CCTCTTATCATTCACAGGGATGTCAAGTCTAATAATATATTGCTGGATGGGGACTTGGAGGCCCAT
GTTGCTGATTTTGGCCTTGCCAAGTTCTTGTACGACCCTGGCGCCTCAGTCCATGTCCTCCATT
GCTGGCTCCTACGGCTACATTGCTCCAGAGTATGCATACACTTTGAAAGTGGACGAGAAAGTGAT
GTGTACAGCTTTGGCGTTGTGCTGCTGGAGCTGATAATAGGGAGGAAGCCAGTGGGAGAGTTTGGA
GACGGGGTGGACATCGTTGGATGGGTCAACAAAACGAGATTGGAGCTCGCTCAGCCGTCGGATGCA
GCGTTGGTGTTGGCAGTGGTGGACCCAAGGTTGAGTGGGTATCCATTGACAAGTGTCATTTACATG
TTCAACATAGCTATGATGTGTGTTAAAGAAATGGGCCCGCTAGGCCTACCATGAGGGAAGTCGTT
CATATGCTCTCAGAGCCTCCTCACTCTGCTACTCACACTCACAACCTAATTAATCTCTAG
```

SEQ ID NO: 220 Glycine max Glyma_NARK_CLV1B LRR-RLK translated amino acid sequence
```
MRSCVCYTLLLFIFFIWLRVATCSSFTDMESLLKLKDSMKGDKAKDDALHDWKFFPSLSAHCFFSG
VKCDRELRVVAINVSFVPLFGHLPPEIGQLDKLENLTVSQNNLTGVLPKELAALTSLKHLNISHNV
FSGHFPGQIILPMTKLEVLDVYDNNFTGPLPVELVKLEKLKYLKLDGNYFSGSIPESYSEFKSLEF
LSLSTNSLSGKIPKSLSKLKTLRYLKLGYNNAYEGGIPPEFGSMKSLRYLDLSSCNLSGEIPPSLA
NLTNLDTLFLQINNLTGTIPSELSAMVSLMSLDLSINDLTGEIPMSFSQLRNLTLMNFFQNNLRGS
VPSFVGELPNLETLQLWDNNFSFVLPPNLGQNGKLKFFDVIKNHFTGLIPRDLCKSGRLQTIMITD
NFFRGPIPNEIGNCKSLTKIRASNNYLNGVVPSGIFKLPSVTIIELANNRFNGELPPEISGESLGI
LTLSNNLFSGKIPPALKNLRALQTLSLDANEFVGEIPGEVFDLPMLTVVNISGNNLTGPIPTTLTR
CVSLTAVDLSRNMLEGKIPKGIKNLTDLSIFNVSINQISGPVPEEIRFMLSLTTLDLSNNNFIGKV
PTGGQFAVFSEKSFAGNPNLCTSHSCPNSSLYPDDALKKRRGPWSLKSTRVIVIVIALGTAALLVA
VTVYMMRRRKMNLAKTWKLTAFQRLNFKAEDVVECLKEENIIGKGGAGIVYRGSMPNGTDVAIKRL
VGAGSGRNDYGFKAEIETLGKIRHRNIMRLLGYVSNKETNLLLYEYMPNGSLGEWLHGAKGGHLKW
EMRYKIAVEAAKGLCYLHHDCSPLIIHRDVKSNNILLDGDLEAHVADFGLAKFLYDPGASQSMSSI
AGSYGYIAPEYAYTLKVDEKSDVYSFGVVLLELIIGRKPVGEFGDGVDIVGWVNKTRLELAQPSDA
ALVLAVVDPRLSGYPLTSVIYMFNIAMMCVKEMGPARPTMREVVHMLSEPPHSATHTHNLINL
```

SEQ ID NO: 221 Lotus japonica Lotja_HAR1 LRR-RLK nucleic acid sequence AB092810.1

```
ATGAGAATCAGAGTGTCTTACTTGTTAGTGCTATGTTTTACCTTAATTTGGTTCAGATGGACAGTG
GTGTACTCTTCATTCAGTGATCTCGATGCACTGCTAAAGCTCAAAGAATCCATGAAGGGAGCCAAA
GCCAAACACCACGCACTCGAAGATTGGAAGTTTTCCACCTCACTCTCAGCACACTGTTCGTTTTCC
GGCGTAACGTGCGACCAGAACTTGCGAGTGGTTGCTCTCAACGTCACGCTGGTTCCGCTTTTCGGC
CACCTTCCGCCGGAGATAGGGTTGTTGGAGAAGTTAGAGAATCTCACCATCTCCATGAACAACCTC
ACTGACCAGCTTCCCTCCGACCTTGCAAGCCTCACCTCCCTCAAGGTCCTCAACATCTCCCACAAC
CTCTTCTCCGGCCAATTCCCTGGTAACATCACCGTTGGCATGACGGAGCTCGAGGCCCTTGATGCC
TACGACAACAGCTTCTCCGGTCCTCTCCCGGAGGAAATCGTCAAGCTCGAGAAACTCAAGTACCTC
CACCTCGCCGGGAACTATTTCTCCGGTACAATACCGGAGAGCTACTCGGAGTTTCAGAGCCTTGAG
TTTCTCGGCTTGAACGCAAACAGCTTAACCGGGAGAGTCCCGGAGAGCTTGGCGAAGTTGAAGACG
TTGAAGGAACTGCACCTCGGTTACTCGAACGCTTACGAAGGTGGAATCCCGCCGGCGTTCGGTTCC
ATGGAGAATCTCCGCCTGCTAGAAATGGCTAACTGCAACCTCACCGGCGAGATTCCACCGAGCCTG
GGGAATCTAACCAAACTCCACTCCTTATTCGTGCAGATGAACAACCTCACCGGAACCATTCCGCCG
GAGCTATCTTCCATGATGAGCCTCATGTCACTGGACCTCTCCATCAACGACCTCACCGGCGAGATC
CCGGAGAGCTTCTCAAAACTGAAGAATCTCACTCTAATGAACTTCTTCCAAAACAAGTTCCGCGGC
TCTCTCCCCTCCTTCATCGGCGACCTTCCAAATCTCGAAACGCTTCAGGTTTGGGAGAACAATTTC
TCCTTCGTGCTGCCGCACAATCTCGGCGGAAACGGAAGATTCTTATACTTCGACGTCACCAAAAAC
CACCTCACCGGGTTGATTCCGCCGGATCTATGCAAAAGCGGGAGGTTGAAAACGTTCATCATCACT
GATAACTTCTTCCGTGGCCCAATTCCCAAGGGAATCGGCGAGTGTAGGTCACTCACGAAGATTCGC
GTGGCTAACAACTTCCTTGACGGTCCAGTTCCACCAGGGGTTTTCCAACTGCCTTCCGTTACGATA
ACGGAATTGAGCAATAACCGCCTCAACGGCGAACTGCCTTCCGTGATTTCAGGCGAATCTCTCGGG
ACGCTCACGCTTTCCAACAACCTCTTCACCGGAAAAATCCCCGCCGCGATGAAAAACCTCAGAGCG
TTGCAGAGCTTATCCCTCGACGCCAATGAGTTCATCGGAGAAATTCCGGGGGGAGTTTTTGAAATC
CCAATGCTCACCAAAGTCAACATCAGCGGCAACAACCTCACAGGTCCGATCCCAACGACGATCACT
CACCGTGCTTCTCTGACGGCGGTAGACCTCAGCCGGAACAACCTCGCCGGCGAGGTTCCGAAGGGG
ATGAAGAATTTGATGGACTTAAGCATTCTGAATCTCTCACGCAACGAGATTCTGGACCGGTTCCT
GATGAGATTCGATTCATGACTAGCCTCACGACGCTGGATCTCTCGAGTAACAATTTCACCGGAACA
GTCCCCACCGGCGGCCAGTTTCTGGTATTCAACTACGACAAGACGTTCGCCGGAAACCCCGAACCTC
TGTTTCCCTCACAGAGCATCCTGTCCTTCTGTCCTCTACGACTCGTTAAGGAAAACCCGCGCCAAA
ACGGCGCGGGTGAGGGCGATTGTGATTGGAATTGCACTCGCCACGGCGGTGTTGCTGGTGGCGGTG
ACGGTGCACGTGGTCAGAAAGCGGAGGCTGCACCGAGCGCAGGCCTGGAAGCTCACCGCGTTCCAG
AGGCTGGAGATCAAGGCGGAGGATGTAGTCGAGTGTTTAAAGGAAGAGAATATAATTGGGAAAGGA
GGAGCAGGCATCGTGTACAGAGGTTCCATGCCGAACGGAACCGACGTGGCGATCAAGCGGTTGGTA
GGGCAGGGAAGTGGGAGGAACGATTACGGTTTCAGGGCGGAGATTGAGACGTTGGGGAAAATCCGG
CACCGGAATATAATGAGGCTTCTGGGGTACGTTTCGAACAAGGATACGAACTTGTTGCTGTATGAG
TACATGCCGAATGGGAGCTTAGGGGAGTGGCTGCACGGTGCGAAGGGTGGGCACTTGCGGTGGGAG
ATGAGGTATAAGATTGCGGTGGAGGCGGCGAGGGGACTCTGCTATATGCACCATGATTGCTCTCCT
CTTATTATTCACAGGGATGTTAAGTCCAACAACATTTTGCTTGATGCTGATTTTGAGGCTCATGTT
GCTGATTTTGGACTTGCTAAGTTTTTGTATGACCCTGGTGCTTCTCAGTCCATGTCCTCCATTGCT
GGCTCCTACGGTTACATTGCTCCAGAGTATGCTTACACGCTGAAAGTGGACGAGAAGAGTGACGTG
TACAGCTTTGGCGTTGTGCTGTTGGAACTGATCATAGGGAGAAAGCCAGTGGGTGAGTTTGGAGAT
GGCGTGGACATCGTTGGATGGGTCAACAAAACCATGTCAGAGCTCTCTCAGCCGTCGGATACTGCA
TTAGTGTTAGCAGTGGTGGACCCTCGCCTCAGTGGATACCCCTTGACAAGTGTCATCCACATGTTC
AACATAGCTATGATGTGTGTGAAGGAAATGGGCCCTGCTAGGCCCACCATGAGGGAAGTTGTTCAT
ATGCTCACTAATCCTCCTCAGTCTAATACCTCCACTCAAGACCTAATTAATCTCTAG
```

FIGURE 13 (continued)

SEQ ID NO: 222 Lotus japonica Lotja_HAR1 LRR-RLK translated amino acid sequence
MRIRVSYLLVLCFTLIWFRWTVVYSSFSDLDALLKLKESMKGAKAKHHALEDWKFSTSLSAHCSFS
GVTCDQNLRVVALNVTLVPLFGHLPPEIGLLEKLENLTISMNNLTDQLPSDLASLTSLKVLNISHN
LFSGQFPGNITVGMTELEALDAYDNSFSGPLPEEIVKLEKLKYLHLAGNYFSGTIPESYSEFQSLE
FLGLNANSLTGRVPESLAKLKTLKELHLGYSNAYEGGIPPAFGSMENLRLLEMANCNLTGEIPPSL
GNLTKLHSLFVQMNNLTGTIPPELSSMMSLMSLDLSINDLTGEIPESFSKLKNLTLMNFFQNKFRG
SLPSFIGDLPNLETLQVWENNFSFVLPHNLGGNGRFLYFDVTKNHLTGLIPPDLCKSGRLKTFIIT
DNFFRGPIPKGIGECRSLTKIRVANNFLDGPVPPGVFQLPSVTITELSNNRLNGELPSVISGESLG
TLTLSNNLFTGKIPAAMKNLRALQSLSLDANEFIGEIPGGVFEIPMLTKVNISGNNLTGPIPTTIT
HRASLTAVDLSRNNLAGEVPKGMKNLMDLSILNLSRNEISGPVPDEIRFMTSLTTLDLSSNNFTGT
VPTGGQFLVFNYDKTFAGNPNLCFPHRASCPSVLYDSLRKTRAKTARVRAIVIGIALATAVLLVAV
TVHVVRKRRLHRAQAWKLTAFQRLEIKAEDVVECLKEENIIGKGGAGIVYRGSMPNGTDVAIKRLV
GQGSGRNDYGFRAEIETLGKIRHRNIMRLLGYVSNKDTNLLLYEYMPNGSLGEWLHGAKGGHLRWE
MRYKIAVEAARGLCYMHHDCSPLIIHRDVKSNNILLDADFEAHVADFGLAKFLYDPGASQSMSSIA
GSYGYIAPEYAYTLKVDEKSDVYSFGVVLLELIIGRKPVGEFGDGVDIVGWVNKTMSELSQPSDTA
LVLAVVDPRLSGYPLTSVIHMFNIAMMCVKEMGPARPTMREVVHMLTNPPQSNTSTQDLINL

SEQ ID NO: 223 Medicago truncatula Medtr_SUNN nucleic acid sequence AY769943
ATGAAAAACATCACATGTTATTTGCTACTATTGTGCATGTTATTTACAACGTGTTATTCATTAAAT
AATGATCTTGATGCGTTGCTAAAGCTAAAAAAATCAATGAAAGGAGAGAAAGCCAAGATGATGCA
CTCAAAGACTGGAAATTTTCAACTTCTGCTTCAGCTCACTGTTCATTTTCCGGTGTAAAATGCGAC
GAAGATCAACGTGTGATTGCTTTGAACGTGACGCAAGTTCCACTCTTCGGACACCTTTCCAAGGAG
ATCGGAGAGTTGAACATGCTCGAGAGCCTTACAATCACTATGGACAATCTCACCGGCGAGCTTCCA
ACTGAGCTATCCAAACTTACTTCTCTTAGAATCCTCAACATCTCTCACAACCTCTTCTCCGGTAAC
TTCCCCGGCAACATCACTTTTGGAATGAAGAAACTTGAGGCTCTAGATGCTTATGACAATAATTTC
GAAGGTCCTCTTCCAGAGGAAATCGTTAGCCTGATGAAACTCAAGTACTTAAGTTTTGCTGGAAAC
TTTTTCTCCGGTACAATACCGGAGAGTTACTCGGAGTTTCAGAAGTTGGAGATTTTAAGGCTGAAC
TATAACAGTTTAACAGGGAAGATTCCTAAGAGTTTGTCGAAGTTAAAGATGCTAAAGGAACTCCAA
TTAGGTTATGAGAATGCTTACTCCGGTGGAATTCCACCGGAGTTAGGTTCAATCAAATCTCTCCGA
TATCTTGAAATTTCTAACGCTAACCTCACCGGAGAAATTCCACCGAGTCTTGGAAATTTAGAAAAC
CTCGACTCCTTGTTTTTGCAAATGAACAACCTCACCGGAACAATTCCACCCGAACTCTCTTCAATG
CGGAGTCTCATGTCGTTGGATCTCTCCATCAACGGACTCTCAGGGGAGATTCCAGAAACCTTCTCA
AAGCTGAAAAATCTCACTCTCATCAATTTCTTCCAGAACAAGCTTCGCGGTTCAATTCCAGCGTTC
ATCGGCGATCTTCCTAACCTCGAAACGCTTCAGGTTTGGGAAAACAATTTCTCTTTTGTATTGCCG
CAGAATCTCGGTTCAAACGGAAAGTTCATATACTTTGACGTTACGAAGAATCACCTCACCGGATTG
ATCCCACCGGAGTTATGCAAATCAAAGAAGTTGAAAACGTTTATCGTTACTGACAACTTCTTCCGC
GGTCCAATACCTAACGGAATTGGCCCGTGTAAGTCACTTGAAAAAATCAGAGTGGCTAATAACTAC
TTGGACGGCCCCGGTCCCACCGGGGATTTTTCAGTTGCCTTCTGTACAGATAATAGAGCTTGGAAAT
AACCGTTTTAACGGCCAACTACCAACGGAGATTTCTGGCAATTCTCTCGGGAATCTCGCTCTTTCT
AACAATTTATTTACCGGGAGGATTCCGGCGTCCATGAAGAATCTCCGATCACTGCAGACGCTGTTA
CTCGATGCCAATCAGTTTCTCGGAGAAATTCCGGCAGAGGTCTTTGCTTTACCGGTGTTGACTAGA
ATCAACATAAGTGGCAATAATCTCACTGGTGGAATTCCAAAGACGGTTACTCAATGTAGTTCACTG
ACTGCAGTTGACTTCAGCCGAAACATGCTTACCGGTGAGGTTCCTAAAGGGATGAAGAATCTGAAG
GTTCTAAGCATTTTTAATGTTTCGCATAATAGCATATCTGGGAAAATCCCTGATGAGATTAGATTC
ATGACGAGTCTAACGACGCTGGATTTATCTTACAACAATTTTACCGGAATTGTCCCCACAGGTGGT
CAGTTTTTGGTCTTCAACGACCGGTCATTTGCCGGAAATCCTAGCCTATGTTTCCCCCACCAAACA

```
ACATGTTCTTCATTGCTCTATCGTTCGAGAAAAAGCCATGCAAAGGAGAAAGCTGTCGTCATAGCA
ATCGTCTTCGCCACAGCGGTGTTAATGGTAATTGTAACACTGCACATGATGAGGAAGAGGAAGCGT
CACATGGCAAAAGCATGGAAGCTAACAGCGTTTCAGAAGTTGGAATTCAGAGCAGAGGAAGTAGTG
GAGTGTCTGAAAGAAGAGAACATAATAGGAAAAGGAGGAGCTGGGATTGTCTACAGAGGGTCCATG
GCAAACGGAACAGACGTTGCGATAAAGCGTTTAGTTGGACAAGGAAGTGGTAGAAATGATTATGGA
TTCAAAGCTGAGATAGAGACATTGGGAAGGATTAGACACAGAAACATAATGAGGCTTTTGGGATAT
GTTTCAAACAAGGATACAAATTTGTTGTTGTATGAGTACATGCCTAATGGTAGTTTAGGTGAGTGG
CTTCATGGTGCAAAAGGTTGTCATTTGAGTTGGGAAATGAGGTACAAAATTGCTGTGGAAGCTGCT
AAGGGACTTTGCTATTTGCACCATGATTGTTCACCTCTTATCATTCATAGGGATGTTAAGTCTAAT
AATATATTGCTTGATGCTGATTTTGAGGCTCATGTTGCTGATTTTGGACTTGCTAAGTTCTTGTAT
GATCCAGGTGCTTCTCAATCCATGTCCTCAATTGCTGGCTCCTACGGCTACATTGCTCCAGAATAT
GCATACACTCTCAAAGTGGATGAAAAAGTGATGTGTATAGTTTCGGAGTGGTGCTATTGGAGCTG
ATAATAGGAAGGAAGCCAGTTGGTGAATTTGGAGATGGAGTAGACATCGTTGGATGGATCAATAAA
ACTGAATTAGAACTTTATCAGCCATCAGATAAAGCATTAGTGTCAGCAGTGGTGGACCCACGACTC
AATGGATACCCTTTGACTAGTGTTATCTACATGTTCAACATAGCTATGATGTGTGTTAAAGAAATG
GGACCTGCAAGGCCTACCATGAGGGAAGTTGTTCATATGCTCACTAATCCACCTCACTCTACAAGT
CACAACTTGATTAATCTCTAG
```

SEQ ID NO: 224 Medicago truncatula Medtr_SUNN translated amino acid sequence

```
MKNITCYLLLLCMLFTTCYSLNNDLDALLKLKKSMKGEKAKDDALKDWKFSTSASAHCSFSGVKCD
EDQRVIALNVTQVPLFGHLSKEIGELNMLESLTITMDNLTGELPTELSKLTSLRILNISHNLFSGN
FPGNITFGMKKLEALDAYDNNFEGPLPEEIVSLMKLKYLSFAGNFFSGTIPESYSEFQKLEILRLN
YNSLTGKIPKSLSKLKMLKELQLGYENAYSGGIPPELGSIKSLRYLEISNANLTGEIPPSLGNLEN
LDSLFLQMNNLTGTIPPELSSMRSLMSLDLSINGLSGEIPETFSKLKNLTLINFFQNKLRGSIPAF
IGDLPNLETLQVWENNFSFVLPQNLGSNGKFIYFDVTKNHLTGLIPPELCKSKKLKTFIVTDNFFR
GPIPNGIGPCKSLEKIRVANNYLDGPVPPGIFQLPSVQIIELGNNRFNGQLPTEISGNSLGNLALS
NNLFTGRIPASMKNLRSLQTLLLDANQFLGEIPAEVFALPVLTRINISGNNLTGGIPKTVTQCSSL
TAVDFSRNMLTGEVPKGMKNLKVLSIFNVSHNSISGKIPDEIRFMTSLTTLDLSYNNFTGIVPTGG
QFLVFNDRSFAGNPSLCFPHQTTCSSLLYRSRKSHAKEKAVVIAIVFATAVLMVIVTLHMMRKRKR
HMAKAWKLTAFQKLEFRAEEVVECLKEENIIGKGGAGIVYRGSMANGTDVAIKRLVGQGSGRNDYG
FKAEIETLGRIRHRNIMRLLGYVSNKDTNLLLYEYMPNGSLGEWLHGAKGCHLSWEMRYKIAVEAA
KGLCYLHHDCSPLIIHRDVKSNNILLDADFEAHVADFGLAKFLYDPGASQSMSSIAGSYGYIAPEY
AYTLKVDEKSDVYSFGVVLLELIIGRKPVGEFGDGVDIVGWINKTELELYQPSDKALVSAVVDPRL
NGYPLTSVIYMFNIAMMCVKEMGPARPTMREVVHMLTNPPHSTSHNLINL
```

SEQ ID NO: 225 Orysa sativa FON1 (floral organ number1) Orysa_FON1 LRR-RLK AB182388

```
ATGCCTCCTACTCTCCTCCTCCTCCTCCTCCTCCCACCCTCCCTCGCCTCCCCCGACCGCGAC
ATCTACGCGCTCGCCAAGCTCAAGGCGGCGCTCGTCCCATCCCCCTCCGCCACCGCCCCACCGCCG
CTCGCCGACTGGGACCCGGCCGCGACCTCCCCGCGCACTGCACCTTCTCCGGCGTCACCTGCGAC
GGCCGCTCCCGCGTCGTCGCCATCAACCTCACCGCCCTCCCGCTCCACTCCGGCTACCTCCCGCCC
GAGATCGCCCTCCTTGACTCCCTCGCCAACCTCACCATCGCCGCCTGCTGCCTCCCCGGCCACGTC
CCCCTCGAGCTCCCCACCCTCCCCTCTCTCCGCCACCTCAACCTCTCCAACAACAACCTTTCCGGC
CACTTCCCCGTCCCCGACTCCGGCGGTGGCGCCTCCCCTACTTCCCCTCGCTCGAGCTCATCGAC
GCTTACAACAACAACCTCTCAGGGTTGCTTCCTCCCTTCTCCGCTTCACACGCTCGCCTCCGCTAC
CTCCACCTCGGCGGCAACTACTTCACCGGCGCAATCCCGGACAGCTATGGCGACCTCGCCGCGCTC
GAGTACCTTGGACTCAACGGCAACACGCTCTCCGGCCATGTCCCCGTCTCCCTCTCCCGCCTCACC
```

```
CGCCTCCGCGAGATGTACATCGGATACTACAACCAGTACGACGGCGGCGTCCCGCCGGAGTTCGGC
GACCTCGGCGCGCTCCTCCGCCTCGACATGAGCAGCTGCAACCTCACCGGCCCCGTCCCGCCGGAG
CTCGGCCGACTCCAGCGCCTCGACACGCTCTTCCTGCAGTGGAACCGCCTCTCCGGCGAGATACCG
CCGCAGCTCGGCGATCTCAGCAGCCTCGCGTCGCTCGACCTCTCCGTCAACGACCTCGCCGGCGAG
ATCCCTCCCAGCCTCGCCAACCTCTCCAACCTCAAGCTCCTCAACCTCTTCCGGAACCACCTCCGC
GGCAGCATACCGGACTTCGTCGCCGGCTTCGCGCAGCTCGAGGTGCTGCAGCTGTGGGACAACAAC
CTCACCGGCAACATCCCCGCCGGGCTCGGGAAGAACGGCCGCCTCAAGACGCTCGACCTGGCCACC
AACCACCTCACCGGCCCCATCCCGGCGGACCTCTGCGCCGGCCGGCGGCTGGAGATGCTCGTGCTC
ATGGAGAACGGCCTGTTCGGCCCCATCCCGGACTCGCTCGGCGACTGCAAGACGCTCACGCGCGTC
CGCCTCGCCAAGAACTTCTTGACCGGCCCGGTTCCCGCCGGGCTCTTCAACCTCCCGCAGGCCAAC
ATGGTGGAGCTCACCGACAACCTGCTCACCGGCGAGCTCCCGGACGTGATCGGCGGCGACAAGATC
GGCATGCTGCTGCTGGGGAACAATGGGATCGGTGGCCGCATCCCTCCGGCCATCGGCAACCTCCCG
GCGCTGCAGACGCTGTCGCTGGAGTCCAACAACTTCTCCGGAGCGCTGCCACCGGAGATCGGCAAT
CTCAAGAACCTGTCCAGGCTCAACGTCAGCGGCAACGCGCTCACCGGCGCCATTCCAGACGAGCTC
ATCCGCTGCGCCTCCCTCGCCGCCGTCGACCTCAGCCGTAACGGCTTCTCCGGCGAGATACCGGAG
AGCATCACGTCGCTCAAGATACTGTGCACGCTGAACGTGTCCAGGAACAGGCTCACCGGCGAGCTC
CCGCCGGAGATGTCCAACATGACGAGCCTCACGACGCTCGACGTGTCGTACAACAGCCTCTCGGGC
CCCGTGCCGATGCAGGGGCAGTTCTTGGTGTTCAACGAGAGCTCGTTCGTCGGCAACCCGGGGCTG
TGCGGCGGCCCCGTGGCCGACGCGTGCCCTCCGTCCATGGCCGGCGGCGGCGGCGGCGCGGGGTCC
CAGCTGCGGCTGCGGTGGGACTCGAAGAAGATGCTGGTGGCGCTGGTGGCGGCGTTCGCGGCGGTG
GCGGTGGCGTTCCTGGGCGCGAGGAAGGGGTGCTCGGCGTGGCGGTCGGCGGCGCGGCGGCGGTCG
GGGGCGTGGAAGATGACGGCGTTCCAGAAGCTGGAGTTCTCGGCGGAGGACGTGGTGGAGTGCGTG
AAGGAGGACAACATCATCGGGAAGGGCGGCGCGGGATCGTGTACCACGGCGTGACGCGCGGGGCG
GAGCTGGCGATCAAGCGGTTGGTGGGCGCGGCGGCGGCGAGCACGACCGGGGGTTCTCGGCGGAG
GTGACGACGCTGGGGAGGATCAGGCACCGGAACATCGTGAGGCTGCTGGGGTTCGTGTCGAACAGG
GAGACGAACCTGCTGCTGTACGAGTACATGCCGAATGGGTCGCTGGGGGAGATGCTCCATGGCGGG
AAGGGGGGGCACCTCGGGTGGAGGCGAGGGCGCGGGTGGCGGCGGAGGCGGCGTGCGGCCTCTGC
TACCTCCACCATGACTGCGCCCCGAGGATCATCCACCGCGACGTCAAGTCCAACAACATCCTCCTC
GACTCCGCCTTCGAGGCGCACGTCGCCGACTTCGGCCTCGCCAAGTTCCTCGGCGGCGCCACCTCC
GAGTGCATGTCCGCCATTGCTGGCTCCTACGGCTACATCGCGCCAGAGTACGCATACACGCTGCGA
GTGGACGAGAAGAGCGACGTGTATAGCTTCGGTGTGGTGCTATTGGAGCTCATCACCGGACGCCGC
CCCGTGGGCGGGTTCGGTGACGGCGTGGACATCGTGCACTGGGTCCGCAAGGTGACCGCCGAGCTG
CCGGACAACTCCGACACGGCGGCCGTCCTCGCCGTGGCCGACCGCCGCCTGACGCCGGAGCCGGTG
GCGCTGATGGTGAACCTGTACAAGGTGGCCATGGCGTGCGTGGAGGAGGCGAGCACGGCCCGGCCC
ACCATGCGCGAGGTCGTCCACATGCTCTCCAACCCAAACTCGGCCCAGCCCAATAGTGGTGACCTC
CTCGTCACCTTCTGA
```

SEQ ID NO: 226 Oryza sativa FON1 (<u>f</u>loral <u>o</u>rgan <u>n</u>umber1) Orysa_FON1 LRR-RLK translated amino acid sequence
```
MPPTLLLLLLLLPPSLASPDRDIYALAKLKAALVPSPSATAPPPLADWDPAATSPAHCTFSGVTCD
GRSRVVAINLTALPLHSGYLPPEIALLDSLANLTIAACCLPGHVPLELPTLPSLRHLNLSNNNLSG
HFPVPDSGGGASPYFPSLELIDAYNNNLSGLLPPFSASHARLRYLHLGNYFTGAIPDSYGDLAAL
EYLGLNGNTLSGHVPVSLSRLTRLREMYIGYYNQYDGGVPPEFGDLGALLRLDMSSCNLTGPVPPE
LGRLQRLDTLFLQWNRLSGEIPPQLGDLSSLASLDLSVNDLAGEIPPSLANLSNLKLLNLFRNHLR
GSIPDFVAGFAQLEVLQLWDNNLTGNIPAGLGKNGRLKTLDLATNHLTGPIPADLCAGRRLEMLVL
MENGLFGPIPDSLGDCKTLTRVRLAKNFLTGPVPAGLFNLPQANMVELTDNLLTGELPDVIGGDKI
GMLLLGNNGIGGRIPPAIGNLPALQTLSLESNNFSGALPPEIGNLKNLSRLNVSGNALTGAIPDEL
IRCASLAAVDLSRNGFSGEIPESITSLKILCTLNVSRNRLTGELPPEMSNMTSLTTLDVSYNSLSG
```

FIGURE 13 (continued)

PVPMQGQFLVFNESSFVGNPGLCGGPVADACPPSMAGGGGGAGSQLRLRWDSKKMLVALVAAFAAV
AVAFLGARKGCSAWRSAARRRSGAWKMTAFQKLEFSAEDVVECVKEDNIIGKGGAGIVYHGVTRGA
ELAIKRLVGRGGGEHDRGFSAEVTTLGRIRHRNIVRLLGFVSNRETNLLLYEYMPNGSLGEMLHGG
KGGHLGWEARARVAAEAACGLCYLHHDCAPRIIHRDVKSNNILLDSAFEAHVADFGLAKFLGGATS
ECMSAIAGSYGYIAPEYAYTLRVDEKSDVYSFGVVLLELITGRRPVGGFGDGVDIVHWVRKVTAEL
PDNSDTAAVLAVADRRLTPEPVALMVNLYKVAMACVEEASTARPTMREVVHMLSNPNSAQPNSGDL
LVTF

SEQ ID NO: 227 Pisum sativa Pissa_LRR-RLK nucleic acid sequence PSA49575
ATGAAAAGTATCACGTGTTATTTGCTGGTATTCTTCTGCGTGTTATTTACACCATGTTTTTCAATA
ACCGATCTCGATGCGTTGCTAAAGCTTAAAGAATCAATGAAAGGAGAGAAATCAAAACATCCCGAT
TCACTCGGAGACTGGAAGTTTTCCGCTTCTGGTTCAGCTCACTGCTCATTTTCCGGTGTAACGTGC
GATCAAGATAACCGAGTGATAACTCTGAACGTGACGCAAGTTCCACTCTTCGGAAGAATTTCTAAG
GAGATTGGAGTGTTGGATAAGCTTGAGAGACTCATCATCACCATGGATAATCTCACTGGCGAGCTT
CCGTTTGAGATATCCAATCTTACCTCTCTTAAAATCCTTAACATCTCTCACAACACCTTCTCTGGT
AACTTCCCCGGCAACATCACTCTCCGTATGACGAAACTTGAGGTTCTAGATGCTTATGACAATAGC
TTCACTGGTCATCTTCCTGAGGAAATCGTCAGCCTCAAGGAACTCACGATCTTATGTCTGGCCGGA
AACTATTTCACCGGTACAATACCCGAGAGTTACTCGGAATTTCAGAAGTTGGAGATTTTAAGCATA
AACGCAAACAGTTTATCGGGGAAGATTCCGAAGAGCTTATCCAAATTAAAGACGCTGAAGGAACTC
CGTTTAGGTTACAACAACGCTTACGATGGCGGAGTTCCACCGGAGTTTGGTTCATTGAAATCTCTC
CGATATCTTGAGGTGTCTAACTGTAACCTCACCGGAGAAATTCCACCGAGTTTTGGAAATTTAGAA
AACCTAGACAGCTTGTTCTTGCAAATGAACAACCTCACCGGAATAATTCCACCGGAACTCTCTTCC
ATGAAGAGTCTCATGTCGTTGGATCTCTCCAACAACGCTCTCTCAGGAGAGATTCCAGAGAGCTTC
TCAAATCTCAAAAGCCTCACTCTCTTGAATTTCTTCCAGAACAAGTTTCGCGGTTCTATTCCGGCA
TTCATAGGCGATCTTCCTAACCTGGAAACGCTTCAGGTTTGGGAAAACAATTTCTCTTTTGTATTG
CCACAAAATCTCGGTTCAAACGGAAAGTTCATTTTCTTCGACGTTACGAAGAATCACCTCACCGGA
TTGATTCCACCGGATTTGTGCAAATCGAAGAAATTGCAAACGTTTATAGTTACGGATAACTTCTTC
CACGGTCCAATCCCTAAAGGAATCGGCGCGTGTAAGTCACTTCTCAAAATCAGAGTTGCTAATAAC
TACTTAGACGGGCCGGTCCCACAAGGGATTTTTCAAATGCCTTCTGTAACGATAATAGAGCTTGGA
AATAACCGTTTTAACGGCCAACTACCTTCTGAAGTTTCCGGCGTTAATCTCGGGATTCTCACTATC
TCTAACAATTTATTCACCGGGAGGATTCCCGCTTCAATGAAGAATCTCATATCACTTCAGACTCTG
TGGCTTGACGCAAATCAGTTCGTCGGAGAAATTCCAAAGGAAGTCTTTGACTTACCAGTGTTAACG
AAGTTCAACATAAGTGGTAACAACCTCACCGGTGTAATCCCAACGACGGTTTCTCAGTGTAGATCG
TTGACAGCCGTTGACTTCAGCCGGAACATGATTACCGGCGAGGTTCCCAGGGGAATGAAGAATCTG
AAGGTTCTCAGCATTTTTAACCTTTCACATAACAACATATCGGGTCTAATCCCGACGAGATTCGA
TTCATGACGAGTCTCACCACGCTGGATCTATCCTACAACAATTTCACCGGAATAGTCCCCACCGGC
GGTCAGTTTTTGGTTTTCAACGACAGGTCGTTTTTCGGAAACCCTAACCTCTGTTTCCCACACCAA
TCCTCATGCTCTTCCTATACCTTTCCCTCGAGTAAAAGCCACGCGAAGGTGAAGGCCATTATTACC
GCAATTGCTCTCGCCACAGCAGTGTTACTGGTAATAGCGACGATGCACATGATGAGGAAGAGAAAG
CTTCATATGGCGAAAGCATGGAAGTTAACAGCATTTCAGAGACTAGACTTCAAAGCAGAGGAAGTT
GTGGAGTGTTTGAAAGAAGAGAACATAATAGGAAAAGGAGGAGCCGGGATCGTGTACAGAGGGTCC
ATGCCCAACGGAACAGACGTAGCGATAAAGCGTTTAGTTGGACAAGGAAGTGGGAGAAACGATTAC
GGTTTCAAAGCAGAGATAGAAACATTGGGTAGAATCAGACACAGAAACATAATGAGGCTATTGGGT
TACGTTTCTAATAAGGACACAAATTTGTTGCTGTATGAGTACATGCCGAATGGTAGTTTAGGGGAA
TGGCTTCATGGTGCAAAAGGCTGTCATTTGAGTTGGGAAATGAGGTATAAAATTGCAGTGGAAGCT
GGTAAAGGACTTTGCTATTTGCACCATGATTGTTCACCTCTTATTATTCATAGGGATGTTAAGTCC
AACAATATATTGCTAGATGCTGATTTTGAAGCCCATGTTGCTGATTTTGGACTTGCAAAGTTTTA

```
TATGACCCAGGTGCTTCTCAGTCCATGTCCTCTATTGCTGGCTCCTACGGCTACATTGCTCCAGAG
TATGCTTATACGTTGAAAGTGGATGAGAAAGCGATGTGTATAGCTTTGGAGTGGTGCTATTGGAG
CTGATCATAGGAAGGAAACCAGTGGGTGAGTTTGGAGATGGAGTGGACATCGTTGGATGGATCAAT
AAAACTGAATTAGAGCTTTATCAGCCGTCAGATAAAGCATTGGTGTCGGCGGTGGTGGACCCGCGG
CTCACTGGATACCCAATGGCAAGTGTTATCTACATGTTCAACATAGCTATGATGTGTGTTAAAGAA
ATGGGACCCGCAAGGCCTACCATGAGGGAAGTAGTTCATATGCTCACTAATCCACCTCAGTCTACC
ACTCATAACAACCTTATTAATCTCTAG
```

SEQ ID NO: 228 Pisum sativa Pissa_LRR-RLK translated amino acid sequence

```
MKSITCYLLVFFCVLFTPCFSITDLDALLKLKESMKGEKSKHPDSLGDWKFSASGSAHCSFSGVTC
DQDNRVITLNVTQVPLFGRISKEIGVLDKLERLIITMDNLTGELPFEISNLTSLKILNISHNTFSG
NFPGNITLRMTKLEVLDAYDNSFTGHLPEEIVSLKELTILCLAGNYFTGTIPESYSEFQKLEILSI
NANSLSGKIPKSLSKLKTLKELRLGYNNAYDGGVPPEFGSLKSLRYLEVSNCNLTGEIPPSFGNLE
NLDSLFLQMNNLTGIIPPELSSMKSLMSLDLSNNALSGEIPESFSNLKSLTLLNFFQNKFRGSIPA
FIGDLPNLETLQVWENNFSFVLPQNLGSNGKFIFFDVTKNHLTGLIPPDLCKSKKLQTFIVTDNFF
HGPIPKGIGACKSLLKIRVANNYLDGPVPQGIFQMPSVTIIELGNNRFNGQLPSEVSGVNLGILTI
SNNLFTGRIPASMKNLISLQTLWLDANQFVGEIPKEVFDLPVLTKFNISGNNLTGVIPTTVSQCRS
LTAVDFSRNMITGEVPRGMKNLKVLSIFNLSHNNISGLIPDEIRFMTSLTTLDLSYNNFTGIVPTG
GQFLVFNDRSFFGNPNLCFPHQSSCSSYTFPSSKSHAKVKAIITAIALATAVLLVIATMHMMRKRK
LHMAKAWKLTAFQRLDFKAEEVVECLKEENIIGKGGAGIVYRGSMPNGTDVAIKRLVGQGSGRNDY
GFKAEIETLGRIRHRNIMRLLGYVSNKDTNLLLYEYMPNGSLGEWLHGAKGCHLSWEMRYKIAVEA
GKGLCYLHHDCSPLIIHRDVKSNNILLDADFEAHVADFGLAKFLYDPGASQSMSSIAGSYGYIAPE
YAYTLKVDEKSDVYSFGVVLLELIIGRKPVGEFGDGVDIVGWINKTELELYQPSDKALVSAVVDPR
LTGYPMASVIYMFNIAMMCVKEMGPARPTMREVVHMLTNPPQSTTHNNLINL
```

SEQ ID NO: 229 Populus tremuloides Poptr_LRR-RLK1 nucleic caid sequence scaff_1514.1

```
ATGAGAACATTTCTGTGCTTTTTTCTTTTACTAGTATTATTGTTCGCTCCTTGCAGTGGATACAGT
GATCTTGAAGTCCTCTTGAAGCTGAAAACCTCCATGTATGGACATAATGGCACTGGCCTTCAAGAT
TGGGTGGCTTCTCCAGCATCTCCCACAGCTCACTGTTACTTCTCTGGAGTCACGTGTGATGAGGAC
TCGCGTGTGGTGTCTCTAAACGTGTCGTTTAGACATCTTCCTGGTTCAATTCCTCCAGAGATTGGG
CTGTTGAACAAGCTTGTGAATCTTACTCTGTCAGGTAATAATCTCACGGGGGGATTTCCAGTGGAG
ATAGCCATGCTGACATCTCTCAGGATTTTGAATATTTCCAACAATGTTATTGCTGGGAATTTCCCC
GGAAAAAATCACTCTTGGCATGGCACTGCTTGAGGTTCTTGATGTTTACAACAATAATTTTACGGGT
GCATTGCCAACTGAAATTGTAAAGCTGAAAAATCTCAAGCATGTTCATCTTGGAGGGAATTTCTTT
TCTGGTACAATACCGGAGGAGTACTCGGAGATTTTGAGCTTGGAGTACTTGGGCTTGAATGGTAAT
GCGCTTTCAGGCAAAGTACCTTCAAGCTTGTCCAGGTGAAGAATCTTAAGAGCTTGTGCGTTGGG
TACTTAACCGTTATGAGGGAGTATTCCACCTGAATTTGGGTCATTAAGTAATCTTGAACTTCTT
GACATGGCTTCCTGTAACCTTGACGGTGAGATTCCTTCCGCTTTAAGTCAATTAACCCATCTGCAT
TCGTTGTTTCTTCAAGTCAATAATCTCACTGGCCATATCCCTCCTGAATTATCTGGTCTAATTAGC
TTGAAATCACTGGATCTTTCGATAAACAACCTCACTGGGGAGATACCAGAGAGTTTTTCAGATTTG
AAAAACATAGAACTGATCAATCTCTTTCAAAACAAGCTGCACGGTCCAATCCCAGAATTTTTTGGT
GATTTTCCGAACCTTGAGGTGCTTCAGGTTTGGGGCAACAACTTCACTTTTGAGCTTCCTCAAAAT
CTTGGCCGGAATGGGAAGCTGATGATGCTGGATGTGTCTATTAATCACTTAACTGGATTGGTCCCG
CGGGATTTATGCAAAGGAGGGAAATTGACGACGTTGATTCTCATGAACAATTTCTTCCTTGGATCG
CTTCCTGATGAAATTGGCCAGTGCAAGTCCTTGCTCAAAATCCGAATAATGAATAATATGTTTTCA
GGAACTATCCCTGCTGGGATATTTAATTTGCCTTTGGCGACACTTGTTGAGTTGAGCAATAACCTT
```

FIGURE 13 (continued)

```
TTCTCTGGCGAGCTTCCACCAGAGATTTCAGGAGATGCACTAGGCCTTTTATCAGTTTCTAACAAT
CGGATCACAGGTAAAATCCCGCCTGCTATTGGGAATCTGAAGAACTTGCAGACTCTGTCACTGGAC
ACGAACAGACTTTCTGGTGAAATTCCTGAAGAAATCGGGGACTGAAGTCCCTCACCAAGATCAAC
ATCCGTGCTAACAACATCAGAGGTGAAATCCCAGCTTCGATTTCCCACTGCACATCACTTACATCC
GTTGATTTCAGTCAAAACAGCCTCAGTGGGGAGATTCCTAAGAAGATTGCCAAACTGAACGATTTG
AGCTTTCTTGATCTCTCTCGAAATCAACTCACTGGTCAACTACCAGGTGAAATTGGATACATGAGA
AGCCTTACATCCCTTAATCTCTCATACAACAATTTATTTGGCAGGATCCCTTCTGCCGGCCAATTC
CTGGCGTTCAATGACAGTTCATTTCTCGGAAATCCAAATCTCTGTGCAGCGAGAAATAATACTTGC
TCCTTCGGTGATCATGGCCATAGGGGGGGGTCTTTTAGTACTTCAAAGCTAATAATCACTGTCATT
GCACTCGTCACTGTTTTGCTGTTAATAGTTGTGACGGTTTACAGATTGAGAAAGAAGAGGCTGCAG
AAATCACGGGCCTGGAAGCTCACTGCATTCCAAAGGCTCGACTTCAAGGCAGAGGACGTGCTTGAG
TGCTTGAAAGAGGAAAACATTATAGGCAAAGGTGGTGCTGGTATTGTCTACCGTGGGTCAATGCCA
GAGGGTGTTGATCATGTAGCTATCAAACGACTTGTTGGTCGAGGCAGCGGAAGAAGTGATCATGGC
TTCTCGGCTGAGATTCAAACTCTTGGAAGAATCAGGCACCGAAATATTGTAAGGCTGTTGGGGTAC
GTATCGAATAAGGATACCAACTTGCTATTGTATGAATACATGCCTAATGGAAGCTTAGGGGAGCTT
TTGCATGGTTCAAAGGGAGGCCATTTGCAGTGGGAGACTAGATACAGAATTGCTGTGGAGGCTGCT
AAGGGACTCTGTTATCTTCACCACGATTGCTCGCCTTTGATTATACATAGGGATGTTAAGTCCAAT
AACATATTACTTGATTCCGATTTTGAGGCTCATGTTGCTGATTTTGGTCTCGCTAAGTTCTTACAA
GATGCAGGCTCATCAGAGTGCATGTCCTCCGTTGCTGGCTCCTATGGTTACATTGCTCCAGAGTAC
GCATACACACTGAAAGTGGACGAAAAGAGTGATGTTTACAGTTTTGGTGTTGTGCTGCTGGAGCTG
ATAGCAGGGAGAAAGCCAGTCGGGGAGTTTGGAGATGGGGTGGACATCGTGAGGTGGGTCAGGAAG
ACCACATCAGAACTCTCTCAGCCATCTGATGCAGCTACAGTCTTGGCAGTTGTGGACCCCAGGCTT
AGTGGGTACCCACTTGCAGGTGTCATTCACTTGTTTAAGATAGCTATGCTGTGTGTTAAAGATGAG
AGCTCAGCCAGGCCCACCATGAGGGAAGTTGTTCACATGCTCACCAATCCTCCACAATCTGCCCCC
AGCCTACTCGCCCTTTAG
```

SEQ ID NO: 230 Populus tremuloides Poptr_LRR-RLK1 translated amino acid sequence

MRTFLCFFLLLVLLFAPCSGYSDLEVLLKLKTSMYGHNGTGLQDWVASPASPTAHCYFSGVTCDED
SRVVSLNVSFRHLPGSIPPEIGLLNKLVNLTLSGNNLTGGFPVEIAMLTSLRILNISNNVIAGNFP
GKITLGMALLEVLDVYNNNFTGALPTEIVKLKNLKHVHLGGNFFSGTIPEEYSEILSLEYLGLNGN
ALSGKVPSSLSRLKNLKSLCVGYFNRYEGSIPPEFGSLSNLELLDMASCNLDGEIPSALSQLTHLH
SLFLQVNNLTGHIPPELSGLISLKSLDLSINNLTGEIPESFSDLKNIELINLFQNKLHGPIPEFFG
DFPNLEVLQVWGNNFTFELPQNLGRNGKLMMLDVSINHLTGLVPRDLCKGGKLTTLILMNNFFLGS
LPDEIGQCKSLLKIRIMNNMFSGTIPAGIFNLPLATLVELSNNLFSGELPPEISGDALGLLSVSNN
RITGKIPPAIGNLKNLQTLSLDTNRLSGEIPEEIWGLKSLTKINIRANNIRGEIPASISHCTSLTS
VDFSQNSLSGEIPKKIAKLNDLSFLDLSRNQLTGQLPGEIGYMRSLTSLNLSYNNLFGRIPSAGQF
LAFNDSSFLGNPNLCAARNNTCSFGDHGHRGGSFSTSKLIITVIALVTVLLIVVTVYRLRKKRLQ
KSRAWKLTAFQRLDFKAEDVLECLKEENIIGKGGAGIVYRGSMPEGVDHVAIKRLVGRGSGRSDHG
FSAEIQTLGRIRHRNIVRLLGYVSNKDTNLLLYEYMPNGSLGELLHGSKGGHLQWETRYRIAVEAA
KGLCYLHHDCSPLIIHRDVKSNNILLDSDFEAHVADFGLAKFLQDAGSSECMSSVAGSYGYIAPEY
AYTLKVDEKSDVYSFGVVLLELIAGRKPVGEFGDGVDIVRWVRKTTSELSQPSDAATVLAVVDPRL
SGYPLAGVIHLFKIAMLCVKDESSARPTMREVVHMLTNPPQSAPSLLAL

FIGURE 13 (continued)

SEQ ID NO: 231 Populus tremuloides Poptr_LRR-RLK2 nucleic acid sequence scaff_II.178

ATGGGAACTCTTCTGTGTTTTCTTCTTCCTTTTCTTGTACTACTGTTCACTGCTTGCAGTGGATAC
AGTGAACTTGAAGTCCTCTTGAAGCTGAAATCTTCCATGTACGGACATAATGGCACTGGCCTTGAA
GATTGGGTGGCTTCTCCTACATCTCCTTCAGCTCATTGTTTCTTCTGGAGTCACGTGTGATGAG
AGCTCACGTGTGGTGTCACTTAATTTGTCGTTCAGACATCTTCCTGGTTCAATTCCTCCAGAGATT
GGGTTGTTGAACAAGCTTGTGAATCTTACTTTGGCCAATGATAATCTCACGGGGGAACTTCCTGCG
GAGATAGCCATGCTTAAATCTCTCAGGATTTTGAACATTTCTGGCAATGCTATTGGTGGGAATTTC
TCTGGAAAGATCACTCCTGGCATGACACAGCTTGAGGTCTTGATATTTACAACAATAATTGCTCG
GGTCCACTGCCAATTGAAATTGCAAACCTGAAAAAACTCAAGCATCTTCACCTGGGAGGGAATTTC
TTTTCTGGTAAAATACCAGAGGAGTACTCGGAGATTATGATCTTGGAGTTCTTAGGCTTGAATGGT
AATGACCTTTCAGGCAAAGTTCCTTCTAGCTTGTCTAAGCTGAAGAATCTCAAGAGCTTGTGCATT
GGGTACTATAACCATTACGAAGGAGGTATTCCACCTGAATTTGGATCATTGAGTAATCTTGAACTT
CTTGACATGGGTTCTTGCAACCTTAATGGTGAGATTCCTTCTACTCTAGGCCAATTAACCCATCTG
CATTCGCTGTTTCTTCAATTCAATAATCTCACTGGATATATCCCTTCGGAATTATCTGGTCTAATT
AGCTTGAAATCACTTGATCTTTCAATCAACAACCTCACTGGGGAGATACCCGAGAGTTTTTCAGCT
TTGAAAAACTTAACACTCCTCAATCTCTTTCAAAACAAGCTGCACGGTCCAATCCCAGACTTTGTT
GGTGATTTTCCAAACCTTGAGGTGCTTCAGGTTTGGGGAAACAACTTCACATTTGAGCTTCCCAAA
CAGCTCGGCCGGAATGGGAAGCTGATGTATCTGGACGTGTCATATAATCACTTGACAGGATTGGTT
CCTCGGGACTTATGCAAGGGAGGGAAATTGAAGACGTTGATTCTCATGAATAATTTCTTCATTGGA
TCACTTCCTGAAGAAATTGGCCAGTGCAAGTCCTTGCTCAAAATCAGAATCATTTGTAATCTCTTT
ACAGGCACTATCCCTGCTGGGATCTTTAATTTACCTTTGGTGACCCAAATTGAGTTGAGCCATAAC
TATTTCTCCGGCGAGCTTCCACCGGAGATTTCAGGAGATGCACTAGGCTCTCTTTCGGTCTCTGAC
AATCGGATTACTGGTAGAATCCCCGGGCTATTGGGAATTTGAAGAGTTTGCAGTTTCTATCTCTG
GAAATGAACAGACTTTCTGGTGAAATTCCTGATGAAATCTTCAGTCTGGAGATCCTCTCCAAGATC
AGCATCCGTGCCAACAACATTAGCGGTGAAATCCCAGCTTCCATGTTCCATTGCACTTCACTTACA
TCCGTTGATTTCAGTCAAAACAGCATCAGTGGGGAGATTCCAAAGGAGATTACTAAACTGAAGGAT
TTGAGTATTCTTGATCTCTCTCGAAATCAGCTTACTGGTCAACTACCAAGTGAAATTCGATACATG
ACAAGTCTTACAACTCTAAACCTCTCCTACAACAATTTATTTGGCCGGATCCCTTCTGTCGGCCAA
TTCCTGGCGTTCAATGACAGCTCATTTCTTGGAAATCCAAATCTCTGTGTAGCAAGAAATGACTCT
TGCTCATTTGGTGGTCATGGCCATAGAAGGTCCTTTAATACTTCAAAGCTAATGATCACTGTCATT
GCTCTTGTCACTGCGTTGCTGTTAATAGCAGTGACAGTTTACAGATTGAGAAAGAAGAATCTGCAG
AAAATCACGGGCCTGGAAGCTCACTGCATTCCAAAGGCTCGATTTCAAAGCAGAGGATGTGCTCGAG
TGCTTGAAAGAGGAAAACATTATAGGCAAAGGTGGCGCTGGGATTGTCTACCGTGGGTCAATGACA
GAGGGTATTGATCATGTAGCTATCAAACGACTTGTTGGTAGAGGCACCGGACGAAACGATCATGGC
TTCTCAGCCGAGATCCAAACACTTGGAAGGATCAGGCACCGAAATATTGTTAGGCTGCTGGGGTAC
GTATCAAATAAGGATACCAACTTGCTGTTGTATGAGTACATGCCAAATGGGAGCTTAGGAGAGCTT
TTGCATGGTTCAAAGGGAGGCCATTTGCAGTGGGAAACCAGGTACAGAATTGCTGTGGAGGCTGCC
AAGGGACTCTGTTATCTTCACCATGATTGCTCTCCTTTGATTATACATAGGGATGTGAAGTCCAAT
AACATATTACTTGATTCGGATTTTGAGGCTCATGTTGCTGATTTTGGGCTGGCCAAGTTCTTGCAA
GATGCAGGTGCATCAGAATGCATGTCCTCTATTGCTGGCTCCTATGGTTACATTGCTCCAGAATAC
GCTTACACATTGAAAGTGGACGAAAAAGTGATGTTTACAGCTGCGGTGTTGTGCTGCTGGAGCTG
ATAGCAGGGAGGAAGCCAGTAGGGAGTTTGGAGATGGGGTGGACATAGTGAGATGGGTCAGGAAG
ACCACGTCAGAACTATCTCAGCCATCCGATGCAGCTTCAGTCTTGGCAGTTGTGGACCCCAGGCTT
AGTGGGTACCCTCTAACAGGTGCCATTCACCTGTTTAAGATAGCTATGTTGTGTGTAAAGATGAG
AGCTCGAACCGGCCTACCATGAGGGAAGTGGTTCACATGCTCACCAATCCTCCACAGTCAGCCTCA
AGCCTCCTCACCCTCTAG

FIGURE 13 (continued)

SEQ ID NO: 232 Populus tremuloides Poptr_LRR-RLK2 translated amino acid sequence
MGTLLCFLLPFLVLLFTACSGYSELEVLLKLKSSMYGHNGTGLEDWVASPTSPSAHCFFSGVTCDE
SSRVVSLNLSFRHLPGSIPPEIGLLNKLVNLTLANDNLTGELPAEIAMLKSLRILNISGNAIGGNF
SGKITPGMTQLEVLDIYNNNCSGPLPIEIANLKKLKHLHLGGNFFSGKIPEEYSEIMILEFLGLNG
NDLSGKVPSSLSKLKNLKSLCIGYYNHYEGGIPPEFGSLSNLELLDMGSCNLNGEIPSTLGQLTHL
HSLFLQFNNLTGYIPSELSGLISLKSLDLSINNLTGEIPESFSALKNLTLLNLFQNKLHGPIPDFV
GDFPNLEVLQVWGNNFTFELPKQLGRNGKLMYLDVSYNHLTGLVPRDLCKGGKLKTLILMNNFFIG
SLPEEIGQCKSLLKIRIICNLFTGTIPAGIFNLPLVTQIELSHNYFSGELPPEISGDALGSLSVSD
NRITGRIPRAIGNLKSLQFLSLEMNRLSGEIPDEIFSLEILSKISIRANNISGEIPASMFHCTSLT
SVDFSQNSISGEIPKEITKLKDLSILDLSRNQLTGQLPSEIRYMTSLTTLNLSYNNLFGRIPSVGQ
FLAFNDSSFLGNPNLCVARNDSCSFGGHGHRRSFNTSKLMITVIALVTALLIAVTVYRLRKKNLQ
KSRAWKLTAFQRLDFKAEDVLECLKEENIIGKGGAGIVYRGSMTEGIDHVAIKRLVGRGTGRNDHG
FSAEIQTLGRIRHRNIVRLLGYVSNKDTNLLLYEYMPNGSLGELLHGSKGGHLQWETRYRIAVEAA
KGLCYLHHDCSPLIIHRDVKSNNILLDSDFEAHVADFGLAKFLQDAGASECMSSIAGSYGYIAPEY
AYTLKVDEKSDVYSCGVVLLELIAGRKPVGEFGDGVDIVRWVRKTTSELSQPSDAASVLAVVDPRL
SGYPLTGAIHLFKIAMLCVKDESSNRPTMREVVHMLTNPPQSASSLLTL

SEQ ID NO: 233 Zea mays Zeama_LRR-RLK translated amino acid sequence
MPPPTFLLGLLLLLLLAAAAPAPASATPERDAYALSRLKASLVPSATNSTSAPLSDWDPAATPPAH
CAFTGVTCDAATSRVVAINLTAVPLHGGALPPEVALLDALASLTVANCYLRGRLPPALASMPALRH
LNLSNNNLSGPFPPPPPAAYFPALEIVDVYNNNLSGPLPPLGAPHARSLRYLHLGGNYFNGSIPDT
FGDLAALEYLGLNGNALSGRVPPSLSRLSRLREMYVGYYNQYSGGVPREFGALQSLVRLDMSSCTL
TGPIPPELARLSRLDTLFLALNQLTGEIPPELGALTSLRSLDLSINDLAGEIPASFAALTNLKLLN
LFRNKLRGEIPAFLGDFPFLEVLQVWDNNLTGPLPPALGRNGRLKTLDVTSNHLTGTIPPDLCAGR
NLQLLVLMDNGFFGSIPESLGDCKTLTRVRLGKNFLTGPVPAGLFDLPQANMLELTDNMLTGELPD
VIAGDKIGMLMLGNNRIGGRIPAAIGNLPALQTLSLESNNFSGSLPPEIGRLRNLTRLNASGNALT
GGIPRELMGCASLGAVDLSRNGLTGEIPDTVTSLKILCTLNVSRNRLSGELPAAMANNTSLTTLDV
SYNQLSGPVPMQGQFLVFNESSFVGNPGLCSACPPSSGGARSPFSLRRWDSKKLLVWLVVLLTLLV
LAVLGARKAHEAWREAARRRSGAWKMTAFQKLDFSADDVVECLKEDNIIGKGGAGIVYHGVTRGGA
ELAIKRLVGRGCGDHDRGFTAEVTTLGRIRHRNIVRLLGFVSNREANLLLYEYMPNGSLGEMLHGG
KGGHLGWEARARVAAEAARGLCYLHHDCAPRIIHRDVKSNNILLDSAFEAHVADFGLAKFLGGGGA
TSECMSAIAGSYGYIAPEYAYTLRVDEKSDVYSFGVVLLELITGRRPVGSFGDGVDIVHWVRKVTA
DAAAAEEPVLLVADRRLAPEPVPLLADLYRVAMACVEEASTARPTMREVVHMLSTSAAAQPDVPHA
LCKVVD

SEQ ID NO: 234 Ipomoea batatas CLV1 like nucleic acid sequence AB162660.1
TTCTCCGGCGTTGCATGCGATCAGGATTCACGAGTCATTTCTTTAGCCATATCCGCTGTTCCGCTC
TTCGGTTCCCTCCCGCCGGAGATTGGACTGCTGGATAGGCTTTTAAACTTAACTCTCACCTCCGTT
AATCTCTCTGGTGCGCTTCCATCGGAGATGGCGAAACTCACATCCATTAAAGCCATTAATATGTCA
AACAATTTGTTGAGCGGCCATTTCCCTGGAGAAATCTTGGTCGGTATGACTGAGCTTCAAGTGTTG
GATGTTTACAATAACAACTTTTCCGAAGGCTTCCTCATGAAGTGGTGAAGTTGAAGAAGCTGAAA
ATTCTCAATCTCGGAGGAAATTACTTCACAGGAGAGATACCGGAAATATACTCTAACATTTCCAGT
TTACAGACTTTAAACTTACAAACAAATAGCCTCACGGGAAATATACCGGCAAGCTTGGCGCAGCTT
CAGAATCTTCGTGAGCTCCGCCTTGGCTACTTGAATACATTTGAAAGAGGCATTCCACCAGAATTA
GGCTCCATCACCACACTTCAAATGCTTGATCTTAGGGAATGCAACCTTTCTGGTGAAATTCCTAAA

FIGURE 13 (continued)

```
AGTTTAGGGAATCTAAAACAGCTATACTTTCTGTATTTGTACGGGAACAGCCTGACAGGTCATATT
CCGGCGGAGCTCTCCGGTTTGGAGAGTTTGGTGCATCTGGACCTTTCAGAAAATAATATGATGGGA
GAAATTCCTCAAAGTTTAGCCGAGTTGAAGAGCCTGGTATTGATAAACTTGTTCAGAAACACGTTC
CAAGGCACAATTCCCGCGTTCATCGGTGATCTACCCAAACTAGAGGTTTTACAGCTTTGGAACAAC
AATTTCACATCCGAGTTACCGGTAAACCTCGGACGAAACCGCCGATTGAGGTTTCTGGACGTTTCG
TCAAACCAAATCAGCGGCAGAGTACCGGAAAATTTGTGTATGGGAGGGAAGCTGGAAGCACTAATT
CTCATGGAAAACAAATTTTCTGGACCGTTTCCTCAAGTCCTGGGCGAGTGCAAGTCCTTGAATGGG
GTTCGTGTTGAGAAGAACTATCTCAATGGAGCCATCCCGCCTGGCTTTCTTCAATTTGCCGTTGGC
TTAATCTACGTTTGTCTCCAAAACAATTACTTCTCCAGCGAGCTTCCGACCAAGATGCTTGCCAAG
AATCTCACAGATCTTGATCTTCACAACAACAGGATAAATGGCCAGATTCCTCCGGCATTCGGAAAT
TTAGAGAACCTCTGGAAGTTATCCCTCCACTCCAACAGATTCTCCGGGAAAATTCCAAATCAAATT
TCACATTTGAAAAGATGGTGACCATGGATTTAAGCAGCAACAGTTTAACAGGTGAAGTTCCAGCC
TCAATTGCTCAGTGTACACAGCTGAATTCCTTTGACTTGAGTGCAAATAATTTAACCGGAAAAATT
CCAAAGGAAATCTCTTCTCTGGAGCGCCTAAATGTACTCAACTTGTCCAGAAATCTACTTACTGGT
TCAGTTCCCAGTGAACTAGGGCTAATGAATAGCTTGACTGTCCTGGATCATTCTTTCAATGATTTT
TCGGGTCCAATACCCACCAATGGACAGTTAGGAGTTTTCGATAACCGGTCTTTCTACGGGAATCCA
AAACTCTTCTATTCACCTCCAAGCTCATCGCCAGTCAATACAACAACCATTCTTGGACCACAAAA
CGAATACTCATAATTACTGTCTTGATTTTGGGTACTGCAGCAGCATTTTTATCTGCTGTTATATGG
GTAAGGTGCATTATTGTTGCGCGAAGAGAAAAGATTATGAAATCCAATAATGCTTGGAAACTAACA
ACATTCAAGAAACTGGAATATAAAGTAGAGGATGTGGTTGAGTGTTTGAAAGAGGAAAACATAATT
GGGCAAGGGGAGCAGGGACAGTATACAAAGGCTCCATGCCCGATGGTGTCATCATAGCAATAAAA
AGGCTAGACAGGCGAGGAACTGGGCGTCGTGATCTTGGTTTCTCTGCTGAAATTAAAACACTGGGA
AGAATCAGGCACCGACACATTATTAGATTACTTGGTTATGCATCTAACAGAGATACTAATTTGTTA
TTGTATGAATACATGCCTAATGGGAGCTTGTCGGGGATCCTGCATGGGACGAATGGGGCCAATTTG
CTTTGGGAGATGCGGTTTCGAATTGCGGTGGAAGCCGCAAAGGGGCTATGTTACTTGCACCATGAT
TGCTCCCCTCCCATTATTCATAGGGACGTAAAGTCTAATAATATTTTACTCACTTCTGATTATATA
GCTTGCATTGCTGATTTTGGGCTGGCTAAATCC
```

SEQ ID NO: 235 Ipomoea batatas CLV1 like translated amino acid sequence
```
FSGVACDQDSRVISLAISAVPLFGSLPPEIGLLDRLLNLTLTSVNLSGALPSEMAKLTSIKAINMS
NNLLSGHFPGEILVGMTELQVLDVYNNNFSGRLPHEVVKLKKLKILNLGGNYFTGEIPEIYSNISS
LQTLNLQTNSLTGNIPASLAQLQNLRELRLGYLNTFERGIPPELGSITTLQMLDLRECNLSGEIPK
SLGNLKQLYFLYLYGNSLTGHIPAELSGLESLVHLDLSENNMMGEIPQSLAELKSLVLINLFRNTF
QGTIPAFIGDLPKLEVLQLWNNNFTSELPVNLGRNRRLRFLDVSSNQISGRVPENLCMGGKLEALI
LMENKFSGPFPQVLGECKSLNGVRVEKNYLNGAIPPGFLQFAVGLIYVCLQNNYFSSELPTKMLAK
NLTDLDLHNNRINGQIPPAFGNLENLWKLSHSNRFSGKIPNQISHLKKMVTMDLSSNSLTGEVPA
SIAQCTQLNSFDLSANNLTGKIPKEISSLERLNVLNLSRNLLTGSVPSELGLMNSLTVLDHSFNDF
SGPIPTNGQLGVFDNRSFYGNPKLFYSPPSSSPVNHNNHSWTTKRILIITVLILGTAAAFLSAVIW
VRCIIVARREKIMKSNNAWKLTTFKKLEYKVEDVVECLKEENIIGQGGAGTVYKGSMPDGVIIAIK
RLDRRGTGRRDLGFSAEIKTLGRIRHRHIIRLLGYASNRDTNLLLYEYMPNGSLSGILHGTNGANL
LWEMRFRIAVEAAKGLCYLHHDCSPPIIHRDVKSNNILLTSDYIACIADFGLAKS
```

SEQ ID NO: 236 Motif 1
```
LXDW
```
where X is any amino acid

FIGURE 13 (continued)

SEQ ID NO: 237 Motif 2
(A/P)HCXF(S/T)GV(S/T/K)CD where X is any amino acid

SEQ ID NO: 238 prm08591
GGGGACAAGTTTGTACAAAAAAGCAGGCTTAAACAATGGCGATGAGACTTTTGAAG

SEQ ID NO: 239 prm08592
GGGGACCACTTTGTACAAGAAAGCTGGGTCGCTACGTAACCAAGAAGTCAC

SEQ ID NO: 240 beta-expansin promoter of Oryza sativa
AAAACCACCGAGGGACCTGATCTGCACCGGTTTTGATAGTTGAGGGACCCGTTGTGTCTGGTTTTC
CGATCGAGGGACGAAAATCGGATTCGGTGTAAAGTTAAGGGACCTCAGATGAACTTATTCCGGAGC
ATGATTGGGAAGGGAGGACATAAGGCCCATGTCGCATGTGTTTGGACGGTCCAGATCTCCAGATCA
CTCAGCAGGATCGGCCGCGTTCGCGTAGCACCCGCGGTTTGATTCGGCTTCCCGCAAGGCGGCGGC
CGGTGGCCGTGCCGCCGTAGCTTCCGCCGGAAGCGAGCACGCCGCCGCCGCCGACCCGGCTCTGCG
TTTGCACCGCCTTGCACGCGATACATCGGGATAGATAGCTACTACTCTCTCCGTTTCACAATGTAA
ATCATTCTACTATTTTCCACATTCATATTGATGTTAATGAATATAGACATATATATCTATTTAGAT
TCATTAACATCAATATGAATGTAGGAAATGCTAGAATGACTTACATTGTGAATTGTGAAATGGACG
AAGTACCTACGATGGATGGATGCAGGATCATGAAAGAATTAATGCAAGATCGTATCTGCCGCATGC
AAAATCTTACTAATTGCGCTGCATATATGCATGACAGCCTGCATGCGGGCGTGTAAGCGTGTTCAT
CCATTAGGAAGTAACCTTGTCATTACTTATACCAGTACTACATACTATATAGTATTGATTTCATGA
GCAAATCTACAAAACTGGAAAGCAATAAGGAATACGGGACTGGAAAAGACTCAACATTAATCACCA
AATATTTCGCCTTCTCCAGCAGAATATATATCTCTCCATCTTGATCACTGTACACACTGACAGTGT
ACGCATAAACGCAGCAGCCAGCTTAACTGTCGTCTCACCGTCGCACACTGGCCTTCCATCTCAGGC
TAGCTTTCTCAGCCACCCATCGTACATGTCAACTCGGCGCGCGCACAGGCACAAATTACGTACAAA
ACGCATGACCAAATCAAAACCACCGGAGAAGAATCGCTCCCGCGCGCGGCGGCGGCGCGCACGTAC
GAATGCACGCACGCACGCCCAACCCCACGACACGATCGCGCGCGACGCCGGCGACACCGGCCATCC
ACCCGCGCCCTCACCTCGCCGACTATAAATACGTAGGCATCTGCTTGATCTTGTCATCCATCTCAC
CACCAAAAAAAAAGGAAAAAAAAACAAAACACACCAAGCCAAATAAAAGCGACAA

SEQ ID NO: 241 C-terminal domain of SEQ ID NO: 212
RLLGYVANKDTNLLLYEYMPNGSLGELLHGSKGGHLQWETRHRVAVEAAKGLCYLHHDCSPLILHR
DVKSNNILLDSDFEAHVADFGLAKFLVDGAASECMSSIAGSYGYIAPEYAYTLKVDEKSDVYSFGV
VLLELIAGKKPVGEFGEGVDIVRWVRNTEEEITQPSDAAIVVAIVDPRLTGYPLTSVIHVFKIAMM
CVEEEAAARPTMREVVHMLTNPPKSVANLIAF FIGURE 13 (continued)

SEQUENCE LISTING

```
<160> NUMBER OF SEQ ID NOS: 241

<210> SEQ ID NO 1
<211> LENGTH: 945
<212> TYPE: DNA
<213> ORGANISM: Arabidopsis thaliana

<400> SEQUENCE: 1
atggatccca agaacctaaa tcgtcaccaa gtaccaaatt tcttgaaccc accaccacca      60
ccgcgaaatc agggtttggt agatgatgat gctgcttctg ctgttgtttc cgacgagaat     120
cgcaaaccaa caactgagat taaagatttc cagatcgtgg tctctgcttc cgacaaagaa     180
ccaaacaaga agagtcagaa tcagaaccag cttggtccta agagaagctc taacaaagac     240
agacacacta aagtcgaagg tagaggtcga cgaattcgga tgcctgctct ttgtgctgct     300 aggattttc aattgactag agaattgggt cataaatctg atggtgaaac tatccagtgg     360
ctgcttcaac aagctgagcc atcgattatt gcagctactg gttcaggaac tataccggcc     420
tctgctttag cttcttcagc tgcaacctct aaccatcatc aaggtgggtc tcttactgct     480
ggtttaatga tcagtcatga cttagatggt gggtctagta gtagtggtag accattaaat     540
tgggggattg gtggcggtga aggagtttct aggtcaagtt taccaactgg gttatggcca     600
aatgtagctg ggtttggttc tggtgtgcca accactggtt taatgagtga aggagctggt     660
tatagaattg ggttcctgg ttttgatttt cctggtgttg gtcatatgag ttttgcatct     720 atttgggtg ggaatcataa tcagatgcct ggacttgagt taggcttgtc tcaagaaggg     780
aatgttggtg ttttgaatcc tcagtctttt actcagattt atcaacagat gggtcaggct     840
caggctcaag ctcaaggtag ggttcttcac catatgcatc ataaccatga agaacatcag     900
caagagagtg gtgagaaaga tgattctcaa ggctcaggtc gttaa                    945

<210> SEQ ID NO 2
<211> LENGTH: 314
<212> TYPE: PRT
```

<213> ORGANISM: Arabidopsis thaliana

<400> SEQUENCE: 2

```
Met Asp Pro Lys Asn Leu Asn Arg His Gln Val Pro Asn Phe Leu Asn
1               5                   10                  15
Pro Pro Pro Pro Arg Asn Gln Gly Leu Val Asp Asp Ala Ala
            20                  25                  30
Ser Ala Val Val Ser Asp Glu Asn Arg Lys Pro Thr Thr Glu Ile Lys
        35                  40                  45
Asp Phe Gln Ile Val Val Ser Ala Ser Asp Lys Glu Pro Asn Lys Lys
    50                  55                  60
Ser Gln Asn Gln Asn Gln Leu Gly Pro Lys Arg Ser Ser Asn Lys Asp
65                  70                  75                  80
Arg His Thr Lys Val Glu Gly Arg Gly Arg Arg Ile Arg Met Pro Ala
                85                  90                  95
Leu Cys Ala Ala Arg Ile Phe Gln Leu Thr Arg Glu Leu Gly His Lys
            100                 105                 110
Ser Asp Gly Glu Thr Ile Gln Trp Leu Leu Gln Gln Ala Glu Pro Ser
        115                 120                 125
Ile Ile Ala Ala Thr Gly Ser Gly Thr Ile Pro Ala Ser Ala Leu Ala
    130                 135                 140
Ser Ser Ala Ala Thr Ser Asn His His Gln Gly Gly Ser Leu Thr Ala
145                 150                 155                 160
Gly Leu Met Ile Ser His Asp Leu Asp Gly Ser Ser Ser Gly
                165                 170                 175
Arg Pro Leu Asn Trp Gly Ile Gly Gly Glu Gly Val Ser Arg Ser
            180                 185                 190
Ser Leu Pro Thr Gly Leu Trp Pro Asn Val Ala Gly Phe Gly Ser Gly
        195                 200                 205
Val Pro Thr Thr Gly Leu Met Ser Glu Gly Ala Gly Tyr Arg Ile Gly
    210                 215                 220
Phe Pro Gly Phe Asp Phe Pro Gly Val Gly His Met Ser Phe Ala Ser
225                 230                 235                 240
Ile Leu Gly Gly Asn His Asn Gln Met Pro Gly Leu Glu Leu Gly Leu
                245                 250                 255
Ser Gln Glu Gly Asn Val Gly Val Leu Asn Pro Gln Ser Phe Thr Gln
            260                 265                 270
Ile Tyr Gln Gln Met Gly Gln Ala Gln Ala Gln Ala Gln Gly Arg Val
        275                 280                 285
Leu His His Met His His Asn His Glu Glu His Gln Gln Glu Ser Gly
    290                 295                 300
Glu Lys Asp Asp Ser Gln Gly Ser Gly Arg
305                 310
```

<210> SEQ ID NO 3
<211> LENGTH: 732
<212> TYPE: DNA
<213> ORGANISM: Arabidopsis thaliana

<400> SEQUENCE: 3

```
atggtcatgg agcccaagaa gaaccaaaat ctaccaagtt tcttaaaccc atcacgacag      60
aatcaggaca acgacaagaa gaggaaacaa acagaggtta aaggtttcga cattgtggtc     120
ggcgaaaaga ggaagaagaa ggagaatgaa gaggaagacc aagaaattca gattctttat     180
gagaaggaga agaagaaacc aaacaaagat cgtcacctta agttgaagg aagaggtcgt      240
```

```
agagttaggt tacctccact ctgtgcagca aggatttatc aattgactaa agaattaggt    300
cacaaatcag atggtgagac tcttgaatgg ttgcttcaac atgctgagcc atcgatactc    360
tctgctactg taaatggtat caaacccact gagtctgttg tttctcaacc tcctctcacg    420
gctgatttga tgatttgtca tagcgttgaa gaagcttcaa ggactcaaat ggaggcaaat    480
gggttgtgga gaaatgaaac aggacagacc attggagggt ttgatctgaa ttacggaatt    540
gggtttgatt tcaatggtgt tccagagatt ggttttggag ataatcaaac gcctggactt    600
gaattaaggc tgtctcaagt tggggttttg aatccacagg ttttcaaca aatgggtaaa     660 gaacagttca gggttcttca tcatcattca catgaagatc agcagcagag tgcagaggaa    720
aatggttcat aa                                                        732

<210> SEQ ID NO 4
<211> LENGTH: 243
<212> TYPE: PRT
<213> ORGANISM: Arabidopsis thaliana

<400> SEQUENCE: 4

Met Val Met Glu Pro Lys Lys Asn Gln Asn Leu Pro Ser Phe Leu Asn
1               5                   10                  15

Pro Ser Arg Gln Asn Gln Asp Asn Asp Lys Lys Arg Lys Gln Thr Glu
                20                  25                  30

Val Lys Gly Phe Asp Ile Val Gly Glu Lys Arg Lys Lys Glu
        35                  40                  45

Asn Glu Glu Glu Asp Gln Glu Ile Gln Ile Leu Tyr Glu Lys Glu Lys
50                  55                  60

Lys Lys Pro Asn Lys Asp Arg His Leu Lys Val Glu Gly Arg Gly Arg
65                  70                  75                  80

Arg Val Arg Leu Pro Pro Leu Cys Ala Ala Arg Ile Tyr Gln Leu Thr
                85                  90                  95

Lys Glu Leu Gly His Lys Ser Asp Gly Glu Thr Leu Glu Trp Leu Leu
                100                 105                 110

Gln His Ala Glu Pro Ser Ile Leu Ser Ala Thr Val Asn Gly Ile Lys
            115                 120                 125

Pro Thr Glu Ser Val Val Ser Gln Pro Pro Leu Thr Ala Asp Leu Met
130                 135                 140

Ile Cys His Ser Val Glu Glu Ala Ser Arg Thr Gln Met Glu Ala Asn
145                 150                 155                 160

Gly Leu Trp Arg Asn Glu Thr Gly Gln Thr Ile Gly Gly Phe Asp Leu
                165                 170                 175

Asn Tyr Gly Ile Gly Phe Asp Phe Asn Gly Val Pro Glu Ile Gly Phe
            180                 185                 190

Gly Asp Asn Gln Thr Pro Gly Leu Glu Leu Arg Leu Ser Gln Val Gly
        195                 200                 205

Val Leu Asn Pro Gln Val Phe Gln Gln Met Gly Lys Glu Gln Phe Arg
    210                 215                 220

Val Leu His His His Ser His Glu Asp Gln Gln Gln Ser Ala Glu Glu
225                 230                 235                 240

Asn Gly Ser

<210> SEQ ID NO 5
<211> LENGTH: 930
<212> TYPE: DNA
<213> ORGANISM: Aquilegia formosa x Aquilegia pubescens

<400> SEQUENCE: 5
```

-continued

```
atggatgatc ttaagaattc atcaaagcaa ccacaagaag tagtaacaag tttcttgaga         60
cattcttcac aacaagagat gggaggagga ggaggagaga ataaacaaac agaaatcaga        120
gattttcaaa tctcaacagt tgttgcagat aaagatggtg gtaagaagca gttagcacca        180
aaaagaactt caaataaaga tagacatact aaggtagatg gaagaggtag aaggataagg        240
atgccagctt tatgtgcagc tagaattttt cagttaacaa gagaattggg tcataaatct        300
gatggagaaa ctatacaatg gttattacaa catgctgaac catcaataat tgccgctaca        360
ggtactggaa ctataccagc ttcagcttta gttcaatcta gtagctcagt ttcacaacag        420
gggaattctg tttcagttgg tttacaaaca agatcagtg aattgggaca tgaaattggg         480
tccagtagta gtaggaccaa ttggaatttg gttagatccc cagtaacaac aagtttatgg        540
ccctctgtca gtggttatgt accagggttt catccttctt caggccaacc gacatcgaat        600
ctgagtagtg atggtttgaa ttatttgcct aaattcggta ttcatggttt cgaaatgcct        660
ggatcaaatt taggtacaat gaatttaaat tcattcatgg gggttggtaa taatcaacaa        720
cttcctggat tggaattagg attatctcaa gatgtgcata ccggggtatt gaatcctcaa        780
gctttacagt tttatcagca gatggttcaa tcaagaggag ttgtcatgca tcaacaacag        840
cagcaccagc aacaacaaca acaacaacag cagcagcagc agcaaccaca tgatgatgat        900
gaggatgatt ctcaaggttc aagacattaa                                         930

<210> SEQ ID NO 6
<211> LENGTH: 309
<212> TYPE: PRT
<213> ORGANISM: Aquilegia formosa x Aquilegia pubescens

<400> SEQUENCE: 6

Met Asp Asp Leu Lys Asn Ser Ser Lys Gln Pro Gln Glu Val Val Thr
  1               5                  10                  15

Ser Phe Leu Arg His Ser Ser Gln Gln Glu Met Gly Gly Gly Gly Gly
                 20                  25                  30

Glu Asn Lys Gln Thr Glu Ile Arg Asp Phe Gln Ile Ser Thr Val Val
             35                  40                  45

Ala Asp Lys Asp Gly Gly Lys Lys Gln Leu Ala Pro Lys Arg Thr Ser
 50                  55                  60

Asn Lys Asp Arg His Thr Lys Val Asp Gly Arg Gly Arg Arg Ile Arg
 65                  70                  75                  80

Met Pro Ala Leu Cys Ala Ala Arg Ile Phe Gln Leu Thr Arg Glu Leu
                 85                  90                  95

Gly His Lys Ser Asp Gly Glu Thr Ile Gln Trp Leu Leu Gln His Ala
            100                 105                 110

Glu Pro Ser Ile Ile Ala Ala Thr Gly Thr Gly Thr Ile Pro Ala Ser
        115                 120                 125

Ala Leu Val Gln Ser Ser Ser Val Ser Gln Gly Asn Ser Val
    130                 135                 140

Ser Val Gly Leu Gln Thr Lys Ile Ser Glu Leu Gly His Glu Ile Gly
145                 150                 155                 160

Ser Ser Ser Ser Arg Thr Asn Trp Asn Leu Val Arg Ser Pro Val Thr
                165                 170                 175

Thr Ser Leu Trp Pro Ser Val Ser Gly Tyr Val Pro Gly Phe His Pro
            180                 185                 190

Ser Ser Gly Gln Pro Thr Ser Asn Leu Ser Ser Asp Gly Leu Asn Tyr
        195                 200                 205
```

```
Leu Pro Lys Phe Gly Ile His Gly Phe Glu Met Pro Gly Ser Asn Leu
    210                 215                 220

Gly Thr Met Asn Leu Asn Ser Phe Met Gly Val Gly Asn Asn Gln Gln
225                 230                 235                 240

Leu Pro Gly Leu Glu Leu Gly Leu Ser Gln Asp Val His Thr Gly Val
                245                 250                 255

Leu Asn Pro Gln Ala Leu Gln Phe Tyr Gln Gln Met Val Gln Ser Arg
            260                 265                 270

Gly Val Val Met His Gln Gln Gln His Gln Gln Gln Gln Gln Gln Gln
            275                 280                 285

Gln Gln Gln Gln Gln Gln Pro His Asp Asp Asp Glu Asp Asp Ser
    290                 295                 300

Gln Gly Ser Arg His
305

<210> SEQ ID NO 7
<211> LENGTH: 1038
<212> TYPE: DNA
<213> ORGANISM: Glycine max

<400> SEQUENCE: 7
atggatccca agggctcaaa gcagcagcca cagcaatcac aggaggtggt accaaacttc      60
ctcagcctcc cccaacagca acaagggaat ccaacaacaa caacatggga gagaacaaa     120
cctgcagagg tgaaggattt ccagatagtg gtagctgaga caaggaaga gagcaagaaa     180
cagcagcaac agttggcacc aaagaggagt tccaacaagg acaggcacac caaggttgaa     240
ggcagggga ggaggataag gatgcctgct ctctgcgcag ccagaatctt ccagttgacc     300
agggaattgg gtcacaaatc tgatggggaa accatccagt ggctcctcca gcaggctgag     360
ccatccatca tagctgccac tgggactggc acaataccag catctgctct tgctgctgct     420
ggaaactcac tctcaccaca agctgcttct ctttcatcat ccttgcacca acatcaacaa     480
aagattgatg aattgggtgg gtcaggggggg agtagtagta gggccagctg gcaaatggtt     540
gggggaatt tggggagacc ccatttgggt gtgggtgtgg ccacagcagc aggcctatgg     600
cccccctcatg tcagtggatt tggatttcaa acaccaccaa caacaacaac accaacaaca     660
acaacatcat catctggtcc atctaatgcc accttagcca ctgagagctc caattacctt     720
cagaaaattg cattccctgg cttttgactg cctacttctg ccactaacat gatgggtcac     780
atgagtttca cctcaatttt gggtggaggt gggggtggtg gggcccagca tatgcctggc     840
ttggagcttg gtctttccca ggatggccat attggggtgt tgaatcaaca ggccttgaac     900
cagatttatc agcagatgaa tcaggctggt agagtgcatc atcatcagca tcagcatcat     960
catcagcatc atcagcagca acaacaccat cagcaaactc ctgctaagga tgattctcaa    1020
ggctcaggag gacagtag                                                 1038

<210> SEQ ID NO 8
<211> LENGTH: 345
<212> TYPE: PRT
<213> ORGANISM: Glycine max

<400> SEQUENCE: 8

Met Asp Pro Lys Gly Ser Lys Gln Gln Pro Gln Gln Ser Gln Glu Val
1               5                   10                  15

Val Pro Asn Phe Leu Ser Leu Pro Gln Gln Gln Gly Asn Thr Asn
            20                  25                  30

Asn Asn Asn Met Gly Glu Asn Lys Pro Ala Glu Val Lys Asp Phe Gln
```

```
                    35                  40                  45
Ile Val Val Ala Glu Asn Lys Glu Ser Lys Lys Gln Gln Gln Gln
 50                  55                  60
Leu Ala Pro Lys Arg Ser Ser Asn Lys Asp Arg His Thr Lys Val Glu
 65                  70                  75                  80
Gly Arg Gly Arg Arg Ile Arg Met Pro Ala Leu Cys Ala Ala Arg Ile
                     85                  90                  95
Phe Gln Leu Thr Arg Glu Leu Gly His Lys Ser Asp Gly Glu Thr Ile
                    100                 105                 110
Gln Trp Leu Leu Gln Gln Ala Glu Pro Ser Ile Ile Ala Ala Thr Gly
                    115                 120                 125
Thr Gly Thr Ile Pro Ala Ser Ala Leu Ala Ala Gly Asn Ser Leu
130                 135                 140
Ser Pro Gln Ala Ala Ser Leu Ser Ser Ser Leu His Gln His Gln Gln
145                 150                 155                 160
Lys Ile Asp Glu Leu Gly Gly Ser Gly Gly Ser Ser Ser Arg Ala Ser
                    165                 170                 175
Trp Gln Met Val Gly Asn Leu Gly Arg Pro His Leu Gly Val Gly
                    180                 185                 190
Val Ala Thr Ala Ala Gly Leu Trp Pro Pro His Val Ser Gly Phe Gly
                    195                 200                 205
Phe Gln Thr Pro Pro Thr Thr Thr Pro Thr Thr Thr Ser Ser
    210                 215                 220
Ser Gly Pro Ser Asn Ala Thr Leu Ala Thr Glu Ser Ser Asn Tyr Leu
225                 230                 235                 240
Gln Lys Ile Ala Phe Pro Gly Phe Asp Leu Pro Thr Ser Ala Thr Asn
                    245                 250                 255
Met Met Gly His Met Ser Phe Thr Ser Ile Leu Gly Gly Gly Gly
                    260                 265                 270
Gly Gly Ala Gln His Met Pro Gly Leu Glu Leu Gly Leu Ser Gln Asp
                    275                 280                 285
Gly His Ile Gly Val Leu Asn Gln Gln Ala Leu Asn Gln Ile Tyr Gln
                    290                 295                 300
Gln Met Asn Gln Ala Gly Arg Val His His His Gln His Gln His His
305                 310                 315                 320
His Gln His His Gln Gln Gln His Gln Gln Thr Pro Ala Lys
                    325                 330                 335
Asp Asp Ser Gln Gly Ser Gly Gly Gln
                    340                 345

<210> SEQ ID NO 9
<211> LENGTH: 903
<212> TYPE: DNA
<213> ORGANISM: Gossypium hirsutum

<400> SEQUENCE: 9
atggatccca agggcgccaa gcagcctcca gaggaagtag ccaacttgtt gagcctgcca      60
ccccaacccc aacagcaaca gcctcaaaac atgggagaga taaagcagc agaaatcaag     120 gatttccaga ttgtggttgc agataaagga aagggaaga agcaacagtt ggccccaaag     180
agaagttcta acaaagacag gcacaccaaa gttgaaggaa gaggtagaag gataaggatg     240
cctgctttat gtgctgctag aatctttcag ttgaccaggg aattgggtca caagtctgat     300
ggggaaacca tacagtggct gttacaacaa gctgaaccat ccataattgc cgccactggg     360
agcggaacaa ttccagcatc agctttggct gcagctggag gctcagtttc acagccaggg     420
```

```
gcctctctat cagcagggtt gcaccaaaag atggaagatt tagggggtc cagtataggg      480 tcagggagca gtaggaccag ttggacaatg gttggtggca atttgggaag accccatcat      540
gtggcgaccg ggttatggcc accagtcagt ggttttgggt ttcagtcatc atctggtccg      600
tctacaacaa atttaggcag tgatagttcc aattatctgc aaaagcttgg gtttccaggt      660
tttgatttgc cagctagtaa catgggtcag ataagtttca cctcaatctt gggcggagct      720
aatcagcagc tcccgggttt ggaacttggg ttatctcaag atggtcatat tggggtctta      780
aatcctcatg ctttgaacca gatttatcag cagatggagc aagctcggat gcaacccccaa      840 catcagcatc agcaccagca acaaccccct gctaaggatg actcccaagg atcgggccag      900
taa                                                                    903
```

```
<210> SEQ ID NO 10
<211> LENGTH: 300
<212> TYPE: PRT
<213> ORGANISM: Gossypium hirsutum

<400> SEQUENCE: 10
```

```
Met Asp Pro Lys Gly Ala Lys Gln Pro Glu Glu Val Ala Asn Leu
1               5                  10                  15

Leu Ser Leu Pro Pro Gln Pro Gln Gln Gln Pro Gln Asn Met Gly
            20                  25                  30

Glu Asn Lys Ala Ala Glu Ile Lys Asp Phe Gln Ile Val Ala Asp
        35                  40                  45

Lys Gly Glu Gly Lys Lys Gln Gln Leu Ala Pro Lys Arg Ser Ser Asn
50                  55                  60

Lys Asp Arg His Thr Lys Val Glu Gly Arg Gly Arg Arg Ile Arg Met
65                  70                  75                  80

Pro Ala Leu Cys Ala Ala Arg Ile Phe Gln Leu Thr Arg Glu Leu Gly
                85                  90                  95

His Lys Ser Asp Gly Glu Thr Ile Gln Trp Leu Leu Gln Gln Ala Glu
            100                 105                 110

Pro Ser Ile Ile Ala Ala Thr Gly Ser Gly Thr Ile Pro Ala Ser Ala
        115                 120                 125

Leu Ala Ala Ala Gly Gly Ser Val Ser Gln Pro Gly Ala Ser Leu Ser
130                 135                 140

Ala Gly Leu His Gln Lys Met Glu Asp Leu Gly Gly Ser Ser Ile Gly
145                 150                 155                 160

Ser Gly Ser Ser Arg Thr Ser Trp Thr Met Val Gly Gly Asn Leu Gly
                165                 170                 175

Arg Pro His His Val Ala Thr Gly Leu Trp Pro Pro Val Ser Gly Phe
            180                 185                 190

Gly Phe Gln Ser Ser Ser Gly Pro Ser Thr Thr Asn Leu Gly Ser Asp
        195                 200                 205

Ser Ser Asn Tyr Leu Gln Lys Leu Gly Phe Pro Gly Phe Asp Leu Pro
    210                 215                 220

Ala Ser Asn Met Gly Gln Ile Ser Phe Thr Ser Ile Leu Gly Gly Ala
225                 230                 235                 240

Asn Gln Gln Leu Pro Gly Leu Glu Leu Gly Leu Ser Gln Asp Gly His
                245                 250                 255

Ile Gly Val Leu Asn Pro His Ala Leu Asn Gln Ile Tyr Gln Gln Met
            260                 265                 270

Glu Gln Ala Arg Met Gln Pro Gln His Gln His Gln Gln Gln
        275                 280                 285
```

```
Pro Pro Ala Lys Asp Asp Ser Gln Gly Ser Gly Gln
    290                 295             300
```

<210> SEQ ID NO 11
<211> LENGTH: 819
<212> TYPE: DNA
<213> ORGANISM: Lycopersicon esculentum

<400> SEQUENCE: 11

```
atggatccca aacaggctaa ccacaacaat attaagccta ctcatgatca gataaaagag    60
ttgcagattt tgaaaaatga tgaaacgaac aaggtggctg ctcccaaaag aaaagatagg   120
catacaaaag ttgaaggtag agggaggaga atacgtatgc cggcgctctg tgcagcaaga   180
atcttccagc ttacgcgcga attgggtcat aaatctgatg gtgagacaat tcagtggctg   240
ctgcagcaag ccgagccttc gattattgct gctactggca cagggacaat acctgcctcg   300
gctttagctg cagcagcctc tgtttctcaa caggggatct ctgtatcagc tggtttaatg   360
attgaatcgg gggcgaatat cgcggggtct ggtagcagta agtagtaa tagtaggacc   420
aattggccaa tgatctgtgg gaattttgga gaccccatt tggctacagc aggaatgtgg   480
cctgcccctg cccctgttgt cactagtttt gggtttcaat cctcatctgc tccatcaagc   540
gcgagtttag gtagtgatag ttcaaattat tacttacaga aaattgggtt tcctggattt   600
gatctgcctg cagctacaag tatgaatccg atgtgtttta cttcaattct tggtggaagt   660
aatcagcaac tgccaggatt ggaactggga ttatctcaag agggtcattt aggggttttg   720
aaccagatat accagcaggc aagaatgcaa catccgcagc agcaacatca acaacaacaa   780
caatctccgg aggaggattc tcaaggatca ggacattaa                          819
```

<210> SEQ ID NO 12
<211> LENGTH: 272
<212> TYPE: PRT
<213> ORGANISM: Lycopersicon esculentum

<400> SEQUENCE: 12

```
Met Asp Pro Lys Gln Ala Asn His Asn Asn Ile Lys Pro Thr His Asp
1               5                   10                  15

Gln Ile Lys Glu Leu Gln Ile Leu Lys Asn Asp Glu Thr Asn Lys Val
            20                  25                  30

Ala Ala Pro Lys Arg Lys Asp Arg His Thr Lys Val Glu Gly Arg Gly
        35                  40                  45

Arg Arg Ile Arg Met Pro Ala Leu Cys Ala Ala Arg Ile Phe Gln Leu
    50                  55                  60

Thr Arg Glu Leu Gly His Lys Ser Asp Gly Glu Thr Ile Gln Trp Leu
65                  70                  75                  80

Leu Gln Gln Ala Glu Pro Ser Ile Ile Ala Ala Thr Gly Thr Gly Thr
                85                  90                  95

Ile Pro Ala Ser Ala Leu Ala Ala Ala Ala Ser Val Ser Gln Gln Gly
            100                 105                 110

Ile Ser Val Ser Ala Gly Leu Met Ile Glu Ser Gly Ala Asn Ile Ala
        115                 120                 125

Gly Ser Gly Ser Ser Arg Ser Ser Asn Ser Arg Thr Asn Trp Pro Met
    130                 135                 140

Ile Cys Gly Asn Phe Gly Arg Pro His Leu Ala Thr Ala Gly Met Trp
145                 150                 155                 160

Pro Ala Pro Ala Pro Val Val Thr Ser Phe Gly Phe Gln Ser Ser Ser
                165                 170                 175
```

```
Ala Pro Ser Ser Ala Ser Leu Gly Ser Asp Ser Ser Asn Tyr Tyr Leu
            180                 185                 190

Gln Lys Ile Gly Phe Pro Gly Phe Asp Leu Pro Ala Ala Thr Ser Met
        195                 200                 205

Asn Pro Met Cys Phe Thr Ser Ile Leu Gly Gly Ser Asn Gln Gln Leu
    210                 215                 220

Pro Gly Leu Glu Leu Gly Leu Ser Gln Glu Gly His Leu Gly Val Leu
225                 230                 235                 240

Asn Gln Ile Tyr Gln Gln Ala Arg Met Gln His Pro Gln Gln His
            245                 250                 255

Gln Gln Gln Gln Gln Ser Pro Glu Glu Asp Ser Gln Gly Ser Gly His
        260                 265                 270
```

<210> SEQ ID NO 13
<211> LENGTH: 966
<212> TYPE: DNA
<213> ORGANISM: Malus domestica

<400> SEQUENCE: 13

```
atggatccca agggctcaaa gcagacacaa gacataccca gcttcttgag ccttccccca    60
caatcacaac cacaacctga gcagcagcag caaccacaac aacaacctca acccaacaac   120
aacatgagcg acaacaaacc tgctgaaatc aaagacttcc agattgtaat cgccgacaaa   180
gatgagtcgg gaaagaagca gttggcgccc aagagaagct ccaacaaaga cagacacact   240
aaagtcgaag gcaggggaag gaggatacgg atgccggccc tctgcgccgc cagaatcttt   300
caattgacca gagagttggg tcacaaatcc gatggggaaa caatccagtg ctcctccag    360
caggccgagc cgtcgattgt tgccaccacc gggaccggga cgattccggc gtcggctttg   420
gcggcggcag gtggctctgt ttcgcaacag gggacttctt tatcagctgg attgcaccaa   480
agatcgatg aattgggggg gtccagtggg ggtaggacca gttgggcaat ggtgggcggg   540
aatttgggga ccccatgt ggcaggggtg ggcgggctat ggccccctgt cagtagcttt    600
gggttccagt catcatctgg tcctccatcg gccaccacaa atctgggcac tgagagttca   660
aattacctgc aaaaaattgg gtttcctggc tttgacttgc ctgtctctaa catgggtccg   720
atgagttttta cttcaatttt gggtgggggc aatcagcagc agcagcagca gcttcctggg   780
ttggaacttg ggttgtcaca ggatggacat attggggttc tgaactctca ggctttgagc   840
cagatttacc agcagatggg gcatgttaga gtgcaccagc agccgccgca gcaccaccac   900
cagcaacacc accaccacca gcagcaaccg ccttccaagg acgattctca aggatccgga   960
cagtag                                                              966
```

<210> SEQ ID NO 14
<211> LENGTH: 321
<212> TYPE: PRT
<213> ORGANISM: Malus domestica

<400> SEQUENCE: 14

```
Met Asp Pro Lys Gly Ser Lys Gln Thr Gln Asp Ile Pro Ser Phe Leu
1               5                   10                  15

Ser Leu Pro Pro Gln Ser Gln Pro Gln Pro Glu Gln Gln Gln Gln Pro
            20                  25                  30

Gln Gln Gln Pro Gln Pro Asn Asn Asn Met Ser Asp Asn Lys Pro Ala
        35                  40                  45

Glu Ile Lys Asp Phe Gln Ile Val Ile Ala Asp Lys Asp Glu Ser Gly
    50                  55                  60
```

| | | | | | | | | | | | | |
|---|---|---|---|---|---|---|---|---|---|---|---|---|
| Lys | Lys | Gln | Leu | Ala | Pro | Lys | Arg | Ser | Ser | Asn | Lys | Asp | Arg | His | Thr |
| 65 | | | | | 70 | | | | 75 | | | | | 80 | |

Lys Lys Gln Leu Ala Pro Lys Arg Ser Ser Asn Lys Asp Arg His Thr
65                  70                  75                  80

Lys Val Glu Gly Arg Gly Arg Ile Arg Met Pro Ala Leu Cys Ala
            85                  90                  95

Ala Arg Ile Phe Gln Leu Thr Arg Glu Leu Gly His Lys Ser Asp Gly
                100                 105                 110

Glu Thr Ile Gln Trp Leu Leu Gln Gln Ala Glu Pro Ser Ile Val Ala
            115                 120                 125

Thr Thr Gly Thr Gly Thr Ile Pro Ala Ser Ala Leu Ala Ala Gly
            130                 135                 140

Gly Ser Val Ser Gln Gln Gly Thr Ser Leu Ser Ala Gly Leu His Gln
145                 150                 155                 160

Lys Ile Asp Glu Leu Gly Gly Ser Ser Gly Arg Thr Ser Trp Ala
                165                 170                 175

Met Val Gly Gly Asn Leu Gly Arg Pro His Val Ala Gly Val Gly Gly
            180                 185                 190

Leu Trp Pro Pro Val Ser Ser Phe Gly Phe Gln Ser Ser Gly Pro
                195                 200                 205

Pro Ser Ala Thr Thr Asn Leu Gly Thr Glu Ser Ser Asn Tyr Leu Gln
210                 215                 220

Lys Ile Gly Phe Pro Gly Phe Asp Leu Pro Val Ser Asn Met Gly Pro
225                 230                 235                 240

Met Ser Phe Thr Ser Ile Leu Gly Gly Gly Asn Gln Gln Gln Gln
            245                 250                 255

Gln Leu Pro Gly Leu Glu Leu Gly Leu Ser Gln Asp Gly His Ile Gly
            260                 265                 270

Val Leu Asn Ser Gln Ala Leu Ser Gln Ile Tyr Gln Gln Met Gly His
            275                 280                 285

Val Arg Val His Gln Pro Pro Gln His His Gln Gln His His
            290                 295                 300

His His Gln Gln Gln Pro Pro Ser Lys Asp Asp Ser Gln Gly Ser Gly
305                 310                 315                 320

Gln

<210> SEQ ID NO 15
<211> LENGTH: 855
<212> TYPE: DNA
<213> ORGANISM: Medicago truncatula

<400> SEQUENCE: 15

```
atggatccca aaactcaaa gcaacaatca caactctcaa acatgggaga gaacaaagaa      60
tcagagacaa aaatcttca aattgtgtta tctgaaacaa caacaaaaga tgaaacaaag     120
aaacaactag caccaaaaag aacatcaaac aaagacagac acacaaaagt tgaaggaaga     180
ggaagaagaa taaggatgcc agctttatgt gcagcaagaa tctttcagct aacaagagag     240
ttaggtcata atcagatgg tgaaacaatt caatggcttt tacaacaatc tgaaccatca     300
atcatagctg caacaggaac aggaacaata ccagcttcag ctttagcttc ttctggtaat     360
actttgacac cacaaggttc atctttgtct tctggtttac agttgaatga taggaatact     420
tgggctcaga cccatcaagc ccatcaggcc catcagggcc atcatgttag ttctacaagt     480
ttatggccac atcatcatgt tggtggattt ggatttcatc aatcatcatc atctggtggt     540
ttagtagcta ctactgttgg tgaaaataat agtggaaatt attttcagaa aattgggttt     600
tctggatttg atatgccaac aggaacaaat ttgggagtgg gagggatgag ttttacttca     660
```

```
attttggggg gtgcaaatca gcagatgcct ggtttggaat tagggttgtc acaagatgga      720
catattggtg tgttgaatca acaagcttta actcagattt atcagcagat tggtcaaaat      780
caaactaggg ttcagcacca gaatcagcag aataataata ctactaagga tgattctcac      840
agttcagaac agtag                                                       855
```

```
<210> SEQ ID NO 16
<211> LENGTH: 284
<212> TYPE: PRT
<213> ORGANISM: Medicago truncatula

<400> SEQUENCE: 16

Met Asp Pro Lys Asn Ser Lys Gln Gln Ser Gln Leu Ser Asn Met Gly
1               5                   10                  15

Glu Asn Lys Glu Ser Glu Thr Lys Asn Leu Gln Ile Val Leu Ser Glu
                20                  25                  30

Thr Thr Thr Lys Asp Glu Thr Lys Lys Gln Leu Ala Pro Lys Arg Thr
            35                  40                  45

Ser Asn Lys Asp Arg His Thr Lys Val Glu Gly Arg Gly Arg Arg Ile
    50                  55                  60

Arg Met Pro Ala Leu Cys Ala Ala Arg Ile Phe Gln Leu Thr Arg Glu
65                  70                  75                  80

Leu Gly His Lys Ser Asp Gly Glu Thr Ile Gln Trp Leu Leu Gln Gln
                85                  90                  95

Ser Glu Pro Ser Ile Ile Ala Ala Thr Gly Thr Gly Thr Ile Pro Ala
                100                 105                 110

Ser Ala Leu Ala Ser Ser Gly Asn Thr Leu Thr Pro Gln Gly Ser Ser
            115                 120                 125

Leu Ser Ser Gly Leu Gln Leu Asn Asp Arg Asn Thr Trp Ala Gln Thr
    130                 135                 140

His Gln Ala His Gln Ala His Gln Gly His His Val Ser Ser Thr Ser
145                 150                 155                 160

Leu Trp Pro His His His Val Gly Gly Phe Gly Phe His Gln Ser Ser
                165                 170                 175

Ser Ser Gly Gly Leu Val Ala Thr Thr Val Gly Glu Asn Asn Ser Gly
                180                 185                 190

Asn Tyr Phe Gln Lys Ile Gly Phe Ser Gly Phe Asp Met Pro Thr Gly
            195                 200                 205

Thr Asn Leu Gly Val Gly Gly Met Ser Phe Thr Ser Ile Leu Gly Gly
    210                 215                 220

Ala Asn Gln Gln Met Pro Gly Leu Glu Leu Gly Leu Ser Gln Asp Gly
225                 230                 235                 240

His Ile Gly Val Leu Asn Gln Ala Leu Thr Gln Ile Tyr Gln Gln
                245                 250                 255

Ile Gly Gln Asn Gln Thr Arg Val Gln His Gln Asn Gln Asn Asn
            260                 265                 270

Asn Thr Thr Lys Asp Asp Ser His Ser Ser Glu Gln
    275                 280
```

```
<210> SEQ ID NO 17
<211> LENGTH: 888
<212> TYPE: DNA
<213> ORGANISM: Nicotiana benthamiana

<400> SEQUENCE: 17
atggatccca agcagccgcc agcgcagtct aacgctatca acattaacaa caatattatg      60
```

```
gttgagtaca ataagcctgt tcatgatcaa ataaaagatg atgaaaccaa gaagcggcag    120
caattggttc ctaaaagaaa agataggcac acaaaagttg aaggcagagg gaggaggata    180
cgtatgcctg ctctttgcgc tgctaggatt ttccaactca cccgcgaatt aggtcataaa    240
tctgatggag agacaatcca gtggctgctg cagcaagccg agccctccat atttgcggcc    300
accgggacag ggaccatccc tgcctcggct ttagctgtag cagccgctgg cccctctgtt    360
tcccaacaga ggacctctgt atctgctggt ttgcataaaa aaatggatga attgggagcg    420
aatatagtcg ggtccgctag tatatgtagt agtagtagta ctagtagggc cagttggcca    480
atgatgattg ggaattttgg aagaccccat ttggccacag caggaatatg gcccggacct    540
actcctgttg tcaatagttt cgcgttacag acagcactga ctcctggatc aagcaccaat    600
ttgggtagtg aaagttccaa ttattaccta caaaagattg gctttcctgg atttgatctg    660
cctgcagcca ccaatatgag tttttacttca attctaggtt ccagtaataa ccagcaattg    720
ccaggtttgg agcttggatt atctcaagac aggggtcata tagggttttt aaactctcaa    780
ggcttgagcc agatatacca ggctagaatt cataatcaac agcagcacca gcaaaatcag    840
catgagcatc tatctcccga ggatgattct cacggatcag gacactaa                 888
```

<210> SEQ ID NO 18
<211> LENGTH: 295
<212> TYPE: PRT
<213> ORGANISM: Nicotiana benthamiana

<400> SEQUENCE: 18

```
Met Asp Pro Lys Gln Pro Pro Ala Gln Ser Asn Ala Ile Asn Ile Asn
1               5                   10                  15

Asn Asn Ile Met Val Glu Tyr Asn Lys Pro Val His Asp Gln Ile Lys
            20                  25                  30

Asp Asp Glu Thr Lys Lys Arg Gln Gln Leu Val Pro Lys Arg Lys Asp
        35                  40                  45

Arg His Thr Lys Val Glu Gly Arg Gly Arg Arg Ile Arg Met Pro Ala
    50                  55                  60

Leu Cys Ala Ala Arg Ile Phe Gln Leu Thr Arg Glu Leu Gly His Lys
65                  70                  75                  80

Ser Asp Gly Glu Thr Ile Gln Trp Leu Leu Gln Gln Ala Glu Pro Ser
                85                  90                  95

Ile Phe Ala Ala Thr Gly Thr Gly Thr Ile Pro Ala Ser Ala Leu Ala
            100                 105                 110

Val Ala Ala Ala Gly Pro Ser Val Ser Gln Gln Arg Thr Ser Val Ser
        115                 120                 125

Ala Gly Leu His Lys Lys Met Asp Glu Leu Gly Ala Asn Ile Val Gly
    130                 135                 140

Ser Ala Ser Ile Cys Ser Ser Ser Thr Ser Arg Ala Ser Trp Pro
145                 150                 155                 160

Met Met Ile Gly Asn Phe Gly Arg Pro His Leu Ala Thr Ala Gly Ile
                165                 170                 175

Trp Pro Gly Pro Thr Pro Val Val Asn Ser Phe Ala Leu Gln Thr Ala
            180                 185                 190

Leu Thr Pro Gly Ser Ser Thr Asn Leu Gly Ser Glu Ser Ser Asn Tyr
        195                 200                 205

Tyr Leu Gln Lys Ile Gly Phe Pro Gly Phe Asp Leu Pro Ala Ala Thr
    210                 215                 220

Asn Met Ser Phe Thr Ser Ile Leu Gly Ser Ser Asn Asn Gln Gln Leu
```

```
              225                 230                 235                 240
Pro Gly Leu Glu Leu Gly Leu Ser Gln Asp Arg Gly His Ile Gly Val
                245                 250                 255
Leu Asn Ser Gln Gly Leu Ser Gln Ile Tyr Gln Ala Arg Ile His Asn
                260                 265                 270
Gln Gln Gln His Gln Gln Asn Gln His Glu His Leu Ser Pro Glu Asp
            275                 280                 285
Asp Ser His Gly Ser Gly His
            290                 295

<210> SEQ ID NO 19
<211> LENGTH: 894
<212> TYPE: DNA
<213> ORGANISM: Ocimum basilicum

<400> SEQUENCE: 19
atggatccga agagctcgaa gcagccgcag gaggtttcga atcacagcaa caccaacagc        60
ttaggcgaaa acaaagcagc ggaaatcaag gattttcaga ttgtagttgc ggagaaggat       120
gattcgaaga agctagccct agctccgaag cgaagctcca acaaggaccg ccacaccaag       180
gtggaaggcc gcggccggcg aattcggatg ccggcgctct gcgccgccag aatcttccaa       240
ttgacccgag aattagggca caaatccgat ggcgagacca tccagtggct cctccagcaa       300
gccgagccgt cgatcatcgc cgccacgggg agcggcacca tccccgcctc cgccctcgcc       360
gcagccgccg gctcgatttc tcagcaaggt agctcgattt cgtctggact ccatcagaaa       420
atcgaggatt taggcgcttc tatgggtggt ggtggggggca ggaatccctg gcctatgatt       480
ggtgggaatc tgagtagacc acatgtgggc gcaagcacag gattatggcc tcccactgga       540
ttcggcttcc agacggcgtc gtcttcttcc tcgtctggtc cgtcaatcgc ggcggagaat       600
cctaattatc tccagaaaat ggggtttgct ggatttgagc tgcccgggaa tatcgggcag       660
atgagtttca cctccatctt aagcggcggc gggcagcagc tgcccggatt ggagctcggc       720
ctttcacaag atggaaatat tgggtttttg aatccgcaag cttttgggca gatttatcag       780
cagattaatc cggcggcgcg tgtggttaac gcacatcaaa atcaccacca acaacaccac       840
catcagcagc cattgtcgtc gaaagatgat gattctcaag aatcaggaca gtag             894

<210> SEQ ID NO 20
<211> LENGTH: 297
<212> TYPE: PRT
<213> ORGANISM: Ocimum basilicum

<400> SEQUENCE: 20

Met Asp Pro Lys Ser Ser Lys Gln Pro Gln Glu Val Ser Asn His Ser
1               5                   10                  15

Asn Thr Asn Ser Leu Gly Glu Asn Lys Ala Ala Glu Ile Lys Asp Phe
            20                  25                  30

Gln Ile Val Val Ala Glu Lys Asp Ser Lys Lys Leu Ala Leu Ala
        35                  40                  45

Pro Lys Arg Ser Ser Asn Lys Asp Arg His Thr Lys Val Glu Gly Arg
    50                  55                  60

Gly Arg Arg Ile Arg Met Pro Ala Leu Cys Ala Ala Arg Ile Phe Gln
65                  70                  75                  80

Leu Thr Arg Glu Leu Gly His Lys Ser Asp Gly Glu Thr Ile Gln Trp
                85                  90                  95

Leu Leu Gln Gln Ala Glu Pro Ser Ile Ile Ala Ala Thr Gly Ser Gly
            100                 105                 110
```

```
Thr Ile Pro Ala Ser Ala Leu Ala Ala Ala Gly Ser Ile Ser Gln
            115                 120                 125
Gln Gly Ser Ser Ile Ser Ser Gly Leu His Gln Lys Ile Glu Asp Leu
    130                 135                 140
Gly Ala Ser Met Gly Gly Gly Gly Arg Asn Pro Trp Pro Met Ile
145                 150                 155                 160
Gly Gly Asn Leu Ser Arg Pro His Val Gly Ala Ser Thr Gly Leu Trp
            165                 170                 175
Pro Pro Thr Gly Phe Gly Phe Gln Thr Ala Ser Ser Ser Ser Ser
            180                 185                 190
Gly Pro Ser Ile Ala Ala Glu Asn Pro Asn Tyr Leu Gln Lys Met Gly
            195                 200                 205
Phe Ala Gly Phe Glu Leu Pro Gly Asn Ile Gly Gln Met Ser Phe Thr
            210                 215                 220
Ser Ile Leu Ser Gly Gly Gln Gln Leu Pro Gly Leu Glu Leu Gly
225                 230                 235                 240
Leu Ser Gln Asp Gly Asn Ile Gly Val Leu Asn Pro Gln Ala Phe Gly
            245                 250                 255
Gln Ile Tyr Gln Ile Asn Pro Ala Ala Arg Val Val Asn Ala His
            260                 265                 270
Gln Asn His His Gln His His His Gln Gln Pro Leu Ser Ser Lys
            275                 280                 285
Asp Asp Asp Ser Gln Glu Ser Gly Gln
            290                 295

<210> SEQ ID NO 21
<211> LENGTH: 954
<212> TYPE: DNA
<213> ORGANISM: Oryza sativa

<400> SEQUENCE: 21
atggacccca aattcccccc accccaccg ctaaacaaaa cggagcccac caccaccacc      60
accaaccagc agcatcacca cgatgagcag cagcagcagc atcgcctcca gattcaagtt     120
catcctcagc agcaggagca gcaggatgga ggtggaggag gagggaagga tcagcagcag     180
cagcagcaga tgcaggtggt ggttgcggcg gcggcggggg agaggaggat gcaggggcta     240
gggccgaagc ggagctcgaa caaggaccgc cacaccaagg tggacgggcg ggggcggcgg     300
atccggatgc cggcgctgtg cgccgcccgg atcttccagc tcacgcggga gctcggccac     360
aagtccgacg gcgagaccgt ccagtggctg ctccagcagg cggagccggc catcgtcgcc     420
gccacgggga ccgggaccat cccggcgtcc gcgctcgcct ccgtcgcccc ctccctccct     480
tcccccaact ccgccctctc caggtcgcac caccaccacc accacatgtg ggcggcagcg     540
ccgcccacgg cgtccgccgg gttcgccggt gcagggttct ccggcgccga ctccggggtg     600
atcgcgggga tcatgcagcg gatggggatc cccgccggga tcgagctcca gggcggggga     660
gcgggggggt tgggggggtgg gggtggcggc ggcggtggcc acatcgggtt cgcgcccatg     720
ttcgccagcc acgcggcggc ggcggcggcc atgccggggc tagagctagg gctctcgcag     780
gacggccaca tcggcgtgct cgccgcgcag tcgctcagcc agttctacca ccaggtcggc     840
gccgccggtc agctgcagca ccagcaccag catcaccatc agcagcagca gcagcagcag     900
gacggggagg acaaccgcga cgacggcgag tccgatgagg agtccgggca gtag            954

<210> SEQ ID NO 22
<211> LENGTH: 317
```

<212> TYPE: PRT
<213> ORGANISM: Oryza sativa

<400> SEQUENCE: 22

Met Asp Pro Lys Phe Pro Pro Pro Pro Leu Asn Lys Thr Glu Pro
1               5                   10                  15

Thr Thr Thr Thr Thr Asn Gln Gln His His Asp Glu Gln Gln Gln
            20                  25                  30

Gln His Arg Leu Gln Ile Gln Val His Pro Gln Gln Glu Gln Gln
        35                  40                  45

Asp Gly Gly Gly Gly Gly Lys Asp Gln Gln Gln Gln Gln Gln Met
    50                  55                  60

Gln Val Val Ala Ala Ala Gly Glu Arg Arg Met Gln Gly Leu
65              70                  75                  80

Gly Pro Lys Arg Ser Ser Asn Lys Asp Arg His Thr Lys Val Asp Gly
                85                  90                  95

Arg Gly Arg Arg Ile Arg Met Pro Ala Leu Cys Ala Ala Arg Ile Phe
                100                 105                 110

Gln Leu Thr Arg Glu Leu Gly His Lys Ser Asp Gly Glu Thr Val Gln
                115                 120                 125

Trp Leu Leu Gln Gln Ala Glu Pro Ala Ile Val Ala Ala Thr Gly Thr
130                 135                 140

Gly Thr Ile Pro Ala Ser Ala Leu Ala Ser Val Ala Pro Ser Leu Pro
145                 150                 155                 160

Ser Pro Asn Ser Ala Leu Ser Arg Ser His His His His His Met
                165                 170                 175

Trp Ala Ala Ala Pro Pro Thr Ala Ser Ala Gly Phe Ala Gly Ala Gly
                180                 185                 190

Phe Ser Gly Ala Asp Ser Gly Val Ile Gly Ile Met Gln Arg Met
                195                 200                 205

Gly Ile Pro Ala Gly Ile Glu Leu Gln Gly Gly Ala Gly Gly Leu
    210                 215                 220

Gly Gly Gly Gly Gly Gly Gly Gly His Ile Gly Phe Ala Pro Met
225                 230                 235                 240

Phe Ala Ser His Ala Ala Ala Ala Ala Met Pro Gly Leu Glu Leu
                245                 250                 255

Gly Leu Ser Gln Asp Gly His Ile Gly Val Leu Ala Ala Gln Ser Leu
                260                 265                 270

Ser Gln Phe Tyr His Gln Val Gly Ala Ala Gly Gln Leu Gln His Gln
                275                 280                 285

His Gln His His His Gln Gln Gln Gln Gln Gln Asp Gly Glu Asp
    290                 295                 300

Asn Arg Asp Asp Gly Glu Ser Asp Glu Glu Ser Gly Gln
305                 310                 315

<210> SEQ ID NO 23
<211> LENGTH: 963
<212> TYPE: DNA
<213> ORGANISM: Populus tremuloides

<400> SEQUENCE: 23
atggatccca agggctctaa ctcaaaaaac ccacatgagt tacccacttt cttgacccac      60 acccacccttt ctcctcctca tcctcctcca caacctcatc ttcaacaacc acaacaactc     120
catagccaaa accaacaaca acccaacatg ggagacaaca aaccagcaga atcaaagac      180 tttcagattg tagtagctga caaagaagag caaaagaaac agttagcacc aaagagaagc     240

```
tcaaacaaag acagacacac aaaagttgaa ggtagaggta gaaggataag gatgccagct    300
ctttgtgcag cgagaatctt tcaattgaca agagaattgg gtcacaaatc tgatggagag    360
acaatacagt ggcttctaca acaagctgaa ccatctataa ttgcagcaac tgggactggt    420
actatacctg catcagcttt agcagctgct ggcggtgcaa tttcacaaca aggagcttct    480
ctttctgctg gtttgcatca aaagattgat gatttaggtg ggtccagtag tagtagggcc    540
agttgggcaa tgttaggtgg caatttaggg agaccccatc atgttactac tgcaggatta    600
tggcccccag ttggaggtta tgggttccag tcatcatcta attccactgg tccatcaaca    660
acaaatatag ggactgaagc tgctgctgct ggtggttcta gttatttgca aaaactcggg    720
tttccagggt ttgacttgcc gggtaacaac atggggccta tgagttttac ttcaattta     780 ggtgggggta cccagcagtt accaggattg aacttgggt tgtcacagga cgggcatatt    840
ggggttttga gtccacaagc tttgaatcag atttatcagc agatgggca tgctagagtg    900 caccagcagc agcatcagca acaaaatcct tctaaagatg attcacaagg atcaggccag    960
tga                                                                 963
```

<210> SEQ ID NO 24
<211> LENGTH: 320
<212> TYPE: PRT
<213> ORGANISM: Populus tremuloides

<400> SEQUENCE: 24

```
Met Asp Pro Lys Gly Ser Asn Ser Lys Asn Pro His Glu Leu Pro Thr
1               5                   10                  15

Phe Leu Thr His Thr His Pro Ser Pro Pro His Pro Pro Gln Pro
            20                  25                  30

His Leu Gln Gln Pro Gln Gln Leu His Ser Gln Asn Gln Gln Gln Pro
        35                  40                  45

Asn Met Gly Asp Asn Lys Pro Ala Glu Ile Lys Asp Phe Gln Ile Val
    50                  55                  60

Val Ala Asp Lys Glu Glu Gln Lys Lys Gln Leu Ala Pro Lys Arg Ser
65                  70                  75                  80

Ser Asn Lys Asp Arg His Thr Lys Val Glu Gly Arg Gly Arg Arg Ile
                85                  90                  95

Arg Met Pro Ala Leu Cys Ala Ala Arg Ile Phe Gln Leu Thr Arg Glu
            100                 105                 110

Leu Gly His Lys Ser Asp Gly Glu Thr Ile Gln Trp Leu Leu Gln Gln
        115                 120                 125

Ala Glu Pro Ser Ile Ile Ala Ala Thr Gly Thr Gly Thr Ile Pro Ala
    130                 135                 140

Ser Ala Leu Ala Ala Ala Gly Gly Ala Ile Ser Gln Gln Gly Ala Ser
145                 150                 155                 160

Leu Ser Ala Gly Leu His Gln Lys Ile Asp Asp Leu Gly Gly Ser Ser
                165                 170                 175

Ser Ser Arg Ala Ser Trp Ala Met Leu Gly Gly Asn Leu Gly Arg Pro
            180                 185                 190

His His Val Thr Thr Ala Gly Leu Trp Pro Pro Val Gly Gly Tyr Gly
        195                 200                 205

Phe Gln Ser Ser Ser Asn Ser Thr Gly Pro Ser Thr Thr Asn Ile Gly
    210                 215                 220

Thr Glu Ala Ala Ala Ala Gly Gly Ser Ser Tyr Leu Gln Lys Leu Gly
225                 230                 235                 240
```

```
Phe Pro Gly Phe Asp Leu Pro Gly Asn Asn Met Gly Pro Met Ser Phe
                245                 250                 255

Thr Ser Ile Leu Gly Gly Gly Thr Gln Gln Leu Pro Gly Leu Glu Leu
            260                 265                 270

Gly Leu Ser Gln Asp Gly His Ile Gly Val Leu Ser Pro Gln Ala Leu
        275                 280                 285

Asn Gln Ile Tyr Gln Gln Met Gly His Ala Arg Val His Gln Gln Gln
    290                 295                 300

His Gln Gln Gln Asn Pro Ser Lys Asp Asp Ser Gln Gly Ser Gly Gln
305                 310                 315                 320

<210> SEQ ID NO 25
<211> LENGTH: 933
<212> TYPE: DNA
<213> ORGANISM: Saccharum officinarum
<220> FEATURE:
<221> NAME/KEY: misc_feature
<222> LOCATION: (699)..(701)
<223> OTHER INFORMATION: n is a, c, g, or t

<400> SEQUENCE: 25
atggacccca agttccccac accccaccg ctaaacaaaa cggagcccac caccgcgacg        60
accaccacca ccacctcgac cgcgcagcag ctggatccta aggactacca gcagcagcag      120
ccggcgcagc accacctgca aatccaaatc caccagccgc cgcagcagga cggggggcggc    180 ggagggaagg agcaacagca gcagctgcag gtggtggcgc agcccgggga gcggaggcag     240
cagccgctcg cgcccaagcg gagctccaac aaggaccgcc acaccaaggt cgatggcagg     300
ggccgccgga tccggatgcc cgcgctgtgc gccgcgcgga tcttccagct cacgcgggag     360
ctcggccaca gtccgacgg cgagaccgtg cagtggctgc tgcagcaggc cgagccggcc      420
atcgtcgccg ccaccggcac gggcaccata ccggcgtccg cgctcgcatc cgtcgcgccc     480
tcgctcccgt cgcccacctc cgggctcgcc aggccgcacc accaccacca tccgcaccac     540
atgtgggcgc cttccgccgc gtccgcgggt ttctcctcgc cctccttcct caattccgcc     600
gccgcaggca cggagacgc cgctggtatc ggcggcatca tgcagcggat ggggatcccc      660
gcgggcctcg agctgccggg aggggggcgcc gctggggcnn ncggctttgc gcccatgttc    720
gctgaacacc ccgcggccat tccggggctc gagcttgccc tctcgcagga cggccacatc    780
gggttgctcg ccgcgcagtc gatcacccag ttctaccacc aggtgggtgc tgccggcggc    840
agcggccaga tgcagcaccc tcacggccac cagcaggagg acggggagga cgaccgcgag    900
gacggcgagt ccgatgatga gtctgggcag tag                                 933

<210> SEQ ID NO 26
<211> LENGTH: 310
<212> TYPE: PRT
<213> ORGANISM: Saccharum officinarum
<220> FEATURE:
<221> NAME/KEY: UNSURE
<222> LOCATION: (234)..(234)
<223> OTHER INFORMATION: Xaa can be any naturally occurring amino acid

<400> SEQUENCE: 26

Met Asp Pro Lys Phe Pro Thr Pro Pro Leu Asn Lys Thr Glu Pro
1               5                   10                  15

Thr Thr Ala Thr Thr Thr Thr Thr Ser Thr Ala Gln Gln Leu Asp
            20                  25                  30

Pro Lys Asp Tyr Gln Gln Gln Gln Pro Ala Gln His His Leu Gln Ile
        35                  40                  45
```

```
Gln Ile His Gln Pro Pro Gln Asp Gly Gly Gly Gly Lys Glu
     50                  55                  60
Gln Gln Gln Gln Leu Gln Val Val Ala Gln Pro Gly Glu Arg Arg Gln
 65                  70                  75                  80
Gln Pro Leu Ala Pro Lys Arg Ser Ser Asn Lys Asp Arg His Thr Lys
                 85                  90                  95
Val Asp Gly Arg Gly Arg Arg Ile Arg Met Pro Ala Leu Cys Ala Ala
            100                 105                 110
Arg Ile Phe Gln Leu Thr Arg Glu Leu Gly His Lys Ser Asp Gly Glu
        115                 120                 125
Thr Val Gln Trp Leu Leu Gln Gln Ala Glu Pro Ala Ile Val Ala Ala
    130                 135                 140
Thr Gly Thr Gly Thr Ile Pro Ala Ser Ala Leu Ala Ser Val Ala Pro
145                 150                 155                 160
Ser Leu Pro Ser Pro Thr Ser Gly Leu Ala Arg Pro His His His
                165                 170                 175
His Pro His His Met Trp Ala Pro Ser Ala Ala Ser Ala Gly Phe Ser
            180                 185                 190
Ser Pro Ser Phe Leu Asn Ser Ala Ala Ala Gly Thr Gly Asp Ala Ala
        195                 200                 205
Gly Ile Gly Gly Ile Met Gln Arg Met Gly Ile Pro Ala Gly Leu Glu
    210                 215                 220
Leu Pro Gly Gly Gly Ala Ala Gly Ala Xaa Gly Phe Ala Pro Met Phe
225                 230                 235                 240
Ala Glu His Pro Ala Ala Ile Pro Gly Leu Glu Leu Ala Leu Ser Gln
                245                 250                 255
Asp Gly His Ile Gly Leu Leu Ala Ala Gln Ser Ile Thr Gln Phe Tyr
            260                 265                 270
His Gln Val Gly Ala Ala Gly Gly Ser Gly Gln Met Gln His Pro His
        275                 280                 285
Gly His Gln Gln Glu Asp Gly Glu Asp Asp Arg Glu Asp Gly Glu Ser
    290                 295                 300
Asp Asp Glu Ser Gly Gln
305                 310

<210> SEQ ID NO 27
<211> LENGTH: 846
<212> TYPE: DNA
<213> ORGANISM: Solanum tuberosum

<400> SEQUENCE: 27
atggatccca agcagcctaa caacaaaaat attaagccta ctcatgatca gataaaagac     60
ttgcagattt tgaaaatga tgaaaccaag aaacagcagc aggtggctgc tcctaaaaga    120
aaagataggc ataccaaagt tgaaggtaga gggaggagga tacgtatgcc tgctctatgt    180
gcagcaagaa tctttcaact tacgcgcgaa ttgggtcata atctgatgg tgagacaatt    240
cagtggctgc tgcagcaagc cgagccttcg attattgctg ctactggcac agggacaatt    300
cctgcatcgg ctttagctgc agcagcatct gtttctcaac aggggatctc tgtatcagct    360
ggtttaatga ttgaatcggg ggcgaatatc gcggggtcag gtagcagtag aagtagtaat    420
agtaggacca attggccaat gatctgtggg aattttggaa gaccccattt ggctacagta    480
ggaatatggc ctgccctgc ccctgttgtc actagttttg ggtttcagtc ctcatctgct    540
ccatcaagcg ccagtttaga cagtgaaagt tcaaactatt acttacagaa aattgggttt    600
cctggatttg atctgcctgc agctacaaat atgaatccta tgagttttac ttcaattctt    660
```

```
ggtggaagta accagcaact gccaggattg gagcttggat tatctcaaga gggtcattta    720
ggggttttga accagatata ccagcaggaa agaatgcaac atccgcagca gcaacaacaa    780
gatcagcatc agcatcagca tcaacaacaa tctccggagg atgattctca aggatcagga    840
cattaa                                                              846
```

<210> SEQ ID NO 28
<211> LENGTH: 281
<212> TYPE: PRT
<213> ORGANISM: Solanum tuberosum

<400> SEQUENCE: 28

```
Met Asp Pro Lys Gln Pro Asn Asn Lys Asn Ile Lys Pro Thr His Asp
1               5                   10                  15

Gln Ile Lys Asp Leu Gln Ile Leu Lys Asn Asp Glu Thr Lys Lys Gln
            20                  25                  30

Gln Gln Val Ala Ala Pro Lys Arg Lys Asp Arg His Thr Lys Val Glu
        35                  40                  45

Gly Arg Gly Arg Arg Ile Arg Met Pro Ala Leu Cys Ala Ala Arg Ile
    50                  55                  60

Phe Gln Leu Thr Arg Glu Leu Gly His Lys Ser Asp Gly Glu Thr Ile
65                  70                  75                  80

Gln Trp Leu Leu Gln Gln Ala Glu Pro Ser Ile Ala Ala Thr Gly
                85                  90                  95

Thr Gly Thr Ile Pro Ala Ser Ala Leu Ala Ala Ala Ser Val Ser
                100                 105                 110

Gln Gln Gly Ile Ser Val Ser Ala Gly Leu Met Ile Glu Ser Gly Ala
        115                 120                 125

Asn Ile Ala Gly Ser Gly Ser Ser Arg Ser Ser Asn Ser Arg Thr Asn
    130                 135                 140

Trp Pro Met Ile Cys Gly Asn Phe Gly Arg Pro His Leu Ala Thr Val
145                 150                 155                 160

Gly Ile Trp Pro Ala Pro Ala Pro Val Val Thr Ser Phe Gly Phe Gln
                165                 170                 175

Ser Ser Ser Ala Pro Ser Ser Ala Ser Leu Asp Ser Glu Ser Ser Asn
            180                 185                 190

Tyr Tyr Leu Gln Lys Ile Gly Phe Pro Gly Phe Asp Leu Pro Ala Ala
        195                 200                 205

Thr Asn Met Asn Pro Met Ser Phe Thr Ser Ile Leu Gly Gly Ser Asn
    210                 215                 220

Gln Gln Leu Pro Gly Leu Glu Leu Gly Leu Ser Gln Glu Gly His Leu
225                 230                 235                 240

Gly Val Leu Asn Gln Ile Tyr Gln Gln Glu Arg Met Gln His Pro Gln
                245                 250                 255

Gln Gln Gln Gln Asp Gln His Gln His Gln Gln Gln Ser Pro
        260                 265                 270

Glu Asp Asp Ser Gln Gly Ser Gly His
    275                 280
```

<210> SEQ ID NO 29
<211> LENGTH: 978
<212> TYPE: DNA
<213> ORGANISM: Sorghum bicolor

<400> SEQUENCE: 29

```
atggacccca gttccccac accccccaccg ctaaacaaaa cggagcccac caccgcgacg    60
```

```
accaccacca cctcgaccgc gcagcagcag cagcagcagc tggatcctaa ggactaccag      120
cagccggcgc agcagcacca cctgcaaatc caaatccacc agccgccgcc gcagcagcag      180
cagcagcagg acggaggcaa ggagcagcag ctgcaggtgg tggcgcagcc cggggagcgg      240
aggcagcagg cgctcgcgcc caagcggagc tccaacaagg accgccacac caaggtcgac      300
ggcaggggcc gccggatccg gatgcccgcg ctgtgcgccg cgcggatctt ccagctcacg      360
cgggaactcg gccacaagtc cgacggcgag accgtgcagt ggctgctgca gcaggccgag      420
ccggccatcg tcgccgccac cggcaccggc accataccgg cgtccgcgct cgcatccgtc      480
gcgccctcgc tcccgtcgcc cacctccggg ctcgccaggc cgcaccacca ccaccacccg      540
caccacatgt gggcgccgtc cgccgcgtcc gcgggttcct cctcgccctc cttcctcaat      600
tccgccgccg cgggcacggg agacgccgct ggtatcggcg gactcatgca gcggatgggg      660
atccccgcgg gtctcgagct gccgggaggc ggcgccgctg gaggcaccct cggcgctggc      720
ggccacatcg gctttgcgcc catgttcgct ggacacgccg cggccatgcc ggggctcgag      780
ctcggcctct cgcaggacgg ccacatcggc gtgctcgcag cgcagtcgat cagccagttc      840
taccaccaag tgggtgctgc tggcggcagc ggccagatgc agcacccgca cggccaccag      900
catcaccatc atcagcagca ggaggacggg gaggacgacc gcgaggacgg cgagtccgat      960
gacgagtctg ggcagtag                                                   978
```

<210> SEQ ID NO 30
<211> LENGTH: 325
<212> TYPE: PRT
<213> ORGANISM: Sorghum bicolor

<400> SEQUENCE: 30

```
Met Asp Pro Lys Phe Pro Thr Pro Pro Leu Asn Lys Thr Glu Pro
 1               5                  10                  15

Thr Thr Ala Thr Thr Thr Thr Ser Thr Ala Gln Gln Gln Gln
            20                  25                  30

Gln Leu Asp Pro Lys Asp Tyr Gln Gln Pro Ala Gln Gln His His Leu
         35                  40                  45

Gln Ile Gln Ile His Gln Pro Pro Gln Gln Gln Gln Gln Asp
     50                  55                  60

Gly Gly Lys Glu Gln Gln Leu Gln Val Val Ala Gln Pro Gly Glu Arg
 65                  70                  75                  80

Arg Gln Gln Ala Leu Ala Pro Lys Arg Ser Ser Asn Lys Asp Arg His
                 85                  90                  95

Thr Lys Val Asp Gly Arg Gly Arg Arg Ile Arg Met Pro Ala Leu Cys
            100                 105                 110

Ala Ala Arg Ile Phe Gln Leu Thr Arg Glu Leu Gly His Lys Ser Asp
        115                 120                 125

Gly Glu Thr Val Gln Trp Leu Leu Gln Gln Ala Glu Pro Ala Ile Val
    130                 135                 140

Ala Ala Thr Gly Thr Gly Thr Ile Pro Ala Ser Ala Leu Ala Ser Val
145                 150                 155                 160

Ala Pro Ser Leu Pro Ser Pro Thr Ser Gly Leu Ala Arg Pro His His
                165                 170                 175

His His His Pro His His Met Trp Ala Pro Ser Ala Ala Ser Ala Gly
            180                 185                 190

Phe Ser Ser Pro Ser Phe Leu Asn Ser Ala Ala Ala Gly Thr Gly Asp
        195                 200                 205
```

```
Ala Ala Gly Ile Gly Gly Leu Met Gln Arg Met Gly Ile Pro Ala Gly
            210                 215                 220

Leu Glu Leu Pro Gly Gly Ala Ala Gly Gly Thr Leu Gly Ala Gly
225                 230                 235                 240

Gly His Ile Gly Phe Ala Pro Met Phe Ala Gly His Ala Ala Met
                245                 250                 255

Pro Gly Leu Glu Leu Gly Leu Ser Gln Asp Gly His Ile Gly Val Leu
            260                 265                 270

Ala Ala Gln Ser Ile Ser Gln Phe Tyr His Gln Val Gly Ala Ala Gly
        275                 280                 285

Gly Ser Gly Gln Met Gln His Pro His Gly His Gln His His His
        290                 295                 300

Gln Gln Gln Glu Asp Gly Glu Asp Asp Arg Glu Asp Gly Glu Ser Asp
305                 310                 315                 320

Asp Glu Ser Gly Gln
            325

<210> SEQ ID NO 31
<211> LENGTH: 891
<212> TYPE: DNA
<213> ORGANISM: Vitis vinifera

<400> SEQUENCE: 31
atggatccca agggctcaaa gcagccgcag gaggtaccaa acttcttgag cctacctcag     60
ccaaacatgg gagagaacaa gccagctgaa gtgaaggact ttcagattgt gattgcagat   120
aaggaagagg gtaagaagca gttggccccc aagaggagct caaacaagga caggcacacc   180
aaggttgaag gcagagggag gagaataagg atgccggctc tttgtgcagc cagaattttt   240
cagttgacta gggaattggg tcacaaatct gacggggaaa ccatacagtg gttgttgcag   300
caggccgagc cgtccataat agcggccact ggtactggga caataccggc gtcggcttta   360
gcggcggcag gaggctctgt gtcgcaacag ggaacttcta tatcagcagg attgcatcaa   420
aagattgatg aattgggggg gtccagtatt gggtcaggga gtagtaggac cagttgggca   480
atggtaggtg caaatttggg gagaccccat gtggccacag gctatggcc cccagtcagt   540 ggttttgggt tcagtcatc atctggacca tcaaccacca atttggggaa tgaaagttcc   600
aattatctgc aaaaaattgc cttccctggg tttgacttgc ctgcaacaaa tctgggtcct   660
atgagtttta cttcaatttt gggtgggagt aaccagcagc ttcctggttt ggagctgggc   720
ctatcacagg atggtcatat tggggttttg aactcacaag ccttaagcca gatttaccag   780
cagatggggc aggccagggt gcaccagcaa cagcagcatc aacatcagca tcagcatcag   840
catcaacagc aacctcctgc taaggatgat tctcaaggtt cagggcagta g            891

<210> SEQ ID NO 32
<211> LENGTH: 296
<212> TYPE: PRT
<213> ORGANISM: Vitis vinifera

<400> SEQUENCE: 32

Met Asp Pro Lys Gly Ser Lys Gln Pro Gln Glu Val Pro Asn Phe Leu
1               5                   10                  15

Ser Leu Pro Gln Pro Asn Met Gly Glu Asn Lys Pro Ala Glu Val Lys
            20                  25                  30

Asp Phe Gln Ile Val Ile Ala Asp Lys Glu Glu Gly Lys Lys Gln Leu
        35                  40                  45

Ala Pro Lys Arg Ser Ser Asn Lys Asp Arg His Thr Lys Val Glu Gly
```

```
              50                  55                  60
Arg Gly Arg Arg Ile Arg Met Pro Ala Leu Cys Ala Ala Arg Ile Phe
 65                  70                  75                  80

Gln Leu Thr Arg Glu Leu Gly His Lys Ser Asp Gly Glu Thr Ile Gln
                 85                  90                  95

Trp Leu Leu Gln Gln Ala Glu Pro Ser Ile Ala Ala Thr Gly Thr
            100                 105                 110

Gly Thr Ile Pro Ala Ser Ala Leu Ala Ala Ala Gly Gly Ser Val Ser
        115                 120                 125

Gln Gln Gly Thr Ser Ile Ser Ala Gly Leu His Gln Lys Ile Asp Glu
    130                 135                 140

Leu Gly Gly Ser Ser Ile Gly Ser Gly Ser Ser Arg Thr Ser Trp Ala
145                 150                 155                 160

Met Val Gly Ala Asn Leu Gly Arg Pro His Val Ala Thr Gly Leu Trp
                165                 170                 175

Pro Pro Val Ser Gly Phe Gly Phe Gln Ser Ser Ser Gly Pro Ser Thr
            180                 185                 190

Thr Asn Leu Gly Asn Glu Ser Ser Asn Tyr Leu Gln Lys Ile Ala Phe
        195                 200                 205

Pro Gly Phe Asp Leu Pro Ala Thr Asn Leu Gly Pro Met Ser Phe Thr
    210                 215                 220

Ser Ile Leu Gly Gly Ser Asn Gln Gln Leu Pro Gly Leu Glu Leu Gly
225                 230                 235                 240

Leu Ser Gln Asp Gly His Ile Gly Val Leu Asn Ser Gln Ala Leu Ser
                245                 250                 255

Gln Ile Tyr Gln Gln Met Gly Gln Ala Arg Val His Gln Gln Gln Gln
            260                 265                 270

His Gln His Gln His Gln His Gln Gln Gln Pro Pro Ala Lys
        275                 280                 285

Asp Asp Ser Gln Gly Ser Gly Gln
    290                 295

<210> SEQ ID NO 33
<211> LENGTH: 975
<212> TYPE: DNA
<213> ORGANISM: Zea mays

<400> SEQUENCE: 33
atggacccca agttccccac accctagcg ctaaacaaaa cggagcccac caccgcgacg      60
accaccacca cctcgaccgc gcagcatcat cagctggatc ctaaggacta ccagcagcag    120
acggcgcagc accaggagca gcagcagcac caccatcacc cccacctgca aatccaaatc    180
caccagccgc cgccgccgcc gcaggacggg ggcggcggag tgaaggagca gcagcagctg    240
ctgcaggtgg tggcgcagcc cggggatcgg aggcagcagg cgctcgcccc caagcggagc    300
tccaacaagg accgccacac caaggtcgac ggcaggggcc gccggatccg gatgccggcg    360
ctctgcgccg cgcggatctt ccagctcacg cgggagctcg ccacaagtc cgacggcgag    420 actgtgcagt ggctgctgca gcaggccgag ccggccatcg tcgccgccac ggcacgggc    480 accataccgg cgtccgcgct cgcctccgtc gcgccctcgc tcccgtcgcc tacctccggg    540
ctcgccaggc cgcaccacca ccaccgcac acatgtgggg cgccgtccgc cggcttctcc    600
tcgccctcct tcctgaattc cgcgggcgcg ggcgacggca ccggtatcgg cggcatcatg    660
cagcggatgg gggtccccgc gggcctggag ctgccgggag cggcgccgc cggcggccac    720 atcggctttg cgcccatgtt cgctggacac gccgcggcca tgccggggct cgagctcggc    780
```

-continued

```
ctctcgcagg acggtcacat cggcgtgctc gccgcgcagt cgatcagcca gttctaccac    840
caggtgggtg ccgctgccgg cggcagtggc cagatgcagc acccgcacgg gcaccagcat    900
caccatcatc agcagcagga ggacggggag gacgaccgcg aggacggcga gtctgatgac    960
gagtctgggc agtag                                                     975
```

<210> SEQ ID NO 34
<211> LENGTH: 324
<212> TYPE: PRT
<213> ORGANISM: Zea mays

<400> SEQUENCE: 34

```
Met Asp Pro Lys Phe Pro Thr Pro Leu Ala Leu Asn Lys Thr Glu Pro
1               5                   10                  15

Thr Thr Ala Thr Thr Thr Thr Ser Thr Ala Gln His His Gln Leu
            20                  25                  30

Asp Pro Lys Asp Tyr Gln Gln Thr Ala Gln His Gln Glu Gln Gln
        35                  40                  45

Gln His His His Pro His Leu Gln Ile Gln Ile His Gln Pro Pro
    50                  55                  60

Pro Pro Pro Gln Asp Gly Gly Gly Val Lys Glu Gln Gln Gln Leu
65              70                  75                  80

Leu Gln Val Val Ala Gln Pro Gly Asp Arg Arg Gln Gln Ala Leu Ala
                85                  90                  95

Pro Lys Arg Ser Ser Asn Lys Asp Arg His Thr Lys Val Asp Gly Arg
            100                 105                 110

Gly Arg Arg Ile Arg Met Pro Ala Leu Cys Ala Ala Arg Ile Phe Gln
        115                 120                 125

Leu Thr Arg Glu Leu Gly His Lys Ser Asp Gly Glu Thr Val Gln Trp
    130                 135                 140

Leu Leu Gln Gln Ala Glu Pro Ala Ile Val Ala Ala Thr Gly Thr Gly
145                 150                 155                 160

Thr Ile Pro Ala Ser Ala Leu Ala Ser Val Ala Pro Ser Leu Pro Ser
                165                 170                 175

Pro Thr Ser Gly Leu Ala Arg Pro His His His Pro His His Met
            180                 185                 190

Trp Ala Pro Ser Ala Gly Phe Ser Ser Pro Ser Phe Leu Asn Ser Ala
        195                 200                 205

Gly Ala Gly Asp Gly Thr Gly Ile Gly Ile Met Gln Arg Met Gly
    210                 215                 220

Val Pro Ala Gly Leu Glu Leu Pro Gly Gly Gly Ala Ala Gly Gly His
225                 230                 235                 240

Ile Gly Phe Ala Pro Met Phe Ala Gly His Ala Ala Ala Met Pro Gly
                245                 250                 255

Leu Glu Leu Gly Leu Ser Gln Asp Gly His Ile Gly Val Leu Ala Ala
            260                 265                 270

Gln Ser Ile Ser Gln Phe Tyr His Gln Val Gly Ala Ala Ala Gly Gly
        275                 280                 285

Ser Gly Gln Met Gln His Pro His Gly His His His His Gln
    290                 295                 300

Gln Gln Glu Asp Gly Glu Asp Asp Arg Glu Asp Gly Glu Ser Asp Asp
305                 310                 315                 320

Glu Ser Gly Gln
```

-continued

```
<210> SEQ ID NO 35
<211> LENGTH: 948
<212> TYPE: DNA
<213> ORGANISM: Zea mays

<400> SEQUENCE: 35
atggacccca agttccccc accccaccg ctaaacaaaa cggagcccac caccgcgacg      60
accaccacca cctcgaccgc gcagcagcag cagcagcagc tggatcctaa ggactaccag     120
cagcagcagc agcagccggc gcagcacctg caaatccaaa tccaccagtc gcagcaggac    180
ggaggcggcg agggaagga gcagcagcag ctgcaggtgg tggcgcagcc cggggagagg    240
aggcagcagg cgctcgcgcc caagcggagc tccaacaagg accgacacac caaggtcgac    300
ggcaggggcc ggcggatccg gatgcccgcg ctctgcgccg cgcggatctt ccagctcacg    360
cgggaactcg gccacaagtc cgacggcgag accgtccagt ggctgctgca gcaggccgag    420
ccggccatcg tcgccgccac cggcacgggc accataccgg cgtccgcgct cgcctccgtc    480
gcgccctcgc tcccgtcgcc cacctccggg ctcgccaggc cgcaccacca catgtgggcg    540
ccgtccgccg gcttctcctc gccctccttc ctgaactctg ccgccgcggg cacgggcgat    600
gccgccggta tcatgcagcg gatggggatc cccgcgggct tcgagctgcc gggagcctcc    660
gccgccggag ccaccctcgg cgccggcggc cacatcggct ttgcgcccat gttcgctgga    720
cacgccgccg ccatgccggg gctcgagctc gggctatcgc aggacggcca catcggcgtg    780
ctcgccgcgc agtcgatcag ccagttctac caccaggtgg gtgctgccgc cggcggcggc    840
ggccagatgc atcacgcgca cgggcaccat catcaccatc accagcagca ggaggacggg    900
gaggacgacc gcgaggacgg cgagtccgat gacgagtctg ggcagtag                 948

<210> SEQ ID NO 36
<211> LENGTH: 315
<212> TYPE: PRT
<213> ORGANISM: Zea mays

<400> SEQUENCE: 36

Met Asp Pro Lys Phe Pro Pro Pro Pro Leu Asn Lys Thr Glu Pro
1               5                   10                  15

Thr Thr Ala Thr Thr Thr Thr Ser Thr Ala Gln Gln Gln Gln Gln
                20                  25                  30

Gln Leu Asp Pro Lys Asp Tyr Gln Gln Gln Gln Gln Pro Ala Gln
                35                  40                  45

His Leu Gln Ile Gln Ile His Gln Ser Gln Gln Asp Gly Gly Gly
            50                  55                  60

Gly Lys Glu Gln Gln Gln Leu Gln Val Val Ala Gln Pro Gly Glu Arg
65                  70                  75                  80

Arg Gln Gln Ala Leu Ala Pro Lys Arg Ser Ser Asn Lys Asp Arg His
                85                  90                  95

Thr Lys Val Asp Gly Arg Gly Arg Arg Ile Arg Met Pro Ala Leu Cys
                100                 105                 110

Ala Ala Arg Ile Phe Gln Leu Thr Arg Glu Leu Gly His Lys Ser Asp
            115                 120                 125

Gly Glu Thr Val Gln Trp Leu Leu Gln Gln Ala Glu Pro Ala Ile Val
    130                 135                 140

Ala Ala Thr Gly Thr Gly Thr Ile Pro Ala Ser Ala Leu Ala Ser Val
145                 150                 155                 160

Ala Pro Ser Leu Pro Ser Pro Thr Ser Gly Leu Ala Arg Pro His His
                165                 170                 175
```

His Met Trp Ala Pro Ser Ala Gly Phe Ser Pro Ser Phe Leu Asn
            180                 185                 190

Ser Ala Ala Gly Thr Gly Asp Ala Gly Ile Met Gln Arg Met
        195                 200                 205

Gly Ile Pro Ala Gly Phe Glu Leu Pro Gly Ala Ser Ala Gly Ala
210                 215                 220

Thr Leu Gly Ala Gly His Ile Gly Phe Ala Pro Met Phe Ala Gly
225                 230                 235                 240

His Ala Ala Met Pro Gly Leu Glu Leu Gly Leu Ser Gln Asp Gly
                245                 250                 255

His Ile Gly Val Leu Ala Ala Gln Ser Ile Ser Gln Phe Tyr His Gln
            260                 265                 270

Val Gly Ala Ala Gly Gly Gly Gln Met His His Ala His Gly
        275                 280                 285

His His His His His Gln Gln Glu Asp Gly Glu Asp Asp Arg
            290                 295                 300

Glu Asp Gly Glu Ser Asp Asp Glu Ser Gly Gln
305                 310                 315

<210> SEQ ID NO 37
<211> LENGTH: 648
<212> TYPE: DNA
<213> ORGANISM: Allium cepa

<400> SEQUENCE: 37
atggatccaa aagaatccca acccaactcg gatcgtcaat tgatgaccca aaccgaatcc      60
attcaagacc cgcaaaaaag agcccttctt gccccaaaac ggacctccaa caaagaccgc     120
cacaccaaag ttgacggccg cggccggagg attcgcatgc ccgctctctg cgccgccaga     180
atcttccagc tgacccgaga actcggccat aaatccgacg gcgagaccgt tcagtggctt     240
ctgcatcatg cagaacctgc catcatcgcc gctaccgggt cggtaccat acccgcatcc      300 gctttagctt cttctcaggc gatgccgaac tctaagcccg acaacagttg ggctgttggg     360
ttatggggag gttttaattc cggatttatg aattccaata atagcagtaa caacaacaat     420
aataatggag tcggccctag ctcgagcaat ttagggtttg tggggatgga gatgacaggg     480
atgagtgggc acatgagctt tacttcaatg ctgggagggc agcctgggcc acaaatgccc     540
gggcttcagt tagggctgtc tcaagatggg catattgggg ttttgaatac acaagggttg     600
aaccattttt tcaacagat gggtcataat gttagggttg gaaatggg                   648

<210> SEQ ID NO 38
<211> LENGTH: 216
<212> TYPE: PRT
<213> ORGANISM: Allium cepa

<400> SEQUENCE: 38

Met Asp Pro Lys Glu Ser Gln Pro Asn Ser Asp Arg Gln Leu Met Thr
1               5                   10                  15

Gln Thr Glu Ser Ile Gln Asp Pro Gln Lys Arg Ala Leu Leu Ala Pro
            20                  25                  30

Lys Arg Thr Ser Asn Lys Asp Arg His Thr Lys Val Asp Gly Arg Gly
        35                  40                  45

Arg Arg Ile Arg Met Pro Ala Leu Cys Ala Ala Arg Ile Phe Gln Leu
    50                  55                  60

Thr Arg Glu Leu Gly His Lys Ser Asp Gly Glu Thr Val Gln Trp Leu
65                  70                  75                  80

Leu His His Ala Glu Pro Ala Ile Ile Ala Ala Thr Gly Ser Gly Thr
                85                  90                  95

Ile Pro Ala Ser Ala Leu Ala Ser Ser Gln Ala Met Pro Asn Ser Lys
            100                 105                 110

Pro Asp Asn Ser Trp Ala Val Gly Leu Trp Gly Gly Phe Asn Ser Gly
        115                 120                 125

Phe Met Asn Ser Asn Asn Ser Ser Asn Asn Asn Asn Asn Asn Gly Val
130                 135                 140

Gly Pro Ser Ser Ser Asn Leu Gly Phe Val Gly Met Glu Met Thr Gly
145                 150                 155                 160

Met Ser Gly His Met Ser Phe Thr Ser Met Leu Gly Gly Gln Pro Gly
                165                 170                 175

Pro Gln Met Pro Gly Leu Gln Leu Gly Leu Ser Gln Asp Gly His Ile
            180                 185                 190

Gly Val Leu Asn Thr Gln Gly Leu Asn His Phe Tyr Gln Gln Met Gly
        195                 200                 205

His Asn Val Arg Val Gly Asn Gly
    210                 215

<210> SEQ ID NO 39
<211> LENGTH: 731
<212> TYPE: DNA
<213> ORGANISM: Brachypodium distachyon

<400> SEQUENCE: 39
atggacccca gtttcctcc tcccccaccg ctaaacaaaa cggagcccac caccggcgtg      60
acgaccacca ccaccacgac ctcccagcag cagctggatc acgagcagta tcaccagccg    120
cagcagcacc tgcaaatcca agtgcaccag cagcagcagg aggaagatgg cggcggggga    180
aaggagcagc agcagcaggt ggtggcggcg gcggggggcgg gggagaggag ggtgcagggg    240
ctggggccga agcggagctc caacaaggac cggcacacca aggtggacgg gcggggggcgg    300 cggatccgga tgccggcgct gtgcgcggcg cggatcttcc agctgacgcg ggagctgggg    360
cacaagtcgg acggggagac ggtccagtgg ctgctgcagc aggcggagcc ggccatcgtc    420
gccgccacag ggtccggcac catacccggcg tccgcgctcg cctcgtcgc gccctcgctg    480 ccttcgccca cctccgcgct cgccaggccg caccaccacc accacctctg ggggccctcg    540 gcggcgggt tctccccggc cgggttcatg aactcggccc cagccggcgc tgactctggg    600
ggcggcctcg gcgggcttat gcagaggata gggcttcccg ccgggatgga gctccctggc    660
ggcggtggtg gggggcacat cgggttcgcg cccatgttcg ccagccacgc ggcggcggcg    720
gcggccatgc c                                                         731

<210> SEQ ID NO 40
<211> LENGTH: 243
<212> TYPE: PRT
<213> ORGANISM: Brachypodium distachyon

<400> SEQUENCE: 40

Met Asp Pro Lys Phe Pro Pro Pro Pro Leu Asn Lys Thr Glu Pro
1               5                  10                  15

Thr Thr Gly Val Thr Thr Thr Thr Thr Thr Ser Gln Gln Gln Leu
            20                  25                  30

Asp His Glu Gln Tyr His Gln Pro Gln Gln His Leu Gln Ile Gln Val
        35                  40                  45

His Gln Gln Gln Gln Glu Glu Asp Gly Gly Gly Gly Lys Glu Gln Gln
    50                  55                  60

Gln Gln Val Val Ala Ala Gly Ala Gly Glu Arg Val Gln Gly
 65                  70                  75                  80

Leu Gly Pro Lys Arg Ser Ser Asn Lys Asp Arg His Thr Lys Val Asp
                 85                  90                  95

Gly Arg Gly Arg Ile Arg Met Pro Ala Leu Cys Ala Ala Arg Ile
            100                 105                 110

Phe Gln Leu Thr Arg Glu Leu Gly His Lys Ser Asp Gly Glu Thr Val
        115                 120                 125

Gln Trp Leu Leu Gln Gln Ala Glu Pro Ala Ile Val Ala Ala Thr Gly
    130                 135                 140

Ser Gly Thr Ile Pro Ala Ser Ala Leu Ala Ser Val Ala Pro Ser Leu
145                 150                 155                 160

Pro Ser Pro Thr Ser Ala Leu Ala Arg Pro His His His His Leu
                165                 170                 175

Trp Gly Pro Ser Ala Ala Gly Phe Ser Pro Ala Gly Phe Met Asn Ser
            180                 185                 190

Ala Pro Ala Gly Ala Asp Ser Gly Gly Leu Gly Gly Leu Met Gln
        195                 200                 205

Arg Ile Gly Leu Pro Ala Gly Met Glu Leu Pro Gly Gly Gly Gly
    210                 215                 220

Gly His Ile Gly Phe Ala Pro Met Phe Ala Ser His Ala Ala Ala Ala
225                 230                 235                 240

Ala Ala Met

<210> SEQ ID NO 41
<211> LENGTH: 768
<212> TYPE: DNA
<213> ORGANISM: Brassica oleracea

<400> SEQUENCE: 41
atggatccca agaacccaaa tccacaccaa gtaccaaact tcttgatacc accaccacaa      60
ccgagagatg cttccgatga caacaaagaa gtaaatgatt ttcagatcgt ggtcgcttcc     120
gacaaagaac cgaacagtaa cggtaagaag cagcttgccc ccaagagaag ctcaaacaaa     180
gacagacaca ccaaagtgga aggtcgcggt cggagaatca ggatgcctgc tctctgcgcg     240
gcaaggattt tcaactgac cagagaattg ggtcacaaat cagacggtga acaatccag      300
tggctgcttc aacaagccga accgtcgctt atcgcagcca ccggttcagg aactgtaccg     360
gcctctgctt tagcctcagc tgcttctgct gtagtctcta accaaggcgg gtctctcact     420
gctggtttga tgatcagtca tcatgactta gactgtggtg gtgggtctag tagtggtaga     480
ccaagttggg gagaaggagg aggagaagta tggccaaatg gagctggtta cagaattggg     540
tttcccggat tgattttcc tggtggagct atgagttttg cttccatttt tggtgctagt     600
ggtggtggta atggtaatca gatgcttgga cttgagttag ggttgtctca ggtagggaat     660
gttggggtct tgaatcaaca gatttatcaa cagatggctc aagctcaggc tcaggctcag     720
ggtagggttc ttcaccatac tcttcatcat aatccaggac atgaagag                 768

<210> SEQ ID NO 42
<211> LENGTH: 256
<212> TYPE: PRT
<213> ORGANISM: Brassica oleracea

<400> SEQUENCE: 42

Met Asp Pro Lys Asn Pro Asn Pro His Gln Val Pro Asn Phe Leu Ile
1               5                   10                  15

Pro Pro Pro Gln Pro Arg Asp Ala Ser Asp Asp Asn Lys Glu Val Asn
              20                  25                  30

Asp Phe Gln Ile Val Val Ala Ser Asp Lys Glu Pro Asn Ser Asn Gly
         35                  40                  45

Lys Lys Gln Leu Ala Pro Lys Arg Ser Ser Asn Lys Asp Arg His Thr
 50                  55                  60

Lys Val Glu Gly Arg Gly Arg Arg Ile Arg Met Pro Ala Leu Cys Ala
 65                  70                  75                  80

Ala Arg Ile Phe Gln Leu Thr Arg Glu Leu Gly His Lys Ser Asp Gly
             85                  90                  95

Glu Thr Ile Gln Trp Leu Leu Gln Gln Ala Glu Pro Ser Leu Ile Ala
            100                 105                 110

Ala Thr Gly Ser Gly Thr Val Pro Ala Ser Ala Leu Ala Ser Ala Ala
            115                 120                 125

Ser Ala Val Val Ser Asn Gln Gly Gly Ser Leu Thr Ala Gly Leu Met
130                 135                 140

Ile Ser His His Asp Leu Asp Cys Gly Gly Gly Ser Ser Ser Gly Arg
145                 150                 155                 160

Pro Ser Trp Gly Glu Gly Gly Gly Glu Val Trp Pro Asn Gly Ala Gly
                165                 170                 175

Tyr Arg Ile Gly Phe Pro Gly Phe Asp Phe Pro Gly Gly Ala Met Ser
            180                 185                 190

Phe Ala Ser Ile Phe Gly Ala Ser Gly Gly Gly Asn Gly Asn Gln Met
            195                 200                 205

Leu Gly Leu Glu Leu Gly Leu Ser Gln Val Gly Asn Val Gly Val Leu
210                 215                 220

Asn Gln Gln Ile Tyr Gln Gln Met Ala Gln Ala Gln Ala Gln Ala Gln
225                 230                 235                 240

Gly Arg Val Leu His His Thr Leu His His Asn Pro Gly His Glu Glu
            245                 250                 255

<210> SEQ ID NO 43
<211> LENGTH: 723
<212> TYPE: DNA
<213> ORGANISM: Brassica rapa

<400> SEQUENCE: 43
agaagctcaa acaaagacag acacatcaaa gtggaaggca ggggtcggag aatcaggatg      60
cctgctctct gcgccgctag gatcttccag ttgactagaa aattgggtca caaatccgac    120
ggcgagacaa tccagtggct gcttcagcag gctgagccgt cgattatcgc agccaccggt    180
tcaggaacta taccggcctc tgctttagcc tcagccgctg ctgctgtatc gagccaccat    240
cttcagggtg gtgggtctct cactgctggt tgatgatca gtcatgagtt ggatggtggg    300
tctagtagtg ggagaccaaa ttggggtgtt ggcgggggag atggagggtc taggtcgagt    360
ttaccaactg gctgtggcc aaatgtagct gggtttggag ctggggtgca gaccatgagt    420
gatggaggtg gttacaggat tgggtttcct gggtttgatt atcctggtgg agctatgagt    480
tttgcgtcca ttcttggtgg tggtagtaac aatcagatgc ctggacttga gttagggttg    540
gctcaggaag ggaatgttgg tgtcttgaat cctcagtctt ttgcacagat ttatcagcag    600
cagatgagtc aggctcaagc tcagggtagg gttcttcacc atactcttca gcataaccca    660
tcacatgagg agcatcagca agagagtggt gagaaagatg attctcaagg gtcagggcgt    720
taa                                                                  723

<210> SEQ ID NO 44
<211> LENGTH: 240
<212> TYPE: PRT
<213> ORGANISM: Brassica rapa

<400> SEQUENCE: 44

```
Arg Ser Ser Asn Lys Asp Arg His Ile Lys Val Glu Gly Arg Gly Arg
1               5                   10                  15
Arg Ile Arg Met Pro Ala Leu Cys Ala Ala Arg Ile Phe Gln Leu Thr
            20                  25                  30
Arg Glu Leu Gly His Lys Ser Asp Gly Glu Thr Ile Gln Trp Leu Leu
        35                  40                  45
Gln Gln Ala Glu Pro Ser Ile Ile Ala Ala Thr Gly Ser Gly Thr Ile
    50                  55                  60
Pro Ala Ser Ala Leu Ala Ser Ala Ala Ala Val Ser Ser His His
65                  70                  75                  80
Leu Gln Gly Gly Gly Ser Leu Thr Ala Gly Leu Met Ile Ser His Glu
                85                  90                  95
Leu Asp Gly Gly Ser Ser Ser Gly Arg Pro Asn Trp Gly Val Gly Gly
            100                 105                 110
Gly Asp Gly Gly Ser Arg Ser Ser Leu Pro Thr Gly Leu Trp Pro Asn
        115                 120                 125
Val Ala Gly Phe Gly Ala Gly Val Gln Thr Met Ser Asp Gly Gly Gly
    130                 135                 140
Tyr Arg Ile Gly Phe Pro Gly Phe Asp Tyr Pro Gly Gly Ala Met Ser
145                 150                 155                 160
Phe Ala Ser Ile Leu Gly Gly Ser Asn Asn Gln Met Pro Gly Leu
                165                 170                 175
Glu Leu Gly Leu Ala Gln Glu Gly Asn Val Gly Val Leu Asn Pro Gln
            180                 185                 190
Ser Phe Ala Gln Ile Tyr Gln Gln Gln Met Ser Gln Ala Gln Ala Gln
        195                 200                 205
Gly Arg Val Leu His His Thr Leu Gln His Asn Pro Ser His Glu Glu
    210                 215                 220
His Gln Gln Glu Ser Gly Glu Lys Asp Asp Ser Gln Gly Ser Gly Arg
225                 230                 235                 240
```

<210> SEQ ID NO 45
<211> LENGTH: 696
<212> TYPE: DNA
<213> ORGANISM: Coffea canephora
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (622)..(622)
<223> OTHER INFORMATION: n is a, c, g, or t

<400> SEQUENCE: 45

```
attttccagc tcaccagaga attgggtcac aaatccgatg gagaaaccat ccaatggctg      60
ttacagcagg ctgaaccatc cattatagcc gccacgggga cggggaccat accggcctcc    120
gctctagccg ctgcggccgc tggagcaggg ggctctgttt ccatgtcagc tgggctgcat    180
cctccaaaga tcagtgctga attgggtgca caccacccc cacacatgga tattgccggg    240
tcaggtcaag gagcgggtag caccggtgct agtaggacca attggccaat ggtcggcggg    300
agtttgttac gagccccca tatgggaatg cccactacaa ctgcagggat atggcccct     360
```

```
acttctgctt ctggtgctgt cagtggtttc gggttccagt catcatcctc ccctgctcca    420
gcagccacca gtttgggcac tgaaagttca aattacctac acaagcttgg gtttcctggt    480
tttgacttgc cagctgcaac taacaacttg ggtcctatga gtttcacctc catcgtgggg    540
gctgctactg accagcagca ncaccttcct ggattggagc tggggctatc acaagatggt    600
catgttgggg ttttgaaccc tncaaccttg agccagattt atcagcatat ggggcaggct    660
cgagcgcacc agcacaacac agcacgagac cacagc                              696
```

<210> SEQ ID NO 46
<211> LENGTH: 232
<212> TYPE: PRT
<213> ORGANISM: Coffea canephora
<220> FEATURE:
<221> NAME/KEY: UNSURE
<222> LOCATION: (187)..(187)
<223> OTHER INFORMATION: Xaa can be any naturally occurring amino acid
<220> FEATURE:
<221> NAME/KEY: UNSURE
<222> LOCATION: (208)..(208)
<223> OTHER INFORMATION: Xaa can be any naturally occurring amino acid

<400> SEQUENCE: 46

```
Ile Phe Gln Leu Thr Arg Glu Leu Gly His Lys Ser Asp Gly Glu Thr
1               5                   10                  15

Ile Gln Trp Leu Leu Gln Ala Glu Pro Ser Ile Ala Ala Thr
            20                  25                  30

Gly Thr Gly Thr Ile Pro Ala Ser Ala Leu Ala Ala Ala Ala Gly
        35                  40                  45

Ala Gly Gly Ser Val Ser Met Ser Ala Gly Leu His Pro Pro Lys Ile
 50                  55                  60

Ser Ala Glu Leu Gly Ala His His Pro Pro His Met Asp Ile Ala Gly
65                  70                  75                  80

Ser Gly Gln Gly Ala Gly Ser Thr Gly Ala Ser Arg Thr Asn Trp Pro
                85                  90                  95

Met Val Gly Gly Ser Leu Leu Arg Ala Pro His Met Gly Met Pro Thr
            100                 105                 110

Thr Thr Ala Gly Ile Trp Pro Pro Thr Ser Ala Ser Gly Ala Val Ser
        115                 120                 125

Gly Phe Gly Phe Gln Ser Ser Ser Pro Ala Pro Ala Ala Thr Ser
130                 135                 140

Leu Gly Thr Glu Ser Ser Asn Tyr Leu His Lys Leu Gly Phe Pro Gly
145                 150                 155                 160

Phe Asp Leu Pro Ala Ala Thr Asn Asn Leu Gly Pro Met Ser Phe Thr
                165                 170                 175

Ser Ile Val Gly Ala Ala Thr Asp Gln Gln Xaa His Leu Pro Gly Leu
            180                 185                 190

Glu Leu Gly Leu Ser Gln Asp Gly His Val Gly Val Leu Asn Pro Xaa
        195                 200                 205

Thr Leu Ser Gln Ile Tyr Gln His Met Gly Gln Ala Arg Ala His Gln
    210                 215                 220

His Asn Thr Ala Arg Asp His Ser
225                 230
```

<210> SEQ ID NO 47
<211> LENGTH: 993
<212> TYPE: DNA
<213> ORGANISM: Helianthus annuus
<220> FEATURE:

<223> OTHER INFORMATION: Also found in Helianthus petiolaris

<400> SEQUENCE: 47

```
tcggccgggg gacccaaagg ctcaaaccta catcatcctc aacagcagcc acatgaggcc      60
tcaagttcaa ccttcttagc ccacccaaac cccaccacaa cagacaacat gggagatcac     120
aacaacaata acatcaacac caacaacctc aacaaacttt ctgaaatcaa agatttccag     180
attacagttt ctgacaaaca agagtctgct accaagaaac aacagttagc ccccaaaaga     240
acctccaata aagacaggca caccaaggtt gaaggaagag gtaggaggat aaggatgcct     300
gctttatgtg ctgcaagaat ctttcagctc actagagagt taggtaacaa atctgatggt     360
gaaactattc aatggctgct acagcaagct gagccttcca ttatagccgc caccggaacc     420
gggacaatcc cggcttctgt gttagccgcc actgggcgg cttcacacgg ggtctcgatt      480
tcggttggct tgcaacaaaa gattgatgaa ttaagcggga gtaataataa cagtaatagt     540
aatattaata ctggtgtcaa ctgtaggacc agttggccaa tggttggtcc agctttgggt     600
gtgggtagac ccactaccca tatggctacg cctacggcta tctggcccgc tgctggattc     660
gggttccagt cctcttcttc gtccccaggt ccatcgggca caatttggg cgtcgaaagt      720
tcgaattact tgcaaaagat ggcgttttcc gggtttgatt tgcccggttc taatatgggt     780
cagatgagtt tttcttcgat tttgggtaat cataatcata atcataatca tcatcagcag     840
cagcttcctg ggctggagct tggactgtcc caggatggtc atttaggggt tttgaatcaa     900
caggctttga atcagatata ccaaatggac cagaccagaa tgcaacaaca gcagacttca     960
aatgataatt ctcaaggttc agaggggcag tag                                  993
```

<210> SEQ ID NO 48
<211> LENGTH: 329
<212> TYPE: PRT
<213> ORGANISM: Helianthus annuus
<220> FEATURE:
<223> OTHER INFORMATION: Also found in Helianthus petiolaris

<400> SEQUENCE: 48

```
Ser Ala Gly Gly Pro Lys Gly Ser Asn Leu His His Pro Gln Gln Gln
1               5                   10                  15

Pro His Glu Ala Ser Ser Ser Thr Phe Leu Ala His Pro Asn Pro Thr
            20                  25                  30

Thr Thr Asp Asn Met Gly Asp His Asn Asn Asn Asn Ile Asn Thr Asn
        35                  40                  45

Asn Leu Asn Lys Leu Ser Glu Ile Lys Asp Phe Gln Ile Thr Val Ser
    50                  55                  60

Asp Lys Gln Glu Ser Ala Thr Lys Lys Gln Gln Leu Ala Pro Lys Arg
65                  70                  75                  80

Thr Ser Asn Lys Asp Arg His Thr Lys Val Glu Gly Arg Gly Arg Arg
                85                  90                  95

Ile Arg Met Pro Ala Leu Cys Ala Ala Arg Ile Phe Gln Leu Thr Arg
            100                 105                 110

Glu Leu Gly Asn Lys Ser Asp Gly Glu Thr Ile Gln Trp Leu Leu Gln
        115                 120                 125

Gln Ala Glu Pro Ser Ile Ile Ala Ala Thr Gly Thr Gly Thr Ile Pro
    130                 135                 140

Ala Ser Val Leu Ala Ala Thr Gly Ala Ala Ser His Gly Val Ser Ile
145                 150                 155                 160

Ser Val Gly Leu Gln Gln Lys Ile Asp Glu Leu Ser Gly Ser Asn Asn
                165                 170                 175
```

```
Asn Ser Asn Ser Asn Ile Asn Thr Gly Val Asn Cys Arg Thr Ser Trp
            180                 185                 190

Pro Met Val Gly Pro Ala Leu Gly Val Gly Arg Pro Thr Thr His Met
            195                 200                 205

Ala Thr Pro Thr Ala Ile Trp Pro Ala Ala Gly Phe Gly Phe Gln Ser
210                 215                 220

Ser Ser Ser Ser Pro Gly Pro Ser Gly Asn Asn Leu Gly Val Glu Ser
225                 230                 235                 240

Ser Asn Tyr Leu Gln Lys Met Ala Phe Ser Gly Phe Asp Leu Pro Gly
            245                 250                 255

Ser Asn Met Gly Gln Met Ser Phe Ser Ser Ile Leu Gly Asn His Asn
            260                 265                 270

His Asn His Asn His His Gln Gln Gln Leu Pro Gly Leu Glu Leu Gly
            275                 280                 285

Leu Ser Gln Asp Gly His Leu Gly Val Leu Asn Gln Gln Ala Leu Asn
290                 295                 300

Gln Ile Tyr Gln Met Asp Thr Arg Met Gln Gln Gln Thr Ser Asn
305                 310                 315                 320

Asp Asn Ser Gln Gly Ser Glu Gly Gln
                325

<210> SEQ ID NO 49
<211> LENGTH: 345
<212> TYPE: DNA
<213> ORGANISM: Hordeum vulgare

<400> SEQUENCE: 49
atcggcggcc tcatgcagcg gatcggcctc cccgccggga tcgagctgcc gggcggcggc      60 gcgggggggca tgggcgggca catcgggttc gcgcccatgt tcgccagcca cgcggcggcc    120
gcaataccgg ggctggagct cggcctgtcg caggagggcc acatcgggt gctcagccag     180 ttctaccacc aggtcggcgg cgccggggcc agcgggcagc tgcagcaccc gcaccctcat    240
cagcaccacc accacgaaca gcaccaccat caccagcagc agcagcagga ggaggacggg    300
gaggaggagc gcgaggacgg cgactccgag gaggagtccg gccag                    345

<210> SEQ ID NO 50
<211> LENGTH: 115
<212> TYPE: PRT
<213> ORGANISM: Hordeum vulgare

<400> SEQUENCE: 50

Ile Gly Gly Leu Met Gln Arg Ile Gly Leu Pro Ala Gly Ile Glu Leu
1               5                   10                  15

Pro Gly Gly Gly Ala Gly Gly Met Gly Gly His Ile Gly Phe Ala Pro
            20                  25                  30

Met Phe Ala Ser His Ala Ala Ala Ile Pro Gly Leu Glu Leu Gly
            35                  40                  45

Leu Ser Gln Glu Gly His Ile Gly Val Leu Ser Gln Phe Tyr His Gln
    50                  55                  60

Val Gly Gly Ala Gly Ala Ser Gly Gln Leu Gln His Pro His Pro His
65                  70                  75                  80

Gln His His His Glu Gln His His Gln Gln Gln Gln
                85                  90                  95

Glu Glu Asp Gly Glu Glu Glu Arg Glu Asp Gly Asp Ser Glu Glu Glu
                100                 105                 110
```

Ser Gly Gln
        115

<210> SEQ ID NO 51
<211> LENGTH: 521
<212> TYPE: DNA
<213> ORGANISM: Linum usitatissimum

<400> SEQUENCE: 51

```
atcatcatca cccatctatt ctcttgtcta tcctctctcc cctgcagctc ttcttatctt      60
gtgcttatgg aacaacaaca acaacaacca aaggtcccaa accaccttga tgatccacac     120
caaaacagca acaaccctct ttcggcaatg aaagacgttc aaatcacatc acttgttcca     180
aacagcagta caaagaagca gcagagttta ggtccgaaga ggagttcgaa caaggacagg     240
cacaagaaag tggacggaag agggagaagg atcaggatgc cagctttatg cgccgctagc     300
atcttccagc tgactcgaga attgggtcac aaatccgacg gcgagaccat ccagtggctt     360
ctgaaccaat ctgagccgtc catcattgca gccaccggca ccgggacaat tccggcctct     420
gctcttgccg ctgcagggtc tctgtttcct aattcggaga tgcaggggag ctctgtttct     480
ttctctgctg ggaacaattg ggcagccttg atgaatgcca a                        521
```

<210> SEQ ID NO 52
<211> LENGTH: 173
<212> TYPE: PRT
<213> ORGANISM: Linum usitatissimum

<400> SEQUENCE: 52

Ile Ile Ile Thr His Leu Phe Ser Cys Leu Ser Ser Leu Pro Cys Ser
1               5                   10                  15

Ser Ser Tyr Leu Val Leu Met Glu Gln Gln Gln Gln Gln Pro Lys Val
            20                  25                  30

Pro Asn His Leu Asp Asp Pro His Gln Asn Ser Asn Asn Pro Leu Ser
        35                  40                  45

Ala Met Lys Asp Val Gln Ile Thr Ser Leu Val Pro Asn Ser Ser Thr
    50                  55                  60

Lys Lys Gln Gln Ser Leu Gly Pro Lys Arg Ser Ser Asn Lys Asp Arg
65                  70                  75                  80

His Lys Lys Val Asp Gly Arg Gly Arg Arg Ile Arg Met Pro Ala Leu
                85                  90                  95

Cys Ala Ala Ser Ile Phe Gln Leu Thr Arg Glu Leu Gly His Lys Ser
            100                 105                 110

Asp Gly Glu Thr Ile Gln Trp Leu Leu Asn Gln Ser Glu Pro Ser Ile
        115                 120                 125

Ile Ala Ala Thr Gly Thr Gly Thr Ile Pro Ala Ser Ala Leu Ala Ala
    130                 135                 140

Ala Gly Ser Ser Val Ser Asn Ser Glu Met Gln Gly Ser Ser Val Ser
145                 150                 155                 160

Phe Ser Ala Gly Asn Asn Trp Ala Ala Leu Met Asn Ala
                165                 170

<210> SEQ ID NO 53
<211> LENGTH: 441
<212> TYPE: DNA
<213> ORGANISM: Lotus corniculatus

<400> SEQUENCE: 53

```
atggatccca agggctcaaa gcagcagaac caggaggttg ttccaaactt ccttcaacaa      60
```

```
caacaacaag ggaacaacaa caacaacatg ggagagaaca aaccatccga ggttaaggat      120
ttccagattg tgattgctga gaaagatgag agcaagaagc agttggcacc aaagaggacc      180
tccaacaagg acagacacac aaaagttgaa ggcaggggaa ggaggataag gatgccagct      240
ctgtgtgcag caagaatctt ccagttgacc agagaattag gtcacaaatc tgatggtgaa      300
accatccagt ggcttctgca gcaggctgag ccatcaatca tagcagccac tggaactgga      360
acaatcccag catctgcttt agcttctgct gctggtaact ctgtttcaca acaggggacc      420
tctttatctg ctggtttgca c                                                441
```

```
<210> SEQ ID NO 54
<211> LENGTH: 147
<212> TYPE: PRT
<213> ORGANISM: Lotus corniculatus

<400> SEQUENCE: 54

Met Asp Pro Lys Gly Ser Lys Gln Gln Asn Gln Glu Val Val Pro Asn
1               5                   10                  15

Phe Leu Gln Gln Gln Gln Gly Asn Asn Asn Asn Met Gly Glu
            20                  25                  30

Asn Lys Pro Ser Glu Val Lys Asp Phe Gln Ile Val Ile Ala Glu Lys
        35                  40                  45

Asp Glu Ser Lys Lys Gln Leu Ala Pro Lys Arg Thr Ser Asn Lys Asp
    50                  55                  60

Arg His Thr Lys Val Glu Gly Arg Gly Arg Arg Ile Arg Met Pro Ala
65                  70                  75                  80

Leu Cys Ala Ala Arg Ile Phe Gln Leu Thr Arg Glu Leu Gly His Lys
                85                  90                  95

Ser Asp Gly Glu Thr Ile Gln Trp Leu Leu Gln Gln Ala Glu Pro Ser
            100                 105                 110

Ile Ile Ala Ala Thr Gly Thr Gly Thr Ile Pro Ala Ser Ala Leu Ala
        115                 120                 125

Ser Ala Ala Gly Asn Ser Val Ser Gln Gln Gly Thr Ser Leu Ser Ala
    130                 135                 140

Gly Leu His
145
```

```
<210> SEQ ID NO 55
<211> LENGTH: 668
<212> TYPE: DNA
<213> ORGANISM: Petunia hybrida

<400> SEQUENCE: 55
gcggcgtcta atatggatc cccgggctgc aggaatcggc acgagagaga aagtagcaag       60
aaacaattag ctccaaaaag aagttcaaac aaagataggc ataaaaaagt agatggtaga      120
ggtagaagaa ttcgtatgcc agctttatgt gctgcaagaa ttttccaatt gactcgtgaa      180
ttgggtcata aaactgatgg tgaaacaatt caatggctgt acaacaagc tgagccttca       240 attattgctg ctactgggac tggtactatt cctgcttcag ttcttgcagc tgctacttcc      300
tctgtttctg aacaggggaa ctctgtttct gctacttctt acattcaag aattgatgat       360 tatggtttgt ttagagctaa ttgggctaat ttaagtagac cccagatgcc tgtttctggt      420
tcttggccta gttttggatc aggatttgtg caaaattcaa gtaatttgag tactcaaatg      480
ttgagttctg ttccaagatt tggctttgag tttactcaaa attcattggg atttaatcag      540
aatcaaaatg ttcctggttt agaacttgga ttatctcaag agggtcgaat tgggaacttg      600
```

```
aattttcaat ctttacaaca gttttatcag caaatagcta cacaaagtgg agatgctgct    660
gctcgagg                                                            668
```

<210> SEQ ID NO 56
<211> LENGTH: 222
<212> TYPE: PRT
<213> ORGANISM: Petunia hybrida

<400> SEQUENCE: 56

```
Ala Ala Ser Lys Tyr Gly Ser Pro Gly Cys Arg Asn Arg His Glu Arg
1               5                   10                  15

Glu Ser Ser Lys Lys Gln Leu Ala Pro Lys Arg Ser Asn Lys Asp
            20                  25                  30

Arg His Lys Lys Val Asp Gly Arg Gly Arg Ile Arg Met Pro Ala
        35                  40                  45

Leu Cys Ala Ala Arg Ile Phe Gln Leu Thr Arg Glu Leu Gly His Lys
    50                  55                  60

Thr Asp Gly Glu Thr Ile Gln Trp Leu Leu Gln Gln Ala Glu Pro Ser
65                  70                  75                  80

Ile Ile Ala Ala Thr Gly Thr Gly Thr Ile Pro Ala Ser Val Leu Ala
                85                  90                  95

Ala Ala Thr Ser Ser Val Ser Glu Gln Gly Asn Ser Val Ser Ala Thr
            100                 105                 110

Ser Leu His Ser Arg Ile Asp Asp Tyr Gly Leu Phe Arg Ala Asn Trp
        115                 120                 125

Ala Asn Leu Ser Arg Pro Gln Met Pro Val Ser Gly Ser Trp Pro Ser
    130                 135                 140

Phe Gly Ser Gly Phe Val Gln Asn Ser Ser Asn Leu Ser Thr Gln Met
145                 150                 155                 160

Leu Ser Ser Val Pro Arg Phe Gly Phe Glu Phe Thr Gln Asn Ser Leu
                165                 170                 175

Gly Phe Asn Gln Asn Gln Asn Val Pro Gly Leu Glu Leu Gly Leu Ser
            180                 185                 190

Gln Glu Gly Arg Ile Gly Asn Leu Asn Phe Gln Ser Leu Gln Gln Phe
        195                 200                 205

Tyr Gln Gln Ile Ala Thr Gln Ser Gly Asp Ala Ala Ala Arg
    210                 215                 220
```

<210> SEQ ID NO 57
<211> LENGTH: 294
<212> TYPE: DNA
<213> ORGANISM: Prunus persica

<400> SEQUENCE: 57

```
gagttcaaat tacatgcaaa agatggcttt cctggctttg acttgcctgt ctccaacatg     60
ggtcctatga gtttcacctc aattttgggt ggtgggagta accaacagct tcctggcttg    120
gagcttgggt tgtctcagga tggtcatatt ggggttttga actcacaagc cttgagccag    180
atttaccagc agatggggca tgctagagta caccagcacc agcaccagca ccagcaccag    240
caccagcacc agcaaccccc tgctaaggat gactctcaag gctcaggaca gtag          294
```

<210> SEQ ID NO 58
<211> LENGTH: 97
<212> TYPE: PRT
<213> ORGANISM: Prunus persica

<400> SEQUENCE: 58

```
Glu Phe Lys Leu His Ala Lys Asp Gly Phe Pro Gly Phe Asp Leu Pro
1               5                  10                  15

Val Ser Asn Met Gly Pro Met Ser Phe Thr Ser Ile Leu Gly Gly
            20                  25                  30

Ser Asn Gln Gln Leu Pro Gly Leu Glu Leu Gly Leu Ser Gln Asp Gly
        35                  40                  45

His Ile Gly Val Leu Asn Ser Gln Ala Leu Ser Gln Ile Tyr Gln Gln
    50                  55                  60

Met Gly His Ala Arg Val His Gln His Gln His Gln His Gln His Gln
65                  70                  75                  80

His Gln His Gln Gln Pro Pro Ala Lys Asp Asp Ser Gly Ser Gly
            85                  90                  95

Gln

<210> SEQ ID NO 59
<211> LENGTH: 936
<212> TYPE: DNA
<213> ORGANISM: Ricinus communis

<400> SEQUENCE: 59
aacccacatg aattacctaa cttcttgact caccctcctc aaccagccct acagcaacaa      60
caacaaccac aacaagaaca caacatcaa aaccagaaac aacagacaaa catgggagag     120
aataaaccag cagaaatcaa agatttccag attgttattg cagataaaga agagcagaag     180
aaacagttag caccaaaaag aagctcaaac aaagacagac atacgaaagt tgaaggaaga     240
gggaggagga taaggatgcc agcactttgt gcagcaagaa tctttcaatt gacaagagaa     300
ttgggtcata aatctgatgg ggaaacaata cagtggttat tacaacaagc tgaaccatct     360
ataattgctg caactgggac aggaacgata ccagcatcag ctttggtagc tgctggtgga     420
tcagtttcac agcaagggac ttctctatca gctggattac accaaaagat tgatgattta     480
ggtgggtcca gtagtattac tagtagtaat agtaggacaa gttgggcaat ggtaggtggc     540
aatttaggga gacccccatca tgtggcaaca acagggttat ggcccccagt tggtggtttt     600
ggattccagt catcatctac tactactggt ccagtaacat caaatttggg aaatgaaagt     660
tctagttatt tgcaaaaaat tgggtttcct gggtttgatt tgccagggaa taatatggga     720
cctatgagtt ttacctcaat cttgggtggg actagcaacc agcagatacc tggtttggag     780
cttgggttgt cacaagatgg tcatattggg gttttgaatt cacaagcttt tagtcagatt     840
tatcagcaga tggggcaggc cagagtgcag caccagcacc agcaccagca ccagcaaaat     900
cctgctaagg atgattctca agggtcagga cagtaa                              936

<210> SEQ ID NO 60
<211> LENGTH: 311
<212> TYPE: PRT
<213> ORGANISM: Ricinus communis

<400> SEQUENCE: 60

Asn Pro His Glu Leu Pro Asn Phe Leu Thr His Pro Pro Gln Pro Ala
1               5                  10                  15

Leu Gln Gln Gln Gln Pro Gln Gln Glu Gln Gln His Gln Asn Gln
            20                  25                  30

Lys Gln Gln Thr Asn Met Gly Glu Asn Lys Pro Ala Glu Ile Lys Asp
        35                  40                  45

Phe Gln Ile Val Ile Ala Asp Lys Glu Glu Gln Lys Lys Gln Leu Ala
    50                  55                  60
```

```
Pro Lys Arg Ser Ser Asn Lys Asp Arg His Thr Lys Val Glu Gly Arg
 65                  70                  75                  80

Gly Arg Arg Ile Arg Met Pro Ala Leu Cys Ala Ala Arg Ile Phe Gln
                 85                  90                  95

Leu Thr Arg Glu Leu Gly His Lys Ser Asp Gly Glu Thr Ile Gln Trp
            100                 105                 110

Leu Leu Gln Gln Ala Glu Pro Ser Ile Ile Ala Thr Gly Thr Gly
        115                 120                 125

Thr Ile Pro Ala Ser Ala Leu Val Ala Ala Gly Gly Ser Val Ser Gln
    130                 135                 140

Gln Gly Thr Ser Leu Ser Ala Gly Leu His Gln Lys Ile Asp Asp Leu
145                 150                 155                 160

Gly Gly Ser Ser Ser Ile Thr Ser Ser Asn Ser Arg Thr Ser Trp Ala
                165                 170                 175

Met Val Gly Gly Asn Leu Gly Arg Pro His His Val Ala Thr Thr Gly
                180                 185                 190

Leu Trp Pro Pro Val Gly Gly Phe Gly Phe Gln Ser Ser Ser Thr Thr
            195                 200                 205

Thr Gly Pro Val Thr Ser Asn Leu Gly Asn Glu Ser Ser Ser Tyr Leu
    210                 215                 220

Gln Lys Ile Gly Phe Pro Gly Phe Asp Leu Pro Gly Asn Asn Met Gly
225                 230                 235                 240

Pro Met Ser Phe Thr Ser Ile Leu Gly Thr Ser Asn Gln Gln Ile
                245                 250                 255

Pro Gly Leu Glu Leu Gly Leu Ser Gln Asp Gly His Ile Gly Val Leu
            260                 265                 270

Asn Ser Gln Ala Phe Ser Gln Ile Tyr Gln Gln Met Gly Gln Ala Arg
        275                 280                 285

Val Gln His Gln His Gln His Gln Gln Asn Pro Ala Lys Asp
    290                 295                 300

Asp Ser Gln Gly Ser Gly Gln
305                 310

<210> SEQ ID NO 61
<211> LENGTH: 231
<212> TYPE: DNA
<213> ORGANISM: Salvia miltiorrhiza

<400> SEQUENCE: 61
agtttcacct caattttgag cggcggcgct cagcagctgc ccggattgga gcttggccta      60
tcacaagatg gaaatattgg cgtgctcaat cctcaagcat tcgggcagtt ttatcagcag     120
atggcaccgg cggcgcgtgt tgcccaccac catcagcagc aacaccacca ccaccatcag     180
cagcagcctt tgtcgcccaa ggatgatgat tctcaagaat caggacagta g              231

<210> SEQ ID NO 62
<211> LENGTH: 76
<212> TYPE: PRT
<213> ORGANISM: Salvia miltiorrhiza

<400> SEQUENCE: 62

Ser Phe Thr Ser Ile Leu Ser Gly Gly Ala Gln Gln Leu Pro Gly Leu
 1               5                  10                  15

Glu Leu Gly Leu Ser Gln Asp Gly Asn Ile Gly Val Leu Asn Pro Gln
            20                  25                  30

Ala Phe Gly Gln Phe Tyr Gln Gln Met Ala Pro Ala Ala Arg Val Ala
        35                  40                  45
```

His His His Gln Gln Gln His His His His Gln Gln Gln Pro Leu
    50                  55                  60
Ser Pro Lys Asp Asp Asp Ser Gln Glu Ser Gly Gln
 65                  70                  75

<210> SEQ ID NO 63
<211> LENGTH: 598
<212> TYPE: DNA
<213> ORGANISM: Zinnia elegans

<400> SEQUENCE: 63
cacacaaagg ttaaaggaag aggtagaaga attaggatgc cagctttatg tgctgcaaga      60
atctttcaac tcactaggga gttaggtaac aaatctgatg gggaaacaat ccagtggctg     120
ctacagcagg ccgagccatc tatcatagca gccactggca ccgggactat cccggcttcc    180
gtgttagcca ccaccggagc ggcttcacac ggagtctcga tttcgtagg attgcaacat      240
aagattgatg tattaggtag tgggaatagt aacactagta ttagtaatag taacagtaat    300
agtaatatct gtggcaacaa ctgtaggacc agttggccta tgggtagacc cacaacccat    360
atggccacgc ctactacagg tatatggccc gcaatgggat acgggtcttc gggtccctcg    420
ggcaacaatt taggggttga aagctcgaat tacctgcaaa agatggcgtt ttccgggttt    480
gaattgcctg gtctaatat gggtcagatg agttttcgt cgattttagg taatcataat      540
catgatcatc atcagcagca gcagcttcct gggttggaac ttgggttgtc ccaagatg      598

<210> SEQ ID NO 64
<211> LENGTH: 199
<212> TYPE: PRT
<213> ORGANISM: Zinnia elegans

<400> SEQUENCE: 64

His Thr Lys Val Lys Gly Arg Gly Arg Arg Ile Arg Met Pro Ala Leu
 1               5                  10                  15

Cys Ala Ala Arg Ile Phe Gln Leu Thr Arg Glu Leu Gly Asn Lys Ser
             20                  25                  30

Asp Gly Glu Thr Ile Gln Trp Leu Leu Gln Gln Ala Glu Pro Ser Ile
         35                  40                  45

Ile Ala Ala Thr Gly Thr Gly Thr Ile Pro Ala Ser Val Leu Ala Thr
     50                  55                  60

Thr Gly Ala Ala Ser His Gly Val Ser Ile Ser Val Gly Leu Gln His
 65                  70                  75                  80

Lys Ile Asp Val Leu Gly Ser Gly Asn Ser Asn Thr Ser Ile Ser Asn
                 85                  90                  95

Ser Asn Ser Asn Ser Asn Ile Cys Gly Asn Asn Cys Arg Thr Ser Trp
            100                 105                 110

Pro Met Gly Arg Pro Thr Thr His Met Ala Thr Pro Thr Thr Gly Ile
        115                 120                 125

Trp Pro Ala Met Gly Tyr Gly Ser Gly Pro Ser Gly Asn Asn Leu
    130                 135                 140

Gly Val Glu Ser Ser Asn Tyr Leu Gln Lys Met Ala Phe Ser Gly Phe
145                 150                 155                 160

Glu Leu Pro Gly Ser Asn Met Gly Gln Met Ser Phe Ser Ile Leu
                165                 170                 175

Gly Asn His Asn His Asp His His Gln Gln Gln Gln Leu Pro Gly Leu
            180                 185                 190

Glu Leu Gly Leu Ser Gln Asp

195

<210> SEQ ID NO 65
<211> LENGTH: 17
<212> TYPE: PRT
<213> ORGANISM: Artificial sequence
<220> FEATURE:
<223> OTHER INFORMATION: consensus C-terminal motif 1
<220> FEATURE:
<221> NAME/KEY: VARIANT
<222> LOCATION: (6)..(6)
<223> OTHER INFORMATION: Xaa is Gly, Arg, or Ala
<220> FEATURE:
<221> NAME/KEY: UNSURE
<222> LOCATION: (10)..(10)
<223> OTHER INFORMATION: Xaa can be any naturally occurring amino acid
<220> FEATURE:
<221> NAME/KEY: UNSURE
<222> LOCATION: (11)..(14)
<223> OTHER INFORMATION: Xaa can be any naturally occurring amino acid
    or no amino acid
<220> FEATURE:
<221> NAME/KEY: VARIANT
<222> LOCATION: (16)..(16)
<223> OTHER INFORMATION: Xaa is Val or Leu

<400> SEQUENCE: 65

Pro Gly Leu Glu Leu Xaa Leu Ser Gln Xaa Xaa Xaa Xaa Xaa Gly Xaa Leu
1               5                   10                  15

<210> SEQ ID NO 66
<211> LENGTH: 69
<212> TYPE: PRT
<213> ORGANISM: Artificial sequence
<220> FEATURE:
<223> OTHER INFORMATION: Conserved TCP domain of SEQ ID NO : 02

<400> SEQUENCE: 66

Lys Asp Arg His Thr Lys Val Glu Gly Arg Gly Arg Arg Ile Arg Met
1               5                   10                  15

Pro Ala Leu Cys Ala Ala Arg Ile Phe Gln Leu Thr Arg Glu Leu Gly
            20                  25                  30

His Lys Ser Asp Gly Glu Thr Ile Gln Trp Leu Leu Gln Gln Ala Glu
        35                  40                  45

Pro Ser Ile Ile Ala Ala Thr Gly Ser Gly Thr Ile Pro Ala Ser Ala
    50                  55                  60

Leu Ala Ser Ser Ala
65

<210> SEQ ID NO 67
<211> LENGTH: 2193
<212> TYPE: DNA
<213> ORGANISM: Oryza sativa

<400> SEQUENCE: 67
aatccgaaaa gtttctgcac cgttttcacc ccctaactaa caatataggg aacgtgtgct     60
aaatataaaa tgagacctta tatatgtagc gctgataact agaactatgc aagaaaaact    120
catccaccta ctttagtggc aatcgggcta aataaaaaag agtcgctaca ctagtttcgt    180
tttccttagt aattaagtgg gaaaatgaaa tcattattgc ttagaatata cgttcacatc    240
tctgtcatga agttaaatta ttcgaggtag ccataattgt catcaaactc ttcttgaata    300
aaaaaatctt tctagctgaa ctcaatgggt aaagagagag attttttta aaaaaatga     360 atgaagatat tctgaacgta ttggcaaaga tttaaacata taattatata attttatagt    420
ttgtgcattc gtcatatcgc acatcattaa ggacatgtct tactccatcc caatttttat    480

```
ttagtaatta aagacaattg acttattttt attatttatc ttttttcgat tagatgcaag    540
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggtttttc acatacaaaa    780 aaaaaagaa ttttgctcgt gcgcgagcgc caatctccca tattgggcac acaggcaaca    840
acagagtggc tgcccacaga acaacccaca aaaaacgatg atctaacgga ggacagcaag    900
tccgcaacaa ccttttaaca gcaggctttg cggccaggag agaggaggag aggcaaagaa    960
aaccaagcat cctcctcctc ccatctataa attcctcccc ccttttcccc tctctatata   1020
ggaggcatcc aagccaagaa gagggagagc accaaggaca cgcgactagc agaagccgag   1080
cgaccgcctt cttcgatcca tatcttccgg tcgagttctt ggtcgatctc ttccctcctc   1140
cacctcctcc tcacagggta tgtgcccttc ggttgttctt ggattattg ttctaggttg    1200 tgtagtacgg gcgttgatgt taggaaaggg gatctgtatc tgtgatgatt cctgttcttg   1260
gatttgggat agaggggttc ttgatgttgc atgttatcgg ttcggtttga ttagtagtat   1320
ggttttcaat cgtctggaga gctctatgga aatgaaatgg tttagggtac ggaatcttgc   1380
gattttgtga gtacctttg tttgaggtaa atcagagca ccggtgatt tgcttggtgt      1440 aataaaagta cggttgtttg gtcctcgatt ctggtagtga tgcttctcga tttgacgaag   1500
ctatcctttg tttattccct attgaacaaa ataatccaa ctttgaagac ggtcccgttg    1560
atgagattga atgattgatt cttaagcctg tccaaaattt cgcagctggc ttgtttagat   1620
acagtagtcc ccatcacgaa attcatgaaa acagttataa tcctcaggaa caggggattc   1680
cctgttcttc cgatttgctt tagtcccaga attttttttc ccaaatatct taaaaagtca   1740
ctttctggtt cagttcaatg aattgattgc tacaaataat gcttttatag cgttatccta   1800
gctgtagttc agttaatagg taataccccct atagtttagt caggagaaga acttatccga   1860
tttctgatct ccattttttaa ttatatgaaa tgaactgtag cataagcagt attcatttgg   1920
attatttttt ttattagctc tcacccccttc attattctga gctgaaagtc tggcatgaac   1980
tgtcctcaat tttgttttca aattcacatc gattatctat gcattatcct cttgtatcta   2040
cctgtagaag tttcttttg gttattcctt gactgcttga ttacagaaag aaatttatga    2100
agctgtaatc gggatagtta tactgcttgt tcttatgatt catttccttt gtgcagttct   2160
tggtgtagct tgccactttc accagcaaag ttc                                 2193
```

<210> SEQ ID NO 68
<211> LENGTH: 53
<212> TYPE: DNA
<213> ORGANISM: Artificial sequence
<220> FEATURE:
<223> OTHER INFORMATION: primer: prm01501

<400> SEQUENCE: 68
ggggacaagt ttgtacaaaa aagcaggctt cacaatggat cccaagaacc taa            53

<210> SEQ ID NO 69
<211> LENGTH: 48
<212> TYPE: DNA
<213> ORGANISM: Artificial sequence
<220> FEATURE:
<223> OTHER INFORMATION: primer: prm01502

<400> SEQUENCE: 69

```
ggggaccact tgtacaaga aagctgggtt tttaacgacc tgagcctt              48
```

<210> SEQ ID NO 70
<211> LENGTH: 924
<212> TYPE: DNA
<213> ORGANISM: Cichorium endivia

<400> SEQUENCE: 70

```
cgggggatc cagagttcaa gcaacaacat cctcaacagc agccatatga ggtttcaagc     60
ttcttaagca tcccgcaacc caccagcaac aacatgggag ataacgacaa cagcaagcct    120
tctgaaatca aagatttaca gattgtaatt cccgacaagg aaaccagcaa gaagcaacaa    180
caattagcac ccaaacgcac atccaacaaa gacaggcata caaaggttga aggccgaggt    240
cgcaggatta ggatgcccgc tctctgtgct gcaagaatct ttcagctgac tcgagaatta    300
ggtcataaat ccgatgggga acaatccag tggctcctac agcaggccga gccttccatt     360
atcgccgcca ccgaactgg aactatcccg gcttcggtgt tagccacagc cggcgcagtt     420
tcacatgggg tttcgacttc ggcgggatta acagaaac ttgacgaatt agttggtgtg      480
ggaaatacta gtgacagctg taggaccagt tggccgattg ttggtccggg ggtgggtaga    540
cccgcaaccc acatggccac tcctttaggt atgtggccaa ccacaaccgg atttgggttt    600
cagtcgcctc cgtcgtcctc tggtccatca tcggccaaca atttgggcat cgaaagctcc    660
aattacttgc aaaagattgc attttctggg tttgatctgc ccggttctaa tctgggcccg    720
atgagttttt cttcgatttt gggtaatcat catcaacagc aacttcccgg gttggagctg    780
ggactgtcac aagatggtca catagggtc ttgaatcaac aagcgctgaa ccagatttac      840
cagatgggtc aggccagaat gcaccatcaa caacaacaac atcaaacttc taaggatgat    900
tctcaaggtt caggggggaca atag                                          924
```

<210> SEQ ID NO 71
<211> LENGTH: 307
<212> TYPE: PRT
<213> ORGANISM: Cichorium endivia

<400> SEQUENCE: 71

```
Arg Gly Asp Pro Glu Phe Lys Gln Gln His Pro Gln Gln Pro Tyr
1               5                  10                  15

Glu Val Ser Ser Phe Leu Ser Ile Pro Gln Pro Thr Ser Asn Asn Met
            20                  25                  30

Gly Asp Asn Asp Asn Ser Lys Pro Ser Glu Ile Lys Asp Leu Gln Ile
        35                  40                  45

Val Ile Pro Asp Lys Glu Thr Ser Lys Gln Gln Gln Leu Ala Pro
    50                  55                  60

Lys Arg Thr Ser Asn Lys Asp Arg His Thr Lys Val Glu Gly Arg Gly
65                  70                  75                  80

Arg Arg Ile Arg Met Pro Ala Leu Cys Ala Ala Arg Ile Phe Gln Leu
                85                  90                  95

Thr Arg Glu Leu Gly His Lys Ser Asp Gly Glu Thr Ile Gln Trp Leu
            100                 105                 110

Leu Gln Gln Ala Glu Pro Ser Ile Ile Ala Ala Thr Gly Thr Gly Thr
        115                 120                 125

Ile Pro Ala Ser Val Leu Ala Thr Ala Gly Ala Val Ser His Gly Val
    130                 135                 140

Ser Thr Ser Ala Gly Leu Gln Gln Lys Leu Asp Glu Leu Val Gly Val
145                 150                 155                 160
```

```
Gly Asn Thr Ser Asp Ser Cys Arg Thr Ser Trp Pro Ile Val Gly Pro
                165                 170                 175

Gly Val Gly Arg Pro Ala Thr His Met Ala Thr Pro Leu Gly Met Trp
            180                 185                 190

Pro Thr Thr Thr Gly Phe Gly Phe Gln Ser Pro Ser Ser Ser Gly
        195                 200                 205

Pro Ser Ser Ala Asn Asn Leu Gly Ile Glu Ser Ser Asn Tyr Leu Gln
    210                 215                 220

Lys Ile Ala Phe Ser Gly Phe Asp Leu Pro Gly Ser Asn Leu Gly Pro
225                 230                 235                 240

Met Ser Phe Ser Ser Ile Leu Gly Asn His His Gln Gln Gln Leu Pro
                245                 250                 255

Gly Leu Glu Leu Gly Leu Ser Gln Asp Gly His Ile Val Leu Asn
            260                 265                 270

Gln Gln Ala Leu Asn Gln Ile Tyr Gln Met Gly Gln Ala Arg Met His
        275                 280                 285

His Gln Gln Gln His Gln Thr Ser Lys Asp Asp Ser Gln Gly Ser
    290                 295                 300

Gly Gly Gln
305

<210> SEQ ID NO 72
<211> LENGTH: 585
<212> TYPE: DNA
<213> ORGANISM: Fragaria vesca

<400> SEQUENCE: 72
accaccggca ccgggacgat cccggcgtcg gctctagcgg cggcaggagg gtctgtatcg      60 cagcaggga gttcaatatc agctggcttg tatcaaaaga cagatgattt agggtccagt     120
ggaggtagga ccagttgggc tatggtggga gggaatttag gaggccccca tgtggctgca     180
gcaactgggc tatggccccc tgctgggttt ggttttttct tcacagtcat cttcatctggt    240 ccatctacta caaatctggg agggactgag agcagctcca attacctcca aaagattggc     300
cttcctgggt ttgacttgcc agtcaccaac atgggaccta tgagcttcac ttcaattctg     360 ggtggggaa gtcaacagct gcctggtttg aacttgggt tgtctcaaga tggccatctt      420
ggggttttga attctcaggc ttaccagatt taccagcaga tgggccatgc tagagtgcac     480
caccatcaac agcagcaaca gcaacaccac cagcagcagc accaaccaca gcaacagcag     540
caagctccgt cttctaagga tgattctcaa ggctcaggac agtag                     585

<210> SEQ ID NO 73
<211> LENGTH: 194
<212> TYPE: PRT
<213> ORGANISM: Fragaria vesca

<400> SEQUENCE: 73

Thr Thr Gly Thr Gly Thr Ile Pro Ala Ser Ala Leu Ala Ala Ala Gly
1               5                   10                  15

Gly Ser Val Ser Gln Gln Gly Ser Ser Ile Ser Ala Gly Leu Tyr Gln
            20                  25                  30

Lys Thr Asp Asp Leu Gly Ser Ser Gly Gly Arg Thr Ser Trp Ala Met
        35                  40                  45

Val Gly Gly Asn Leu Gly Arg Pro His Val Ala Ala Thr Gly Leu
    50                  55                  60

Trp Pro Pro Ala Gly Phe Gly Phe Ser Ser Gln Ser Ser Ser Ser Gly
```

```
                65                  70                  75                  80
Pro Ser Thr Thr Asn Leu Gly Gly Thr Glu Ser Ser Asn Tyr Leu
                        85                  90                  95

Gln Lys Ile Gly Leu Pro Gly Phe Asp Leu Pro Val Thr Asn Met Gly
            100                 105                 110

Pro Met Ser Phe Thr Ser Ile Leu Gly Gly Ser Gln Gln Leu Pro
        115                 120                 125

Gly Leu Glu Leu Gly Leu Ser Gln Asp Gly His Leu Gly Val Leu Asn
    130                 135                 140

Ser Gln Ala Tyr Gln Ile Tyr Gln Gln Met Gly His Ala Arg Val His
145                 150                 155                 160

His His Gln Gln Gln Gln Gln His His Gln Gln His Gln His
                165                 170                 175

Gln Gln Gln Gln Gln Ala Pro Ser Ser Lys Asp Asp Ser Gln Gly Ser
            180                 185                 190

Gly Gln

<210> SEQ ID NO 74
<211> LENGTH: 818
<212> TYPE: DNA
<213> ORGANISM: Juglans hindsii x Juglans regia

<400> SEQUENCE: 74
ccaagggctc aacaacagca aagcagccac aacaagtacc aaacttcttg agcctcccac      60
aaccacaaca acaacctaac atgggtgaga acaagcctgc tgaaatcaaa gacttccaga     120
ttgtgattgc tgacaaagaa gagggcaaga agcagttggc ccccaagaga agctcaaaca     180
aagaccggca caccaaagtt gaaggcaggg aaggagaat aaggatgcca gctcttttgtg     240 cagcgaggat ttttcaattg accagagaat tgggccacaa atctgatgga gaaaccatac     300
agtggctgtt acagcaggct gagccatcga taatagcagc cactgggact ggaaccatac     360
cggcttcagc tttagcagcg gcagggggtt ctgtatcaca gcaggggggcc tctctatcag     420 ctggattgca ccaaaagatt gatgatttgg gggggtccag tatcgggtta gggagtagga     480
ccagttgggc aatggtaggt gggaatttag ggagacccca tgtggccaca gggctatggc     540
ccccggtcag tgggtttggg tttcagtcat catctggtcc atcgactgcg aatttgggaa     600
gtgagagttc aaattacctg caaaagattg gcttccctgg ctttgacttg ccagccaccc     660
ctatgagttt cacctcaata ttgggtggga ataatcagca gctaccggga ttggagctcg     720
gcttatccca agatggtcat atcggggttt tgaacccaca agccttgagt cagatttatc     780
aacagatggg gcaggctaga gtgcagcagc aacagcaa                             818

<210> SEQ ID NO 75
<211> LENGTH: 272
<212> TYPE: PRT
<213> ORGANISM: Juglans hindsii x Juglans regia

<400> SEQUENCE: 75

Lys Gly Ser Thr Thr Ala Lys Gln Pro Gln Gln Val Pro Asn Phe Leu
1               5                   10                  15

Ser Leu Pro Gln Pro Gln Gln Gln Pro Asn Met Gly Glu Asn Lys Pro
            20                  25                  30

Ala Glu Ile Lys Asp Phe Gln Ile Val Ile Ala Asp Lys Glu Glu Gly
        35                  40                  45

Lys Lys Gln Leu Ala Pro Lys Arg Ser Ser Asn Lys Asp Arg His Thr
    50                  55                  60
```

Lys Val Glu Gly Arg Gly Arg Ile Arg Met Pro Ala Leu Cys Ala
65                  70                  75                  80

Ala Arg Ile Phe Gln Leu Thr Arg Glu Leu Gly His Lys Ser Asp Gly
            85                  90                  95

Glu Thr Ile Gln Trp Leu Leu Gln Ala Glu Pro Ser Ile Ile Ala
        100                 105                 110

Ala Thr Gly Thr Gly Thr Ile Pro Ala Ser Ala Leu Ala Ala Gly
        115                 120                 125

Gly Ser Val Ser Gln Gln Gly Ala Ser Leu Ser Ala Gly Leu His Gln
        130                 135                 140

Lys Ile Asp Asp Leu Gly Gly Ser Ser Ile Gly Leu Gly Ser Arg Thr
145                 150                 155                 160

Ser Trp Ala Met Val Gly Gly Asn Leu Gly Arg Pro His Val Ala Thr
                165                 170                 175

Gly Leu Trp Pro Pro Val Ser Gly Phe Gly Phe Gln Ser Ser Ser Gly
            180                 185                 190

Pro Ser Thr Ala Asn Leu Gly Ser Glu Ser Ser Asn Tyr Leu Gln Lys
        195                 200                 205

Ile Gly Phe Pro Gly Phe Asp Leu Pro Ala Thr Pro Met Ser Phe Thr
210                 215                 220

Ser Ile Leu Gly Gly Asn Asn Gln Gln Leu Pro Gly Leu Glu Leu Gly
225                 230                 235                 240

Leu Ser Gln Asp Gly His Ile Gly Val Leu Asn Pro Gln Ala Leu Ser
                245                 250                 255

Gln Ile Tyr Gln Gln Met Gly Gln Ala Arg Val Gln Gln Gln Gln
        260                 265                 270

<210> SEQ ID NO 76
<211> LENGTH: 474
<212> TYPE: DNA
<213> ORGANISM: Panax ginseng

<400> SEQUENCE: 76
tcagcagggc tgtatcagaa aattgatgaa ttgggcgggt ctagtagtag gagcagttgg      60
ccaatggttg gtgggaattt gggaagaccc catatggcca cagcaggatt atggcccgct     120
gctgcagtcg gtggctatgg gtttcagtca tcatcatctg gtccatcgac aaccaatttg     180
ggacatgaaa gttcaaatta cttgcaaaaa attgggtttt ctgggtttga cttgccagcc     240
accaatttgg gtcctatgag ttttgcctca attttgggtg caagtaatca gcagctccct     300
ggtttggagc ttggcctctc acaagatgga catattgggg ttttgtgccc tcaagccttg     360
acccagattt accagcagat gggaaatgat agaatgcacc agcaacagca acaacagcac     420
cggaatcacc agcaggcatc tcccaaggat gaatctcaag ggtcaggaga gtag           474

<210> SEQ ID NO 77
<211> LENGTH: 157
<212> TYPE: PRT
<213> ORGANISM: Panax ginseng

<400> SEQUENCE: 77

Ser Ala Gly Leu Tyr Gln Lys Ile Asp Glu Leu Gly Gly Ser Ser Ser
1               5                   10                  15

Arg Ser Ser Trp Pro Met Val Gly Gly Asn Leu Gly Arg Pro His Met
            20                  25                  30

Ala Thr Ala Gly Leu Trp Pro Ala Ala Val Gly Gly Tyr Gly Phe
        35                  40                  45

```
Gln Ser Ser Ser Ser Gly Pro Ser Thr Thr Asn Leu Gly His Glu Ser
    50                  55                  60

Ser Asn Tyr Leu Gln Lys Ile Gly Phe Ser Gly Phe Asp Leu Pro Ala
65                  70                  75                  80

Thr Asn Leu Gly Pro Met Ser Phe Ala Ser Ile Leu Gly Ala Ser Asn
                85                  90                  95

Gln Gln Leu Pro Gly Leu Glu Leu Gly Leu Ser Gln Asp Gly His Ile
            100                 105                 110

Gly Val Leu Cys Pro Gln Ala Leu Thr Gln Ile Tyr Gln Gln Met Gly
        115                 120                 125

Asn Asp Arg Met His Gln Gln Gln Gln His Arg Asn His Gln
130                 135                 140

Gln Ala Ser Pro Lys Asp Glu Ser Gln Gly Ser Gly Glu
145                 150                 155

<210> SEQ ID NO 78
<211> LENGTH: 582
<212> TYPE: DNA
<213> ORGANISM: Poncirus trifoliata

<400> SEQUENCE: 78 gaaccatccta tcatcgctgc tacaggaact gggactattc cagcctctat gcttgcagct      60
gcagggcct  ctgtttctga acaggggaac tctgtttcag caggcttgca tacaaaaata     120
gaagggttgg gaccaggtgt tgggtccatt aatagggcca actggacaat gatgagtgca     180
aattttggaa ggtctcaaat tccaagtgga gtttggccaa atataaatgg aactgggtct     240
gggtttattc aaaattctgg ccagttgact tcaaattttg gaagtgaaaa tttgagtgca     300
aatccaaaat ttgggttcca cgggattgaa tttccaaata tgaatatggg tttgatgagt     360
ttctcctcta tgttgagcgg tgctagccat caaattcctg gcttggagct tggtctctca     420
caggatgcgc atgtgggggt gatgaattct caagctataa gccagttcta tcaacagatg     480
gggcatcaca gaagcgcttc aggatccttg aatcagcagc atcagcatca gcaacaaatt     540
tctgataagg atgattctca gggatcagga tcaaagcagt ag                        582

<210> SEQ ID NO 79
<211> LENGTH: 193
<212> TYPE: PRT
<213> ORGANISM: Poncirus trifoliata

<400> SEQUENCE: 79

Glu Pro Ser Ile Ile Ala Ala Thr Gly Thr Gly Thr Ile Pro Ala Ser
1               5                   10                  15

Met Leu Ala Ala Ala Gly Ala Ser Val Ser Glu Gln Gly Asn Ser Val
            20                  25                  30

Ser Ala Gly Leu His Thr Lys Ile Glu Gly Leu Gly Pro Gly Val Gly
        35                  40                  45

Ser Ile Asn Arg Ala Asn Trp Thr Met Met Ser Ala Asn Phe Gly Arg
    50                  55                  60

Ser Gln Ile Pro Ser Gly Val Trp Pro Asn Ile Asn Gly Thr Gly Ser
65                  70                  75                  80

Gly Phe Ile Gln Asn Ser Gly Gln Leu Thr Ser Asn Phe Gly Ser Glu
                85                  90                  95

Asn Leu Ser Ala Asn Pro Lys Phe Gly Phe His Gly Ile Glu Phe Pro
            100                 105                 110

Asn Met Asn Met Gly Leu Met Ser Phe Ser Ser Met Leu Ser Gly Ala
```

```
                115                120                125
Ser His Gln Ile Pro Gly Leu Glu Leu Gly Leu Ser Gln Asp Ala His
        130                135                140

Val Gly Val Met Asn Ser Gln Ala Ile Ser Gln Phe Tyr Gln Gln Met
145                150                155                160

Gly His His Arg Ser Ala Ser Gly Ser Leu Asn Gln His Gln His
                165                170                175

Gln Gln Gln Ile Ser Asp Lys Asp Asp Ser Gly Ser Gly Ser Lys
        180                185                190

Gln

<210> SEQ ID NO 80
<211> LENGTH: 933
<212> TYPE: DNA
<213> ORGANISM: Chlamydomonas reinhardtii

<400> SEQUENCE: 80
atgcgctcag ccgttctaca acgcggccag gcgcggcgag tgtcttgccg ggttcgggcg      60
gatggttcgg gcgtggattc gctgccctcg accagcgcca gcagcagcgc acgccctctc     120
attgatcgcc gtcagctcct gaccggtgct gctgcgtcgg tcataacctt cgttggctgc     180
ccttgccccc tgtgcaagcc tggggaggca aaggccgcag cttggaacta tggcgaagtt     240
gcgggtccgc caacctggaa gggtgtgtgt gcgacgggca agcgccagtc gcccatcaac     300
atcccgttga acacatcggc gccgaaggtc gacgcggaga tgggcgaatt cgatttcgcc     360
tacggcagct tcgagaagtg cgacgtgctg aacacgggac acagcaccat gcaggtgaac     420
ttccccgctg caacctggc gttcattggc aacatggagc tggagctgct gcagttccac     480
ttccacgcgc cctcggagca cgccatggat ggccgccgtt acgccatgga ggcgcatctg     540
gtgcacaaga taaaagcac cggcaaccta gctgtgctgg cattatgct ggagcccggc     600 ggcctgatca agaacccggc gctgtccact gctctggagg tggcgcccga ggtgcccctg     660
gccaagaagc cctcgcccaa gggcatcaac cccgtcatgc tgctgcccaa gaagagcaag     720
gccgggacac ggccgttcgt gcactaccct ggctcgctta ccacgccccc gtgttcggag     780
ggggtggact ggtttgtgtt catgcagccc atcaaggtgc ccgacagcca gatcctggac     840
ttcatgcgct tcgtgggcga caacaagaca tacgccacca acgcggcc actgcagctg     900 ctcaacagcc gcctggtcga atacgagctg tga                                  933

<210> SEQ ID NO 81
<211> LENGTH: 310
<212> TYPE: PRT
<213> ORGANISM: Chlamydomonas reinhardtii

<400> SEQUENCE: 81

Met Arg Ser Ala Val Leu Gln Arg Gly Gln Ala Arg Arg Val Ser Cys
1               5                   10                  15

Arg Val Arg Ala Asp Gly Ser Gly Val Asp Ser Leu Pro Ser Thr Ser
                20                  25                  30

Ala Ser Ser Ser Ala Arg Pro Leu Ile Asp Arg Arg Gln Leu Leu Thr
            35                  40                  45

Gly Ala Ala Ala Ser Val Ile Thr Phe Val Gly Cys Pro Cys Pro Leu
        50                  55                  60

Cys Lys Pro Gly Glu Ala Lys Ala Ala Ala Trp Asn Tyr Gly Glu Val
65                  70                  75                  80

Ala Gly Pro Pro Thr Trp Lys Gly Val Cys Ala Thr Gly Lys Arg Gln
```

```
                        85                  90                  95
Ser Pro Ile Asn Ile Pro Leu Asn Thr Ser Ala Pro Lys Val Asp Ala
                100                 105                 110

Glu Met Gly Glu Phe Asp Phe Ala Tyr Gly Ser Phe Glu Lys Cys Asp
            115                 120                 125

Val Leu Asn Thr Gly His Ser Thr Met Gln Val Asn Phe Pro Ala Gly
        130                 135                 140

Asn Leu Ala Phe Ile Gly Asn Met Glu Leu Glu Leu Leu Gln Phe His
145                 150                 155                 160

Phe His Ala Pro Ser Glu His Ala Met Asp Gly Arg Arg Tyr Ala Met
                165                 170                 175

Glu Ala His Leu Val His Lys Asn Lys Ser Thr Gly Asn Leu Ala Val
            180                 185                 190

Leu Gly Ile Met Leu Glu Pro Gly Gly Leu Ile Lys Asn Pro Ala Leu
        195                 200                 205

Ser Thr Ala Leu Glu Val Ala Pro Glu Val Pro Leu Ala Lys Lys Pro
210                 215                 220

Ser Pro Lys Gly Ile Asn Pro Val Met Leu Leu Pro Lys Lys Ser Lys
225                 230                 235                 240

Ala Gly Thr Arg Pro Phe Val His Tyr Pro Gly Ser Leu Thr Thr Pro
                245                 250                 255

Pro Cys Ser Glu Gly Val Asp Trp Val Phe Met Gln Pro Ile Lys
            260                 265                 270

Val Pro Asp Ser Gln Ile Leu Asp Phe Met Arg Phe Val Gly Asp Asn
        275                 280                 285

Lys Thr Tyr Ala Thr Asn Thr Arg Pro Leu Gln Leu Leu Asn Ser Arg
        290                 295                 300

Leu Val Glu Tyr Glu Leu
305                 310

<210> SEQ ID NO 82
<211> LENGTH: 1383
<212> TYPE: DNA
<213> ORGANISM: Chlamydomonas reinhardtii

<400> SEQUENCE: 82
cttttgtaga cccacttgtc agtgggcact gcccctagaa gcggcttctt gaccagagaa    60
gatgcgctca gccgttctac aacgcggcca ggcgcggcga gtgtcttgcc gggttcgggc   120
ggatggttcg ggcgtggatt cgctgccctc gaccagcgcc agcagcagcg cacgccctct   180
cattgatcgc cgtcagctcc tgaccggtgc tgctgcgtcg gtcataacct tcgttggctg   240
cccttgcccc ctgtgcaagc ctggggaggc aaaggccgca gcttggaact atggcgaagt   300
tgcgggtccg ccaacctgga agggtgtgtg tgcgacgggc aagcgccagt cgcccatcaa   360
catcccgttg aacacatcgg cgccgaaggt cgacgcggag atgggcgaat cgatttcgc   420
ctacggcagc ttcgagaagt gcgacgtgct gaacacggga cacggcacca tgcaggtgaa   480
cttccccgct ggcaacctgg cgttcattgg caacatggag ctggagctgc tgcagttcca   540
cttccacgcg ccctcggagc acgccatgga tggccgccgt tacgccatgg aggcgcatct   600
ggtgcacaag aataaaagca ccggcaacct agctgtgctg gcattatgc tggagcccgg   660
cggcctgatc aagaacccgg cgctgtccac tgctctggag gtggcgcccg aggtgcccct   720
ggccaagaag ccctcgccca agggcatcaa ccccgtcatg ctgctgccca agaagagcaa   780
ggccgggaca cggccgttcg tgcactaccc tggctcgctt accacgcccc cgtgttcgga   840
```

```
gggggtggac tggtttgtgt tcatgcagcc catcaaggtg cccgacagcc agatcctgga    900
cttcatgcgc ttcgtgggcg acaacaagac atacgccacc aacacgcggc cactgcagct    960
gctcaacagc cgcctggtcg aatacgagct gtgagcggac acgagtgtgc tagggtcagt   1020
gagcagcgtg tgaacatgaa gattacaagt ttgctgacag agagcgggcg gagtgcccat   1080
gcatcgcatc gtaacagccc gcgaagtacg acttaacatg acataaaagt gcaatgcgca   1140
tattgactgg tttggcccac ggtggggaag gcgtacgcgc ggttccatca agcagccttt   1200
ggggaggcat cgccttgcac gcacttgccg tatgtaggcg tgctggtgaa tgaggtatgg   1260
ggcgagagac ccgcgaacta aacttaagta gattacccat gtatccttta tttggcttgc   1320
gtgccctctc aattggggca ccgatgcagg ggctggaagg ccccgtgtaa cacatgacac   1380
tca                                                                 1383
```

<210> SEQ ID NO 83
<211> LENGTH: 310
<212> TYPE: PRT
<213> ORGANISM: Chlamydomonas reinhardtii

<400> SEQUENCE: 83

```
Met Arg Ser Ala Val Leu Gln Arg Gly Gln Ala Arg Arg Val Ser Cys
1               5                   10                  15

Arg Val Arg Ala Asp Gly Ser Gly Val Asp Ser Leu Pro Ser Thr Ser
            20                  25                  30

Ala Ser Ser Ser Ala Arg Pro Leu Ile Asp Arg Arg Gln Leu Leu Thr
        35                  40                  45

Gly Ala Ala Ala Ser Val Ile Thr Phe Val Gly Cys Pro Cys Pro Leu
    50                  55                  60

Cys Lys Pro Gly Glu Ala Lys Ala Ala Trp Asn Tyr Gly Glu Val
65                  70                  75                  80

Ala Gly Pro Pro Thr Trp Lys Gly Val Cys Ala Thr Gly Lys Arg Gln
                85                  90                  95

Ser Pro Ile Asn Ile Pro Leu Asn Thr Ser Ala Pro Lys Val Asp Ala
            100                 105                 110

Glu Met Gly Glu Phe Asp Phe Ala Tyr Gly Ser Phe Glu Lys Cys Asp
        115                 120                 125

Val Leu Asn Thr Gly His Gly Thr Met Gln Val Asn Phe Pro Ala Gly
    130                 135                 140

Asn Leu Ala Phe Ile Gly Asn Met Glu Leu Glu Leu Gln Phe His
145                 150                 155                 160

Phe His Ala Pro Ser Glu His Ala Met Asp Gly Arg Arg Tyr Ala Met
                165                 170                 175

Glu Ala His Leu Val His Lys Asn Lys Ser Thr Gly Asn Leu Ala Val
            180                 185                 190

Leu Gly Ile Met Leu Glu Pro Gly Gly Leu Ile Lys Asn Pro Ala Leu
        195                 200                 205

Ser Thr Ala Leu Glu Val Ala Pro Glu Val Pro Leu Ala Lys Lys Pro
    210                 215                 220

Ser Pro Lys Gly Ile Asn Pro Val Met Leu Leu Pro Lys Lys Ser Lys
225                 230                 235                 240

Ala Gly Thr Arg Pro Phe Val His Tyr Pro Gly Ser Leu Thr Thr Pro
                245                 250                 255

Pro Cys Ser Glu Gly Val Asp Trp Phe Val Phe Met Gln Pro Ile Lys
            260                 265                 270

Val Pro Asp Ser Gln Ile Leu Asp Phe Met Arg Phe Val Gly Asp Asn
```

```
                275              280              285
Lys Thr Tyr Ala Thr Asn Thr Arg Pro Leu Gln Leu Leu Asn Ser Arg
            290              295              300

Leu Val Glu Tyr Glu Leu
305              310

<210> SEQ ID NO 84
<211> LENGTH: 1244
<212> TYPE: DNA
<213> ORGANISM: Arabidopsis thaliana

<400> SEQUENCE: 84
caaaattcat gtgttagttc ttcttcttta caaaattgag tttaaactgt tttattacta      60
atccaaatga ggaatcactt tgcactatta atagaaaata atacacaacc aaacatctaa     120
aagatactat aatagtagag atcaaagacc tgagcaaaaa ctgaaagaaa aaaaaaaaa     180 aaaaaaaaga cttctcctca aaatggcgt ttacactagg tggaagagct cgtcgtctag     240
tctctgcaac atcagttcat caaaatggtt gcttacacaa actgcaacaa attggatcgg     300
atcggtttca gcttggtgaa gcaaaagcaa taagattact acccaggtga taagataaag     360
tttggtcttt atagttcttt aaaaaaaaaa gtgaatcaaa gaataaagac agagattact     420 ctgtttttt gtatcatagg agaacaaaca tggttcaaga attaggaatc agggaagaat     480
ttatggatct aaacagagaa acagagacaa gttatgattt tctggatgaa atgagacaca     540
gatttctgaa attcaagaga caaaagtatc taccggagat agaaaagttt aaagctttgg     600
ccatagctca atcaccaaag gtaatggtga taggatgtgc agattcaagg gtatgtccat     660
cttatgtact aggatttcaa cctggtgaag cttttactat ccgaaatgtc gccaatctcg     720
ttaccccggt tcagaatgga ccaacagaaa ccaactcggc tcttgagttt gcggtcacca     780
ctcttcaggt tgagaacatt atagttatgg gtcatagcaa ttgtggagga attgcagcac     840
ttatgagtca tcaaaaccac caagggcaac actctagttt agtagaaagg tgggttatga     900
atgggaaagc cgctaagtta agaacacaat tagcttcatc acatttatcc tttgatgaac     960
aatgcagaaa ctgtgagaag gaatctataa aggattctgt gatgaatttg ataacttatt    1020
catggataag agatagagta aagagaggtg aagtcaagat tcatggatgt tattacaatt    1080
tgtcagattg tagtcttgag aagtggagat taagttcaga caagactaac tatggattct    1140
atatttcaga cagagagata tggagttgag taaatattga caatcctca gttctaatat    1200 tcagatgtat ctttgtacat acgaaatgat atttacacaa ttgg                      1244

<210> SEQ ID NO 85
<211> LENGTH: 286
<212> TYPE: PRT
<213> ORGANISM: Arabidopsis thaliana

<400> SEQUENCE: 85

Met Ala Phe Thr Leu Gly Gly Arg Ala Arg Arg Leu Val Ser Ala Thr
1               5                   10                  15

Ser Val His Gln Asn Gly Cys Leu His Lys Leu Gln Gln Ile Gly Ser
            20                  25                  30

Asp Arg Phe Gln Leu Gly Glu Ala Lys Ala Ile Arg Leu Leu Pro Arg
        35                  40                  45

Arg Thr Asn Met Val Gln Glu Leu Gly Ile Arg Glu Glu Phe Met Asp
    50                  55                  60

Leu Asn Arg Glu Thr Glu Thr Ser Tyr Asp Phe Leu Asp Glu Met Arg
65                  70                  75                  80
```

```
His Arg Phe Leu Lys Phe Lys Arg Gln Lys Tyr Leu Pro Glu Ile Glu
                85                  90                  95

Lys Phe Lys Ala Leu Ala Ile Ala Gln Ser Pro Lys Val Met Val Ile
            100                 105                 110

Gly Cys Ala Asp Ser Arg Val Cys Pro Ser Tyr Val Leu Gly Phe Gln
            115                 120                 125

Pro Gly Glu Ala Phe Thr Ile Arg Asn Val Ala Asn Leu Val Thr Pro
130                 135                 140

Val Gln Asn Gly Pro Thr Glu Thr Asn Ser Ala Leu Glu Phe Ala Val
145                 150                 155                 160

Thr Thr Leu Gln Val Glu Asn Ile Ile Val Met Gly His Ser Asn Cys
                165                 170                 175

Gly Gly Ile Ala Ala Leu Met Ser His Gln Asn His Gln Gly Gln His
            180                 185                 190

Ser Arg Trp Val Met Asn Gly Lys Ala Ala Lys Leu Arg Thr Gln Leu
            195                 200                 205

Ala Ser Ser His Leu Ser Phe Asp Glu Gln Cys Arg Asn Cys Glu Lys
210                 215                 220

Glu Ser Ile Lys Asp Ser Val Met Asn Leu Ile Thr Tyr Ser Trp Ile
225                 230                 235                 240

Arg Asp Arg Val Lys Arg Gly Glu Val Lys Ile His Gly Cys Tyr Tyr
                245                 250                 255

Asn Leu Ser Asp Cys Ser Leu Glu Lys Trp Arg Leu Ser Ser Asp Lys
            260                 265                 270

Thr Asn Tyr Gly Phe Tyr Ile Ser Asp Arg Glu Ile Trp Ser
            275                 280                 285

<210> SEQ ID NO 86
<211> LENGTH: 801
<212> TYPE: DNA
<213> ORGANISM: Medicago truncatula

<400> SEQUENCE: 86
atggcaaatc aatcatctga gctagccatt gaacaactga agaagcttct cagagagaag      60
gaggaactta tggggtggc cacagcaaaa attgagcagc ttatagttga attacaggga     120
tgtcatccaa atccaattga acctgctgat cagagaatca ttgatggttt tacgtacttc     180
aagctcaaca atttcaacaa gaacccggaa ctgtatgatc gacttgctaa aggccagtct     240
cccaagttta tggtatttgc ttgttccgac tctcgagtga gtccctctgt tatcctgaac     300
tttcaacctg gtgaagcttt catggttcga acattgctaa acatggtccc tccatttaat     360
cagttaagat acagtggagt tggtgcaacc cttgagtatg ctattacagc tctaaaggtg     420
gagaacatct tggttattgg acatagtcgc tgcggcggaa tctcaaggct tatgaatcat     480
ccagaggatg ttctgctccc atatgacttc atagatgatt gggtgaaaat tggtttatct     540
tccaaagtca aggttttgaa agaacatgaa cgctgtgatt tcaagaaaca atgcaaattc     600
tgtgaaatgg aatcagtgaa taactcatta gtgaacctga gacatatcc atatgttgat     660 agagaaataa ggaacaagaa cttagctctg ttgggaggtt actatgattt tgtgagtgga     720
gaattcaagc tttggaagta taagaatcat gtcactgaac tgttaccat ccctctaaaa     780 ggccttgaca tgaccatcta a                                               801

<210> SEQ ID NO 87
<211> LENGTH: 266
<212> TYPE: PRT
```

<213> ORGANISM: Medicago truncatula

<400> SEQUENCE: 87

```
Met Ala Asn Gln Ser Ser Glu Leu Ala Ile Glu Gln Leu Lys Lys Leu
1               5                   10                  15
Leu Arg Glu Lys Glu Leu Asn Gly Val Ala Thr Ala Lys Ile Glu
            20                  25                  30
Gln Leu Ile Val Glu Leu Gln Gly Cys His Pro Asn Pro Ile Glu Pro
        35                  40                  45
Ala Asp Gln Arg Ile Ile Asp Gly Phe Thr Tyr Phe Lys Leu Asn Asn
    50                  55                  60
Phe Asn Lys Asn Pro Glu Leu Tyr Asp Arg Leu Ala Lys Gly Gln Ser
65                  70                  75                  80
Pro Lys Phe Met Val Phe Ala Cys Ser Asp Ser Arg Val Ser Pro Ser
                85                  90                  95
Val Ile Leu Asn Phe Gln Pro Gly Glu Ala Phe Met Val Arg Asn Ile
            100                 105                 110
Ala Asn Met Val Pro Pro Phe Asn Gln Leu Arg Tyr Ser Gly Val Gly
        115                 120                 125
Ala Thr Leu Glu Tyr Ala Ile Thr Ala Leu Lys Val Glu Asn Ile Leu
    130                 135                 140
Val Ile Gly His Ser Arg Cys Gly Gly Ile Ser Arg Leu Met Asn His
145                 150                 155                 160
Pro Glu Asp Gly Ser Ala Pro Tyr Asp Phe Ile Asp Asp Trp Val Lys
                165                 170                 175
Ile Gly Leu Ser Ser Lys Val Lys Val Leu Lys Glu His Glu Arg Cys
            180                 185                 190
Asp Phe Lys Glu Gln Cys Lys Phe Cys Glu Met Glu Ser Val Asn Asn
        195                 200                 205
Ser Leu Val Asn Leu Lys Thr Tyr Pro Tyr Val Asp Arg Glu Ile Arg
    210                 215                 220
Asn Lys Asn Leu Ala Leu Leu Gly Gly Tyr Tyr Asp Phe Val Ser Gly
225                 230                 235                 240
Glu Phe Lys Leu Trp Lys Tyr Lys Asn His Val Thr Glu Pro Val Thr
                245                 250                 255
Ile Pro Leu Lys Gly Leu Asp Met Thr Ile
            260                 265
```

<210> SEQ ID NO 88
<211> LENGTH: 774
<212> TYPE: DNA
<213> ORGANISM: Medicago truncatula

<400> SEQUENCE: 88

```
atggcaaatc aatcatctga gctagccatt gaacaactga agaagcttct cagagagaaa      60
gaggaactta atgaggtggc cactgcaaaa attgaggaaa ttatagttga gttgcaggga     120
tgtcatccac aaccaattga tcctgctgag cagagaatca ttgatggttt tacttacttc     180
aagctcaaca atttcgacaa ggaccggaaa ttgtatgatc gacttgctaa aggacaatcc     240
cccaagttta tggtatttgc ttgttctgac tctagagtga gtccctctat tatcctgaac     300
tttcaacctg gagaagcttt catggtccga aacattgcta acatggtccc tccatttaat     360
cagttaagat acagtggagt tggtgcaacc cttgagtatg ctattacagc tctaaaggtg     420
gagaacatct tggttattgg acatagtcgc tgcggcggta tatcaaggct tatgagtcat     480
ccagaggatg gttctgctcc atatgacttc atagatgatt gggtgaaaat tggtttacct     540
```

| | | |
|---|---|---|
| tctaaagtca aggtcctgaa agaacataaa ttctgtgatt tcgagcaaca atgtgaattt | | 600 |
| tgtgaaatgg aatcagtgaa taactcatta gtgaaccttc agacatatcc atatgttgat | | 660 |
| gcagaaataa ggaacaagaa cttagcacta ttgggggggtt actatgactt tgtgagtgga | | 720 |
| gaattcaagt tttggaagta taagactcat attactgaac ccattacaat ctga | | 774 |

<210> SEQ ID NO 89
<211> LENGTH: 257
<212> TYPE: PRT
<213> ORGANISM: Medicago truncatula

<400> SEQUENCE: 89

```
Met Ala Asn Gln Ser Ser Glu Leu Ala Ile Glu Gln Leu Lys Lys Leu
1               5                   10                  15

Leu Arg Glu Lys Glu Leu Asn Glu Val Ala Thr Ala Lys Ile Glu
            20                  25                  30

Glu Ile Ile Val Glu Leu Gln Gly Cys His Pro Gln Pro Ile Asp Pro
        35                  40                  45

Ala Glu Gln Arg Ile Ile Asp Gly Phe Thr Tyr Phe Lys Leu Asn Asn
    50                  55                  60

Phe Asp Lys Asp Arg Lys Leu Tyr Asp Arg Leu Ala Lys Gly Gln Ser
65                  70                  75                  80

Pro Lys Phe Met Val Phe Ala Cys Ser Asp Ser Arg Val Ser Pro Ser
                85                  90                  95

Ile Ile Leu Asn Phe Gln Pro Gly Glu Ala Phe Met Val Arg Asn Ile
            100                 105                 110

Ala Asn Met Val Pro Pro Phe Asn Gln Leu Arg Tyr Ser Gly Val Gly
        115                 120                 125

Ala Thr Leu Glu Tyr Ala Ile Thr Ala Leu Lys Val Glu Asn Ile Leu
    130                 135                 140

Val Ile Gly His Ser Arg Cys Gly Gly Ile Ser Arg Leu Met Ser His
145                 150                 155                 160

Pro Glu Asp Gly Ser Ala Pro Tyr Asp Phe Ile Asp Asp Trp Val Lys
                165                 170                 175

Ile Gly Leu Pro Ser Lys Val Lys Val Leu Lys Glu His Lys Phe Cys
            180                 185                 190

Asp Phe Glu Gln Gln Cys Glu Phe Cys Glu Met Glu Ser Val Asn Asn
        195                 200                 205

Ser Leu Val Asn Leu Gln Thr Tyr Pro Tyr Val Asp Ala Glu Ile Arg
    210                 215                 220

Asn Lys Asn Leu Ala Leu Leu Gly Gly Tyr Tyr Asp Phe Val Ser Gly
225                 230                 235                 240

Glu Phe Lys Phe Trp Lys Tyr Lys Thr His Ile Thr Glu Pro Ile Thr
                245                 250                 255

Ile
```

<210> SEQ ID NO 90
<211> LENGTH: 1100
<212> TYPE: DNA
<213> ORGANISM: Arabidopsis thaliana

<400> SEQUENCE: 90

| | | |
|---|---|---|
| ttcttcgata aggattttac tctccagaga aagaaaaaaa aaacctcctc tgcttttgtg | | 60 |
| atcctttaag gaaaagacg aaatggcaac ggaatcgtac gaagccgcca ttaaggact | | 120 |
| caatgatctt ctcagtacga aagcggatct cggaaacgtc gccgccgcga agatcaaagc | | 180 |

```
gttgacggcg gagctaaagg agcttgactc aagcaattca gacgcaattg aacgaatcaa    240
gaccggtttt actcaattca aaaccgagaa atatttgaag aatagtactt tgttcaatca    300
tcttgccaag actcagaccc caaagtttct ggtgtttgct tgctctgatt ctcgagtttg    360
tccatctcac atcttgaatt tccaacctgg tgaggctttt gttgtcagaa acatagccaa    420
tatggttcca ccttttgacc agaagagaca ctctggagtt ggcgccgccg ttgaatacgc    480
agttgtacat ctcaaggtgg agaacatttt ggtgataggc catagctgct gtggtggtat    540
taagggactc atgtccattg aagatgatgc tgccccaact caaagtgact tcattgaaaa    600
ttgggtgaag ataggcgcat cagcgaggaa caagatcaag gaggaacata aagacttgag    660
ctacgatgat caatgcaaca agtgtgaaa ggaagctgtg aacgtatcgc ttggaaactt    720
gctttcgtac ccattcgtga gagctgaggt ggtgaagaac acacttgcaa taagaggagg    780
tcactacaat ttcgtcaaag gaacgtttga tctctgggag ctcgatttca agaccactcc    840
tgcttttgcc ttctcttaag aaagaaagct accggaacat ataaaactct tttgagataa    900
aaaaagacac tttgactcat cttttcttcat tctctcatgt tgatgattcc tctccaactt    960
ctttgatttc ttttttgttaa ttcaaaactt caactttgct gcttctattt caaaagctca   1020
aacaataaag ctgtaaccaa cgtttgaaac ttctatattt gtctaattga tgtttgaacg   1080
aagatttgaa ctttccttct                                               1100

<210> SEQ ID NO 91
<211> LENGTH: 280
<212> TYPE: PRT
<213> ORGANISM: Arabidopsis thaliana

<400> SEQUENCE: 91

Met Ala Pro Ala Phe Gly Lys Cys Phe Met Phe Cys Cys Ala Lys Thr
1               5                   10                  15

Ser Pro Glu Lys Asp Glu Met Ala Thr Glu Ser Tyr Glu Ala Ala Ile
            20                  25                  30

Lys Gly Leu Asn Asp Leu Leu Ser Thr Lys Ala Asp Leu Gly Asn Val
        35                  40                  45

Ala Ala Ala Lys Ile Lys Ala Leu Thr Ala Glu Leu Lys Glu Leu Asp
    50                  55                  60

Ser Ser Asn Ser Asp Ala Ile Glu Arg Ile Lys Thr Gly Phe Thr Gln
65                  70                  75                  80

Phe Lys Thr Glu Lys Tyr Leu Lys Asn Ser Thr Leu Phe Asn His Leu
                85                  90                  95

Ala Lys Thr Gln Thr Pro Lys Phe Leu Val Phe Ala Cys Ser Asp Ser
            100                 105                 110

Arg Val Cys Pro Ser His Ile Leu Asn Phe Gln Pro Gly Glu Ala Phe
        115                 120                 125

Val Val Arg Asn Ile Ala Asn Met Val Pro Pro Phe Asp Gln Lys Arg
    130                 135                 140

His Ser Gly Val Gly Ala Ala Val Glu Tyr Ala Val His Leu Lys
145                 150                 155                 160

Val Glu Asn Ile Leu Val Ile Gly His Ser Cys Gly Gly Ile Lys
                165                 170                 175

Gly Leu Met Ser Ile Glu Asp Asp Ala Ala Pro Thr Gln Ser Asp Phe
            180                 185                 190

Ile Glu Asn Trp Val Lys Ile Gly Ala Ser Ala Arg Asn Lys Ile Lys
        195                 200                 205
```

```
Glu Glu His Lys Asp Leu Ser Tyr Asp Asp Gln Cys Asn Lys Cys Glu
        210                 215                 220

Lys Glu Ala Val Asn Val Ser Leu Gly Asn Leu Leu Ser Tyr Pro Phe
225                 230                 235                 240

Val Arg Ala Glu Val Lys Asn Thr Leu Ala Ile Arg Gly Gly His
            245                 250                 255

Tyr Asn Phe Val Lys Gly Thr Phe Asp Leu Trp Glu Leu Asp Phe Lys
            260                 265                 270

Thr Thr Pro Ala Phe Ala Phe Ser
            275                 280

<210> SEQ ID NO 92
<211> LENGTH: 1748
<212> TYPE: DNA
<213> ORGANISM: Oryza sativa

<400> SEQUENCE: 92
```

| | | | | |
|---|---|---|---|---|
| atcattttc taaaaagaa aatcgctgcc tcgacctcgg tttctccgtc gcatcgccgt | 60 |
| cgtgctcgct gcctcgctct accccgtaaa atcccccccg gccgttgccg cgcgaagctt | 120 |
| ttccctccca caaatgcccg agaccccgac cacgacgacc accacccgcg cgagcaccgg | 180 |
| gacatcctca catggctcct agtctgctcc gccccgcctc ccgtgcctc aacctcgcgc | 240 |
| cccccaccgc cgacggcccc ggccggagcc gctccgctgt gacgatcggt ggttcgaggc | 300 |
| cgctcagcgt ttccctgcgt gtgggaggat ctagccggag ggactttccg tgtaccacaa | 360 |
| tggcctcaag agatcattct ggtttgactc gacagctttt agattttcaa catggtacag | 420 |
| tagatgagat agatggggaa catgatccat tcatggagtt gaaagcaagg ttcatggact | 480 |
| tcaagcacag gaattgtgtg gataatattt ctaactatca aaatcttgct cagcagcaaa | 540 |
| caccaaagtt catggtggtt gcttgtgctg attctagggt atgtccttca agtgttttgg | 600 |
| ggtttcagcc cggggaagca tttactgtcc gtaatatagc aaatttggta ccaccatatc | 660 |
| agcatggtgc ttcagagact agcgctgcac tggagttcgc tgtcaacaca ctagaggtag | 720 |
| agaatgtatt agtggtaggt cacagccgtt gtggtggtat ccaagcacta atgagtatga | 780 |
| aaagtaagca agatgattcg caatctagaa gctttatcag agattgggtg tcaattgcaa | 840 |
| agagtgcaag gttaagtacg gaagcagcag ctggaaattt gaattttgaa ttacagtgca | 900 |
| aacattgtga aaaggaatca attaatagct cactgttgaa cttgttaaca taccccttgga | 960 |
| tagagaaaag ggtgaatgaa ggaactttga gccttcatgg gggctattac aatttttattg | 1020 |
| attgcacatt cgagaagtgg aaattagtat accgccaagg gttggaaggt ggaagcaagt | 1080 |
| atgccataaa gaataggact acctggtctt gatcaagagg cattgcttac ctgggtaaat | 1140 |
| ttcactctgc cccctgcagt ttagcatggt tttgctttgc cactgtgctg tccattttca | 1200 |
| ttgcactttg ctccattgtg gtattgacat tctgcaagaa cgagtcccag tatcaagtca | 1260 |
| ctgttacggt gttgttggta ccattgatta acataacact tgacggccat acttggtcat | 1320 |
| gttgtatgtt atcagcttca cagaggtaca tgtggcactt taacagttat ttgatacagt | 1380 |
| gactaggctg cagttgagcg aaaccacaat ggagtgaagt gcaacagaaa tgaacattat | 1440 |
| ggcagcaaag tgaaagtttg tcaaactgcc ggggacaaag tgaattttgt ccaaatatcc | 1500 |
| ctgtattatt ttctgcttag aagcatcata ttaattcaat aagctgcaaa ctcatattca | 1560 |
| taccaaaaac atgtacgatc ttgccacatt tggcaaatta ttgtgttgta tcatttatcg | 1620 |
| tgtaattgca aaaataagat agagcttgt aatctggtgt gccgggcagc tgctgtatca | 1680 |
| atataataat tctcaaatag ttgaaacaat gttgtgttta aagttcaatc tttactgttc | 1740 | ttttgtcg                                                                1748

<210> SEQ ID NO 93
<211> LENGTH: 306
<212> TYPE: PRT
<213> ORGANISM: Oryza sativa

<400> SEQUENCE: 93

Met Ala Pro Ser Leu Leu Arg Pro Ala Ser Pro Cys Leu Asn Leu Ala
1               5                   10                  15

Pro Pro Thr Ala Asp Gly Pro Gly Arg Ser Arg Ser Ala Val Thr Ile
            20                  25                  30

Gly Gly Ser Arg Pro Leu Ser Val Ser Leu Arg Val Gly Gly Ser Ser
        35                  40                  45

Arg Arg Asp Phe Pro Cys Thr Thr Met Ala Ser Arg Asp His Ser Gly
    50                  55                  60

Leu Thr Arg Gln Leu Leu Asp Phe Gln His Gly Thr Val Asp Glu Ile
65                  70                  75                  80

Asp Gly Glu His Asp Pro Phe Met Glu Leu Lys Ala Arg Phe Met Asp
                85                  90                  95

Phe Lys His Arg Asn Cys Val Asp Asn Ile Ser Asn Tyr Gln Asn Leu
            100                 105                 110

Ala Gln Gln Thr Pro Lys Phe Met Val Val Ala Cys Ala Asp Ser
        115                 120                 125

Arg Val Cys Pro Ser Ser Val Leu Gly Phe Gln Pro Gly Glu Ala Phe
    130                 135                 140

Thr Val Arg Asn Ile Ala Asn Leu Val Pro Pro Tyr Gln His Gly Ala
145                 150                 155                 160

Ser Glu Thr Ser Ala Ala Leu Glu Phe Ala Val Asn Thr Leu Glu Val
                165                 170                 175

Glu Asn Val Leu Val Val Gly His Ser Arg Cys Gly Gly Ile Gln Ala
            180                 185                 190

Leu Met Ser Met Lys Ser Lys Gln Asp Asp Ser Gln Ser Arg Ser Phe
        195                 200                 205

Ile Arg Asp Trp Val Ser Ile Ala Lys Ser Ala Arg Leu Ser Thr Glu
    210                 215                 220

Ala Ala Ala Gly Asn Leu Asn Phe Glu Leu Gln Cys Lys His Cys Glu
225                 230                 235                 240

Lys Glu Ser Ile Asn Ser Ser Leu Leu Asn Leu Leu Thr Tyr Pro Trp
                245                 250                 255

Ile Glu Lys Arg Val Asn Glu Gly Thr Leu Ser Leu His Gly Gly Tyr
            260                 265                 270

Tyr Asn Phe Ile Asp Cys Thr Phe Glu Lys Trp Lys Leu Val Tyr Arg
        275                 280                 285

Gln Gly Leu Glu Gly Gly Ser Lys Tyr Ala Ile Lys Asn Arg Thr Thr
    290                 295                 300

Trp Ser
305

<210> SEQ ID NO 94
<211> LENGTH: 1997
<212> TYPE: DNA
<213> ORGANISM: Oryza sativa

<400> SEQUENCE: 94
agcagcaatg gtgtcctccc atgcagccat cgtcttcttc ctcgtcgccg cgtcgtcgct     60

```
cctctcatac ggtgaggcgg cgccgaagat gacggcggtg gcggcggact acgggtaccc      120
ggcggactac gggtacgcgg cggggagcaa gctggggccg gagaactggg ggaagctgag      180
cccggcgtac aagctgtgcg gcgacggcaa gaagcagtcg cccatcgaca tcgtcaccaa      240
gcaggccatc tccaacccca acctcgactc actcaaccgc acctacaccg cctccgacgg      300
caccctcgtc aacaacggca aggacatctt ggcaagccat ctaacctaac tagctagacc      360
tacctacatt gggattttt tgaatttgt ttttattttt aattctaaaa acaaacattt       420
ctcattcata ttttcaatat ctgaaccttt tgaccacggg ttggcgtggc aaaataatac      480
tgccatgtca gtctgaatac acggtgtggt agaaataaat tttcatgctg gttttaggtg      540
acgtgatatg ttattttacc atggtaggca ggttggcgtg gccaaaagat tcagattttg      600
gaaataaatt taagaaaggt ttgttttga ataaaaaaa tttagaaaag ttcaagaaaa        660
aaataaaaaa aaattctcca ttgggaaaac tctattcatc ccttcaagag atatcccctt      720 attttttgcat gtcacttaaa aagtcattaa aaattttgaa aaaatttagt agcatatgta     780
atatgtcact tcacaataca tattcaaatt caacttgtac atatagaaac aaaaataaca     840
aatttgacta tgaatagaac gcataattca cggttaaatt tattattttt gtttcgaatt     900
gtataagaat tttaacttgc gtgtctgtga aagatatat catatattga tctatcttga      960 tgatttttt tttaattttt cgataacgtt ttgaacgtca tgcacaaaac gagaggatgt      1020
cccccgaggg acaaaaatcc acttcccctg cattgttgca ttatccaatg gagctagcta     1080
gcagagattt gattgattgg catatcgaac catggcgcag atggagttcg agccagacaa     1140
ggtggggacg gtgacggtga acggcaaggt gtacagcttc aggcgggtgc actggcacgc     1200
gccgtcggag cacaccatca acggggagaa gcacccgctg gagctccaga tggtgcacgc     1260
tgccgccgac ggcagcctcg ccgtcatcgc catcctctac aagtacggcg ccccggactc     1320
cttctacttc cagctcaaga ggaagctcgc cgagctcgcc gccgacggct gcagcttcgg     1380
cgaggagaac gcccaggtcg ccctcggcct cgtccacctc cgctcgctgc agaagcggac     1440
ggggagctac ttccgctacg ccggctcgct gacggcgccg ccgtgcaccg aggacgtctt     1500
ctggagcgtg ctcggcaaga tcaggcagat cagccaggag caggtcgccc tcatcaccgc     1560
gctgctcccc gccggcggcg cgaggccgac gcagccgctc aacggccgca ccgtgcagtt     1620
ctacaacccg cccaacagca ccatctcctt caaggtctag tagccccagg cccaatgggc     1680
tttggcccat ttatatatac tatatggggtt gcattgggct gcacaggccc tgaaattgat     1740
tgaaggatct caatttttga gattttctt gtttctggag aaaaaaaatt catgtactgt      1800
tgcttagata ggcccttatc tatagtatag taacatatgt atatgaattt aattttagga     1860
tttggaaaca tggttgctta tcctcacttg gaattaggct tttaaaagtc gagcacatgt     1920
gcacttgttt tcattcaaa cattagcctg tcgcatagat agtctttttc ttaataatta      1980
gagctgattt gaatttt                                                    1997
```

<210> SEQ ID NO 95
<211> LENGTH: 182
<212> TYPE: PRT
<213> ORGANISM: Oryza sativa

<400> SEQUENCE: 95

Met Ala Gln Met Glu Phe Glu Pro Asp Lys Val Gly Thr Val Thr Val
1               5                   10                  15

Asn Gly Lys Val Tyr Ser Phe Arg Arg Val His Trp His Ala Pro Ser
            20                  25                  30

Glu His Thr Ile Asn Gly Glu Lys His Pro Leu Glu Leu Gln Met Val
              35                  40                  45

His Ala Ala Ala Asp Gly Ser Leu Ala Val Ile Ala Ile Leu Tyr Lys
 50                  55                  60

Tyr Gly Ala Pro Asp Ser Phe Tyr Phe Gln Leu Lys Arg Lys Leu Ala
 65                  70                  75                  80

Glu Leu Ala Ala Asp Gly Cys Ser Phe Gly Glu Glu Asn Ala Gln Val
                 85                  90                  95

Ala Leu Gly Leu Val His Leu Arg Ser Leu Gln Lys Arg Thr Gly Ser
             100                 105                 110

Tyr Phe Arg Tyr Ala Gly Ser Leu Thr Ala Pro Pro Cys Thr Glu Asp
             115                 120                 125

Val Phe Trp Ser Val Leu Gly Lys Ile Arg Gln Ile Ser Gln Glu Gln
         130                 135                 140

Val Ala Leu Ile Thr Ala Leu Leu Pro Ala Gly Gly Ala Arg Pro Thr
145                 150                 155                 160

Gln Pro Leu Asn Gly Arg Thr Val Gln Phe Tyr Asn Pro Pro Asn Ser
                 165                 170                 175

Thr Ile Ser Phe Lys Val
             180

<210> SEQ ID NO 96
<211> LENGTH: 1497
<212> TYPE: DNA
    <213> ORGANISM: Dunaliella salina

<400> SEQUENCE: 96
atggcgcgcc tcgcgctgtt aggcgccgcg ctactatgcg ccctggcggt ctcgacgcaa      60
gggtcacctg aggggcatgg cactaagact gagatgatgg gcgctggaag gctgctccag     120
caagggcctc ataccaacag cgaccccccc tacaactaca actgccatgg ctttgactgg     180
gcggcttcca gttcaagtgc cgaaattact gagctgtgcg acagcccagc atcaagtttt     240
ccagtggccg actgtgatgg ggacatgcag agcccaatca acatcgtgac gagcgagctt     300
gcagacccga ctgaccgcag cggcgtgtct ggcatcaacc tgagaggcat gggctcctcg     360
gattttgtgc tgcgaagcaa cgtcaagttg aacatcgagc aagacatgaa gatcagctgg     420
gacgcgccca cgtccggcaa cctgcccacc atcatgatcg acggcacaga gcagcgattc     480
cagcccatcc agctttactt ccaccacttt gccagtgagc acaccatcaa tgggcagctc     540
taccctcttg atgcccacct tgtcatggct tcccttgatg accccaacca gctggctgtc     600
atcggcacca tgtataagta tggcaatggc gatgacttcc tggcgcgcct gttcggcaag     660
gttgaggatg cacttgagga gcgtgatgat gtgtcttacg gcagcaaaga agtgccaatt     720
gacatggaga tcagcccgaa agaccatgtc ctgccccagt cctccctgga gtacgctggc     780
tacgacggca gcctgaccac ccctccctgc agtgaggtgg tgaagtggca cgtgttcacc     840
agccccagga ccatctccat cgaccagctg aagacatttg agagggtctc cttcaacgcg     900
caccccaatg aagccatccc caccaacaac cgcgtgatcc agcctctcgg caccagggct     960
gtctaccgct acgaggctac agccatggat gactccggcg atggcaccgg caacgctgac    1020
gagctgtctt ctcccacgac cgtcacagca acctacgaca tcatggtctc aggcaccgct    1080
agcagcctgg cggacatgtt caacaatgga gctcgtctgg acaatggcgg ttttggtcct    1140
gatgaccagg cagaggctga cctgctgcgc cagatccagc ggcgtgcacg tgcaaactct    1200
ggtgctgaag cgctgaggt ggtccgcatg atgaagttca cagctgccct tggccgtcgc    1260

```
aggctcaacc agcagggcgc ggcagcagag atggacatca ggtactactt tgagggtagc    1320
accgatcaag aagaggctac atcagctgtg aatggcatga acccctcttc gctgggcagc    1380
tccagcagtg gcctgactga tgtgcagcag actgaggtaa cctcttctgc cagcagcctg    1440
cgtgctggcc tgggcttggt tgtggcagcc ttcttcggtg ctgcattggc actgtga       1497
```

<210> SEQ ID NO 97
<211> LENGTH: 498
<212> TYPE: PRT
<213> ORGANISM: Dunaliella salina

<400> SEQUENCE: 97

| Met | Ala | Arg | Leu | Ala | Leu | Leu | Gly | Ala | Ala | Leu | Leu | Cys | Ala | Leu | Ala |
|---|---|---|---|---|---|---|---|---|---|---|---|---|---|---|---|
| 1 | | | | 5 | | | | | 10 | | | | | 15 | |

| Val | Ser | Thr | Gln | Gly | Ser | Pro | Glu | Gly | His | Gly | Thr | Lys | Thr | Glu | Met |
| | | | 20 | | | | | 25 | | | | | 30 | | |

| Met | Gly | Ala | Gly | Arg | Leu | Leu | Gln | Gln | Gly | Pro | His | Thr | Asn | Ser | Asp |
| | | | 35 | | | | | 40 | | | | | 45 | | |

| Pro | Pro | Tyr | Asn | Tyr | Asn | Cys | His | Gly | Phe | Asp | Trp | Ala | Ala | Ser | Ser |
| | 50 | | | | | 55 | | | | | 60 | | | | |

| Ser | Ser | Ala | Glu | Ile | Thr | Glu | Leu | Cys | Asp | Ser | Pro | Ala | Ser | Ser | Phe |
| 65 | | | | | 70 | | | | | 75 | | | | | 80 |

| Pro | Val | Ala | Asp | Cys | Asp | Gly | Asp | Met | Gln | Ser | Pro | Ile | Asn | Ile | Val |
| | | | | 85 | | | | | 90 | | | | | 95 | |

| Thr | Ser | Glu | Leu | Ala | Asp | Pro | Thr | Asp | Arg | Ser | Gly | Val | Ser | Gly | Ile |
| | | | 100 | | | | | 105 | | | | | 110 | | |

| Asn | Leu | Arg | Gly | Met | Gly | Ser | Ser | Asp | Phe | Val | Leu | Arg | Ser | Asn | Val |
| | | | 115 | | | | | 120 | | | | | 125 | | |

| Lys | Leu | Asn | Ile | Glu | Gln | Asp | Met | Lys | Ile | Ser | Trp | Asp | Ala | Pro | Thr |
| | 130 | | | | | 135 | | | | | 140 | | | | |

| Ser | Gly | Asn | Leu | Pro | Thr | Ile | Met | Ile | Asp | Gly | Thr | Glu | Gln | Arg | Phe |
| 145 | | | | | 150 | | | | | 155 | | | | | 160 |

| Gln | Pro | Ile | Gln | Leu | Tyr | Phe | His | His | Phe | Ala | Ser | Glu | His | Thr | Ile |
| | | | | 165 | | | | | 170 | | | | | 175 | |

| Asn | Gly | Gln | Leu | Tyr | Pro | Leu | Asp | Ala | His | Leu | Val | Met | Ala | Ser | Leu |
| | | | 180 | | | | | 185 | | | | | 190 | | |

| Asp | Asp | Pro | Asn | Gln | Leu | Ala | Val | Ile | Gly | Thr | Met | Tyr | Lys | Tyr | Gly |
| | | | 195 | | | | | 200 | | | | | 205 | | |

| Asn | Gly | Asp | Asp | Phe | Leu | Ala | Arg | Leu | Phe | Gly | Lys | Val | Glu | Asp | Ala |
| | 210 | | | | | 215 | | | | | 220 | | | | |

| Leu | Glu | Glu | Arg | Asp | Asp | Val | Ser | Tyr | Gly | Ser | Lys | Glu | Val | Pro | Ile |
| 225 | | | | | 230 | | | | | 235 | | | | | 240 |

| Asp | Met | Glu | Ile | Ser | Pro | Lys | Asp | His | Val | Leu | Pro | Gln | Ser | Ser | Leu |
| | | | | 245 | | | | | 250 | | | | | 255 | |

| Glu | Tyr | Ala | Gly | Tyr | Asp | Gly | Ser | Leu | Thr | Thr | Pro | Cys | Ser | Glu |
| | | | 260 | | | | | 265 | | | | | 270 | |

| Val | Val | Lys | Trp | His | Val | Phe | Thr | Ser | Pro | Arg | Thr | Ile | Ser | Ile | Asp |
| | | | 275 | | | | | 280 | | | | | 285 | | |

| Gln | Leu | Lys | Thr | Phe | Glu | Arg | Val | Ser | Phe | Asn | Ala | His | Pro | Asn | Glu |
| | 290 | | | | | 295 | | | | | 300 | | | | |

| Ala | Ile | Pro | Thr | Asn | Asn | Arg | Val | Ile | Gln | Pro | Leu | Gly | Thr | Arg | Ala |
| 305 | | | | | 310 | | | | | 315 | | | | | 320 |

| Val | Tyr | Arg | Tyr | Glu | Ala | Thr | Ala | Met | Asp | Asp | Ser | Gly | Asp | Gly | Thr |
| | | | | 325 | | | | | 330 | | | | | 335 | |

```
Gly Asn Ala Asp Glu Leu Ser Ser Pro Thr Thr Val Thr Ala Thr Tyr
            340                 345                 350

Asp Ile Met Val Ser Gly Thr Ala Ser Ser Leu Ala Asp Met Phe Asn
            355                 360                 365

Asn Gly Ala Arg Leu Asp Asn Gly Gly Phe Gly Pro Asp Asp Gln Ala
        370                 375                 380

Glu Ala Asp Leu Leu Arg Gln Ile Gln Arg Arg Ala Arg Ala Asn Ser
385                 390                 395                 400

Gly Ala Glu Gly Ala Glu Val Val Arg Met Met Lys Phe Thr Ala Ala
                405                 410                 415

Leu Gly Arg Arg Arg Leu Asn Gln Gln Gly Ala Ala Glu Met Asp
            420                 425                 430

Ile Arg Tyr Tyr Phe Glu Gly Ser Thr Asp Gln Glu Glu Ala Thr Ser
            435                 440                 445

Ala Val Asn Gly Met Asn Pro Ser Ser Leu Gly Ser Ser Ser Ser Gly
        450                 455                 460

Leu Thr Asp Val Gln Gln Thr Glu Val Thr Ser Ser Ala Ser Ser Leu
465                 470                 475                 480

Arg Ala Gly Leu Gly Leu Val Val Ala Ala Phe Phe Gly Ala Ala Leu
                485                 490                 495

Ala Leu

<210> SEQ ID NO 98
<211> LENGTH: 1668
<212> TYPE: DNA
<213> ORGANISM: Dunaliella salina

<400> SEQUENCE: 98
atggcgaggc tcgtcctgct agggcgttg ctcggcgcgc tgtgtgccac ggctgttcaa      60
ggctccctgg atggctctca ggttgaggcg gtctaggaa ggcagctcac acaggacaag     120
ccccatgagt acaactacaa cagacatggc atcgactgga gggacgaggg cctggacaac     180
tgcgctggct ccatgcagag ccccatcaac atcgacatgg ccactttgaa ccgtggcgag     240
gagcgcagcg atgtgagcgg cctctacctc aatggcctcg cctcgcccgc ctacgatgtc     300
gccgccgacg tgacagtgaa cgcggagcag acatgaaga tcaccttcaa ggacgtcgcg     360
cagaacaaca tgcctgccat caagatcgac ggcagcgaca tgctcttcaa gcccgtgcag     420
ctgcacttcc accacttcct cagcgagcac gccatcaacg cgcgcacta ccctctggag     480 gcgcaccttg tgatggggga cgcaagcggc aacaccaacc agctggcggt gctgggcatc     540
atgtaccagt acggcgagca gcctgacgac ttcgtccggc gcttgcagac gaagaccatt     600
gatgagatcg cgaccaacgg tgctgggtac ggagagactg tgaacgtcac cgacttgtct     660
gtgaacatca tgaaggatgt gctgccccc acccaccaca actacgtggg ctacgacggg     720
agcctgacca cgccccgtg cgatgagagg gtgaagtggc acgtgttcac cgagcccagg     780
accatcacaa ctgggcagct ggagaagttc ctgatgatca aaagcgcgg ccacactgat     840 gcgatcgtca ccaacaaccg catcgtgcag cccattggca ggcctctgta ccactacaag     900
cccacacccg ccagctacaa ctacgcgcgc aagggcattg actggaggga ggctggcctg     960
gacaactgtg ctggtgacag gcagagcccc atcaacattg acacaaccga tctccaacct    1020
ggcgctgtct ctggcatcag cctgaacggc ctggagtcac agagcttcac attcaccgac    1080
gcctacgtga acctggagca ggacatgaag gtcagcttca ccgccccac aaacaacctg    1140 cccactgtca acatcgatgg gaacgacgag tcgttcaggc ccatccagct gcacttccac    1200
```

-continued

```
cacttctcca gcgagcacac cgtggatggc atgatctacc ccctggaggc ccaccttgtg   1260
atggcatccc aggccgagaa cagcaaccag ctggcagtca ttgccatctt ctaccagtac   1320
ggcagtgagg ctgatgactt cctgaccagg ctgcacaccg aggccatcag cgctcagcaa   1380
ggcaacgcca actggggcga caacaacgtg cccatcaacc tgcccatcac cttcgccacg   1440
gatttgatgc ccagcagtac tgagcactgg gcctatgagg gcagcttgac cacccccacct  1500 tgcgatgaga gggtgaggtg gattgtgatg aaggagccca ggaccaccac tgctgagcag   1560
atggagacct tcaagactgc caccgtgaac gcccactacg ctgccgagat tgtcaacaac   1620
cgcgcgattc aggagcgcaa cagcaggcct attagcagta tcccttaa              1668
```

<210> SEQ ID NO 99
<211> LENGTH: 555
<212> TYPE: PRT
<213> ORGANISM: Dunaliella salina

<400> SEQUENCE: 99

```
Met Ala Arg Leu Val Leu Leu Gly Ala Leu Gly Ala Leu Cys Ala
1               5                   10                  15

Thr Ala Val Gln Gly Ser Leu Asp Gly Ser Gln Val Glu Ala Gly Leu
            20                  25                  30

Gly Arg Gln Leu Thr Gln Asp Lys Pro His Glu Tyr Asn Tyr Asn Arg
        35                  40                  45

His Gly Ile Asp Trp Arg Asp Glu Gly Leu Asp Asn Cys Ala Gly Ser
    50                  55                  60

Met Gln Ser Pro Ile Asn Ile Asp Met Ala Thr Leu Asn Arg Gly Glu
65                  70                  75                  80

Glu Arg Ser Asp Val Ser Gly Leu Tyr Leu Asn Gly Leu Ala Ser Pro
                85                  90                  95

Ala Tyr Asp Val Ala Ala Asp Val Thr Val Asn Ala Glu Gln Asp Met
            100                 105                 110

Lys Ile Thr Phe Lys Asp Val Ala Gln Asn Asn Met Pro Ala Ile Lys
        115                 120                 125

Ile Asp Gly Ser Asp Met Leu Phe Lys Pro Val Gln Leu His Phe His
    130                 135                 140

His Phe Leu Ser Glu His Ala Ile Asn Gly Ala His Tyr Pro Leu Glu
145                 150                 155                 160

Ala His Leu Val Met Gly Asp Ala Ser Gly Asn Thr Asn Gln Leu Ala
                165                 170                 175

Val Leu Gly Ile Met Tyr Gln Tyr Gly Glu Gln Pro Asp Asp Phe Val
            180                 185                 190

Arg Arg Leu Gln Thr Lys Thr Ile Asp Glu Ile Ala Thr Asn Gly Ala
        195                 200                 205

Gly Tyr Gly Glu Thr Val Asn Val Thr Asp Leu Ser Val Asn Ile Met
    210                 215                 220

Lys Asp Val Leu Pro Pro Thr His His Asn Tyr Val Gly Tyr Asp Gly
225                 230                 235                 240

Ser Leu Thr Thr Pro Pro Cys Asp Glu Arg Val Lys Trp His Val Phe
                245                 250                 255

Thr Glu Pro Arg Thr Ile Thr Thr Gly Gln Leu Glu Lys Phe Leu Met
            260                 265                 270

Ile Thr Lys Arg Gly His Thr Asp Ala Ile Val Thr Asn Asn Arg Ile
        275                 280                 285

Val Gln Pro Ile Gly Arg Pro Leu Tyr His Tyr Lys Pro Thr Pro Ala
    290                 295                 300
```

```
Ser Tyr Asn Tyr Ala Arg Lys Gly Ile Asp Trp Arg Glu Ala Gly Leu
305                 310                 315                 320

Asp Asn Cys Ala Gly Asp Arg Gln Ser Pro Ile Asn Ile Asp Thr Thr
            325                 330                 335

Asp Leu Gln Pro Gly Ala Val Ser Gly Ile Ser Leu Asn Gly Leu Glu
        340                 345                 350

Ser Gln Ser Phe Thr Phe Thr Asp Ala Tyr Val Asn Leu Glu Gln Asp
    355                 360                 365

Met Lys Val Ser Phe Thr Ala Pro Thr Asn Asn Leu Pro Thr Val Asn
370                 375                 380

Ile Asp Gly Asn Asp Glu Ser Phe Arg Pro Ile Gln Leu His Phe His
385                 390                 395                 400

His Phe Ser Ser Glu His Thr Val Asp Gly Met Ile Tyr Pro Leu Glu
            405                 410                 415

Ala His Leu Val Met Ala Ser Gln Ala Glu Asn Ser Asn Gln Leu Ala
        420                 425                 430

Val Ile Ala Ile Phe Tyr Gln Tyr Gly Ser Glu Ala Asp Asp Phe Leu
    435                 440                 445

Thr Arg Leu His Thr Glu Ala Ile Ser Ala Gln Gln Gly Asn Ala Asn
450                 455                 460

Trp Gly Asp Asn Val Pro Ile Asn Leu Pro Ile Thr Phe Ala Thr
465                 470                 475                 480

Asp Leu Met Pro Ser Ser Thr Glu His Trp Ala Tyr Glu Gly Ser Leu
            485                 490                 495

Thr Thr Pro Pro Cys Asp Glu Arg Val Arg Trp Ile Val Met Lys Glu
        500                 505                 510

Pro Arg Thr Thr Thr Ala Glu Gln Met Glu Thr Phe Lys Thr Ala Thr
    515                 520                 525

Val Asn Ala His Tyr Ala Ala Glu Ile Val Asn Asn Arg Ala Ile Gln
530                 535                 540

Glu Arg Asn Ser Arg Pro Ile Ser Ser Ile Pro
545                 550                 555

<210> SEQ ID NO 100
<211> LENGTH: 1125
<212> TYPE: DNA
<213> ORGANISM: Chlamydomonas reinhardtii

<400> SEQUENCE: 100
atggcgcgta ctggcgctct actcctggcc gcgctggcgc ttgcgggctg cgcgcaggct     60
tgcatctaca gttcggcac gtcgccggac tccaaggcca ctcacacagg cgaccactgg    120
gatcatagtc tcaatggcga gaactgggag ggcaaggacg gcgcgggcaa ccctggggtc    180
tgcaagactg gccgcaagca gtcgcccatc aacgtgcccc agtaccatgt cctggacggg    240
aagggttcca agattgccac cggcctgcag acccagtggt cgtaccctga cctgatgtcc    300
aacggcagct cggttcaagt catcaacaac ggccacacca tccaggtgca gtggacctac    360
gactacgccg ccatgccaca catcgccatc cctgccatgc gcaaccagag caaccgcatc    420
gtggacgtgc tggagatgcg ccccaacgac gcctccgacc gcgtgactgc cgtgcccacc    480
cagttccact ccactccac tcggagcac ctgctggcgg caagatctt ctcctcttgag    540 ttgcacattg tgcacaaggt gactgacaag ctagaggcct gcaagggcgg ctgcttcagc    600
gtcaccggca tcctgttcca gctcgacaac ggccccgata cgagctgct tgagcccacg    660 cgcgagggca ccttcaccaa cctgccggcg ggcaccacca tcaagctggg tgagctgctg    720
```

```
cccagcgacc gcgactacgt cacctacgag ggcagcctca ccaccccgcc ctgcagcgag    780
ggcctgctgt ggcacgtcat gacccagccg cagcgcatca gcttcggcca gtggaaccgc    840
taccgcctgg ctgtgggcga aggagtgc aactccacgg agaccgatgc tgcccacgcg       900
gacgccggcc atcatcacca ccaccaccgc cgcctgctgc acaaccacgc gcacctggag    960
gaggtgcctg ccgccacctc cgagcccaag cactacttcc gccgcgtgat ggaggagacc   1020 gagaacccg atgcttacac ctgcacgacc gttgcctttg gccagaactt ccgcaacgcc    1080
cagtacgcca acggccgcac catcaagctg gcccgctacg agtaa                   1125
```

<210> SEQ ID NO 101
<211> LENGTH: 380
<212> TYPE: PRT
<213> ORGANISM: Chlamydomonas reinhardtii

<400> SEQUENCE: 101

```
Met Ala Arg Thr Gly Ala Leu Leu Ala Ala Leu Ala Leu Ala Gly
 1               5                  10                  15

Cys Ala Gln Ala Cys Ile Tyr Lys Phe Gly Thr Ser Pro Asp Ser Lys
                20                  25                  30

Ala Thr His Thr Gly Asp His Trp Asp His Ser Leu Asn Gly Glu Asn
            35                  40                  45

Trp Glu Gly Lys Asp Gly Ala Gly Asn Pro Trp Val Cys Lys Thr Gly
        50                  55                  60

Arg Lys Gln Ser Pro Ile Asn Val Pro Gln Tyr His Val Leu Asp Gly
65                  70                  75                  80

Lys Gly Ser Lys Ile Ala Thr Gly Leu Gln Thr Gln Trp Ser Tyr Pro
                85                  90                  95

Asp Leu Met Ser Asn Gly Ser Ser Val Gln Val Ile Asn Asn Gly His
            100                 105                 110

Thr Ile Gln Val Gln Trp Thr Tyr Asp Tyr Ala Gly His Ala Thr Ile
        115                 120                 125

Ala Ile Pro Ala Met Arg Asn Gln Ser Asn Arg Ile Val Asp Val Leu
    130                 135                 140

Glu Met Arg Pro Asn Asp Ala Ser Asp Arg Val Thr Ala Val Pro Thr
145                 150                 155                 160

Gln Phe His Phe His Ser Thr Ser Glu His Leu Leu Ala Gly Lys Ile
                165                 170                 175

Phe Pro Leu Glu Leu His Ile Val His Lys Val Thr Asp Lys Leu Glu
            180                 185                 190

Ala Cys Lys Gly Gly Cys Phe Ser Val Thr Gly Ile Leu Phe Gln Leu
        195                 200                 205

Asp Asn Gly Pro Asp Asn Glu Leu Leu Glu Pro Ile Phe Ala Asn Met
    210                 215                 220

Pro Thr Arg Glu Gly Thr Phe Thr Asn Leu Pro Ala Gly Thr Thr Ile
225                 230                 235                 240

Lys Leu Gly Glu Leu Leu Pro Ser Asp Arg Asp Tyr Val Thr Tyr Glu
                245                 250                 255

Gly Ser Leu Thr Thr Pro Pro Cys Ser Glu Gly Leu Leu Trp His Val
            260                 265                 270

Met Thr Gln Pro Gln Arg Ile Ser Phe Gly Gln Trp Asn Arg Tyr Arg
        275                 280                 285

Leu Ala Val Gly Glu Lys Glu Cys Asn Ser Thr Glu Thr Asp Ala Ala
    290                 295                 300
```

```
His Ala Asp Ala Gly His His His His Arg Arg Leu Leu His
305                 310                 315                 320

Asn His Ala His Leu Glu Glu Val Pro Ala Thr Ser Glu Pro Lys
                325                 330                 335

His Tyr Phe Arg Arg Val Met Glu Glu Thr Glu Asn Pro Asp Ala Tyr
            340                 345                 350

Thr Cys Thr Thr Val Ala Phe Gly Gln Asn Phe Arg Asn Ala Gln Tyr
        355                 360                 365

Ala Asn Gly Arg Thr Ile Lys Leu Ala Arg Tyr Glu
    370                 375                 380

<210> SEQ ID NO 102
<211> LENGTH: 1134
<212> TYPE: DNA
<213> ORGANISM: Chlamydomonas reinhardtii

<400> SEQUENCE: 102
atggcgcgta ctggcgctct actcctggtc gcgctggcgc ttgcgggctg cgcgcaggct      60
tgcatctaca agttcggcac gtcgccggac tccaaggcca ccgtttcggg tgatcactgg     120
gaccatggcc tcaacggcga gaactgggag ggcaaggacg cgcaggcaa cgcctgggtt     180 tgcaagactg gccgcaagca gtcgcccatc aacgtgcccc agtaccaggt cctggacggg     240
aagggttcca gattgccaa cggcctgcag acccagtggt cgtaccctga cctgatgtcc     300
aacggcacct cggtccaagt catcaacaac ggccacacca tccaggtgca gtggacttac     360
aactacgccg ccatgccac catcgccatc cctgccatgc acaaccagac caaccgcatc     420
gtggacgtgc tggagatgcg ccccaacgac gccgccgacc gcgtgactgc cgtgcccacc     480
cagttccact ccactccac ctcggagcac ctgctggcgg caagatcta tccccttgag     540 ttgcacattg tgcaccaggt gactgagaag ctggaggcct gcaagggcgg ctgcttcagc     600
gtcaccggca tcctgttcca gctcgacaac ggccccgata cgagctgct tgagcccatc     660 tttgcgaaca tgccctcgcg cgagggcacc ttcagcaacc tgccggcggg caccaccatc     720
aagctgggtg agctgctgcc cagcgaccgc gactacgtaa cgtacgaggg cagcctcacc     780
accccgccct gcagcgaggg cctgctgtgg cacgtcatga cccagccgca gcgcatcagc     840
ttcggccagt ggaaccgcta ccgcctggct gtgggcctga aggagtgcaa ctccacggag     900
accgccgcgg acgccggcca ccaccaccac caccgccgcc tgctgcacaa ccacgcgcac     960
ctggaggagt gcctgccgc cacctccgag cccaagcact acttccgccg cgtgatgctg    1020
gccgagtccg cgaaccccga tgcctacacc tgcaaggccg ttgcctttgg ccagaacttc    1080 cgcaacccccc agtacgccaa cggccgcacc atcaagctgg cccgctatca ctaa          1134

<210> SEQ ID NO 103
<211> LENGTH: 377
<212> TYPE: PRT
<213> ORGANISM: Chlamydomonas reinhardtii

<400> SEQUENCE: 103

Met Ala Arg Thr Gly Ala Leu Leu Val Ala Leu Ala Leu Ala Gly
1                 5                 10                  15

Cys Ala Gln Ala Cys Ile Tyr Lys Phe Gly Thr Ser Pro Asp Ser Lys
            20                  25                  30

Ala Thr Val Ser Gly Asp His Trp Asp His Gly Leu Asn Gly Glu Asn
        35                  40                  45

Trp Glu Gly Lys Asp Gly Ala Gly Asn Ala Trp Val Cys Lys Thr Gly
    50                  55                  60
```

Arg Lys Gln Ser Pro Ile Asn Val Pro Gln Tyr Gln Val Leu Asp Gly
65                  70                  75                  80

Lys Gly Ser Lys Ile Ala Asn Gly Leu Gln Thr Gln Trp Ser Tyr Pro
            85                  90                  95

Asp Leu Met Ser Asn Gly Thr Ser Val Gln Val Ile Asn Asn Gly His
            100                 105                 110

Thr Ile Gln Val Gln Trp Thr Tyr Asn Tyr Ala Gly His Ala Thr Ile
        115                 120                 125

Ala Ile Pro Ala Met His Asn Gln Thr Asn Arg Ile Val Asp Val Leu
130                 135                 140

Glu Met Arg Pro Asn Asp Ala Ala Asp Arg Val Thr Ala Val Pro Thr
145                 150                 155                 160

Gln Phe His Phe His Ser Thr Ser Glu His Leu Leu Ala Gly Lys Ile
                165                 170                 175

Tyr Pro Leu Glu Leu His Ile Val His Gln Val Thr Glu Lys Leu Glu
            180                 185                 190

Ala Cys Lys Gly Gly Cys Phe Ser Val Thr Gly Ile Leu Phe Gln Leu
        195                 200                 205

Asp Asn Gly Pro Asp Asn Glu Leu Leu Glu Pro Ile Phe Ala Asn Met
210                 215                 220

Pro Ser Arg Glu Gly Thr Phe Ser Asn Leu Pro Ala Gly Thr Thr Ile
225                 230                 235                 240

Lys Leu Gly Glu Leu Leu Pro Ser Asp Arg Asp Tyr Val Thr Tyr Glu
            245                 250                 255

Gly Ser Leu Thr Thr Pro Pro Cys Ser Glu Gly Leu Leu Trp His Val
            260                 265                 270

Met Thr Gln Pro Gln Arg Ile Ser Phe Gly Gln Trp Asn Arg Tyr Arg
        275                 280                 285

Leu Ala Val Gly Leu Lys Glu Cys Asn Ser Thr Glu Thr Ala Ala Asp
290                 295                 300

Ala Gly His His His His His Arg Arg Leu Leu His Asn His Ala His
305                 310                 315                 320

Leu Glu Glu Val Pro Ala Ala Thr Ser Glu Pro Lys His Tyr Phe Arg
            325                 330                 335

Arg Val Met Leu Ala Glu Ser Ala Asn Pro Asp Ala Tyr Thr Cys Lys
        340                 345                 350

Ala Val Ala Phe Gly Gln Asn Phe Arg Asn Pro Gln Tyr Ala Asn Gly
        355                 360                 365

Arg Thr Ile Lys Leu Ala Arg Tyr His
370                 375

<210> SEQ ID NO 104
<211> LENGTH: 810
<212> TYPE: DNA
<213> ORGANISM: Physcomitrella patens

<400> SEQUENCE: 104
atggcgagcc aacttgtgca ggcagtggcc gctgttgtgg ttctgcaatg catctccgca     60
agctgggttg gcgcgtgggc aggatcggct caggctgagg aggtgacga ggtgcactgg    120 gactacagcg gtgggtcgca tgggccaggt ggctgggggtg acctgaaggc cgagtggggt   180
gtgtgcaagt cgggcagccg gcagtccccg atcgccatca cggcgctcga cctggtcaca   240
gaccgcagtc tggggaagct ggatgccaag taccggaaga gagttcatgc cactctttac    300
aacagcgggc atgggctga ggtgagcatg ccagccggct cgggacgctt gaggatcggt    360

-continued

```
ggcgagacgt accgacccgt ccagttccac atccacatgc ccagcgagca cacaatcatg      420
aaccagagtt tcccgctgga gctccacttg gtgcacaagt ccgatgatgg gaagcttgcg      480
gtgatcgggt tcctgtttga ggaaggaggc gagagcgaat tcctggccca gttcgcacat      540
gaggtgccat cgtcaaatag cccaggcgtg aaggtcgact tggggcacat caagatgatg      600
aagccggaga ggaactacgg cacttacatg ggatccctca ccaccccacc atgcgcggag      660
ggtgtcacct ggattctgtc gttgttcaac tttcaaacgg cgtccgcgga acagctggct      720
aagctccggg cttctgtgcc gaagggacac aacaaccgtc caaccttcgg cagcgccgga      780
aggggtttcc gcatgcgcac caacgcttga                                      810
```

<210> SEQ ID NO 105
<211> LENGTH: 269
<212> TYPE: PRT
<213> ORGANISM: Physcomitrella patens

<400> SEQUENCE: 105

```
Met Ala Ser Gln Leu Val Gln Ala Val Ala Val Val Leu Gln
1               5                   10                  15

Cys Ile Ser Ala Ser Trp Val Gly Trp Ala Gly Ser Ala Gln Ala
                20                  25                  30

Glu Gly Gly Asp Glu Val His Trp Asp Tyr Ser Gly Ser His Gly
            35                  40                  45

Pro Gly Gly Trp Gly Asp Leu Lys Ala Glu Trp Gly Val Cys Lys Ser
        50                  55                  60

Gly Ser Arg Gln Ser Pro Ile Ala Ile Thr Ala Leu Asp Leu Val Thr
65                  70                  75                  80

Asp Arg Ser Leu Gly Lys Leu Asp Ala Lys Tyr Arg Lys Arg Val His
                85                  90                  95

Ala Thr Leu Tyr Asn Ser Gly His Gly Ala Glu Val Ser Met Pro Ala
            100                 105                 110

Gly Ser Gly Arg Leu Arg Ile Gly Gly Glu Thr Tyr Arg Pro Val Gln
        115                 120                 125

Phe His Ile His Met Pro Ser Glu His Thr Ile Met Asn Gln Ser Phe
    130                 135                 140

Pro Leu Glu Leu His Leu Val Lys Ser Asp Asp Gly Lys Leu Ala
145                 150                 155                 160

Val Ile Gly Phe Leu Phe Glu Glu Gly Gly Glu Ser Glu Phe Leu Ala
                165                 170                 175

Gln Phe Ala His Glu Val Pro Ser Ser Asn Ser Pro Gly Val Lys Val
            180                 185                 190

Asp Leu Gly His Ile Lys Met Met Lys Pro Glu Arg Asn Tyr Gly Thr
        195                 200                 205

Tyr Met Gly Ser Leu Thr Thr Pro Pro Cys Ala Glu Gly Val Thr Trp
    210                 215                 220

Ile Leu Ser Leu Phe Asn Phe Gln Thr Ala Ser Ala Glu Gln Leu Ala
225                 230                 235                 240

Lys Leu Arg Ala Ser Val Pro Lys Gly His Asn Asn Arg Pro Thr Phe
                245                 250                 255

Gly Ser Ala Gly Arg Gly Phe Arg Met Arg Thr Asn Ala
            260                 265
```

<210> SEQ ID NO 106
<211> LENGTH: 1519
<212> TYPE: DNA

<213> ORGANISM: Arabidopsis thaliana

<400> SEQUENCE: 106

```
aaatagagaa gctcttcaag tatccgatgt ttttgtttaa tcaacaagag gcggagatac      60
gggagaaatt gcatgtgtaa tcataaaatg tagatgttag cttcgtcgtt tttactatag     120
tttagttctc ttcttcttct tttttcgtca ttacaatctc tttcttaatt tacttcttct     180
tgatagtata attaagttgt ttgtaataat ctgtacaaag atgttgtgtt ctcataaaaa     240
attcaatttt gtaaagaagc tctacatgtt ccttgctctg taaacatggt ccccttttgg     300
actacagttt ctcgaaatgg ctcatcagac tcagagacga ctctccaatc tgcttcaaaa     360
gccacaaaac agtataaata tccttctctt cgtccctctc atcgcctgtc tctcctcttc     420
ctcttcccgt tccatttatc cgcaaacgga gcttgttttc ggtgcacctg cttcagccac     480
ttcaaacttg gtataaactg agaaggatgg gaaacgaatc atatgaagac gccatcgaag     540
ctctcaagaa gcttctcatt gagaaggatg atctgaagga tgtagctgcg gccaaggtga     600
agaagatcac ggcggagctt caggcagcct cgtcatcgga cagcaaatct tttgatcccg     660
tcgaacgaat taaggaaggc ttcgtcacct tcaagaagga gaaatacgag accaatcctg     720
cttttgtatgg tgagctcgcc aaaggtcaaa gcccaaagta catggtgttt gcttgttcgg     780
actcacgagt gtgcccatca cacgtactag acttccatcc tggagatgcc ttcgtggttc     840
gtaatatcgc caatatggtt cctccttttg acaaggtcaa atatgcagga gttggagccg     900
ccattgaata cgctgtcttg cacttaaggt tggaaaacat tgtggtgata gggcacagtg     960
catgtggtgg catcaagggg cttatgtcat ttcctcttga cggaaacaac tctactgact    1020
tcatagagga ttgggtcaaa atctgtttac cagcaaagtc aaaagttttg gcagaaagtg    1080
aaagttcagc atttgaagac caatgtggcc gatgcgaaag ggaggcagtg aatgtgtcac    1140
tagcaaacct attgacatat ccatttgtga gagaaggagt tgtgaaagga acacttgctt    1200
tgaagggagg ctactatgac tttgttaatg gctcctttga gctttgggag ctccagtttg    1260
gaatttcccc cgttcattct atatgaacta acacatcacc atcaccatcg ctaccaccac    1320
catcacaaac atcatcatcg tcgtcatcat catgatcagc atcttcatat ataaatgttt    1380
tactcttatt taattgctac ttgtaatggt atacatttac ttgcgatgag cttcttttcc    1440
ttcattatcc agttataaaa taaataaata aatcatgttt actttcacag atatcgtttt    1500
gctgaagttg ctttgattt                                                 1519
```

<210> SEQ ID NO 107
<211> LENGTH: 259
<212> TYPE: PRT
<213> ORGANISM: Arabidopsis thaliana

<400> SEQUENCE: 107

```
Met Gly Asn Glu Ser Tyr Glu Asp Ala Ile Glu Ala Leu Lys Lys Leu
1               5                  10                  15

Leu Ile Glu Lys Asp Asp Leu Lys Asp Val Ala Ala Lys Val Lys
        20                  25                  30

Lys Ile Thr Ala Glu Leu Gln Ala Ala Ser Ser Ser Asp Ser Lys Ser
    35                  40                  45

Phe Asp Pro Val Glu Arg Ile Lys Glu Gly Phe Val Thr Phe Lys Lys
    50                  55                  60

Glu Lys Tyr Glu Thr Asn Pro Ala Leu Tyr Gly Glu Leu Ala Lys Gly
65                  70                  75                  80

Gln Ser Pro Lys Tyr Met Val Phe Ala Cys Ser Asp Ser Arg Val Cys
```

|  | 85 | 90 | 95 |  |

Pro Ser His Val Leu Asp Phe His Pro Gly Asp Ala Phe Val Val Arg
             100                 105                 110

Asn Ile Ala Asn Met Val Pro Pro Phe Asp Lys Val Lys Tyr Ala Gly
             115                 120                 125

Val Gly Ala Ala Ile Glu Tyr Ala Val Leu His Leu Lys Val Glu Asn
             130                 135                 140

Ile Val Val Ile Gly His Ser Ala Cys Gly Gly Ile Lys Gly Leu Met
145                 150                 155                 160

Ser Phe Pro Leu Asp Gly Asn Asn Ser Thr Asp Phe Ile Glu Asp Trp
             165                 170                 175

Val Lys Ile Cys Leu Pro Ala Lys Ser Lys Val Leu Ala Glu Ser Glu
             180                 185                 190

Ser Ser Ala Phe Glu Asp Gln Cys Gly Arg Cys Glu Arg Glu Ala Val
             195                 200                 205

Asn Val Ser Leu Ala Asn Leu Leu Thr Tyr Pro Phe Val Arg Glu Gly
             210                 215                 220

Val Val Lys Gly Thr Leu Ala Leu Lys Gly Gly Tyr Tyr Asp Phe Val
225                 230                 235                 240

Asn Gly Ser Phe Glu Leu Trp Glu Leu Gln Phe Gly Ile Ser Pro Val
             245                 250                 255

His Ser Ile

<210> SEQ ID NO 108
<211> LENGTH: 1770
<212> TYPE: DNA
<213> ORGANISM: Dunaliella salina

<400> SEQUENCE: 108

```
atgggatccc gccgcatcac cctcttgggg gctctgttcg ctgtcctggc ggtcgcaatc      60
gaagggcgta ccctgcttac acacaacctg aaggccgagg ctgctgagac agtggatgca     120
gtgagctctg tggtagctgg ttctgcaggc aggcagttgc tggtgagtga gcctcacgac     180
tacaactatg agaaagttgg cttttgattgg acgggggggg tctgcgtcaa taccgggacc     240
agcaagcaga gcccaatcaa cattgagact gacagcctgg ctgaggaatc agagaggctg     300
gggaccgcgg atgacacttc acgcctggcc ttgaagggcc tactgtcttc atcctaccag     360
ctgaccagcg aagtggcaat caacctggag caggatatgc agttttcttt taatgcgcct     420
gatgaagact tgcctcaact tactattggt ggggttgtcc acaccttcaa gcctgtgcaa     480
atccactttc accactttgc cagcgagcac gctattgacg ccagcttta tcctcttgag     540
gcccacatgg tgatggcatc ccagaatgac ggctctgacc agcttgctgt cattggcatc     600
atgtacaagt acggggaaga agatcctttc ctcaaaaggc tgcaagaaac tgcacagagc     660
aatggcgaag ctgccgacaa aaatgtggag ctgaactcgt tttccatcaa tgtggccagg     720
gatttgctgc tgagtcagac ctgacctac tatggatatg atggtagctt gactacccc      780
ggttgtgatg agcgagtgaa gtggcatgtg ttcaaggagg caaggactgt ctcagtggcg     840
cagctcaagg tgttttcaga ggtcacgctg ctgcccacc tgaagctac ggttaccaac       900
aaccgtgtca ttcagccgct caatggcagg aaggtctacg agtacaaggg tgaacccaac     960
gacaagtaca actatgtcca gcatggcttt gactggcgcg ataatggctt ggatagctgt    1020
gctggcgacg tccagagccc tattgacatc gtgaccagca ctttgcaagc tggatcttct    1080
cggagtgatg tttctagtgt caacctgaat gacttgaaca ccgacgcgtt cacgctgacc    1140
```

```
ggcaacactg tgaatattgg gcaaggcatg caaatcaatt ttggtgaccc ccctgcgggt    1200
gacctgcccg tcatcagaat tggtactagg gacgtcactt tcaggcccct ccaggtgcac    1260
tggcacttct ttttgagtga gcacactgtg gatggagtgc actaccccct ggaagctcat    1320
attgttatga aggacaatga caaccttggt gattctgccg ccagcttgc tgtcatcggt     1380 attatgtaca agtacggcga tgcagacccc ttcattactg atatgcagaa gagggtgtca    1440
gataaaattg catcaggtgc catcacctat ggacaatcag gagtgtctct gaacaatcct    1500
gatgatccct tcaatgtcaa catcaagaat aatttcctgc cctctgagct tggatatgct    1560
ggctacgatg gcagcctgac caccccctcct tgctctgaga ttgtgaagtg catgtgttc    1620 ctggagccta ggactgtttc agtggagcag atggaggtct ttgcagatgt gactctgaac    1680
tctaatccag gtgcgaccgt gacaaccaac cgaatgatcc agccactgga gggtaggact    1740
gtgtacggat ataacggtgc tgctgcttaa                                     1770
```

<210> SEQ ID NO 109
<211> LENGTH: 589
<212> TYPE: PRT
<213> ORGANISM: Dunaliella salina

<400> SEQUENCE: 109

```
Met Gly Ser Arg Arg Ile Thr Leu Leu Gly Ala Leu Phe Ala Val Leu
1               5                   10                  15

Ala Val Ala Ile Glu Gly Arg Thr Leu Leu Thr His Asn Leu Lys Ala
            20                  25                  30

Glu Ala Ala Glu Thr Val Asp Ala Val Ser Ser Val Ala Gly Ser
        35                  40                  45

Ala Gly Arg Gln Leu Leu Val Ser Glu Pro His Asp Tyr Asn Tyr Glu
    50                  55                  60

Lys Val Gly Phe Asp Trp Thr Gly Gly Val Cys Val Asn Thr Gly Thr
65                  70                  75                  80

Ser Lys Gln Ser Pro Ile Asn Ile Glu Thr Asp Ser Leu Ala Glu Glu
                85                  90                  95

Ser Glu Arg Leu Gly Thr Ala Asp Asp Thr Ser Arg Leu Ala Leu Lys
            100                 105                 110

Gly Leu Leu Ser Ser Ser Tyr Gln Leu Thr Ser Glu Val Ala Ile Asn
        115                 120                 125

Leu Glu Gln Asp Met Gln Phe Ser Phe Asn Ala Pro Asp Glu Asp Leu
    130                 135                 140

Pro Gln Leu Thr Ile Gly Gly Val Val His Thr Phe Lys Pro Val Gln
145                 150                 155                 160

Ile His Phe His His Phe Ala Ser Glu His Ala Ile Asp Gly Gln Leu
                165                 170                 175

Tyr Pro Leu Glu Ala His Met Val Met Ala Ser Gln Asn Asp Gly Ser
            180                 185                 190

Asp Gln Leu Ala Val Ile Gly Ile Met Tyr Lys Tyr Gly Glu Glu Asp
        195                 200                 205

Pro Phe Leu Lys Arg Leu Gln Glu Thr Ala Gln Ser Asn Gly Glu Ala
    210                 215                 220

Gly Asp Lys Asn Val Glu Leu Asn Ser Phe Ser Ile Asn Val Ala Arg
225                 230                 235                 240

Asp Leu Leu Pro Glu Ser Asp Leu Thr Tyr Tyr Gly Tyr Asp Gly Ser
                245                 250                 255

Leu Thr Thr Pro Gly Cys Asp Glu Arg Val Lys Trp His Val Phe Lys
            260                 265                 270
```

```
Glu Ala Arg Thr Val Ser Val Ala Gln Leu Lys Val Phe Ser Glu Val
            275                 280                 285

Thr Leu Ala Ala His Pro Glu Ala Thr Val Thr Asn Asn Arg Val Ile
        290                 295                 300

Gln Pro Leu Asn Gly Arg Lys Val Tyr Glu Tyr Lys Gly Glu Pro Asn
305                 310                 315                 320

Asp Lys Tyr Asn Tyr Val Gln His Gly Phe Asp Trp Arg Asp Asn Gly
                325                 330                 335

Leu Asp Ser Cys Ala Gly Asp Val Gln Ser Pro Ile Asp Ile Val Thr
            340                 345                 350

Ser Thr Leu Gln Ala Gly Ser Ser Arg Ser Asp Val Ser Ser Val Asn
        355                 360                 365

Leu Met Thr Leu Asn Thr Asp Ala Phe Thr Leu Thr Gly Asn Thr Val
    370                 375                 380

Asn Ile Gly Gln Gly Met Gln Ile Asn Phe Gly Asp Pro Pro Ala Gly
385                 390                 395                 400

Asp Leu Pro Val Ile Arg Ile Gly Thr Arg Asp Val Thr Phe Arg Pro
                405                 410                 415

Leu Gln Val His Trp His Phe Phe Leu Ser Glu His Thr Val Asp Gly
            420                 425                 430

Val His Tyr Pro Leu Glu Ala His Ile Val Met Lys Asp Asn Asp Asn
        435                 440                 445

Leu Gly Asp Ser Ala Gly Gln Leu Ala Val Ile Gly Ile Met Tyr Lys
    450                 455                 460

Tyr Gly Asp Ala Asp Pro Phe Ile Thr Asp Met Gln Lys Arg Val Ser
465                 470                 475                 480

Asp Lys Ile Ala Ser Gly Ala Ile Thr Tyr Gly Gln Ser Gly Val Ser
                485                 490                 495

Leu Asn Asn Pro Asp Asp Pro Phe Asn Val Asn Ile Lys Asn Asn Phe
            500                 505                 510

Leu Pro Ser Glu Leu Gly Tyr Ala Gly Tyr Asp Gly Ser Leu Thr Thr
        515                 520                 525

Pro Pro Cys Ser Glu Ile Val Lys Trp His Val Phe Leu Glu Pro Arg
    530                 535                 540

Thr Val Ser Val Glu Gln Met Glu Val Phe Ala Asp Val Thr Leu Asn
545                 550                 555                 560

Ser Asn Pro Gly Ala Thr Val Thr Thr Asn Arg Met Ile Gln Pro Leu
                565                 570                 575

Glu Gly Arg Thr Val Tyr Gly Tyr Asn Gly Ala Ala Ala
            580                 585

<210> SEQ ID NO 110
<211> LENGTH: 693
<212> TYPE: DNA
<213> ORGANISM: Arabidopsis thaliana

<400> SEQUENCE: 110
atgaagatta tgatgatgat taagctctgc ttcttctcca tgtccctcat ctgcattgca      60
cctgcagatg ctcagacaga aggagtagtg tttggatata aaggcaaaaa tggaccaaac     120 caatgggac acttaaaccc tcacttcacc acatgcgcgg tcggtaaatt gcaatctcca     180
attgatattc aaaggaggca aatattttac aaccacaaat tgaattcaat acaccgtgaa     240
tactacttca caaacgcaac actagtgaac cacgtctgta atgttgccat gttcttcggg     300
gagggagcag gagatgtgat aatagaaaac aagaactata ccttactgca aatgcattgg     360
```

```
cacactcctt ctgaacatca cctccatgga gtccaatatg cagctgagct gcacatggta    420
caccaagcaa aagatggaag ctttgctgtg gtggcaagtc tcttcaaaat cggcactgaa    480 gagccttttcc tctctcagat gaaggagaaa ttggtgaagc taaaggaaga gagactcaaa    540
gggaaccaca cagcacaagt ggaagtagga agaatcgaca caagacacat tgaacgtaag    600
actcgaaagt actacagata cattggttca ctcactactc ctccttgctc cgagaacgtt    660
tcttggacca tccttggcaa ggtaatcttt taa                                 693
```

<210> SEQ ID NO 111
<211> LENGTH: 284
<212> TYPE: PRT
<213> ORGANISM: Arabidopsis thaliana

<400> SEQUENCE: 111

```
Met Lys Ile Met Met Ile Lys Leu Cys Phe Phe Ser Met Ser Leu
1               5                   10                  15

Ile Cys Ile Ala Pro Ala Asp Ala Gln Thr Glu Gly Val Val Phe Gly
            20                  25                  30

Tyr Lys Gly Lys Asn Gly Pro Asn Gln Trp Gly His Leu Asn Pro His
        35                  40                  45

Phe Thr Thr Cys Ala Val Gly Lys Leu Gln Ser Pro Ile Asp Ile Gln
    50                  55                  60

Arg Arg Gln Ile Phe Tyr Asn His Lys Leu Asn Ser Ile His Arg Glu
65                  70                  75                  80

Tyr Tyr Phe Thr Asn Ala Thr Leu Val Asn His Val Cys Asn Val Ala
                85                  90                  95

Met Phe Phe Gly Glu Gly Ala Gly Asp Val Ile Ile Glu Asn Lys Asn
            100                 105                 110

Tyr Thr Leu Leu Gln Met His Trp His Thr Pro Ser Glu His His Leu
        115                 120                 125

His Gly Val Gln Tyr Ala Ala Glu Leu His Met Val His Gln Ala Lys
    130                 135                 140

Asp Gly Ser Phe Ala Val Val Ala Ser Leu Phe Lys Ile Gly Thr Glu
145                 150                 155                 160

Glu Pro Phe Leu Ser Gln Met Lys Glu Lys Leu Val Lys Leu Lys Glu
                165                 170                 175

Glu Arg Leu Lys Gly Asn His Thr Ala Gln Val Glu Val Gly Arg Ile
            180                 185                 190

Asp Thr Arg His Ile Glu Arg Lys Thr Arg Lys Tyr Tyr Arg Tyr Ile
        195                 200                 205

Gly Ser Leu Thr Thr Pro Pro Cys Ser Glu Asn Val Ser Trp Thr Ile
    210                 215                 220

Leu Gly Lys Val Arg Ser Met Ser Lys Glu Gln Val Glu Leu Leu Arg
225                 230                 235                 240

Ser Pro Leu Asp Thr Ser Phe Lys Asn Asn Ser Arg Pro Cys Gln Pro
                245                 250                 255

Leu Asn Gly Arg Arg Val Glu Met Phe His Asp His Glu Arg Val Asp
            260                 265                 270

Lys Lys Glu Thr Gly Asn Lys Lys Lys Pro Asn
        275                 280
```

<210> SEQ ID NO 112
<211> LENGTH: 1053
<212> TYPE: DNA
<213> ORGANISM: Arabidopsis thaliana

<400> SEQUENCE: 112

```
atgaagatat catcactagg atgggtctta gtccttatct tcatctctat taccattgtt      60
tcgagtgcac cagcacctaa acctcctaaa cctaagcctg caccagcacc tacacctcct     120
aaacctaagc ccacaccagc acctacacct cctaaaccta gcccaaaacc agcacctaca     180
cctcctaaac ctaagcctgc accagcacct acacctccta aacctaagcc cgcaccagca     240
cctacacctc taaacctaa gcccaaacca gcacctacac ctcctaatcc taagcccaca     300
ccagcaccta cacctcctaa acctaagcct gcaccagcac cagcaccaac accagcaccg     360
aaacctaaac ctgcacctaa accagcacca ggtggagaag ttgaggacga aaccgagttt     420
agctacgaga cgaaaggaaa caaggggcca gcgaaatggg gaacactaga tgcagagtgg     480
aaaatgtgtg gaataggcaa aatgcaatct cctattgatc ttcgggacaa aaatgtggta     540
gttagtaata aatttggatt gcttcgtagc cagtatctgc cttctaatac caccattaag     600
aacagaggtc atgatatcat gttgaaattc aaaggaggaa ataaaggtat tggtgtcact     660
atccgtggta ctagatatca acttcaacaa cttcattggc actctccttc cgaacataca     720
atcaatggca aaaggtttgc gctagaggaa cacttggttc atgagagcaa agataaacgc     780
tacgctgttg tcgcattctt atacaatctc ggagcatctg accctttttct cttttcgttg     840
gaaaaacaat tgaagaagat aactgataca catgcgtccg aggaacatat tcgcactgtg     900
tcaagtaaac aagtgaagct tctccgtgtg gctgtacacg atgcttcaga ttcaaatgcc     960
aggccgcttc aagcagtcaa taagcgcaag gtatattat acaaaccaaa ggttaagtta    1020
atgaagaaat actgtaatat aagttcttac tag                                 1053
```

<210> SEQ ID NO 113
<211> LENGTH: 350
<212> TYPE: PRT
<213> ORGANISM: Arabidopsis thaliana

<400> SEQUENCE: 113

```
Met Lys Ile Ser Ser Leu Gly Trp Val Leu Val Leu Ile Phe Ile Ser
1               5                   10                  15
Ile Thr Ile Val Ser Ser Ala Pro Ala Pro Lys Pro Pro Lys Pro Lys
                20                  25                  30
Pro Ala Pro Ala Pro Thr Pro Pro Lys Pro Lys Pro Thr Pro Ala Pro
            35                  40                  45
Thr Pro Pro Lys Pro Lys Pro Lys Pro Ala Pro Thr Pro Pro Lys Pro
        50                  55                  60
Lys Pro Ala Pro Ala Pro Thr Pro Pro Lys Pro Ala Pro Ala
65                  70                  75                  80
Pro Thr Pro Pro Lys Pro Lys Pro Lys Pro Ala Pro Thr Pro Pro Asn
                85                  90                  95
Pro Lys Pro Thr Pro Ala Pro Thr Pro Pro Lys Pro Lys Pro Ala Pro
            100                 105                 110
Ala Pro Ala Pro Thr Pro Ala Pro Lys Pro Lys Pro Ala Pro Lys Pro
        115                 120                 125
Ala Pro Gly Gly Glu Val Glu Asp Glu Thr Glu Phe Ser Tyr Glu Thr
    130                 135                 140
Lys Gly Asn Lys Gly Pro Ala Lys Trp Gly Thr Leu Asp Ala Glu Trp
145                 150                 155                 160
Lys Met Cys Gly Ile Gly Lys Met Gln Ser Pro Ile Asp Leu Arg Asp
                165                 170                 175
```

```
Lys Asn Val Val Val Ser Asn Lys Phe Gly Leu Leu Arg Ser Gln Tyr
                180                 185                 190

Leu Pro Ser Asn Thr Thr Ile Lys Asn Arg Gly His Asp Ile Met Leu
                195                 200                 205

Lys Phe Lys Gly Gly Asn Lys Gly Ile Gly Val Thr Ile Arg Gly Thr
    210                 215                 220

Arg Tyr Gln Leu Gln Gln Leu His Trp His Ser Pro Ser Glu His Thr
225                 230                 235                 240

Ile Asn Gly Lys Arg Phe Ala Leu Glu Glu His Leu Val His Glu Ser
                245                 250                 255

Lys Asp Lys Arg Tyr Ala Val Val Ala Phe Leu Tyr Asn Leu Gly Ala
                260                 265                 270

Ser Asp Pro Phe Leu Phe Ser Leu Glu Lys Gln Leu Lys Lys Ile Thr
                275                 280                 285

Asp Thr His Ala Ser Glu Glu His Ile Arg Thr Val Ser Ser Lys Gln
                290                 295                 300

Val Lys Leu Leu Arg Val Ala Val His Asp Ala Ser Asp Ser Asn Ala
305                 310                 315                 320

Arg Pro Leu Gln Ala Val Asn Lys Arg Lys Val Tyr Leu Tyr Lys Pro
                325                 330                 335

Lys Val Lys Leu Met Lys Lys Tyr Cys Asn Ile Ser Ser Tyr
                340                 345                 350

<210> SEQ ID NO 114
<211> LENGTH: 834
<212> TYPE: DNA
<213> ORGANISM: Arabidopsis thaliana

<400> SEQUENCE: 114
atgaaaacca ttatcctttt tgtaacattt cttgctcttt cttcttcatc tctagccgat     60
gagacagaga ctgaatttca ttacaaaccc ggtgagatag ccgatccctc gaaatggagc    120
agtatcaagg ctgaatggaa aatttgcggg acagggaaga ggcaatcgcc aatcaatctt    180
actccaaaaa tagctcgcat tgttcacaat tctacagaga ttcttcagac atattacaaa    240
cctgtagagg ctattcttaa gaaccgtgga ttcgacatga aggttaagtg ggaagacgat    300
gcagggaaga tcgtgatcaa tgataccgac tataaattgg ttcaaagcca ctggcacgca    360
ccttcagagc attttctcga tggacagagg ttggcaatgg aacttcacat ggtacacaaa    420
agtgtagaag gcacttggc agtgattgga gttctcttca gagaaggaga accaaatgct    480
ttcatttcgc ggatcatgga caagatccat aagatcgcag acgtacaaga tggagaggtc    540
agcatcggaa agatagatcc aagagaattt ggatgggatc ttacaaagtt ttatgaatac    600
agaggttctc tcacgactcc tccttgcacg gaagatgtca tgtggaccat catcaacaag    660
gtggggactg tttcacgtga gcaaattgat gtattgacag atgctcgtcg cggtggttat    720
gagaagaacg cgagaccagc tcaacctctg aacggacgtc tggtttattt aaacgagcag    780
tccagtccaa gtccaactcc acggctaaga ataccacgag ttggtccggt ctaa          834

<210> SEQ ID NO 115
<211> LENGTH: 277
<212> TYPE: PRT
<213> ORGANISM: Arabidopsis thaliana

<400> SEQUENCE: 115

Met Lys Thr Ile Ile Leu Phe Val Thr Phe Leu Ala Leu Ser Ser Ser
1               5                   10                  15
```

```
Ser Leu Ala Asp Glu Thr Glu Thr Glu Phe His Tyr Lys Pro Gly Glu
         20                  25                  30

Ile Ala Asp Pro Ser Lys Trp Ser Ile Lys Ala Glu Trp Lys Ile
         35                  40                  45

Cys Gly Thr Gly Lys Arg Gln Ser Pro Ile Asn Leu Thr Pro Lys Ile
 50                  55                  60

Ala Arg Ile Val His Asn Ser Thr Glu Ile Leu Gln Thr Tyr Tyr Lys
 65                  70                  75                  80

Pro Val Glu Ala Ile Leu Lys Asn Arg Gly Phe Asp Met Lys Val Lys
                 85                  90                  95

Trp Glu Asp Asp Ala Gly Lys Ile Val Ile Asn Asp Thr Asp Tyr Lys
                100                 105                 110

Leu Val Gln Ser His Trp His Ala Pro Ser Glu His Phe Leu Asp Gly
             115                 120                 125

Gln Arg Leu Ala Met Glu Leu His Met Val His Lys Ser Val Glu Gly
        130                 135                 140

His Leu Ala Val Ile Gly Val Leu Phe Arg Glu Gly Glu Pro Asn Ala
145                 150                 155                 160

Phe Ile Ser Arg Ile Met Asp Lys Ile His Lys Ile Ala Asp Val Gln
                165                 170                 175

Asp Gly Glu Val Ser Ile Gly Lys Ile Asp Pro Arg Glu Phe Gly Trp
            180                 185                 190

Asp Leu Thr Lys Phe Tyr Glu Tyr Arg Gly Ser Leu Thr Thr Pro Pro
        195                 200                 205

Cys Thr Glu Asp Val Met Trp Thr Ile Ile Asn Lys Val Gly Thr Val
210                 215                 220

Ser Arg Glu Gln Ile Asp Val Leu Thr Asp Ala Arg Arg Gly Gly Tyr
225                 230                 235                 240

Glu Lys Asn Ala Arg Pro Ala Gln Pro Leu Asn Gly Arg Leu Val Tyr
                245                 250                 255

Leu Asn Glu Gln Ser Ser Pro Ser Pro Thr Pro Arg Leu Arg Ile Pro
            260                 265                 270

Arg Val Gly Pro Val
        275

<210> SEQ ID NO 116
<211> LENGTH: 825
<212> TYPE: DNA
<213> ORGANISM: Nicotiana langsdorffii x Nicotiana sanderae

<400> SEQUENCE: 116
atgaggatgg cagcaataac caaaatgttg ttcatttcgt ttcttttcct ttcaagtgta      60
tttcttgcaa ggtccggaga agttgatgat gagagtgaat ttagttacga tgaaaaaagt     120
gagaatggac cagctaattg gggcaatatt cgtccagatt ggaaagaatg tagtggcaaa     180
ttgcagtctc ctattgatat ttttgacttg agggctgaag tagtttcaaa cttgagaata     240
cttcaaaagg actacaaacc atcgaatgcc actctcttga acagaggtca tgatataatg     300
ttgagattgg atgatggagg atacttgaag ataaatgaaa ctcaatatca actcaagcaa     360
ttgcattggc acacccttc  tgaacacact atcaatggag aaaggtttaa tttggaggct     420
catttggtac atgaaagtaa taatggaaag tttgttgtca ttggaatagt ctacgagatc     480
ggattatggc ctgatccctt cttatctatg atagagaacg atttgaaagt tcctgctaat     540
aaaaaaggta tagagagagg cattggaatt attgatccaa atcaaataaa attggatggc     600
aaaaaatatt ttaggtatat tggctcactt acaacacctc cttgcaccga aggtgttgtc     660
```

```
tggataattg atagaaaggt aaaaactgta accagaagac aaataaaact actccaagaa        720
gctgttcatg atggatttga aaccaacgct agaccaactc aaccagaaaa cgaacgttat        780
atcaactcaa cataccattc ctttggtatt gaaaagcagc agtga                       825
```

```
<210> SEQ ID NO 117
<211> LENGTH: 274
<212> TYPE: PRT
<213> ORGANISM: Nicotiana langsdorffii x Nicotiana sanderae

<400> SEQUENCE: 117
```

Met Arg Met Ala Ala Ile Thr Lys Met Leu Phe Ile Ser Phe Leu Phe
1               5                   10                  15

Leu Ser Ser Val Phe Leu Ala Arg Ser Gly Glu Val Asp Asp Glu Ser
            20                  25                  30

Glu Phe Ser Tyr Asp Glu Lys Ser Glu Asn Gly Pro Ala Asn Trp Gly
        35                  40                  45

Asn Ile Arg Pro Asp Trp Lys Glu Cys Ser Gly Lys Leu Gln Ser Pro
    50                  55                  60

Ile Asp Ile Phe Asp Leu Arg Ala Glu Val Val Ser Asn Leu Arg Ile
65                  70                  75                  80

Leu Gln Lys Asp Tyr Lys Pro Ser Asn Ala Thr Leu Leu Asn Arg Gly
                85                  90                  95

His Asp Ile Met Leu Arg Leu Asp Asp Gly Gly Tyr Leu Lys Ile Asn
            100                 105                 110

Glu Thr Gln Tyr Gln Leu Lys Gln Leu His Trp His Thr Pro Ser Glu
        115                 120                 125

His Thr Ile Asn Gly Glu Arg Phe Asn Leu Glu Ala His Leu Val His
    130                 135                 140

Glu Ser Asn Asn Gly Lys Phe Val Val Ile Gly Ile Val Tyr Glu Ile
145                 150                 155                 160

Gly Leu Trp Pro Asp Pro Phe Leu Ser Met Ile Glu Asn Asp Leu Lys
                165                 170                 175

Val Pro Ala Asn Lys Lys Gly Ile Glu Arg Gly Ile Gly Ile Ile Asp
            180                 185                 190

Pro Asn Gln Ile Lys Leu Asp Gly Lys Lys Tyr Phe Arg Tyr Ile Gly
        195                 200                 205

Ser Leu Thr Thr Pro Pro Cys Thr Glu Gly Val Val Trp Ile Ile Asp
    210                 215                 220

Arg Lys Val Lys Thr Val Thr Arg Gln Ile Lys Leu Leu Gln Glu
225                 230                 235                 240

Ala Val His Asp Gly Phe Glu Thr Asn Ala Arg Pro Thr Gln Pro Glu
                245                 250                 255

Asn Glu Arg Tyr Ile Asn Ser Thr Tyr His Ser Phe Gly Ile Glu Lys
            260                 265                 270

Gln Gln

```
<210> SEQ ID NO 118
<211> LENGTH: 993
<212> TYPE: DNA
<213> ORGANISM: Flaveria bidentis

<400> SEQUENCE: 118
atgtcggccg cctctgcttt cgccatgaat gcgccttcgt tcgtcaacgc ttcgtcgctg        60
aagaaagcgt ctacttcagc tagatctggt gtgttgtccg ccagatttac gtgcaattcg       120
```

-continued

```
tcgtcgtcgt cgtcttcgtc tgcaactcct ccgagtctca ttcgtaacga gcctgttttc    180
gctgctcccg cgcccatcat cacaccgaat tggaccgaag acggaaatga atcatacgaa    240
gaagccattg acgcgctcaa gaaaacgctc attgaaaagg gtgagttaga accagttgcc    300
gctacaagaa tcgaccaaat cacagctcaa gccgcagcac ccgacaccaa agctccattt    360
gaccctgttg agaggatcaa atccggcttc gtgaagttca agacagagaa attcgtcaca    420
aacccagcct tgtacgatga gcttgctaaa ggccaaagcc caaagttcat ggtgtttgca    480
tgctcagact cgcgtgtttg cccgtcacac gttcttgatt tccagcccgg tgaggcgttt    540
gttgttcgta acgttgccaa catggtccct cctttgacaa gaccaaaata ttctggagta    600
ggagctgctg ttgagtatgc agttttgcat ctaaaggtac aagaaatctt tgtaattggg    660
catagccgtt gtgaggaat  caagggtctc atgactttcc cagacgaagg acctcactca    720
accgatttca tcgaagattg ggtgaaagtg tgtctccccg cgaagtcaaa agtggtagca    780
gaacacaacg gcacacatct tgatgatcaa tgtgtactat gtgaaaagga agctgtgaac    840
gtgtcgcttg aaacctgtt  gacataccca tttgtaaggg atggattgag gaacaagaca    900
ctcgcgctca agggtggtca ctatgacttt gttaacggga cctttgagct gtgggcactt    960
gactttgggc tttcgtctcc tacctctgta tga                                 993
```

<210> SEQ ID NO 119
<211> LENGTH: 330
<212> TYPE: PRT
<213> ORGANISM: Flaveria bidentis

<400> SEQUENCE: 119

```
Met Ser Ala Ala Ser Ala Phe Ala Met Asn Ala Pro Ser Phe Val Asn
1               5                   10                  15

Ala Ser Ser Leu Lys Lys Ala Ser Thr Ser Ala Arg Ser Gly Val Leu
            20                  25                  30

Ser Ala Arg Phe Thr Cys Asn Ser Ser Ser Ser Ser Ser Ser Ser Ala
        35                  40                  45

Thr Pro Pro Ser Leu Ile Arg Asn Glu Pro Val Phe Ala Ala Pro Ala
    50                  55                  60

Pro Ile Ile Thr Pro Asn Trp Thr Glu Asp Gly Asn Glu Ser Tyr Glu
65                  70                  75                  80

Glu Ala Ile Asp Ala Leu Lys Lys Thr Leu Ile Glu Lys Gly Glu Leu
                85                  90                  95

Glu Pro Val Ala Ala Thr Arg Ile Asp Gln Ile Thr Ala Gln Ala Ala
            100                 105                 110

Ala Pro Asp Thr Lys Ala Pro Phe Asp Pro Val Glu Arg Ile Lys Ser
        115                 120                 125

Gly Phe Val Lys Phe Lys Thr Glu Lys Phe Val Thr Asn Pro Ala Leu
    130                 135                 140

Tyr Asp Glu Leu Ala Lys Gly Gln Ser Pro Lys Phe Met Val Phe Ala
145                 150                 155                 160

Cys Ser Asp Ser Arg Val Cys Pro Ser His Val Leu Asp Phe Gln Pro
                165                 170                 175

Gly Glu Ala Phe Val Val Arg Asn Val Ala Asn Met Val Pro Pro Phe
            180                 185                 190

Asp Lys Thr Lys Tyr Ser Gly Val Gly Ala Ala Val Glu Tyr Ala Val
        195                 200                 205

Leu His Leu Lys Val Gln Glu Ile Phe Val Ile Gly His Ser Arg Cys
    210                 215                 220
```

```
Gly Gly Ile Lys Gly Leu Met Thr Phe Pro Asp Glu Gly Pro His Ser
225                 230                 235                 240

Thr Asp Phe Ile Glu Asp Trp Val Lys Val Cys Leu Pro Ala Lys Ser
            245                 250                 255

Lys Val Val Ala Glu His Asn Gly Thr His Leu Asp Asp Gln Cys Val
        260                 265                 270

Leu Cys Glu Lys Glu Ala Val Asn Val Ser Leu Gly Asn Leu Leu Thr
    275                 280                 285

Tyr Pro Phe Val Arg Asp Gly Leu Arg Asn Lys Thr Leu Ala Leu Lys
290                 295                 300

Gly Gly His Tyr Asp Phe Val Asn Gly Thr Phe Glu Leu Trp Ala Leu
305                 310                 315                 320

Asp Phe Gly Leu Ser Ser Pro Thr Ser Val
                325                 330

<210> SEQ ID NO 120
<211> LENGTH: 975
<212> TYPE: DNA
<213> ORGANISM: Hordeum vulgare

<400> SEQUENCE: 120
atgtcgttgc agattgggcg gacagagagg gcccggtccc cggtctttgt ctttgcacac      60
aagcggcaac tgctccatgg acggtgtagt accatcgaca atgcaaattg cagcacctgc     120
agcatgaaaa tcaatagcac ttgtacattg acggccctgc cgattgccgc actgcctggg     180
ccacgtacta cctcacacta ctcgaccgcc gcggctaact ggtgctacgc aaccgtcgcg     240
ccccgtgccc gctcctccac catcgccgcc agcctcggca ccccgcgcc ctcctcctcc      300
gcctccttcc gccccaagct catcaggacc accccgtcc aggccgcgcc cgtcgcacct      360
gcattgatgg acgccgccgt ggagcgcctc aagaccgggt tcgagaagtt caagaccgag     420
gtctacgaca agaagcccga tttcttcgag ccgctcaagg ccggccaggc gcccaagtac     480
atggtgttcg cgtgcgccga ctcgcgtgtg tgcccgtcgg tcaccctggg ccttgagccc     540
ggtgaggcct tcaccatccg caacatcgcc aacatggtcc cggcctactg caagaacaag     600
tacgccggtg ttggatcggc catcgaatac gccgtctgcg cgctcaaggt tgaggtcatc     660
gtggtgattg ccacagccg ctgccggtgga atcaaggctc tgctctcgct caaggatggc     720
gcagacgact ccttccactt cgttgaggac tgggtcagga tcgggttccc ggccaagaag     780
aaggtgcaga ctgagtgcgc ctccatgcct ttcgatgacc agtgcaccgt cctggagaag     840
gaggccgtca acgtgtccct ccagaacctc ttgacctacc cgttcgtcaa ggagggtgtg     900
accaacggaa ccctcaagct cgtcggcggc cactacgact tcgtctccgg caagttcgaa     960
acatgggagc agtaa                                                     975

<210> SEQ ID NO 121
<211> LENGTH: 324
<212> TYPE: PRT
<213> ORGANISM: Hordeum vulgare

<400> SEQUENCE: 121

Met Ser Leu Gln Ile Gly Arg Thr Glu Arg Ala Arg Ser Pro Val Phe
1               5                   10                  15

Val Phe Ala His Lys Arg Gln Leu Leu His Gly Arg Cys Ser Thr Ile
            20                  25                  30

Asp Asn Ala Asn Cys Ser Thr Cys Ser Met Lys Ile Asn Ser Thr Cys
        35                  40                  45
```

Thr Leu Thr Ala Leu Pro Ile Ala Ala Leu Pro Gly Pro Arg Thr Thr
50                  55                  60

Ser His Tyr Ser Thr Ala Ala Asn Trp Cys Tyr Ala Thr Val Ala
65                  70                  75                  80

Pro Arg Ala Arg Ser Ser Thr Ile Ala Ala Ser Leu Gly Thr Pro Ala
                85                  90                  95

Pro Ser Ser Ser Ala Ser Phe Arg Pro Lys Leu Ile Arg Thr Thr Pro
                100                 105                 110

Val Gln Ala Ala Pro Val Ala Pro Ala Leu Met Asp Ala Ala Val Glu
                115                 120                 125

Arg Leu Lys Thr Gly Phe Glu Lys Phe Lys Thr Glu Val Tyr Asp Lys
                130                 135                 140

Lys Pro Asp Phe Phe Glu Pro Leu Lys Ala Gly Gln Ala Pro Lys Tyr
145                 150                 155                 160

Met Val Phe Ala Cys Ala Asp Ser Arg Val Cys Pro Ser Val Thr Leu
                165                 170                 175

Gly Leu Glu Pro Gly Glu Ala Phe Thr Ile Arg Asn Ile Ala Asn Met
                180                 185                 190

Val Pro Ala Tyr Cys Lys Asn Lys Tyr Ala Gly Val Gly Ser Ala Ile
                195                 200                 205

Glu Tyr Ala Val Cys Ala Leu Lys Val Glu Val Ile Val Ile Gly
210                 215                 220

His Ser Arg Cys Gly Gly Ile Lys Ala Leu Leu Ser Leu Lys Asp Gly
225                 230                 235                 240

Ala Asp Asp Ser Phe His Phe Val Glu Asp Trp Val Arg Ile Gly Phe
                245                 250                 255

Pro Ala Lys Lys Lys Val Gln Thr Glu Cys Ala Ser Met Pro Phe Asp
                260                 265                 270

Asp Gln Cys Thr Val Leu Glu Lys Glu Ala Val Asn Val Ser Leu Gln
                275                 280                 285

Asn Leu Leu Thr Tyr Pro Phe Val Lys Glu Gly Val Thr Asn Gly Thr
                290                 295                 300

Leu Lys Leu Val Gly Gly His Tyr Asp Phe Val Ser Gly Lys Phe Glu
305                 310                 315                 320

Thr Trp Glu Gln

<210> SEQ ID NO 122
<211> LENGTH: 804
<212> TYPE: DNA
<213> ORGANISM: Chlamydomonas reinhardtii

<400> SEQUENCE: 122
atgtcgtcgc ggaatgtcgc taccgctctg cgcatgttcg cgaccctcgg tccgagccag      60
gctggcgagg cctcggccat gatgggcacc ggctcggcgc tgctcgcgca gcgcgcggcc     120
gccctgggcg gcgcctcggc tgttaacaag ggctgcagct gccgctgcgg ccgcgtggcg     180
tgcatgggcg cgtgcatgcc gatgcgccac ctccacgccc accccaaccc gccctcggac     240
cccgaccagg ccctggagta ccttcgcgag ggcaacaagc gcttcgtgaa caacaagccg     300
cacgactcgc accccacgcg caacctggac cgcgtcaagg ccaccgccgc gggccagaag     360
cccttcgccc ccttcctgtc ctgcgccgac tcgcgcgtgc ctgtcgagat catcttcgac     420
cagggcttcg gtgacgtgtt cgtgacgcgc gtggccggca acatcgtgac caacgagatc     480
acggcgtcgc tggagttcgg cacggccgtc ctgggctcca aggtgctcat ggtgctgggc     540
cacagcgctt gcggcgccgt ggcggccacc atgaacggcg ccgccgtgcc tggcgtcatc     600

```
tcctctctct actacagcat cagcccggcc tgcaagaagg ctcaggctgg cgacgttgac    660
ggtgccattg ccgagaacgt caaggtccag atggagcagc tcaaggtgtc gcccgtgctg    720
caggggctcg tgaaggaggg caagctcaag atcgtgggcg cgtgtacga cctggccacc     780 ggcaaggtga ccgagatcgc ctaa                                           804

<210> SEQ ID NO 123
<211> LENGTH: 267
<212> TYPE: PRT
<213> ORGANISM: Chlamydomonas reinhardtii

<400> SEQUENCE: 123

Met Ser Ser Arg Asn Val Ala Thr Ala Leu Arg Met Phe Ala Thr Leu
1               5                   10                  15

Gly Pro Ser Gln Ala Gly Glu Ala Ser Ala Met Met Gly Thr Gly Ser
                20                  25                  30

Ala Leu Leu Ala Gln Arg Ala Ala Ala Leu Gly Gly Ala Ser Ala Val
            35                  40                  45

Asn Lys Gly Cys Ser Cys Arg Cys Gly Arg Val Ala Cys Met Gly Ala
        50                  55                  60

Cys Met Pro Met Arg His Leu His Ala His Pro Asn Pro Pro Ser Asp
65                  70                  75                  80

Pro Asp Gln Ala Leu Glu Tyr Leu Arg Glu Gly Asn Lys Arg Phe Val
                85                  90                  95

Asn Asn Lys Pro His Asp Ser His Pro Thr Arg Asn Leu Asp Arg Val
            100                 105                 110

Lys Ala Thr Ala Ala Gly Gln Lys Pro Phe Ala Phe Leu Ser Cys
        115                 120                 125

Ala Asp Ser Arg Val Pro Val Glu Ile Ile Phe Asp Gln Gly Phe Gly
    130                 135                 140

Asp Val Phe Val Thr Arg Val Ala Gly Asn Ile Val Thr Asn Glu Ile
145                 150                 155                 160

Thr Ala Ser Leu Glu Phe Gly Thr Ala Val Leu Gly Ser Lys Val Leu
                165                 170                 175

Met Val Leu Gly His Ser Ala Cys Gly Ala Val Ala Ala Thr Met Asn
            180                 185                 190

Gly Ala Ala Val Pro Gly Val Ile Ser Ser Leu Tyr Tyr Ser Ile Ser
        195                 200                 205

Pro Ala Cys Lys Lys Ala Gln Ala Gly Asp Val Asp Gly Ala Ile Ala
    210                 215                 220

Glu Asn Val Lys Val Gln Met Glu Gln Leu Lys Val Ser Pro Val Leu
225                 230                 235                 240

Gln Gly Leu Val Lys Glu Gly Lys Leu Lys Ile Val Gly Gly Val Tyr
                245                 250                 255

Asp Leu Ala Thr Gly Lys Val Thr Glu Ile Ala
            260                 265

<210> SEQ ID NO 124
<211> LENGTH: 846
<212> TYPE: DNA
<213> ORGANISM: Oryza sativa

<400> SEQUENCE: 124
ggagcgcgcc gtgcaccgcc tctcacaatg tcgaccgccg ccgccgccgc cgctgcccag     60
agctggtgct tcgccactgt caccccgcgc tcccgcgcca cagtcgtcgc cagcctcgcc    120
```

```
tccccatcac cgtcctcctc ctcctcctcc tccaacagca gcaacctccc ggccccttc    180 cgccccgcc tcatccgcaa caccccgtc ttcgccgccc ccgtcgcccc cgccgcgatg     240
gacgccgccg tcgaccgcct caaggatggg ttcgccaagt tcaagaccga gttctatgac   300
aagaagccgg agctcttcga gccgctcaag gccggccagg cacccaagta catggtgttc   360
tcgtgcgccg actctcgcgt gtgcccgtcg gtgaccatgg gcctggagcc cggcgaggcc   420
ttcaccgtcc gcaacatcgc caacatggtc cagcttact gcaagatcaa gcacgctggc    480
gtcgggtcgg ccatcgagta cgccgtctgc gccctcaagg tcgaactcat cgtggtgatt   540
ggccacagcc gctgcggtgg aatcaaggcc ctcctctcac tcaaggatgg agcaccagac   600
tccttccact tcgtcgagga ctgggtcagg accggtttcc ccgccaagaa gaaggttcag   660
accgagcacg cctcgctgcc tttcgatgac caatgcgcca tcttggagaa ggaggccgtg   720
aaccaatccc tggagaacct caagacctac ccgttcgtca aggaggggat cgccaacggc   780
accctcaagc tcgtcggcgg ccactacgac ttcgtctccg gcaacttgga cttatgggag   840
ccctaa                                                              846

<210> SEQ ID NO 125
<211> LENGTH: 273
<212> TYPE: PRT
<213> ORGANISM: Oryza sativa

<400> SEQUENCE: 125

Met Ser Thr Ala Ala Ala Ala Ala Ala Gln Ser Trp Cys Phe Ala
1               5                   10                  15

Thr Val Thr Pro Arg Ser Arg Ala Thr Val Val Ala Ser Leu Ala Ser
                20                  25                  30

Pro Ser Pro Ser Ser Ser Ser Ser Ser Asn Ser Ser Asn Leu
            35                  40                  45

Pro Ala Pro Phe Arg Pro Arg Leu Ile Arg Asn Thr Pro Val Phe Ala
        50                  55                  60

Ala Pro Val Ala Pro Ala Ala Met Asp Ala Ala Val Asp Arg Leu Lys
65                  70                  75                  80

Asp Gly Phe Ala Lys Phe Lys Thr Glu Phe Tyr Asp Lys Lys Pro Glu
                85                  90                  95

Leu Phe Glu Pro Leu Lys Ala Gly Gln Ala Pro Lys Tyr Met Val Phe
            100                 105                 110

Ser Cys Ala Asp Ser Arg Val Cys Pro Ser Val Thr Met Gly Leu Glu
        115                 120                 125

Pro Gly Glu Ala Phe Thr Val Arg Asn Ile Ala Asn Met Val Pro Ala
130                 135                 140

Tyr Cys Lys Ile Lys His Ala Gly Val Gly Ser Ala Ile Glu Tyr Ala
145                 150                 155                 160

Val Cys Ala Leu Lys Val Glu Leu Ile Val Val Ile Gly His Ser Arg
                165                 170                 175

Cys Gly Gly Ile Lys Ala Leu Leu Ser Leu Lys Asp Gly Ala Pro Asp
            180                 185                 190

Ser Phe His Phe Val Glu Asp Trp Val Arg Thr Gly Phe Pro Ala Lys
        195                 200                 205

Lys Lys Val Gln Thr Glu His Ala Ser Leu Pro Phe Asp Asp Gln Cys
    210                 215                 220

Ala Ile Leu Glu Lys Glu Ala Val Asn Gln Ser Leu Glu Asn Leu Lys
225                 230                 235                 240

Thr Tyr Pro Phe Val Lys Glu Gly Ile Ala Asn Gly Thr Leu Lys Leu
```

```
                245                 250                 255
Val Gly Gly His Tyr Asp Phe Val Ser Gly Asn Leu Asp Leu Trp Glu
            260                 265                 270

Pro

<210> SEQ ID NO 126
<211> LENGTH: 993
<212> TYPE: DNA
<213> ORGANISM: Arabidopsis thaliana

<400> SEQUENCE: 126
atggtcccct tttggactac agtttctcga aatggctcat cagactcaga gacgactctc     60
caatctgctt caaaagccac aaaacagtat aaatatcctt ctcttcgtcc ctctcatcgc    120
ctgtctctcc tcttcctctt cccgttccat ttatccgcaa acggagcttg ttttcggtgc    180
acctgcttca gccacttcaa acttgaactg agaaggatgg gaaacgaatc atatgaagac    240
gccatcgaag ctctcaagaa gcttctcatt gagaaggatg atctgaagga tgtagctgcg    300
gccaaggtga agaagatcac ggcggagctt caggcagcct cgtcatcgga cagcaaatct    360
tttgatcccg tcgaacgaat taaggaaggc ttcgtcacct tcaagaagga gaaatacgag    420
accaatcctg ctttgtatgg tgagctcgcc aaaggtcaaa gcccaaagta catggtgttt    480
gcttgttcgg actcacgagt gtgcccatca cacgtactag acttccatcc tggagatgcc    540
ttcgtggttc gtaatatcgc caatatggtt cctccttttg acaaggtcaa atatgcagga    600
gttggagccg ccattgaata cgctgtcttg caccttaagg tggaaaacat tgtggtgata    660
gggcacagtg catgtggtgg catcaagggg cttatgtcat ttcctcttga cggaaacaac    720
tctactgact tcatagagga ttgggtcaaa atctgtttac cagcaaagtc aaaagttttg    780
gcagaaagtg aaagttcagc atttgaagac caatgtggcc gatgcgaaag ggcagtgaat    840
gtgtcactag caaacctatt gacatatcca tttgtgagag aaggagttgt gaaaggaaca    900
cttgctttga agggaggcta ctatgacttt gttaatggct cctttgagct ttgggagctc    960
cagtttggaa tttcccccgt tcattctata tga                                 993

<210> SEQ ID NO 127
<211> LENGTH: 347
<212> TYPE: PRT
<213> ORGANISM: Arabidopsis thaliana

<400> SEQUENCE: 127

Met Ser Thr Ala Pro Leu Ser Gly Phe Phe Leu Thr Ser Leu Ser Pro
1               5                   10                  15

Ser Gln Ser Ser Leu Gln Lys Leu Ser Leu Arg Thr Ser Thr Val
            20                  25                  30

Ala Cys Leu Pro Pro Ala Ser Ser Ser Ser Ser Ser Ser Ser
        35                  40                  45

Ser Ser Arg Ser Val Pro Thr Leu Ile Arg Asn Glu Pro Val Phe Ala
    50                  55                  60

Ala Pro Ala Pro Ile Ile Ala Pro Tyr Trp Ser Glu Glu Met Gly Thr
65                  70                  75                  80

Glu Ala Tyr Asp Glu Ala Ile Glu Ala Leu Lys Lys Leu Leu Ile Glu
                85                  90                  95

Lys Glu Glu Leu Lys Thr Val Ala Ala Ala Lys Val Glu Gln Ile Thr
            100                 105                 110

Ala Ala Leu Gln Thr Gly Thr Ser Ser Asp Lys Lys Ala Phe Asp Pro
        115                 120                 125
```

| | | | | | | | | | | | | |
|---|---|---|---|---|---|---|---|---|---|---|---|---|
| Val | Glu | Thr | Ile | Lys | Gln | Gly | Phe | Ile | Lys | Phe | Lys | Lys | Glu | Lys | Tyr |
| | 130 | | | | 135 | | | | | 140 | | | | | |

Val Glu Thr Ile Lys Gln Gly Phe Ile Lys Phe Lys Lys Glu Lys Tyr
            130                 135                 140

Glu Thr Asn Pro Ala Leu Tyr Gly Glu Leu Ala Lys Gly Gln Ser Pro
145                 150                 155                 160

Lys Tyr Met Val Phe Ala Cys Ser Asp Ser Arg Val Cys Pro Ser His
                165                 170                 175

Val Leu Asp Phe Gln Pro Gly Asp Ala Phe Val Val Arg Asn Ile Ala
            180                 185                 190

Asn Met Val Pro Pro Phe Asp Lys Val Lys Tyr Gly Gly Val Gly Ala
            195                 200                 205

Ala Ile Glu Tyr Ala Val Leu His Leu Lys Val Glu Asn Ile Val Val
210                 215                 220

Ile Gly His Ser Ala Cys Gly Gly Ile Lys Gly Leu Met Ser Phe Pro
225                 230                 235                 240

Leu Asp Gly Asn Asn Ser Thr Asp Phe Ile Glu Asp Trp Val Lys Ile
            245                 250                 255

Cys Leu Pro Ala Lys Ser Lys Val Ile Ser Glu Leu Gly Asp Ser Ala
            260                 265                 270

Phe Glu Asp Gln Cys Gly Arg Cys Glu Arg Glu Ala Val Asn Val Ser
            275                 280                 285

Leu Ala Asn Leu Leu Thr Tyr Pro Phe Val Arg Glu Gly Leu Val Lys
290                 295                 300

Gly Thr Leu Ala Leu Lys Gly Gly Tyr Tyr Asp Phe Val Lys Gly Ala
305                 310                 315                 320

Phe Glu Leu Trp Gly Leu Glu Phe Gly Leu Ser Glu Thr Ser Ser Val
            325                 330                 335

Lys Asp Val Ala Thr Ile Leu His Trp Lys Leu
            340                 345

<210> SEQ ID NO 128
<211> LENGTH: 990
<212> TYPE: DNA
<213> ORGANISM: Flaveria pringlei

<400> SEQUENCE: 128

```
atgtcgaccg cctctgcttt cgccattaat gcgccttcgt tcgtcaacgc ttcgtcgctg      60
aagaagtcgt cttcttcagc cagatctggt gtgttgtccg ccagatttac gtgcaattcg     120
tcgtcgtctt cttcgtctgc tactcctccg agtctcattc gtaacgagcc tgttttcgct     180
gctccggctc ctatcatcac accgaattgg accgaagatg gaaatgaatc atacgaggaa     240
gccattgacg cactcaagaa aatgctcatt gaaaagggtg agttagaacc agttgccgct     300
gcaagaatcg accaaatcac agctcaagcc gcagcacccg acaccaaagc tccatttgac     360
cctgttgaga ggatcaaatc cggcttcgtg aagttcaaga cagagaaatt cgtcacaaac     420
ccggtcttgt acgatgagct tgctaaaggc caaagcccaa agttcatggt gtttgcatgc     480
tcagactcgc gtgtttgccc atcacacgtt cttgatttcc agcccggtga ggcgtttgtt     540
gtccgtaacg ttgccaacat ggtccctccc tttgacaaga ccaaatattc tggagtagga     600
gctgctgttg agtatgcagt tttgcatcta aaggtacaag aaatatttgt aattgggcat     660
agccgttgtg gagggatcaa gggtctcatg actttcccag acgaaggacc tcactcaacc     720
gatttcatcg aagattgggt gaaagtatgt ctccccgcga agtcaaaagt ggtagcagaa     780
cacaacggca cacatcttga tgatcaatgt gtactatgtg aaaaggaagc tgtgaacgtg     840
tcgcttggaa acctgttgac atacccattt gtaagggatg gattgaggaa caatacactc     900
```

```
gcgctcaagg gtggtcacta tgactttgtt aacgggacct ttgagctgtg ggcacttgac      960
tttggccttt cgtctcctac ctctgtatga                                       990
```

<210> SEQ ID NO 129
<211> LENGTH: 329
<212> TYPE: PRT
<213> ORGANISM: Flaveria pringlei

<400> SEQUENCE: 129

```
Met Ser Thr Ala Ser Ala Phe Ala Ile Asn Ala Pro Ser Phe Val Asn
1               5                   10                  15

Ala Ser Ser Leu Lys Lys Ser Ser Ser Ala Arg Ser Gly Val Leu
            20                  25                  30

Ser Ala Arg Phe Thr Cys Asn Ser Ser Ser Ser Ser Ala Thr
        35                  40                  45

Pro Pro Ser Leu Ile Arg Asn Glu Pro Val Phe Ala Ala Pro Ala Pro
50                  55                  60

Ile Ile Thr Pro Asn Trp Thr Glu Asp Gly Asn Glu Ser Tyr Glu Glu
65                  70                  75                  80

Ala Ile Asp Ala Leu Lys Lys Met Leu Ile Glu Lys Gly Glu Leu Glu
                85                  90                  95

Pro Val Ala Ala Ala Arg Ile Asp Gln Ile Thr Ala Gln Ala Ala Ala
            100                 105                 110

Pro Asp Thr Lys Ala Pro Phe Asp Pro Val Glu Arg Ile Lys Ser Gly
        115                 120                 125

Phe Val Lys Phe Lys Thr Glu Lys Phe Val Thr Asn Pro Val Leu Tyr
130                 135                 140

Asp Glu Leu Ala Lys Gly Gln Ser Pro Lys Phe Met Val Phe Ala Cys
145                 150                 155                 160

Ser Asp Ser Arg Val Cys Pro Ser His Val Leu Asp Phe Gln Pro Gly
                165                 170                 175

Glu Ala Phe Val Val Arg Asn Val Ala Asn Met Val Pro Pro Phe Asp
            180                 185                 190

Lys Thr Lys Tyr Ser Gly Val Gly Ala Ala Val Glu Tyr Ala Val Leu
        195                 200                 205

His Leu Lys Val Gln Glu Ile Phe Val Ile Gly His Ser Arg Cys Gly
210                 215                 220

Gly Ile Lys Gly Leu Met Thr Phe Pro Asp Glu Gly Pro His Ser Thr
225                 230                 235                 240

Asp Phe Ile Glu Asp Trp Val Lys Val Cys Leu Pro Ala Lys Ser Lys
                245                 250                 255

Val Val Ala Glu His Asn Gly Thr His Leu Asp Asp Gln Cys Val Leu
            260                 265                 270

Cys Glu Lys Glu Ala Val Asn Val Ser Leu Gly Asn Leu Leu Thr Tyr
        275                 280                 285

Pro Phe Val Arg Asp Gly Leu Arg Asn Asn Thr Leu Ala Leu Lys Gly
290                 295                 300

Gly His Tyr Asp Phe Val Asn Gly Thr Phe Glu Leu Trp Ala Leu Asp
305                 310                 315                 320

Phe Gly Leu Ser Ser Pro Thr Ser Val
                325
```

<210> SEQ ID NO 130
<211> LENGTH: 993
<212> TYPE: DNA

<213> ORGANISM: Flaveria linearis

<400> SEQUENCE: 130

```
atgtcgaccg cctctgcttt cgccattaac gcgccttcgt tcgtcaacgc ttcatcgctg    60
aagaagtcgt cgacttcttc agccagatct ggtgtgttgt ccgccagatt tacgtgcaat   120
tcgtcgtcgt cttcttcgtc tgcaactcct ccgagtctca ttcgtaacga gcctgttttc   180
gctgccccgg cgcccatcat aacaccgaat tggaccgaag acggaaatga atcatacgag   240
gaagccattg acgcactcaa gaaaatgctc attgaaaagg gtgagttaga acccgttgcc   300
gctgcaagaa tcgaccaaat cacagctcaa gccgcagcac ccgacaccaa agctccattc   360
gaccctgttg agaggatcaa atccggcttc gtgaagttca agacagagaa attcgtaaca   420
aacccagccc tgtacgatga gcttgctaaa ggccaaagcc caaagttcat ggtgtttgca   480
tgctcagact cgcgtgtttg cccatcacac gttcttgatt tccagcccgg tgaggcgttt   540
gttgtccgta acgttgccaa catggtccct ccctttgaca agaccaaata ttctggagta   600
ggagctgctg ttgagtatgc agttttgcat ctaaaggtac aagaaatatt tgtaattggg   660
catagccgtt gcggagggat caagggtctc atgactttcc cagacgaagg acctcactca   720
actgatttca tcgaagattg ggtgaaagta tgcctccccg caaagtcaaa agtggtagca   780
gaacacaacg gcacacatct tgatgatcaa tgtgtacaat gtgaaaagga agctgtgaac   840
gtgtcgcttg aaacctgtt gacatacca tttgtaaggg atggtttgag gaacaataca   900
ctcgcgctca agggtggtca ctatgatttt gttaacggga cctttgagct gtgggcactt   960
gactttgggc tttcgtctcc tacctctgta tga                                993
```

<210> SEQ ID NO 131
<211> LENGTH: 330
<212> TYPE: PRT
<213> ORGANISM: Flaveria linearis

<400> SEQUENCE: 131

```
Met Ser Thr Ala Ser Ala Phe Ala Ile Asn Ala Pro Ser Phe Val Asn
1               5                   10                  15

Ala Ser Ser Leu Lys Lys Ser Ser Thr Ser Ser Ala Arg Ser Gly Val
            20                  25                  30

Leu Ser Ala Arg Phe Thr Cys Asn Ser Ser Ser Ser Ser Ser Ser Ala
        35                  40                  45

Thr Pro Pro Ser Leu Ile Arg Asn Glu Pro Val Phe Ala Ala Pro Ala
    50                  55                  60

Pro Ile Ile Thr Pro Asn Trp Thr Glu Asp Gly Asn Glu Ser Tyr Glu
65                  70                  75                  80

Glu Ala Ile Asp Ala Leu Lys Lys Met Leu Ile Glu Lys Gly Glu Leu
                85                  90                  95

Glu Pro Val Ala Ala Ala Arg Ile Asp Gln Ile Thr Ala Gln Ala Ala
            100                 105                 110

Ala Pro Asp Thr Lys Ala Pro Phe Asp Pro Val Glu Arg Ile Lys Ser
        115                 120                 125

Gly Phe Val Lys Phe Lys Thr Glu Lys Phe Val Thr Asn Pro Ala Leu
    130                 135                 140

Tyr Asp Glu Leu Ala Lys Gly Gln Ser Pro Lys Phe Met Val Phe Ala
145                 150                 155                 160

Cys Ser Asp Ser Arg Val Cys Pro Ser His Val Leu Asp Phe Gln Pro
                165                 170                 175

Gly Glu Ala Phe Val Val Arg Asn Val Ala Asn Met Val Pro Pro Phe
```

-continued

```
                      180                 185                 190
Asp Lys Thr Lys Tyr Ser Gly Val Gly Ala Ala Val Glu Tyr Ala Val
                  195                 200                 205
Leu His Leu Lys Val Gln Glu Ile Phe Val Ile Gly His Ser Arg Cys
              210                 215                 220
Gly Gly Ile Lys Gly Leu Met Thr Phe Pro Asp Gly Pro His Ser
225                 230                 235                 240
Thr Asp Phe Ile Glu Asp Trp Val Lys Val Cys Leu Pro Ala Lys Ser
                  245                 250                 255
Lys Val Val Ala Glu His Asn Gly Thr His Leu Asp Asp Gln Cys Val
              260                 265                 270
Gln Cys Glu Lys Glu Ala Val Asn Val Ser Leu Gly Asn Leu Leu Thr
          275                 280                 285
Tyr Pro Phe Val Arg Asp Gly Leu Arg Asn Asn Thr Leu Ala Leu Lys
      290                 295                 300
Gly Gly His Tyr Asp Phe Val Asn Gly Thr Phe Glu Leu Trp Ala Leu
305                 310                 315                 320
Asp Phe Gly Leu Ser Ser Pro Thr Ser Val
                  325                 330

<210> SEQ ID NO 132
<211> LENGTH: 993
<212> TYPE: DNA
<213> ORGANISM: Flaveria brownii

<400> SEQUENCE: 132
atgtcgaccg cctctgcttt cgccactaac gtgccttcgt tcgtcaacgc ttcatcgctg      60
aagaagtcgt ccacttcttc agccagatct ggtgtgttgt ccgccaaatt tacgtgcaat     120
tcgtcgtcgt cttcttcgtc tgcaactcct ccgagtctca ttcgtaacga gcctgttttc     180
gctgctccgg cgcccatcat cacaccgaat tggaccgaag acggaaatga atcatacgag     240
gaagccattg acgcactcaa gaaaatgctc attgaaaagg gtgagttaga accagttgcg     300
gctgcaagaa tcgaccaaat cacagctcaa gccgcggcac ccgacaccaa agctccattc     360
gaccctgttg agaggatcaa atccggcttc gtgaagttca agactgagaa attcgtaaca     420
aacccagccc tgtacgatga gcttgctaaa ggccaaagcc caaagttcat ggtgtttgca     480
tgctcagact cgcgtgtttg cccatcacac gttcttgatt ccagcccgg tgaggcgttt      540 gttgtccgta acgttgccaa catggtccct ccctttgaca agaccaaata ttctggagta     600
ggagctgctg ttgagtatgc agttttgcat ctgaaggtac aagaaatatt tgtaattggg     660
catagccgtt gcggagggat caagggtctc atgactttcc cagacgaagg acctcactca     720
accgatttca tcgaagattg ggtgaaagta tgcctccccg cgaagtcaaa gtggtagca      780 gaacacaacg gcacacatct tgatgatcaa tgtgtactat gtgaaaagga agctgtgaac     840
gtgtcgcttg gaaacctgtt gacatacccca tttgtaaggg atggtttgag gaacaataca     900
ctcgcgctca agggtggtca ctatgatttt gttaacggga cctttgagct gtgggcactt     960
gactttgggc tttcgtctcc tacctctgta tga                                  993

<210> SEQ ID NO 133
<211> LENGTH: 330
<212> TYPE: PRT
<213> ORGANISM: Flaveria brownii

<400> SEQUENCE: 133

Met Ser Thr Ala Ser Ala Phe Ala Thr Asn Val Pro Ser Phe Val Asn
```

```
                1               5              10              15
Ala Ser Ser Leu Lys Lys Ser Thr Ser Ser Ala Arg Ser Gly Val
                  20              25              30

Leu Ser Ala Lys Phe Thr Cys Asn Ser Ser Ser Ser Ser Ser Ala
                  35              40                  45

Thr Pro Pro Ser Leu Ile Arg Asn Glu Pro Val Phe Ala Ala Pro Ala
                50              55              60

Pro Ile Ile Thr Pro Asn Trp Thr Glu Asp Gly Asn Glu Ser Tyr Glu
 65              70              75                  80

Glu Ala Ile Asp Ala Leu Lys Lys Met Leu Ile Glu Lys Gly Glu Leu
                  85              90              95

Glu Pro Val Ala Ala Ala Arg Ile Asp Gln Ile Thr Ala Gln Ala Ala
                 100             105             110

Ala Pro Asp Thr Lys Ala Pro Phe Asp Pro Val Glu Arg Ile Lys Ser
                 115             120             125

Gly Phe Val Lys Phe Lys Thr Glu Lys Phe Val Thr Asn Pro Ala Leu
                 130             135             140

Tyr Asp Glu Leu Ala Lys Gly Gln Ser Pro Lys Phe Met Val Phe Ala
145                 150             155             160

Cys Ser Asp Ser Arg Val Cys Pro Ser His Val Leu Asp Phe Gln Pro
                 165             170             175

Gly Glu Ala Phe Val Val Arg Asn Val Ala Asn Met Val Pro Pro Phe
                 180             185             190

Asp Lys Thr Lys Tyr Ser Gly Val Gly Ala Ala Val Glu Tyr Ala Val
                 195             200             205

Leu His Leu Lys Val Gln Glu Ile Phe Val Ile Gly His Ser Arg Cys
 210             215             220

Gly Gly Ile Lys Gly Leu Met Thr Phe Pro Asp Glu Gly Pro His Ser
225             230             235             240

Thr Asp Phe Ile Glu Asp Trp Val Lys Val Cys Leu Pro Ala Lys Ser
                 245             250             255

Lys Val Val Ala Glu His Asn Gly Thr His Leu Asp Asp Gln Cys Val
                 260             265             270

Leu Cys Glu Lys Glu Ala Val Asn Val Ser Leu Gly Asn Leu Leu Thr
                 275             280             285

Tyr Pro Phe Val Arg Asp Gly Leu Arg Asn Asn Thr Leu Ala Leu Lys
                 290             295             300

Gly Gly His Tyr Asp Phe Val Asn Gly Thr Phe Glu Leu Trp Ala Leu
305             310             315             320

Asp Phe Gly Leu Ser Ser Pro Thr Ser Val
                 325             330

<210> SEQ ID NO 134
<211> LENGTH: 969
<212> TYPE: DNA
<213> ORGANISM: Nicotiana paniculata

<400> SEQUENCE: 134
atgtcaactg cttccattaa cagttgcctt actatctccc cagctcaagc ttcccttaag      60
aaaccaattc gtcctgttgc ttttgctagg cttagcaaca cctcttcttc ttcttcttcc     120
gttcccagtc tcatcagaaa cgagcccgtc ttcgccgccc caactcccat catcaacccc     180
attttgagag aagaaatggc aaaggaatcc tatgagcagg ccattgctgc actcgagaaa     240
ctcctcagcg aaaaaggaga acttggacca attgctgcag caagagttga ccagattaca     300
```

-continued

```
gctgaattgc aatcatcaga tggcagcaaa ccattcgacc ctgttgagca catgaaagct    360
ggctttattc acttcaaaac tgagaaatac gagaagaacc cagccttata tggggaacta    420
tcaaaaggcc agagcccaa gttcatggtc tttgcctgct ctgactctcg agtgtgccca     480
tcacatgttc tgaacttcca acctggtgag gctttcgtgg tccgaaacat cgccaacatg    540
gtccccgctt atgacaagac cagatactct ggtgtcggag cagctatcga atacgctgtt    600
ctccacctta aggtagagaa cattgttgtc attggccaca gcgcatgtgg aggtatcaaa    660
ggtctcatgt ctctatctgc agatggttct gaatcaactg cctttattga ggattgggtg    720
aaaattggtt tacctgccaa ggccaaggtg gagggtgaac acgcggataa atgttttgca    780
gatcaatgca cagcttgtga aggaagct gtgaatgtgt cacttggaaa tttgctgacc       840
tatccatttg tgagagaagg tttggtgaag aaaacactag cattgaaggg aggtcactat     900
gattttgtga atggaggatt tgagctgtgg ggacttgagt tcggtctttc tccttctctt     960
tccgtatga                                                             969
```

<210> SEQ ID NO 135
<211> LENGTH: 322
<212> TYPE: PRT
<213> ORGANISM: Nicotiana paniculata

<400> SEQUENCE: 135

```
Met Ser Thr Ala Ser Ile Asn Ser Cys Leu Thr Ile Ser Pro Ala Gln
1               5                   10                  15

Ala Ser Leu Lys Lys Pro Ile Arg Pro Val Ala Phe Ala Arg Leu Ser
            20                  25                  30

Asn Thr Ser Ser Ser Ser Ser Val Pro Ser Leu Ile Arg Asn Glu
        35                  40                  45

Pro Val Phe Ala Ala Pro Thr Pro Ile Ile Asn Pro Ile Leu Arg Glu
    50                  55                  60

Glu Met Ala Lys Glu Ser Tyr Glu Gln Ala Ile Ala Ala Leu Glu Lys
65                  70                  75                  80

Leu Leu Ser Glu Lys Gly Glu Leu Gly Pro Ile Ala Ala Ala Arg Val
                85                  90                  95

Asp Gln Ile Thr Ala Glu Leu Gln Ser Ser Asp Gly Ser Lys Pro Phe
            100                 105                 110

Asp Pro Val Glu His Met Lys Ala Gly Phe Ile His Phe Lys Thr Glu
        115                 120                 125

Lys Tyr Glu Lys Asn Pro Ala Leu Tyr Gly Glu Leu Ser Lys Gly Gln
    130                 135                 140

Ser Pro Lys Phe Met Val Phe Ala Cys Ser Asp Ser Arg Val Cys Pro
145                 150                 155                 160

Ser His Val Leu Asn Phe Gln Pro Gly Glu Ala Phe Val Val Arg Asn
                165                 170                 175

Ile Ala Asn Met Val Pro Ala Tyr Asp Lys Thr Arg Tyr Ser Gly Val
            180                 185                 190

Gly Ala Ala Ile Glu Tyr Ala Val Leu His Leu Lys Val Glu Asn Ile
        195                 200                 205

Val Val Ile Gly His Ser Ala Cys Gly Gly Ile Lys Gly Leu Met Ser
    210                 215                 220

Leu Ser Ala Asp Gly Ser Glu Ser Thr Ala Phe Ile Glu Asp Trp Val
225                 230                 235                 240

Lys Ile Gly Leu Pro Ala Lys Ala Lys Val Glu Gly Glu His Ala Asp
                245                 250                 255
```

Lys Cys Phe Ala Asp Gln Cys Thr Ala Cys Glu Lys Glu Ala Val Asn
              260                 265                 270

Val Ser Leu Gly Asn Leu Leu Thr Tyr Pro Phe Val Arg Glu Gly Leu
            275                 280                 285

Val Lys Lys Thr Leu Ala Leu Lys Gly Gly His Tyr Asp Phe Val Asn
            290                 295                 300

Gly Gly Phe Glu Leu Trp Gly Leu Glu Phe Gly Leu Ser Pro Ser Leu
305                 310                 315                 320

Ser Val

<210> SEQ ID NO 136
<211> LENGTH: 966
<212> TYPE: DNA
<213> ORGANISM: Nicotiana tabacum

<400> SEQUENCE: 136
atgtcaactg cttccattaa cagttgcctt actatctccc ctgctcaagc ttcccttaag    60
aaaccaactc gtcctgttgc ttttgcaagg cttagcaact cttcttcttc tacttctgtt   120
cccagtctca tcagaaacga gcccgtcttc gccgccccta ctcccatcat caacccattt   180
ttgagagaag aaatggcaaa ggaatcctat gagcaggcca ttgctgcact cgagaaactc   240
ctcagcgaaa aggagaact tggaccaatt gctgcagcaa gagttgacca gattacagct   300
gaattgcaat catcagatgg cagcaaacca ttcgaccctg ttgagcacat gaaagctggc   360
tttattcact tcaaaactga gaatacgag aagaacccag ccttatatgg ggaactatca   420
aaaggccaga gccccaagtt catggtcttt gcctgctctg actctcgagt gtgcccatca   480
catgtcctga acttccaacc tggtgaggct ttcgtggtcc gaaacatcgc caacatggtc   540
cctgcttatg acaagaccag atactccgga gtcggagcag ctatcgaata cgctgttctt   600
caccttaagg tagagaacat tgttgtcatt ggccatagcg catgtggagg tatcaaaggt   660
ctcatgtctt tacctgcaga tggttctgaa tcaactgcct tcattgagga ttgggtgaaa   720
attggtttac tgccaaggc gaaggtgcag ggtgaacacg tggataaatg ttttgcagat   780
caatgcacag cttgtgagaa ggaagctgtg aatgtgtcac ttggaaattt gctgacctat   840
ccatttgtga gaagggtttt ggtgaagaaa acactagcat tgaagggagg tcactatgat   900
ttcgtgaatg gaggatttga gctgtgggga cttgagttcg gtctttctcc ttctctttcc   960
gtatga                                                             966

<210> SEQ ID NO 137
<211> LENGTH: 321
<212> TYPE: PRT
<213> ORGANISM: Nicotiana tabacum

<400> SEQUENCE: 137

Met Ser Thr Ala Ser Ile Asn Ser Cys Leu Thr Ile Ser Pro Ala Gln
1               5                   10                  15

Ala Ser Leu Lys Lys Pro Thr Arg Pro Val Ala Phe Ala Arg Leu Ser
            20                  25                  30

Asn Ser Ser Ser Ser Thr Ser Val Pro Ser Leu Ile Arg Asn Glu Pro
        35                  40                  45

Val Phe Ala Ala Pro Thr Pro Ile Ile Asn Pro Ile Leu Arg Glu Glu
    50                  55                  60

Met Ala Lys Glu Ser Tyr Glu Gln Ala Ile Ala Ala Leu Glu Lys Leu
65                  70                  75                  80

Leu Ser Glu Lys Gly Glu Leu Gly Pro Ile Ala Ala Ala Arg Val Asp

|   |   |   | 85 |   |   |   | 90 |   |   |   | 95 |   |
|---|---|---|---|---|---|---|---|---|---|---|---|---|

Gln Ile Thr Ala Glu Leu Gln Ser Ser Asp Gly Ser Lys Pro Phe Asp
             100                 105                 110

Pro Val Glu His Met Lys Ala Gly Phe Ile His Phe Lys Thr Glu Lys
         115                 120                 125

Tyr Glu Lys Asn Pro Ala Leu Tyr Gly Glu Leu Ser Lys Gly Gln Ser
     130                 135                 140

Pro Lys Phe Met Val Phe Ala Cys Ser Asp Ser Arg Val Cys Pro Ser
145                 150                 155                 160

His Val Leu Asn Phe Gln Pro Gly Glu Ala Phe Val Val Arg Asn Ile
                 165                 170                 175

Ala Asn Met Val Pro Ala Tyr Asp Lys Thr Arg Tyr Ser Gly Val Gly
             180                 185                 190

Ala Ala Ile Glu Tyr Ala Val Leu His Leu Lys Val Glu Asn Ile Val
         195                 200                 205

Val Ile Gly His Ser Ala Cys Gly Gly Ile Lys Gly Leu Met Ser Leu
     210                 215                 220

Pro Ala Asp Gly Ser Glu Ser Thr Ala Phe Ile Glu Asp Trp Val Lys
225                 230                 235                 240

Ile Gly Leu Pro Ala Lys Ala Lys Val Gln Gly Glu His Val Asp Lys
                 245                 250                 255

Cys Phe Ala Asp Gln Cys Thr Ala Cys Glu Lys Glu Ala Val Asn Val
             260                 265                 270

Ser Leu Gly Asn Leu Leu Thr Tyr Pro Phe Val Arg Glu Gly Leu Val
         275                 280                 285

Lys Lys Thr Leu Ala Leu Lys Gly Gly His Tyr Asp Phe Val Asn Gly
     290                 295                 300

Gly Phe Glu Leu Trp Gly Leu Glu Phe Gly Leu Ser Pro Ser Leu Ser
305                 310                 315                 320

Val

<210> SEQ ID NO 138
<211> LENGTH: 963
<212> TYPE: DNA
<213> ORGANISM: Populus tremula x Populus tremuloides

<400> SEQUENCE: 138

```
atgtcgactg cttcgattaa cagctggtgt ctcacctctg tctctgcctc taagaaatca    60
ctacccgcat acgtccttc agtctttgca agcctcaact cctctgtttc tcctcctacc   120
cttatcagaa accagcctgt tttcgcagcc cctgctccta ttctctatcc acggagaggc   180
gaagaaatgg gaaacgacta caacgaggcc attgaatctc tcaagaaact cctcagtgac   240
aaggaagagc tgaaaactgt agcagctgcg aaagtggagc agataacagc tgaattacaa   300
accgtctcat cttctgaccc caaggcattc gatcctgttg agaagattaa atccggattc   360
attcacttca gaaggagaaa atatgacaag aatccgggac tgtactccga gcttgccaaa   420
ggccaaagcc ccaagtttat ggtgtttgca tgctcggatt cccgggtttg cccgtcccat   480
gtgcttgatt ccaaccagg ggaagctttt gtggtccgca atgttgcgaa tatggtcccg   540
ccatacgata agactaagta cgctggagtt ggggcagcga tagtacgc agttttgcat   600 ctgaaggtgg aatacattgt ggtcatcgga cacagcgcct gtggtggaat taagggcctc   660
atgtccttcc cgtatgatgg aacaacatca actgatttca tagaagactg ggtcaaagtc   720
tgctacaatg ccaagaccaa gattttagca gaacatgcca actcaccttt cccagacatg   780
```

```
tgtacacaat gtgaaaagga ggcagtgaac gtgtccatcg acacttgct cacctacccg   840 tttgtgagag atggcttggt gaacaaaact ctaggactga agggtggtta ttatgatttt   900
gtcaaaggca gttttgagct ctgggggctt gagtacagcc tctccccctc tctctccgta   960
tga                                                                963
```

```
<210> SEQ ID NO 139
<211> LENGTH: 320
<212> TYPE: PRT
<213> ORGANISM: Populus tremula x Populus tremuloides

<400> SEQUENCE: 139
```

Met Ser Thr Ala Ser Ile Asn Ser Trp Cys Leu Thr Ser Val Ser Ala
1               5                   10                  15

Ser Lys Lys Ser Leu Pro Ala Leu Arg Pro Ser Val Phe Ala Ser Leu
            20                  25                  30

Asn Ser Ser Val Ser Pro Pro Thr Leu Ile Arg Asn Gln Pro Val Phe
        35                  40                  45

Ala Ala Pro Ala Pro Ile Leu Tyr Pro Arg Arg Gly Glu Glu Met Gly
    50                  55                  60

Asn Asp Tyr Asn Glu Ala Ile Glu Ser Leu Lys Lys Leu Leu Ser Asp
65                  70                  75                  80

Lys Glu Glu Leu Lys Thr Val Ala Ala Ala Lys Val Glu Gln Ile Thr
                85                  90                  95

Ala Glu Leu Gln Thr Val Ser Ser Ser Asp Pro Lys Ala Phe Asp Pro
            100                 105                 110

Val Glu Lys Ile Lys Ser Gly Phe Ile His Phe Lys Glu Lys Lys Tyr
        115                 120                 125

Asp Lys Asn Pro Gly Leu Tyr Ser Glu Leu Ala Lys Gly Gln Ser Pro
    130                 135                 140

Lys Phe Met Val Phe Ala Cys Ser Asp Ser Arg Val Cys Pro Ser His
145                 150                 155                 160

Val Leu Asp Phe Gln Pro Gly Glu Ala Phe Val Val Arg Asn Val Ala
                165                 170                 175

Asn Met Val Pro Pro Tyr Asp Lys Thr Lys Tyr Ala Gly Val Gly Ala
            180                 185                 190

Ala Ile Glu Tyr Ala Val Leu His Leu Lys Val Glu Tyr Ile Val Val
        195                 200                 205

Ile Gly His Ser Ala Cys Gly Gly Ile Lys Gly Leu Met Ser Phe Pro
    210                 215                 220

Tyr Asp Gly Thr Thr Ser Thr Asp Phe Ile Glu Asp Trp Val Lys Val
225                 230                 235                 240

Cys Tyr Asn Ala Lys Thr Lys Ile Leu Ala Glu His Ala Asn Ser Pro
                245                 250                 255

Phe Pro Asp Met Cys Thr Gln Cys Glu Lys Glu Ala Val Asn Val Ser
            260                 265                 270

Ile Gly His Leu Leu Thr Tyr Pro Phe Val Arg Asp Gly Leu Val Asn
        275                 280                 285

Lys Thr Leu Gly Leu Lys Gly Tyr Tyr Asp Phe Val Lys Gly Ser
    290                 295                 300

Phe Glu Leu Trp Gly Leu Glu Tyr Ser Leu Ser Pro Ser Leu Ser Val
305                 310                 315                 320

```
<210> SEQ ID NO 140
<211> LENGTH: 963
<212> TYPE: DNA
```

<213> ORGANISM: Populus tremula x Populus tremuloides

<400> SEQUENCE: 140

```
atgtcgactg cttcgattaa cagctggtgt ctcacctctg tctctccctc taagaaatca      60
ctacccgcat tacgtccttc agtctttgca agcctcaact cctctgtttc tcctcctacc     120
cttatcagaa accagcctgt tttcgcagcc cctgctccta ttctctatcc acggagaggc     180
gaagaaatgg gaaacgacta caacgaggcc attgaatctc tcaagaaact cctcagtgat     240
aaggaggagc tgaaaactgt agcagctgcg aaagtggagc agataacagc tgaattacaa     300
accgtctcat cttctgaccc caaggcattc gatcctgttg agaagattaa atccggattc     360
attcacttca agaaggagaa atatgacaag aatccgggac tgtactccga gcttgccaaa     420
ggccaaagcc ccaagtttat ggtgtttgca tgctcggatt cccgggtttg cccgtcccat     480
gtgcttgatt tccaaccggg ggaagctttt gtggtccgca atgttgcgaa tatggtcccg     540
ccatacgata agactaagta cgctggagtt ggggcagcga tagagtacgc agttttgcat     600
ctgaaggtgg aatacattgt ggtcatcgga cacagcgcct gtggtggaat taagggcctc     660
atgtccttcc cgtatgatgg aacaacatca actgatttca tagaagactg ggtcaaagtc     720
tgctacaatg ccaagaccaa gattttagca gaacatgcca actcaccttt cccagacatg     780
tgtacacaat gtgaaaagga ggcagtgaac gtgtccctcg acacttgct cacctacccg      840
tttgtgagag atggcttggt gaacaaaact ctaggcctta agggtggtta ttatgatttt     900
gtcaaaggaa gttttgagct ctggggcctt gagtacagcc tctctccctc tctctccgta     960
tga                                                                   963
```

<210> SEQ ID NO 141
<211> LENGTH: 320
<212> TYPE: PRT
<213> ORGANISM: Populus tremula

<400> SEQUENCE: 141

```
Met Ser Thr Ala Ser Ile Asn Ser Trp Cys Leu Thr Ser Val Ser Pro
1               5                   10                  15

Ser Lys Lys Ser Leu Pro Ala Leu Arg Pro Ser Val Phe Ala Ser Leu
                20                  25                  30

Asn Ser Val Ser Pro Pro Thr Leu Ile Arg Asn Gln Pro Val Phe
            35                  40                  45

Ala Ala Pro Ala Pro Ile Leu Tyr Pro Arg Arg Gly Glu Glu Met Gly
        50                  55                  60

Asn Asp Tyr Asn Glu Ala Ile Glu Ser Leu Lys Lys Leu Leu Ser Asp
65                  70                  75                  80

Lys Glu Glu Leu Lys Thr Val Ala Ala Ala Lys Val Glu Gln Ile Thr
                85                  90                  95

Ala Glu Leu Gln Thr Val Ser Ser Ser Asp Pro Lys Ala Phe Asp Pro
            100                 105                 110

Val Glu Lys Ile Lys Ser Gly Phe Ile His Phe Lys Lys Glu Lys Tyr
        115                 120                 125

Asp Lys Asn Pro Gly Leu Tyr Ser Glu Leu Ala Lys Gly Gln Ser Pro
    130                 135                 140

Lys Phe Met Val Phe Ala Cys Ser Asp Ser Arg Val Cys Pro Ser His
145                 150                 155                 160

Val Leu Asp Phe Gln Pro Gly Glu Ala Phe Val Val Arg Asn Val Ala
                165                 170                 175

Asn Met Val Pro Pro Tyr Asp Lys Thr Lys Tyr Ala Gly Val Gly Ala
```

```
                    180                 185                 190
Ala Ile Glu Tyr Ala Val Leu His Leu Lys Val Glu Tyr Ile Val Val
            195                 200                 205

Ile Gly His Ser Ala Cys Gly Gly Ile Lys Gly Leu Met Ser Phe Pro
            210                 215                 220

Tyr Asp Gly Thr Thr Ser Thr Asp Phe Ile Glu Asp Trp Val Lys Val
225                 230                 235                 240

Cys Tyr Asn Ala Lys Thr Lys Ile Leu Ala Glu His Ala Asn Ser Pro
            245                 250                 255

Phe Pro Asp Met Cys Thr Gln Cys Glu Lys Glu Ala Val Asn Val Ser
            260                 265                 270

Leu Gly His Leu Leu Thr Tyr Pro Phe Val Arg Asp Gly Leu Val Asn
            275                 280                 285

Lys Thr Leu Gly Leu Lys Gly Tyr Tyr Asp Phe Val Lys Gly Ser
            290                 295                 300

Phe Glu Leu Trp Gly Leu Glu Tyr Ser Leu Ser Pro Ser Leu Ser Val
305                 310                 315                 320

<210> SEQ ID NO 142
<211> LENGTH: 777
<212> TYPE: DNA
<213> ORGANISM: Arabidopsis thaliana

<400> SEQUENCE: 142
atgtcgacag agtcgtacga agacgccatt aaaagactcg agagcttct cagtaagaaa     60 tcggatctcg ggaacgtggc agccgcaaag atcaagaagt taacggatga gttagaggaa    120
cttgattcca acaagttaga tgccgtagaa cgaatcaaat ccggatttct ccatttcaag    180
actaataatt atgagaagaa tcctactttg tacaattcac ttgccaagag ccagaccccc    240
aagtttttgg tgtttgcttg tgcggattca cgagttagtc catctcacat cttgaatttc    300
caacttgggg aagccttcat cgttagaaac attgcaaaca tggtgccacc ttatgacaag    360
acaaagcact ctaatgttgg tgcggccctt gaatatccaa ttacagtcct caacgtggag    420
aacattcttg ttattggaca cagctgttgt ggtggaataa agggactcat ggccattgaa    480
gataatacag ctcccactaa gaccgagttc atagaaaact ggatccagat ctgtgcaccg    540
gccaagaaca ggatcaagca ggattgtaaa gacctaagct tgaagatca gtgcaccaac    600 tgtgagaagg aagccgtgaa cgtgtccttg gggaatcttt tgtcttaccc attcgtgaga    660
gaaagagtgg tgaagaacaa gcttgccata gagagctc actatgattt cgtaaaagga    720
acgtttgatc tttgggaact tgacttcaag actaccctg cctttgcctt gtcttaa      777

<210> SEQ ID NO 143
<211> LENGTH: 258
<212> TYPE: PRT
<213> ORGANISM: Arabidopsis thaliana

<400> SEQUENCE: 143

Met Ser Thr Glu Ser Tyr Glu Asp Ala Ile Lys Arg Leu Gly Glu Leu
1               5                   10                  15

Leu Ser Lys Lys Ser Asp Leu Gly Asn Val Ala Ala Ala Lys Ile Lys
            20                  25                  30

Lys Leu Thr Asp Glu Leu Glu Glu Leu Asp Ser Asn Lys Leu Asp Ala
        35                  40                  45

Val Glu Arg Ile Lys Ser Gly Phe Leu His Phe Lys Thr Asn Asn Tyr
    50                  55                  60
```

```
Glu Lys Asn Pro Thr Leu Tyr Asn Ser Leu Ala Lys Ser Gln Thr Pro
 65                  70                  75                  80

Lys Phe Leu Val Phe Ala Cys Ala Asp Ser Arg Val Ser Pro Ser His
                 85                  90                  95

Ile Leu Asn Phe Gln Leu Gly Glu Ala Phe Ile Val Arg Asn Ile Ala
            100                 105                 110

Asn Met Val Pro Pro Tyr Asp Lys Thr Lys His Ser Asn Val Gly Ala
        115                 120                 125

Ala Leu Glu Tyr Pro Ile Thr Val Leu Asn Val Glu Asn Ile Leu Val
    130                 135                 140

Ile Gly His Ser Cys Cys Gly Gly Ile Lys Gly Leu Met Ala Ile Glu
145                 150                 155                 160

Asp Asn Thr Ala Pro Thr Lys Thr Glu Phe Ile Glu Asn Trp Ile Gln
                165                 170                 175

Ile Cys Ala Pro Ala Lys Asn Arg Ile Lys Gln Asp Cys Lys Asp Leu
            180                 185                 190

Ser Phe Glu Asp Gln Cys Thr Asn Cys Glu Lys Glu Ala Val Asn Val
        195                 200                 205

Ser Leu Gly Asn Leu Leu Ser Tyr Pro Phe Val Arg Glu Arg Val Val
    210                 215                 220

Lys Asn Lys Leu Ala Ile Arg Gly Ala His Tyr Asp Phe Val Lys Gly
225                 230                 235                 240

Thr Phe Asp Leu Trp Glu Leu Asp Phe Lys Thr Thr Pro Ala Phe Ala
                245                 250                 255

Leu Ser

<210> SEQ ID NO 144
<211> LENGTH: 960
<212> TYPE: DNA
<213> ORGANISM: Spinacia oleracea

<400> SEQUENCE: 144
atgtctacta ttaacggctg cctcacctct atctctcctt cccgtactca attgaaaaat      60
acctccactt taaggccaac tttcattgct aacagcaggg ttaacccttc ttcttctgtt     120
cctccttccc ttattagaaa ccagcccgtt ttcgccgccc cgcccctat catcacccct      180
actttgaaag aagatatggc atacgaagaa gccatcgctg cccttaagaa gcttctaagc     240
gagaagggag aacttgaaaa tgaagccgca tcaaggtgg cacagataac atctgagtta      300
gccgacggtg gcacaccatc cgccagttac ccggttcaga gaattaagga agggtttatc     360
aaattcaaga aggagaaata cgagaaaaat ccagcattgt atggtgagct ttctaagggc     420
caagctccca gtttatggt gtttgcgtgc tcagactccc gtgtgtgtcc ctcgcacgta      480
ctagatttcc agcccggtga ggctttcatg gttcgcaaca tcgccaacat ggtgccagtg     540
tttgacaagg acaaatacgc tggagtcgga gcagccattg aatacgcagt gttgcacctt     600
aaggtggaga acattgtcgt gattggacac agtgcttgtg gtggaatcaa ggggcttatg     660
tctttcccag atgcaggacc aaccacaact gattttattg aggattgggt caaaatctgc     720
ttgcctgcca agcacaaggt gttagccgag catggtaatg caactttcgc tgaacaatgc     780
acccattgtg aaaaggaagc tgtgaatgta tctctcggaa acttgttgac ttacccattt     840
gtaagagatg gtttggtgaa gaagactcta gctttgcagg gtggttacta cgattttgtc     900
aatggatcat cgagctatg gggactcgaa tacggcctct ctccttccca atctgtatga     960

<210> SEQ ID NO 145
```

<211> LENGTH: 319
<212> TYPE: PRT
<213> ORGANISM: Spinacia oleracea

<400> SEQUENCE: 145

```
Met Ser Thr Ile Asn Gly Cys Leu Thr Ser Ile Ser Pro Ser Arg Thr
  1               5                  10                  15

Gln Leu Lys Asn Thr Ser Thr Leu Arg Pro Thr Phe Ile Ala Asn Ser
             20                  25                  30

Arg Val Asn Pro Ser Ser Val Pro Pro Ser Leu Ile Arg Asn Gln
         35                  40                  45

Pro Val Phe Ala Ala Pro Ala Pro Ile Ile Thr Pro Thr Leu Lys Glu
     50                  55                  60

Asp Met Ala Tyr Glu Glu Ala Ile Ala Ala Leu Lys Lys Leu Leu Ser
 65                  70                  75                  80

Glu Lys Gly Glu Leu Glu Asn Glu Ala Ala Ser Lys Val Ala Gln Ile
                 85                  90                  95

Thr Ser Glu Leu Ala Asp Gly Gly Thr Pro Ser Ala Ser Tyr Pro Val
            100                 105                 110

Gln Arg Ile Lys Glu Gly Phe Ile Lys Phe Lys Glu Lys Tyr Glu
        115                 120                 125

Lys Asn Pro Ala Leu Tyr Gly Glu Leu Ser Lys Gly Gln Ala Pro Lys
    130                 135                 140

Phe Met Val Phe Ala Cys Ser Asp Ser Arg Val Cys Pro Ser His Val
145                 150                 155                 160

Leu Asp Phe Gln Pro Gly Glu Ala Phe Met Val Arg Asn Ile Ala Asn
                165                 170                 175

Met Val Pro Val Phe Asp Lys Asp Lys Tyr Ala Gly Val Gly Ala Ala
            180                 185                 190

Ile Glu Tyr Ala Val Leu His Leu Lys Val Glu Asn Ile Val Val Ile
        195                 200                 205

Gly His Ser Ala Cys Gly Gly Ile Lys Gly Leu Met Ser Phe Pro Asp
    210                 215                 220

Ala Gly Pro Thr Thr Thr Asp Phe Ile Glu Asp Trp Val Lys Ile Cys
225                 230                 235                 240

Leu Pro Ala Lys His Lys Val Leu Ala Glu His Gly Asn Ala Thr Phe
                245                 250                 255

Ala Glu Gln Cys Thr His Cys Glu Lys Glu Ala Val Asn Val Ser Leu
            260                 265                 270

Gly Asn Leu Leu Thr Tyr Pro Phe Val Arg Asp Gly Leu Val Lys Lys
        275                 280                 285

Thr Leu Ala Leu Gln Gly Gly Tyr Tyr Asp Phe Val Asn Gly Ser Phe
    290                 295                 300

Glu Leu Trp Gly Leu Glu Tyr Gly Leu Ser Pro Ser Gln Ser Val
305                 310                 315
```

<210> SEQ ID NO 146
<211> LENGTH: 987
<212> TYPE: DNA
<213> ORGANISM: Pisum sativum

<400> SEQUENCE: 146

```
atgtctacct cttcaataaa cggctttagt ctttcttctt tgtcccctgc caaaacttct    60
accaaaagaa ctacattgag acccttgtt tctgcatctc ttaacacttc ttcttcatct   120
tcttcctcga ctttcccttc tcttattcaa gacaagccgg ttttcgcttc ttcttctcct   180
```

```
atcatcaccc cagtttgag agaagaaatg ggaaagggct atgatgaagc tattgaagaa      240
ctccaaaagt tgttgaggga gaagactgaa ctgaaagcca cagctgctga gaaggttgag      300
caaatcacag ctcagctagg aacaacatca tcatctgatg gcattccaaa atctgaagcc      360
tctgaaagga tcaaaactgg tttccttcac ttcaagaaag agaaatatga caagaatcca      420
gctttgtatg gtgaacttgc caaaggccaa agccctccgt ttatggtgtt tgcatgttca      480
gactcaagag tctgcccatc tcatgtgcta gatttccagc caggtgaagc ctttgtggtc      540
agaaatgttg ctaacttggt tccaccatat gaccaggcaa aatatgccgg aactggtgct      600
gcaattgagt acgcagttct gcatctcaag gtttccaaca ttgttgtcat tggacacagt      660
gcttgtggtg gtattaaggg acttttgtcc tttccatttg atggaaccta ctccactgat      720
ttcattgagt agtgggtcaa aattggttta cctgcaaagg cgaaggtgaa agcacaaacat    780 ggagatgcac cttttgcaga gctatgcaca cactgtgaga aggaagctgt gaatgcttcc      840
cttggaaacc ttctcaccta cccatttgtg agagagggat tggtgaacaa gacattggca      900
ctcaaaggag gatactatga cttttgtgaaaa ggatcctttg agctttgggg acttgaattt     960
ggcctttcgt ccactttctc cgtatga                                           987
```

<210> SEQ ID NO 147
<211> LENGTH: 328
<212> TYPE: PRT
<213> ORGANISM: Pisum sativum

<400> SEQUENCE: 147

```
Met Ser Thr Ser Ser Ile Asn Gly Phe Ser Leu Ser Ser Leu Ser Pro
1               5                   10                  15

Ala Lys Thr Ser Thr Lys Arg Thr Thr Leu Arg Pro Phe Val Ser Ala
                20                  25                  30

Ser Leu Asn Thr Ser Ser Ser Ser Ser Ser Thr Phe Pro Ser Leu
                35                  40                  45

Ile Gln Asp Lys Pro Val Phe Ala Ser Ser Pro Ile Ile Thr Pro
            50                  55                  60

Val Leu Arg Glu Glu Met Gly Lys Gly Tyr Asp Glu Ala Ile Glu Glu
65                  70                  75                  80

Leu Gln Lys Leu Leu Arg Glu Lys Thr Glu Leu Lys Ala Thr Ala Ala
                85                  90                  95

Glu Lys Val Glu Gln Ile Thr Ala Gln Leu Gly Thr Thr Ser Ser Ser
                100                 105                 110

Asp Gly Ile Pro Lys Ser Glu Ala Ser Glu Arg Ile Lys Thr Gly Phe
            115                 120                 125

Leu His Phe Lys Lys Glu Lys Tyr Asp Lys Asn Pro Ala Leu Tyr Gly
        130                 135                 140

Glu Leu Ala Lys Gly Gln Ser Pro Pro Phe Met Val Phe Ala Cys Ser
145                 150                 155                 160

Asp Ser Arg Val Cys Pro Ser His Val Leu Asp Phe Gln Pro Gly Glu
                165                 170                 175

Ala Phe Val Val Arg Asn Val Ala Asn Leu Val Pro Pro Tyr Asp Gln
                180                 185                 190

Ala Lys Tyr Ala Gly Thr Gly Ala Ala Ile Glu Tyr Ala Val Leu His
            195                 200                 205

Leu Lys Val Ser Asn Ile Val Val Ile Gly His Ser Ala Cys Gly Gly
        210                 215                 220

Ile Lys Gly Leu Leu Ser Phe Pro Phe Asp Gly Thr Tyr Ser Thr Asp
225                 230                 235                 240
```

Phe Ile Glu Glu Trp Val Lys Ile Gly Leu Pro Ala Lys Ala Lys Val
                245                 250                 255

Lys Ala Gln His Gly Asp Ala Pro Phe Ala Glu Leu Cys Thr His Cys
            260                 265                 270

Glu Lys Glu Ala Val Asn Ala Ser Leu Gly Asn Leu Leu Thr Tyr Pro
        275                 280                 285

Phe Val Arg Glu Gly Leu Val Asn Lys Thr Leu Ala Leu Lys Gly Gly
    290                 295                 300

Tyr Tyr Asp Phe Val Lys Gly Ser Phe Glu Leu Trp Gly Leu Glu Phe
305                 310                 315                 320

Gly Leu Ser Ser Thr Phe Ser Val
                325

<210> SEQ ID NO 148
<211> LENGTH: 996
<212> TYPE: DNA
<213> ORGANISM: Medicago truncatula

<400> SEQUENCE: 148
atgtctacct cttccataaa cggctttagt ctctcttctt tgtccctac aaaaacttct        60 attaaaaaag ttacattgag acctattgtt tctgcatctc ttaactcttc ttcttcttcc     120
tcttccactt ctaacttccc ttctcttatt caagacaagc ctgttttgc ttcatcttct      180 tctcctatca tcaccccagt tttgagagaa gaaatgggaa agggctatga tgaagctatt     240
gaagaactcc aaaaattgtt gagggagaag actgaattga agccacagc agctgaaaag      300 gttgagcaaa ttacagctca gctaggaaca acagcatcag ctgatggtgt tccaacatct     360
gatcaagcct cagagaggat caaaactggt ttccttcact tcaagaaaga gaatatgac     420 acaaaaccag ctttgtatgg tgaacttgcc aaaggccaag ccccccgtt tatggtgttt     480 gcatgctcag actcaagagt ctgcccatct catgtgctag acttccagcc aggagaagct     540
tttgtggtca gaaatgttgc taacatggtt ccaccatatg accaggcaaa atatgctgga    600
actggatctg caattgagta tgctgttctg catctcaagg tttccaacat tgtggtcatt    660
ggacacagtg cttgtggtgg tattaagggg cttttgtctt ttccatttga tggagcctac    720
tccactgatt tcattgagga gtgggtcaaa attggtttac ctgcaaaggc aaaggtgaag    780
gcaaagcatg gagatgcacc ttttggagag ctatgcacac actgtgagaa ggaagctgtg    840
aatgtttctc ttggaaacct tctaacctac ccatttgtga gagggatt ggtgaacaaa      900 acattggcac taaaggagg atactatgac tttgtgaaag gatcttttga gctttgggga    960
cttgaatttg gcctttcttc aactttctcc gtatga                              996

<210> SEQ ID NO 149
<211> LENGTH: 331
<212> TYPE: PRT
<213> ORGANISM: Medicago truncatula

<400> SEQUENCE: 149

Met Ser Thr Ser Ser Ile Asn Gly Phe Ser Leu Ser Ser Leu Ser Pro
1               5                   10                  15

Thr Lys Thr Ser Ile Lys Lys Val Thr Leu Arg Pro Ile Val Ser Ala
            20                  25                  30

Ser Leu Asn Ser Ser Ser Ser Ser Ser Thr Ser Asn Phe Pro Ser
        35                  40                  45

Leu Ile Gln Asp Lys Pro Val Phe Ala Ser Ser Ser Pro Ile Ile
    50                  55                  60

```
Thr Pro Val Leu Arg Glu Glu Met Gly Lys Gly Tyr Asp Glu Ala Ile
 65                  70                  75                  80

Glu Glu Leu Gln Lys Leu Leu Arg Glu Lys Thr Glu Leu Lys Ala Thr
             85                  90                  95

Ala Ala Glu Lys Val Glu Gln Ile Thr Ala Gln Leu Gly Thr Thr Ala
        100                 105                 110

Ser Ala Asp Gly Val Pro Thr Ser Asp Gln Ala Ser Glu Arg Ile Lys
        115                 120                 125

Thr Gly Phe Leu His Phe Lys Lys Glu Lys Tyr Asp Thr Lys Pro Ala
    130                 135                 140

Leu Tyr Gly Glu Leu Ala Lys Gly Gln Ala Pro Pro Phe Met Val Phe
145                 150                 155                 160

Ala Cys Ser Asp Ser Arg Val Cys Pro Ser His Val Leu Asp Phe Gln
                165                 170                 175

Pro Gly Glu Ala Phe Val Val Arg Asn Val Ala Asn Met Val Pro Pro
            180                 185                 190

Tyr Asp Gln Ala Lys Tyr Ala Gly Thr Gly Ser Ala Ile Glu Tyr Ala
        195                 200                 205

Val Leu His Leu Lys Val Ser Asn Ile Val Val Ile Gly His Ser Ala
    210                 215                 220

Cys Gly Gly Ile Lys Gly Leu Leu Ser Phe Pro Phe Asp Gly Ala Tyr
225                 230                 235                 240

Ser Thr Asp Phe Ile Glu Glu Trp Val Lys Ile Gly Leu Pro Ala Lys
                245                 250                 255

Ala Lys Val Lys Ala Lys His Gly Asp Ala Pro Phe Gly Glu Leu Cys
            260                 265                 270

Thr His Cys Glu Lys Glu Ala Val Asn Val Ser Leu Gly Asn Leu Leu
        275                 280                 285

Thr Tyr Pro Phe Val Arg Glu Gly Leu Val Asn Lys Thr Leu Ala Leu
    290                 295                 300

Lys Gly Gly Tyr Tyr Asp Phe Val Lys Gly Ser Phe Glu Leu Trp Gly
305                 310                 315                 320

Leu Glu Phe Gly Leu Ser Ser Thr Phe Ser Val
                325                 330
```

<210> SEQ ID NO 150
<211> LENGTH: 471
<212> TYPE: DNA
<213> ORGANISM: Medicago truncatula

<400> SEQUENCE: 150

```
atggtatttg cttgctctga ctctagagtg agtccctcta ttatcctgaa ctttcaacat    60
ggagaagctt tcatggtccg aaacattgct aacatggtcc ctacatttaa tcaggtggag   120
aacatcttgg ttattggaca tagtcgctgc ggtggaatct caaggcttat gccttccaga   180
ggatggctgc tccataatga ttgggtgaaa attggtttat ctttcaaagt caaggttctg   240
aaagaacatg aatgctgtga tttcaaagaa caatgcaaat tttgtgaaat ggaatcagtg   300
aataattcat tagtgaacct gaagacatat ctatatgttg atagagaagt aaggaacaag   360
aacttagcac tattgggagg ttactatgat tttgtgaatg agaattcaa gctctggaag   420
tataagaccc atgtcactaa acccattaca atcccctcta aaagaccttg a             471
```

<210> SEQ ID NO 151
<211> LENGTH: 156
<212> TYPE: PRT

<213> ORGANISM: Medicago truncatula

<400> SEQUENCE: 151

```
Met Val Phe Ala Cys Ser Asp Ser Arg Val Ser Pro Ser Ile Ile Leu
1               5                   10                  15
Asn Phe Gln His Gly Glu Ala Phe Met Val Arg Asn Ile Ala Asn Met
            20                  25                  30
Val Pro Thr Phe Asn Gln Val Glu Asn Ile Leu Val Ile Gly His Ser
        35                  40                  45
Arg Cys Gly Gly Ile Ser Arg Leu Met Pro Ser Arg Gly Trp Leu Leu
    50                  55                  60
His Asn Asp Trp Val Lys Ile Gly Leu Ser Phe Lys Val Lys Val Leu
65                  70                  75                  80
Lys Glu His Glu Cys Cys Asp Phe Lys Glu Gln Cys Lys Phe Cys Glu
                85                  90                  95
Met Glu Ser Val Asn Asn Ser Leu Val Asn Leu Lys Thr Tyr Leu Tyr
            100                 105                 110
Val Asp Arg Glu Val Arg Asn Lys Asn Leu Ala Leu Leu Gly Gly Tyr
        115                 120                 125
Tyr Asp Phe Val Asn Gly Glu Phe Lys Leu Trp Lys Tyr Lys Thr His
    130                 135                 140
Val Thr Lys Pro Ile Thr Ile Pro Ser Lys Arg Pro
145                 150                 155
```

<210> SEQ ID NO 152
<211> LENGTH: 828
<212> TYPE: DNA
<213> ORGANISM: Arabidopsis thaliana

<400> SEQUENCE: 152

```
atggtgaact actcatcaat cagttgcatc ttctttgtgg ctctgtttag tattttcaca      60
attgtttcga tttcgagtgc tgcttcaagt cacggagaag ttgaggacga acgcgagttt     120
aactacaaga agaacgatga gaaggggcca gagagatggg gagaacttaa accggaatgg     180
gaaatgtgtg aaaaggaga gatgcaatct cccatagatc ttatgaacga gagagttaac     240
attgtttctc atcttggaag gcttaataga gactataatc cttcaaatgc aactcttaag     300
aacagaggcc atgacatcat gttaaaattt gaagatggag caggaactat aagatcaat     360
ggttttgaat atgaacttca acagcttcac tggcactctc cgtctgaaca tactattaat     420
ggaagaaggt ttgcacttga gctgcatatg gttcacgaag gcaggaatag aagaatggct     480
gttgtgactg tgttgtacaa gatcggaaga gcagatactt ttatcagatc gttggagaaa     540
gaattagagg gcattgctga atggaggag gctgagaaaa atgtaggaat gattgatccc     600
accaaaatta agatcggaag cagaaaatat tacagataca ctggttcact taccactcct     660
ccttgcactc aaaacgttac ttggagcgtc gttagaaagg ttaggaccgt gacaagaaaa     720
caagtgaagc tcctccgcgt ggcagtgcac gatgatgcta attcgaatgc gaggccggtt     780
caaccaacca acaagcgcat agtgcactta tacagaccaa tagtttaa                   828
```

<210> SEQ ID NO 153
<211> LENGTH: 275
<212> TYPE: PRT
<213> ORGANISM: Arabidopsis thaliana

<400> SEQUENCE: 153

```
Met Val Asn Tyr Ser Ser Ile Ser Cys Ile Phe Phe Val Ala Leu Phe
1               5                   10                  15
```

Ser Ile Phe Thr Ile Val Ser Ile Ser Ser Ala Ala Ser Ser His Gly
        20                  25                  30

Glu Val Glu Asp Glu Arg Glu Phe Asn Tyr Lys Lys Asn Asp Glu Lys
            35                  40                  45

Gly Pro Glu Arg Trp Gly Leu Lys Pro Glu Trp Glu Met Cys Gly
 50                  55                  60

Lys Gly Glu Met Gln Ser Pro Ile Asp Leu Met Asn Glu Arg Val Asn
 65                  70                  75                  80

Ile Val Ser His Leu Gly Arg Leu Asn Arg Asp Tyr Asn Pro Ser Asn
                85                  90                  95

Ala Thr Leu Lys Asn Arg Gly His Asp Ile Met Leu Lys Phe Glu Asp
                100                 105                 110

Gly Ala Gly Thr Ile Lys Ile Asn Gly Phe Glu Tyr Glu Leu Gln Gln
            115                 120                 125

Leu His Trp His Ser Pro Ser Glu His Thr Ile Asn Gly Arg Arg Phe
        130                 135                 140

Ala Leu Glu Leu His Met Val His Glu Gly Arg Asn Arg Arg Met Ala
145                 150                 155                 160

Val Val Thr Val Leu Tyr Lys Ile Gly Arg Ala Asp Thr Phe Ile Arg
                165                 170                 175

Ser Leu Glu Lys Glu Leu Glu Gly Ile Ala Glu Met Glu Glu Ala Glu
            180                 185                 190

Lys Asn Val Gly Met Ile Asp Pro Thr Lys Ile Lys Ile Gly Ser Arg
        195                 200                 205

Lys Tyr Tyr Arg Tyr Thr Gly Ser Leu Thr Thr Pro Pro Cys Thr Gln
210                 215                 220

Asn Val Thr Trp Ser Val Val Arg Lys Val Arg Thr Val Thr Arg Lys
225                 230                 235                 240

Gln Val Lys Leu Leu Arg Val Ala Val His Asp Asp Ala Asn Ser Asn
                245                 250                 255

Ala Arg Pro Val Gln Pro Thr Asn Lys Arg Ile Val His Leu Tyr Arg
            260                 265                 270

Pro Ile Val
        275

<210> SEQ ID NO 154
<211> LENGTH: 987
<212> TYPE: DNA
<213> ORGANISM: Flaveria pringlei

<400> SEQUENCE: 154
atgtatgcta cagctgccgc atttgcaccc tccttcacca cctcccgccg caaaccgtca      60
tcgtcgtctt ccaccgtatc cacttgcttt gcaaggctta gcaacagcgc tcagtcgtcg     120
tcgtcgtctg ccactccacc acccagcctc atccgtaatc agcccgtttt tgccgccccg     180
actcccatca tcaccccac tgtgagagga gacatgggaa gtgaatcata tgatgaggca      240
attgctgcac tcaagaagct tttaagtgaa aaggaggagt tggcacctgt ggctgctgcc     300
aaaatcgacg aaatcacggc ccaacttcaa actctcgaca ccaaacctgc atttgacgcg     360
gtcgagagga tcaaaaccgg gtttgccaag ttcaagaccg agaaataccta gacaaatcca   420 gctttgtacg atgaactttc caaggccag agcccaaaat ttatggtttt tgcatgctct     480
gactctcgag tttgcccgtc acacgtgctg gatttccaac ccggtgaggc gtttgtggtc     540
cgtaacgtag ccaacattgt cccccccttt gataagctta aatacgctgg agtaggatcc     600

```
gcagtcgagt atgcagttct gcatctcaag gtggagcaga tagtcgtaat tgggcatagt    660
aaatgtggtg ggatcaaggg tctgatgact tccccgatg agggaccgac cagcaccgac     720
ttcattgagg actgggtcag agttggtctc cctgcaaagt caaaggtgaa agcggagcat    780
ggaagtgcat cacttgatga tcaatgtgta tcctgcgaga aggaggcggt gaatgtgtct    840
cttgcaaacc tgttgactta cccgtttgtg agaaacggat tgatgaacaa acattggcg    900 ctcaagggtg cacactatga ctttgttaac ggggcctttg agttgtgggg gcttgatttc    960
agcctttcgc ctcctacctc ggcataa                                        987
```

<210> SEQ ID NO 155
<211> LENGTH: 328
<212> TYPE: PRT
<213> ORGANISM: Flaveria pringlei

<400> SEQUENCE: 155

```
Met Tyr Ala Thr Ala Ala Ala Phe Ala Pro Ser Phe Thr Thr Ser Arg
1               5                   10                  15

Arg Lys Pro Ser Ser Ser Ser Thr Val Ser Thr Cys Phe Ala Arg
            20                  25                  30

Leu Ser Asn Ser Ala Gln Ser Ser Ser Ser Ala Thr Pro Pro
        35                  40                  45

Ser Leu Ile Arg Asn Gln Pro Val Phe Ala Ala Thr Pro Ile Ile
    50                  55                  60

Thr Pro Thr Val Arg Gly Asp Met Gly Ser Glu Ser Tyr Asp Glu Ala
65                  70                  75                  80

Ile Ala Ala Leu Lys Lys Leu Leu Ser Glu Lys Glu Glu Leu Ala Pro
                85                  90                  95

Val Ala Ala Ala Lys Ile Asp Glu Ile Thr Ala Gln Leu Gln Thr Leu
            100                 105                 110

Asp Thr Lys Pro Ala Phe Asp Ala Val Glu Arg Ile Lys Thr Gly Phe
        115                 120                 125

Ala Lys Phe Lys Thr Glu Lys Tyr Leu Thr Asn Pro Ala Leu Tyr Asp
    130                 135                 140

Glu Leu Ser Lys Gly Gln Ser Pro Lys Phe Met Val Phe Ala Cys Ser
145                 150                 155                 160

Asp Ser Arg Val Cys Pro Ser His Val Leu Asp Phe Gln Pro Gly Glu
                165                 170                 175

Ala Phe Val Val Arg Asn Val Ala Asn Ile Val Pro Pro Phe Asp Lys
            180                 185                 190

Leu Lys Tyr Ala Gly Val Gly Ser Ala Val Glu Tyr Ala Val Leu His
        195                 200                 205

Leu Lys Val Glu Gln Ile Val Val Ile Gly His Ser Lys Cys Gly Gly
    210                 215                 220

Ile Lys Gly Leu Met Thr Phe Pro Asp Glu Gly Pro Thr Ser Thr Asp
225                 230                 235                 240

Phe Ile Glu Asp Trp Val Arg Val Gly Leu Pro Ala Lys Ser Lys Val
                245                 250                 255

Lys Ala Glu His Gly Ser Ala Ser Leu Asp Asp Gln Cys Val Ser Cys
            260                 265                 270

Glu Lys Glu Ala Val Asn Val Ser Leu Ala Asn Leu Leu Thr Tyr Pro
        275                 280                 285

Phe Val Arg Asn Gly Leu Met Asn Lys Thr Leu Ala Leu Lys Gly Ala
    290                 295                 300

His Tyr Asp Phe Val Asn Gly Ala Phe Glu Leu Trp Gly Leu Asp Phe
```

305                 310                 315                 320
Ser Leu Ser Pro Pro Thr Ser Ala
            325

<210> SEQ ID NO 156
<211> LENGTH: 996
<212> TYPE: DNA
<213> ORGANISM: Flaveria linearis

<400> SEQUENCE: 156
atgtatgcca cagctgccgc attaattgca ccctccttca ccacctctct ccgcaaaccg      60
tcatcgtcgt cttccaccgt atccgctccc ttcgcaaggc taattaccaa caactcgctg     120
gcgtcgtcgt cgttgtctgc cactccacca ccgagcctca tccgtaacca gcccgttttt     180
gccgccccga ctcccatcat cacccccact gtgagaggag acatgggaag tgaatcatat     240
gacgaggcaa ttgctgcact gaagaagctt ttaagtgaaa gggaggattt ggcacctgtg     300
gctgctgcaa aaatcgacga aatcacctcc aacttcaaa cgctcgacac caaacccgca     360
tttgacgcgg tcgagaggat caaaaccggc tttgccaagt tcaagaccga gaaatacttg     420
acaaatccag ctttgtacga tgaactttcc aaaggccaga gcccaaaatt tatggttttt     480
gcatgctctg actctcgagt ttgcccgtca cacgtgctcg atttccaacc tggtgaggcg     540
tttgtggtcc gtaacgtagc caacattgtc ccccccttg ataagcttaa atatgctgga     600
gtaggatccg ctgtcgagta tgcagttttg catctcaagg tggagcagat agttgtaatt     660
gggcatagta atgtggtgg gatcaaggt ctgatgactt ccggacga aggaccgaca      720 agcaccgact tcattgagga ctgggtcaga gttggtctcc ctgcaaagtc aaaggtgaaa     780
gcggagcatg aagtgcatc aattgatgat caatgtgtat cctgcgagaa ggaggcggtg     840
aatgtgtctc ttgcaaacct gttgacttac ccgtttgtga aaacggatt gataaacaaa     900 acattggcgc tcaagggtgc acactatgac tttgttaacg ggacctttga gttgtggggg     960
cttgatttct gcctttcgcc tcctacctcg gcataa                              996

<210> SEQ ID NO 157
<211> LENGTH: 331
<212> TYPE: PRT
<213> ORGANISM: Flaveria linearis

<400> SEQUENCE: 157

Met Tyr Ala Thr Ala Ala Ala Leu Ile Ala Pro Ser Phe Thr Thr Ser
1               5                   10                  15

Leu Arg Lys Pro Ser Ser Ser Ser Thr Val Ser Ala Pro Phe Ala
            20                  25                  30

Arg Leu Ile Thr Asn Asn Ser Leu Ala Ser Ser Leu Ser Ala Thr
        35                  40                  45

Pro Pro Pro Ser Leu Ile Arg Asn Gln Pro Val Phe Ala Ala Pro Thr
    50                  55                  60

Pro Ile Ile Thr Pro Thr Val Arg Gly Asp Met Gly Ser Glu Ser Tyr
65                  70                  75                  80

Asp Glu Ala Ile Ala Ala Leu Lys Lys Leu Leu Ser Glu Arg Glu Asp
                85                  90                  95

Leu Ala Pro Val Ala Ala Ala Lys Ile Asp Glu Ile Thr Ser Gln Leu
            100                 105                 110

Gln Thr Leu Asp Thr Lys Pro Ala Phe Asp Ala Val Glu Arg Ile Lys
        115                 120                 125

Thr Gly Phe Ala Lys Phe Lys Thr Glu Lys Tyr Leu Thr Asn Pro Ala

```
                130               135               140
Leu Tyr Asp Glu Leu Ser Lys Gly Gln Ser Pro Lys Phe Met Val Phe
145                 150                 155                 160

Ala Cys Ser Asp Ser Arg Val Cys Pro Ser His Val Leu Asp Phe Gln
                165                 170                 175

Pro Gly Glu Ala Phe Val Val Arg Asn Val Ala Asn Ile Val Pro Pro
            180                 185                 190

Phe Asp Lys Leu Lys Tyr Ala Gly Val Gly Ser Ala Val Glu Tyr Ala
        195                 200                 205

Val Leu His Leu Lys Val Glu Gln Ile Val Val Ile Gly His Ser Lys
    210                 215                 220

Cys Gly Gly Ile Lys Gly Leu Met Thr Phe Pro Asp Glu Gly Pro Thr
225                 230                 235                 240

Ser Thr Asp Phe Ile Glu Asp Trp Val Arg Val Gly Leu Pro Ala Lys
                245                 250                 255

Ser Lys Val Lys Ala Glu His Gly Ser Ala Ser Ile Asp Gln Cys
                260                 265                 270

Val Ser Cys Glu Lys Glu Ala Val Asn Val Ser Leu Ala Asn Leu Leu
        275                 280                 285

Thr Tyr Pro Phe Val Arg Asn Gly Leu Ile Asn Lys Thr Leu Ala Leu
    290                 295                 300

Lys Gly Ala His Tyr Asp Phe Val Asn Gly Thr Phe Glu Leu Trp Gly
305                 310                 315                 320

Leu Asp Phe Cys Leu Ser Pro Pro Thr Ser Ala
                325                 330

<210> SEQ ID NO 158
<211> LENGTH: 828
<212> TYPE: DNA
<213> ORGANISM: Arabidopsis thaliana

<400> SEQUENCE: 158
atgggaaccc taggcagagc attttactcg gtcggttttt ggatccgtga gactggtcaa      60
gctcttgatc gcctcggttg tcgccttcaa ggcaaaaatt acttccgaga caactgtca     120
aggcatcgga cactgatgaa tgtatttgat aaggctccga ttgtggacaa ggaagctttt     180
gtggcaccaa gcgcctcagt tattggggac gttcacattg gaagaggatc gtccatttgg     240
tatggatgcg tattacgagg cgatgtgaac accgtaagtg ttgggtcagg aactaatatt     300
caggacaact cacttgtgca tgtggcaaaa tcaaacttaa gcgggaaggt gcacccaacc     360
ataattggag acaatgtaac cattggtcat agtgctgttt acatggatg tactgttgag     420
gatgagacct ttattgggat gggtgcgaca cttcttgatg gggtcgttgt tgaaaagcat     480
gggatggttg ctgctggtgc acttgtacga caaaacacca gaattccttc tggagaggta     540
tggggaggaa acccagcaag gttcctcagg aagctcactg atgaggaaat tgcttttatc     600
tctcagtcag caacaaacta ctcaaacctc gcacaggctc acgctgcaga gaatgcaaag     660
ccattaaatg tgattgagtt cgagaaggtt ctacgcaaga agcatgctct aaaggacgag     720
gagtatgact caatgctcgg aatagtgaga gaaactccac cagagcttaa cctccctaac     780
acatactgc tgataaaga aaccaagcgt ccttctaatg tgaactga                    828

<210> SEQ ID NO 159
<211> LENGTH: 275
<212> TYPE: PRT
<213> ORGANISM: Arabidopsis thaliana
```

<400> SEQUENCE: 159

```
Met Gly Thr Leu Gly Arg Ala Phe Tyr Ser Val Gly Phe Trp Ile Arg
 1               5                  10                  15
Glu Thr Gly Gln Ala Leu Asp Arg Leu Gly Cys Arg Leu Gln Gly Lys
            20                  25                  30
Asn Tyr Phe Arg Glu Gln Leu Ser Arg His Arg Thr Leu Met Asn Val
        35                  40                  45
Phe Asp Lys Ala Pro Ile Val Asp Lys Asp Ala Phe Val Ala Pro Ser
50                  55                  60
Ala Ser Val Ile Gly Asp Val His Ile Gly Arg Gly Ser Ser Ile Trp
65                  70                  75                  80
Tyr Gly Cys Val Leu Arg Gly Asp Val Asn Thr Val Ser Val Gly Ser
                85                  90                  95
Gly Thr Asn Ile Gln Asp Asn Ser Leu Val His Val Ala Lys Ser Asn
            100                 105                 110
Leu Ser Gly Lys Val His Pro Thr Ile Ile Gly Asp Asn Val Thr Ile
        115                 120                 125
Gly His Ser Ala Val Leu His Gly Cys Thr Val Glu Asp Glu Thr Phe
130                 135                 140
Ile Gly Met Gly Ala Thr Leu Leu Asp Gly Val Val Glu Lys His
145                 150                 155                 160
Gly Met Val Ala Ala Gly Ala Leu Val Arg Gln Asn Thr Arg Ile Pro
                165                 170                 175
Ser Gly Glu Val Trp Gly Gly Asn Pro Ala Arg Phe Leu Arg Lys Leu
            180                 185                 190
Thr Asp Glu Glu Ile Ala Phe Ile Ser Gln Ser Ala Thr Asn Tyr Ser
        195                 200                 205
Asn Leu Ala Gln Ala His Ala Ala Glu Asn Ala Lys Pro Leu Asn Val
210                 215                 220
Ile Glu Phe Glu Lys Val Leu Arg Lys His Ala Leu Lys Asp Glu
225                 230                 235                 240
Glu Tyr Asp Ser Met Leu Gly Ile Val Arg Glu Thr Pro Pro Glu Leu
                245                 250                 255
Asn Leu Pro Asn Asn Ile Leu Pro Asp Lys Glu Thr Lys Arg Pro Ser
            260                 265                 270
Asn Leu Asn
        275
```

<210> SEQ ID NO 160
<211> LENGTH: 874
<212> TYPE: DNA
<213> ORGANISM: Gossypium hirsutum

<400> SEQUENCE: 160

```
catttcgagc tttgtttcct aatcactcgc ccgctgcgca atcaccgatc aaagctgaag      60
atgggaagcc ttgaaaagc aatatacacc gtcggattct ggattcggga gaccggtcag     120
gctctcgatc gcctaggctg ccgcctacaa ggcaactatt ttttccagga gcaactttct     180
aggcatcgga ctctgatgaa cgtatttgat aaatctcctc tggtggacaa ggatgcattt     240
gtagcccta gcgcatctgt cattggcgat gttcaggtgg aagaggatc atctatttgg       300
tatggatgtg ttttaagggg ggatgtcaac agcattagtg ttggatctgg aactaatata     360
caagacaact cccttgtgca tgttgcaaag tctaatctaa gtgggaaagt gctaccaact     420
aacattggaa acaatgttac tgtaggtcat agtgctgttt tacatggctg taccgttgag    480
```

```
gatgaagcat tgttggcat gggagccaca cttcttgatg gtgtagttgt ggaaaaacat    540
gctatggttg ctgctggagc ccttgtaaga cagaatacaa ggatccctgc tggagaggtg    600
tggggaggca atcctgctaa attcctgagg aagctaactg aagaagagat agcgtttatt    660
tcccagtcag ccaccaatta taccaacctt gcacaggtac atgctgctga aatgcaaaa     720 cccttttgatg aaattgaatt tgagaaaatt cttcgcaaga agtttgcgaa gagggatgaa   780
gagtatgact caatgctggg tgttgtccgt gaaactccac cagaactaat tcttccagac   840
aatgtcctac cagataaaga gcaaaagtcc tctc                                874
```

<210> SEQ ID NO 161
<211> LENGTH: 273
<212> TYPE: PRT
<213> ORGANISM: Gossypium hirsutum

<400> SEQUENCE: 161

```
Met Gly Ser Leu Gly Lys Ala Ile Tyr Thr Val Gly Phe Trp Ile Arg
1               5                   10                  15

Glu Thr Gly Gln Ala Leu Asp Arg Leu Gly Cys Arg Leu Gln Gly Asn
            20                  25                  30

Tyr Phe Phe Gln Glu Gln Leu Ser Arg His Arg Thr Leu Met Asn Val
        35                  40                  45

Phe Asp Lys Ser Pro Leu Val Asp Lys Asp Ala Phe Val Ala Pro Ser
    50                  55                  60

Ala Ser Val Ile Gly Asp Val Gln Val Gly Arg Gly Ser Ser Ile Trp
65                  70                  75                  80

Tyr Gly Cys Val Leu Arg Gly Asp Val Asn Ser Ile Ser Val Gly Ser
                85                  90                  95

Gly Thr Asn Ile Gln Asp Asn Ser Leu Val His Val Ala Lys Ser Asn
            100                 105                 110

Leu Ser Gly Lys Val Leu Pro Thr Asn Ile Gly Asn Asn Val Thr Val
        115                 120                 125

Gly His Ser Ala Val Leu His Gly Cys Thr Val Glu Asp Glu Ala Phe
    130                 135                 140

Val Gly Met Gly Ala Thr Leu Leu Asp Gly Val Val Glu Lys His
145                 150                 155                 160

Ala Met Val Ala Ala Gly Ala Leu Val Arg Gln Asn Thr Arg Ile Pro
                165                 170                 175

Ala Gly Glu Val Trp Gly Gly Asn Pro Ala Lys Phe Leu Arg Lys Leu
            180                 185                 190

Thr Glu Glu Glu Ile Ala Phe Ile Ser Gln Ser Ala Thr Asn Tyr Thr
        195                 200                 205

Asn Leu Ala Gln Val His Ala Ala Glu Asn Ala Lys Pro Phe Asp Glu
    210                 215                 220

Ile Glu Phe Glu Lys Val Leu Arg Lys Lys Phe Ala Lys Arg Asp Glu
225                 230                 235                 240

Glu Tyr Asp Ser Met Leu Gly Val Val Arg Glu Thr Pro Pro Glu Leu
                245                 250                 255

Ile Leu Pro Asp Asn Val Leu Pro Asp Lys Glu Gln Lys Ser Ser Gln
            260                 265                 270

Lys
```

<210> SEQ ID NO 162
<211> LENGTH: 1217
<212> TYPE: DNA
<213> ORGANISM: Lycopersicon esculentum

<400> SEQUENCE: 162

```
aggcatgtgg tattcactat tctgccctac caattactct gtggaaagcc ttcatttctc    60
actcaatcgt cccttttgct acacaaacac cttgactgca cagctctact gatcagaaag   120
agggctaaac cgaaagaaga agaaggagga ggtcaaacat gggaaccctc gggaaagcaa   180
tttactccct gggatccatc gttcgagcga ccggcaaagc tcttgatcgc gtcggaaatc   240
gcctacaagg cagctcccac atagaggaac acctgtccag gcatcggact cttatgaacg   300
tattcgataa agctccggtg gtggataagg atgtatttgt agctccaggt gcctcagtca   360
ttggagatgt ccatgtggga cgcaattcat ctatttggta tggatgtgta ctaagaggtg   420
atgttaacag catcagtgtc ggatctggta ccaatataca ggacaactcc cttgttcatg   480
tggccaaatc aaatataagt caaaaggtgc tgcccaccat catagggaac aatgttactg   540
ttggtcatag tgctgttgta catggctgca ccattgagga tgaggccttc attggtatgg   600
gggccacact gcttgatggt gttcatgtag agaaacatgc catggttgct gcaggagccc   660
ttgtgaaaca gaacacaagg attccctccg gagaggtatg ggcaggcaat cccgctaagt   720
ttctgaggaa gctaactgat gaagagatag ccttcattgc tcagtcagca accaactact   780
gtaaccttgc tcgtgtccat gcagctgaga actccaagtc ctttgacgaa attgaatttg   840
aaaagatgct tcgtaagaag tatgccaaac gtgatgagga atatgattct atgattggtg   900
ttgtccgtga acacctccc gagcttgtac ttcctgataa tatcctcccc gaaaaagctg   960
ctaagagcat cgcccaatga gatcagtgcc caagcaactc tctctttttt tgctttccag  1020
agatttattt tacaccgtga gcatctgtat ggagaacagt catggatatt ggctgttacc  1080
cttccaaata atatcaaact tattggatag catcggtacg tcactgcttt gtagttaaga  1140
cttttgcccc ttatttccca gaaattcttc agcttggaaa aggaagttac gcccgaaaaa  1200
aaaaaaaaaa aaaaaaa                                                 1217
```

<210> SEQ ID NO 163
<211> LENGTH: 273
<212> TYPE: PRT
<213> ORGANISM: Lycopersicon esculentum

<400> SEQUENCE: 163

```
Met Gly Thr Leu Gly Lys Ala Ile Tyr Ser Leu Gly Ser Ile Val Arg
1               5                   10                  15

Ala Thr Gly Lys Ala Leu Asp Arg Val Gly Asn Arg Leu Gln Gly Ser
            20                  25                  30

Ser His Ile Glu Glu His Leu Ser Arg His Arg Thr Leu Met Asn Val
        35                  40                  45

Phe Asp Lys Ala Pro Val Val Asp Lys Asp Val Phe Val Ala Pro Gly
    50                  55                  60

Ala Ser Val Ile Gly Asp Val His Val Gly Arg Asn Ser Ser Ile Trp
65                  70                  75                  80

Tyr Gly Cys Val Leu Arg Gly Asp Val Asn Ser Ile Ser Val Gly Ser
                85                  90                  95

Gly Thr Asn Ile Gln Asp Asn Ser Leu Val His Val Ala Lys Ser Asn
            100                 105                 110

Ile Ser Gln Lys Val Leu Pro Thr Ile Ile Gly Asn Asn Val Thr Val
        115                 120                 125

Gly His Ser Ala Val Val His Gly Cys Thr Ile Glu Asp Glu Ala Phe
    130                 135                 140
```

```
Ile Gly Met Gly Ala Thr Leu Leu Asp Gly Val His Val Glu Lys His
145                 150                 155                 160

Ala Met Val Ala Ala Gly Ala Leu Val Lys Gln Asn Thr Arg Ile Pro
                165                 170                 175

Ser Gly Glu Val Trp Ala Gly Asn Pro Ala Lys Phe Leu Arg Lys Leu
            180                 185                 190

Thr Asp Glu Glu Ile Ala Phe Ile Ala Gln Ser Ala Thr Asn Tyr Cys
        195                 200                 205

Asn Leu Ala Arg Val His Ala Ala Glu Asn Ser Lys Ser Phe Asp Glu
    210                 215                 220

Ile Glu Phe Glu Lys Met Leu Arg Lys Lys Tyr Ala Lys Arg Asp Glu
225                 230                 235                 240

Glu Tyr Asp Ser Met Ile Gly Val Val Arg Glu Thr Pro Pro Glu Leu
                245                 250                 255

Val Leu Pro Asp Asn Ile Leu Pro Glu Lys Ala Ala Lys Ser Ile Ala
            260                 265                 270

Gln

<210> SEQ ID NO 164
<211> LENGTH: 1962
<212> TYPE: DNA
<213> ORGANISM: Zea mays

<400> SEQUENCE: 164
atgtacacat tgcccgtccg tgccaccaca tccagcatcg tgccagcctg ccaccccgc     60 gccgtcctcc tcctccggct ccggccccca ggctcaggct catccggaac gccccgtctt    120
cgccgccccg ccaccgtcgt gggcatggac cccaccgtcg agcgcttgaa gagcgggttc    180
cagaagttca agaccgaggt ctatgacaag aagccggagc tgttcgagcc tctcaagtcc    240
ggccagagcc caggtacat ggtgttcgcc tgctccgact cccgcgtgtg cccgtcggtg     300
acactgggac tgcagcccgg cgaggcattc accgtccgca catcgcttc catggtccca     360 ccctacgaca agatcaagta cgccggcaca gggtccgcca tcgagtacgc cgtgtgcgcg    420
ctcaaggtgc aggtcatcgt ggtcattggc cacagctgct gcggtggcat cagggcgctc    480
ctctccctca aggacggcgc gcccgacaac ttcaccttcg tggaggactg gtcaggatc     540 ggcagccctg ccaagaacaa ggtgaagaaa gagcacgcgt ccgtgccgtt cgatgaccag    600
tgctccatcc tggagaagga ggccgtgaac gtgtcgctcc agaacctcaa gagctacccc    660
ttcgtcaagg aagggctggc cggcgggacg ctcaagctgg ttggcgccca ctacagcttc    720
gtcaaagggc agttcgtcac atgggagcct cccaggacg ccatcgagcg cttgacgagc     780
ggcttccagc agttcaaggt caatgtctat gacaagaagc cggagctttt cgggcctctc    840
aagtccggcc aggcccccaa gtacatggtg ttcgcctgct ccgactcccg tgtgtgcccg    900
tcggtgaccc tgggcctgca gcccgcgaag gccttcaccg ttcgcaacat cgccgccatg    960
gtcccaggct acgacaagac caagtacacc ggcatcgggt ccgccatcga gtacgctgtg   1020
tgcgccctca aggtggaggt cctcgtggtc attggccata gctgctgcgg tggcatcagg   1080
gcgctcctct ccctcaagga cggcgcgccc gacaacttcc acttcgtgga ggactgggtc   1140
aggatcggca gccctgccaa gaacaaggtg aagaaagagc acgcgtccgt gccgttcgat   1200
gaccagtgct ccatcctgga aggaggcc gtgaacgtgt cgctccagaa cctcaagagc     1260
taccccttgg tcaaggaagg ctggccggc gggacgtcaa gtggttggcc ccactacgac    1320
ttcgttaaag ggcagttcgt cacatgggag cctccccagg acgccatcga gcgcttgacg   1380
```

-continued

```
agcggcttcc agcagttcaa ggtcaatgtc tatgacaaga agccggagct tttcgggcct    1440
ctcaagtccg gccaggcccc caagtacatg gtgttcgcct gctccgactc ccgtgtgtcc    1500
ccgtcggtga ccctgggcct gcagcccggc gaggccttca ccgttcgcaa catcgccgcc    1560
atggtccccg gctacgacaa gaccaagtac accggcatcg gtccgccat cgagtacgct     1620 gtgtgcgccc tcaaggtgga ggtcctcgtg gtcattggcc atagctgctg cggtggcatc    1680
agggcgctcc tctcactcca ggacggcgca cctgacacct ccacttcgt cgaggactgg     1740 gttaagatcg ccttcattgc caagatgaag gtaaagaaag agcacgcctc ggtgccgttc    1800
gatgaccagt ggtccattct cgagaaggag gccgtgaacg tgtccctgga aacctcaag    1860 acctacccct tcgtcaagga agggcttgca aatgggaccc tcaagctgat cggcgcccac    1920
tacgactttg tctcaggaga gttcctcaca tggaaaaagt ga                       1962
```

<210> SEQ ID NO 165
<211> LENGTH: 653
<212> TYPE: PRT
<213> ORGANISM: Zea mays

<400> SEQUENCE: 165

```
Met Tyr Thr Leu Pro Val Arg Ala Thr Thr Ser Ser Ile Val Pro Ala
1               5                   10                  15

Cys His Pro Arg Ala Val Leu Leu Arg Leu Arg Pro Pro Gly Ser
            20                  25                  30

Gly Ser Ser Gly Thr Pro Arg Leu Arg Arg Pro Ala Thr Val Val Gly
        35                  40                  45

Met Asp Pro Thr Val Glu Arg Leu Lys Ser Gly Phe Gln Lys Phe Lys
    50                  55                  60

Thr Glu Val Tyr Asp Lys Lys Pro Glu Leu Phe Glu Pro Leu Lys Ser
65                  70                  75                  80

Gly Gln Ser Pro Arg Tyr Met Val Phe Ala Cys Ser Asp Ser Arg Val
                85                  90                  95

Cys Pro Ser Val Thr Leu Gly Leu Gln Pro Gly Glu Ala Phe Thr Val
            100                 105                 110

Arg Asn Ile Ala Ser Met Val Pro Pro Tyr Asp Lys Ile Lys Tyr Ala
        115                 120                 125

Gly Thr Gly Ser Ala Ile Glu Tyr Ala Val Cys Ala Leu Lys Val Gln
    130                 135                 140

Val Ile Val Val Ile Gly His Ser Cys Cys Gly Gly Ile Arg Ala Leu
145                 150                 155                 160

Leu Ser Leu Lys Asp Gly Ala Pro Asp Asn Phe Thr Phe Val Glu Asp
                165                 170                 175

Trp Val Arg Ile Gly Ser Pro Ala Lys Asn Lys Val Lys Lys Glu His
            180                 185                 190

Ala Ser Val Pro Phe Asp Asp Gln Cys Ser Ile Leu Glu Lys Glu Ala
        195                 200                 205

Val Asn Val Ser Leu Gln Asn Leu Lys Ser Tyr Pro Phe Val Lys Glu
    210                 215                 220

Gly Leu Ala Gly Gly Thr Leu Lys Leu Val Gly Ala His Tyr Ser Phe
225                 230                 235                 240

Val Lys Gly Gln Phe Val Thr Trp Glu Pro Pro Gln Asp Ala Ile Glu
                245                 250                 255

Arg Leu Thr Ser Gly Phe Gln Gln Phe Lys Val Asn Val Tyr Asp Lys
            260                 265                 270

Lys Pro Glu Leu Phe Gly Pro Leu Lys Ser Gly Gln Ala Pro Lys Tyr
```

```
                      275                 280                 285
Met Val Phe Ala Cys Ser Asp Ser Arg Val Cys Pro Ser Val Thr Leu
290                 295                 300

Gly Leu Gln Pro Ala Lys Ala Phe Thr Val Arg Asn Ile Ala Ala Met
305                 310                 315                 320

Val Pro Gly Tyr Asp Lys Thr Lys Tyr Thr Gly Ile Gly Ser Ala Ile
                325                 330                 335

Glu Tyr Ala Val Cys Ala Leu Lys Val Glu Val Leu Val Ile Gly
                340                 345                 350

His Ser Cys Cys Gly Gly Ile Arg Ala Leu Leu Ser Leu Lys Asp Gly
                355                 360                 365

Ala Pro Asp Asn Phe His Phe Val Glu Asp Trp Val Arg Ile Gly Ser
370                 375                 380

Pro Ala Lys Asn Lys Val Lys Lys Glu His Ala Ser Val Pro Phe Asp
385                 390                 395                 400

Asp Gln Cys Ser Ile Leu Glu Lys Glu Ala Val Asn Val Ser Leu Gln
                405                 410                 415

Asn Leu Lys Ser Tyr Pro Leu Val Lys Glu Gly Leu Ala Gly Gly Thr
                420                 425                 430

Ser Ser Gly Trp Pro His Tyr Asp Phe Val Lys Gly Gln Phe Val Thr
                435                 440                 445

Trp Glu Pro Pro Gln Asp Ala Ile Glu Arg Leu Thr Ser Gly Phe Gln
450                 455                 460

Gln Phe Lys Val Asn Val Tyr Asp Lys Lys Pro Glu Leu Phe Gly Pro
465                 470                 475                 480

Leu Lys Ser Gly Gln Ala Pro Lys Tyr Met Val Phe Ala Cys Ser Asp
                485                 490                 495

Ser Arg Val Ser Pro Ser Val Thr Leu Gly Leu Gln Pro Gly Glu Ala
                500                 505                 510

Phe Thr Val Arg Asn Ile Ala Ala Met Val Pro Gly Tyr Asp Lys Thr
                515                 520                 525

Lys Tyr Thr Gly Ile Gly Ser Ala Ile Glu Tyr Ala Val Cys Ala Leu
530                 535                 540

Lys Val Glu Val Leu Val Ile Gly His Ser Cys Cys Gly Gly Ile
545                 550                 555                 560

Arg Ala Leu Leu Ser Leu Gln Asp Gly Ala Pro Asp Thr Phe His Phe
                565                 570                 575

Val Glu Asp Trp Val Lys Ile Ala Phe Ile Ala Lys Met Lys Val Lys
                580                 585                 590

Lys Glu His Ala Ser Val Pro Phe Asp Asp Gln Trp Ser Ile Leu Glu
                595                 600                 605

Lys Glu Ala Val Asn Val Ser Leu Glu Asn Leu Lys Thr Tyr Pro Phe
                610                 615                 620

Val Lys Glu Gly Leu Ala Asn Gly Thr Leu Lys Leu Ile Gly Ala His
625                 630                 635                 640

Tyr Asp Phe Val Ser Gly Glu Phe Leu Thr Trp Lys Lys
                645                 650

<210> SEQ ID NO 166
<211> LENGTH: 1920
<212> TYPE: DNA
<213> ORGANISM: Zea mays

<400> SEQUENCE: 166
atgtacacat tgcccgtccg tgccaccaca tccagcatcg tcgccagcct cgccaccccc         60
```

```
gcgccgtcct cctcctccgg ctccggccgc cccaggctca ggctcatccg gaacgccccc    120
gtcttcgccg cccccgccac cgtctgtaaa cgggacggcg ggcagctgag gagtcaaacg    180
agagagatcg agagagaaag aaagggaggg catccaccag ccggcgggca taagagggga    240
ggagagagag gccagagaag aggaggagaa gaagaagaag atgagcagct gcctctgcct    300
tccgaaaaaa aaggagggc cagcgaagga gaagccgtcc acagataccc ccacctcgtc    360
actccttcag aaccagaagc cctccaacct ccacctcctc cctccaaggc ttcctccaag    420
ggcatggacc ccaccgtcga gcgcttgaag agcgggttcc agaagttcaa gaccgaggtc    480
tatgacaaga agccggagct gttcgagcct ctcaagtccg ccagagccc caggtacatg    540 gtgttcgcct gctccgactc ccgcgtgtgc ccgtcggtga cactgggact gcagcccggc    600
gaggcattca ccgtccgcaa catcgcttcc atggtcccac cctacgacaa gatcaagtac    660
gccggcacag gtccgccat cgagtacgcc gtgtgcgcgc tcaaggtgca ggtcatcgtg    720
gtcattggcc acagctgctg cggtggcatc agggcgctcc tctccctcaa ggacggcgcg    780
cccgacaact tcaccttcgt ggaggactgg gtcaggatcg cagccctgc caagaacaag    840 gtgaagaaag agcacgcgtc cgtgccgttc gatgaccagt gctccatcct ggagaaggag    900
gccgtgaacg tgtcgctcca gaacctcaag agctacccct cgtcaagga agggctggcc    960 ggcgggacgc tcaagctggt tggcgcccac tcacacttcg tcaaagggca gttcgtcaca   1020
tgggagcctc cccaggacgc catcgagcgc ttgacgagcg gcttccagca gttcaaggtc   1080
aatgtctatg acaagaagcc ggagcttttc gggcctctca gtccggcca ggcccccaag   1140 tacatggtgt tcgcctgctc cgactcccgt gtgtgcccgt cggtgaccct gggcctgcag   1200
ccgggcgagg ccttcaccgt tcgcaacatc gccgccatgg tcccaggcta cgacaagacc   1260
aagtacaccg gcatcgggtc cgccatcgag tacgctgtgt gcgccctcaa ggtggaggtc   1320
ctcgtggtca ttggccatag ctgctgcggt ggcatcaggg cgctcctctc actccaggac   1380
ggcgcagcct acaccttcca cttcgtcgag gactgggtta agatcggctt cattgccaag   1440
atgaaggtaa agaaagagca cgcctcggtg ccgttcgatg accagtgctc cattctcgag   1500
aaggaggccg tgaacgtgtc cctggagaac ctcaagacct accccttcgt caaggaaggg   1560
cttgcaaatg ggaccctcaa gctgatcggc gcccactacg actttgtctc aggagagttc   1620
ctcacatgga aaaagtgaaa aactagggct aaggcaattc taccggcccg ccgactctgc   1680
atcatcataa tatatatact ataactatac tactagctac ctaccgatag tcacccgagc   1740
aatgtgaatg cgtcgagtac tatctgtttt ctgcatctac atatatatac cggatcaaca   1800
atcgcccaat gtgaatgtaa taagcaatat catttctac cacttttcat tcctaacgct   1860
gaggcttttt atgtactata tcttatatga tgaataataa tatgaccgcc ttgtgatcta   1920
```

<210> SEQ ID NO 167
<211> LENGTH: 545
<212> TYPE: PRT
<213> ORGANISM: Zea mays

<400> SEQUENCE: 167

Met Tyr Thr Leu Pro Val Arg Ala Thr Thr Ser Ser Ile Val Ala Ser
1               5                   10                  15

Leu Ala Thr Pro Ala Pro Ser Ser Ser Ser Gly Ser Gly Arg Pro Arg
            20                  25                  30

Leu Arg Leu Ile Arg Asn Ala Pro Val Phe Ala Ala Pro Ala Thr Val
        35                  40                  45

```
Cys Lys Arg Asp Gly Gly Gln Leu Arg Ser Gln Thr Arg Glu Ile Glu
     50                  55                  60

Arg Glu Arg Lys Gly Gly His Pro Pro Ala Gly Gly His Lys Arg Gly
 65                  70                  75                  80

Gly Glu Arg Gly Gln Arg Arg Gly Gly Glu Glu Glu Asp Glu Gln
                 85                  90                  95

Leu Pro Leu Pro Ser Glu Lys Lys Gly Gly Ala Ser Glu Gly Glu Ala
                100                 105                 110

Val His Arg Tyr Pro His Leu Val Thr Pro Ser Glu Pro Glu Ala Leu
            115                 120                 125

Gln Pro Pro Pro Pro Ser Lys Ala Ser Ser Lys Gly Met Asp Pro
        130                 135                 140

Thr Val Glu Arg Leu Lys Ser Gly Phe Gln Lys Phe Lys Thr Glu Val
145                 150                 155                 160

Tyr Asp Lys Lys Pro Glu Leu Phe Glu Pro Leu Lys Ser Gly Gln Ser
                165                 170                 175

Pro Arg Tyr Met Val Phe Ala Cys Ser Asp Ser Arg Val Cys Pro Ser
            180                 185                 190

Val Thr Leu Gly Leu Gln Pro Gly Glu Ala Phe Thr Val Arg Asn Ile
            195                 200                 205

Ala Ser Met Val Pro Pro Tyr Asp Lys Ile Lys Tyr Ala Gly Thr Gly
    210                 215                 220

Ser Ala Ile Glu Tyr Ala Val Cys Ala Leu Lys Val Gln Val Ile Val
225                 230                 235                 240

Val Ile Gly His Ser Cys Cys Gly Gly Ile Arg Ala Leu Leu Ser Leu
                245                 250                 255

Lys Asp Gly Ala Pro Asp Asn Phe Thr Phe Val Glu Asp Trp Val Arg
            260                 265                 270

Ile Gly Ser Pro Ala Lys Asn Lys Val Lys Lys Glu His Ala Ser Val
                275                 280                 285

Pro Phe Asp Asp Gln Cys Ser Ile Leu Glu Lys Glu Ala Val Asn Val
    290                 295                 300

Ser Leu Gln Asn Leu Lys Ser Tyr Pro Phe Val Lys Glu Gly Leu Ala
305                 310                 315                 320

Gly Gly Thr Leu Lys Leu Val Gly Ala His Ser His Phe Val Lys Gly
                325                 330                 335

Gln Phe Val Thr Trp Glu Pro Pro Gln Asp Ala Ile Glu Arg Leu Thr
            340                 345                 350

Ser Gly Phe Gln Gln Phe Lys Val Asn Val Tyr Asp Lys Lys Pro Glu
            355                 360                 365

Leu Phe Gly Pro Leu Lys Ser Gly Gln Ala Pro Lys Tyr Met Val Phe
    370                 375                 380

Ala Cys Ser Asp Ser Arg Val Cys Pro Ser Val Thr Leu Gly Leu Gln
385                 390                 395                 400

Pro Gly Glu Ala Phe Thr Val Arg Asn Ile Ala Ala Met Val Pro Gly
                405                 410                 415

Tyr Asp Lys Thr Lys Tyr Thr Gly Ile Gly Ser Ala Ile Glu Tyr Ala
            420                 425                 430

Val Cys Ala Leu Lys Val Glu Val Leu Val Val Ile Gly His Ser Cys
                435                 440                 445

Cys Gly Gly Ile Arg Ala Leu Leu Ser Leu Gln Asp Gly Ala Ala Tyr
    450                 455                 460

Thr Phe His Phe Val Glu Asp Trp Val Lys Ile Gly Phe Ile Ala Lys
465                 470                 475                 480
```

```
Met Lys Val Lys Lys Glu His Ala Ser Val Pro Phe Asp Asp Gln Cys
                485                 490                 495

Ser Ile Leu Glu Lys Glu Ala Val Asn Val Ser Leu Glu Asn Leu Lys
            500                 505                 510

Thr Tyr Pro Phe Val Lys Glu Gly Leu Ala Asn Gly Thr Leu Lys Leu
        515                 520                 525

Ile Gly Ala His Tyr Asp Phe Val Ser Gly Phe Leu Thr Trp Lys
    530                 535                 540

Lys
545

<210> SEQ ID NO 168
<211> LENGTH: 1208
<212> TYPE: DNA
<213> ORGANISM: Urochloa panicoides

<400> SEQUENCE: 168
gggcagcccg cactttaatg tcggcattgg ccatccgtgc agcccgtcc agcatcatcg      60 ccagcgtccg caccccgcg ctctccgccc gccgccgccc aggctcgtc ggcaacgccg     120 ccgccgccaa cgccgtcgtg taaaccggcc ggcgcacggg gagctcgaaa gtcaaacgag    180
agactagaga gagggggcg agaagtacta gtaggtcgaa gccggctgtg ataaaaagag    240
gagaagatga gcgggtgcct ctgcctcccc ggctacaaaa agaagaccat ggaccccgtc    300
gagcgcttgc agagcgggtt caagcagttc aagagcgagg tctacgacaa gaagccggag    360
ctgttcgagc cactcaagga aggccaggcc cccacgtaca tggtgttcgc ctgctccgac    420
tcccgttgct gcccgtcggt gaccctcggc ctgaagcccg cgaggccttt accgtccgc    480 aacatcgccg ccatggtccc accctacgac aagaatcggt acaccggcat cgggtccgcc    540
atcgagtacg ccgtctgcgc cctcaaggtc aaggtcctca ccgtcatcgg ccacagccgc    600
tgcggtggca tcaaggcgct cctctcaatg caggacggcg cagccgacaa cttccacttc    660
gtcgaggact gggtcaggat cggcttcctc gccaagaaga aggttctcac cgaccacccc    720
atggctccct tcgacgacca gtgctccatc ttggagaagg aggccgtcaa cgtctccctg    780
tacaacctcc tgacctaccc ctgggtgaag aaggtgtgt ccaacggctc cctcaagctg    840
gtcggcggcc actacgactt cgtcaagggc gcgttcgtca catgggagaa ataagccacc    900
cgatttacaa ctcctacacc atcatacata tatacatacg tacatcgtct cccgatatgc    960 acccatccg acgtgaatgg gtggagtgct cactacctat tttcggccgc tacatacggg   1020
atcgtcgtcc ttctatgtga atgtaataag caatagcatc ctctaccgct ttaatttcta   1080
taaggccgag cttttatt taccatatga tgcataattt gaccgccttg tggtcaaaag   1140
acatcaccaa tatatgtata agccttcttc ataataatat ataatcatca agtgtttacc   1200
tttttatt                                                           1208

<210> SEQ ID NO 169
<211> LENGTH: 157
<212> TYPE: PRT
<213> ORGANISM: Urochloa panicoides

<400> SEQUENCE: 169

Met Ser Gly Cys Leu Cys Leu Pro Gly Tyr Lys Lys Thr Met Asp
1               5                   10                  15

Pro Val Glu Arg Leu Gln Ser Gly Phe Lys Gln Phe Lys Ser Glu Val
            20                  25                  30
```

```
Tyr Asp Lys Lys Pro Glu Leu Phe Glu Pro Leu Lys Glu Gly Gln Ala
            35                  40                  45

Pro Thr Tyr Met Val Phe Ala Cys Ser Asp Ser Arg Cys Cys Pro Ser
        50                  55                  60

Val Thr Leu Gly Leu Lys Pro Gly Glu Ala Phe Thr Val Arg Asn Ile
 65                 70                  75                  80

Ala Ala Met Val Pro Pro Tyr Asp Lys Asn Arg Tyr Thr Gly Ile Gly
                85                  90                  95

Ser Ala Ile Glu Tyr Ala Val Cys Ala Leu Lys Val Lys Val Leu Thr
            100                 105                 110

Val Ile Gly His Ser Arg Cys Gly Gly Ile Lys Ala Leu Leu Ser Met
            115                 120                 125

Gln Asp Gly Ala Ala Asp Asn Phe His Phe Val Glu Asp Trp Val Arg
        130                 135                 140

Ile Gly Phe Leu Ala Lys Lys Lys Val Leu Thr Asp His
145                 150                 155
```

<210> SEQ ID NO 170
<211> LENGTH: 1034
<212> TYPE: DNA
<213> ORGANISM: Urochloa panicoides

<400> SEQUENCE: 170

```
ccgcactgga atgtcggcat tggccatccg ctcagccccg tccagcatca tcgccagcgt    60
ccgcacccc gcgcaccgcc gccccgggct cgtcaggaac gccgccgcca ccaccgccga   120
gttgaccatg accccgtcg agcgcttgca gagcggcttc aagcagttca gagcgaggt   180
ctatgacaag aagccggagc tgttcgagcc actcaaggaa ggccaggccc ccacgtacat   240
ggtgttcgcc tgctccgact ctcgttgctg cccgtcggtg accctcggcc tgaagcccgg   300
cgaggccttc accgtccgca acatcgccgc catggtccca ccctacgaca gaaccggta   360
caccggcatc gggtccgcca tcgagtacgc cgtctgcgcc ctcaaggtca aggtcctcac   420
cgtcatcggc cacagccgct gcggtggcat caaggcgctc ctctccatgc aggatggcgc   480
agccgacaac ttccacttcg tcgaggattg ggtcaggatc ggcttcctcg cgaagaagaa   540
ggttctgacc gaccacccca tggctccgtt cgatgaccag tgctccatct tggagaagga   600
ggcagtcaac gtctccctct acaacctcct gacctacccc tgggtgaagg aaggcgtgtc   660
caacgggtcc ctcaagctgg tcggcggcca ctacgacttc gtcaaggggg cgttcgtcac   720
atgggagaaa taagccaccc gattacagc tcctacacca ccgtacatac atacgtacat   780
cccgatatgt accccatccg acgtgaacgg gtggagtact tactactacc tattttcggc   840
cgctacgtac cgggtcgtcg ttctatgtga atgtaataag caatagcatt ctctaccgct   900
ttaatttcta aggccgagct ttttatttat gtaccgtatg atgcataatt tgacctcctt   960
gtggtcaaaa gacatcagct atatatgtat aagtcttctt cataatataa tcataaagtg  1020
tttaccttt tact                                                    1034
```

<210> SEQ ID NO 171
<211> LENGTH: 240
<212> TYPE: PRT
<213> ORGANISM: Urochloa panicoides

<400> SEQUENCE: 171

```
Met Ser Ala Leu Ala Ile Arg Ser Ala Pro Ser Ile Ile Ala Ser
 1               5                  10                  15

Val Arg Thr Pro Ala His Arg Arg Pro Gly Leu Val Arg Asn Ala Ala
```

```
            20                  25                  30
Ala Thr Thr Ala Glu Leu Thr Met Asp Pro Val Glu Arg Leu Gln Ser
         35                  40                  45
Gly Phe Lys Gln Phe Lys Ser Glu Val Tyr Asp Lys Pro Glu Leu
     50                  55                  60
Phe Glu Pro Leu Lys Glu Gly Gln Ala Pro Thr Tyr Met Val Phe Ala
 65                  70                  75                  80
Cys Ser Asp Ser Arg Cys Cys Pro Ser Val Thr Leu Gly Leu Lys Pro
                 85                  90                  95
Gly Glu Ala Phe Thr Val Arg Asn Ile Ala Ala Met Val Pro Pro Tyr
             100                 105                 110
Asp Lys Asn Arg Tyr Thr Gly Ile Gly Ser Ala Ile Glu Tyr Ala Val
             115                 120                 125
Cys Ala Leu Lys Val Lys Val Leu Thr Val Ile Gly His Ser Arg Cys
         130                 135                 140
Gly Gly Ile Lys Ala Leu Leu Ser Met Gln Asp Gly Ala Ala Asp Asn
145                 150                 155                 160
Phe His Phe Val Glu Asp Trp Val Arg Ile Gly Phe Leu Ala Lys Lys
                 165                 170                 175
Lys Val Leu Thr Asp His Pro Met Ala Pro Phe Asp Asp Gln Cys Ser
             180                 185                 190
Ile Leu Glu Lys Glu Ala Val Asn Val Ser Leu Tyr Asn Leu Leu Thr
         195                 200                 205
Tyr Pro Trp Val Lys Glu Gly Val Ser Asn Gly Ser Leu Lys Leu Val
     210                 215                 220
Gly Gly His Tyr Asp Phe Val Lys Gly Ala Phe Val Thr Trp Glu Lys
225                 230                 235                 240

<210> SEQ ID NO 172
<211> LENGTH: 795
<212> TYPE: DNA
<213> ORGANISM: Chlamydomonas reinhardtii

<400> SEQUENCE: 172
atgggatgcg gtgccagcgt gcctcagaat ggtggaggag ctcccgttac gcgggttatg    60
cccgcgccag cacaaccagt gtctgaggcg caatcggcaa tcagcttcca accatcgcgc   120
agcaaccgca gcagccttga aaagatcaat tcgctcacgg atagggcatc gcctgagcag   180
gtgctgcaga acctgctgga cggcaacatg cgcttcctgg atgcgccgt cgcgcatccc    240 caccaggact tcagccgcgt gcaggccatt aaggccaagc aaaagcccct cgcggccatc   300
ctgggctgcg ccgactctcg cgtgcctgcg gaaattgtgt cgaccaagg ctttggcgac    360 gtgttcgtgt gccgtgtcgc cggcaacatt gctacgccag aggagatcgc cagtctggag   420
tatgccgtgc ttgacctcgg agttaaggtg gtgatggtcc tcggacacac acgctgcgga   480
gccgtgaagg ctgcactttc aggcaaggcg ttccccggct tcatcgacac gctggtggac   540
cacctggacg tcgccatcag ccgcgtcaac agcatgagcg ccaaggcgca ccaggccatc   600
aaggacggcg acgtggacat gctggaccgc gtggtgaagg agaacgtcaa gtaccaggtg   660
cagcggtgcc agcgctccgt catcatccag gaggggttgc agaaggggaa cctgctgctg   720
gcgggcgccg tgtacgacct ggacacgggc aaggtgcacg tcagcgtcac caagggcggc   780
agcagcgccg agtag                                                    795

<210> SEQ ID NO 173
<211> LENGTH: 264
```

```
<212> TYPE: PRT
<213> ORGANISM: Chlamydomonas reinhardtii

<400> SEQUENCE: 173

Met Gly Cys Gly Ala Ser Val Pro Gln Asn Gly Gly Ala Pro Val
1               5                   10                  15

Thr Arg Val Met Pro Ala Pro Ala Gln Pro Val Ser Glu Ala Gln Ser
            20                  25                  30

Ala Ile Ser Phe Gln Pro Ser Arg Ser Asn Arg Ser Ser Leu Glu Lys
        35                  40                  45

Ile Asn Ser Leu Thr Asp Arg Ala Ser Pro Glu Gln Val Leu Gln Asn
    50                  55                  60

Leu Leu Asp Gly Asn Met Arg Phe Leu Asp Gly Ala Val Ala His Pro
65              70                  75                  80

His Gln Asp Phe Ser Arg Val Gln Ala Ile Lys Ala Lys Gln Lys Pro
                85                  90                  95

Leu Ala Ala Ile Leu Gly Cys Ala Asp Ser Arg Val Pro Ala Glu Ile
            100                 105                 110

Val Phe Asp Gln Gly Phe Gly Asp Val Phe Val Cys Arg Val Ala Gly
        115                 120                 125

Asn Ile Ala Thr Pro Glu Glu Ile Ala Ser Leu Glu Tyr Ala Val Leu
    130                 135                 140

Asp Leu Gly Val Lys Val Met Val Leu Gly His Thr Arg Cys Gly
145                 150                 155                 160

Ala Val Lys Ala Ala Leu Ser Gly Lys Ala Phe Pro Gly Phe Ile Asp
                165                 170                 175

Thr Leu Val Asp His Leu Asp Val Ala Ile Ser Arg Val Asn Ser Met
            180                 185                 190

Ser Ala Lys Ala His Gln Ala Ile Lys Asp Gly Asp Val Asp Met Leu
        195                 200                 205

Asp Arg Val Val Lys Glu Asn Val Lys Tyr Gln Val Gln Arg Cys Gln
    210                 215                 220

Arg Ser Val Ile Ile Gln Glu Gly Leu Gln Lys Gly Asn Leu Leu Leu
225                 230                 235                 240

Ala Gly Ala Val Tyr Asp Leu Asp Thr Gly Lys Val His Val Ser Val
                245                 250                 255

Thr Lys Gly Gly Ser Ser Ala Glu
            260

<210> SEQ ID NO 174
<211> LENGTH: 939
<212> TYPE: DNA
<213> ORGANISM: Chlamydomonas reinhardtii

<400> SEQUENCE: 174
atgtcgctat tcaagtctag cctgcctgcg ggcttcctat tccctatcg gcaccccaag    60 gccaagggc ttgttgaggg cacgctttat ggactgggct ccctgtttcg cggcgtgggc   120
gccgcgctgg atgagctggg ctctatggtt cagggccctc agggtagtgt caaggaccac   180
gtccagccta acctggcgtt tgcaccagtg caccgcaagc cggatgtgcc cgttaacgcg   240
ggccaggtgt gcccgctcc acccgctgct gctcgcacgc tgaaaatcaa ggaggtggtt   300
gtgcccaaca agcacagcac cgcgttcgtg gctgccaacg ccaatgtgct cgggaacgtt   360
aagctggggg cgggctcatc ggtgtggtat ggcgccgtgc tgcgcggtga cgtgaacggc   420
attgaggtgg gcgccaacag caacatccag gacaacgcca tcgtgcacgt gtccaagtac   480
```

```
agcatggacg gcacggcacg gcccaccgtc atcggcaaca atgtgaccat tggccacgcc    540
gccacggtgc acgcctgcac cattgaggac aactgcctgg tgggcatggg cgccaccgtg    600
ctcgacggag cgacggtcaa gagcggctcc atcgtggctg ccggcgccgt ggtgccgccc    660
aacaccacca tccctcgggg ccaggtgtgg gccggctcgc ccgccaagtt cctgcgccac    720
ctggagccgg aggaggccag cttcatcggc aagtctgcca gctgctacgc cgagctgtcc    780
gccatccaca gttcgagca gagcaagacg tttgaggagc agtacacgga gagctgcatc    840
atcaaggacc gcgccgctct ggccgacccg tcaaactcag tgcaccagat gtgggagtac    900
gacagccaga cggcgttggt ggcccgcgcc aagaggtag                           939
```

<210> SEQ ID NO 175
<211> LENGTH: 312
<212> TYPE: PRT
<213> ORGANISM: Chlamydomonas reinhardtii

<400> SEQUENCE: 175

```
Met Ser Leu Phe Lys Ser Ser Leu Pro Ala Gly Phe Leu Phe Pro Tyr
1               5                   10                  15

Arg His Pro Lys Ala Lys Gly Leu Val Glu Gly Thr Leu Tyr Gly Leu
            20                  25                  30

Gly Ser Leu Phe Arg Gly Val Gly Ala Ala Leu Asp Glu Leu Gly Ser
        35                  40                  45

Met Val Gln Gly Pro Gln Gly Ser Val Lys Asp His Val Gln Pro Asn
    50                  55                  60

Leu Ala Phe Ala Pro Val His Arg Lys Pro Asp Val Pro Val Asn Ala
65                  70                  75                  80

Gly Gln Val Val Pro Ala Pro Ala Ala Arg Thr Leu Lys Ile
                85                  90                  95

Lys Glu Val Val Val Pro Asn Lys His Ser Thr Ala Phe Val Ala Ala
                100                 105                 110

Asn Ala Asn Val Leu Gly Asn Val Lys Leu Gly Ala Gly Ser Ser Val
            115                 120                 125

Trp Tyr Gly Ala Val Leu Arg Gly Asp Val Asn Gly Ile Glu Val Gly
    130                 135                 140

Ala Asn Ser Asn Ile Gln Asp Asn Ala Ile Val His Val Ser Lys Tyr
145                 150                 155                 160

Ser Met Asp Gly Thr Ala Arg Pro Thr Val Ile Gly Asn Asn Val Thr
                165                 170                 175

Ile Gly His Ala Ala Thr Val His Ala Cys Thr Ile Glu Asp Asn Cys
            180                 185                 190

Leu Val Gly Met Gly Ala Thr Val Leu Asp Gly Ala Thr Val Lys Ser
        195                 200                 205

Gly Ser Ile Val Ala Ala Gly Ala Val Val Pro Pro Asn Thr Thr Ile
    210                 215                 220

Pro Ser Gly Gln Val Trp Ala Gly Ser Pro Ala Lys Phe Leu Arg His
225                 230                 235                 240

Leu Glu Pro Glu Glu Ala Ser Phe Ile Gly Lys Ser Ala Ser Cys Tyr
                245                 250                 255

Ala Glu Leu Ser Ala Ile His Lys Phe Glu Gln Ser Lys Thr Phe Glu
            260                 265                 270

Glu Gln Tyr Thr Glu Ser Cys Ile Ile Lys Asp Arg Ala Ala Leu Ala
        275                 280                 285

Asp Pro Ser Asn Ser Val His Gln Met Trp Glu Tyr Asp Ser Gln Thr
    290                 295                 300
```

Ala Leu Val Ala Arg Ala Lys Arg
    305                 310

<210> SEQ ID NO 176
<211> LENGTH: 1238
<212> TYPE: DNA
<213> ORGANISM: Oryza sativa

<400> SEQUENCE: 176

```
ggggctcatc tctctctctc tcactcttct ccctcttctc accaccagac gccatcaaac      60
ccctacctcc cgcggcggcg gcggcggcgg cggccggcgg cgagctccgg acagacagag     120
gagggcgcga gcggagaggg cgaggaggga aggagggagg gaggcgacag gcatggggac     180
cctcgggcgc gcgatctaca cggtgtggga agtggatccg cggcacgggg caggccatgga    240
ccgcctcgga tccaccatcc agggcggcct ccgcgtcgag gagcagcttt caaggcatcg     300
cacgatcatg aacatatttg agaaagagcc cagagtccac aaggatgttt ttgttgctcc     360
cagtgcagct gtgattggcg atgttgagat cggacatgga tcctcaatct ggtacggctc     420
cattttaaga ggtgatgtca acagcattca tattggatct ggatcaaata tacaagacaa     480
ttcccttgta catgttgcaa aagctaacat cagcgggaag gttctcccaa ccataattgg     540
aaacaatgtt acaataggtc atagtgctgt tctgcacgca tgcaccgtcg aggatgaagc     600
ttttgttggt atgggtgcca ctctgcttga tggagtggtc gttgaaaagc acagcatggt     660
tggtgcagga tcgcttgtta agcagaacac aaggattcct tctggagagg tctgggtcgg     720
taatcctgcc aagttcctaa gaaagcttac tgaagaggag atagcgttca ttgctcagtc     780
agcaacgaac tacatcaatc tggcccaagt ccatgctgcc gagaattcca agaccttcga     840
cgagatcgag ctcgagaaga tgctgaggaa aaagtatgcc cacaaagacg aggagtatga     900
ttcgatgctc ggcgtggtcc gtgagatccc gccggagctc atcctcccgg acaacatcct     960
cccaaacaag gctcagaagg ctgttgctca ctgaatgttt tgtcaagctc ccgcttggga    1020
aaagcttggt tttttttgtta cgtgttttga cctggaacaa catttgacac atgtcttttg    1080
atctcattgt ctgttttca agcccaataa gaatttgggt cgagcattgt tttaggatcg     1140
accatataca gtacctctct ttgcattaca atgaagagca gttaatttgg gtcacttttt    1200
acatctttac tgaagtagaa acgcgtcctc tgtctgtg                            1238
```

<210> SEQ ID NO 177
<211> LENGTH: 273
<212> TYPE: PRT
<213> ORGANISM: Oryza sativa

<400> SEQUENCE: 177

Met Gly Thr Leu Gly Arg Ala Ile Tyr Thr Val Gly Lys Trp Ile Arg
1               5                   10                  15

Gly Thr Gly Gln Ala Met Asp Arg Leu Gly Ser Thr Ile Gln Gly Gly
            20                  25                  30

Leu Arg Val Asp Glu Gln Leu Ser Arg His Arg Thr Ile Met Asn Ile
        35                  40                  45

Phe Glu Lys Glu Pro Arg Val His Lys Asp Val Phe Val Ala Pro Ser
    50                  55                  60

Ala Ala Val Ile Gly Asp Ile Glu Ile Gly His Gly Ser Ser Ile Trp
65                  70                  75                  80

Tyr Gly Ser Ile Leu Arg Gly Asp Val Asn Ser Ile His Ile Gly Val
                85                  90                  95

```
Gly Thr Asn Ile Gln Asp Asn Ser Leu Val His Val Ser Lys Ala Asn
                100                 105                 110

Ile Ser Gly Lys Val Leu Pro Thr Ile Ile Gly Asn Asn Val Thr Ile
            115                 120                 125

Gly His Ser Ala Val Leu His Ala Cys Ile Val Glu Asp Glu Ala Phe
    130                 135                 140

Val Gly Met Gly Ala Thr Leu Leu Asp Gly Val Val Glu Lys His
145                 150                 155                 160

Ser Met Val Gly Ala Gly Ser Leu Val Lys Gln Asn Thr Arg Ile Pro
                165                 170                 175

Ser Gly Glu Val Trp Val Gly Asn Pro Ala Lys Phe Leu Arg Lys Leu
            180                 185                 190

Thr Glu Glu Glu Ile Ala Phe Ile Ala Gln Ser Ala Thr Asn Tyr Ile
            195                 200                 205

Asn Leu Ala Gln Val His Ala Ala Glu Asn Ser Lys Thr Phe Asp Glu
    210                 215                 220

Ile Glu Leu Glu Lys Met Leu Arg Lys Lys Tyr Ala His Lys Asp Glu
225                 230                 235                 240

Glu Tyr Asp Ser Met Leu Gly Val Val Arg Glu Ile Pro Pro Glu Leu
                245                 250                 255

Ile Leu Pro Asp Asn Ile Leu Pro Asn Lys Ala Gln Lys Ala Val Ala
            260                 265                 270

His

<210> SEQ ID NO 178
<211> LENGTH: 657
<212> TYPE: DNA
<213> ORGANISM: Oryza sativa

<400> SEQUENCE: 178
atgggttcga ctcgcctcct cgtactgctc gccgccgctt ccctcctcct cgccaccgcc      60
gtcccggcag ccagagcaca ggaagaaact gatcacgagg aggagttcac gtacatcagc     120
ggggacgaga aggggccgga gcactggggc aagctgaagc cggagtgggc gcagtgcggc     180
gccggcgaga tgcagtcgcc gatcgacctc tcccacgagc gggtcaagct ggtgcgcgac     240
ctcggctacc tcgacgactc ctaccgcgcc gccgaggcct ccatcgtcaa ccgcggccac     300
gacatcatgg tcaggttcga cggcgacgcc ggcagcgtcg tcatcaacgg caccgcctac     360
tacctccgcc agctccactg cactccccc accgagcaca cgtcgacgg ccgcaggtac      420 gacatggagc tgcacatggt ccacgagagc gccgagaaga aggccgccgt gatcggcctc     480
ctctacgagg tcggccgccc cgaccgcttc ctccaaaaga tggagccata tctcaagatg     540
attgcggaca aggaggacag ggccgccttg cacgcagggg gtggtctgga cgattgtcaa     600
gagggttcgc accgtgtcga ggtatcagct cgaccttctc agggaagctg tgcatga       657

<210> SEQ ID NO 179
<211> LENGTH: 275
<212> TYPE: PRT
<213> ORGANISM: Oryza sativa

<400> SEQUENCE: 179

Met Gly Ser Thr Arg Leu Leu Val Leu Leu Ala Ala Ala Ser Leu Leu
1               5                   10                  15

Leu Ala Thr Ala Val Pro Ala Ala Arg Ala Gln Glu Glu Thr Asp His
                20                  25                  30

Glu Lys Glu Phe Thr Tyr Ile Ser Gly Asp Glu Lys Gly Pro Glu His
```

```
                 35                  40                  45
Trp Gly Lys Leu Lys Pro Glu Trp Ala Gln Cys Gly Ala Gly Glu Met
 50                  55                  60

Gln Ser Pro Ile Asp Leu Ser His Glu Arg Val Lys Leu Val Arg Asp
 65                  70                  75                  80

Leu Gly Tyr Leu Asp Asp Ser Tyr Arg Ala Glu Ala Ser Ile Val
                 85                  90                  95

Asn Arg Gly His Asp Ile Met Val Arg Phe Asp Gly Asp Ala Gly Ser
                100                 105                 110

Val Val Ile Asn Gly Thr Ala Tyr Tyr Leu Arg Gln Leu His Trp His
                115                 120                 125

Ser Pro Thr Glu His Ser Val Asp Gly Arg Arg Tyr Asp Met Glu Leu
 130                 135                 140

His Met Val His Glu Ser Ala Glu Lys Lys Ala Ala Val Ile Gly Leu
 145                 150                 155                 160

Leu Tyr Glu Val Gly Arg Pro Asp Arg Phe Leu Gln Lys Met Glu Pro
                165                 170                 175

Tyr Leu Lys Met Ile Ala Asp Lys Glu Asp Arg Glu Glu Lys Val Gly
                180                 185                 190

Met Ile Asp Pro Arg Gly Ala Arg Gly Arg Ala Ser Val Tyr Tyr Arg
                195                 200                 205

Tyr Met Gly Ser Leu Thr Thr Pro Pro Cys Thr Gln Gly Val Val Trp
                210                 215                 220

Thr Ile Val Lys Arg Val Arg Thr Val Ser Arg Tyr Gln Leu Asp Leu
225                 230                 235                 240

Leu Arg Glu Ala Val His Asp Glu Met Glu Asn Asn Ala Arg Pro Leu
                245                 250                 255

Gln Ala Val Asn Asn Arg Asp Ile Ser Ile Phe Arg Pro Tyr Pro His
                260                 265                 270

Lys Arg Tyr
        275

<210> SEQ ID NO 180
<211> LENGTH: 822
<212> TYPE: DNA
<213> ORGANISM: Dioscorea cayenensis

<400> SEQUENCE: 180
atgagttcat ccaccttct  ccatctcctc ctcctctcct ccctcctctt ctcttgcctt       60
ccaaatgcaa aacctcagca agctgaggat gagtttagct acattgaagg aagtcctaat      120
ggtcctgaaa actggggaaa tcttaaaaag gagtgggaga cttgtggcaa aggcatggag      180
cagtcaccca ttcaattgcg tgataacaga gtgatattcg atcaaacttt gggggagctg      240
agaagaaatt atagagccgc tgaagcaaca ttaaggaaca gtggacatga tgtattggtg      300
gaatttgagg gtaatgctgg ttcactatcc atcaatcgag ttgcatacca actcaagcga      360
attcattttc actccccttc agagcatgaa atgaatggcg aaaggtttga ccttgaggca      420
cagctggtcc atgagagcca agaccaaaag agagcagtgg tttctattct tttcagattt      480
ggacgtgctg atacattcct ctcagatctt gaagacttta tcaagcagtt tagcagtagc      540
cagaagaatg aaataaatgc aggagttgtg atccaaatc  aattacagtt tgatgactgt      600
gcatatttta gatacatggg ctcattcaca gctccacctt gcactgaagg tatttcatgg      660
accgtcatga ggaaggttgc aactgttttca ccaaggcaag tacttctgtt gaagcaggca      720
gtgaatgaaa atgctataaa caatgcgaga ccacttcaac caaccaatta ccgctccgtt      780
```
ttttactttg aacagctgaa atcgaagctt ggtgtcatat aa   822

<210> SEQ ID NO 181
<211> LENGTH: 273
<212> TYPE: PRT
<213> ORGANISM: Dioscorea cayenensis

<400> SEQUENCE: 181

Met Ser Ser Ser Thr Leu Leu His Leu Leu Leu Ser Leu Leu
1               5                   10                  15

Phe Ser Cys Leu Pro Asn Ala Lys Pro Gln Gln Ala Glu Asp Glu Phe
            20                  25                  30

Ser Tyr Ile Glu Gly Ser Pro Asn Gly Pro Glu Asn Trp Gly Asn Leu
        35                  40                  45

Lys Lys Glu Trp Glu Thr Cys Gly Lys Gly Met Glu Gln Ser Pro Ile
    50                  55                  60

Gln Leu Arg Asp Asn Arg Val Ile Phe Asp Gln Thr Leu Gly Glu Leu
65              70                  75                  80

Arg Arg Asn Tyr Arg Ala Ala Glu Ala Thr Leu Arg Asn Ser Gly His
                85                  90                  95

Asp Val Leu Val Glu Phe Glu Gly Asn Ala Gly Ser Leu Ser Ile Asn
            100                 105                 110

Arg Val Ala Tyr Gln Leu Lys Arg Ile His Phe His Ser Pro Ser Glu
        115                 120                 125

His Glu Met Asn Gly Glu Arg Phe Asp Leu Glu Ala Gln Leu Val His
    130                 135                 140

Glu Ser Gln Asp Gln Lys Arg Ala Val Val Ser Ile Leu Phe Arg Phe
145                 150                 155                 160

Gly Arg Ala Asp Thr Phe Leu Ser Asp Leu Glu Asp Phe Ile Lys Gln
                165                 170                 175

Phe Ser Ser Gln Lys Asn Glu Ile Asn Ala Gly Val Val Asp Pro
            180                 185                 190

Asn Gln Leu Gln Phe Asp Asp Cys Ala Tyr Phe Arg Tyr Met Gly Ser
        195                 200                 205

Phe Thr Ala Pro Pro Cys Thr Glu Gly Ile Ser Trp Thr Val Met Arg
    210                 215                 220

Lys Val Ala Thr Val Ser Pro Arg Gln Val Leu Leu Lys Gln Ala
225                 230                 235                 240

Val Asn Glu Asn Ala Ile Asn Asn Ala Arg Pro Leu Gln Pro Thr Asn
                245                 250                 255

Tyr Arg Ser Val Phe Tyr Phe Glu Gln Leu Lys Ser Lys Leu Gly Val
            260                 265                 270

Ile

<210> SEQ ID NO 182
<211> LENGTH: 807
<212> TYPE: DNA
<213> ORGANISM: Dioscorea batatas

<400> SEQUENCE: 182
atgagttcat ccaccttct ccatctcctc ctcctctcct cctcctctt ctcttgcctt      60 gcaaatgtag aggatgagtt tagctacatt gaaggaaatc ctaatggtcc tgaaaactgg    120
ggaaatctta aaccggagtg ggagacttgt ggcaaaggca tggagcagtc acccattcag    180
ttgcgtgata acagagtgat attcgatcaa actttgggga ggttgagaag aaattacaga    240

-continued

```
gccgttgatg caagattaag gaacagtgga catgatgtat tggtggaatt taagggtaat    300
gctggttcac tatcaatcaa tcgagttgca taccaactca agcgaattca ttttcactcc    360
ccttcagagc atgaaatgaa tggcgaaagg tttgaccttg aggcacagct ggttcatgag    420
agccaagatc aaaagagagc agtggtttct attcttttca tatttggacg tgctgaccca    480
ttcctctcag atcttgaaga ctttatcaag cagtttagca gtagccagaa gaatgaaata    540
aatgcaggag ttgtggatcc aaatcaatta cagattgatg actctgcata ttatagatac    600
atgggctcat tcacagctcc accttgcact gaaggtattt catggaccgt catgaggaag    660
gttgcaactg tttcaccaag acaagtactg ctgttgaagc aggcagtgaa tgaaaatgct    720
ataaacaatg caagaccact tcaaccaacc aatttccgct ccgttttttta ctttgaacag    780
ctgaaatcga aggtttgtgc catataa                                         807
```

<210> SEQ ID NO 183
<211> LENGTH: 268
<212> TYPE: PRT
<213> ORGANISM: Dioscorea batatas

<400> SEQUENCE: 183

```
Met Ser Ser Ser Thr Leu Leu His Leu Leu Leu Ser Leu Leu
1               5                   10                  15

Phe Ser Cys Leu Ala Asn Val Glu Asp Glu Phe Ser Tyr Ile Glu Gly
            20                  25                  30

Asn Pro Asn Gly Pro Glu Asn Trp Gly Asn Leu Lys Pro Glu Trp Glu
        35                  40                  45

Thr Cys Gly Lys Gly Met Glu Gln Ser Pro Ile Gln Leu Arg Asp Asn
    50                  55                  60

Arg Val Ile Phe Asp Gln Thr Leu Gly Arg Leu Arg Asn Tyr Arg
65                  70                  75                  80

Ala Val Asp Ala Arg Leu Arg Asn Ser Gly His Asp Val Leu Glu
                85                  90                  95

Phe Lys Gly Asn Ala Gly Ser Leu Ser Ile Asn Arg Val Ala Tyr Gln
            100                 105                 110

Leu Lys Arg Ile His Phe His Ser Pro Ser Glu His Glu Met Asn Gly
        115                 120                 125

Glu Arg Phe Asp Leu Glu Ala Gln Leu Val His Glu Ser Gln Asp Gln
    130                 135                 140

Lys Arg Ala Val Val Ser Ile Leu Phe Ile Phe Gly Arg Ala Asp Pro
145                 150                 155                 160

Phe Leu Ser Asp Leu Glu Asp Phe Ile Lys Gln Phe Ser Ser Gln
            165                 170                 175

Lys Asn Glu Ile Asn Ala Gly Val Val Asp Pro Asn Gln Leu Gln Ile
        180                 185                 190

Asp Asp Ser Ala Tyr Tyr Arg Tyr Met Gly Ser Phe Thr Ala Pro Pro
    195                 200                 205

Cys Thr Glu Gly Ile Ser Trp Thr Val Met Arg Lys Val Ala Thr Val
210                 215                 220

Ser Pro Arg Gln Val Leu Leu Leu Lys Gln Ala Val Asn Glu Asn Ala
225                 230                 235                 240

Ile Asn Asn Ala Arg Pro Leu Gln Pro Thr Asn Phe Arg Ser Val Phe
            245                 250                 255

Tyr Phe Glu Gln Leu Lys Ser Lys Val Cys Ala Ile
        260                 265
```

<210> SEQ ID NO 184
<211> LENGTH: 822
<212> TYPE: DNA
<213> ORGANISM: Dioscorea alata

<400> SEQUENCE: 184

```
atgagttcat ccacccttt tccatctctt ctcctctcct ccctcctctt ctcttgcttt       60
tcaaatgcaa ggcttgatgg cgatgatgac tttagctaca ttgaaggaag tcctaatggt      120
cctgaaaact ggggaaatct tagaccggag tggaagactt gtggctatgg catggagcag      180
tcacccatta atttgtgtga tgatagagtg atacggactc caactttggg gaagctgaga      240
acaagttatc aggctgctcg tgcaacagtg aagaacaatg gacatgatat aatggtgtac      300
tttaaaagtg atgctggtac acaattcatc aatcaagtag agtaccaact caaacgaatt      360
cattttcact ccccatcaga acatgcactc agtggtgaaa ggtatgacct tgaggttcag      420
atggtccatg agagccaaga tcaaggagag cagtaattg ctattatgtt cagatttgga       480
cgttctgacc cattcctccc agaccttgaa gactttatca gccagataag cagacgtgag      540
accaatgaag tagatgcagg agttgtggat ccaaggcaat tattacagtt tgatgaccct      600
gcatattata gatacatggg ctcatacaca gctccacctt gcactgaaga tattacatgg      660
accgttatta agaagcttgg aactgtttca ccaaagcaag tactgatgtt gaagcaagca      720
gtgaatgaaa attctatgaa caatgcaagg ccacttcaac cactgaaatt tcgcaccgtt      780
tttttctatc cgcgtcagaa atctgatcat gttgccatat aa                        822
```

<210> SEQ ID NO 185
<211> LENGTH: 273
<212> TYPE: PRT
<213> ORGANISM: Dioscorea alata

<400> SEQUENCE: 185

Met Ser Ser Ser Thr Leu Phe His Leu Phe Leu Ser Ser Leu Leu
1               5                   10                  15

Phe Ser Cys Phe Ser Asn Ala Arg Leu Asp Gly Asp Asp Phe Ser
                20                  25                  30

Tyr Ile Glu Gly Ser Pro Asn Gly Pro Glu Asn Trp Gly Asn Leu Arg
            35                  40                  45

Pro Glu Trp Lys Thr Cys Gly Tyr Gly Met Glu Gln Ser Pro Ile Asn
    50                  55                  60

Leu Cys Asp Asp Arg Val Ile Arg Thr Pro Thr Leu Gly Lys Leu Arg
65                  70                  75                  80

Thr Ser Tyr Gln Ala Ala Arg Ala Thr Val Lys Asn Asn Gly His Asp
                85                  90                  95

Ile Met Val Tyr Phe Lys Ser Asp Ala Gly Thr Gln Phe Ile Asn Gln
            100                 105                 110

Val Glu Tyr Gln Leu Lys Arg Ile His Phe His Ser Pro Ser Glu His
        115                 120                 125

Ala Leu Ser Gly Glu Arg Tyr Asp Leu Glu Val Gln Met Val His Glu
    130                 135                 140

Ser Gln Asp Gln Arg Arg Ala Val Ile Ala Ile Met Phe Arg Phe Gly
145                 150                 155                 160

Arg Ser Asp Pro Phe Leu Pro Asp Leu Glu Asp Phe Ile Ser Gln Ile
                165                 170                 175

Ser Arg Arg Glu Thr Asn Glu Val Asp Ala Gly Val Val Asp Pro Arg
            180                 185                 190

Gln Leu Leu Gln Phe Asp Asp Pro Ala Tyr Tyr Arg Tyr Met Gly Ser

```
                195                 200                 205
Tyr Thr Ala Pro Pro Cys Thr Glu Asp Ile Thr Trp Thr Val Ile Lys
        210                 215                 220

Lys Leu Gly Thr Val Ser Pro Lys Gln Val Leu Met Leu Lys Gln Ala
225                 230                 235                 240

Val Asn Glu Asn Ser Met Asn Asn Ala Arg Pro Leu Gln Pro Leu Lys
                245                 250                 255

Phe Arg Thr Val Phe Phe Tyr Pro Arg Gln Lys Ser Asp His Val Ala
            260                 265                 270

Ile

<210> SEQ ID NO 186
<211> LENGTH: 831
<212> TYPE: DNA
<213> ORGANISM: Oryza sativa

<400> SEQUENCE: 186
atgagtactt cagctcgccg cctcctcctc ctcgccggcg ccgctgccgc catcgcactc      60
ctgctctcgg ccactgcccc ggtggccgga gccgaggacg acggctacag ctacatccct     120
ggctcaccca gggggccgca gaactggggc agcctgaagc cggaatgggc cacctgcagc     180
agcggcaaga tgcagtcgcc gatcaacctc ggcctcctcg acctcacctt ggctcccggc     240
ctcggcaacc tcaactacac ctaccagaac gccaacgcct ccgtcgtcaa ccgtggccac     300
gacatcatgg tcaggtttga cggcgacgcc ggtagcctaa agataaatgg cacggcgtac     360
cagctccggc agatgcactg gcacacgccg tcggagcaca ccatcgatgg ccggaggtac     420
gacatggagc tgcacatggt gcacctcaac gcccagaacc aggccgccgt cattggcatc     480
ctctacacca tcggcacccg ggacgagttt ctgcaaaagc tagagcctta tataattgag     540
atatcaaagc aagaaggcaa agagagagtg atcattggtg gggcggatcc aaatgtagcc     600
aagggacagg ataccgtgta ctaccgctac atgggctcct ttaccacacc accttgcact     660
gagggagtca tctggaccgt tgtcaggaag gtgcgcaccg tgtcactgtc ccaaatcaca     720
cttctcaagg cagctgtgct cacgggtaac gagaacaacg cgagacccct tcagggcgtg     780
aacaacaggg agattgacct gttccttcct ctccctctca tcaacaactg a              831

<210> SEQ ID NO 187
<211> LENGTH: 276
<212> TYPE: PRT
<213> ORGANISM: Oryza sativa

<400> SEQUENCE: 187

Met Ser Thr Ser Ala Arg Arg Leu Leu Leu Ala Gly Ala Ala Ala
1               5                   10                  15

Ala Ile Ala Leu Leu Leu Ser Ala Thr Ala Pro Val Ala Gly Ala Glu
            20                  25                  30

Asp Asp Gly Tyr Ser Tyr Ile Pro Gly Ser Pro Arg Gly Pro Gln Asn
        35                  40                  45

Trp Gly Ser Leu Lys Pro Glu Trp Ala Thr Cys Ser Ser Gly Lys Met
    50                  55                  60

Gln Ser Pro Ile Asn Leu Gly Leu Leu Asp Leu Thr Leu Ala Pro Gly
65                  70                  75                  80

Leu Gly Asn Leu Asn Tyr Thr Tyr Gln Asn Ala Asn Ala Ser Val Val
                85                  90                  95

Asn Arg Gly His Asp Ile Met Val Arg Phe Asp Gly Asp Ala Gly Ser
            100                 105                 110
```

```
Leu Lys Ile Asn Gly Thr Ala Tyr Gln Leu Arg Gln Met His Trp His
        115                 120                 125

Thr Pro Ser Glu His Thr Ile Asp Gly Arg Arg Tyr Asp Met Glu Leu
    130                 135                 140

His Met Val His Leu Asn Ala Gln Asn Gln Ala Val Ile Gly Ile
145                 150                 155                 160

Leu Tyr Thr Ile Gly Thr Arg Asp Glu Phe Leu Gln Lys Leu Glu Pro
            165                 170                 175

Tyr Ile Ile Glu Ile Ser Lys Gln Glu Gly Lys Glu Arg Val Ile Ile
            180                 185                 190

Gly Gly Ala Asp Pro Asn Val Ala Lys Gly Gln Asp Thr Val Tyr Tyr
        195                 200                 205

Arg Tyr Met Gly Ser Phe Thr Thr Pro Pro Cys Thr Glu Gly Val Ile
    210                 215                 220

Trp Thr Val Val Arg Lys Val Arg Thr Val Ser Leu Ser Gln Ile Thr
225                 230                 235                 240

Leu Leu Lys Ala Ala Val Leu Thr Gly Asn Glu Asn Asn Ala Arg Pro
                245                 250                 255

Leu Gln Gly Val Asn Asn Arg Glu Ile Asp Leu Phe Leu Pro Leu Pro
            260                 265                 270

Leu Ile Asn Asn
        275

<210> SEQ ID NO 188
<211> LENGTH: 846
<212> TYPE: DNA
<213> ORGANISM: Oryza sativa

<400> SEQUENCE: 188
atggtgtctc tccgcgcggc catcgtcctc gtcgtcgccg cctcgtcggt cgccgtcgcc      60
ttctctcatg cggaagggaa cgaggggccg gacttcacct acatcgaagg cgccatggac     120
gggccgtcga actgggggaa gctgagcccg gagtacagga tgtgcggcga ggggaggtcg     180
cagtcgccga tcgacatcaa caccaagacc gtcgtcccgc gctcggacct cgacacgctg     240
gaccgcaact acaacgccgt gaacgccacc atcgtcaaca acggcaagga catcaccatg     300
aagttccacg gcgaggtcgg ccaggtgatc atcgccggga agccgtacag gttccaggcg     360
atccactggc acgcgccgtc ggagcacacc atcaacggca ggcgcttccc gctcgagctc     420
cacctcgtcc acaagtccga cgccgacggc ggcctcgccg tcatctccgt cctctacaag     480
ctcggcgccc cggactcctt ctacctccag ttcaaggacc acctcgccga gctcggcgcc     540
gacgagtgcg acttcagcaa ggaggaggcc cacgtcgccg ccgggctggt gcagatgagg     600
tcgctgcaga agcgcacggg gagctacttc cggtacggcg gctcgctgac gacgccgccg     660
tgcggcgaga acgtggtgtg gagcgtgctc gggaaggtga gggagatcag ccaggagcag     720
ctgcacctgc tcatgtcgcc attgccgacc aaggacgcca ggccggcgca gccgctcaat     780
ggcagggccg tcttctacta caacccgccg ggcagcgccg tctccttcca ggaattcgcc     840
aagtga                                                                846

<210> SEQ ID NO 189
<211> LENGTH: 281
<212> TYPE: PRT
<213> ORGANISM: Oryza sativa

<400> SEQUENCE: 189
```

```
Met Val Ser Leu Arg Ala Ala Ile Val Leu Val Ala Ala Ser Ser
1               5                   10                  15

Val Ala Val Ala Phe Ser His Ala Glu Gly Asn Glu Gly Pro Asp Phe
            20                  25                  30

Thr Tyr Ile Glu Gly Ala Met Asp Gly Pro Ser Asn Trp Gly Lys Leu
        35                  40                  45

Ser Pro Glu Tyr Arg Met Cys Gly Glu Gly Arg Ser Gln Ser Pro Ile
    50                  55                  60

Asp Ile Asn Thr Lys Thr Val Val Pro Arg Ser Asp Leu Asp Thr Leu
65                  70                  75                  80

Asp Arg Asn Tyr Asn Ala Val Asn Ala Thr Ile Val Asn Gly Lys
                85                  90                  95

Asp Ile Thr Met Lys Phe His Gly Glu Val Gly Gln Val Ile Ile Ala
                100                 105                 110

Gly Lys Pro Tyr Arg Phe Gln Ala Ile His Trp His Ala Pro Ser Glu
            115                 120                 125

His Thr Ile Asn Gly Arg Arg Phe Pro Leu Glu Leu His Leu Val His
    130                 135                 140

Lys Ser Asp Ala Asp Gly Gly Leu Ala Val Ile Ser Val Leu Tyr Lys
145                 150                 155                 160

Leu Gly Ala Pro Asp Ser Phe Tyr Leu Gln Phe Lys Asp His Leu Ala
                165                 170                 175

Glu Leu Gly Ala Asp Glu Cys Asp Phe Ser Lys Glu Ala His Val
                180                 185                 190

Ala Ala Gly Leu Val Gln Met Arg Ser Leu Gln Lys Arg Thr Gly Ser
            195                 200                 205

Tyr Phe Arg Tyr Gly Gly Ser Leu Thr Thr Pro Pro Cys Gly Glu Asn
    210                 215                 220

Val Val Trp Ser Val Leu Gly Lys Val Arg Glu Ile Ser Gln Glu Gln
225                 230                 235                 240

Leu His Leu Leu Met Ser Pro Leu Pro Thr Lys Asp Ala Arg Pro Ala
                245                 250                 255

Gln Pro Leu Asn Gly Arg Ala Val Phe Tyr Tyr Asn Pro Pro Gly Ser
            260                 265                 270

Ala Val Ser Phe Gln Glu Phe Ala Lys
            275                 280

<210> SEQ ID NO 190
<211> LENGTH: 804
<212> TYPE: DNA
<213> ORGANISM: Arabidopsis thaliana

<400> SEQUENCE: 190
atggatacca acgcaaaaac aattttcttc atggctatgt gtttcatcta tctatctttc     60
cctaatattt cacacgctca ttctgaagtc gacgacgaaa ctccatttac ttacgaacaa    120
aaaacggaaa agggaccaga gggatggggc aaaataaatc cgcactggaa agtttgtaac    180
accggaagat atcaatcccc gatcgatctt actaacgaaa gagtcagtct tattcatgat    240
caagcatgga caagacaata taaccagct ccggctgtaa ttacaaacag aggccatgac    300
attatggtat catggaaagg agatgctggg aagatgacaa tacggaaaac ggatttta at    360 ttggtgcaat gccattggca ttcaccttct gagcataccg ttaacggaac taggtacgac    420
ctagagcttc acatggttca cacgagtgca cgaggcagaa ctgcggttat cggagttctt    480
tacaaattag gcgaacctaa tgaattcctc accaagctac taaatggaat aaaagcagtg    540
```

```
ggaaataaag agataaatct agggatgatt gatccacgag agattaggtt tcaaacaaga    600
aaattctata gatacattgg ctctctcact gttcctcctt gcactgaagg cgtcatttgg    660
actgtcgtca aaagggtgaa cacaatatca atggagcaaa ttacagctct taggcaagcc    720
gttgacgatg gatttgagac aaattcaaga ccggttcaag actcaaaggg aagatcagtt    780
tggttctatg atccaaatgt ttga                                            804
```

<210> SEQ ID NO 191
<211> LENGTH: 267
<212> TYPE: PRT
<213> ORGANISM: Arabidopsis thaliana

<400> SEQUENCE: 191

```
Met Asp Thr Asn Ala Lys Thr Ile Phe Phe Met Ala Met Cys Phe Ile
1               5                   10                  15

Tyr Leu Ser Phe Pro Asn Ile Ser His Ala His Ser Glu Val Asp Asp
            20                  25                  30

Glu Thr Pro Phe Thr Tyr Glu Gln Lys Thr Glu Lys Gly Pro Glu Gly
        35                  40                  45

Trp Gly Lys Ile Asn Pro His Trp Lys Val Cys Asn Thr Gly Arg Tyr
    50                  55                  60

Gln Ser Pro Ile Asp Leu Thr Asn Glu Arg Val Ser Leu Ile His Asp
65                  70                  75                  80

Gln Ala Trp Thr Arg Gln Tyr Lys Pro Ala Pro Ala Val Ile Thr Asn
                85                  90                  95

Arg Gly His Asp Ile Met Val Ser Trp Lys Gly Asp Ala Gly Lys Met
            100                 105                 110

Thr Ile Arg Lys Thr Asp Phe Asn Leu Val Gln Cys His Trp His Ser
        115                 120                 125

Pro Ser Glu His Thr Val Asn Gly Thr Arg Tyr Asp Leu Glu Leu His
    130                 135                 140

Met Val His Thr Ser Ala Arg Gly Arg Thr Ala Val Ile Gly Val Leu
145                 150                 155                 160

Tyr Lys Leu Gly Glu Pro Asn Glu Phe Leu Thr Lys Leu Leu Asn Gly
                165                 170                 175

Ile Lys Ala Val Gly Asn Lys Glu Ile Asn Leu Gly Met Ile Asp Pro
            180                 185                 190

Arg Glu Ile Arg Phe Gln Thr Arg Lys Phe Tyr Arg Tyr Ile Gly Ser
        195                 200                 205

Leu Thr Val Pro Pro Cys Thr Glu Gly Val Ile Trp Thr Val Val Lys
    210                 215                 220

Arg Val Asn Thr Ile Ser Met Glu Gln Ile Thr Ala Leu Arg Gln Ala
225                 230                 235                 240

Val Asp Asp Gly Phe Glu Thr Asn Ser Arg Pro Val Gln Asp Ser Lys
                245                 250                 255

Gly Arg Ser Val Trp Phe Tyr Asp Pro Asn Val
            260                 265
```

<210> SEQ ID NO 192
<211> LENGTH: 792
<212> TYPE: DNA
<213> ORGANISM: Arabidopsis thaliana

<400> SEQUENCE: 192

```
atgaaacaca ttttttttaa ctcgtgtata accaaaaaaa atatagagga cgaaacgcag    60
tttaactacg agaagaaagg agagaagggg ccagagaact ggggaagact aaagccagag    120
```

-continued

```
tgggcaatgt gtggaaaagg caacatgcag tctccgattg atcttacgga caaaagagtc    180
ttgattgatc ataatcttgg ataccttcgt agccagtatt taccttcaaa tgccaccatt    240
aagaacagag gccatgatat catgatgaaa tttgaaggag gaaatgcagg tttaggtatc    300
actattaatg gtactgaata taaacttcaa cagattcatt ggcactctcc ttccgaacac    360
acactcaatg gcaaaggtt tgttcttgag gaacacatgg ttcatcagag caaagatgga    420
cgcaacgctg ttgtcgcttt cttttacaaa ttgggaaaac ctgactattt tctcctcacg    480
ttggaaagat acttgaagag gataactgat acacacgaat cccaggaatt tgtcgagatg    540
gttcatccta gaacattcgg ttttgaatca aaacactatt atagatttat cggatcactt    600
acaactccac cgtgttctga aaatgtgatt tggacgattt ccaaagagat gaggactgtg    660
acattaaaac aattgatcat gcttcgagtg actgtacacg atcaatctaa ctcaaatgct    720
agaccgcttc agcgtaaaaa tgagcgtccg gtggcacttt ataccaac atggcatagt     780 aaactatatt aa                                                       792
```

<210> SEQ ID NO 193
<211> LENGTH: 263
<212> TYPE: PRT
<213> ORGANISM: Arabidopsis thaliana

<400> SEQUENCE: 193

```
Met Lys His Ile Phe Phe Asn Ser Cys Ile Thr Lys Lys Asn Ile Glu
1               5                   10                  15

Asp Glu Thr Gln Phe Asn Tyr Glu Lys Lys Gly Glu Lys Gly Pro Glu
            20                  25                  30

Asn Trp Gly Arg Leu Lys Pro Glu Trp Ala Met Cys Gly Lys Gly Asn
        35                  40                  45

Met Gln Ser Pro Ile Asp Leu Thr Asp Lys Arg Val Leu Ile Asp His
    50                  55                  60

Asn Leu Gly Tyr Leu Arg Ser Gln Tyr Leu Pro Ser Asn Ala Thr Ile
65                  70                  75                  80

Lys Asn Arg Gly His Asp Ile Met Met Lys Phe Glu Gly Gly Asn Ala
                85                  90                  95

Gly Leu Gly Ile Thr Ile Asn Gly Thr Glu Tyr Lys Leu Gln Gln Ile
            100                 105                 110

His Trp His Ser Pro Ser Glu His Thr Leu Asn Gly Lys Arg Phe Val
        115                 120                 125

Leu Glu Glu His Met Val His Gln Ser Lys Asp Gly Arg Asn Ala Val
    130                 135                 140

Val Ala Phe Phe Tyr Lys Leu Gly Lys Pro Asp Tyr Phe Leu Leu Thr
145                 150                 155                 160

Leu Glu Arg Tyr Leu Lys Arg Ile Thr Asp Thr His Glu Ser Gln Glu
                165                 170                 175

Phe Val Glu Met Val His Pro Arg Thr Phe Gly Phe Glu Ser Lys His
            180                 185                 190

Tyr Tyr Arg Phe Ile Gly Ser Leu Thr Thr Pro Pro Cys Ser Glu Asn
        195                 200                 205

Val Ile Trp Thr Ile Ser Lys Glu Met Arg Thr Val Thr Leu Lys Gln
    210                 215                 220

Leu Ile Met Leu Arg Val Thr Val His Asp Gln Ser Asn Ser Asn Ala
225                 230                 235                 240

Arg Pro Leu Gln Arg Lys Asn Glu Arg Pro Val Ala Leu Tyr Ile Pro
                245                 250                 255
```

Thr Trp His Ser Lys Leu Tyr
                260

<210> SEQ ID NO 194
<211> LENGTH: 275
<212> TYPE: PRT
<213> ORGANISM: Adonis aestivalis

<400> SEQUENCE: 194

Met Gly Thr Leu Gly Lys Ala Ile Tyr Thr Val Gly Phe Trp Ile Arg
1               5                   10                  15

Glu Thr Gly Gln Ala Ile Asp Arg Leu Gly Ser Arg Leu Gln Gly Asn
            20                  25                  30

Tyr Tyr Phe His Glu Gln Leu Ser Arg His Arg Thr Leu Met Asn Ile
        35                  40                  45

Phe Asp Lys Ala Pro Val Val Asp Lys Asp Ala Phe Ile Ala Pro Ser
    50                  55                  60

Ala Ser Val Ile Gly Asp Val Gln Val Gly Arg Ser Ser Ile Trp
65                  70                  75                  80

Tyr Gly Cys Val Leu Arg Gly Asp Val Asn Ser Ile Ser Val Gly Ser
                85                  90                  95

Gly Thr Asn Ile Gln Asp Asn Ser Leu Val His Val Ala Lys Ser Asn
            100                 105                 110

Leu Ser Gly Lys Val Leu Pro Thr Ile Ile Gly Asn Asn Val Thr Val
        115                 120                 125

Gly His Ser Ala Val Leu His Gly Cys Thr Val Gln Asp Ser Ala Phe
    130                 135                 140

Val Gly Met Gly Ala Thr Leu Leu Asp Gly Val Val Val Glu Asn His
145                 150                 155                 160

Ala Met Val Ala Ala Gly Ala Leu Val Arg Gln Asn Thr Arg Ile Pro
                165                 170                 175

Lys Gly Glu Val Trp Gly Gly Asn Pro Ala Lys Phe Leu Arg Lys Leu
            180                 185                 190

Thr Glu Glu Glu Ile Ala Phe Ile Ser Gln Ser Ala Thr Asn Tyr Thr
        195                 200                 205

Asn Leu Ala Gln Val His Ala Ala Glu Asn Ala Lys Thr Phe Glu Glu
    210                 215                 220

Ile Glu Phe Glu Lys Leu Leu Arg Lys Lys Phe Ala Arg Lys Asp Glu
225                 230                 235                 240

Glu Tyr Asp Ser Met Leu Gly Val Val Arg Glu Thr Pro Gln Glu Leu
                245                 250                 255

Ile Leu Pro Asp Asn Ile Leu Ala Asp Lys Gln Ser Pro Lys Ala Val
            260                 265                 270

Ser Ser Ser
        275

<210> SEQ ID NO 195
<211> LENGTH: 276
<212> TYPE: PRT
<213> ORGANISM: Glycine max

<400> SEQUENCE: 195

Met Gly Thr Leu Gly Arg Ala Ile Tyr Ser Val Gly Asn Trp Ile Arg
1               5                   10                  15

Gly Thr Gly Gln Ala Ile Asp Arg Leu Gly Ser Leu Leu Gln Gly Gly
            20                  25                  30

```
Tyr Tyr Val Gln Glu Gln Leu Ser Arg His Arg Thr Leu Met Asp Ile
         35                  40                  45

Phe Asp Lys Ala Pro Val Val Asp Glu Asp Val Phe Val Ala Pro Ser
 50                  55                  60

Ala Ser Val Ile Gly Asp Val Gln Leu Gly Arg Gly Ser Ser Ile Trp
 65                  70                  75                  80

Tyr Gly Val Val Leu Arg Gly Asp Val Asn Ser Ile Arg Val Gly Asn
                 85                  90                  95

Gly Thr Asn Ile Gln Asp Asn Ser Leu Val His Val Ala Lys Ser Asn
                100                 105                 110

Leu Ser Gly Lys Val Leu Pro Thr Ile Ile Gly Asp Asn Val Thr Val
            115                 120                 125

Gly His Ser Ala Val Ile His Gly Cys Thr Val Glu Asp Glu Ala Phe
130                 135                 140

Val Gly Met Gly Ala Ile Leu Leu Asp Gly Val Val Val Glu Lys Asn
145                 150                 155                 160

Ala Met Val Ala Ala Gly Ala Leu Val Arg Gln Asn Thr Arg Ile Pro
                165                 170                 175

Ser Gly Glu Val Trp Ala Gly Asn Pro Ala Lys Phe Leu Arg Lys Leu
            180                 185                 190

Thr Asp Glu Glu Ile Ala Phe Ile Ser Gln Ser Ala Thr Asn Tyr Thr
195                 200                 205

Asn Leu Ala Gln Val His Ala Ala Glu Asn Ser Lys Ser Phe Asp Glu
            210                 215                 220

Ile Glu Phe Glu Lys Val Leu Arg Lys Lys Phe Ala Arg Lys Asp Glu
225                 230                 235                 240

Glu Tyr Asp Ser Met Leu Gly Val Val Arg Glu Ile Pro Pro Glu Leu
                245                 250                 255

Ile Leu Pro Asp Asn Val Leu Pro Asp Lys Ala Glu Lys Ala Leu Lys
            260                 265                 270

Lys Ser Gly Ile
275

<210> SEQ ID NO 196
<211> LENGTH: 276
<212> TYPE: PRT
<213> ORGANISM: Brassica napus

<400> SEQUENCE: 196

Met Gly Thr Leu Gly Arg Val Ile Tyr Thr Val Gly Lys Trp Ile Arg
 1               5                  10                  15

Gly Ser Gly Gln Ala Leu Asp Arg Val Gly Ser Ile Leu Gln Gly Ser
             20                  25                  30

His Arg Leu Glu Glu His Leu Ser Arg His Arg Thr Leu Met Asn Val
         35                  40                  45

Phe Asp Lys Ser Pro Leu Val Asp Lys Asp Val Phe Val Ala Pro Ser
 50                  55                  60

Ala Ser Val Ile Gly Asp Val Gln Ile Gly Lys Gly Ser Ser Ile Trp
 65                  70                  75                  80

Tyr Gly Cys Val Leu Arg Gly Asp Val Asn Asn Ile Ser Val Gly Ser
                 85                  90                  95

Gly Thr Asn Ile Gln Asp Asn Ser Leu Val His Val Ala Lys Thr Asn
                100                 105                 110

Leu Gly Gly Lys Val Leu Pro Thr Ile Gly Asp Asn Val Thr Val
            115                 120                 125
```

```
Gly His Ser Ala Val Ile His Gly Cys Thr Val Glu Asp Glu Ala Phe
        130                 135                 140

Val Gly Met Gly Ala Thr Leu Leu Asp Gly Val Val Glu Lys His
145                 150                 155                 160

Ala Met Val Ala Ala Gly Ser Leu Val Arg Glu Asn Thr Arg Ile Pro
                    165                 170                 175

Ser Gly Glu Val Trp Gly Gly Asn Pro Ala Lys Phe Met Arg Lys Leu
            180                 185                 190

Thr Asp Glu Glu Ile Ala Tyr Ile Ser Lys Ser Ala Glu Asn Tyr Ile
            195                 200                 205

Asn Leu Ala His Ile His Ala Ala Glu Asn Ser Lys Ser Phe Glu Glu
    210                 215                 220

Ile Glu Val Glu Arg Ala Leu Arg Lys Lys Tyr Ala Arg Lys Asp Glu
225                 230                 235                 240

Asp Tyr Asp Ser Met Leu Gly Ile Val Arg Glu Thr Pro Ala Glu Leu
                    245                 250                 255

Ile Leu Pro Asp Asn Val Leu Pro Glu Lys Thr Thr Thr Arg Val Pro
                260                 265                 270

Thr Thr His Tyr
        275

<210> SEQ ID NO 197
<211> LENGTH: 273
<212> TYPE: PRT
<213> ORGANISM: Zea mays

<400> SEQUENCE: 197

Met Gly Thr Leu Gly Arg Ala Ile Phe Thr Val Gly Lys Trp Ile Arg
1               5                   10                  15

Gly Thr Gly Gln Ala Met Asp Arg Leu Gly Ser Thr Ile Gln Gly Gly
            20                  25                  30

Leu Arg Val Glu Glu Gln Val Ser Arg His Arg Thr Ile Met Asn Ile
        35                  40                  45

Phe Glu Lys Glu Pro Arg Ile His Arg Asp Val Phe Val Ala Pro Ser
50                  55                  60

Ala Ala Val Ile Gly Asp Val Glu Ile Gly His Gly Ser Ser Ile Trp
65                  70                  75                  80

Tyr Gly Ser Ile Leu Arg Gly Asp Val Asn Ser Ile His Ile Gly Ser
                85                  90                  95

Gly Thr Asn Ile Gln Asp Asn Ser Leu Val His Val Ser Lys Ala Asn
            100                 105                 110

Ile Ser Gly Lys Val Leu Pro Thr Ile Ile Gly Ser Asn Val Thr Val
        115                 120                 125

Gly His Ser Ala Val Leu His Ala Cys Thr Ile Glu Asp Glu Ala Phe
    130                 135                 140

Val Gly Met Gly Ala Thr Leu Leu Asp Gly Val Val Val Glu Lys His
145                 150                 155                 160

Ser Met Val Gly Ala Gly Ser Leu Val Lys Gln Asn Thr Arg Ile Pro
                165                 170                 175

Ser Gly Glu Val Trp Val Gly Asn Pro Ala Lys Phe Leu Arg Lys Leu
            180                 185                 190

Thr Glu Glu Glu Ile Ala Phe Ile Ala Gln Ser Ala Thr Asn Tyr Ile
            195                 200                 205

Asn Leu Ala Gln Val His Ala Ala Glu Asn Ala Lys Ser Phe Asp Glu
    210                 215                 220
```

Ile Glu Leu Glu Lys Met Leu Arg Lys Lys Tyr Ala His Lys Asp Glu
225                 230                 235                 240

Glu Tyr Asp Ser Met Leu Gly Val Val Arg Glu Ile Pro Pro Gln Leu
            245                 250                 255

Ile Leu Pro Asp Asn Ile Leu Pro His Asn Ala Gln Lys Ala Val Ala
        260                 265                 270

Arg

<210> SEQ ID NO 198
<211> LENGTH: 274
<212> TYPE: PRT
<213> ORGANISM: Triticum aestivum

<400> SEQUENCE: 198

Met Gly Thr Leu Gly Arg Ala Ile Tyr Thr Val Gly Lys Trp Ile Arg
1               5                   10                  15

Gly Thr Gly Gln Ala Met Asp Arg Leu Gly Ser Thr Ile Gln Gly Gly
            20                  25                  30

Leu Arg Thr Glu Glu Gln Val Ser Arg His Arg Thr Val Met Ser Ile
        35                  40                  45

Phe Asp Lys Glu Pro Arg Ile Asn Lys Asp Val Phe Val Ala Pro Ser
50                  55                  60

Ala Ser Val Ile Gly Asp Val Glu Ile Gly His Gly Ser Ser Ile Trp
65                  70                  75                  80

Tyr Gly Ser Val Leu Arg Gly Asp Val Asn Ser Ile Arg Ile Gly Ser
                85                  90                  95

Gly Ser Asn Ile Gln Asp Asn Ser Leu Val His Val Ala Lys Thr Asn
            100                 105                 110

Ile Ser Gly Lys Val Leu Pro Thr Ile Ile Gly Ser Asn Val Thr Val
        115                 120                 125

Gly His Ser Ala Val Leu His Ala Cys Thr Ile Glu Asp Glu Ala Phe
    130                 135                 140

Val Gly Met Gly Ala Thr Leu Leu Asp Gly Val Val Glu Lys His
145                 150                 155                 160

Ser Met Val Gly Ala Gly Ser Leu Val Lys Gln Asn Thr Arg Ile Pro
                165                 170                 175

Ser Gly Glu Val Trp Val Gly Asn Pro Ala Lys Phe Leu Arg Lys Leu
            180                 185                 190

Thr Glu Glu Glu Ile Thr Phe Ile Ala Gln Ser Ala Ala Asn Tyr Ile
        195                 200                 205

Asn Leu Ala His Val His Ala Thr Glu Asn Ser Lys Ser Phe Asp Glu
    210                 215                 220

Ile Glu Leu Glu Lys Lys Leu Arg Lys Lys Phe Ala His Lys Asp Glu
225                 230                 235                 240

Glu Tyr Asp Ser Met Leu Gly Val Val Arg Glu Ile Pro Pro Gln Leu
            245                 250                 255

Ile Leu Pro Asp Asn Ile Leu Pro Asp Lys Ala Pro Lys Ala Ala Val
        260                 265                 270

Ala His

<210> SEQ ID NO 199
<211> LENGTH: 270
<212> TYPE: PRT
<213> ORGANISM: Glycine max

<400> SEQUENCE: 199

Met Gly Thr Leu Gly Arg Val Phe Tyr Ala Val Gly Phe Trp Ile Arg
1               5                   10                  15

Glu Thr Gly Gln Ala Ile Asp Arg Leu Gly Ser Arg Leu Gln Gly Asn
            20                  25                  30

Tyr Leu Phe Gln Glu Gln Leu Ser Arg His Arg Pro Leu Met Asn Leu
            35                  40                  45

Phe Asp Lys Ala Pro Ser Val His Arg Asp Ala Phe Val Ala Pro Ser
50                  55                  60

Ala Ser Leu Leu Gly Asp Val His Val Gly Pro Ala Ser Ser Ile Trp
65                  70                  75                  80

Tyr Gly Cys Val Leu Arg Gly Asp Val Asn Ser Ile Thr Ile Gly Ser
                85                  90                  95

Gly Thr Asn Ile Gln Asp Asn Ser Leu Val His Val Ala Lys Ser Asn
                100                 105                 110

Leu Ser Gly Lys Val Leu Pro Thr Ile Ile Gly Asp Asn Val Thr Val
            115                 120                 125

Gly His Ser Ala Val Leu Gln Gly Cys Thr Val Glu Asp Glu Ala Phe
            130                 135                 140

Ile Gly Met Gly Ala Thr Leu Leu Asp Gly Val Tyr Val Glu Lys His
145                 150                 155                 160

Ala Met Val Ala Ala Gly Ala Leu Val Arg Gln Asn Thr Arg Ile Pro
                165                 170                 175

Tyr Gly Glu Val Trp Gly Gly Asn Pro Ala Arg Phe Leu Arg Lys Leu
                180                 185                 190

Thr Glu Asp Glu Met Thr Phe Ser Gln Ser Ala Leu Asn Tyr Ser
            195                 200                 205

Asn Leu Ala Gln Ala His Ser Ala Glu Asn Ala Lys Gly Leu Asp Glu
            210                 215                 220

Thr Glu Phe Val Lys Val Leu His Lys Lys Phe Ala Arg His Gly Asp
225                 230                 235                 240

Glu Tyr His Ser Val Leu Gly Gly Val Gln Glu Thr Pro Thr Glu Leu
                245                 250                 255

Lys Ser Ser Asp Asn Val Leu Leu Asp Lys Val Pro Lys Ala
            260                 265                 270

<210> SEQ ID NO 200
<211> LENGTH: 307
<212> TYPE: PRT
<213> ORGANISM: Hordeum vulgare

<400> SEQUENCE: 200

Met Ala Lys Ala Ser Tyr Ala Val Gly Phe Trp Ile Arg Glu Thr Gly
1               5                   10                  15

Gln Ala Leu Asp Arg Leu Gly Cys Arg Leu Gln Gly Asn Tyr Phe Phe
            20                  25                  30

His Glu Gln Ile Ser Arg His Arg Thr Leu Met Asn Ile Phe Asp Lys
            35                  40                  45

Ala Pro His Val His Lys Glu Ala Phe Val Ala Pro Ser Ala Ser Leu
50                  55                  60

Ile Gly Asp Val Glu Val Gly Lys Gly Ser Ser Ile Trp Tyr Gly Cys
65                  70                  75                  80

Val Leu Arg Gly Asp Ala Asn Asn Val Gln Val Gly Ser Gly Thr Asn
                85                  90                  95

Ile Gln Asp Asn Ser Val Val His Val Ala Lys Ser Asn Leu Ser Gly
                100                 105                 110

```
Lys Val Phe Pro Thr Ile Ile Gly Asp Asn Val Thr Gly His Ser
            115                 120                 125

Ala Val Leu Gln Gly Cys Thr Val Glu Asp Glu Ala Phe Val Gly Met
130                 135                 140

Gly Ala Thr Leu Leu Asp Gly Val Val Glu Lys His Gly Met Val
145                 150                 155                 160

Ala Ala Gly Ala Leu Val Arg Gln Asn Thr Arg Ile Pro Cys Gly Glu
                165                 170                 175

Val Trp Gly Gly Asn Pro Ala Lys Phe Leu Arg Lys Leu Thr Asp Glu
                180                 185                 190

Glu Ile Ala Phe Ile Ala Glu Ser Ala Ala Asn Tyr Ser Asn Leu Ala
            195                 200                 205

Lys Ala His Ala Val Glu Asn Ala Lys Pro Val Glu Lys Ile Asp Phe
210                 215                 220

Glu Lys Val Leu Arg Lys Val Ala His Gln Asp Glu Glu His Gly
225                 230                 235                 240

Ser Met Leu Gly Ala Thr Arg Lys Ser Leu Gln Ser Trp Arg Arg Pro
                245                 250                 255

Val Leu Leu Leu Arg Pro Asn Lys Leu Cys Leu Ser Val Phe Leu Ser
                260                 265                 270

Phe Phe Gly Ala Phe Thr Ile Phe Ser Leu Asn Ser Tyr Ile Leu Ser
            275                 280                 285

Val His Leu Val Trp Gln Phe Lys Ile Ile Ser Ile Leu Gly Arg
290                 295                 300

Ala Met Phe
305

<210> SEQ ID NO 201
<211> LENGTH: 279
<212> TYPE: PRT
<213> ORGANISM: Zea mays

<400> SEQUENCE: 201

Met Val Ser Ser Ser Arg Ala Val Val Val Val Gly Leu Leu Val
1               5                   10                  15

Ala Ala Ser Ser Leu Ala Val Ala Ala Ser Asp Gly Gly Pro Thr
                20                  25                  30

Tyr Gly Tyr Thr Ala Gly Ser Pro Asp Gly Pro Glu Asn Trp Gly Lys
            35                  40                  45

Leu Ser Pro Ala Tyr Lys Leu Cys Gly Gln Gly Lys Gln Gln Ser Pro
50                  55                  60

Ile Asp Ile Val Thr Lys Gln Ala Val Pro Thr Ala Thr Leu Asp Thr
65                  70                  75                  80

Leu Asn Arg Thr Tyr Gly Ala Thr Asn Ala Thr Leu Ile Asn Asp Gly
                85                  90                  95

His Asp Ile Thr Met Ala Leu Glu Gly Lys Val Gly Thr Val Thr Val
            100                 105                 110

Asn Gly Lys Ala Tyr Ser Phe Glu Lys Leu His Trp His Ser Pro Ser
        115                 120                 125

Asp His Thr Ile Asn Gly Gln Arg Phe Pro Leu Glu Leu His Leu Val
    130                 135                 140

His Arg Ser Ala Asp Gly Ala Leu Ala Val Ile Gly Ile Leu Tyr Gln
145                 150                 155                 160

Leu Gly Ala Pro Asp Ser Phe Tyr Tyr Gln Leu Lys Arg Gln Leu Gly
                165                 170                 175
```

```
Glu Met Ala Gln Asp Arg Cys Asp Phe Ala Glu Glu Glu Ser Arg
            180                 185                 190

Val Glu Ala Gly Leu Ile His Leu Arg Ser Leu Gln Lys Arg Thr Gly
            195                 200                 205

Ser Tyr Phe Arg Tyr Thr Gly Ser Leu Thr Val Pro Pro Cys Thr Glu
            210                 215                 220

Asn Val Val Trp Ser Val Leu Gly Lys Val Arg Gln Ile Ser Gln Asp
225                 230                 235                 240

Gln Leu Gln Leu Leu Lys Ala Pro Leu Pro Gly Ser Asp Ala Arg Pro
            245                 250                 255

Thr Gln Pro Leu Asn Gly Arg Thr Val Gln Phe Tyr Asn Pro Pro Asn
            260                 265                 270

Ser Thr Ile Ser Phe Gln Ile
            275

<210> SEQ ID NO 202
<211> LENGTH: 274
<212> TYPE: PRT
<213> ORGANISM: Brassica napus

<400> SEQUENCE: 202

Met Lys Arg Pro Ser Ile Val Arg Val Ile Phe Leu Ile Val Ile Ser
1               5                   10                  15

Ile Thr Thr Ala Ser Gly Ser Pro Asp His Gly Glu Val Glu Asp Glu
            20                  25                  30

Thr Glu Phe Asn Tyr Glu Lys Gly Gly Glu Lys Gly Pro Glu Lys Trp
            35                  40                  45

Gly Thr Leu Lys Pro Glu Trp Lys Met Cys Gly Asn Gly Thr Met Gln
        50                  55                  60

Ser Pro Ile Asp Leu Thr Asp Lys Arg Val Phe Ile Asp His Asn Leu
65                  70                  75                  80

Gly Pro Leu Arg Ser His Tyr Leu Pro Ser Asn Ala Thr Ile Lys Asn
                85                  90                  95

Arg Gly His Asp Ile Met Leu Glu Phe Glu Gly Gly Asn Ala Gly Met
            100                 105                 110

Gly Ile Ile Ile Asn Gly Thr Val Tyr Gln Leu Gln Gln Leu His Trp
            115                 120                 125

His Ser Pro Ser Glu His Thr Ile Asn Gly Lys Arg Phe Val Leu Glu
            130                 135                 140

Gln His Met Leu His Gln Ser Lys Asp Gly Arg Leu Ala Val Val Ala
145                 150                 155                 160

Phe Leu Tyr Ser Leu Gly Arg Pro Asp Ser Phe Leu Leu Ser Leu Glu
                165                 170                 175

Arg Gln Leu Lys Arg Ile Thr Asp Ala His Gly Ser Glu Asp Phe Val
            180                 185                 190

Ser Trp Ile Asp Pro Arg Ala Val Asn Phe Lys Thr Arg Leu Tyr Tyr
            195                 200                 205

Arg Tyr Leu Gly Ser Leu Thr Thr Pro Pro Cys Ser Glu Asn Val Thr
            210                 215                 220

Trp Ser Ile Ser Arg Glu Met Arg Thr Val Thr Leu Lys Gln Leu Asp
225                 230                 235                 240

Leu Leu Arg Val Ser Val His Asp Gln Ser Asn Thr Asn Ala Arg Pro
                245                 250                 255

Leu Gln Arg Gln Asn Gly Arg Pro Val Lys Phe Tyr Leu Pro Ala Trp
            260                 265                 270
```

His Ile

```
<210> SEQ ID NO 203
<211> LENGTH: 17
<212> TYPE: PRT
<213> ORGANISM: Artificial sequence
<220> FEATURE:
<223> OTHER INFORMATION: motif 1 of a CAH3 polypeptide
<220> FEATURE:
<221> NAME/KEY: VARIANT
<222> LOCATION: (1)..(1)
<223> OTHER INFORMATION: Xaa is Ser or Thr
<220> FEATURE:
<221> NAME/KEY: VARIANT
<222> LOCATION: (3)..(3)
<223> OTHER INFORMATION: Xaa is His or Asn
<220> FEATURE:
<221> NAME/KEY: UNSURE
<222> LOCATION: (4)..(4)
<223> OTHER INFORMATION: Xaa can be any naturally occurring amino acid
<220> FEATURE:
<221> NAME/KEY: VARIANT
<222> LOCATION: (5)..(5)
<223> OTHER INFORMATION: Xaa is Leu, Ile, Val, or Met
<220> FEATURE:
<221> NAME/KEY: UNSURE
<222> LOCATION: (6)..(9)
<223> OTHER INFORMATION: Xaa can be any naturally occurring amino acid
<220> FEATURE:
<221> NAME/KEY: VARIANT
<222> LOCATION: (10)..(10)
<223> OTHER INFORMATION: Xaa is Phe, Tyr, Leu, or His
<220> FEATURE:
<221> NAME/KEY: UNSURE
<222> LOCATION: (11)..(12)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: Xaa is Glu or Asp
<220> FEATURE:
<221> NAME/KEY: UNSURE
<222> LOCATION: (14)..(14)
<223> OTHER INFORMATION: Xaa can be any naturally occurring amino acid
<220> FEATURE:
<221> NAME/KEY: VARIANT
<222> LOCATION: (15)..(15)
<223> OTHER INFORMATION: Xaa is His or Gln
<220> FEATURE:
<221> NAME/KEY: VARIANT
<222> LOCATION: (16)..(16)
<223> OTHER INFORMATION: Xaa is Leu, Ile, Val, Met, Phe, or Ala
<220> FEATURE:
<221> NAME/KEY: VARIANT
<222> LOCATION: (17)..(17)
<223> OTHER INFORMATION: Xaa is Leu, Ile, Val, Met, Phe, or Ala

<400> SEQUENCE: 203

Xaa Glu Xaa Xaa Xaa Xaa Xaa Xaa Xaa Xaa Xaa Xaa Xaa Xaa Xaa Xaa
 1               5                   10                  15

Xaa

<210> SEQ ID NO 204
<211> LENGTH: 7
<212> TYPE: PRT
<213> ORGANISM: Artificial sequence
<220> FEATURE:
<223> OTHER INFORMATION: motif 2 of a CAH3 polypeptide
<220> FEATURE:
<221> NAME/KEY: VARIANT
<222> LOCATION: (1)..(1)
<223> OTHER INFORMATION: Xaa is Leu, Asn, Tyr, Met, Thr, Phe, Ala, or
      Arg
<220> FEATURE:
<221> NAME/KEY: VARIANT
<222> LOCATION: (2)..(2)
```

```
<223> OTHER INFORMATION: Xaa is Ala, Val, or Ser
<220> FEATURE:
<221> NAME/KEY: VARIANT
<222> LOCATION: (4)..(4)
<223> OTHER INFORMATION: Xaa is Val, Ile, Leu, or Thr
<220> FEATURE:
<221> NAME/KEY: VARIANT
<222> LOCATION: (5)..(5)
<223> OTHER INFORMATION: Xaa is Ala, Thr, Gly, or Ser
<220> FEATURE:
<221> NAME/KEY: VARIANT
<222> LOCATION: (6)..(6)
<223> OTHER INFORMATION: Xaa is Phe, Val, Ile, Ser, or Thr
<220> FEATURE:
<221> NAME/KEY: VARIANT
<222> LOCATION: (7)..(7)
<223> OTHER INFORMATION: Xaa is Leu, Phe, Val, or Met

<400> SEQUENCE: 204

Xaa Xaa Val Xaa Xaa Xaa Xaa
1               5

<210> SEQ ID NO 205
<211> LENGTH: 16
<212> TYPE: PRT
<213> ORGANISM: Artificial sequence
<220> FEATURE:
<223> OTHER INFORMATION: motif 3 of a CAH3 polypeptide
<220> FEATURE:
<221> NAME/KEY: VARIANT
<222> LOCATION: (1)..(1)
<223> OTHER INFORMATION: Xaa is Tyr or Phe
<220> FEATURE:
<221> NAME/KEY: VARIANT
<222> LOCATION: (2)..(2)
<223> OTHER INFORMATION: Xaa is Tyr, Phe, Val, Gly, or Ala
<220> FEATURE:
<221> NAME/KEY: VARIANT
<222> LOCATION: (3)..(3)
<223> OTHER INFORMATION: Xaa is Arg, Glu, Gly, Thr, or His
<220> FEATURE:
<221> NAME/KEY: VARIANT
<222> LOCATION: (4)..(4)
<223> OTHER INFORMATION: Xaa is Tyr or Phe
<220> FEATURE:
<221> NAME/KEY: UNSURE
<222> LOCATION: (5)..(5)
<223> OTHER INFORMATION: Xaa can be any naturally occurring amino acid
<220> FEATURE:
<221> NAME/KEY: VARIANT
<222> LOCATION: (8)..(8)
<223> OTHER INFORMATION: Xaa is Leu, Phe, or Tyr
<220> FEATURE:
<221> NAME/KEY: VARIANT
<222> LOCATION: (10)..(10)
<223> OTHER INFORMATION: Xaa is Thr, Val, or Ala
<220> FEATURE:
<221> NAME/KEY: VARIANT
<222> LOCATION: (14)..(14)
<223> OTHER INFORMATION: Xaa is Ser, Thr, Gly, Asp, or Ala
<220> FEATURE:
<221> NAME/KEY: VARIANT
<222> LOCATION: (15)..(15)
<223> OTHER INFORMATION: Xaa is Glu or Gln
<220> FEATURE:
<221> NAME/KEY: VARIANT
<222> LOCATION: (16)..(16)
<223> OTHER INFORMATION: Xaa is Asn, Gly, Asp, or Arg

<400> SEQUENCE: 205

Xaa Xaa Xaa Xaa Xaa Gly Ser Xaa Thr Xaa Pro Pro Cys Xaa Xaa Xaa
1               5                   10                  15

<210> SEQ ID NO 206
<211> LENGTH: 1416
<212> TYPE: DNA
```

<213> ORGANISM: Oryza sativa

<400> SEQUENCE: 206

```
cccacgcgtc cgcccacgcg tccgggacac cagaaacata gtacacttga gctcactcca    60
aactcaaaca ctcacaccaa tggctctcca agttcaggcc gcactcctgc cctctgctct   120
ctctgtcccc aagaagggta acttgagcgc ggtggtgaag gagccggggt tccttagcgt   180
gagcagaagg ccaagaagcc gtcgctggtg gtgaggcgg tggcgacgcg gcgggccggt   240
ggcgagcccc ggcgcgggca cgtcgaaggc ggacgggaag aagacgctgc ggcaggggt   300
ggtggtgatc accggcgcgt cgtcgggct cgggctcgcg gcggcgaagg cgcttggcgg   360
agacggggaa gtggcacgtg gtgatggcgt tccgcgactt tcctgaaggc ggcgacggcg   420
gcgaaggcgg cggggatggc ggcggggagc tacaccgtca tgcacctgga cctcgcctcc   480
ctcgacagcg tccgccagtt cgtggacaac ttccggcgct ccggcatgcc gctcgacgcg   540
ctggtgtgca acgccgcaca tctaccggcc gacggcgcgg caaccgacgt tcaacgccga   600
cgggtacgag atgagcgtcg gggtgaacca cctgggccac ttcctcctcg cccgcctcat   660
gctcgacgac ctcaagaaat ccgactaccc gtcgcggcgg ctcatcatcc tcggctccat   720
caccggcaac accaacacct tcgccggcaa cgtccctccc aaggccgggc taggcgacct   780
ccggggctc gccggcggc tccgcggca gaacgggtcg gcgatgatcg acggcgcgga   840
gagcttcgac ggcgccaagg cgtacaagga cagcaagatc tgtaacatgc tgacgatgca   900
ggagttccac cggagattcc acgaggagac cgggatcacg ttcgcgtcgc tgtacccggg   960
gtgcatcgcg acgacgggct tgttccgcga gcacatcccg ctgttccggc tgctgttccc  1020
gccgttccag cggttcgtga cgaagggtt cgtgtcggag gcggagtccg ggaagcggct  1080
ggcgcaggtg gtgggcgacc cgagcctgac caagtccggc gtgtactgga gctggaacaa  1140
ggactcggcg tcgttcgaga ccagctctc gcaggaggcc agcgacccgg agaaggccag  1200
gaagctctgg gacctcagcg agaagctcgt cggcctcgtc tgagttatt attttaccat  1260
tcgttttcaac tgttaatttc ttcggggttt agggggtttc agctttcagt gagagaggcc  1320
tgtcaagtga tgtacaatta gtaatttttt tttacccgac aaatcatgca ataaaaccac  1380
aggcttacat tatcgatttg tccacctaaa ttaagt                              1416
```

<210> SEQ ID NO 207
<211> LENGTH: 51
<212> TYPE: DNA
<213> ORGANISM: Artificial sequence
<220> FEATURE:
<223> OTHER INFORMATION: primer: prm8571

<400> SEQUENCE: 207

```
ggggacaagt ttgtacaaaa aagcaggctt aaacaatgcg ctcagccgtt c             51
```

<210> SEQ ID NO 208
<211> LENGTH: 50
<212> TYPE: DNA
<213> ORGANISM: Artificial sequence
<220> FEATURE:
<223> OTHER INFORMATION: primer: prm8572

<400> SEQUENCE: 208

```
ggggaccact ttgtacaaga aagctgggtc tcactgaccc tagcacactc                50
```

<210> SEQ ID NO 209
<211> LENGTH: 2253
<212> TYPE: DNA

<213> ORGANISM: Arabidopsis thaliana

<400> SEQUENCE: 209

```
atggcgatga gacttttgaa gactcatctt ctgtttctgc atctgtatct attttctca      60
ccatgtttcg cttacactga catggaagtt cttctcaatc tcaaatcctc catgattggt    120
cctaaaggac acggtctcca cgactggatt cactcatctt ctccggatgc tcactgttct    180
ttctccggcg tctcatgtga cgacgatgct cgtgttatct ctctcaacgt ctccttcact    240
cctttgtttg gtacaatctc accagagatt gggatgttga ctcatttggt gaatctaact    300
ttagctgcca acaacttcac cggtgaatta ccattggaga tgaagagtct aacttctctc    360
aaggttttga atatctccaa caatggtaac cttactggaa cattccctgg agagatttta    420
aaagctatgg ttgatcttga agttcttgac acttataaca acaatttcaa cggtaagtta    480
ccaccggaga tgtcagagct taagaagctt aaatacctct ctttcggtgg aaatttcttc    540
agcggagaga ttccagagag ttatggagat attcaaagct tagagtatct tggtctcaac    600
ggagctggac tctccggtaa atctccggcg tttctttccc gcctcaagaa cttaagagaa    660
atgtatattg ctactacaa cagctacacc ggtggtgttc caccggagtt cggtggttta    720
acaaagcttg agatcctcga catggcgagc tgtacactca ccggagagat tccgacgagt    780
ttaagtaacc tgaaacatct acatactctg tttcttcaca tcaacaactt aaccggtcat    840
ataccaccgg agctttccgg tttagtcagc ttgaaatctc tcgatttatc aatcaatcag    900
ttaaccggag aaatccctca agcttcatc aatctcggaa acattactct aatcaatctc    960
ttcagaaaca atctctacgg acaaatacca gaggccatcg gagaattacc aaaactcgaa   1020
gtcttcgaag tatgggagaa caatttcacg ttacaattac cggcgaatct tggccggaac   1080
gggaatctaa taaagcttga tgtctctgat aatcatctca ccggacttat ccccaaggac   1140
ttatgcagag gtgagaaatt agagatgtta attctctcta acaacttctt ctttggtcca   1200
attccagaag agcttggtaa atgcaaatcc ttaaccaaaa tcagaatcgt taagaatctt   1260
ctcaacggca ctgttccggc ggggcttttc aatctaccgt tagttacgat tatcgaactc   1320
actgataatt tcttctccgg tgaacttccg gtaacgatgt ccggcgatgt tctcgatcag   1380
atttacctct ctaacaactg gttttccggc gagattccac ctgcgattgg taatttcccc   1440
aatctacaga ctctattctt agatcggaac cgatttcgcg gcaacattcc gagagaaatc   1500
ttcgaattga agcatttatc gaggatcaac acaagtgcga acaacatcac cggcggtatt   1560
ccagattcaa tctctcgctg ctcaacttta atctccgtcg atctcagccg taaccgaatc   1620
aacggagaaa tccctaaagg gatcaacaac gtgaaaaact taggaactct aaatatctcc   1680
ggtaatcaat taaccggttc aatccctacc ggaatcggaa acatgacgag tttaacaact   1740
ctcgatctct ctttcaacga tctctccggt agagtaccac tcggtggtca attcttggtg   1800
ttcaacgaaa cttccttcgc cggaaacact tacctctgtc ccctcaccg tgtctcttgc    1860
ccaacacggc aggacaaac tccgatcac aatcacacgg cgttgttctc accgtcaagg    1920
atcgtaatca cggttatcgc agcgatcacc ggtttgatcc taatcagtgt agcgattcgt    1980
cagatgaata agaagaagaa ccagaaatct ctcgcctgga aactaatcgc cttccagaaa   2040
ctagatttca aatctgaaga cgttctcgag tgtcttaaag aagagaacat aatcggtaaa   2100
ggcggagctg gaattgtcta ccgtggatca atgccaaaca acgtagacgt cgcgattaaa   2160
cgactcgttg gccgtgggac cgggaggagc gatcatggat tcacggcgga gattcaaact   2220
ttggggagaa tccgccaccg tcacatagtg tga                                 2253
```

<210> SEQ ID NO 210
<211> LENGTH: 750
<212> TYPE: PRT
<213> ORGANISM: Arabidopsis thaliana

<400> SEQUENCE: 210

```
Met Ala Met Arg Leu Leu Lys Thr His Leu Leu Phe Leu His Leu Tyr
1               5                   10                  15

Leu Phe Phe Ser Pro Cys Phe Ala Tyr Thr Asp Met Glu Val Leu Leu
            20                  25                  30

Asn Leu Lys Ser Ser Met Ile Gly Pro Lys Gly His Gly Leu His Asp
        35                  40                  45

Trp Ile His Ser Ser Ser Pro Asp Ala His Cys Ser Phe Ser Gly Val
    50                  55                  60

Ser Cys Asp Asp Asp Ala Arg Val Ile Ser Leu Asn Val Ser Phe Thr
65                  70                  75                  80

Pro Leu Phe Gly Thr Ile Ser Pro Glu Ile Gly Met Leu Thr His Leu
                85                  90                  95

Val Asn Leu Thr Leu Ala Ala Asn Asn Phe Thr Gly Glu Leu Pro Leu
            100                 105                 110

Glu Met Lys Ser Leu Thr Ser Leu Lys Val Leu Asn Ile Ser Asn Asn
        115                 120                 125

Gly Asn Leu Thr Gly Thr Phe Pro Gly Glu Ile Leu Lys Ala Met Val
    130                 135                 140

Asp Leu Glu Val Leu Asp Thr Tyr Asn Asn Phe Asn Gly Lys Leu
145                 150                 155                 160

Pro Pro Glu Met Ser Glu Leu Lys Lys Leu Lys Tyr Leu Ser Phe Gly
                165                 170                 175

Gly Asn Phe Phe Ser Gly Glu Ile Pro Glu Ser Tyr Gly Asp Ile Gln
            180                 185                 190

Ser Leu Glu Tyr Leu Gly Leu Asn Gly Ala Gly Leu Ser Gly Lys Ser
        195                 200                 205

Pro Ala Phe Leu Ser Arg Leu Lys Asn Leu Arg Glu Met Tyr Ile Gly
    210                 215                 220

Tyr Tyr Asn Ser Tyr Thr Gly Val Pro Glu Phe Gly Leu
225                 230                 235                 240

Thr Lys Leu Glu Ile Leu Asp Met Ala Ser Cys Thr Leu Thr Gly Glu
                245                 250                 255

Ile Pro Thr Ser Leu Ser Asn Leu Lys His Leu His Thr Leu Phe Leu
            260                 265                 270

His Ile Asn Asn Leu Thr Gly His Ile Pro Pro Glu Leu Ser Gly Leu
        275                 280                 285

Val Ser Leu Lys Ser Leu Asp Leu Ser Ile Asn Gln Leu Thr Gly Glu
    290                 295                 300

Ile Pro Gln Ser Phe Ile Asn Leu Gly Asn Ile Thr Leu Ile Asn Leu
305                 310                 315                 320

Phe Arg Asn Asn Leu Tyr Gly Gln Ile Pro Glu Ala Ile Gly Glu Leu
                325                 330                 335

Pro Lys Leu Glu Val Phe Glu Val Trp Glu Asn Asn Phe Thr Leu Gln
            340                 345                 350

Leu Pro Ala Asn Leu Gly Arg Asn Gly Asn Leu Ile Lys Leu Asp Val
        355                 360                 365

Ser Asp Asn His Leu Thr Gly Leu Ile Pro Lys Asp Leu Cys Arg Gly
    370                 375                 380
```

| | | | | | | | | | | | | | | |
|---|---|---|---|---|---|---|---|---|---|---|---|---|---|---|
|Glu|Lys|Leu|Glu|Met|Leu|Ile|Leu|Ser|Asn|Asn|Phe|Phe|Phe|Gly|Pro|
|385| | | |390| | | |395| | | |400| | |

Ile Pro Glu Glu Leu Gly Lys Cys Lys Ser Leu Thr Lys Ile Arg Ile
            405                 410                 415

Val Lys Asn Leu Leu Asn Gly Thr Val Pro Ala Gly Leu Phe Asn Leu
        420                 425                 430

Pro Leu Val Thr Ile Ile Glu Leu Thr Asp Asn Phe Phe Ser Gly Glu
            435                 440                 445

Leu Pro Val Thr Met Ser Gly Asp Val Leu Asp Gln Ile Tyr Leu Ser
        450                 455                 460

Asn Asn Trp Phe Ser Gly Glu Ile Pro Ala Ile Gly Asn Phe Pro
465                 470                 475                 480

Asn Leu Gln Thr Leu Phe Leu Asp Arg Asn Arg Phe Arg Gly Asn Ile
            485                 490                 495

Pro Arg Glu Ile Phe Glu Leu Lys His Leu Ser Arg Ile Asn Thr Ser
            500                 505                 510

Ala Asn Asn Ile Thr Gly Gly Ile Pro Asp Ser Ile Ser Arg Cys Ser
        515                 520                 525

Thr Leu Ile Ser Val Asp Leu Ser Arg Asn Arg Ile Asn Gly Glu Ile
    530                 535                 540

Pro Lys Gly Ile Asn Asn Val Lys Asn Leu Gly Thr Leu Asn Ile Ser
545                 550                 555                 560

Gly Asn Gln Leu Thr Gly Ser Ile Pro Thr Gly Ile Gly Asn Met Thr
            565                 570                 575

Ser Leu Thr Thr Leu Asp Leu Ser Phe Asn Asp Leu Ser Gly Arg Val
        580                 585                 590

Pro Leu Gly Gly Gln Phe Leu Val Phe Asn Glu Thr Ser Phe Ala Gly
        595                 600                 605

Asn Thr Tyr Leu Cys Leu Pro His Arg Val Ser Cys Pro Thr Arg Pro
        610                 615                 620

Gly Gln Thr Ser Asp His Asn His Thr Ala Leu Phe Ser Pro Ser Arg
625                 630                 635                 640

Ile Val Ile Thr Val Ile Ala Ala Ile Thr Gly Leu Ile Leu Ile Ser
            645                 650                 655

Val Ala Ile Arg Gln Met Asn Lys Lys Asn Gln Lys Ser Leu Ala
        660                 665                 670

Trp Lys Leu Ile Ala Phe Gln Lys Leu Asp Phe Lys Ser Glu Asp Val
    675                 680                 685

Leu Glu Cys Leu Lys Glu Glu Asn Ile Ile Gly Lys Gly Gly Ala Gly
            690                 695                 700

Ile Val Tyr Arg Gly Ser Met Pro Asn Asn Val Asp Val Ala Ile Lys
705                 710                 715                 720

Arg Leu Val Gly Arg Gly Thr Gly Arg Ser Asp His Gly Phe Thr Ala
            725                 730                 735

Glu Ile Gln Thr Leu Gly Arg Ile Arg His Arg His Ile Val
        740                 745                 750

<210> SEQ ID NO 211
<211> LENGTH: 2943
<212> TYPE: DNA
<213> ORGANISM: Arabidopsis thaliana

<400> SEQUENCE: 211
atggcgatga gacttttgaa gactcatctt ctgtttctgc atctgtatct attttctca      60 ccatgtttcg cttacactga catggaagtt cttctcaatc tcaaatcctc catgattggt    120

```
cctaaaggac acggtctcca cgactggatt cactcatctt ctccggatgc tcactgttct     180
ttctccggcg tctcatgtga cgacgatgct cgtgttatct ctctcaacgt ctccttcact     240
cctttgtttg gtacaatctc accagagatt gggatgttga ctcatttggt gaatctaact     300
ttagctgcca acaacttcac cggtgaatta ccattggaga tgaagagtct aacttctctc     360
aaggttttga atatctccaa caatggtaac cttactggaa cattccctgg agagatttta     420
aaagctatgg ttgatcttga agttcttgac acttataaca acaatttcaa cggtaagtta     480
ccaccggaga tgtcagagct taagaagctt aaatacctct ctttcggtgg aaatttcttc     540
agcggagaga ttccagagag ttatggagat attcaaagct tagagtatct tggtctcaac     600
ggagctggac tctccggtaa atctccggcg tttctttccc gcctcaagaa cttaagagaa     660
atgtatattg gctactacaa cagctacacc ggtggtgttc cacgcgagtt cggtggttta     720
acaaagcttg agatcctcga catggcgagc tgtacactca ccggagagat tccgacgagt     780
ttaagtaacc tgaaacatct acatactctg tttcttcaca tcaacaactt aaccggtcat     840
ataccaccgg agcttttccgg tttagtcagc ttgaaatctc tcgatttatc aatcaatcag     900
ttaaccggag aaatccctca aagcttcatc aatctcggaa acattactct aatcaatctc     960
ttcagaaaca atctctacgg acaaatacca gaggccatcg gagaattacc aaaactcgaa    1020
gtcttcgaag tatgggagaa caatttcacg ttacaattac cggcgaatct tggccggaac    1080
gggaatctaa taagcttga tgtctctgat aatcatctca ccggacttat ccccaaggac    1140
ttatgcagag gtgagaaatt agagatgtta attctctcta caacttctt ctttggtcca    1200 attccagaag agcttggtaa atgcaaatcc ttaaccaaaa tcagaatcgt taagaatctt    1260
ctcaacggca ctgttccggc ggggcttttc aatctaccgt tagttacgat tatcgaactc    1320
actgataatt tcttctccgg tgaacttccg gtaacgatgt ccggcgatgt tctcgatcag    1380
atttacctct ctaacaactg gttttccggc gagattccac ctgcgattgg taatttcccc    1440
aatctacaga ctctattctt agatcggaac cgatttcgcg gcaacattcc gagagaaatc    1500
ttcgaattga agcatttatc gaggatcaac acaagtgcga acaacatcac cggcggtatt    1560
ccagattcaa tctctcgctg ctcaaccttta atctccgtcg atctcagccg taaccgaatc    1620
aacggagaaa tccctaaagg gatcaacaac gtgaaaaact taggaactct aaatatctcc    1680
ggtaatcaat taaccggttc aatccctacc ggaatcggaa acatgacgag tttaacaact    1740
ctcgatctct ctttcaacga tctctccggt agagtaccac tcggtggtca attcttggtg    1800
ttcaacgaaa cttccttcgc cggaaacact tacctctgtc tccctcaccg tgtctcttgt    1860
ccaacacggc caggacaaac ctccgatcac aatcacacgg cgttgttctc accgtcaagg    1920
atcgtaatca cggttatcgc agcgatcacc ggtttgatcc taatcagtgt agcgattcgt    1980
cagatgaata agaagaagaa ccagaaatct ctcgcctgga aactaaccgc cttccagaaa    2040
ctagatttca atctgaagga cgttctcgag tgtcttaaag aagagaacat aatcggtaaa    2100
ggcggagctg gaattgtcta ccgtggatca atgccaaaca acgtagacgt cgcgattaaa    2160
cgactcgttg gccgtgggac cgggaggagc gatcatggat tcacggcgga gattcaaact    2220
ttggggagaa tccgccaccg tcacatagtg agacttcttg gttacgtagc gaacaaggat    2280
acgaatctcc ttctttatga gtacatgcct aatgaagcc ttgagagct tttgcatgga    2340 tctaaaggtg gtcatcttca atgggagacg agacatagag tagccgtgga agctgcaaag    2400
ggcttgtgtt atcttcacca tgattgttca ccattgatct tgcatagaga tgttaagtcc    2460
aataacattc ttttggactc tgattttgaa gcccatgttg ctgattttgg gcttgctaag    2520
```

```
ttcttagttg atggtgctgc ttctgagtgt atgtcttcaa ttgctggctc ttatggatac    2580
atcgccccag agtatgcata taccttgaaa gtggacgaga agagtgatgt gtatagtttc    2640
ggagtggttt tgttggagtt aatagctggg aagaaacctg ttggtgaatt tggagaagga    2700
gtggatatag ttaggtgggt gaggaacacg gaagaggaga taactcagcc atcggatgct    2760
gctattgttg ttgcgattgt tgacccgagg ttgactggtt acccgttgac aagtgtgatt    2820
catgtgttca agatcgcaat gatgtgtgtg gaggaagaag ccgcggcaag gcctacgatg    2880
agggaagttg tgcacatgct cactaaccct cctaaatccg tggcgaactt gatcgcgttc    2940
tga                                                                  2943
```

<210> SEQ ID NO 212
<211> LENGTH: 980
<212> TYPE: PRT
<213> ORGANISM: Arabidopsis thaliana

<400> SEQUENCE: 212

```
Met Ala Met Arg Leu Leu Lys Thr His Leu Phe Leu His Leu Tyr
1               5                   10                  15

Leu Phe Phe Ser Pro Cys Phe Ala Tyr Thr Asp Met Glu Val Leu Leu
                20                  25                  30

Asn Leu Lys Ser Ser Met Ile Gly Pro Lys Gly His Gly Leu His Asp
            35                  40                  45

Trp Ile His Ser Ser Ser Pro Asp Ala His Cys Ser Phe Ser Gly Val
        50                  55                  60

Ser Cys Asp Asp Asp Ala Arg Val Ile Ser Leu Asn Val Ser Phe Thr
65                  70                  75                  80

Pro Leu Phe Gly Thr Ile Ser Pro Glu Ile Gly Met Leu Thr His Leu
                85                  90                  95

Val Asn Leu Thr Leu Ala Ala Asn Asn Phe Thr Gly Glu Leu Pro Leu
            100                 105                 110

Glu Met Lys Ser Leu Thr Ser Leu Lys Val Leu Asn Ile Ser Asn Asn
        115                 120                 125

Gly Asn Leu Thr Gly Thr Phe Pro Gly Glu Ile Leu Lys Ala Met Val
    130                 135                 140

Asp Leu Glu Val Leu Asp Thr Tyr Asn Asn Phe Asn Gly Lys Leu
145                 150                 155                 160

Pro Pro Glu Met Ser Glu Leu Lys Lys Leu Lys Tyr Leu Ser Phe Gly
                165                 170                 175

Gly Asn Phe Phe Ser Gly Glu Ile Pro Glu Ser Tyr Gly Asp Ile Gln
            180                 185                 190

Ser Leu Glu Tyr Leu Gly Leu Asn Gly Ala Gly Leu Ser Gly Lys Ser
        195                 200                 205

Pro Ala Phe Leu Ser Arg Leu Lys Asn Leu Arg Glu Met Tyr Ile Gly
    210                 215                 220

Tyr Tyr Asn Ser Tyr Thr Gly Gly Val Pro Arg Glu Phe Gly Leu
225                 230                 235                 240

Thr Lys Leu Glu Ile Leu Asp Met Ala Ser Cys Thr Leu Thr Gly Glu
                245                 250                 255

Ile Pro Thr Ser Leu Ser Asn Leu Lys His Leu His Thr Leu Phe Leu
            260                 265                 270

His Ile Asn Asn Leu Thr Gly His Ile Pro Pro Glu Leu Ser Gly Leu
        275                 280                 285

Val Ser Leu Lys Ser Leu Asp Leu Ser Ile Asn Gln Leu Thr Gly Glu
```

```
              290                 295                 300
Ile Pro Gln Ser Phe Ile Asn Leu Gly Asn Ile Thr Leu Ile Asn Leu
305                 310                 315                 320

Phe Arg Asn Asn Leu Tyr Gly Gln Ile Pro Glu Ala Ile Gly Glu Leu
                    325                 330                 335

Pro Lys Leu Glu Val Phe Glu Val Trp Glu Asn Asn Phe Thr Leu Gln
                    340                 345                 350

Leu Pro Ala Asn Leu Gly Arg Asn Gly Asn Leu Ile Lys Leu Asp Val
                    355                 360                 365

Ser Asp Asn His Leu Thr Gly Leu Ile Pro Lys Asp Leu Cys Arg Gly
370                 375                 380

Glu Lys Leu Glu Met Leu Ile Leu Ser Asn Asn Phe Phe Gly Pro
385                 390                 395                 400

Ile Pro Glu Glu Leu Gly Lys Cys Lys Ser Leu Thr Lys Ile Arg Ile
                    405                 410                 415

Val Lys Asn Leu Leu Asn Gly Thr Val Pro Ala Gly Leu Phe Asn Leu
                    420                 425                 430

Pro Leu Val Thr Ile Ile Glu Leu Thr Asp Asn Phe Phe Ser Gly Glu
                    435                 440                 445

Leu Pro Val Thr Met Ser Gly Asp Val Leu Asp Gln Ile Tyr Leu Ser
450                 455                 460

Asn Asn Trp Phe Ser Gly Glu Ile Pro Ala Ile Gly Asn Phe Pro
465                 470                 475                 480

Asn Leu Gln Thr Leu Phe Leu Asp Arg Asn Arg Phe Arg Gly Asn Ile
                    485                 490                 495

Pro Arg Glu Ile Phe Glu Leu Lys His Leu Ser Arg Ile Asn Thr Ser
                    500                 505                 510

Ala Asn Asn Ile Thr Gly Gly Ile Pro Asp Ser Ile Ser Arg Cys Ser
                    515                 520                 525

Thr Leu Ile Ser Val Asp Leu Ser Arg Asn Arg Ile Asn Gly Glu Ile
                    530                 535                 540

Pro Lys Gly Ile Asn Asn Val Lys Asn Leu Gly Thr Leu Asn Ile Ser
545                 550                 555                 560

Gly Asn Gln Leu Thr Gly Ser Ile Pro Thr Gly Ile Gly Asn Met Thr
                    565                 570                 575

Ser Leu Thr Thr Leu Asp Leu Ser Phe Asn Asp Leu Ser Gly Arg Val
                    580                 585                 590

Pro Leu Gly Gly Gln Phe Leu Val Phe Asn Glu Thr Ser Phe Ala Gly
                    595                 600                 605

Asn Thr Tyr Leu Cys Leu Pro His Arg Val Ser Cys Pro Thr Arg Pro
610                 615                 620

Gly Gln Thr Ser Asp His Asn His Thr Ala Leu Phe Ser Pro Ser Arg
625                 630                 635                 640

Ile Val Ile Thr Val Ile Ala Ala Ile Thr Gly Leu Ile Leu Ile Ser
                    645                 650                 655

Val Ala Ile Arg Gln Met Asn Lys Lys Asn Gln Lys Ser Leu Ala
                    660                 665                 670

Trp Lys Leu Thr Ala Phe Gln Lys Leu Asp Phe Lys Ser Glu Asp Val
                    675                 680                 685

Leu Glu Cys Leu Lys Glu Glu Asn Ile Ile Gly Lys Gly Gly Ala Gly
                    690                 695                 700

Ile Val Tyr Arg Gly Ser Met Pro Asn Asn Val Asp Val Ala Ile Lys
705                 710                 715                 720
```

```
Arg Leu Val Gly Arg Gly Thr Gly Arg Ser Asp His Gly Phe Thr Ala
            725                 730                 735
Glu Ile Gln Thr Leu Gly Arg Ile Arg His Arg His Ile Val Arg Leu
        740                 745                 750
Leu Gly Tyr Val Ala Asn Lys Asp Thr Asn Leu Leu Leu Tyr Glu Tyr
    755                 760                 765
Met Pro Asn Gly Ser Leu Gly Glu Leu Leu His Gly Ser Lys Gly Gly
770                 775                 780
His Leu Gln Trp Glu Thr Arg His Arg Val Ala Val Glu Ala Ala Lys
785                 790                 795                 800
Gly Leu Cys Tyr Leu His His Asp Cys Ser Pro Leu Ile Leu His Arg
            805                 810                 815
Asp Val Lys Ser Asn Asn Ile Leu Leu Asp Ser Asp Phe Glu Ala His
        820                 825                 830
Val Ala Asp Phe Gly Leu Ala Lys Phe Leu Val Asp Gly Ala Ala Ser
    835                 840                 845
Glu Cys Met Ser Ser Ile Ala Gly Ser Tyr Gly Tyr Ile Ala Pro Glu
850                 855                 860
Tyr Ala Tyr Thr Leu Lys Val Asp Glu Lys Ser Asp Val Tyr Ser Phe
865                 870                 875                 880
Gly Val Val Leu Leu Glu Leu Ile Ala Gly Lys Lys Pro Val Gly Glu
            885                 890                 895
Phe Gly Glu Gly Val Asp Ile Val Arg Trp Val Arg Asn Thr Glu Glu
        900                 905                 910
Glu Ile Thr Gln Pro Ser Asp Ala Ala Ile Val Ala Ile Val Asp
    915                 920                 925
Pro Arg Leu Thr Gly Tyr Pro Leu Thr Ser Val Ile His Val Phe Lys
930                 935                 940
Ile Ala Met Met Cys Val Glu Glu Ala Ala Arg Pro Thr Met
945                 950                 955                 960
Arg Glu Val Val His Met Leu Thr Asn Pro Pro Lys Ser Val Ala Asn
            965                 970                 975
Leu Ile Ala Phe
        980

<210> SEQ ID NO 213
<211> LENGTH: 2964
<212> TYPE: DNA
<213> ORGANISM: Brassica napus

<400> SEQUENCE: 213
atggcgatga gacttttgaa gactcacctt ctgtttctcc atcttcacta cgttatctcg      60
attttgcttc tatctttctc accatgcttc gcttccactg acatggacca tctcctcacc     120
ctcaaatcgt ccatggtcgg ccccaacggc acggcctcc acgactgggt tcgctcccct     180
tctccctcag ctcactgttc tttctccggc gtttcctgcg acggcgacgc tcgtgtcatc     240
tccctcaacg tctctttcac tcctctcttc ggaaccatct ccccggagat tgggatgctg     300
gaccgtctcg tgaatctgac gttagctgct aataatttct ccggtatgct cccgttggag     360
atgaagagtc tcacttctct aaaggttctc aacatctcca caacgtgaa cctcaacgga     420
accttccccg gagagattct cactcccatg gtcgacctcg aagtcctcga cgcgtacaac     480
aacaacttca caggcccact accgccggag atccccgggc tcaagaagct gagacacctc     540
tctctcggag gaaacttctt aaccggagaa atcccagaga gttacggaga tatccagagc     600
ttggagtatc ttggcctcaa cggagccgga ctctccggcg aatctccggc gttcttgtct     660
```

```
cgcctcaaga atcttaaaga aatgtacgtc ggctacttca acagctacac cggcggcgta    720
ccgccggagt tcggtgaatt gacaaaccta gaggttctcg acatggcgag ctgtacactc    780
acgggagaga ttccgacgac tctgagtaat ctaaaacatt tgcacacttt gtttctccac    840
atcaacaact taaccggaaa catccctccg gaactctccg gtttaatcag cttaaaatct    900
ctagacctct caataaacca gctaaccgga gagattcctc agagcttcat ctccctctgg    960
aacatcactc tcgtcaacct cttcagaaac aatctccacg ggcccatacc tgagttcatc   1020
ggagacatgc cgaacctcca agtcctccag gtgtgggaga acaacttcac gctagagcta   1080
ccggcgaatc tcggccggaa cgggaatctg aaaaagctcg acgtctctga taaccatctc   1140
accggactca tccccatgga tttgtgcaga ggcgggaagc tggagacgct ggtgctctcc   1200
gacaacttct tcttcggctc gatccctgag aagctaggtc gatgcaaatc gctaaacaag   1260
atcagaatcg tcaagaatct cctcaacggt acggttccgg cgggactatt cactctaccg   1320
ctcgttacca tcatcgagct caccgataac ttcttctccg gggagcttcc ggggagatg    1380 tcaggcgacc ttctcgatca tatctactta tctaacaatt ggtttaccgg tttaatcccc   1440
ccggctatcg gtaattttaa aaatctacag gatttattct tagaccggaa ccggtttagc   1500
gggaatattc cgagagaagt tttcgagtta aagcatctca ctaagatcaa cacgagtgct   1560
aacaacctca ccgcgacat ccctgactcg atctcgcgat gcacttcctt aatctccgtc   1620
gatctcagcc gtaaccgaat cggcggagat atcccgaaag acatccacga cgtgattaac   1680
ttaggaactc tcaatctctc cgggaatcaa ctcaccggct cgatcccgat cggaatcggg   1740
aagatgacga gcttaaccac tctcgatctc tccttcaacg acctctcggg gcgagtccca   1800
ctcggcggcc agttcctagt cttcaacgac acttccttcg ccggaaaccc ttacctctgc   1860
ctccctcgcc acgtctcgtg cctcacgcgt cccggccaaa cctccgatcg catccacacg   1920
gcgctgttct cgccgtcgag gatcgccatc acgataatcg cagcggtcac ggcgctgatc   1980
ctcatcagcg tcgcgattcg tcagatgaac aagaagaagc acgagagatc cctctcctgg   2040
aagctaaccg ccttccagcg gctcgatttc aaggcggaag acgtcctcga gtgcctccaa   2100
gaggagaaca taatcggcaa aggcggagcg gggatcgtct accgcggatc catgccgaac   2160
aacgtagacg tcgcgatcaa acgcctcgtg ggacgcggaa cagggaggag cgatcacgga   2220
ttcacggcgg agattcagac gctagggagg atccgccacc gtcacatcgt gagactcctc   2280
ggatacgtgg cgaacaggga cacgaacctg cttctctacg agtacatgcc taacgggagc   2340
ctcggcgagc ttttgcacgg gtctaaagga ggtcatcttc agtgggagac gaggcacaga   2400
gtagccgttg aagcggcgaa aggactgtgt tatcttcacc atgactgttc gccgttgatc   2460
ttgcatagag acgttaagtc caataacatt ttactggact ctgattttga ggcccatgtt   2520
gctgattttg ggcttgctaa gttcttactg gacggtgctg cttccgagtg tatgtcttcg   2580
atagctggat cctatggata catcgctcca gagtatgctt acactctcaa agtggatgag   2640
aagagtgatg tttatagttt tggagtggtg ttattggagc tgatagctgg aagaaaccg    2700 gttggtgagt ttggggaagg agtggatata gtgaggtggg tgaggaacac ggagggtgag   2760
atacctcagc cgtcggatgc agctactgtt gttgcgatcg tcgaccagag gttgactggt   2820
tacccgttga ctagtgtgat tcacgtgttc aagatacgaa tgatgtgtgt ggaggatgag   2880
gcaacgacaa ggccgacgat gagggaagtt gtgcacatgc tcactaaccc tcccaagtcc   2940
gtgactaact tgatcgcctt ctga                                          2964
```

<210> SEQ ID NO 214
<211> LENGTH: 987
<212> TYPE: PRT
<213> ORGANISM: Brassica napus

<400> SEQUENCE: 214

```
Met Ala Met Arg Leu Leu Lys Thr His Leu Leu Phe Leu His Leu His
1               5                   10                  15

Tyr Val Ile Ser Ile Leu Leu Leu Ser Phe Ser Pro Cys Phe Ala Ser
            20                  25                  30

Thr Asp Met Asp His Leu Leu Thr Leu Lys Ser Ser Met Val Gly Pro
        35                  40                  45

Asn Gly His Gly Leu His Asp Trp Val Arg Ser Pro Ser Pro Ser Ala
    50                  55                  60

His Cys Ser Phe Ser Gly Val Ser Cys Asp Gly Asp Ala Arg Val Ile
65                  70                  75                  80

Ser Leu Asn Val Ser Phe Thr Pro Leu Phe Gly Thr Ile Ser Pro Glu
                85                  90                  95

Ile Gly Met Leu Asp Arg Leu Val Asn Leu Thr Leu Ala Ala Asn Asn
            100                 105                 110

Phe Ser Gly Met Leu Pro Leu Glu Met Lys Ser Leu Thr Ser Leu Lys
        115                 120                 125

Val Leu Asn Ile Ser Asn Asn Val Asn Leu Asn Gly Thr Phe Pro Gly
    130                 135                 140

Glu Ile Leu Thr Pro Met Val Asp Leu Glu Val Leu Asp Ala Tyr Asn
145                 150                 155                 160

Asn Asn Phe Thr Gly Pro Leu Pro Pro Glu Ile Pro Gly Leu Lys Lys
                165                 170                 175

Leu Arg His Leu Ser Leu Gly Gly Asn Phe Leu Thr Gly Glu Ile Pro
            180                 185                 190

Glu Ser Tyr Gly Asp Ile Gln Ser Leu Glu Tyr Leu Gly Leu Asn Gly
        195                 200                 205

Ala Gly Leu Ser Gly Glu Ser Pro Ala Phe Leu Ser Arg Leu Lys Asn
    210                 215                 220

Leu Lys Glu Met Tyr Val Gly Tyr Phe Asn Ser Tyr Thr Gly Gly Val
225                 230                 235                 240

Pro Pro Glu Phe Gly Glu Leu Thr Asn Leu Glu Val Leu Asp Met Ala
                245                 250                 255

Ser Cys Thr Leu Thr Gly Glu Ile Pro Thr Thr Leu Ser Asn Leu Lys
            260                 265                 270

His Leu His Thr Leu Phe Leu His Ile Asn Asn Leu Thr Gly Asn Ile
        275                 280                 285

Pro Pro Glu Leu Ser Gly Leu Ile Ser Leu Lys Ser Leu Asp Leu Ser
    290                 295                 300

Ile Asn Gln Leu Thr Gly Glu Ile Pro Gln Ser Phe Ile Ser Leu Trp
305                 310                 315                 320

Asn Ile Thr Leu Val Asn Leu Phe Arg Asn Asn Leu His Gly Pro Ile
                325                 330                 335

Pro Glu Phe Ile Gly Asp Met Pro Asn Leu Gln Val Leu Gln Val Trp
            340                 345                 350

Glu Asn Asn Phe Thr Leu Glu Leu Pro Ala Asn Leu Gly Arg Asn Gly
        355                 360                 365

Asn Leu Lys Lys Leu Asp Val Ser Asp Asn His Leu Thr Gly Leu Ile
    370                 375                 380

Pro Met Asp Leu Cys Arg Gly Gly Lys Leu Glu Thr Leu Val Leu Ser
```

```
            385                 390                 395                 400

Asp Asn Phe Phe Phe Gly Ser Ile Pro Glu Lys Leu Gly Arg Cys Lys
                405                 410                 415

Ser Leu Asn Lys Ile Arg Ile Val Lys Asn Leu Leu Asn Gly Thr Val
                420                 425                 430

Pro Ala Gly Leu Phe Thr Leu Pro Leu Val Thr Ile Ile Glu Leu Thr
                435                 440                 445

Asp Asn Phe Phe Ser Gly Glu Leu Pro Gly Glu Met Ser Gly Asp Leu
            450                 455                 460

Leu Asp His Ile Tyr Leu Ser Asn Asn Trp Phe Thr Gly Leu Ile Pro
465                 470                 475                 480

Pro Ala Ile Gly Asn Phe Lys Asn Leu Gln Asp Leu Phe Leu Asp Arg
                485                 490                 495

Asn Arg Phe Ser Gly Asn Ile Pro Arg Glu Val Phe Glu Leu Lys His
                500                 505                 510

Leu Thr Lys Ile Asn Thr Ser Ala Asn Asn Leu Thr Gly Asp Ile Pro
            515                 520                 525

Asp Ser Ile Ser Arg Cys Thr Ser Leu Ile Ser Val Asp Leu Ser Arg
            530                 535                 540

Asn Arg Ile Gly Gly Asp Ile Pro Lys Asp Ile His Asp Val Ile Asn
545                 550                 555                 560

Leu Gly Thr Leu Asn Leu Ser Gly Asn Gln Leu Thr Gly Ser Ile Pro
                565                 570                 575

Ile Gly Ile Gly Lys Met Thr Ser Leu Thr Thr Leu Asp Leu Ser Phe
                580                 585                 590

Asn Asp Leu Ser Gly Arg Val Pro Leu Gly Gly Gln Phe Leu Val Phe
                595                 600                 605

Asn Asp Thr Ser Phe Ala Gly Asn Pro Tyr Leu Cys Leu Pro Arg His
            610                 615                 620

Val Ser Cys Leu Thr Arg Pro Gly Gln Thr Ser Asp Arg Ile His Thr
625                 630                 635                 640

Ala Leu Phe Ser Pro Ser Arg Ile Ala Ile Thr Ile Ala Ala Val
                645                 650                 655

Thr Ala Leu Ile Leu Ile Ser Val Ala Ile Arg Gln Met Asn Lys Lys
                660                 665                 670

Lys His Glu Arg Ser Leu Ser Trp Lys Leu Thr Ala Phe Gln Arg Leu
            675                 680                 685

Asp Phe Lys Ala Glu Asp Val Leu Glu Cys Leu Gln Glu Glu Asn Ile
            690                 695                 700

Ile Gly Lys Gly Gly Ala Gly Ile Val Tyr Arg Gly Ser Met Pro Asn
705                 710                 715                 720

Asn Val Asp Val Ala Ile Lys Arg Leu Val Gly Arg Gly Thr Gly Arg
                725                 730                 735

Ser Asp His Gly Phe Thr Ala Glu Ile Gln Thr Leu Gly Arg Ile Arg
                740                 745                 750

His Arg His Ile Val Arg Leu Leu Gly Tyr Val Ala Asn Arg Asp Thr
                755                 760                 765

Asn Leu Leu Leu Tyr Glu Tyr Met Pro Asn Gly Ser Leu Gly Glu Leu
            770                 775                 780

Leu His Gly Ser Lys Gly Gly His Leu Gln Trp Glu Thr Arg His Arg
785                 790                 795                 800

Val Ala Val Glu Ala Ala Lys Gly Leu Cys Tyr Leu His His Asp Cys
                805                 810                 815
```

```
Ser Pro Leu Ile Leu His Arg Asp Val Lys Ser Asn Asn Ile Leu Leu
            820                 825                 830
Asp Ser Asp Phe Glu Ala His Val Ala Asp Phe Gly Leu Ala Lys Phe
        835                 840                 845
Leu Leu Asp Gly Ala Ala Ser Glu Cys Met Ser Ile Ala Gly Ser
    850                 855                 860
Tyr Gly Tyr Ile Ala Pro Glu Tyr Ala Tyr Thr Leu Lys Val Asp Glu
865                 870                 875                 880
Lys Ser Asp Val Tyr Ser Phe Gly Val Val Leu Glu Leu Ile Ala
                885                 890                 895
Gly Lys Lys Pro Val Gly Glu Phe Gly Glu Gly Val Asp Ile Val Arg
                900                 905                 910
Trp Val Arg Asn Thr Glu Gly Glu Ile Pro Gln Pro Ser Asp Ala Ala
            915                 920                 925
Thr Val Ala Ile Val Asp Gln Arg Leu Thr Gly Tyr Pro Leu Thr
    930                 935                 940
Ser Val Ile His Val Phe Lys Ile Ala Met Met Cys Val Glu Asp Glu
945                 950                 955                 960
Ala Thr Thr Arg Pro Thr Met Arg Glu Val Val His Met Leu Thr Asn
                965                 970                 975
Pro Pro Lys Ser Val Thr Asn Leu Ile Ala Phe
            980                 985

<210> SEQ ID NO 215
<211> LENGTH: 2925
<212> TYPE: DNA
<213> ORGANISM: Eucalyptus grandis

<400> SEQUENCE: 215
atggcggcga cggcggcgaa accgccctgc aagcccgctt cctacttctg cttctcctcc    60
tccttctgcc tcctcctctt cgtctcggct tccctcgcgc agagcgacct cgacgtgctc   120
ctgcagctca gggccgccct ggccgcgccc aactcgaccg ccctccacga ctgggtcggc   180
ccctcctcct cctcctcatc ctcctcgtcg ccgccgccct tccgcattg ctccttcacc    240 ggggtcacgt gcgacgccgg ctcccgggtc gtgtctctca acctcactga cgtccgcctc   300
ttcggccgcg tccccgcga aatcggcctc tccgcgacc tcgtcaacct cacgctcacc     360
agctgcaacc tctcggggac cctcccgccg gagctcggca acctgaccga gctcgaagtc   420
ctcgacgtgt acgacaacaa cttcacggcc cagctgccgc cggaggtggt ggggctgaag   480
aagctgaagt ggctcaacct cgccggcaat tacttcttcg gcgagatacc ggaggtttac   540
tcggagatgg agagcctgga gtacctgggc ctgcaggcga accagctgag cggcagagtc   600
ccggcgagcc tcgcgaagct gaagaacctc cagtggctct acctgggcta cttcaacacg   660
tacgatggcg agattccggc ggagttcggg tctatgaaag agctcagacg cctcgacttg   720
gcgagctgcg gcctctccgg cgagattccg gtgagcctga gcgagctaaa gaagttagac   780
tctctgttcc tccagtggaa caacctcatg gcgttatcc ccccgagct ctcgaagatg     840 ttgagcctca tgtccctcga cctctccaac aattacctca ctggagtgat tccggcgacc   900
ttcgccgaac tcaagaacct gactctgctc aacctgttcg cgaaccacct ggaaggccag   960
atccccgagt tcgtgggcga gcttccgaac ctggagaccc tccaggtttg ggcaacaac    1020 ttcacgatga tgttgccagc ggggctaggg aggaacggga ggctgctata cgtcgacgtc   1080
acgcagaacc acttcaccgg cacgatccct cgggaattgt gccggggagg gaggctcaag   1140
actctgatcc tgaccaacaa ctcgttcttt gggcccatcc ctgatgaatt cggggagtgc   1200
```

```
aagtcgctga ccaaagtccg agtcggcaag aactttctcg acgggacgat tcctcggggg   1260
atcttcaacc tgccgcaagc aactataatc gagcttaacg acaatctctt ctccggcgag   1320
ctcccggcgc agatgtccgg cgagaacttg gtcatcctgt cgctctcgaa caaccggatt   1380
tccggtgaga tccctccggc gattggcaac ttcagcggcc tgcgtactct gttactggac   1440
gcgaacaggt tctccggcaa gattcccagc gagcttttct cgccgaggtt cctactgagg   1500
gtgaacatca gcgggaacag catcagcggc aggattcctg gttcggtcac tgggtgcact   1560
tctctggcag ccccttgattt gagcaggaac aatctcgctg gcgagattcc gaacggcttg   1620
tctagcctga aagtgttggc cgtcctcaat ctgtcgagca acagattgac cggtccagtt   1680
ccaaaggaaa ttggcatcat gaccagcctc aatacgctcg atttgtcctt caacgatctc   1740 tccgcgaag tcccccacga aggccagttc ctcgtcttca agaactcctc cttcgccgga   1800
aaccagaaac tctgctcgcc aggccgcttc tcttgcccctt cgcggtcaag tgcctcgcgc   1860
acttcctcga gggttgtgat cacggcaatc tcactcgtga ccgcggcgct gctcatcacc   1920
gtcacggtct accaggtcct gaagaggagg cggcagggct cgagagcctg aagctcact    1980 gccttccaga agctcggctt caaggccgag gacgtgctca agtgcctgga ggaggagaat   2040
atcatcggca aggtggcgc ggggatcgtc taccgcgggt cgatgcccaa cgggacggac    2100
gtcgccatca gcagctggc gggacgggc ggcaacgggc tcagcgacca cggcttctcc    2160
gcggagattc agaccctcgg tcggatccgg caccggaaca tcgtgaggct cctcggatac    2220
ctctccaaca aggacaccaa cctgttgctg tacgagtaca tgcccaatgg gagcttaggg    2280
gagctgttgc atggttcgaa aggcggccac ttgcagtggg agacgcggta tcggatcgcc    2340
gtggaggccg cgaaggggct gtgctacctc caccacgatt gcttgccgct gataattcat    2400
cgagacgtga agtcgaacaa cattctgctg gattcggact tcgaggcgca cgtcgctgat    2460
ttcgggctgg ccaagttctt gcaggacgcc ggcgcatcgg agtgcatgtc gtccgtggcc    2520
ggttcctacg gctacatagc cccagaatac gcctacacgc tgaaagtgga cgagaagagc    2580
gacgtgtaca gcttcggggt cgtgctgctg gagctgatag ccgggaggaa gccggtgggg    2640
gagtttggcg acggcgtgga catcgtgagg tgggtgaaga ccgcgtcgga ccccctcccg    2700
cagccgccgt cggacgcggc cttggtgctg gccgtgatcg accgcaggct gggcgggtac    2760
cccatcgcga gcgtgatcca cctcttcaag atcgcgtgcc ggtgcgtcga ggaggagagt    2820
tccgagaggc ccaccatgag agaagtcgtc cacatgctga caaacccgcc tctgtccgcc    2880
accaccttcg ccgtcggcgc caccccggac ctcatcaaac tgtag                   2925
```

<210> SEQ ID NO 216
<211> LENGTH: 974
<212> TYPE: PRT
<213> ORGANISM: Eucalyptus grandis

<400> SEQUENCE: 216

Met Ala Ala Thr Ala Ala Lys Pro Pro Cys Lys Pro Ala Ser Tyr Phe
1               5                   10                  15

Cys Phe Ser Ser Ser Phe Cys Leu Leu Leu Phe Val Ser Ala Ser Leu
                20                  25                  30

Ala Gln Ser Asp Leu Asp Val Leu Leu Gln Leu Arg Ala Ala Leu Ala
            35                  40                  45

Ala Pro Asn Ser Thr Ala Leu His Asp Trp Val Gly Pro Ser Ser
        50                  55                  60

Ser Ser Ser Ser Ser Ser Pro Pro Pro Phe Pro His Cys Ser Phe Thr

-continued

```
                65                  70                  75                  80
Gly Val Thr Cys Asp Ala Gly Ser Arg Val Ser Leu Asn Leu Thr
                    85                  90                  95
Asp Val Arg Leu Phe Gly Arg Val Pro Arg Glu Ile Gly Leu Leu Arg
                    100                 105                 110
Asp Leu Val Asn Leu Thr Leu Thr Ser Cys Asn Leu Ser Gly Thr Leu
                    115                 120                 125
Pro Pro Glu Leu Gly Asn Leu Thr Glu Leu Val Leu Asp Val Tyr
    130                 135                 140
Asp Asn Asn Phe Thr Ala Gln Leu Pro Pro Glu Val Val Gly Leu Lys
145                 150                 155                 160
Lys Leu Lys Trp Leu Asn Leu Ala Gly Asn Tyr Phe Phe Gly Glu Ile
                    165                 170                 175
Pro Glu Val Tyr Ser Glu Met Glu Ser Leu Glu Tyr Leu Gly Leu Gln
                    180                 185                 190
Ala Asn Gln Leu Ser Gly Arg Val Pro Ala Ser Leu Ala Lys Leu Lys
                    195                 200                 205
Asn Leu Gln Trp Leu Tyr Leu Gly Tyr Phe Asn Thr Tyr Asp Gly Glu
    210                 215                 220
Ile Pro Ala Glu Phe Gly Ser Met Lys Glu Leu Arg Arg Leu Asp Leu
225                 230                 235                 240
Ala Ser Cys Gly Leu Ser Gly Glu Ile Pro Val Ser Leu Ser Glu Leu
                    245                 250                 255
Lys Lys Leu Asp Ser Leu Phe Leu Gln Trp Asn Asn Leu Met Gly Val
                    260                 265                 270
Ile Pro Pro Glu Leu Ser Lys Met Leu Ser Leu Met Ser Leu Asp Leu
                    275                 280                 285
Ser Asn Asn Tyr Leu Thr Gly Val Ile Pro Ala Thr Phe Ala Glu Leu
    290                 295                 300
Lys Asn Leu Thr Leu Leu Asn Leu Phe Ala Asn His Leu Glu Gly Gln
305                 310                 315                 320
Ile Pro Glu Phe Val Gly Glu Leu Pro Asn Leu Glu Thr Leu Gln Val
                    325                 330                 335
Trp Gly Asn Asn Phe Thr Met Met Leu Pro Ala Gly Leu Gly Arg Asn
                    340                 345                 350
Gly Arg Leu Leu Tyr Val Asp Val Thr Gln Asn His Phe Thr Gly Thr
                    355                 360                 365
Ile Pro Arg Glu Leu Cys Arg Gly Gly Arg Leu Lys Thr Leu Ile Leu
                    370                 375                 380
Thr Asn Asn Ser Phe Phe Gly Pro Ile Pro Asp Glu Phe Gly Glu Cys
385                 390                 395                 400
Lys Ser Leu Thr Lys Val Arg Val Gly Lys Asn Phe Leu Asp Gly Thr
                    405                 410                 415
Ile Pro Arg Gly Ile Phe Asn Leu Pro Gln Ala Thr Ile Ile Glu Leu
                    420                 425                 430
Asn Asp Asn Leu Phe Ser Gly Glu Leu Pro Ala Gln Met Ser Gly Glu
                    435                 440                 445
Asn Leu Val Ile Leu Ser Leu Ser Asn Asn Arg Ile Ser Gly Glu Ile
                    450                 455                 460
Pro Pro Ala Ile Gly Asn Phe Ser Gly Leu Arg Thr Leu Leu Leu Asp
465                 470                 475                 480
Ala Asn Arg Phe Ser Gly Lys Ile Pro Ser Glu Leu Phe Ser Pro Arg
                    485                 490                 495
```

-continued

```
Phe Leu Leu Arg Val Asn Ile Ser Gly Asn Ser Ile Ser Gly Arg Ile
            500                 505                 510

Pro Gly Ser Val Thr Gly Cys Thr Ser Leu Ala Ala Leu Asp Leu Ser
            515                 520                 525

Arg Asn Asn Leu Ala Gly Glu Ile Pro Asn Gly Leu Ser Ser Leu Lys
            530                 535                 540

Val Leu Ala Val Leu Asn Leu Ser Ser Asn Arg Leu Thr Gly Pro Val
545                 550                 555                 560

Pro Lys Glu Ile Gly Ile Met Thr Ser Leu Asn Thr Leu Asp Leu Ser
                565                 570                 575

Phe Asn Asp Leu Ser Gly Glu Val Pro His Glu Gly Gln Phe Leu Val
            580                 585                 590

Phe Lys Asn Ser Ser Phe Ala Gly Asn Gln Lys Leu Cys Ser Pro Gly
            595                 600                 605

Arg Phe Ser Cys Pro Ser Arg Ser Ser Ala Ser Arg Thr Ser Ser Arg
            610                 615                 620

Val Val Ile Thr Ala Ile Ser Leu Val Thr Ala Ala Leu Leu Ile Thr
625                 630                 635                 640

Val Thr Val Tyr Gln Val Leu Lys Arg Arg Gln Gly Ser Arg Ala
                645                 650                 655

Trp Lys Leu Thr Ala Phe Gln Lys Leu Gly Phe Lys Ala Glu Asp Val
                660                 665                 670

Leu Lys Cys Leu Glu Glu Asn Ile Ile Gly Lys Gly Gly Ala Gly
            675                 680                 685

Ile Val Tyr Arg Gly Ser Met Pro Asn Gly Thr Asp Val Ala Ile Lys
            690                 695                 700

Gln Leu Ala Gly Arg Gly Gly Asn Gly Leu Ser Asp His Gly Phe Ser
705                 710                 715                 720

Ala Glu Ile Gln Thr Leu Gly Arg Ile Arg His Arg Asn Ile Val Arg
                725                 730                 735

Leu Leu Gly Tyr Leu Ser Asn Lys Asp Thr Asn Leu Leu Leu Tyr Glu
            740                 745                 750

Tyr Met Pro Asn Gly Ser Leu Gly Glu Leu Leu His Gly Ser Lys Gly
            755                 760                 765

Gly His Leu Gln Trp Glu Thr Arg Tyr Arg Ile Ala Val Glu Ala Ala
    770                 775                 780

Lys Gly Leu Cys Tyr Leu His His Asp Cys Leu Pro Leu Ile Ile His
785                 790                 795                 800

Arg Asp Val Lys Ser Asn Asn Ile Leu Leu Asp Ser Asp Phe Glu Ala
                805                 810                 815

His Val Ala Asp Phe Gly Leu Ala Lys Phe Leu Gln Asp Ala Gly Ala
            820                 825                 830

Ser Glu Cys Met Ser Ser Val Ala Gly Ser Tyr Gly Tyr Ile Ala Pro
            835                 840                 845

Glu Tyr Ala Tyr Thr Leu Lys Val Asp Glu Lys Ser Asp Val Tyr Ser
            850                 855                 860

Phe Gly Val Val Leu Leu Glu Leu Ile Ala Gly Arg Lys Pro Val Gly
865                 870                 875                 880

Glu Phe Gly Asp Gly Val Asp Ile Val Arg Trp Val Lys Thr Ala Ser
                885                 890                 895

Asp Pro Leu Pro Gln Pro Ser Asp Ala Ala Leu Val Leu Ala Val
            900                 905                 910

Ile Asp Arg Arg Leu Gly Gly Tyr Pro Ile Ala Ser Val Ile His Leu
            915                 920                 925
```

```
Phe Lys Ile Ala Cys Arg Cys Val Glu Glu Ser Ser Glu Arg Pro
        930                 935                 940

Thr Met Arg Glu Val Val His Met Leu Thr Asn Pro Pro Leu Ser Ala
945                 950                 955                 960

Thr Thr Phe Ala Val Gly Ala Thr Pro Asp Leu Ile Lys Leu
            965                 970

<210> SEQ ID NO 217
<211> LENGTH: 2946
<212> TYPE: DNA
<213> ORGANISM: Glycine max

<400> SEQUENCE: 217
```

| | | | | |
|---|---|---|---|---|
| atgagaagct | gtgtgtgtta | cacgctttta | ttgtttgttt | tcttcatatg | gctacacgtg | 60 |
| gcaacgtgtt | cttcgttcag | tgacatggat | gcgctgctga | agctgaagga | gtccatgaag | 120 |
| ggagacagag | ccaaagacga | cgcgctccat | gactggaagt | tttccacgtc | gctttctgca | 180 |
| cactgtttct | tttcaggtgt | atcttgcgac | caagaacttc | gagttgttgc | tatcaacgtc | 240 |
| tcctttgttc | ctctcttcgg | ccacgttccg | ccggagatcg | gagaattgga | caaacttgaa | 300 |
| aacctcacca | tctcgcagaa | caacctcacc | ggcgaacttc | caaggagct | cgccgccctc | 360 |
| acttccctca | gcaccctcaa | catctctcac | aacgtcttct | ccggctattt | tcccggcaaa | 420 |
| ataattcttc | cgatgaccga | actcgaggtc | ctcgacgtct | acgacaacaa | cttcaccgga | 480 |
| tcgcttccgg | aagagttcgt | gaaactggag | aaattgaaat | acctgaagct | cgacggaaac | 540 |
| tatttctccg | gaagcatacc | ggagagttac | tcggagttta | gagcttgga | gttttaagc | 600 |
| ttaagcacca | atagcttatc | ggggaatatt | ccgaagagtt | tgtctaagtt | gaagacgctg | 660 |
| aggattctca | agctcggata | caacaacgct | tacgaaggcg | gaattccacc | ggagttcggc | 720 |
| accatggaat | ctctgaaata | ccttgacctc | tcaagctgca | acctcagcgg | cgagattcca | 780 |
| ccgagtctag | caaatatgag | aaacctcgac | acgttgttct | tgcaaatgaa | taacctcacc | 840 |
| ggaaccattc | cgtctgagct | ctccgacatg | gtgagcctca | tgtcactgga | tctctccttc | 900 |
| aacggcctca | ccggggagat | accgacgcgc | ttctctcagc | tgaaaaacct | cactctgatg | 960 |
| aacttcttcc | acaacaatct | ccgaggctca | gttccctcct | tcgtcggcga | gcttcctaat | 1020 |
| ctggaaacgc | tgcagctctg | ggagaacaat | ttctcctctg | agctcccgca | gaacctgggg | 1080 |
| caaaacggga | agttcaagtt | cttcgacgtc | acgaagaatc | acttcagcgg | gttgatccct | 1140 |
| cgggatttgt | gcaagagtgg | gaggttacaa | acgttcttga | tcacagataa | cttcttccat | 1200 |
| ggtccaatcc | ctaacgagat | tgctaactgc | aagtctctaa | ccaagatccg | agcctccaat | 1260 |
| aactaccta | acggcgcagt | tccgtcaggg | atttcaagc | taccttccgt | cacgataatc | 1320 |
| gagttggcca | ataaccgttt | taacggagaa | ctgcctcccg | aaatttccgg | cgattcactc | 1380 |
| gggattctca | ctcttttccaa | caacttattc | actgggaaaa | ttcccccagc | gttgaagaac | 1440 |
| ttaagggcac | tgcagactct | gtcacttgac | acgaacgaat | tccttggaga | aatcccgggg | 1500 |
| gaggttttg | acctaccaat | gctgactgtg | gtcaacataa | gcggcaacaa | tctcaccgga | 1560 |
| ccaatcccaa | cgacgtttac | tcgctgcgtt | tcactcgccg | ccgttgatct | tagccggaac | 1620 |
| atgcttgacg | gggagattcc | caaggggatg | aaaaacctaa | cggatttaag | catttcaat | 1680 |
| gtgtcgataa | accaaatctc | agggtcagtc | ccagacgaga | ttcgcttcat | gttgagtctc | 1740 |
| accacgctgg | atctctccta | caacaatttc | atcggcaagg | tccctaccgg | tggtcagttt | 1800 |
| ttggtcttca | gcgacaaatc | ctttgcaggg | aacccgaatc | tctgtagttc | ccactcttgc | 1860 |

```
cctaattcct cgttgaagaa gagacgcggc ccttggagtt tgaaatcgac gagggtgatc   1920
gtcatggtga ttgcactggc cactgcggcg attctcgtgg cggggacgga gtacatgagg   1980
aggaggagga agctgaagct tgcgatgacg tggaagctga cggggttcca gcggctgaac   2040
ttgaaagccg aggaggtggt ggagtgtcta aaagaagaga acataatagg aaaaggagga   2100
gcagggatcg tgtaccgcgg gtccatgaga acggaagcg acgtggcaat aaagcggttg   2160
gttggagcgg ggagtggaag gaacgattac gggttcaaag cggagataga acggtgggg   2220
aagataaggc acaggaacat aatgaggctt ttgggttacg tgtcgaacaa ggagacgaac   2280
ttgcttctgt atgagtacat gccgaatggg agcttagggg agtggctgca tggtgccaag   2340
ggaggtcatt taaagtggga atgaggtac aagattgcgg tggaagctgc aaagggacta   2400
tgctatttgc accatgattg ttcccctctt atcattcaca gggatgtcaa gtctaataat   2460
atattgctcg atgctcactt tgaggctcat gttgctgatt ttggccttgc caagttcttg   2520
tacgaccttg gctcctctca gtccatgtcc tccattgctg gctcctacgg ctacattgct   2580
ccagagtatg cttacacttt gaaagtggac gagaaaagtg atgtgtacag ctttggcgtg   2640
gtgctgttgg aactgataat agggaggaag ccagttggtg agtttggaga cggggtggac   2700
atcgttggat gggtcaacaa aacgagattg gagctctctc agccgtcgga tgcagcagta   2760
gtgttggcag tggtggaccc aaggcttagt gggtatccat tgataagtgt catttacatg   2820
ttcaacatag ctatgatgtg tgttaaagaa gtgggggccca ctaggcctac catgagggaa   2880
gtagttcata tgctctcaaa tcctcctcac tttaccactc acactcacaa cctaattaat   2940
ctctag                                                            2946

<210> SEQ ID NO 218
<211> LENGTH: 981
<212> TYPE: PRT
<213> ORGANISM: Glycine max

<400> SEQUENCE: 218

Met Arg Ser Cys Val Cys Tyr Thr Leu Leu Leu Phe Val Phe Phe Ile
1               5                   10                  15

Trp Leu His Val Ala Thr Cys Ser Ser Phe Ser Asp Met Asp Ala Leu
            20                  25                  30

Leu Lys Leu Lys Glu Ser Met Lys Gly Asp Arg Ala Lys Asp Asp Ala
        35                  40                  45

Leu His Asp Trp Lys Phe Ser Thr Ser Leu Ser Ala His Cys Phe Phe
    50                  55                  60

Ser Gly Val Ser Cys Asp Gln Glu Leu Arg Val Val Ala Ile Asn Val
65                  70                  75                  80

Ser Phe Val Pro Leu Phe Gly His Val Pro Pro Glu Ile Gly Glu Leu
                85                  90                  95

Asp Lys Leu Glu Asn Leu Thr Ile Ser Gln Asn Asn Leu Thr Gly Glu
            100                 105                 110

Leu Pro Lys Glu Leu Ala Ala Leu Thr Ser Leu Lys His Leu Asn Ile
        115                 120                 125

Ser His Asn Val Phe Ser Gly Tyr Phe Pro Gly Lys Ile Ile Leu Pro
    130                 135                 140

Met Thr Glu Leu Glu Val Leu Asp Val Tyr Asp Asn Asn Phe Thr Gly
145                 150                 155                 160

Ser Leu Pro Glu Glu Phe Val Lys Leu Glu Lys Leu Lys Tyr Leu Lys
                165                 170                 175

Leu Asp Gly Asn Tyr Phe Ser Gly Ser Ile Pro Glu Ser Tyr Ser Glu
```

```
                180                 185                 190
Phe Lys Ser Leu Glu Phe Leu Ser Leu Ser Thr Asn Ser Leu Ser Gly
            195                 200                 205
Asn Ile Pro Lys Ser Leu Ser Lys Leu Lys Thr Leu Arg Ile Leu Lys
210                 215                 220
Leu Gly Tyr Asn Asn Ala Tyr Glu Gly Gly Ile Pro Pro Glu Phe Gly
225                 230                 235                 240
Thr Met Glu Ser Leu Lys Tyr Leu Asp Leu Ser Ser Cys Asn Leu Ser
            245                 250                 255
Gly Glu Ile Pro Pro Ser Leu Ala Asn Met Arg Asn Leu Asp Thr Leu
            260                 265                 270
Phe Leu Gln Met Asn Asn Leu Thr Gly Thr Ile Pro Ser Glu Leu Ser
            275                 280                 285
Asp Met Val Ser Leu Met Ser Leu Asp Leu Ser Phe Asn Gly Leu Thr
            290                 295                 300
Gly Glu Ile Pro Thr Arg Phe Ser Gln Leu Lys Asn Leu Thr Leu Met
305                 310                 315                 320
Asn Phe Phe His Asn Asn Leu Arg Gly Ser Val Pro Ser Phe Val Gly
                325                 330                 335
Glu Leu Pro Asn Leu Glu Thr Leu Gln Leu Trp Glu Asn Asn Phe Ser
            340                 345                 350
Ser Glu Leu Pro Gln Asn Leu Gly Gln Asn Gly Lys Phe Lys Phe Phe
            355                 360                 365
Asp Val Thr Lys Asn His Phe Ser Gly Leu Ile Pro Arg Asp Leu Cys
            370                 375                 380
Lys Ser Gly Arg Leu Gln Thr Phe Leu Ile Thr Asp Asn Phe Phe His
385                 390                 395                 400
Gly Pro Ile Pro Asn Glu Ile Ala Asn Cys Lys Ser Leu Thr Lys Ile
                405                 410                 415
Arg Ala Ser Asn Asn Tyr Leu Asn Gly Ala Val Pro Ser Gly Ile Phe
            420                 425                 430
Lys Leu Pro Ser Val Thr Ile Ile Glu Leu Ala Asn Asn Arg Phe Asn
            435                 440                 445
Gly Glu Leu Pro Pro Glu Ile Ser Gly Asp Ser Leu Gly Ile Leu Thr
            450                 455                 460
Leu Ser Asn Asn Leu Phe Thr Gly Lys Ile Pro Ala Leu Lys Asn
465                 470                 475                 480
Leu Arg Ala Leu Gln Thr Leu Ser Leu Asp Thr Asn Glu Phe Leu Gly
            485                 490                 495
Glu Ile Pro Gly Glu Val Phe Asp Leu Pro Met Leu Thr Val Val Asn
            500                 505                 510
Ile Ser Gly Asn Asn Leu Thr Gly Pro Ile Pro Thr Thr Phe Thr Arg
            515                 520                 525
Cys Val Ser Leu Ala Ala Val Asp Leu Ser Arg Asn Met Leu Asp Gly
            530                 535                 540
Glu Ile Pro Lys Gly Met Lys Asn Leu Thr Asp Leu Ser Ile Phe Asn
545                 550                 555                 560
Val Ser Ile Asn Gln Ile Ser Gly Ser Val Pro Asp Glu Ile Arg Phe
                565                 570                 575
Met Leu Ser Leu Thr Thr Leu Asp Leu Ser Tyr Asn Asn Phe Ile Gly
            580                 585                 590
Lys Val Pro Thr Gly Gly Gln Phe Leu Val Phe Ser Asp Lys Ser Phe
            595                 600                 605
```

```
Ala Gly Asn Pro Asn Leu Cys Ser Ser His Ser Cys Pro Asn Ser Ser
        610                 615                 620
Leu Lys Lys Arg Arg Gly Pro Trp Ser Leu Lys Ser Thr Arg Val Ile
625                 630                 635                 640
Val Met Val Ile Ala Leu Ala Thr Ala Ala Ile Leu Val Ala Gly Thr
                    645                 650                 655
Glu Tyr Met Arg Arg Arg Arg Lys Leu Lys Leu Ala Met Thr Trp Lys
                660                 665                 670
Leu Thr Gly Phe Gln Arg Leu Asn Leu Lys Ala Glu Val Val Glu
            675                 680                 685
Cys Leu Lys Glu Glu Asn Ile Ile Gly Lys Gly Ala Gly Ile Val
        690                 695                 700
Tyr Arg Gly Ser Met Arg Asn Gly Ser Asp Val Ala Ile Lys Arg Leu
705                 710                 715                 720
Val Gly Ala Gly Ser Gly Arg Asn Asp Tyr Gly Phe Lys Ala Glu Ile
                    725                 730                 735
Glu Thr Val Gly Lys Ile Arg His Arg Asn Ile Met Arg Leu Leu Gly
                740                 745                 750
Tyr Val Ser Asn Lys Glu Thr Asn Leu Leu Tyr Glu Tyr Met Pro
            755                 760                 765
Asn Gly Ser Leu Gly Glu Trp Leu His Gly Ala Lys Gly Gly His Leu
        770                 775                 780
Lys Trp Glu Met Arg Tyr Lys Ile Ala Val Glu Ala Ala Lys Gly Leu
785                 790                 795                 800
Cys Tyr Leu His His Asp Cys Ser Pro Leu Ile Ile His Arg Asp Val
                    805                 810                 815
Lys Ser Asn Asn Ile Leu Leu Asp Ala His Phe Glu Ala His Val Ala
                820                 825                 830
Asp Phe Gly Leu Ala Lys Phe Leu Tyr Asp Leu Gly Ser Ser Gln Ser
            835                 840                 845
Met Ser Ser Ile Ala Gly Ser Tyr Gly Tyr Ile Ala Pro Glu Tyr Ala
        850                 855                 860
Tyr Thr Leu Lys Val Asp Glu Lys Ser Asp Val Tyr Ser Phe Gly Val
865                 870                 875                 880
Val Leu Leu Glu Leu Ile Ile Gly Arg Lys Pro Val Gly Glu Phe Gly
                    885                 890                 895
Asp Gly Val Asp Ile Val Gly Trp Val Asn Lys Thr Arg Leu Glu Leu
                900                 905                 910
Ser Gln Pro Ser Asp Ala Ala Val Leu Ala Val Val Asp Pro Arg
            915                 920                 925
Leu Ser Gly Tyr Pro Leu Ile Ser Val Ile Tyr Met Phe Asn Ile Ala
        930                 935                 940
Met Met Cys Val Lys Glu Val Gly Pro Thr Arg Pro Thr Met Arg Glu
945                 950                 955                 960
Val Val His Met Leu Ser Asn Pro Pro His Phe Thr Thr His Thr His
                    965                 970                 975
Asn Leu Ile Asn Leu
            980
```

<210> SEQ ID NO 219
<211> LENGTH: 2964
<212> TYPE: DNA
<213> ORGANISM: Glycine max

<400> SEQUENCE: 219

```
atgagaagct gtgtgtgcta cacgctatta ttgtttattt tcttcatatg gctgcgcgtg      60
gcaacgtgct cttcgttcac tgacatggaa tcgcttctga agctgaagga ctccatgaaa     120
ggagataaag ccaaagacga cgctctccat gactggaagt ttttcccctc gctttctgca     180
cactgtttct tttcaggcgt aaaatgcgac cgagaacttc gagtcgttgc tatcaacgtc     240
tcgtttgttc ctctcttcgg tcaccttccg ccggagatcg gacaattgga caaactcgag     300
aacctcaccg tctcgcagaa caacctcacc ggcgtacttc caaggagct cgccgccctc      360 acttccctca agcacctcaa catctctcac aacgtcttct ccggccattt ccccggccaa     420
attatccttc cgatgacgaa actggaggtc ctcgacgtct acgacaacaa cttcaccgga     480
ccgcttcccg tagagttggt gaaactggag aaattaaaat acctgaagct cgacggaaac     540
tatttctccg gcagcatacc ggagagttac tcggagttta agagcttgga gttttaagc      600 ttaagcacca atagcttatc ggggaagatt cccaagagtt gtcgaagtt gaagacgctg      660 aggtacctaa aactcggata caacaacgct tacgaaggtg aattccacc ggagtttggc      720 agcatgaaat ctctgagata ccttgacctc tctagctgca acctcagcgg cgagattcca     780
ccgagccttg caaatctgac aaaccttgac acgttgttcc tgcaaattaa caacctcacc     840
ggaaccattc cgtcggagct ctccgctatg gtgagcctca tgtcacttga tctctccatc     900
aacgacctca ccggtgagat accgatgagc ttctcacagc ttagaaacct cactctcatg     960
aacttcttcc aaaacaatct tcgcggctca gttccgtcct tcgtcggcga gcttccgaat    1020
ctggaaacgc tgcagctctg ggataacaac ttctccttcg tgctacctcc gaaccttggg    1080
caaaacggca agttaaagtt cttcgacgtc atcaagaatc acttcaccgg gttgatccct    1140
cgagatttgt gtaagagtgg gaggttacaa acgatcatga tcacagataa cttcttccgc    1200
ggtccaatcc ctaacgagat tggtaactgc aagtctctca ccaagatccg agcctccaat    1260 aactaccta acggcgtggt tccgtcaggg attttcaaac taccttctgt cacgataatc     1320
gagctggcca ataaccgttt taacggcgaa ctgcctcctg agatttccgg cgaatccctg    1380
gggattctca ctctttccaa caacttattc agtgggaaaa ttcccccagc gttgaagaac    1440
ttgagggcac tgcagactct ctcacttgac gcaaacgagt tcgttggaga ataccgggga    1500 gaggttttg acctaccgat gctgactgtg tcaacataa gcggcaacaa tctaaccgga      1560
ccaatcccaa cgacgttgac tcgctgcgtt tcactcaccg ccgtgaccct cagccggaac    1620
atgcttgaag gaagattcc gaagggaatc aaaaacctca cggacttgag cattttcaat     1680
gtgtcgataa accaaatttc agggccagtc cctgaggaga ttcgcttcat gttgagtctc    1740
accacattgg atctatccaa caacaatttc atcggcaagg tcccaaccgg gggtcagttc    1800
gcggtcttca gcgagaaatc ctttgcaggg aaccccaacc tctgtacctc ccactcttgc    1860
ccgaattcct cgttgtaccc tgacgacgcc ttgaagaaga ggcgcggccc ttggagtttg    1920
aaatccacga gggtgatagt catcgtgatt gcactgggca cagccgcgct gctggtggcg    1980
gtgacggtgt acatgatgag gaggaggaag atgaaccttg cgaagacgtg aagctgacg     2040 gcgttccagc ggctgaactt caaagccgag acgtggtgg agtgtctgaa ggaggagaac    2100
ataataggaa aaggaggggc aggatcgtg taccgcgggt ccatgccaaa cggaacagac    2160
gtggcgataa agcggttggt tggggcgggg agtggaagga acgattacgg attcaaagcg    2220
gagatagaaa cgctggggaa gataaggcac aggaacataa tgaggctttt aggttacgtg    2280
tcgaacaagg agacgaactt gctgctgtat gagtacatgc caaatgggag cttagggga a    2340 tggctgcatg gtgccaaagg agggcacttg aagtgggaaa tgaggtacaa gattgcggtg    2400
```

-continued

```
gaagctgcta agggactgtg ctatttgcac catgattgtt ccctctttat cattcacagg    2460
gatgtcaagt ctaataatat attgctggat ggggacttgg aggcccatgt tgctgatttt    2520
ggccttgcca agttcttgta cgaccctggc gcctctcagt ccatgtcctc cattgctggc    2580
tcctacggct acattgctcc agagtatgca tacactttga aagtggacga gaaaagtgat    2640
gtgtacagct ttggcgttgt gctgctggag ctgataatag ggaggaagcc agtgggagag    2700
tttggagacg gggtggacat cgttggatgg gtcaacaaaa cgagattgga gctcgctcag    2760
ccgtcggatg cagcgttggt gttggcagtg gtggacccaa ggttgagtgg gtatccattg    2820
acaagtgtca tttacatgtt caacatagct atgatgtgtg ttaaagaaat ggggcccgct    2880
aggcctacca tgagggaagt cgttcatatg ctctcagagc ctcctcactc tgctactcac    2940
actcacaacc taattaatct ctag                                           2964
```

<210> SEQ ID NO 220
<211> LENGTH: 987
<212> TYPE: PRT
<213> ORGANISM: Glycine max

<400> SEQUENCE: 220

```
Met Arg Ser Cys Val Cys Tyr Thr Leu Leu Phe Ile Phe Phe Ile
1               5                   10                  15

Trp Leu Arg Val Ala Thr Cys Ser Ser Phe Thr Asp Met Glu Ser Leu
        20                  25                  30

Leu Lys Leu Lys Asp Ser Met Lys Gly Asp Lys Ala Lys Asp Asp Ala
            35                  40                  45

Leu His Asp Trp Lys Phe Phe Pro Ser Leu Ser Ala His Cys Phe Phe
        50                  55                  60

Ser Gly Val Lys Cys Asp Arg Glu Leu Arg Val Val Ala Ile Asn Val
65                  70                  75                  80

Ser Phe Val Pro Leu Phe Gly His Leu Pro Pro Glu Ile Gly Gln Leu
                85                  90                  95

Asp Lys Leu Glu Asn Leu Thr Val Ser Gln Asn Asn Leu Thr Gly Val
            100                 105                 110

Leu Pro Lys Glu Leu Ala Ala Leu Thr Ser Leu Lys His Leu Asn Ile
        115                 120                 125

Ser His Asn Val Phe Ser Gly His Phe Pro Gly Gln Ile Ile Leu Pro
    130                 135                 140

Met Thr Lys Leu Glu Val Leu Asp Val Tyr Asp Asn Asn Phe Thr Gly
145                 150                 155                 160

Pro Leu Pro Val Glu Leu Val Lys Leu Glu Lys Leu Lys Tyr Leu Lys
                165                 170                 175

Leu Asp Gly Asn Tyr Phe Ser Gly Ser Ile Pro Glu Ser Tyr Ser Glu
            180                 185                 190

Phe Lys Ser Leu Glu Phe Leu Ser Leu Ser Thr Asn Ser Leu Ser Gly
        195                 200                 205

Lys Ile Pro Lys Ser Leu Ser Lys Leu Lys Thr Leu Arg Tyr Leu Lys
    210                 215                 220

Leu Gly Tyr Asn Asn Ala Tyr Glu Gly Gly Ile Pro Pro Glu Phe Gly
225                 230                 235                 240

Ser Met Lys Ser Leu Arg Tyr Leu Asp Leu Ser Cys Asn Leu Ser
                245                 250                 255

Gly Glu Ile Pro Pro Ser Leu Ala Asn Leu Thr Asn Leu Asp Thr Leu
            260                 265                 270

Phe Leu Gln Ile Asn Asn Leu Thr Gly Thr Ile Pro Ser Glu Leu Ser
```

```
                    275                 280                 285
Ala Met Val Ser Leu Met Ser Leu Asp Leu Ser Ile Asn Asp Leu Thr
290                 295                 300

Gly Glu Ile Pro Met Ser Phe Ser Gln Leu Arg Asn Leu Thr Leu Met
305                 310                 315                 320

Asn Phe Phe Gln Asn Asn Leu Arg Gly Ser Val Pro Ser Phe Val Gly
                    325                 330                 335

Glu Leu Pro Asn Leu Glu Thr Leu Gln Leu Trp Asp Asn Asn Phe Ser
                340                 345                 350

Phe Val Leu Pro Pro Asn Leu Gly Gln Asn Gly Lys Leu Lys Phe Phe
                355                 360                 365

Asp Val Ile Lys Asn His Phe Thr Gly Leu Ile Pro Arg Asp Leu Cys
        370                 375                 380

Lys Ser Gly Arg Leu Gln Thr Ile Met Ile Thr Asp Asn Phe Phe Arg
385                 390                 395                 400

Gly Pro Ile Pro Asn Glu Ile Gly Asn Cys Lys Ser Leu Thr Lys Ile
                    405                 410                 415

Arg Ala Ser Asn Asn Tyr Leu Asn Gly Val Val Pro Ser Gly Ile Phe
                420                 425                 430

Lys Leu Pro Ser Val Thr Ile Ile Glu Leu Ala Asn Asn Arg Phe Asn
                435                 440                 445

Gly Glu Leu Pro Pro Glu Ile Ser Gly Glu Ser Leu Gly Ile Leu Thr
450                 455                 460

Leu Ser Asn Asn Leu Phe Ser Gly Lys Ile Pro Pro Ala Leu Lys Asn
465                 470                 475                 480

Leu Arg Ala Leu Gln Thr Leu Ser Leu Asp Ala Asn Glu Phe Val Gly
                    485                 490                 495

Glu Ile Pro Gly Glu Val Phe Asp Leu Pro Met Leu Thr Val Val Asn
                500                 505                 510

Ile Ser Gly Asn Asn Leu Thr Gly Pro Ile Pro Thr Thr Leu Thr Arg
                515                 520                 525

Cys Val Ser Leu Thr Ala Val Asp Leu Ser Arg Asn Met Leu Glu Gly
530                 535                 540

Lys Ile Pro Lys Gly Ile Lys Asn Leu Thr Asp Leu Ser Ile Phe Asn
545                 550                 555                 560

Val Ser Ile Asn Gln Ile Ser Gly Pro Val Pro Glu Glu Ile Arg Phe
                    565                 570                 575

Met Leu Ser Leu Thr Thr Leu Asp Leu Ser Asn Asn Asn Phe Ile Gly
                580                 585                 590

Lys Val Pro Thr Gly Gly Gln Phe Ala Val Phe Ser Glu Lys Ser Phe
                595                 600                 605

Ala Gly Asn Pro Asn Leu Cys Thr Ser His Ser Cys Pro Asn Ser Ser
                610                 615                 620

Leu Tyr Pro Asp Asp Ala Leu Lys Lys Arg Arg Gly Pro Trp Ser Leu
625                 630                 635                 640

Lys Ser Thr Arg Val Ile Val Ile Val Ile Ala Leu Gly Thr Ala Ala
                    645                 650                 655

Leu Leu Val Ala Val Thr Val Tyr Met Met Arg Arg Arg Lys Met Asn
                660                 665                 670

Leu Ala Lys Thr Trp Lys Leu Thr Ala Phe Gln Arg Leu Asn Phe Lys
                675                 680                 685

Ala Glu Asp Val Val Glu Cys Leu Lys Glu Glu Asn Ile Ile Gly Lys
690                 695                 700
```

```
Gly Gly Ala Gly Ile Val Tyr Arg Gly Ser Met Pro Asn Gly Thr Asp
705                 710                 715                 720
Val Ala Ile Lys Arg Leu Val Gly Ala Gly Ser Gly Arg Asn Asp Tyr
            725                 730                 735
Gly Phe Lys Ala Glu Ile Glu Thr Leu Gly Lys Ile Arg His Arg Asn
        740                 745                 750
Ile Met Arg Leu Leu Gly Tyr Val Ser Asn Lys Glu Thr Asn Leu Leu
    755                 760                 765
Leu Tyr Glu Tyr Met Pro Asn Gly Ser Leu Gly Glu Trp Leu His Gly
770                 775                 780
Ala Lys Gly Gly His Leu Lys Trp Glu Met Arg Tyr Lys Ile Ala Val
785                 790                 795                 800
Glu Ala Ala Lys Gly Leu Cys Tyr Leu His His Asp Cys Ser Pro Leu
            805                 810                 815
Ile Ile His Arg Asp Val Lys Ser Asn Asn Ile Leu Leu Asp Gly Asp
        820                 825                 830
Leu Glu Ala His Val Ala Asp Phe Gly Leu Ala Lys Phe Leu Tyr Asp
    835                 840                 845
Pro Gly Ala Ser Gln Ser Met Ser Ser Ile Ala Gly Ser Tyr Gly Tyr
850                 855                 860
Ile Ala Pro Glu Tyr Ala Tyr Thr Leu Lys Val Asp Glu Lys Ser Asp
865                 870                 875                 880
Val Tyr Ser Phe Gly Val Val Leu Leu Glu Leu Ile Ile Gly Arg Lys
            885                 890                 895
Pro Val Gly Glu Phe Gly Asp Gly Val Asp Ile Val Gly Trp Val Asn
        900                 905                 910
Lys Thr Arg Leu Glu Leu Ala Gln Pro Ser Asp Ala Ala Leu Val Leu
    915                 920                 925
Ala Val Val Asp Pro Arg Leu Ser Gly Tyr Pro Leu Thr Ser Val Ile
930                 935                 940
Tyr Met Phe Asn Ile Ala Met Met Cys Val Lys Glu Met Gly Pro Ala
945                 950                 955                 960
Arg Pro Thr Met Arg Glu Val Val His Met Leu Ser Glu Pro Pro His
            965                 970                 975
Ser Ala Thr His Thr His Asn Leu Ile Asn Leu
        980                 985

<210> SEQ ID NO 221
<211> LENGTH: 2961
<212> TYPE: DNA
<213> ORGANISM: Lotus japonica

<400> SEQUENCE: 221
atgagaatca gagtgtctta cttgttagtg ctatgtttta ccttaatttg gttcagatgg      60
acagtggtgt actcttcatt cagtgatctc gatgcactgc taaagctcaa agaatccatg     120
aagggagcca agccaaaaca ccacgcactc gaagattgga agttttccac ctcactctca     180
gcacactgtt cgttttccgg cgtaacgtgc gaccagaact tgcgagtggt tgctctcaac     240
gtcacgctgg ttccgctttt cggccacctt ccgccggaga tagggttgtt ggagaagtta     300
gagaatctca ccatctccat gaacaacctc actgaccagc ttccctccga ccttgcaagc     360
ctcacctccc tcaaggtcct caacatctcc acaacctct tctccggcca attccctggt     420
aacatcaccg ttggcatgac ggagctcgag gcccttgatg cctacgacaa cagcttctcc     480
ggtcctctcc cggaggaaat cgtcaagctc gagaaactca gtacctcca cctcgccggg     540
```

-continued

```
aactatttct ccggtacaat accggagagc tactcggagt ttcagagcct tgagtttctc    600
ggcttgaacg caaacagctt aaccgggaga gtcccggaga gcttggcgaa gttgaagacg    660
ttgaaggaac tgcacctcgg ttactcgaac gcttacgaag gtggaatccc gccggcgttc    720
ggttccatgg agaatctccg cctgctagaa atggctaact gcaacctcac cggcgagatt    780
ccaccgagcc tggggaatct aaccaaactc cactccttat tcgtgcagat gaacaacctc    840
accgaaccat tccgccgga gctatcttcc atgatgagcc tcatgtcact ggacctctcc     900
atcaacgacc tcaccggcga gatcccggag agcttctcaa aactgaagaa tctcactcta    960
atgaacttct ccaaaacaa gttccgcggc tctctcccct ccttcatcgg cgaccttcca   1020
aatctcgaaa cgcttcaggt ttgggagaac aatttctcct tcgtgctgcc gcacaatctc   1080
ggcggaaacg gaagattctt atacttcgac gtcaccaaaa accacctcac cgggttgatt   1140
ccgccggatc tatgcaaaag cgggaggttg aaaacgttca tcatcactga taacttcttc   1200
cgtggcccaa ttcccaaggg aatcggcgag tgtaggtcac tcacgaagat tcgcgtggct   1260
aacaacttcc ttgacggtcc agttccacca ggggttttcc aactgccttc cgttacgata   1320
acggaattga gcaataaccg cctcaacggc gaactgcctt ccgtgatttc aggcgaatct   1380
ctcgggacgc tcacgctttc caacaacctc ttcaccggaa aaatccccgc cgcgatgaaa   1440
aacctcagag cgttgcagag cttatccctc gacgccaatg agttcatcgg agaaattccg   1500
ggggggagttt ttgaaatccc aatgctcacc aaagtcaaca tcagcggcaa caacctcaca   1560
ggtccgatcc caacgacgat cactcaccgt gcttctctga cggcggtaga cctcagccgg   1620
aacaacctcg ccggcgaggt tccgaagggg atgaagaatt tgatggactt aagcattctg   1680
aatctctcac gcaacgagat ttctggaccg gttcctgatg agattcgatt catgactagc   1740
ctcacgacgc tggatctctc gagtaacaat ttcaccggaa cagtccccac cggcggccag   1800
tttctggtat tcaactacga caagacgttc gccggaaacc cgaacctctg tttccctcac   1860
agagcatcct gtccttctgt cctctacgac tcgttaagga aaacccgcgc caaaacggcg   1920
cgggtgaggg cgattgtgat tggaattgca ctcgccacgg cggtgttgct ggtggcggtg   1980
acggtgcacg tggtcagaaa gcggaggctg caccgagcgc aggcctggaa gctcaccgcg   2040
ttccagaggc tggagatcaa ggcggaggat gtagtcgagt gtttaaagga agagaatata   2100
attgggaaag gaggagcagg catcgtgtac agaggttcca tgccgaacgg aaccgacgtg   2160
gcgatcaagc ggttggtagg gcagggaagt gggaggaacg attacggttt cagggcggag   2220
attgagacgt tggggaaaat ccggcaccgg aatataatga ggcttctggg gtacgtttcg   2280
aacaaggata cgaacttgtt gctgtatgag tacatgccga atgggagctt aggggagtgg   2340
ctgcacggtg cgaaggggtgg gcacttgcgg tgggagatga ggtataagat tgcggtggag   2400
gcggcgaggg gactctgcta tatgcaccat gattgctctc ctcttattat tcacagggat   2460
gttaagtcca acaacatttt gcttgatgct gattttgagg ctcatgttgc tgattttgga   2520
cttgctaagt ttttgtatga ccctggtgct tctcagtcca tgtcctccat tgctggctcc   2580
tacggttaca ttgctccaga gtatgcttac acgctgaaag tggacgagaa gagtgacgtg   2640
tacagctttg gcgttgtgct gttggaactg atcataggga gaaagccagt gggtgagttt   2700
ggagatggcg tggacatcgt tggatgggtc aacaaaacca tgtcagagct ctctcagccg   2760
tcggatactg cattagtgtt agcagtggtg gaccctcgcc tcagtggata ccccttgaca   2820
agtgtcatcc acatgttcaa catagctatg atgtgtgtga aggaaatggg ccctgctagg   2880
cccaccatga gggaagttgt tcatatgctc actaatcctc ctcagtctaa tacctccact   2940
```
caagacctaa ttaatctcta g                                      2961

<210> SEQ ID NO 222
<211> LENGTH: 986
<212> TYPE: PRT
<213> ORGANISM: Lotus japonica

<400> SEQUENCE: 222

Met Arg Ile Arg Val Ser Tyr Leu Leu Val Leu Cys Phe Thr Leu Ile
1               5                   10                  15

Trp Phe Arg Trp Thr Val Val Tyr Ser Ser Phe Ser Asp Leu Asp Ala
            20                  25                  30

Leu Leu Lys Leu Lys Glu Ser Met Lys Gly Ala Lys Ala Lys His His
        35                  40                  45

Ala Leu Glu Asp Trp Lys Phe Ser Thr Ser Leu Ser Ala His Cys Ser
    50                  55                  60

Phe Ser Gly Val Thr Cys Asp Gln Asn Leu Arg Val Val Ala Leu Asn
65                  70                  75                  80

Val Thr Leu Val Pro Leu Phe Gly His Leu Pro Pro Glu Ile Gly Leu
                85                  90                  95

Leu Glu Lys Leu Glu Asn Leu Thr Ile Ser Met Asn Asn Leu Thr Asp
            100                 105                 110

Gln Leu Pro Ser Asp Leu Ala Ser Leu Thr Ser Leu Lys Val Leu Asn
        115                 120                 125

Ile Ser His Asn Leu Phe Ser Gly Gln Phe Pro Gly Asn Ile Thr Val
    130                 135                 140

Gly Met Thr Glu Leu Glu Ala Leu Asp Ala Tyr Asp Asn Ser Phe Ser
145                 150                 155                 160

Gly Pro Leu Pro Glu Glu Ile Val Lys Leu Lys Leu Lys Tyr Leu
                165                 170                 175

His Leu Ala Gly Asn Tyr Phe Ser Gly Thr Ile Pro Glu Ser Tyr Ser
            180                 185                 190

Glu Phe Gln Ser Leu Glu Phe Leu Gly Leu Asn Ala Asn Ser Leu Thr
        195                 200                 205

Gly Arg Val Pro Glu Ser Leu Ala Lys Leu Lys Thr Leu Lys Glu Leu
    210                 215                 220

His Leu Gly Tyr Ser Asn Ala Tyr Glu Gly Gly Ile Pro Pro Ala Phe
225                 230                 235                 240

Gly Ser Met Glu Asn Leu Arg Leu Leu Glu Met Ala Asn Cys Asn Leu
                245                 250                 255

Thr Gly Glu Ile Pro Pro Ser Leu Gly Asn Leu Thr Lys Leu His Ser
            260                 265                 270

Leu Phe Val Gln Met Asn Asn Leu Thr Gly Thr Ile Pro Pro Glu Leu
        275                 280                 285

Ser Ser Met Met Ser Leu Met Ser Leu Asp Leu Ser Ile Asn Asp Leu
    290                 295                 300

Thr Gly Glu Ile Pro Glu Ser Phe Ser Lys Leu Lys Asn Leu Thr Leu
305                 310                 315                 320

Met Asn Phe Phe Gln Asn Lys Phe Arg Gly Ser Leu Pro Ser Phe Ile
                325                 330                 335

Gly Asp Leu Pro Asn Leu Glu Thr Leu Gln Val Trp Glu Asn Asn Phe
            340                 345                 350

Ser Phe Val Leu Pro His Asn Leu Gly Gly Asn Gly Arg Phe Leu Tyr
        355                 360                 365

Phe Asp Val Thr Lys Asn His Leu Thr Gly Leu Ile Pro Pro Asp Leu

```
            370                 375                 380
Cys Lys Ser Gly Arg Leu Lys Thr Phe Ile Ile Thr Asp Asn Phe Phe
385                 390                 395                 400

Arg Gly Pro Ile Pro Lys Gly Ile Gly Glu Cys Arg Ser Leu Thr Lys
                405                 410                 415

Ile Arg Val Ala Asn Asn Phe Leu Asp Gly Pro Val Pro Pro Gly Val
                420                 425                 430

Phe Gln Leu Pro Ser Val Thr Ile Thr Glu Leu Ser Asn Asn Arg Leu
                435                 440                 445

Asn Gly Glu Leu Pro Ser Val Ile Ser Gly Ser Leu Gly Thr Leu
450                 455                 460

Thr Leu Ser Asn Asn Leu Phe Thr Gly Lys Ile Pro Ala Ala Met Lys
465                 470                 475                 480

Asn Leu Arg Ala Leu Gln Ser Leu Ser Leu Asp Ala Asn Glu Phe Ile
                485                 490                 495

Gly Glu Ile Pro Gly Gly Val Phe Glu Ile Pro Met Leu Thr Lys Val
                500                 505                 510

Asn Ile Ser Gly Asn Asn Leu Thr Gly Pro Ile Pro Thr Thr Ile Thr
                515                 520                 525

His Arg Ala Ser Leu Thr Ala Val Asp Leu Ser Arg Asn Asn Leu Ala
                530                 535                 540

Gly Glu Val Pro Lys Gly Met Lys Asn Leu Met Asp Leu Ser Ile Leu
545                 550                 555                 560

Asn Leu Ser Arg Asn Glu Ile Ser Gly Pro Val Pro Asp Glu Ile Arg
                565                 570                 575

Phe Met Thr Ser Leu Thr Thr Leu Asp Leu Ser Ser Asn Asn Phe Thr
                580                 585                 590

Gly Thr Val Pro Thr Gly Gly Gln Phe Leu Val Phe Asn Tyr Asp Lys
                595                 600                 605

Thr Phe Ala Gly Asn Pro Asn Leu Cys Phe Pro His Arg Ala Ser Cys
                610                 615                 620

Pro Ser Val Leu Tyr Asp Ser Leu Arg Lys Thr Arg Ala Lys Thr Ala
625                 630                 635                 640

Arg Val Arg Ala Ile Val Ile Gly Ile Ala Leu Ala Thr Ala Val Leu
                645                 650                 655

Leu Val Ala Val Thr Val His Val Val Arg Lys Arg Leu His Arg
                660                 665                 670

Ala Gln Ala Trp Lys Leu Thr Ala Phe Gln Arg Leu Glu Ile Lys Ala
                675                 680                 685

Glu Asp Val Val Glu Cys Leu Lys Glu Glu Asn Ile Ile Gly Lys Gly
                690                 695                 700

Gly Ala Gly Ile Val Tyr Arg Gly Ser Met Pro Asn Gly Thr Asp Val
705                 710                 715                 720

Ala Ile Lys Arg Leu Val Gly Gln Gly Ser Gly Arg Asn Asp Tyr Gly
                725                 730                 735

Phe Arg Ala Glu Ile Glu Thr Leu Gly Lys Ile Arg His Arg Asn Ile
                740                 745                 750

Met Arg Leu Leu Gly Tyr Val Ser Asn Lys Asp Thr Asn Leu Leu Leu
                755                 760                 765

Tyr Glu Tyr Met Pro Asn Gly Ser Leu Gly Glu Trp Leu His Gly Ala
                770                 775                 780

Lys Gly Gly His Leu Arg Trp Glu Met Arg Tyr Lys Ile Ala Val Glu
785                 790                 795                 800
```

| | | | | | | | | | | | |
|---|---|---|---|---|---|---|---|---|---|---|---|
|Ala|Ala|Arg|Gly|Leu|Cys|Tyr|Met|His|His|Asp|Cys|Ser|Pro|Leu|Ile|
| | | | |805| | | | |810| | | | |815| |

Ala Ala Arg Gly Leu Cys Tyr Met His His Asp Cys Ser Pro Leu Ile
                805                 810                 815

Ile His Arg Asp Val Lys Ser Asn Asn Ile Leu Leu Asp Ala Asp Phe
            820                 825                 830

Glu Ala His Val Ala Asp Phe Gly Leu Ala Lys Phe Leu Tyr Asp Pro
        835                 840                 845

Gly Ala Ser Gln Ser Met Ser Ser Ile Ala Gly Ser Tyr Gly Tyr Ile
    850                 855                 860

Ala Pro Glu Tyr Ala Tyr Thr Leu Lys Val Asp Glu Lys Ser Asp Val
865                 870                 875                 880

Tyr Ser Phe Gly Val Val Leu Leu Glu Leu Ile Ile Gly Arg Lys Pro
                885                 890                 895

Val Gly Glu Phe Gly Asp Gly Val Asp Ile Val Gly Trp Val Asn Lys
            900                 905                 910

Thr Met Ser Glu Leu Ser Gln Pro Ser Asp Thr Ala Leu Val Leu Ala
        915                 920                 925

Val Val Asp Pro Arg Leu Ser Gly Tyr Pro Leu Thr Ser Val Ile His
    930                 935                 940

Met Phe Asn Ile Ala Met Met Cys Val Lys Glu Met Gly Pro Ala Arg
945                 950                 955                 960

Pro Thr Met Arg Glu Val Val His Met Leu Thr Asn Pro Pro Gln Ser
                965                 970                 975

Asn Thr Ser Thr Gln Asp Leu Ile Asn Leu
            980                 985

<210> SEQ ID NO 223
<211> LENGTH: 2925
<212> TYPE: DNA
<213> ORGANISM: Medicago truncatula

<400> SEQUENCE: 223

```
atgaaaaaca tcacatgtta tttgctacta ttgtgcatgt tatttacaac gtgttattca      60
ttaaataatg atcttgatgc gttgctaaag ctaaaaaaat caatgaaagg agagaaagcc     120
aaagatgatg cactcaaaga ctggaaattt tcaacttctg cttcagctca ctgttcattt     180
tccggtgtaa atgcgacga agatcaacgt gtgattgctt tgaacgtgac gcaagttcca     240
ctcttcggac acctttccaa ggagatcgga gagttgaaca tgctcgagag ccttacaatc     300
actatggaca atctcaccgg cgagcttcca actgagctat ccaaacttac ttctcttaga     360
atcctcaaca tctctcacaa cctcttctcc ggtaacttcc ccggcaacat cacttttgga     420
atgaagaaac ttgaggctct agatgcttat gacaataatt tcgaaggtcc tcttccagag     480
gaaatcgtta gcctgatgaa actcaagtac ttaagttttg ctggaaactt tttctccggt     540
acaataccgg agagttactc ggagtttcag aagttggaga ttttaaggct gaactataac     600
agtttaacag ggaagattcc taagagtttg tcgaagttaa agatgctaaa ggaactccaa     660
ttaggttatg agaatgctta ctccggtgga attccaccgg agttaggttc aatcaaatct     720
ctccgatatc ttgaaatttc taacgctaac ctcaccggag aaattccacc gagtcttgga     780
aatttagaaa acctcgactc cttgtttttg caaatgaaca acctcaccgg aacaattcca     840
cccgaactct cttcaatgcg gagtctcatg tcgttggatc tctccatcaa cggactctca     900
ggggagattc cagaaacctt ctcaaagctg aaaaatctca ctctcatcaa tttcttccag     960
aacaagcttc gcggttcaat tccagcgttc atcggcgatc ttcctaacct cgaaacgctt    1020
caggtttggg aaaacaattt ctctttttgta ttgccgcaga atctcggttc aaacggaaag    1080
```

```
ttcatatact tgacgttac gaagaatcac ctcaccggat tgatcccacc ggagttatgc    1140
aaatcaaaga agttgaaaac gtttatcgtt actgacaact tcttccgcgg tccaatacct    1200
aacggaattg gcccgtgtaa gtcacttgaa aaaatcagag tggctaataa ctacttggac    1260
ggcccggtcc caccggggat ttttcagttg ccttctgtac agataataga gcttggaaat    1320
aaccgtttta acggccaact accaacggag atttctggca attctctcgg gaatctcgct    1380
ctttctaaca atttatttac cgggaggatt ccggcgtcca tgaagaatct ccgatcactg    1440
cagacgctgt tactcgatgc caatcagttt ctcgagaaa ttccggcaga ggtctttgct    1500
ttaccggtgt tgactagaat caacataagt ggcaataatc tcactggtgg aattccaaag    1560
acggttactc aatgtagttc actgactgca gttgacttca gccgaaacat gcttaccggt    1620
gaggttccta aagggatgaa gaatctgaag gttctaagca ttttttaatgt ttcgcataat    1680 agcatatctg gaaaatccc tgatgagatt agattcatga cgagtctaac gacgctggat    1740
ttatcttaca acaattttac cggaattgtc cccacaggtg gtcagttttt ggtcttcaac    1800
gaccggtcat ttgccggaaa tcctagccta tgtttccccc accaaacaac atgttcttca    1860
ttgctctatc gttcgagaaa aagccatgca aaggagaaag ctgtcgtcat agcaatcgtc    1920
ttcgccacag cggtgttaat ggtaattgta acactgcaca tgatgaggaa gaggaagcgt    1980
cacatggcaa aagcatggaa gctaacagcg tttcagaagt tggaattcag agcagaggaa    2040
gtagtggagt gtctgaaaga agaacata ataggaaaag gaggagctgg gattgtctac    2100
agagggtcca tggcaaacgg aacagacgtt gcgataaagc gtttagttgg acaaggaagt    2160
ggtagaaatg attatggatt caaagctgag atagagacat tgggaaggat tagacacaga    2220
aacataatga ggcttttggg atatgtttca aacaaggata caaatttgtt gttgtatgag    2280
tacatgccta atggtagttt aggtgagtgg cttcatggtg caaaaggttg tcatttgagt    2340
tgggaaatga ggtacaaaat tgctgtggaa gctgctaagg actttgcta tttgcaccat    2400 gattgttcac ctcttatcat tcataggat gttaagtcta ataatatat gcttgatgct    2460 gatttttgagg ctcatgttgc tgattttgga cttgctaagt tcttgtatga tccaggtgct    2520
tctcaatcca tgtcctcaat tgctggctcc tacggctaca ttgctccaga atatgcatac    2580
actctcaaag tggatgaaaa aagtgatgtg tatagtttcg gagtggtgct attggagctg    2640
ataataggaa ggaagccagt tggtgaattt ggagatggag tagacatcgt tggatggatc    2700
aataaaactg aattagaact ttatcagcca tcagataaag cattagtgtc agcagtggtg    2760
gacccacgac tcaatggata ccctttgact agtgttatct acatgttcaa catagctatg    2820
atgtgtgtta agaaatggg acctgcaagg cctaccatga gggaagttgt tcatatgctc    2880
actaatccac ctcactctac aagtcacaac ttgattaatc tctag                   2925
```

<210> SEQ ID NO 224
<211> LENGTH: 974
<212> TYPE: PRT
<213> ORGANISM: Medicago truncatula

<400> SEQUENCE: 224

Met Lys Asn Ile Thr Cys Tyr Leu Leu Leu Cys Met Leu Phe Thr
1               5                   10                  15

Thr Cys Tyr Ser Leu Asn Asn Asp Leu Asp Ala Leu Leu Lys Leu Lys
                20                  25                  30

Lys Ser Met Lys Gly Glu Lys Ala Lys Asp Asp Ala Leu Lys Asp Trp
            35                  40                  45

Lys Phe Ser Thr Ser Ala Ser Ala His Cys Ser Phe Ser Gly Val Lys

```
              50                  55                  60
Cys Asp Glu Asp Gln Arg Val Ile Ala Leu Asn Val Thr Gln Val Pro
 65                  70                  75                  80

Leu Phe Gly His Leu Ser Lys Glu Ile Gly Glu Leu Asn Met Leu Glu
                 85                  90                  95

Ser Leu Thr Ile Thr Met Asp Asn Leu Thr Gly Glu Leu Pro Thr Glu
                100                 105                 110

Leu Ser Lys Leu Thr Ser Leu Arg Ile Leu Asn Ile Ser His Asn Leu
                115                 120                 125

Phe Ser Gly Asn Phe Pro Gly Asn Ile Thr Phe Gly Met Lys Lys Leu
                130                 135                 140

Glu Ala Leu Asp Ala Tyr Asp Asn Asn Phe Glu Gly Pro Leu Pro Glu
145                 150                 155                 160

Glu Ile Val Ser Leu Met Lys Leu Lys Tyr Leu Ser Phe Ala Gly Asn
                165                 170                 175

Phe Phe Ser Gly Thr Ile Pro Glu Ser Tyr Ser Glu Phe Gln Lys Leu
                180                 185                 190

Glu Ile Leu Arg Leu Asn Tyr Asn Ser Leu Thr Gly Lys Ile Pro Lys
                195                 200                 205

Ser Leu Ser Lys Leu Lys Met Leu Lys Glu Leu Gln Leu Gly Tyr Glu
210                 215                 220

Asn Ala Tyr Ser Gly Gly Ile Pro Pro Glu Leu Gly Ser Ile Lys Ser
225                 230                 235                 240

Leu Arg Tyr Leu Glu Ile Ser Asn Ala Asn Leu Thr Gly Glu Ile Pro
                245                 250                 255

Pro Ser Leu Gly Asn Leu Glu Asn Leu Asp Ser Leu Phe Leu Gln Met
                260                 265                 270

Asn Asn Leu Thr Gly Thr Ile Pro Pro Glu Leu Ser Ser Met Arg Ser
                275                 280                 285

Leu Met Ser Leu Asp Leu Ser Ile Asn Gly Leu Ser Gly Glu Ile Pro
                290                 295                 300

Glu Thr Phe Ser Lys Leu Lys Asn Leu Thr Leu Ile Asn Phe Phe Gln
305                 310                 315                 320

Asn Lys Leu Arg Gly Ser Ile Pro Ala Phe Ile Gly Asp Leu Pro Asn
                325                 330                 335

Leu Glu Thr Leu Gln Val Trp Glu Asn Asn Phe Ser Phe Val Leu Pro
                340                 345                 350

Gln Asn Leu Gly Ser Asn Gly Lys Phe Ile Tyr Phe Asp Val Thr Lys
                355                 360                 365

Asn His Leu Thr Gly Leu Ile Pro Pro Glu Leu Cys Lys Ser Lys Lys
                370                 375                 380

Leu Lys Thr Phe Ile Val Thr Asp Asn Phe Phe Arg Gly Pro Ile Pro
385                 390                 395                 400

Asn Gly Ile Gly Pro Cys Lys Ser Leu Glu Lys Ile Arg Val Ala Asn
                405                 410                 415

Asn Tyr Leu Asp Gly Pro Val Pro Pro Gly Ile Phe Gln Leu Pro Ser
                420                 425                 430

Val Gln Ile Ile Glu Leu Gly Asn Asn Arg Phe Asn Gly Gln Leu Pro
                435                 440                 445

Thr Glu Ile Ser Gly Asn Ser Leu Gly Asn Leu Ala Leu Ser Asn Asn
                450                 455                 460

Leu Phe Thr Gly Arg Ile Pro Ala Ser Met Lys Asn Leu Arg Ser Leu
465                 470                 475                 480
```

-continued

```
Gln Thr Leu Leu Leu Asp Ala Asn Gln Phe Leu Gly Glu Ile Pro Ala
            485                 490                 495
Glu Val Phe Ala Leu Pro Val Leu Thr Arg Ile Asn Ile Ser Gly Asn
            500                 505                 510
Asn Leu Thr Gly Gly Ile Pro Lys Thr Val Thr Gln Cys Ser Ser Leu
            515                 520                 525
Thr Ala Val Asp Phe Ser Arg Asn Met Leu Thr Gly Glu Val Pro Lys
        530                 535                 540
Gly Met Lys Asn Leu Lys Val Leu Ser Ile Phe Asn Val Ser His Asn
545                 550                 555                 560
Ser Ile Ser Gly Lys Ile Pro Asp Glu Ile Arg Phe Met Thr Ser Leu
                565                 570                 575
Thr Thr Leu Asp Leu Ser Tyr Asn Asn Phe Thr Gly Ile Val Pro Thr
            580                 585                 590
Gly Gly Gln Phe Leu Val Phe Asn Asp Arg Ser Phe Ala Gly Asn Pro
            595                 600                 605
Ser Leu Cys Phe Pro His Gln Thr Thr Cys Ser Ser Leu Leu Tyr Arg
            610                 615                 620
Ser Arg Lys Ser His Ala Lys Glu Lys Ala Val Val Ile Ala Ile Val
625                 630                 635                 640
Phe Ala Thr Ala Val Leu Met Val Ile Val Thr Leu His Met Met Arg
                645                 650                 655
Lys Arg Lys Arg His Met Ala Lys Ala Trp Lys Leu Thr Ala Phe Gln
            660                 665                 670
Lys Leu Glu Phe Arg Ala Glu Val Val Glu Cys Leu Lys Glu Glu
            675                 680                 685
Asn Ile Ile Gly Lys Gly Gly Ala Gly Ile Val Tyr Arg Gly Ser Met
690                 695                 700
Ala Asn Gly Thr Asp Val Ala Ile Lys Arg Leu Val Gly Gln Gly Ser
705                 710                 715                 720
Gly Arg Asn Asp Tyr Gly Phe Lys Ala Glu Ile Glu Thr Leu Gly Arg
                725                 730                 735
Ile Arg His Arg Asn Ile Met Arg Leu Leu Gly Tyr Val Ser Asn Lys
            740                 745                 750
Asp Thr Asn Leu Leu Leu Tyr Glu Tyr Met Pro Asn Gly Ser Leu Gly
            755                 760                 765
Glu Trp Leu His Gly Ala Lys Gly Cys His Leu Ser Trp Glu Met Arg
            770                 775                 780
Tyr Lys Ile Ala Val Glu Ala Ala Lys Gly Leu Cys Tyr Leu His His
785                 790                 795                 800
Asp Cys Ser Pro Leu Ile Ile His Arg Asp Val Lys Ser Asn Asn Ile
                805                 810                 815
Leu Leu Asp Ala Asp Phe Glu Ala His Val Ala Asp Phe Gly Leu Ala
            820                 825                 830
Lys Phe Leu Tyr Asp Pro Gly Ala Ser Gln Ser Met Ser Ser Ile Ala
            835                 840                 845
Gly Ser Tyr Gly Tyr Ile Ala Pro Glu Tyr Ala Tyr Thr Leu Lys Val
            850                 855                 860
Asp Glu Lys Ser Asp Val Tyr Ser Phe Gly Val Val Leu Leu Glu Leu
865                 870                 875                 880
Ile Ile Gly Arg Lys Pro Val Gly Glu Phe Gly Asp Gly Val Asp Ile
                885                 890                 895
Val Gly Trp Ile Asn Lys Thr Glu Leu Glu Leu Tyr Gln Pro Ser Asp
            900                 905                 910
```

```
Lys Ala Leu Val Ser Ala Val Val Asp Pro Arg Leu Asn Gly Tyr Pro
        915                 920                 925

Leu Thr Ser Val Ile Tyr Met Phe Asn Ile Ala Met Met Cys Val Lys
        930                 935                 940

Glu Met Gly Pro Ala Arg Pro Thr Met Arg Glu Val Val His Met Leu
945                 950                 955                 960

Thr Asn Pro Pro His Ser Thr Ser His Asn Leu Ile Asn Leu
                965                 970

<210> SEQ ID NO 225
<211> LENGTH: 2985
<212> TYPE: DNA
<213> ORGANISM: Oryza sativa

<400> SEQUENCE: 225
```

| | | | | | |
|---|---|---|---|---|---|
| atgcctccta | ctctcctcct | cctcctcctc | ctcctcccac | cctccctcgc | ctcccccgac | 60 |
| cgcgacatct | acgcgctcgc | caagctcaag | gcggcgctcg | tcccatcccc | ctccgccacc | 120 |
| gccccaccgc | cgctcgccga | ctgggacccg | gccgcgacct | ccccgcgca | ctgcaccttc | 180 |
| tccggcgtca | cctgcgacgg | ccgctcccgc | gtcgtcgcca | tcaacctcac | cgccctcccg | 240 |
| ctccactccg | gctacctccc | gcccgagatc | gccctccttg | actccctcgc | caacctcacc | 300 |
| atcgccgcct | gctgcctccc | cggccacgtc | ccctcgagc | tccccaccct | ccctctctc | 360 |
| cgccacctca | acctctccaa | caacaacctt | tccggccact | tccccgtccc | cgactccggc | 420 |
| ggtggcgcct | cccctactt | cccctcgctc | gagctcatcg | acgcttacaa | caacaacctc | 480 |
| tcagggttgc | ttcctccctt | ctccgcttca | cacgctcgcc | tccgctacct | ccacctcggc | 540 |
| ggcaactact | tcaccggcgc | aatcccggac | agctatggcg | acctcgccgc | gctcgagtac | 600 |
| cttggactca | acggcaacac | gctctccggc | catgtccccg | tctccctctc | ccgcctcacc | 660 |
| cgcctccgcg | agatgtacat | cggatactac | aaccagtacg | acggcggcgt | cccgccggag | 720 |
| ttcggcgacc | tcggcgcgct | cctccgcctc | gacatgagca | gctgcaacct | caccggcccc | 780 |
| gtcccgccgg | agctcggccg | actccagcgc | ctcgacacgc | tcttcctgca | gtggaaccgc | 840 |
| ctctccggcg | agataccgcc | gcagctcggc | gatctcagca | gcctcgcgtc | gctcgacctc | 900 |
| tccgtcaacg | acctcgccgg | cgagatccct | cccagcctcg | ccaacctctc | caacctcaag | 960 |
| ctcctcaacc | tcttccggaa | ccacctccgc | ggcagcatac | cggacttcgt | cgccggcttc | 1020 |
| gcgcagctcg | aggtgctgca | gctgtgggac | aacaacctca | ccggcaacat | ccccgccggg | 1080 |
| ctcgggaaga | acggccgcct | caagacgctc | gacctggcca | ccaaccacct | caccggcccc | 1140 |
| atcccggcgg | acctctgcgc | cggcggcgg | ctggagatgc | tcgtgctcat | ggagaacggc | 1200 |
| ctgttcggcc | ccatcccgga | ctcgctcggc | gactgcaaga | cgctcacgcg | cgtccgcctc | 1260 |
| gccaagaact | tcttgaccgg | cccggttccc | gccgggctct | tcaacctccc | gcaggccaac | 1320 |
| atggtggagc | tcaccgacaa | cctgctcacc | ggcgagctcc | cggacgtgat | cggcggcgac | 1380 |
| aagatcggca | tgctgctgct | ggggaacaat | gggatcggtg | ccgcatccc | tccggccatc | 1440 |
| ggcaacctcc | cggcgctgca | gacgctgtcg | ctggagtcca | caacttctc | cggagcgctg | 1500 |
| ccaccggaga | tcggcaatct | caagaacctg | tccaggctca | acgtcagcgg | caacgcgctc | 1560 |
| accggcgcca | ttccagacga | gctcatccgc | tgcgcctccc | tcgccgccgt | cgacctcagc | 1620 |
| cgtaacggct | tctccggcga | gataccggag | agcatcacgt | cgctcaagat | actgtgcacg | 1680 |
| ctgaacgtgt | ccaggaacag | gctcaccggc | gagctcccgc | cggagatgtc | caacatgacg | 1740 |
| agcctcacga | cgctcgacgt | gtcgtacaac | agcctctcgg | gccccgtgcc | gatgcagggg | 1800 |

```
cagttcttgg tgttcaacga gagctcgttc gtcggcaacc cggggctgtg cggcggcccc    1860
gtggccgacg cgtgccctcc gtccatggcc ggcggcggcg gcggcgcggg gtcccagctg    1920
cggctgcggt gggactcgaa gaagatgctg gtggcgctgg tggcggcgtt cgcggcggtg    1980
gcggtggcgt tcctgggcgc gaggaagggg tgctcggcgt ggcggtcggc ggcgcggcgg    2040
cggtcggggg cgtggaagat gacggcgttc cagaagctgg agttctcggc ggaggacgtg    2100
gtggagtgcg tgaaggagga caacatcatc gggaagggcg gcgcggggat cgtgtaccac    2160
ggcgtgacgc gcggggcgga gctggcgatc aagcggttgg tggggcgcgg cggcggcgag    2220
cacgaccggg ggttctcggc ggaggtgacg acgctgggga ggatcaggca ccggaacatc    2280
gtgaggctgc tggggttcgt gtcgaacagg gagacgaacc tgctgctgta cgagtacatg    2340
ccgaatgggt cgctggggga gatgctccat ggcgggaagg gggggcacct cgggtgggag    2400
gcgagggcgc gggtggcggc ggaggcggcg tgcggcctct gctacctcca ccatgactgc    2460
gccccgagga tcatccaccg cgacgtcaag tccaacaaca tcctcctcga ctccgccttc    2520
gaggcgcacg tcgccgactt cggcctcgcc aagttcctcg gcggcgccac ctccgagtgc    2580
atgtccgcca ttgctggctc ctacggctac atcgcgccag agtacgcata cacgctgcga    2640
gtggacgaga gagcgacgt gtatagcttc ggtgtggtgc tattggagct catcaccgga    2700
cgccgccccg tgggcgggtt cggtgacggc gtggacatcg tgcactgggt ccgcaaggtg    2760
accgccgagc tgccggacaa ctccgacacg gcggccgtcc tcgccgtggc cgaccgccgc    2820
ctgacgccgg agccggtggc gctgatggtg aacctgtaca aggtggccat ggcgtgcgtg    2880
gaggaggcga gcacggcccg gcccaccatg cgcgaggtcg tccacatgct ctccaaccca    2940
aactcggccc agcccaatag tggtgacctc ctcgtcacct tctga                   2985
```

<210> SEQ ID NO 226
<211> LENGTH: 994
<212> TYPE: PRT
<213> ORGANISM: Oryza sativa

<400> SEQUENCE: 226

```
Met Pro Pro Thr Leu Leu Leu Leu Leu Leu Leu Pro Pro Ser Leu
1               5                   10                  15

Ala Ser Pro Asp Arg Asp Ile Tyr Ala Leu Ala Lys Leu Lys Ala Ala
            20                  25                  30

Leu Val Pro Ser Pro Ser Ala Thr Ala Pro Pro Leu Ala Asp Trp
        35                  40                  45

Asp Pro Ala Ala Thr Ser Pro Ala His Cys Thr Phe Ser Gly Val Thr
    50                  55                  60

Cys Asp Gly Arg Ser Arg Val Val Ala Ile Asn Leu Thr Ala Leu Pro
65                  70                  75                  80

Leu His Ser Gly Tyr Leu Pro Pro Glu Ile Ala Leu Leu Asp Ser Leu
                85                  90                  95

Ala Asn Leu Thr Ile Ala Ala Cys Cys Leu Pro Gly His Val Pro Leu
            100                 105                 110

Glu Leu Pro Thr Leu Pro Ser Leu Arg His Leu Asn Leu Ser Asn Asn
        115                 120                 125

Asn Leu Ser Gly His Phe Pro Val Pro Asp Ser Gly Gly Ala Ser
    130                 135                 140

Pro Tyr Phe Pro Ser Leu Glu Leu Ile Asp Ala Tyr Asn Asn Asn Leu
145                 150                 155                 160

Ser Gly Leu Leu Pro Pro Phe Ser Ala Ser His Ala Arg Leu Arg Tyr
```

```
                        165                 170                 175
Leu His Leu Gly Gly Asn Tyr Phe Thr Gly Ala Ile Pro Asp Ser Tyr
            180                 185                 190

Gly Asp Leu Ala Ala Leu Glu Tyr Leu Gly Leu Asn Gly Asn Thr Leu
            195                 200                 205

Ser Gly His Val Pro Val Ser Leu Ser Arg Leu Thr Arg Leu Arg Glu
            210                 215                 220

Met Tyr Ile Gly Tyr Tyr Asn Gln Tyr Asp Gly Gly Val Pro Pro Glu
225                 230                 235                 240

Phe Gly Asp Leu Gly Ala Leu Leu Arg Leu Asp Met Ser Ser Cys Asn
                245                 250                 255

Leu Thr Gly Pro Val Pro Pro Glu Leu Gly Arg Leu Gln Arg Leu Asp
                260                 265                 270

Thr Leu Phe Leu Gln Trp Asn Arg Leu Ser Gly Glu Ile Pro Pro Gln
                275                 280                 285

Leu Gly Asp Leu Ser Ser Leu Ala Ser Leu Asp Leu Ser Val Asn Asp
                290                 295                 300

Leu Ala Gly Glu Ile Pro Pro Ser Leu Ala Asn Leu Ser Asn Leu Lys
305                 310                 315                 320

Leu Leu Asn Leu Phe Arg Asn His Leu Arg Gly Ser Ile Pro Asp Phe
                325                 330                 335

Val Ala Gly Phe Ala Gln Leu Glu Val Leu Gln Leu Trp Asp Asn Asn
                340                 345                 350

Leu Thr Gly Asn Ile Pro Ala Gly Leu Gly Lys Asn Gly Arg Leu Lys
                355                 360                 365

Thr Leu Asp Leu Ala Thr Asn His Leu Thr Gly Pro Ile Pro Ala Asp
                370                 375                 380

Leu Cys Ala Gly Arg Arg Leu Glu Met Leu Val Leu Met Glu Asn Gly
385                 390                 395                 400

Leu Phe Gly Pro Ile Pro Asp Ser Leu Gly Asp Cys Lys Thr Leu Thr
                405                 410                 415

Arg Val Arg Leu Ala Lys Asn Phe Leu Thr Gly Pro Val Pro Ala Gly
                420                 425                 430

Leu Phe Asn Leu Pro Gln Ala Asn Met Val Glu Leu Thr Asp Asn Leu
                435                 440                 445

Leu Thr Gly Glu Leu Pro Asp Val Ile Gly Gly Asp Lys Ile Gly Met
                450                 455                 460

Leu Leu Leu Gly Asn Asn Gly Ile Gly Gly Arg Ile Pro Pro Ala Ile
465                 470                 475                 480

Gly Asn Leu Pro Ala Leu Gln Thr Leu Ser Leu Glu Ser Asn Asn Phe
                485                 490                 495

Ser Gly Ala Leu Pro Pro Glu Ile Gly Asn Leu Lys Asn Leu Ser Arg
                500                 505                 510

Leu Asn Val Ser Gly Asn Ala Leu Thr Gly Ala Ile Pro Asp Glu Leu
                515                 520                 525

Ile Arg Cys Ala Ser Leu Ala Ala Val Asp Leu Ser Arg Asn Gly Phe
                530                 535                 540

Ser Gly Glu Ile Pro Glu Ser Ile Thr Ser Leu Lys Ile Leu Cys Thr
545                 550                 555                 560

Leu Asn Val Ser Arg Asn Arg Leu Thr Gly Glu Leu Pro Pro Glu Met
                565                 570                 575

Ser Asn Met Thr Ser Leu Thr Thr Leu Asp Val Ser Tyr Asn Ser Leu
                580                 585                 590
```

```
Ser Gly Pro Val Pro Met Gln Gly Gln Phe Leu Val Phe Asn Glu Ser
    595                 600                 605
Ser Phe Val Gly Asn Pro Gly Leu Cys Gly Gly Pro Val Ala Asp Ala
610                 615                 620
Cys Pro Pro Ser Met Ala Gly Gly Gly Gly Ala Gly Ser Gln Leu
625                 630                 635                 640
Arg Leu Arg Trp Asp Ser Lys Lys Met Leu Val Ala Leu Val Ala Ala
            645                 650                 655
Phe Ala Ala Val Ala Val Ala Phe Leu Gly Ala Arg Lys Gly Cys Ser
                660                 665                 670
Ala Trp Arg Ser Ala Ala Arg Arg Arg Ser Gly Ala Trp Lys Met Thr
                    675                 680                 685
Ala Phe Gln Lys Leu Glu Phe Ser Ala Glu Asp Val Val Glu Cys Val
690                 695                 700
Lys Glu Asp Asn Ile Ile Gly Lys Gly Gly Ala Gly Ile Val Tyr His
705                 710                 715                 720
Gly Val Thr Arg Gly Ala Glu Leu Ala Ile Lys Arg Leu Val Gly Arg
                725                 730                 735
Gly Gly Gly Glu His Asp Arg Gly Phe Ser Ala Glu Val Thr Thr Leu
            740                 745                 750
Gly Arg Ile Arg His Arg Asn Ile Val Arg Leu Leu Gly Phe Val Ser
        755                 760                 765
Asn Arg Glu Thr Asn Leu Leu Leu Tyr Glu Tyr Met Pro Asn Gly Ser
770                 775                 780
Leu Gly Glu Met Leu His Gly Gly Lys Gly Gly His Leu Gly Trp Glu
785                 790                 795                 800
Ala Arg Ala Arg Val Ala Ala Glu Ala Cys Gly Leu Cys Tyr Leu
                805                 810                 815
His His Asp Cys Ala Pro Arg Ile Ile His Arg Asp Val Lys Ser Asn
                820                 825                 830
Asn Ile Leu Leu Asp Ser Ala Phe Glu Ala His Val Ala Asp Phe Gly
        835                 840                 845
Leu Ala Lys Phe Leu Gly Gly Ala Thr Ser Glu Cys Met Ser Ala Ile
    850                 855                 860
Ala Gly Ser Tyr Gly Tyr Ile Ala Pro Glu Tyr Ala Tyr Thr Leu Arg
865                 870                 875                 880
Val Asp Glu Lys Ser Asp Val Tyr Ser Phe Gly Val Val Leu Leu Glu
            885                 890                 895
Leu Ile Thr Gly Arg Arg Pro Val Gly Gly Phe Gly Asp Gly Val Asp
                900                 905                 910
Ile Val His Trp Val Arg Lys Val Thr Ala Glu Leu Pro Asp Asn Ser
        915                 920                 925
Asp Thr Ala Ala Val Leu Ala Val Ala Asp Arg Arg Leu Thr Pro Glu
930                 935                 940
Pro Val Ala Leu Met Val Asn Leu Tyr Lys Val Ala Met Ala Cys Val
945                 950                 955                 960
Glu Glu Ala Ser Thr Ala Arg Pro Thr Met Arg Glu Val Val His Met
                965                 970                 975
Leu Ser Asn Pro Asn Ser Ala Gln Pro Asn Ser Gly Asp Leu Leu Val
            980                 985                 990
Thr Phe

<210> SEQ ID NO 227
<211> LENGTH: 2931
```

<212> TYPE: DNA
<213> ORGANISM: Pisum sativa

<400> SEQUENCE: 227

```
atgaaaagta tcacgtgtta tttgctggta ttcttctgcg tgttatttac accatgtttt      60
tcaataaccg atctcgatgc gttgctaaag cttaaagaat caatgaaagg agagaaatca     120
aaacatcccg attcactcgg agactggaag ttttccgctt ctggttcagc tcactgctca     180
ttttccggtg taacgtgcga tcaagataac cgagtgataa ctctgaacgt gacgcaagtt     240
ccactcttcg gaagaatttc taaggagatt ggagtgttgg ataagcttga gagactcatc     300
atcaccatgg ataatctcac tggcgagctt ccgtttgaga tatccaatct tacctctctt     360
aaaatcctta acatctctca caacaccttc tctggtaact tccccggcaa catcactctc     420
cgtatgacga aacttgaggt tctagatgct tatgacaata gcttcactgg tcatcttcct     480
gaggaaatcg tcagcctcaa ggaactcacg atcttatgtc tggccggaaa ctatttcacc     540
ggtacaatac ccgagagtta ctcggaattt cagaagttgg agattttaag cataaacgca     600
aacagtttat cggggaagat tccgaagagc ttatccaaat taaagacgct gaaggaactc     660
cgtttaggtt acaacaacgc ttacgatggc ggagttccac cggagtttgg ttcattgaaa     720
tctctccgat atcttgaggt gtctaactgt aacctcaccg agaaattcc accgagtttt     780
ggaaatttag aaaacctaga cagcttgttc ttgcaaatga caacctcac cggaataatt     840
ccaccggaac tctcttccat gaagagtctc atgtcgttgg atctctccaa caacgctctc     900
tcaggagaga ttccagagag cttctcaaat ctcaaaagcc tcactctctt gaatttcttc     960
cagaacaagt ttcgcggttc tattccggca ttcataggcg atcttcctaa cctggaaacg    1020
cttcaggttt gggaaaacaa tttctctttt gtattgccac aaaatctcgg ttcaaacgga    1080
aagttcattt tcttcgacgt tacgaagaat cacctcaccg gattgattcc accggatttg    1140
tgcaaatcga agaaattgca aacgtttata gttacggata acttcttcca cggtccaatc    1200
cctaaaggaa tcggcgcgtg taagtcactt ctcaaaatca gagttgctaa taactactta    1260
gacgggccgg tcccacaagg gattttttcaa atgccttctg taacgataat agagcttgga    1320
aataaccgtt ttaacggcca actaccttct gaagtttccg gcgttaatct cgggattctc    1380
actatctcta acaatttatt caccgggagg attcccgctt caatgaagaa tctcatatca    1440
cttcagactc tgtggcttga cgcaaatcag ttcgtcggag aaattccaaa ggaagtcttt    1500
gacttaccag tgttaacgaa gttcaacata agtggtaaca acctcaccgg tgtaatccca    1560
acgacggttt ctcagtgtag atcgttgaca gccgttgact tcagccggaa catgattacc    1620
ggcgaggttc ccaggggaat gaagaatctg aaggttctca gcattttaa cctttcacat    1680
aacaacatat cgggtctaat ccccgacgag attcgattca tgacgagtct caccacgctg    1740
gatctatcct acaacaattt caccggaata gtccccaccg gcggtcagtt tttggttttc    1800
aacgacaggt cgttttcgg aaaccctaac ctctgtttcc cacaccaatc ctcatgctct    1860
tcctataccct ttccctcgag taaaagccac gcgaaggtga aggccattat taccgcaatt    1920
gctctcgcca cagcagtgtt actggtaata gcgacgatgc acatgatgag gaagagaaag    1980
cttcatatgg cgaaagcatg gaagttaaca gcatttcaga gactagactt caaagcagag    2040
gaagttgtgg agtgtttgaa agaagagaac ataataggaa aaggaggagc cgggatcgtg    2100
tacagagggt ccatgcccaa cggaacagac gtagcgataa agcgtttagt tggacaagga    2160
agtgggagaa acgattacgg tttcaaagca gagatagaaa cattgggtag aatcagacac    2220
agaaacataa tgaggctatt gggttacgtt tctaataagg acacaaattt gttgctgtat    2280
```

-continued

```
gagtacatgc cgaatggtag tttaggggaa tggcttcatg gtgcaaaagg ctgtcatttg    2340
agttgggaaa tgaggtataa aattgcagtg gaagctggta aaggactttg ctatttgcac    2400
catgattgtt cacctcttat tattcatagg gatgttaagt ccaacaatat attgctagat    2460
gctgattttg aagcccatgt tgctgatttt ggacttgcaa agttttata tgacccaggt     2520 gcttctcagt ccatgtcctc tattgctggc tcctacggct acattgctcc agagtatgct    2580
tatacgttga aagtggatga gaaaagcgat gtgtatagct ttggagtggt gctattggag    2640
ctgatcatag gaaggaaacc agtgggtgag tttggagatg gagtggacat cgttggatgg    2700
atcaataaaa ctgaattaga gctttatcag ccgtcagata aagcattggt gtcggcggtg    2760
gtggacccgc ggctcactgg atacccaatg gcaagtgtta tctacatgtt caacatagct    2820
atgatgtgtg ttaaagaaat gggacccgca aggcctacca tgaggaagt agttcatatg     2880 ctcactaatc cacctcagtc taccactcat aacaaccta ttaatctcta g               2931
```

<210> SEQ ID NO 228
<211> LENGTH: 976
<212> TYPE: PRT
<213> ORGANISM: Pisum sativa

<400> SEQUENCE: 228

```
Met Lys Ser Ile Thr Cys Tyr Leu Leu Val Phe Phe Cys Val Leu Phe
 1               5                  10                  15

Thr Pro Cys Phe Ser Ile Thr Asp Leu Asp Ala Leu Leu Lys Leu Lys
            20                  25                  30

Glu Ser Met Lys Gly Glu Lys Ser Lys His Pro Asp Ser Leu Gly Asp
        35                  40                  45

Trp Lys Phe Ser Ala Ser Gly Ser Ala His Cys Ser Phe Ser Gly Val
    50                  55                  60

Thr Cys Asp Gln Asp Asn Arg Val Ile Thr Leu Asn Val Thr Gln Val
65                  70                  75                  80

Pro Leu Phe Gly Arg Ile Ser Lys Glu Ile Gly Val Leu Asp Lys Leu
                85                  90                  95

Glu Arg Leu Ile Ile Thr Met Asp Asn Leu Thr Gly Glu Leu Pro Phe
            100                 105                 110

Glu Ile Ser Asn Leu Thr Ser Leu Lys Ile Leu Asn Ile Ser His Asn
        115                 120                 125

Thr Phe Ser Gly Asn Phe Pro Gly Asn Ile Thr Leu Arg Met Thr Lys
    130                 135                 140

Leu Glu Val Leu Asp Ala Tyr Asp Asn Ser Phe Thr Gly His Leu Pro
145                 150                 155                 160

Glu Glu Ile Val Ser Leu Lys Glu Leu Thr Ile Leu Cys Leu Ala Gly
                165                 170                 175

Asn Tyr Phe Thr Gly Thr Ile Pro Glu Ser Tyr Ser Glu Phe Gln Lys
            180                 185                 190

Leu Glu Ile Leu Ser Ile Asn Ala Asn Ser Leu Ser Gly Lys Ile Pro
        195                 200                 205

Lys Ser Leu Ser Lys Leu Lys Thr Leu Lys Glu Leu Arg Leu Gly Tyr
    210                 215                 220

Asn Asn Ala Tyr Asp Gly Gly Val Pro Pro Glu Phe Gly Ser Leu Lys
225                 230                 235                 240

Ser Leu Arg Tyr Leu Glu Val Ser Asn Cys Asn Leu Thr Gly Glu Ile
                245                 250                 255

Pro Pro Ser Phe Gly Asn Leu Glu Asn Leu Asp Ser Leu Phe Leu Gln
```

```
                260             265             270
Met Asn Asn Leu Thr Gly Ile Ile Pro Pro Glu Leu Ser Ser Met Lys
        275             280             285
Ser Leu Met Ser Leu Asp Leu Ser Asn Asn Ala Leu Ser Gly Glu Ile
        290             295             300
Pro Glu Ser Phe Ser Asn Leu Lys Ser Leu Thr Leu Asn Phe Phe
305             310             315             320
Gln Asn Lys Phe Arg Gly Ser Ile Pro Ala Phe Ile Gly Asp Leu Pro
                325             330             335
Asn Leu Glu Thr Leu Gln Val Trp Glu Asn Asn Phe Ser Phe Val Leu
        340             345             350
Pro Gln Asn Leu Gly Ser Asn Gly Lys Phe Ile Phe Asp Val Thr
        355             360             365
Lys Asn His Leu Thr Gly Leu Ile Pro Pro Asp Leu Cys Lys Ser Lys
        370             375             380
Lys Leu Gln Thr Phe Ile Val Thr Asp Asn Phe Phe His Gly Pro Ile
385             390             395             400
Pro Lys Gly Ile Gly Ala Cys Lys Ser Leu Leu Lys Ile Arg Val Ala
                405             410             415
Asn Asn Tyr Leu Asp Gly Pro Val Pro Gln Gly Ile Phe Gln Met Pro
        420             425             430
Ser Val Thr Ile Ile Glu Leu Gly Asn Asn Arg Phe Asn Gly Gln Leu
        435             440             445
Pro Ser Glu Val Ser Gly Val Asn Leu Gly Ile Leu Thr Ile Ser Asn
        450             455             460
Asn Leu Phe Thr Gly Arg Ile Pro Ala Ser Met Lys Asn Leu Ile Ser
465             470             475             480
Leu Gln Thr Leu Trp Leu Asp Ala Asn Gln Phe Val Gly Glu Ile Pro
                485             490             495
Lys Glu Val Phe Asp Leu Pro Val Leu Thr Lys Phe Asn Ile Ser Gly
        500             505             510
Asn Asn Leu Thr Gly Val Ile Pro Thr Thr Val Ser Gln Cys Arg Ser
        515             520             525
Leu Thr Ala Val Asp Phe Ser Arg Asn Met Ile Thr Gly Glu Val Pro
        530             535             540
Arg Gly Met Lys Asn Leu Lys Val Leu Ser Ile Phe Asn Leu Ser His
545             550             555             560
Asn Asn Ile Ser Gly Leu Ile Pro Asp Glu Ile Arg Phe Met Thr Ser
                565             570             575
Leu Thr Thr Leu Asp Leu Ser Tyr Asn Asn Phe Thr Gly Ile Val Pro
        580             585             590
Thr Gly Gly Gln Phe Leu Val Phe Asn Asp Arg Ser Phe Phe Gly Asn
        595             600             605
Pro Asn Leu Cys Phe Pro His Gln Ser Ser Cys Ser Ser Tyr Thr Phe
        610             615             620
Pro Ser Ser Lys Ser His Ala Lys Val Lys Ala Ile Ile Thr Ala Ile
625             630             635             640
Ala Leu Ala Thr Ala Val Leu Leu Val Ile Ala Thr Met His Met Met
                645             650             655
Arg Lys Arg Lys Leu His Met Ala Lys Ala Trp Lys Leu Thr Ala Phe
                660             665             670
Gln Arg Leu Asp Phe Lys Ala Glu Glu Val Val Glu Cys Leu Lys Glu
        675             680             685
```

```
Glu Asn Ile Ile Gly Lys Gly Gly Ala Gly Ile Val Tyr Arg Gly Ser
            690                 695                 700
Met Pro Asn Gly Thr Asp Val Ala Ile Lys Arg Leu Val Gly Gln Gly
705                 710                 715                 720
Ser Gly Arg Asn Asp Tyr Gly Phe Lys Ala Glu Ile Glu Thr Leu Gly
                725                 730                 735
Arg Ile Arg His Arg Asn Ile Met Arg Leu Leu Gly Tyr Val Ser Asn
            740                 745                 750
Lys Asp Thr Asn Leu Leu Leu Tyr Glu Tyr Met Pro Asn Gly Ser Leu
        755                 760                 765
Gly Glu Trp Leu His Gly Ala Lys Gly Cys His Leu Ser Trp Glu Met
770                 775                 780
Arg Tyr Lys Ile Ala Val Glu Ala Gly Lys Gly Leu Cys Tyr Leu His
785                 790                 795                 800
His Asp Cys Ser Pro Leu Ile Ile His Arg Asp Val Lys Ser Asn Asn
                805                 810                 815
Ile Leu Leu Asp Ala Asp Phe Glu Ala His Val Ala Asp Phe Gly Leu
            820                 825                 830
Ala Lys Phe Leu Tyr Asp Pro Gly Ala Ser Gln Ser Met Ser Ser Ile
        835                 840                 845
Ala Gly Ser Tyr Gly Tyr Ile Ala Pro Glu Tyr Ala Tyr Thr Leu Lys
850                 855                 860
Val Asp Glu Lys Ser Asp Val Tyr Ser Phe Gly Val Val Leu Leu Glu
865                 870                 875                 880
Leu Ile Ile Gly Arg Lys Pro Val Gly Glu Phe Gly Asp Gly Val Asp
                885                 890                 895
Ile Val Gly Trp Ile Asn Lys Thr Glu Leu Glu Leu Tyr Gln Pro Ser
            900                 905                 910
Asp Lys Ala Leu Val Ser Ala Val Asp Pro Arg Leu Thr Gly Tyr
        915                 920                 925
Pro Met Ala Ser Val Ile Tyr Met Phe Asn Ile Ala Met Met Cys Val
930                 935                 940
Lys Glu Met Gly Pro Ala Arg Pro Thr Met Arg Glu Val His Met
945                 950                 955                 960
Leu Thr Asn Pro Pro Gln Ser Thr Thr His Asn Asn Leu Ile Asn Leu
                965                 970                 975
```

<210> SEQ ID NO 229
<211> LENGTH: 2922
<212> TYPE: DNA
<213> ORGANISM: Populus tremuloides

<400> SEQUENCE: 229

```
atgagaacat tctgtgctt ttttctttta ctagtattat tgttcgctcc ttgcagtgga      60
tacagtgatc ttgaagtcct cttgaagctg aaaacctcca tgtatggaca taatggcact     120
ggccttcaag attgggtggc ttctccagca tctcccacag ctcactgtta cttctctgga    180
gtcacgtgtg atgaggactc gcgtgtggtg tctctaaacg tgtcgtttag acatcttcct    240
ggttcaattc ctccagagat tgggctgttg aacaagcttg tgaatcttac tctgtcaggt    300
aataatctca cggggggatt tccagtggag atagccatgc tgacatctct caggattttg    360
aatatttcca acaatgttat tgctgggaat ttccccggaa aaatcactct tggcatggca    420
ctgcttgagg tcttgatgt ttacaacaat aattttacgg gtgcattgcc aactgaaatt    480
gtaaagctga aaaatctcaa gcatgttcat cttggaggga atttcttttc tggtacaata   540
```

```
ccggaggagt actcggagat tttgagcttg gagtacttgg gcttgaatgg taatgcgctt      600
tcaggcaaag taccttcaag cttgtccagg ttgaagaatc ttaagagctt gtgcgttggg      660
tactttaacc gttatgaggg gagtattcca cctgaatttg ggtcattaag taatcttgaa      720
cttcttgaca tggcttcctg taaccttgac ggtgagattc cttccgcttt aagtcaatta      780
acccatctgc attcgttgtt tcttcaagtc aataatctca ctggccatat ccctcctgaa      840
ttatctggtc taattagctt gaaatcactg gatctttcga taaacaacct cactggggag      900
ataccagaga gtttttcaga tttgaaaaac atagaactga tcaatctctt tcaaaacaag      960
ctgcacggtc caatcccaga atttttggt gattttccga accttgaggt gcttcaggtt     1020
tggggcaaca acttcacttt tgagcttcct caaaatcttg gccggaatgg gaagctgatg     1080
atgctggatg tgtctattaa tcacttaact ggattggtcc cgcgggattt atgcaaagga     1140
gggaaattga cgacgttgat tctcatgaac aatttcttcc ttggatcgct tcctgatgaa     1200
attggccagt gcaagtcctt gctcaaaatc cgaataatga ataatatgtt ttcaggaact     1260
atccctgctg ggatatttaa tttgcctttg gcgacacttg ttgagttgag caataacctt     1320
ttctctggcg agcttccacc agagatttca ggagatgcac taggccttt atcagtttct      1380
aacaatcgga tcacaggtaa atcccgcct gctattggga atctgaagaa cttgcagact      1440
ctgtcactgg acacgaacag actttctggt gaaattcctg aagaaatctg gggactgaag     1500
tccctcacca agatcaacat ccgtgctaac aacatcagag gtgaaatccc agcttcgatt     1560
tcccactgca catcacttac atccgttgat ttcagtcaaa acagcctcag tggggagatt     1620
cctaagaaga ttgccaaact gaacgatttg agctttcttg atctctctcg aaatcaactc     1680
actggtcaac taccaggtga aattggatac atgagaagcc ttacatccct taatctctca     1740
tacaacaatt tatttggcag gatcccttct gccggccaat tcctggcgtt caatgacagt     1800
tcatttctcg gaaatccaaa tctctgtgca gcgagaaata atacttgctc cttcggtgat     1860
catggccata ggggggggtc ttttagtact tcaaagctaa taatcactgt cattgcactc     1920
gtcactgttt tgctgttaat agttgtgacg gtttacagat tgagaaagaa gaggctgcag     1980
aaatcacggg cctggaagct cactgcattc caaaggctcg acttcaaggc agaggacgtg     2040
cttgagtgct tgaaagagga aaacattata ggcaaaggtg gtgctggtat tgtctaccgt     2100
gggtcaatgc cagagggtgt tgatcatgta gctatcaaac gacttgttgg tcgaggcagc     2160
ggaagaagtg atcatggctt ctcggctgag attcaaactc ttggaagaat caggcaccga     2220
aatattgtaa ggctgttggg gtacgtatcg aataaggata ccaacttgct attgtatgaa     2280
tacatgccta atggaagctt aggggagctt ttgcatggtt caaagggagg ccatttgcag     2340
tgggagacta gatacagaat tgctgtggag gctgctaagg gactctgtta tcttcaccac     2400
gattgctcgc ctttgattat acatagggat gttaagtcca ataacatatt acttgattcc     2460
gattttgagg ctcatgttgc tgattttggt ctcgctaagt tcttacaaga tgcaggctca     2520
tcagagtgca tgtcctccgt tgctggctcc tatggttaca ttgctccaga gtacgcatac     2580
acactgaaag tggacgaaaa gagtgatgtt tacagttttg gtgttgtgct gctggagctg     2640
atagcaggga gaaagccagt cggggagttt ggagatgggg tggacatcgt gaggtgggtc     2700
aggaagacca catcagaact ctctcagcca tctgatgcag ctacagtctt ggcagttgtg     2760
gaccccaggc ttagtgggta cccacttgca ggtgtcattc acttgtttaa gatagctatg     2820
ctgtgtgtta aagatgagag ctcagccagg cccaccatga gggaagttgt tcacatgctc     2880
accaatcctc cacaatctgc ccccagccta ctcgccctt ag                        2922
```

```
<210> SEQ ID NO 230
<211> LENGTH: 973
<212> TYPE: PRT
<213> ORGANISM: Populus tremuloides

<400> SEQUENCE: 230
```

| | | | | | | | | | | | | | | |
|---|---|---|---|---|---|---|---|---|---|---|---|---|---|---|
| Met | Arg | Thr | Phe | Leu | Cys | Phe | Phe | Leu | Leu | Val | Leu | Leu | Phe | Ala |
| 1 | | | | 5 | | | | | 10 | | | | | 15 |

| | | | | | | | | | | | | | | |
|---|---|---|---|---|---|---|---|---|---|---|---|---|---|---|
| Pro | Cys | Ser | Gly | Tyr | Ser | Asp | Leu | Glu | Val | Leu | Leu | Lys | Leu | Lys | Thr |
| | | | 20 | | | | | 25 | | | | | 30 |

| | | | | | | | | | | | | | | |
|---|---|---|---|---|---|---|---|---|---|---|---|---|---|---|
| Ser | Met | Tyr | Gly | His | Asn | Gly | Thr | Gly | Leu | Gln | Asp | Trp | Val | Ala | Ser |
| | | 35 | | | | | 40 | | | | | 45 |

Pro Ala Ser Pro Thr Ala His Cys Tyr Phe Ser Gly Val Thr Cys Asp
       50                  55                  60

Glu Asp Ser Arg Val Val Ser Leu Asn Val Ser Phe Arg His Leu Pro
65                  70                  75                  80

Gly Ser Ile Pro Pro Glu Ile Gly Leu Leu Asn Lys Leu Val Asn Leu
                85                  90                  95

Thr Leu Ser Gly Asn Asn Leu Thr Gly Gly Phe Pro Val Glu Ile Ala
            100                 105                 110

Met Leu Thr Ser Leu Arg Ile Leu Asn Ile Ser Asn Asn Val Ile Ala
            115                 120                 125

Gly Asn Phe Pro Gly Lys Ile Thr Leu Gly Met Ala Leu Leu Glu Val
130                 135                 140

Leu Asp Val Tyr Asn Asn Asn Phe Thr Gly Ala Leu Pro Thr Glu Ile
145                 150                 155                 160

Val Lys Leu Lys Asn Leu Lys His Val His Leu Gly Gly Asn Phe Phe
                165                 170                 175

Ser Gly Thr Ile Pro Glu Glu Tyr Ser Glu Ile Leu Ser Leu Glu Tyr
            180                 185                 190

Leu Gly Leu Asn Gly Asn Ala Leu Ser Gly Lys Val Pro Ser Ser Leu
            195                 200                 205

Ser Arg Leu Lys Asn Leu Lys Ser Leu Cys Val Gly Tyr Phe Asn Arg
210                 215                 220

Tyr Glu Gly Ser Ile Pro Pro Glu Phe Gly Ser Leu Ser Asn Leu Glu
225                 230                 235                 240

Leu Leu Asp Met Ala Ser Cys Asn Leu Asp Gly Glu Ile Pro Ser Ala
                245                 250                 255

Leu Ser Gln Leu Thr His Leu His Ser Leu Phe Leu Gln Val Asn Asn
            260                 265                 270

Leu Thr Gly His Ile Pro Pro Glu Leu Ser Gly Leu Ile Ser Leu Lys
            275                 280                 285

Ser Leu Asp Leu Ser Ile Asn Asn Leu Thr Gly Glu Ile Pro Glu Ser
290                 295                 300

Phe Ser Asp Leu Lys Asn Ile Glu Leu Ile Asn Leu Phe Gln Asn Lys
305                 310                 315                 320

Leu His Gly Pro Ile Pro Glu Phe Phe Gly Asp Phe Pro Asn Leu Glu
                325                 330                 335

Val Leu Gln Val Trp Gly Asn Asn Phe Thr Phe Glu Leu Pro Gln Asn
            340                 345                 350

Leu Gly Arg Asn Gly Lys Leu Met Met Leu Asp Val Ser Ile Asn His
            355                 360                 365

Leu Thr Gly Leu Val Pro Arg Asp Leu Cys Lys Gly Gly Lys Leu Thr
370                 375                 380

-continued

Thr Leu Ile Leu Met Asn Asn Phe Phe Leu Gly Ser Leu Pro Asp Glu
385                 390                 395                 400

Ile Gly Gln Cys Lys Ser Leu Leu Lys Ile Arg Ile Met Asn Asn Met
            405                 410                 415

Phe Ser Gly Thr Ile Pro Ala Gly Ile Phe Asn Leu Pro Leu Ala Thr
        420                 425                 430

Leu Val Glu Leu Ser Asn Asn Leu Phe Ser Gly Glu Leu Pro Pro Glu
    435                 440                 445

Ile Ser Gly Asp Ala Leu Gly Leu Leu Ser Val Ser Asn Asn Arg Ile
450                 455                 460

Thr Gly Lys Ile Pro Pro Ala Ile Gly Asn Leu Lys Asn Leu Gln Thr
465                 470                 475                 480

Leu Ser Leu Asp Thr Asn Arg Leu Ser Gly Glu Ile Pro Glu Glu Ile
                485                 490                 495

Trp Gly Leu Lys Ser Leu Thr Lys Ile Asn Ile Arg Ala Asn Asn Ile
            500                 505                 510

Arg Gly Glu Ile Pro Ala Ser Ile Ser His Cys Thr Ser Leu Thr Ser
        515                 520                 525

Val Asp Phe Ser Gln Asn Ser Leu Ser Gly Ile Pro Lys Lys Ile
    530                 535                 540

Ala Lys Leu Asn Asp Leu Ser Phe Leu Asp Leu Ser Arg Asn Gln Leu
545                 550                 555                 560

Thr Gly Gln Leu Pro Gly Glu Ile Gly Tyr Met Arg Ser Leu Thr Ser
                565                 570                 575

Leu Asn Leu Ser Tyr Asn Asn Leu Phe Gly Arg Ile Pro Ser Ala Gly
            580                 585                 590

Gln Phe Leu Ala Phe Asn Asp Ser Ser Phe Leu Gly Asn Pro Asn Leu
        595                 600                 605

Cys Ala Ala Arg Asn Asn Thr Cys Ser Phe Gly Asp His Gly His Arg
    610                 615                 620

Gly Gly Ser Phe Ser Thr Ser Lys Leu Ile Ile Thr Val Ile Ala Leu
625                 630                 635                 640

Val Thr Val Leu Leu Leu Ile Val Val Thr Val Tyr Arg Leu Arg Lys
                645                 650                 655

Lys Arg Leu Gln Lys Ser Arg Ala Trp Lys Leu Thr Ala Phe Gln Arg
            660                 665                 670

Leu Asp Phe Lys Ala Glu Asp Val Leu Glu Cys Leu Lys Glu Glu Asn
        675                 680                 685

Ile Ile Gly Lys Gly Gly Ala Gly Ile Val Tyr Arg Gly Ser Met Pro
    690                 695                 700

Glu Gly Val Asp His Val Ala Ile Lys Arg Leu Val Gly Arg Gly Ser
705                 710                 715                 720

Gly Arg Ser Asp His Gly Phe Ser Ala Glu Ile Gln Thr Leu Gly Arg
                725                 730                 735

Ile Arg His Arg Asn Ile Val Arg Leu Leu Gly Tyr Val Ser Asn Lys
            740                 745                 750

Asp Thr Asn Leu Leu Leu Tyr Glu Tyr Met Pro Asn Gly Ser Leu Gly
        755                 760                 765

Glu Leu Leu His Gly Ser Lys Gly Gly His Leu Gln Trp Glu Thr Arg
    770                 775                 780

Tyr Arg Ile Ala Val Glu Ala Ala Lys Gly Leu Cys Tyr Leu His His
785                 790                 795                 800

Asp Cys Ser Pro Leu Ile Ile His Arg Asp Val Lys Ser Asn Asn Ile
                805                 810                 815

```
Leu Leu Asp Ser Asp Phe Glu Ala His Val Ala Asp Phe Gly Leu Ala
            820                 825                 830

Lys Phe Leu Gln Asp Ala Gly Ser Ser Glu Cys Met Ser Ser Val Ala
        835                 840                 845

Gly Ser Tyr Gly Tyr Ile Ala Pro Glu Tyr Ala Tyr Thr Leu Lys Val
    850                 855                 860

Asp Glu Lys Ser Asp Val Tyr Ser Phe Gly Val Val Leu Leu Glu Leu
865                 870                 875                 880

Ile Ala Gly Arg Lys Pro Val Gly Glu Phe Gly Asp Gly Val Asp Ile
                885                 890                 895

Val Arg Trp Val Arg Lys Thr Thr Ser Glu Leu Ser Gln Pro Ser Asp
            900                 905                 910

Ala Ala Thr Val Leu Ala Val Val Asp Pro Arg Leu Ser Gly Tyr Pro
        915                 920                 925

Leu Ala Gly Val Ile His Leu Phe Lys Ile Ala Met Leu Cys Val Lys
    930                 935                 940

Asp Glu Ser Ser Ala Arg Pro Thr Met Arg Glu Val Val His Met Leu
945                 950                 955                 960

Thr Asn Pro Pro Gln Ser Ala Pro Ser Leu Leu Ala Leu
                965                 970

<210> SEQ ID NO 231
<211> LENGTH: 2922
<212> TYPE: DNA
<213> ORGANISM: Populus tremuloides

<400> SEQUENCE: 231
atgggaactc ttctgtgttt tcttcttcct tttcttgtac tactgttcac tgcttgcagt      60
ggatacagtg aacttgaagt cctcttgaag ctgaaatctt ccatgtacgg acataatggc     120
actggccttg aagattgggt ggcttctcct acatctcctt cagctcattg tttcttctct     180
ggagtcacgt gtgatgagag ctcacgtgtg gtgtcactta atttgtcgtt cagacatctt     240
cctggttcaa ttcctccaga gattgggttg ttgaacaagc ttgtgaatct tactttggcc     300
aatgataatc tcacggggga acttcctgcg agatagcca tgcttaaatc tctcaggatt      360
ttgaacattt ctggcaatgc tattggtggg aatttctctg aaagatcac tcctggcatg      420 acacagcttg aggttcttga tatttacaac aataattgct cgggtccact gccaattgaa     480
attgcaaacc tgaaaaaact caagcatctt cacctgggag ggaatttctt ttctggtaaa     540
ataccagagg agtactcgga gattatgatc ttggagttct taggcttgaa tggtaatgac     600
ctttcaggca agttccttc tagcttgtct aagctgaaga atctcaagag cttgtgcatt      660
gggtactata accattacga aggaggtatt ccacctgaat ttggatcatt gagtaatctt     720
gaacttcttg acatgggttc ttgcaacctt aatggtgaga ttccttctac tctaggccaa     780
ttaacccatc tgcattcgct gtttcttcaa ttcaataatc tcactggata tatcccttcg     840
gaattatctg gtctaattag cttgaaatca cttgatcttt caatcaacaa cctcactggg     900
gagatacccg agagttttc agctttgaaa aacttaacac tcctcaatct ctttcaaaac     960
aagctgcacg tccaatccc agactttgtt ggtgattttc caaaccttga ggtgcttcag    1020
gtttggggaa acaacttcac atttgagctt cccaaacagc tcggccggaa tgggaagctg    1080
atgtatctgg acgtgtcata taatcacttg acaggattgg ttcctcggga cttatgcaag    1140
ggagggaaat tgaagacgtt gattctcatg aataatttct tcattggatc acttcctgaa    1200
gaaattggcc agtgcaagtc cttgctcaaa atcagaatca tttgtaatct ctttacaggc    1260
```

```
actatccctg ctgggatctt taatttacct tggtgaccc aaattgagtt gagccataac      1320
tatttctccg gcgagcttcc accggagatt tcaggagatg cactaggctc tctttcggtc      1380
tctgacaatc ggattactgg tagaatcccc cgggctattg gaatttgaa gagtttgcag       1440
tttctatctc tggaaatgaa cagactttct ggtgaaattc ctgatgaaat cttcagtctg      1500
gagatcctct ccaagatcag catccgtgcc aacaacatta gcggtgaaat cccagcttcc      1560
atgttccatt gcacttcact acatccgtt gatttcagtc aaaacagcat cagtggggag       1620
attccaaagg agattactaa actgaaggat tgagtattc ttgatctctc tcgaaatcag       1680
cttactggtc aactaccaag tgaaattcga tacatgacaa gtcttacaac tctaaacctc      1740
tcctacaaca atttatttgg ccggatccct tctgtcggcc aattcctggc gttcaatgac      1800
agctcatttc ttggaaatcc aaatctctgt gtagcaagaa atgactcttg ctcatttggt      1860
ggtcatggcc atagaaggtc ctttaatact tcaaagctaa tgatcactgt cattgctctt      1920
gtcactgcgt tgctgttaat agcagtgaca gtttacagat tgagaaagaa gaatctgcag      1980
aaatcacggg cctggaagct cactgcattc caaaggctcg atttcaaagc agaggatgtg      2040
ctcgagtgct tgaaagagga aaacattata ggcaaaggtg gcgctgggat tgtctaccgt      2100
gggtcaatga cagagggtat tgatcatgta gctatcaaac gacttgttgg tagaggcacc      2160
ggacgaaacg atcatggctt ctcagccgag atccaaacac ttggaaggat caggcaccga      2220
aatattgtta ggctgctggg gtacgtatca ataaggata ccaacttgct gttgtatgag       2280
tacatgccaa atgggagctt aggagagctt ttgcatggtt caagggagg ccatttgcag       2340
tgggaaacca ggtacagaat tgctgtggag gctgccaagg gactctgtta tcttcaccat      2400
gattgctctc ctttgattat acataggat gtgaagtcca ataacatatt acttgattcg       2460
gattttgagg ctcatgttgc tgattttggg ctggccaagt tcttgcaaga tgcaggtgca      2520
tcagaatgca tgtcctctat tgctggctcc tatggttaca ttgctccaga atacgcttac      2580
acattgaaag tggacgaaaa aagtgatgtt tacagctgcg gtgttgtgct gctggagctg      2640
atagcaggga ggaagccagt aggggagttt ggagatgggg tggacatagt gagatgggtc      2700
aggaagacca cgtcagaact atctcagcca tccgatgcag cttcagtctt ggcagttgtg      2760
gacccccaggc ttagtgggta ccctctaaca ggtgccattc acctgtttaa gatagctatg      2820
ttgtgtgtaa aagatgagag ctcgaaccgg cctaccatga gggaagtggt tcacatgctc      2880
accaatcctc cacagtcagc ctcaagcctc ctcaccctct ag                         2922
```

<210> SEQ ID NO 232
<211> LENGTH: 973
<212> TYPE: PRT
<213> ORGANISM: Populus tremuloides

<400> SEQUENCE: 232

```
Met Gly Thr Leu Leu Cys Phe Leu Leu Pro Phe Leu Val Leu Leu Phe
1               5                   10                  15

Thr Ala Cys Ser Gly Tyr Ser Glu Leu Glu Val Leu Leu Lys Leu Lys
            20                  25                  30

Ser Ser Met Tyr Gly His Asn Gly Thr Gly Leu Glu Asp Trp Val Ala
        35                  40                  45

Ser Pro Thr Ser Pro Ser Ala His Cys Phe Phe Ser Gly Val Thr Cys
    50                  55                  60

Asp Glu Ser Ser Arg Val Val Ser Leu Asn Leu Ser Phe Arg His Leu
65                  70                  75                  80
```

-continued

```
Pro Gly Ser Ile Pro Pro Glu Ile Gly Leu Leu Asn Lys Leu Val Asn
            85                  90                  95
Leu Thr Leu Ala Asn Asp Asn Leu Thr Gly Glu Leu Pro Ala Glu Ile
            100                 105                 110
Ala Met Leu Lys Ser Leu Arg Ile Leu Asn Ile Ser Gly Asn Ala Ile
            115                 120                 125
Gly Gly Asn Phe Ser Gly Lys Ile Thr Pro Gly Met Thr Gln Leu Glu
            130                 135                 140
Val Leu Asp Ile Tyr Asn Asn Cys Ser Gly Pro Leu Pro Ile Glu
145                 150                 155                 160
Ile Ala Asn Leu Lys Lys Leu Lys His Leu His Leu Gly Gly Asn Phe
                165                 170                 175
Phe Ser Gly Lys Ile Pro Glu Glu Tyr Ser Glu Ile Met Ile Leu Glu
            180                 185                 190
Phe Leu Gly Leu Asn Gly Asn Asp Leu Ser Gly Lys Val Pro Ser Ser
            195                 200                 205
Leu Ser Lys Leu Lys Asn Leu Lys Ser Leu Cys Ile Gly Tyr Tyr Asn
    210                 215                 220
His Tyr Glu Gly Gly Ile Pro Pro Glu Phe Gly Ser Leu Ser Asn Leu
225                 230                 235                 240
Glu Leu Leu Asp Met Gly Ser Cys Asn Leu Asn Gly Glu Ile Pro Ser
                245                 250                 255
Thr Leu Gly Gln Leu Thr His Leu His Ser Leu Phe Leu Gln Phe Asn
            260                 265                 270
Asn Leu Thr Gly Tyr Ile Pro Ser Glu Leu Ser Gly Leu Ile Ser Leu
            275                 280                 285
Lys Ser Leu Asp Leu Ser Ile Asn Asn Leu Thr Gly Glu Ile Pro Glu
290                 295                 300
Ser Phe Ser Ala Leu Lys Asn Leu Thr Leu Leu Asn Leu Phe Gln Asn
305                 310                 315                 320
Lys Leu His Gly Pro Ile Pro Asp Phe Val Gly Asp Phe Pro Asn Leu
                325                 330                 335
Glu Val Leu Gln Val Trp Gly Asn Asn Phe Thr Phe Glu Leu Pro Lys
            340                 345                 350
Gln Leu Gly Arg Asn Gly Lys Leu Met Tyr Leu Asp Val Ser Tyr Asn
            355                 360                 365
His Leu Thr Gly Leu Val Pro Arg Asp Leu Cys Lys Gly Gly Lys Leu
    370                 375                 380
Lys Thr Leu Ile Leu Met Asn Asn Phe Phe Ile Gly Ser Leu Pro Glu
385                 390                 395                 400
Glu Ile Gly Gln Cys Lys Ser Leu Leu Lys Ile Arg Ile Ile Cys Asn
                405                 410                 415
Leu Phe Thr Gly Thr Ile Pro Ala Gly Ile Phe Asn Leu Pro Leu Val
            420                 425                 430
Thr Gln Ile Glu Leu Ser His Asn Tyr Phe Ser Gly Glu Leu Pro Pro
            435                 440                 445
Glu Ile Ser Gly Asp Ala Leu Gly Ser Leu Ser Val Ser Asp Asn Arg
    450                 455                 460
Ile Thr Gly Arg Ile Pro Arg Ala Ile Gly Asn Leu Lys Ser Leu Gln
465                 470                 475                 480
Phe Leu Ser Leu Glu Met Asn Arg Leu Ser Gly Glu Ile Pro Asp Glu
                485                 490                 495
Ile Phe Ser Leu Glu Ile Leu Ser Lys Ile Ser Ile Arg Ala Asn Asn
            500                 505                 510
```

```
Ile Ser Gly Glu Ile Pro Ala Ser Met Phe His Cys Thr Ser Leu Thr
        515                 520                 525
Ser Val Asp Phe Ser Gln Asn Ser Ile Ser Gly Glu Ile Pro Lys Glu
    530                 535                 540
Ile Thr Lys Leu Lys Asp Leu Ser Ile Leu Asp Leu Ser Arg Asn Gln
545                 550                 555                 560
Leu Thr Gly Gln Leu Pro Ser Glu Ile Arg Tyr Met Thr Ser Leu Thr
                565                 570                 575
Thr Leu Asn Leu Ser Tyr Asn Leu Phe Gly Arg Ile Pro Ser Val
        580                 585                 590
Gly Gln Phe Leu Ala Phe Asn Asp Ser Ser Phe Leu Gly Asn Pro Asn
        595                 600                 605
Leu Cys Val Ala Arg Asn Asp Ser Cys Ser Phe Gly Gly His Gly His
        610                 615                 620
Arg Arg Ser Phe Asn Thr Ser Lys Leu Met Ile Thr Val Ile Ala Leu
625                 630                 635                 640
Val Thr Ala Leu Leu Leu Ile Ala Val Thr Val Tyr Arg Leu Arg Lys
                645                 650                 655
Lys Asn Leu Gln Lys Ser Arg Ala Trp Lys Leu Thr Ala Phe Gln Arg
                660                 665                 670
Leu Asp Phe Lys Ala Glu Asp Val Leu Glu Cys Leu Lys Glu Glu Asn
                675                 680                 685
Ile Ile Gly Lys Gly Gly Ala Gly Ile Val Tyr Arg Gly Ser Met Thr
        690                 695                 700
Glu Gly Ile Asp His Val Ala Ile Lys Arg Leu Val Gly Arg Gly Thr
705                 710                 715                 720
Gly Arg Asn Asp His Gly Phe Ser Ala Glu Ile Gln Thr Leu Gly Arg
                725                 730                 735
Ile Arg His Arg Asn Ile Val Arg Leu Leu Gly Tyr Val Ser Asn Lys
                740                 745                 750
Asp Thr Asn Leu Leu Leu Tyr Glu Tyr Met Pro Asn Gly Ser Leu Gly
        755                 760                 765
Glu Leu Leu His Gly Ser Lys Gly Gly His Leu Gln Trp Glu Thr Arg
        770                 775                 780
Tyr Arg Ile Ala Val Glu Ala Ala Lys Gly Leu Cys Tyr Leu His His
785                 790                 795                 800
Asp Cys Ser Pro Leu Ile Ile His Arg Asp Val Lys Ser Asn Asn Ile
                805                 810                 815
Leu Leu Asp Ser Asp Phe Glu Ala His Val Ala Asp Phe Gly Leu Ala
                820                 825                 830
Lys Phe Leu Gln Asp Ala Gly Ala Ser Glu Cys Met Ser Ser Ile Ala
        835                 840                 845
Gly Ser Tyr Gly Tyr Ile Ala Pro Glu Tyr Ala Tyr Thr Leu Lys Val
        850                 855                 860
Asp Glu Lys Ser Asp Val Tyr Ser Cys Gly Val Val Leu Leu Glu Leu
865                 870                 875                 880
Ile Ala Gly Arg Lys Pro Val Gly Glu Phe Gly Asp Gly Val Asp Ile
                885                 890                 895
Val Arg Trp Val Arg Lys Thr Thr Ser Glu Leu Ser Gln Pro Ser Asp
                900                 905                 910
Ala Ala Ser Val Leu Ala Val Val Asp Pro Arg Leu Ser Gly Tyr Pro
        915                 920                 925
Leu Thr Gly Ala Ile His Leu Phe Lys Ile Ala Met Leu Cys Val Lys
```

```
                930             935             940
Asp Glu Ser Ser Asn Arg Pro Thr Met Arg Glu Val Val His Met Leu
945                 950                 955                 960

Thr Asn Pro Pro Gln Ser Ala Ser Ser Leu Leu Thr Leu
                965                 970

<210> SEQ ID NO 233
<211> LENGTH: 996
<212> TYPE: PRT
<213> ORGANISM: Zea mays

<400> SEQUENCE: 233

Met Pro Pro Pro Thr Phe Leu Leu Gly Leu Leu Leu Leu Leu Leu Leu
1               5                   10                  15

Ala Ala Ala Ala Pro Ala Pro Ala Ser Ala Thr Pro Glu Arg Asp Ala
            20                  25                  30

Tyr Ala Leu Ser Arg Leu Lys Ala Ser Leu Val Pro Ser Ala Thr Asn
        35                  40                  45

Ser Thr Ser Ala Pro Leu Ser Asp Trp Asp Pro Ala Ala Thr Pro Pro
50                  55                  60

Ala His Cys Ala Phe Thr Gly Val Thr Cys Asp Ala Ala Thr Ser Arg
65                  70                  75                  80

Val Val Ala Ile Asn Leu Thr Ala Val Pro Leu His Gly Gly Ala Leu
                85                  90                  95

Pro Pro Glu Val Ala Leu Leu Asp Ala Leu Ala Ser Leu Thr Val Ala
            100                 105                 110

Asn Cys Tyr Leu Arg Gly Arg Leu Pro Pro Ala Leu Ala Ser Met Pro
        115                 120                 125

Ala Leu Arg His Leu Asn Leu Ser Asn Asn Asn Leu Ser Gly Pro Phe
130                 135                 140

Pro Pro Pro Pro Pro Ala Ala Tyr Phe Pro Ala Leu Glu Ile Val Asp
145                 150                 155                 160

Val Tyr Asn Asn Asn Leu Ser Gly Pro Leu Pro Leu Gly Ala Pro
                165                 170                 175

His Ala Arg Ser Leu Arg Tyr Leu His Leu Gly Gly Asn Tyr Phe Asn
            180                 185                 190

Gly Ser Ile Pro Asp Thr Phe Gly Asp Leu Ala Ala Leu Glu Tyr Leu
        195                 200                 205

Gly Leu Asn Gly Asn Ala Leu Ser Gly Arg Val Pro Pro Ser Leu Ser
210                 215                 220

Arg Leu Ser Arg Leu Arg Glu Met Tyr Val Gly Tyr Tyr Asn Gln Tyr
225                 230                 235                 240

Ser Gly Gly Val Pro Arg Glu Phe Gly Ala Leu Gln Ser Leu Val Arg
                245                 250                 255

Leu Asp Met Ser Ser Cys Thr Leu Thr Gly Pro Ile Pro Pro Glu Leu
            260                 265                 270

Ala Arg Leu Ser Arg Leu Asp Thr Leu Phe Leu Ala Leu Asn Gln Leu
        275                 280                 285

Thr Gly Glu Ile Pro Pro Glu Leu Gly Ala Leu Thr Ser Leu Arg Ser
290                 295                 300

Leu Asp Leu Ser Ile Asn Asp Leu Ala Gly Glu Ile Pro Ala Ser Phe
305                 310                 315                 320

Ala Ala Leu Thr Asn Leu Lys Leu Leu Asn Leu Phe Arg Asn Lys Leu
                325                 330                 335

Arg Gly Glu Ile Pro Ala Phe Leu Gly Asp Phe Pro Phe Leu Glu Val
```

```
                340                 345                 350
Leu Gln Val Trp Asp Asn Asn Leu Thr Gly Pro Leu Pro Ala Leu
        355                 360                 365
Gly Arg Asn Gly Arg Leu Lys Thr Leu Asp Val Thr Ser Asn His Leu
        370                 375                 380
Thr Gly Thr Ile Pro Pro Asp Leu Cys Ala Gly Arg Asn Leu Gln Leu
385                 390                 395                 400
Leu Val Leu Met Asp Asn Gly Phe Phe Gly Ser Ile Pro Glu Ser Leu
                405                 410                 415
Gly Asp Cys Lys Thr Leu Thr Arg Val Arg Leu Gly Lys Asn Phe Leu
                420                 425                 430
Thr Gly Pro Val Pro Ala Gly Leu Phe Asp Leu Pro Gln Ala Asn Met
                435                 440                 445
Leu Glu Leu Thr Asp Asn Met Leu Thr Gly Glu Leu Pro Asp Val Ile
        450                 455                 460
Ala Gly Asp Lys Ile Gly Met Leu Met Leu Gly Asn Asn Arg Ile Gly
465                 470                 475                 480
Gly Arg Ile Pro Ala Ala Ile Gly Asn Leu Pro Ala Leu Gln Thr Leu
                485                 490                 495
Ser Leu Glu Ser Asn Asn Phe Ser Gly Ser Leu Pro Pro Glu Ile Gly
                500                 505                 510
Arg Leu Arg Asn Leu Thr Arg Leu Asn Ala Ser Gly Asn Ala Leu Thr
        515                 520                 525
Gly Gly Ile Pro Arg Glu Leu Met Gly Cys Ala Ser Leu Gly Ala Val
        530                 535                 540
Asp Leu Ser Arg Asn Gly Leu Thr Gly Glu Ile Pro Asp Thr Val Thr
545                 550                 555                 560
Ser Leu Lys Ile Leu Cys Thr Leu Asn Val Ser Arg Asn Arg Leu Ser
                565                 570                 575
Gly Glu Leu Pro Ala Ala Met Ala Asn Asn Thr Ser Leu Thr Thr Leu
                580                 585                 590
Asp Val Ser Tyr Asn Gln Leu Ser Gly Pro Val Pro Met Gln Gly Gln
                595                 600                 605
Phe Leu Val Phe Asn Glu Ser Ser Phe Val Gly Asn Pro Gly Leu Cys
        610                 615                 620
Ser Ala Cys Pro Pro Ser Ser Gly Gly Ala Arg Ser Pro Phe Ser Leu
625                 630                 635                 640
Arg Arg Trp Asp Ser Lys Lys Leu Leu Val Trp Leu Val Leu Leu
                645                 650                 655
Thr Leu Leu Val Leu Ala Val Leu Gly Ala Arg Lys Ala His Glu Ala
        660                 665                 670
Trp Arg Glu Ala Ala Arg Arg Ser Gly Ala Trp Lys Met Thr Ala
        675                 680                 685
Phe Gln Lys Leu Asp Phe Ser Ala Asp Val Val Glu Cys Leu Lys
        690                 695                 700
Glu Asp Asn Ile Ile Gly Lys Gly Gly Ala Gly Ile Val Tyr His Gly
705                 710                 715                 720
Val Thr Arg Gly Gly Ala Glu Leu Ala Ile Lys Arg Leu Val Gly Arg
                725                 730                 735
Gly Cys Gly Asp His Asp Arg Gly Phe Thr Ala Glu Val Thr Thr Leu
                740                 745                 750
Gly Arg Ile Arg His Arg Asn Ile Val Arg Leu Leu Gly Phe Val Ser
        755                 760                 765
```

```
Asn Arg Glu Ala Asn Leu Leu Leu Tyr Glu Tyr Met Pro Asn Gly Ser
        770                 775                 780

Leu Gly Glu Met Leu His Gly Gly Lys Gly Gly His Leu Gly Trp Glu
785                 790                 795                 800

Ala Arg Ala Arg Val Ala Ala Glu Ala Ala Arg Gly Leu Cys Tyr Leu
                805                 810                 815

His His Asp Cys Ala Pro Arg Ile Ile His Arg Asp Val Lys Ser Asn
            820                 825                 830

Asn Ile Leu Leu Asp Ser Ala Phe Glu Ala His Val Ala Asp Phe Gly
        835                 840                 845

Leu Ala Lys Phe Leu Gly Gly Gly Ala Thr Ser Glu Cys Met Ser
850                 855                 860

Ala Ile Ala Gly Ser Tyr Gly Tyr Ile Ala Pro Glu Tyr Ala Tyr Thr
865                 870                 875                 880

Leu Arg Val Asp Glu Lys Ser Asp Val Tyr Ser Phe Gly Val Val Leu
                885                 890                 895

Leu Glu Leu Ile Thr Gly Arg Arg Pro Val Gly Ser Phe Gly Asp Gly
            900                 905                 910

Val Asp Ile Val His Trp Val Arg Lys Val Thr Ala Asp Ala Ala
        915                 920                 925

Ala Glu Glu Pro Val Leu Leu Val Ala Asp Arg Arg Leu Ala Pro Glu
    930                 935                 940

Pro Val Pro Leu Leu Ala Asp Leu Tyr Arg Val Ala Met Ala Cys Val
945                 950                 955                 960

Glu Glu Ala Ser Thr Ala Arg Pro Thr Met Arg Glu Val Val His Met
                965                 970                 975

Leu Ser Thr Ser Ala Ala Ala Gln Pro Asp Val Pro His Ala Leu Cys
            980                 985                 990

Lys Val Val Asp
        995
```

<210> SEQ ID NO 234
<211> LENGTH: 2343
<212> TYPE: DNA
<213> ORGANISM: Ipomoea batatas

<400> SEQUENCE: 234

```
ttctccggcg ttgcatgcga tcaggattca cgagtcattt ctttagccat atccgctgtt    60
ccgctcttcg gttccctccc gccggagatt ggactgctgg ataggctttt aaacttaact   120
ctcacctccg ttaatctctc tggtgcgctt ccatcggaga tggcgaaact cacatccatt   180
aaagccatta atatgtcaaa caatttgttg agcggccatt tccctggaga atcttggtc    240
ggtatgactg agcttcaagt gttggatgtt tacaataaca acttttccgg aaggcttcct   300
catgaagtgg tgaagttgaa gaagctgaaa attctcaatc tcggaggaaa ttacttcaca   360
ggagagatac cggaaatata ctctaacatt ccagtttac agactttaaa cttacaaaca    420
aatagcctca cggaaatat accggcaagc ttggcgcagc ttcagaatct tcgtgagctc    480
cgccttggct acttgaatac atttgaaaga ggcattccac cagaattagg ctccatcacc   540
acacttcaaa tgcttgatct tagggaatgc aaccttttctg gtgaaattcc taaaagttta   600
gggaatctaa aacagctata ctttctgtat tgtacgggaa cagcctgac aggtcatatt    660
ccggcggagc tctccggttt ggagagtttg gtgcatctgg acctttcaga aaataatatg   720
atgggagaaa ttcctcaaag tttagccgag ttgaagagcc tggtattgat aaacttgttc   780
agaaacacgt tccaaggcac aattcccgcg ttcatcggtg atctacccaa actagaggtt   840
```

-continued

```
ttacagctttt ggaacaacaa tttcacatcc gagttaccgg taaacctcgg acgaaaccgc    900
cgattgaggt ttctggacgt ttcgtcaaac caaatcagcg gcagagtacc ggaaaatttg    960
tgtatgggag ggaagctgga agcactaatt ctcatggaaa acaaattttc tggaccgttt   1020
cctcaagtcc tgggcgagtg caagtccttg aatggggttc gtgttgagaa gaactatctc   1080
aatggagcca tcccgcctgg ctttcttcaa tttgccgttg gcttaatcta cgtttgtctc   1140
caaaacaatt acttctccag cgagcttccg accaagatgc ttgccaagaa tctcacagat   1200
cttgatcttc acaacaacag gataaatggc cagattcctc cggcattcgg aaatttagag   1260
aacctctgga agttatccct ccactccaac agattctccg ggaaaattcc aaatcaaatt   1320
tcacatttga aaaagatggt gaccatggat ttaagcagca acagtttaac aggtgaagtt   1380
ccagcctcaa ttgctcagtg tacacagctg aattcctttg acttgagtgc aaataattta   1440
accggaaaaa ttccaaagga aatctcttct ctggagcgcc taaatgtact caacttgtcc   1500
agaaatctac ttactggttc agttcccagt gaactagggc taatgaatag cttgactgtc   1560
ctggatcatt ctttcaatga ttttcgggt ccaatacccca ccaatggaca gttaggagtt   1620
ttcgataacc ggtctttcta cgggaatcca aaactcttct attcacctcc aagctcatcg   1680
ccagtcaatc acaacaacca ttcttggacc acaaaacgaa tactcataat tactgtcttg   1740
attttgggta ctgcagcagc attttttatct gctgttatat gggtaaggtg cattattgtt   1800
gcgcgaagag aaaagattat gaaatccaat aatgcttgga aactaacaac attcaagaaa   1860
ctggaatata agtagagga tgtggttgag tgtttgaaag aggaaaacat aattgggcaa   1920
gggggagcag ggacagtata caaaggctcc atgcccgatg gtgtcatcat agcaataaaa   1980
aggctagaca ggcgaggaac tgggcgtcgt gatcttggtt tctctgctga aattaaaaca   2040
ctgggaagaa tcaggcaccg acacattatt agattacttg gttatgcatc taacagagat   2100
actaatttgt tattgtatga atacatgcct aatgggagct tgtcgggat cctgcatggg   2160
acgaatgggg ccaatttgct ttgggagatg cggtttcgaa ttgcggtgga agccgcaaag   2220
gggctatgtt acttgcacca tgattgctcc cctcccatta ttcataggga cgtaaagtct   2280
aataatattt tactcacttc tgattatata gcttgcattg ctgattttgg gctggctaaa   2340
tcc                                                                 2343
```

<210> SEQ ID NO 235
<211> LENGTH: 781
<212> TYPE: PRT
<213> ORGANISM: Ipomoea batatas

<400> SEQUENCE: 235

```
Phe Ser Gly Val Ala Cys Asp Gln Asp Ser Arg Val Ile Ser Leu Ala
1               5                   10                  15

Ile Ser Ala Val Pro Leu Phe Gly Ser Leu Pro Pro Glu Ile Gly Leu
            20                  25                  30

Leu Asp Arg Leu Leu Asn Leu Thr Leu Thr Ser Val Asn Leu Ser Gly
        35                  40                  45

Ala Leu Pro Ser Glu Met Ala Lys Leu Thr Ser Ile Lys Ala Ile Asn
    50                  55                  60

Met Ser Asn Asn Leu Leu Ser Gly His Phe Pro Gly Glu Ile Leu Val
65                  70                  75                  80

Gly Met Thr Glu Leu Gln Val Leu Asp Val Tyr Asn Asn Asn Phe Ser
                85                  90                  95

Gly Arg Leu Pro His Glu Val Val Lys Leu Lys Lys Leu Lys Ile Leu
```

```
                       100                 105                 110
Asn Leu Gly Gly Asn Tyr Phe Thr Gly Glu Ile Pro Glu Ile Tyr Ser
                115                 120                 125
Asn Ile Ser Ser Leu Gln Thr Leu Asn Leu Gln Thr Asn Ser Leu Thr
                130                 135                 140
Gly Asn Ile Pro Ala Ser Leu Ala Gln Leu Gln Asn Leu Arg Glu Leu
145                 150                 155                 160
Arg Leu Gly Tyr Leu Asn Thr Phe Glu Arg Gly Ile Pro Glu Leu
                165                 170                 175
Gly Ser Ile Thr Thr Leu Gln Met Leu Asp Leu Arg Glu Cys Asn Leu
                180                 185                 190
Ser Gly Glu Ile Pro Lys Ser Leu Gly Asn Leu Lys Gln Leu Tyr Phe
                195                 200                 205
Leu Tyr Leu Tyr Gly Asn Ser Leu Thr Gly His Ile Pro Ala Glu Leu
210                 215                 220
Ser Gly Leu Glu Ser Leu Val His Leu Asp Leu Ser Glu Asn Asn Met
225                 230                 235                 240
Met Gly Glu Ile Pro Gln Ser Leu Ala Glu Leu Lys Ser Leu Val Leu
                245                 250                 255
Ile Asn Leu Phe Arg Asn Thr Phe Gln Gly Thr Ile Pro Ala Phe Ile
                260                 265                 270
Gly Asp Leu Pro Lys Leu Glu Val Leu Gln Leu Trp Asn Asn Phe
                275                 280                 285
Thr Ser Glu Leu Pro Val Asn Leu Gly Arg Asn Arg Arg Leu Arg Phe
                290                 295                 300
Leu Asp Val Ser Ser Asn Gln Ile Ser Gly Arg Val Pro Glu Asn Leu
305                 310                 315                 320
Cys Met Gly Gly Lys Leu Glu Ala Leu Ile Leu Met Glu Asn Lys Phe
                325                 330                 335
Ser Gly Pro Phe Pro Gln Val Leu Gly Glu Cys Lys Ser Leu Asn Gly
                340                 345                 350
Val Arg Val Glu Lys Asn Tyr Leu Asn Gly Ala Ile Pro Pro Gly Phe
                355                 360                 365
Leu Gln Phe Ala Val Gly Leu Ile Tyr Val Cys Leu Gln Asn Asn Tyr
                370                 375                 380
Phe Ser Ser Glu Leu Pro Thr Lys Met Leu Ala Lys Asn Leu Thr Asp
385                 390                 395                 400
Leu Asp Leu His Asn Asn Arg Ile Asn Gly Gln Ile Pro Pro Ala Phe
                405                 410                 415
Gly Asn Leu Glu Asn Leu Trp Lys Leu Ser Leu His Ser Asn Arg Phe
                420                 425                 430
Ser Gly Lys Ile Pro Asn Gln Ile Ser His Leu Lys Lys Met Val Thr
                435                 440                 445
Met Asp Leu Ser Ser Asn Ser Leu Thr Gly Glu Val Pro Ala Ser Ile
                450                 455                 460
Ala Gln Cys Thr Gln Leu Asn Ser Phe Asp Leu Ser Ala Asn Leu
465                 470                 475                 480
Thr Gly Lys Ile Pro Lys Glu Ile Ser Ser Leu Glu Arg Leu Asn Val
                485                 490                 495
Leu Asn Leu Ser Arg Asn Leu Leu Thr Gly Ser Val Pro Ser Glu Leu
                500                 505                 510
Gly Leu Met Asn Ser Leu Thr Val Leu Asp His Ser Phe Asn Asp Phe
                515                 520                 525
```

```
Ser Gly Pro Ile Pro Thr Asn Gly Gln Leu Gly Val Phe Asp Asn Arg
            530                 535                 540

Ser Phe Tyr Gly Asn Pro Lys Leu Phe Tyr Ser Pro Pro Ser Ser Ser
545                 550                 555                 560

Pro Val Asn His Asn Asn His Ser Trp Thr Thr Lys Arg Ile Leu Ile
                565                 570                 575

Ile Thr Val Leu Ile Leu Gly Thr Ala Ala Ala Phe Leu Ser Ala Val
            580                 585                 590

Ile Trp Val Arg Cys Ile Ile Val Ala Arg Arg Glu Lys Ile Met Lys
        595                 600                 605

Ser Asn Asn Ala Trp Lys Leu Thr Thr Phe Lys Lys Leu Glu Tyr Lys
    610                 615                 620

Val Glu Asp Val Val Glu Cys Leu Lys Glu Glu Asn Ile Ile Gly Gln
625                 630                 635                 640

Gly Gly Ala Gly Thr Val Tyr Lys Gly Ser Met Pro Asp Gly Val Ile
                645                 650                 655

Ile Ala Ile Lys Arg Leu Asp Arg Arg Gly Thr Gly Arg Arg Asp Leu
            660                 665                 670

Gly Phe Ser Ala Glu Ile Lys Thr Leu Gly Arg Ile Arg His Arg His
        675                 680                 685

Ile Ile Arg Leu Leu Gly Tyr Ala Ser Asn Arg Asp Thr Asn Leu Leu
    690                 695                 700

Leu Tyr Glu Tyr Met Pro Asn Gly Ser Leu Ser Gly Ile Leu His Gly
705                 710                 715                 720

Thr Asn Gly Ala Asn Leu Leu Trp Glu Met Arg Phe Arg Ile Ala Val
                725                 730                 735

Glu Ala Ala Lys Gly Leu Cys Tyr Leu His His Asp Cys Ser Pro Pro
            740                 745                 750

Ile Ile His Arg Asp Val Lys Ser Asn Asn Ile Leu Leu Thr Ser Asp
        755                 760                 765

Tyr Ile Ala Cys Ile Ala Asp Phe Gly Leu Ala Lys Ser
    770                 775                 780

<210> SEQ ID NO 236
<211> LENGTH: 4
<212> TYPE: PRT
<213> ORGANISM: Artificial sequence
<220> FEATURE:
<223> OTHER INFORMATION: motif 1 of a CLV1 polypeptide
<220> FEATURE:
<221> NAME/KEY: UNSURE
<222> LOCATION: (2)..(2)
<223> OTHER INFORMATION: Xaa can be any naturally occurring amino acid

<400> SEQUENCE: 236

Leu Xaa Asp Trp
1

<210> SEQ ID NO 237
<211> LENGTH: 11
<212> TYPE: PRT
<213> ORGANISM: Artificial sequence
<220> FEATURE:
<223> OTHER INFORMATION: motif 2 of a CLV1 polypeptide
<220> FEATURE:
<221> NAME/KEY: VARIANT
<222> LOCATION: (1)..(1)
<223> OTHER INFORMATION: Xaa is Ala or Pro
<220> FEATURE:
<221> NAME/KEY: UNSURE
<222> LOCATION: (4)..(4)
<223> OTHER INFORMATION: Xaa can be any naturally occurring amino acid
```

```
<220> FEATURE:
<221> NAME/KEY: VARIANT
<222> LOCATION: (6)..(6)
<223> OTHER INFORMATION: Xaa is Ser or Thr
<220> FEATURE:
<221> NAME/KEY: VARIANT
<222> LOCATION: (9)..(9)
<223> OTHER INFORMATION: Xaa is Ser, Thr, or Lys

<400> SEQUENCE: 237

Xaa His Cys Xaa Phe Xaa Gly Val Xaa Cys Asp
1               5                   10

<210> SEQ ID NO 238
<211> LENGTH: 56
<212> TYPE: DNA
<213> ORGANISM: Artificial sequence
<220> FEATURE:
<223> OTHER INFORMATION: primer: prm08591

<400> SEQUENCE: 238
ggggacaagt ttgtacaaaa aagcaggctt aaacaatggc gatgagactt ttgaag        56

<210> SEQ ID NO 239
<211> LENGTH: 51
<212> TYPE: DNA
<213> ORGANISM: Artificial sequence
<220> FEATURE:
<223> OTHER INFORMATION: primer: prm08592

<400> SEQUENCE: 239
ggggaccact ttgtacaaga aagctgggtc gctacgtaac caagaagtca c             51

<210> SEQ ID NO 240
<211> LENGTH: 1243
<212> TYPE: DNA
<213> ORGANISM: Oryza sativa

<400> SEQUENCE: 240
aaaaccaccg agggacctga tctgcaccgg ttttgatagt tgagggaccc gttgtgtctg      60
gttttccgat cgagggacga aaatcggatt cggtgtaaag ttaagggacc tcagatgaac     120
ttattccgga gcatgattgg gaagggagga cataaggccc atgtcgcatg tgtttggacg     180
gtccagatct ccagatcact cagcaggatc ggccgcgttc gcgtagcacc cgcggtttga     240
ttcggcttcc cgcaaggcgg cggccggtgg ccgtgccgcc gtagcttccg ccggaagcga     300
gcacgccgcc gccgccgacc cggctctgcg tttgcaccgc cttgcacgcg atacatcggg     360
atagatagct actactctct ccgtttcaca atgtaaatca ttctactatt ttccacattc     420
atattgatgt taatgaatat agacatatat atctatttag attcattaac atcaatatga     480
atgtaggaaa tgctagaatg acttacattg tgaattgtga aatggacgaa gtacctacga     540
tggatggatg caggatcatg aaagaattaa tgcaagatcg tatctgccgc atgcaaaatc     600
ttactaattg cgctgcatat atgcatgaca gcctgcatgc gggcgtgtaa gcgtgttcat     660
ccattaggaa gtaaccttgt cattacttat accagtacta catactatat agtattgatt     720
tcatgagcaa atctacaaaa ctggaaagca ataaggaata cgggactgga aaagactcaa     780
cattaatcac caaatatttc gccttctcca gcagaatata tatctctcca tcttgatcac     840
tgtacacact gacagtgtac gcataaacgc agcagccagc ttaactgtcg tctcaccgtc     900
gcacactggc cttccatctc aggctagctt tctcagccac ccatcgtaca tgtcaactcg     960
gcgcgcgcac aggcacaaat tacgtacaaa acgcatgacc aaatcaaaac caccggagaa    1020
```

```
gaatcgctcc cgcgcgcggc ggcggcgcgc acgtacgaat gcacgcacgc acgcccaacc    1080
ccacgacacg atcgcgcgcg acgccggcga caccggccat ccacccgcgc cctcacctcg    1140
ccgactataa atacgtaggc atctgcttga tcttgtcatc catctcacca ccaaaaaaaa    1200
aggaaaaaaa aacaaaacac accaagccaa ataaaagcga caa                     1243
```

```
<210> SEQ ID NO 241
<211> LENGTH: 230
<212> TYPE: PRT
<213> ORGANISM: Artificial sequence
<220> FEATURE:
<223> OTHER INFORMATION: C-terminal domain of SEQ ID NO: 212

<400> SEQUENCE: 241

Arg Leu Leu Gly Tyr Val Ala Asn Lys Asp Thr Asn Leu Leu Leu Tyr
1               5                  10                  15

Glu Tyr Met Pro Asn Gly Ser Leu Gly Glu Leu Leu His Gly Ser Lys
            20                  25                  30

Gly Gly His Leu Gln Trp Glu Thr Arg His Arg Val Ala Val Glu Ala
        35                  40                  45

Ala Lys Gly Leu Cys Tyr Leu His His Asp Cys Ser Pro Leu Ile Leu
    50                  55                  60

His Arg Asp Val Lys Ser Asn Asn Ile Leu Leu Asp Ser Asp Phe Glu
65                  70                  75                  80

Ala His Val Ala Asp Phe Gly Leu Ala Lys Phe Leu Val Asp Gly Ala
                85                  90                  95

Ala Ser Glu Cys Met Ser Ser Ile Ala Gly Ser Tyr Gly Tyr Ile Ala
            100                 105                 110

Pro Glu Tyr Ala Tyr Thr Leu Lys Val Asp Glu Lys Ser Asp Val Tyr
        115                 120                 125

Ser Phe Gly Val Val Leu Leu Glu Leu Ile Ala Gly Lys Lys Pro Val
    130                 135                 140

Gly Glu Phe Gly Glu Gly Val Asp Ile Val Arg Trp Val Arg Asn Thr
145                 150                 155                 160

Glu Glu Glu Ile Thr Gln Pro Ser Asp Ala Ala Ile Val Val Ala Ile
                165                 170                 175

Val Asp Pro Arg Leu Thr Gly Tyr Pro Leu Thr Ser Val Ile His Val
            180                 185                 190

Phe Lys Ile Ala Met Met Cys Val Glu Glu Glu Ala Ala Ala Arg Pro
        195                 200                 205

Thr Met Arg Glu Val Val His Met Leu Thr Asn Pro Pro Lys Ser Val
    210                 215                 220

Ala Asn Leu Ile Ala Phe
225                 230
```

TRANSGENIC PLANTS COMPRISING AS TRANSGENE A CLASS I TCP OR CLAVATA 1 (CLV1) OR CAH3 POLYPEPTIDE HAVING INCREASED SEED YIELD AND A METHOD FOR MAKING THE SAME

RELATED APPLICATIONS

This application is a national stage application (under 35 U.S.C. §371) of PCT/EP2007/062720, filed Nov. 22, 2007, which claims benefit of European application 06124785.4, filed Nov. 24, 2006, European Application 06125156.7, filed Nov. 30, 2006, U.S. Provisional Application 60/868,381, filed Dec. 4, 2006, European Application 06126018.8, filed Dec. 13, 2006, U.S. Provisional Application 60/883,166, filed Jan. 3, 2007, and U.S. Provisional Application 60/883,170, filed Jan. 3, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Revised_Sequence_List__14546__00047_US. The size of the text file is 551 KB, and the text file was created on Apr 24, 2010.

The present invention relates generally to the field of molecular biology and concerns a method for enhancing various economically important yield-related traits in plants. More specifically, the present invention concerns a method for enhancing various economically important yield-related traits in plants relative to control plants, by increasing expression in a plant of a nucleic acid sequence encoding a Yield-Enhancing Polypeptide (YEP). The YEP may be a Class I TCP or a CAH3 or a Clavata1 (CLV1) polypeptide with a non-functional C-terminal domain. The present invention also concerns plants having increased expression of a nucleic acid sequence encoding a YEP, which plants have enhanced yield-related traits in plants relative to control plants. The invention also provides constructs useful in the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing the above-mentioned factors may therefore contribute to increasing crop yield.

The ability to increase plant yield would have many applications in areas such as agriculture, including in the production of ornamental plants, arboriculture, horticulture and forestry. Increasing yield may also find use in the production of algae for use in bioreactors (for the biotechnological production of substances such as pharmaceuticals, antibodies or vaccines, or for the bioconversion of organic waste) and other such areas.

Depending on the end use, the modification of certain yield traits may be favoured over others. For example, for applications such as forage or wood production, or bio-fuel resource, an increase in the vegetative parts of a plant may be desirable, and for applications such as flour, starch or oil production, an increase in seed parameters may be particularly desirable. Even amongst the seed parameters, some may be favoured over others, depending on the application. Various mechanisms may contribute to increasing seed yield, whether that is in the form of increased seed size or increased seed number.

Seed yield is a particularly important trait, since the seeds of many plants are important for human and animal nutrition. Crops such as, corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, stalks, leaves and stems into the growing seed. The endosperm, in particular, assimilates the metabolic precursors of carbohydrates, oils and proteins and synthesizes them into storage macromolecules to fill out the grain.

Another important trait for many crops is early vigour. Improving early vigour is an important objective of modern rice breeding programs in both temperate and tropical rice cultivars. Long roots are important for proper soil anchorage in water-seeded rice. Where rice is sown directly into flooded fields, and where plants must emerge rapidly through water, longer shoots are associated with vigour. Where drill-seeding is practiced, longer mesocotyls and coleoptiles are important for good seedling emergence. The ability to engineer early vigour into plants would be of great importance in agriculture. For example, poor early vigour has been a limitation to the introduction of maize (*Zea mays* L.) hybrids based on Corn Belt germplasm in the European Atlantic.

A further important trait is that of improved abiotic stress tolerance. Abiotic stress is a primary cause of crop loss worldwide, reducing average yields for most major crop plants by more than 50% (Wang et al., Planta (2003) 218: 1-14). Abiotic stresses may be caused by drought, salinity, extremes of temperature, chemical toxicity and oxidative stress. The ability to improve plant tolerance to abiotic stress would be of great economic advantage to farmers worldwide and would allow for the cultivation of crops during adverse conditions and in territories where cultivation of crops may not otherwise be possible.

Another economically important trait is that of increased biomass. Plant biomass is yield for forage crops like alfalfa, silage corn and hay. Many proxies for yield have been used in grain crops. Chief amongst these are estimates of plant size.

Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679). In this way a standard environment is used as a proxy for the diverse and dynamic environments encountered at different locations and times by crops in the field.

Harvest index, the ratio of seed yield to aboveground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73). Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

One approach to increasing yield (seed yield and/or biomass) in plants may be through modification of the inherent growth mechanisms of a plant, such as the cell cycle or various signalling pathways involved in plant growth or in defense mechanisms.

It has now been found that various yield-related traits may be improved in plants by modulating expression in a plant of a nucleic acid encoding a Yield-Enahancing Polypeptide (YEP) in a plant, wherein the YEP is either a Class I TCP or a CAH3 or a Clavata1 (CLV1) polypeptide with a non-functional C-terminal domain.

BACKGROUND

Tcp

Transcription factors are usually defined as proteins that show sequence-specific DNA binding affinity and that are capable of activating and/or repressing transcription. The *Arabidopsis thaliana* genome codes for at least 1533 transcriptional regulators, accounting for ~5.9% of its estimated total number of genes (Riechmann et al. (2000) Science 290: 2105-2109). The TCP family of transcription factors is named after its first characterized members (teosinte-branched1 (TB1), cycloidea (CYC) and PCNA factor (PCF); Cubas P et al. (1999) Plant J 18(2): 215-22). In *Arabidopsis thaliana*, more than 20 members of the TCP family polypeptides have been identified, and classified based on sequence similarity in the TCP domain into Class I (also called Group I or PCF group) transcription factors that positively regulate gene expression, and Class II (also called Group II or CYC-TB1 group) transcription factors that negatively regulate proliferation. All TCP transcription factors are characterized by a non-canonical predicted basic-Helix-Loop-Helix (bHLH), that is required for both DNA binding and homo- and heterodimerization (see Cubas et al. above).

One Class I TCP polypeptide, AtTCP20 (also named PCF1 orthologue), binds to the promoter of cell cycle and ribosomal protein genes, as reported in Li et al. (2005) PNAS 102(36): 12978-83). International Patent Application WO0036124 provides a nucleic acid sequence encoding a Class I TCP polypeptide (named VBDBP) and the corresponding polypeptide sequence. Expression vectors and transgenic plants comprising the aforementioned VBDBP nucleic acid sequence are described. In International Patent Application WO2004031349, transgenic *Arabidopsis thaliana* plants overexpressing (using a 35CaMV promoter) a nucleic acid sequence encoding a Class I TCP polypeptide (named G1938) are characterized. Retarded plant growth rate and development are observed.

CAH3

Carbonic anhydrase catalyses the reversible reaction $H_2CO_3 \leftrightharpoons H_2O + CO_2$. There are 3 classes of carbonic anhydrases (alpha, beta and gamma), phylogenetically unrelated but sharing some similarities at the active site. In plants, all three classes exist. Carbonic anhydrases are present in chloroplasts, mitochondria (mostly gamma class) and cytosol, and may represent up to 2% of total soluble proteins in leaves. Carbonic anhydrase is important for ensuring efficient photosynthesis by maintaining $CO_2$ concentration in cells at a suitable level. It is known that at atmospheric $O_2$ and $CO_2$ pressure, ribulose bisphosphate carboxylase (Rubisco) works at 30% of its total capacity, hence there is interest in improving the $CO_2$ uptake mechanism in plants. Carbonic anhydrase expression is co-regulated with the expression of Rubisco, and plants generally maintain a constant carbonic anhydrase versus Rubisco ratio. It is furthermore reported that carbonic anhydrase may also limit photorespiration by providing C-skeletons for nitrogen assimilation under certain conditions. In plants with a C3 type of photosynthesis, most of the carbonic anhydrase activity is localized to the stroma of the mesophyll chloroplasts, whereas in C4 plants, most of the carbonic anhydrase is found in the cytoplasm of mesophyll cells.

The idea of using carbonic anhydrase for increasing $CO_2$ assimilation has been formulated many times. In WO9511979, it is postulated that transforming a monocotyledonous plant with a carbonic anhydrase from a monocotyledonous plant the ability of carbon dioxide fixation would be improved and would result in accelerated plant growth. Other documents disclose methods for mimicking a C4 type photosynthesis in C3 plants thereby improving the efficiency of photosynthesis (for example U.S. Pat. Nos. 6,610,913, 6,831,217 or US 20030233670). In these approaches, a C4-like pathway is introduced in C3 plants by introducing and expressing a combination of various enzyme activities (such as phosphoenolpyruvate carboxylase (PEPC) or pyruvate orthophosphate dikinase (PPDK)) from C4 plants to increase $CO_2$ fixation; expression of these genes is under control of C4 regulatory sequences, typically their native promoters. Although predicted however, these attempts did not result yet in plants with increased yield.

Clavata

Leucine-rich repeat receptor-like kinases (LRR-RLKs) are polypeptides involved in two biological functions in plants, i.e., growth and development on one hand, and defense response on the other. LRR-RLKs are transmembrane polypeptides involved in signal transduction, with from N-terminus to C-terminus: (i) a signal peptide for ER subcellular targeting; (ii) an extracellular receptor domain to perceive signals; (iii) a transmembrane domain; and (iv) an intracellular cytoplasmic serine/threonine kinase domain that can phosphorylate downstream target proteins, be phosphorylated by itself (autophosphorylation) or by other kinases, or be dephosphorylated by phosphatases.

LRR-RLKs comprise the largest group within the plant receptor-like kinase (RLK) superfamily, and the *Arabidopsis* genome alone contains over 200 LRR-RLK genes. Members of this family have been categorized into subfamilies based on both the identity of the extracellular domains and the phylogenetic relationships between the kinase domains of subfamily members (Shiu & Bleecker (2001) Proc Natl Aced Sc USA 98(19): 10763-10768). The subfamily LRR XI comprises one of the most studied LRR-RLK, Clavata1 (CLV1; Leyser et al., (2002) Development 116:397-403), involved in the control of shoot, inflorescence, and floral meristem size.

The shoot apical meristem can initiate organs and secondary meristems throughout the life of a plant. A few cells located in the central zone of the meristem act as pluripotent stem cells. They divide slowly, thereby displacing daughter cells outwards to the periphery where they eventually become incorporated into organ primordia and differentiate. The maintenance of a functional meristem requires coordination between the loss of stem cells from the meristem through differentiation and replacement of cells through division. In *Arabidopsis*, the Clavata (CLV1, CLV2, and CLV3) genes play a critical role in this process, by limiting the size of the stem cell pool in these meristems.

Clavata1 mutants have been identified in *Arabidopsis* (Leyser et al. see above; Clark et al., (1993) Development 119: 397-418; Diévart et al., (2003) Plant Cell 15: 1198-1211), in rice (Suzaki et al., (2004) Development 131: 5649-5657), and in corn (Bommert et al., (2004) Development 132: 1235-1245). All mutants present an enlargement of the aboveground meristems of all types (vegetative, inflorescence, floral) due to ectopic accumulation of stem cells, leading often to abnormal phyllotaxy, inflorescence fasciation and extra floral organs and whorls. This phenotypic severity varies between the different *Arabidopsis* mutants, the weaker alleles presenting only a small increase in stem cell number, whereas the strong alleles have more than 1000 fold more stem cells compared with the wild type (Dievart et al., (2004) supra).

The number of carpels formed per flower and the extent of growth of the ectopic whorls are sensitive indicators of clv1 mutant severity (Clarke et al., (1993) Development 119: 397-418). Two weak *Arabidopsis* mutants, clv1-6 and clv1-7, contain lesions after the transmembrane domain, leaving the possibility that the polypeptides these alleles encode are actually expressed and located to the plasma membrane (Clarke et al., (1993) supra).

Transgenic *Arabidopsis* plants expressing the nucleic acid sequence encoding the full length CLV1 polypeptide under the control of the ERECTA promoter (ER; for broad expression within the meristems and developing organ primordial) do not present a disrupted meristem (Clarke et al., (1993) supra). Granted U.S. Pat. No. 5,859,338 provides for an isolated nucleic acid sequence encoding a Clavata1 protein, and modified nucleic acid sequences encoding a modified Clavata1 protein, and describes expression vectors comprising the aforementioned isolated nucleic acid sequences, and plants and plant cells comprising the aforementioned isolated nucleic acid sequences.

DEFINITIONS

Polypeptide(s)/Protein(s)

The terms "polypeptide" and "protein" are used interchangeably herein and refer to amino acids in a polymeric form of any length, linked together by peptide bonds.

Polynucleotide(s)/Nucleic Acid(s)/Nucleic Acid Sequence(s)/Nucleotide Sequence(s)

The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

Coding Sequence

A "coding sequence" is a nucleic acid sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleic acid sequences or genomic DNA, whether with or without.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

Orthologue(s)/Paralogue(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The Tm is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA hybrids (Meinkoth and Wahl, Anal. Biochem., 138: 267-284, 1984):

$$T_m = 81.5°C. + 16.6 \times \log_{10}[Na^+]^a + 0.41 \times \%[G/C^b] - 500 \times [L^c]^{-1} - 0.61 \times \% \text{ formamide}$$

2) DNA-RNA or RNA-RNA hybrids:

$$Tm = 79.8 + 18.5(\log_{10}[Na^+]^a) + 0.58(\% G/C^b) + 11.8(\% G/C^b)^2 - 820/L^c$$

3) oligo-DNA or oligo-RNA$^d$ hybrids:

For <20 nucleotides: $T_m = 2(I_n)$

For 20-35 nucleotides: $T_m = 22 + 1.46(I_n)$ $^a$ or for other monovalent cation, but only accurate in the 0.01-0.4 M range.
$^b$ only accurate for % GC in the 30% to 75% range.
$^c$ L=length of duplex in base pairs.
$^d$ oligo, oligonucleotide; $I_n$,=effective length of primer=2× (no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 µg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3$^{rd}$ Edition, Cold Spring Harbor Laboratory Press, CSH, New York or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex (2005) BMC Bioinformatics 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (IN-DELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acids or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. Control sequences may be promoters, enhancers, silencers, intron sequences, 3'UTR and/or 5'UTR regions and/or RNA stabilizing elements.

The term "promoter" typically refers to a nucleic acid control sequence located upstream from the transcriptional start of a gene and which is involved in recognising and binding of RNA polymerase and other proteins, thereby directing transcription of an operably linked nucleic acid.

Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about $1/10,000$ transcripts to about $1/100,000$ transcripts, to about $1/500,0000$ transcripts per cell. Conversely, a "strong promoter" drives expression of a coding sequence at high level, or at about $1/10$ transcripts to about $1/100$ transcripts to about $1/1000$ transcripts per cell.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table 2a below gives examples of constitutive promoters.

TABLE 2a

Examples of constitutive promoters

| Gene Source | Reference |
|---|---|
| Actin | McElroy et al, Plant Cell, 2: 163-171, 1990 |
| HMGP | WO 2004/070039 |
| CAMV 35S | Odell et al, Nature, 313: 810-812, 1985 |
| CaMV 19S | Nilsson et al., Physiol. Plant. 100: 456-462, 1997 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| 34S FMV | Sanger et al., Plant. Mol. Biol., 14, 1990: 433-443 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |
| nos | Shaw et al. (1984) Nucleic Acids Res. 12(20): 7831-7846 |
| V-ATPase | WO 01/14572 |
| Super promoter | WO 95/14098 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

Examples of root-specific promoters are listed in Table 2b below:

TABLE 2b

Examples of root-specific promoters

| Gene Source | Reference |
| --- | --- |
| RCc3 | Plant Mol Biol. 1995 Jan; 27(2): 237-48 |
| *Arabidopsis* PHT1 | Kovama et al., 2005; Mudge et al. (2002, Plant J. 31: 341) |
| Medicago phosphate transporter | Xiao et al., 2006 |
| *Arabidopsis* Pyk10 | Nitz et al. (2001) Plant Sci 161(2): 337-346 |
| root-expressible genes | Tingey et al., EMBO J. 6: 1, 1987. |
| tobacco auxin-inducible gene | Van der Zaal et al., Plant Mol. Biol. 16, 983, 1991. |
| β-tubulin | Oppenheimer, et al., Gene 63: 87, 1988. |
| tobacco root-specific genes | Conkling, et al., Plant Physiol. 93: 1203, 1990. |
| *B. napus* G1-3b gene | U.S. Pat. No. 5,401,836 |
| SbPRP1 | Suzuki et al., Plant Mol. Biol. 21: 109-119, 1993. |
| LRX1 | Baumberger et al. 2001, Genes & Dev. 15: 1128 |
| BTG-26 *Brassica napus* | US 20050044585 |
| LeAMT1 (tomato) | Lauter et al. (1996, PNAS 3: 8139) |
| The LeNRT1-1 (tomato) | Lauter et al. (1996, PNAS 3: 8139) |
| class I patatin gene (potato) | Liu et al., Plant Mol. Biol. 153: 386-395, 1991. |
| KDC1 (*Daucus carota*) | Downey et al. (2000, J. Biol. Chem. 275: 39420) |
| TobRB7 gene | W Song (1997) PhD Thesis, North Carolina State University, Raleigh, NC USA |
| OsRAB5a (rice) | Wang et al. 2002, Plant Sci. 163: 273 |
| ALF5 (*Arabidopsis*) | Diener et al. (2001, Plant Cell 13: 1625) |
| NRT2;1Np (*N. plumbaginifolia*) | Quesada et al. (1997, Plant Mol. Biol. 34: 265) |

A seed-specific promoter is transcriptionally active predominantly in seed tissue, but not necessarily exclusively in seed tissue (in cases of leaky expression). The seed-specific promoter may be active during seed development and/or during germination. The seed specific promoter may be endosperm and/or aleurone and/or embryo specific. Examples of seed-specific promoters (endosperm/aleurone/embryo specific) are shown in Tables 2c-f below. Further examples of seed-specific promoters are given in Qing Qu and Takaiwa (Plant Biotechnol. J. 2, 113-125, 2004), which disclosure is incorporated by reference herein as if fully set forth.

TABLE 2c

Examples of seed-specific promoters

| Gene source | Reference |
| --- | --- |
| seed-specific genes | Simon et al., Plant Mol. Biol. 5: 191, 1985; Scofield et al., J. Biol. Chem. 262: 12202, 1987.; Baszczynski et al., Plant Mol. Biol. 14: 633, 1990. |
| Brazil Nut albumin | Pearson et al., Plant Mol. Biol. 18: 235-245, 1992. |
| legumin | Ellis et al., Plant Mol. Biol. 10: 203-214, 1988. |
| glutelin (rice) | Takaiwa et al., Mol. Gen. Genet. 208: 15-22, 1986; Takaiwa et al., FEBS Letts. 221: 43-47, 1987. |
| zein | Matzke et al Plant Mol Biol, 14(3): 323-32 1990 |
| napA | Stalberg et al, Planta 199: 515-519, 1996. |
| wheat LMW and HMW glutenin-1 | Mol Gen Genet 216: 81-90, 1989; NAR 17: 461-2, 1989 |
| wheat SPA | Albani et al, Plant Cell, 9: 171-184, 1997 |
| wheat α,β,γ-gliadins | EMBO J. 3: 1409-15, 1984 |
| barley Itr1 promoter | Diaz et al. (1995) Mol Gen Genet 248(5): 592-8 |
| barley B1, C, D, hordein | Theor Appl Gen 98: 1253-62, 1999; Plant J 4: 343-55, 1993; Mol Gen Genet 250: 750-60, 1996 |
| barley DOF | Mena et al, The Plant Journal, 116(1): 53-62, 1998 |
| blz2 | EP99106056.7 |
| synthetic promoter | Vicente-Carbajosa et al., Plant J. 13: 629-640, 1998. |
| rice prolamin NRP33 | Wu et al, Plant Cell Physiology 39(8) 885-889, 1998 |
| rice a-globulin Glb-1 | Wu et al, Plant Cell Physiology 39(8) 885-889, 1998 |
| rice OSH1 | Sato et al, Proc. Natl. Acad. Sci. USA, 93: 8117-8122, 1996 |
| rice α-globulin REB/OHP-1 | Nakase et al. Plant Mol. Biol. 33: 513-522, 1997 |
| rice ADP-glucose pyrophosphorylase | Trans Res 6: 157-68, 1997 |
| maize ESR gene family | Plant J 12: 235-46, 1997 |
| *sorghum* α-kafirin | DeRose et al., Plant Mol. Biol 32: 1029-35, 1996 |
| KNOX | Postma-Haarsma et al, Plant Mol. Biol. 39: 257-71, 1999 |
| rice oleosin | Wu et al, J. Biochem. 123: 386, 1998 |
| sunflower oleosin | Cummins et al., Plant Mol. Biol. 19: 873-876, 1992 |
| PRO0117, putative rice 40S ribosomal protein | WO 2004/070039 |

TABLE 2c-continued

Examples of seed-specific promoters

| Gene source | Reference |
| --- | --- |
| PRO0136, rice alanine aminotransferase | unpublished |
| PRO0147, trypsin inhibitor ITR1 (barley) | unpublished |
| PRO0151, rice WSI18 | WO 2004/070039 |
| PRO0175, rice RAB21 | WO 2004/070039 |
| PRO005 | WO 2004/070039 |
| PRO0095 | WO 2004/070039 |
| α-amylase (Amy32b) | Lanahan et al, Plant Cell 4: 203-211, 1992; Skriver et al, Proc Natl Acad Sci USA 88: 7266-7270, 1991 |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

TABLE 2d examples of endosperm-specific promoters

| Gene source | Reference |
| --- | --- |
| glutelin (rice) | Takaiwa et al. (1986) Mol Gen Genet 208: 15-22; Takaiwa et al. (1987) FEBS Letts. 221: 43-47 |
| zein | Matzke et al., (1990) Plant Mol Biol 14(3): 323-32 |
| wheat LMW and HMW glutenin-1 | Colot et al. (1989) Mol Gen Genet 216: 81-90, Anderson et al. (1989) NAR 17: 461-2 |
| wheat SPA | Albani et al. (1997) Plant Cell 9: 171-184 |
| wheat gliadins | Rafalski et al. (1984) EMBO 3: 1409-15 |
| barley Itr1 promoter | Diaz et al. (1995) Mol Gen Genet 248(5): 592-8 |
| barley B1, C, D, hordein | Cho et al. (1999) Theor Appl Genet 98: 1253-62; Muller et al. (1993) Plant J 4: 343-55; Sorenson et al. (1996) Mol Gen Genet 250: 750-60 |
| barley DOF | Mena et al, (1998) Plant J 116(1): 53-62 |
| blz2 | Onate et al. (1999) J Biol Chem 274(14): 9175-82 |
| synthetic promoter | Vicente-Carbajosa et al. (1998) Plant J 13: 629-640 |
| rice prolamin NRP33 | Wu et al, (1998) Plant Cell Physiol 39(8) 885-889 |
| rice globulin Glb-1 | Wu et al. (1998) Plant Cell Physiol 39(8) 885-889 |
| rice globulin REB/OHP-1 | Nakase et al. (1997) Plant Molec Biol 33: 513-522 |
| rice ADP-glucose pyrophosphorylase | Russell et al. (1997) Trans Res 6: 157-68 |
| maize ESR gene family | Opsahl-Ferstad et al. (1997) Plant J 12: 235-46 |
| *sorghum* kafirin | DeRose et al. (1996) Plant Mol Biol 32: 1029-35 |

TABLE 2e

Examples of embryo specific promoters:

| Gene source | Reference |
| --- | --- |
| rice OSH1 | Sato et al, Proc. Natl. Acad. Sci. USA, 93: 8117-8122, 1996 |
| KNOX | Postma-Haarsma et al, Plant Mol. Biol. 39: 257-71, 1999 |
| PRO0151 | WO 2004/070039 |
| PRO0175 | WO 2004/070039 |
| PRO005 | WO 2004/070039 |
| PRO0095 | WO 2004/070039 |

TABLE 2f

Examples of aleurone-specific promoters:

| Gene source | Reference |
| --- | --- |
| α-amylase (Amy32b) | Lanahan et al, Plant Cell 4: 203-211, 1992; Skriver et al, Proc Natl Acad Sci USA 88: 7266-7270, 1991 |
| cathepsin β-like gene | Cejudo et al, Plant Mol Biol 20: 849-856, 1992 |
| Barley Ltp2 | Kalla et al., Plant J. 6: 849-60, 1994 |
| Chi26 | Leah et al., Plant J. 4: 579-89, 1994 |
| Maize B-Peru | Selinger et al., Genetics 149; 1125-38, 1998 |

A green tissue-specific promoter as defined herein is a promoter that is transcriptionally active predominantly in green tissue, substantially to the exclusion of any other parts of a plant, whilst still allowing for any leaky expression in these other plant parts.

Examples of green tissue-specific promoters which may be used to perform the methods of the invention are shown in Table 2g below.

TABLE 2g

Examples of green tissue-specific promoters

| Gene | Expression | Reference |
| --- | --- | --- |
| Maize Orthophosphate dikinase | Leaf specific | Fukayama et al., 2001 |
| Maize Phosphoenolpyruvate | Leaf specific | Kausch et al., 2001 |

TABLE 2g-continued

Examples of green tissue-specific promoters

| Gene | Expression | Reference |
| --- | --- | --- |
| carboxylase | | |
| Rice Phosphoenolpyruvate carboxylase | Leaf specific | Liu et al., 2003 |
| Rice small subunit Rubisco | Leaf specific | Nomura et al., 2000 |
| rice beta expansin EXBP9 | Shoot specific | WO 2004/070039 |
| Pigeonpea small subunit Rubisco | Leaf specific | Panguluri et al., 2005 |
| Pea RBCS3A | Leaf specific | |

Another example of a tissue-specific promoter is a meristem-specific promoter, which is transcriptionally active predominantly in meristematic tissue, substantially to the exclusion of any other parts of a plant, whilst still allowing for any leaky expression in these other plant parts. Examples of green meristem-specific promoters which may be used to perform the methods of the invention are shown in Table 2h below.

TABLE 2h

Examples of meristem-specific promoters

| Gene source | Expression pattern | Reference |
| --- | --- | --- |
| rice OSH1 | Shoot apical meristem, from embryo globular stage to seedling stage | Sato et al. (1996) Proc. Natl. Acad. Sci. USA, 93: 8117-8122 |
| Rice metallothionein | Meristem specific | BAD87835.1 |
| WAK1 & WAK 2 | Shoot and root apical meristems, and in expanding leaves and sepals | Wagner & Kohorn (2001) Plant Cell 13(2): 303-318 |

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Modulation

The term "modulation" means in relation to expression or gene expression, a process in which the expression level is changed by said gene expression in comparison to the control plant, the expression level may be increased or decreased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased yield and/or increased growth of the plants.

Expression

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

Increased Expression/Overexpression

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell. biol. 8: 4395-4405; Callis et al. (1987) Genes Dev 1:1183-1200). Such intron enhancement of gene expression is typically greatest when placed near the 5' end of the transcription unit. Use of the maize introns Adh1-5 intron 1, 2, and 6, the Bronze-1 intron are known in the art. For general information see: The Maize Handbook, Chapter 116, Freeling and Walbot, Eds., Springer, N.Y. (1994).

Endogenous Gene

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene). For example, a transgenic plant containing such a transgene may encounter a substantial reduction of the transgene expression and/or substantial reduction of expression of the endogenous gene. The isolated gene may be isolated from an organism or may be manmade, for example by chemical synthesis.

Decreased Expression

Reference herein to "decreased epression" or "reduction or substantial elimination" of expression is taken to mean a decrease in endogenous gene expression and/or polypeptide levels and/or polypeptide activity relative to control plants. The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control plants.

For the reduction or substantial elimination of expression an endogenous gene in a plant, a sufficient length of substantially contiguous nucleotides of a nucleic acid sequence is required. In order to perform gene silencing, this may be as little as 20, 19, 18, 17, 16, 15, 14, 13, 12, 11, 10 or fewer nucleotides, alternatively this may be as much as the entire gene (including the 5' and/or 3' UTR, either in part or in whole). The stretch of substantially contiguous nucleotides may be derived from the nucleic acid encoding the protein of interest (target gene), or from any nucleic acid capable of encoding an orthologue, paralogue or homologue of the protein of interest. Preferably, the stretch of substantially contiguous nucleotides is capable of forming hydrogen bonds with the target gene (either sense or antisense strand), more preferably, the stretch of substantially contiguous nucleotides has, in increasing order of preference, 50%, 60%, 70%, 80%, 85%, 90%, 95%, 96%, 97%, 98%, 99%, 100% sequence identity to the target gene (either sense or antisense strand). A nucleic acid sequence encoding a (functional) polypeptide is not a requirement for the various methods discussed herein for the reduction or substantial elimination of expression of an endogenous gene.

This reduction or substantial elimination of expression may be achieved using routine tools and techniques. A preferred method for the reduction or substantial elimination of endogenous gene expression is by introducing and expressing in a plant a genetic construct into which the nucleic acid (in this case a stretch of substantially contiguous nucleotides derived from the gene of interest, or from any nucleic acid capable of encoding an orthologue, paralogue or homologue of any one of the protein of interest) is cloned as an inverted repeat (in part or completely), separated by a spacer (non-coding DNA).

In such a preferred method, expression of the endogenous gene is reduced or substantially eliminated through RNA-mediated silencing using an inverted repeat of a nucleic acid or a part thereof (in this case a stretch of substantially contiguous nucleotides derived from the gene of interest, or from any nucleic acid capable of encoding an orthologue, paralogue or homologue of the protein of interest), preferably capable of forming a hairpin structure. The inverted repeat is cloned in an expression vector comprising control sequences. A non-coding DNA nucleic acid sequence (a spacer, for example a matrix attachment region fragment (MAR), an intron, a polylinker, etc.) is located between the two inverted nucleic acids forming the inverted repeat. After transcription of the inverted repeat, a chimeric RNA with a self-complementary structure is formed (partial or complete). This double-stranded RNA structure is referred to as the hairpin RNA (hpRNA). The hpRNA is processed by the plant into siRNAs that are incorporated into an RNA-induced silencing complex (RISC). The RISC further cleaves the mRNA transcripts, thereby substantially reducing the number of mRNA transcripts to be translated into polypeptides. For further general details see for example, Grierson et al. (1998) WO 98/53083; Waterhouse et al. (1999) WO 99/53050).

Performance of the methods of the invention does not rely on introducing and expressing in a plant a genetic construct into which the nucleic acid is cloned as an inverted repeat, but any one or more of several well-known "gene silencing" methods may be used to achieve the same effects.

One such method for the reduction of endogenous gene expression is RNA-mediated silencing of gene expression (downregulation). Silencing in this case is triggered in a plant by a double stranded RNA sequence (dsRNA) that is substantially similar to the target endogenous gene. This dsRNA is further processed by the plant into about 20 to about 26 nucleotides called short interfering RNAs (siRNAs). The siRNAs are incorporated into an RNA-induced silencing complex (RISC) that cleaves the mRNA transcript of the endogenous target gene, thereby substantially reducing the number of mRNA transcripts to be translated into a polypeptide. Preferably, the double stranded RNA sequence corresponds to a target gene.

Another example of an RNA silencing method involves the introduction of nucleic acid sequences or parts thereof (in this case a stretch of substantially contiguous nucleotides derived from the gene of interest, or from any nucleic acid capable of encoding an orthologue, paralogue or homologue of the protein of interest) in a sense orientation into a plant. "Sense orientation" refers to a DNA sequence that is homologous to an mRNA transcript thereof. Introduced into a plant would therefore be at least one copy of the nucleic acid sequence. The additional nucleic acid sequence will reduce expression of the endogenous gene, giving rise to a phenomenon known as co-suppression. The reduction of gene expression will be more pronounced if several additional copies of a nucleic acid sequence are introduced into the plant, as there is a positive correlation between high transcript levels and the triggering of co-suppression.

Another example of an RNA silencing method involves the use of antisense nucleic acid sequences. An "antisense" nucleic acid sequence comprises a nucleotide sequence that is complementary to a "sense" nucleic acid sequence encoding a protein, i.e. complementary to the coding strand of a double-stranded cDNA molecule or complementary to an mRNA transcript sequence. The antisense nucleic acid sequence is preferably complementary to the endogenous gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire nucleic acid sequence (in this case a stretch of substantially contiguous nucleotides derived from the gene of interest, or from any nucleic acid capable of encoding an orthologue, paralogue or homologue of the protein of interest), but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine substituted nucleotides may be used. Examples of modified nucleotides that may be used to generate the antisense nucleic acid sequences are well known in the art. Known nucleotide modifications include methylation, cyclization and 'caps' and substitution of one or more of the naturally occurring nucleotides with an analogue such as inosine. Other modifications of nucleotides are well known in the art.

The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention (whether introduced into a plant or generated in situ) hybridize with or bind to mRNA transcripts and/or genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using the vectors described herein.

According to a further aspect, the antisense nucleic acid sequence is an a-anomeric nucleic acid sequence. An a-anomeric nucleic acid sequence forms specific double-stranded hybrids with complementary RNA in which, contrary to the usual b-units, the strands run parallel to each other (Gaultier et al. (1987) Nucl Ac Res 15: 6625-6641). The antisense nucleic acid sequence may also comprise a 2'-o-methylribonucleotide (Inoue et al. (1987) Nucl Ac Res 15, 6131-6148) or a chimeric RNA-DNA analogue (Inoue et al. (1987) FEBS Lett. 215, 327-330).

The reduction or substantial elimination of endogenous gene expression may also be performed using ribozymes. Ribozymes are catalytic RNA molecules with ribonuclease activity that are capable of cleaving a single-stranded nucleic acid sequence, such as an mRNA, to which they have a complementary region. Thus, ribozymes (e.g., hammerhead ribozymes (described in Haselhoff and Gerlach (1988) Nature 334, 585-591) can be used to catalytically cleave mRNA transcripts encoding a polypeptide, thereby substantially reducing the number of mRNA transcripts to be translated into a polypeptide. A ribozyme having specificity for a nucleic acid sequence can be designed (see for example: Cech et al. U.S. Pat. No. 4,987,071; and Cech et al. U.S. Pat. No. 5,116,742). Alternatively, mRNA transcripts corresponding to a nucleic acid sequence can be used to select a catalytic RNA having a specific ribonuclease activity from a pool of RNA molecules (Bartel and Szostak (1993) Science 261, 1411-1418). The use of ribozymes for gene silencing in plants is known in the art (e.g., Atkins et al. (1994) WO 94/00012; Lenne et al. (1995) WO 95/03404; Lutziger et al. (2000) WO 00/00619; Prinsen et al. (1997) WO 97/13865 and Scott et al. (1997) WO 97/38116).

Gene silencing may also be achieved by insertion mutagenesis (for example, T-DNA insertion or transposon insertion) or by strategies as described by, among others, Angell and Baulcombe ((1999) Plant J 20(3): 357-62), (Amplicon VIGS WO 98/36083), or Baulcombe (WO 99/15682).

Gene silencing may also occur if there is a mutation on an endogenous gene and/or a mutation on an isolated gene/nucleic acid subsequently introduced into a plant. The reduction or substantial elimination may be caused by a non-functional polypeptide. For example, the polypeptide may bind to various interacting proteins; one or more mutation(s) and/or truncation(s) may therefore provide for a polypeptide that is still able to bind interacting proteins (such as receptor proteins) but that cannot exhibit its normal function (such as signalling ligand).

A further approach to gene silencing is by targeting nucleic acid sequences complementary to the regulatory region of the gene (e.g., the promoter and/or enhancers) to form triple helical structures that prevent transcription of the gene in target cells. See Helene, C., Anticancer Drug Res. 6, 569-84, 1991; Helene et al., Ann. N.Y. Acad. Sci. 660, 27-36 1992; and Maher, L. J. Bioassays 14, 807-15, 1992.

Other methods, such as the use of antibodies directed to an endogenous polypeptide for inhibiting its function in planta, or interference in the signalling pathway in which a polypeptide is involved, will be well known to the skilled man. In particular, it can be envisaged that manmade molecules may be useful for inhibiting the biological function of a target polypeptide, or for interfering with the signalling pathway in which the target polypeptide is involved.

Alternatively, a screening program may be set up to identify in a plant population natural variants of a gene, which variants encode polypeptides with reduced activity. Such natural variants may also be used for example, to perform homologous recombination.

Artificial and/or natural microRNAs (miRNAs) may be used to knock out gene expression and/or mRNA translation. Endogenous miRNAs are single stranded small RNAs of typically 19-24 nucleotides long. They function primarily to regulate gene expression and/or mRNA translation. Most plant microRNAs (miRNAs) have perfect or near-perfect complementarity with their target sequences. However, there are natural targets with up to five mismatches. They are processed from longer non-coding RNAs with characteristic fold-back structures by double-strand specific RNases of the Dicer family. Upon processing, they are incorporated in the RNA-induced silencing complex (RISC) by binding to its main component, an Argonaute protein. mRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA overexpression are thus often reflected in decreased mRNA levels of target genes.

Artificial microRNAs (amiRNAs), which are typically 21 nucleotides in length, can be genetically engineered specifically to negatively regulate gene expression of single or multiple genes of interest. Determinants of plant microRNA target selection are well known in the art. Empirical parameters for target recognition have been defined and can be used to aid in the design of specific amiRNAs, (Schwab et al., Dev. Cell 8, 517-527, 2005). Convenient tools for design and generation of amiRNAs and their precursors are also available to the public (Schwab et al., Plant Cell 18, 1121-1133, 2006).

For optimal performance, the gene silencing techniques used for reducing expression in a plant of an endogenous gene requires the use of nucleic acid sequences from monocotyledonous plants for transformation of monocotyledonous plants, and from dicotyledonous plants for transformation of dicotyledonous plants. Preferably, a nucleic acid sequence from any given plant species is introduced into that same species. For example, a nucleic acid sequence from rice is transformed into a rice plant. However, it is not an absolute requirement that the nucleic acid sequence to be introduced originates from the same plant species as the plant in which it will be introduced. It is sufficient that there is substantial homology between the endogenous target gene and the nucleic acid to be introduced.

Described above are examples of various methods for the reduction or substantial elimination of expression in a plant of an endogenous gene. A person skilled in the art would readily be able to adapt the aforementioned methods for silencing so as to achieve reduction of expression of an endogenous gene in a whole plant or in parts thereof through the use of an appropriate promoter, for example.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen. Genet. 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet. 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol. Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

T-DNA Activation Tagging

T-DNA activation tagging (Hayashi et al. Science (1992) 1350-1353), involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

TILLING

The term "TILLING" is an abbreviation of "Targeted Induced Local Lesions In Genomes" and refers to a mutagenesis technology useful to generate and/or identify nucleic acids encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet. 5(2): 145-50).

Homologous Recombination

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J. 9(10): 3077-84) but also for crop plants, for example rice (Terada et al. (2002) Nat Biotech 20(10): 1030-4; Iida and Terada (2004) Curr Opin Biotech 15(2): 132-8), and approaches exist that are generally applicable regardless of the target organism (Miller et al, Nature Biotechnol. 25, 778-785, 2007).

Yield

The term "yield" in general means a measurable produce of economic value, typically related to a specified crop, to an area, and to a period of time. Individual plant parts directly contribute to yield based on their number, size and/or weight, or the actual yield is the yield per square meter for a crop and year, which is determined by dividing total production (includes both harvested and appraised production) by planted square meters. The term "yield" of a plant may relate to vegetative biomass (root and/or shoot biomass), to reproductive organs, and/or to propagules (such as seeds) of that plant.

Early Vigour

"Early vigour" refers to active healthy well-balanced growth especially during early stages of plant growth, and may result from increased plant fitness due to, for example, the plants being better adapted to their environment (i.e. optimizing the use of energy resources and partitioning between shoot and root). Plants having early vigour also show increased seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

Increase/Improve/Enhance

The terms "increase", "improve" or "enhance" are interchangeable and shall mean in the sense of the application at least a 3%, 4%, 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per square meter; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased yield may also result in modified architecture, or may occur because of modified architecture.

Greenness Index

The "greenness index" as used herein is calculated from digital images of plants. For each pixel belonging to the plant object on the image, the ratio of the green value versus the red value (in the RGB model for encoding color) is calculated. The greenness index is expressed as the percentage of pixels for which the green-to-red ratio exceeds a given threshold. Under normal growth conditions, under salt stress growth conditions, and under reduced nutrient availability growth conditions, the greenness index of plants is measured in the last imaging before flowering. In contrast, under drought stress growth conditions, the greenness index of plants is measured in the first imaging after drought.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida), Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera), Eleusine coracana, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max), Gossypium hirsutum, Helianthus* spp. (e.g. *Helianthus annuus), Hemerocallis fulva, Hibiscus* spp., *Hordeum* spp. (e.g. *Hordeum vulgare), Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme), Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia), Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum), Sorghum bicolor, Spinacia* spp., *Syzygium* spp., *Tagetes* spp., *Tamarindus indica, Theobroma cacao, Trifolium* spp., *Triticosecale rimpaui, Triticum* spp. (e.g. *Triticum aestivum, Triticum durum, Triticum turgidum, Triticum hybernum, Triticum macha, Triticum sativum* or *Triticum vulgare), Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

DETAILED DESCRIPTION OF THE INVENTION

Class I TCP

Surprisingly, it has now been found that increasing expression in a plant of a nucleic acid sequence encoding a YEP, which YEP is a Class I TCP polypeptide, gives plants having increased seed yield relative to control plants. The particular type of Class I TCP polypeptides suitable for increasing seed yield in plants is described in detail below.

The present invention provides a method for increasing seed yield in plants relative to control plants, comprising increasing expression in a plant of a nucleic acid sequence encoding a Class I TCP polypeptide.

In the context of this embodiment, any reference to a "polypeptide useful in the methods of the invention" is taken to mean a Class I TCP polypeptide as defined herein. Any reference hereinafter to a "nucleic acid sequence useful in the methods of the invention" is taken to mean a nucleic acid sequence capable of encoding such a Class I TCP polypeptide.

The terms "polypeptide" and "protein" are used interchangeably herein and refer to amino acids in a polymeric form of any length. The terms are also defined in the "Definitions" section herein. The terms "polynucleotide(s)", "nucleic acid sequence(s)", "nucleotide sequence(s)" are also defined in the "Defintions" section herein The increase in seed yield achieved by performing the methods of the invention is an increase relative to control plants. The term "control plants" is defined in the "Defintions" section herein.

A preferred method for increasing expression of a nucleic acid sequence encoding a Class I TCP polypeptide is by introducing and expressing in a plant a nucleic acid sequence encoding a Class I TCP polypeptide useful in the methods of the invention as defined below.

The nucleic acid sequence to be introduced into a plant (and therefore useful in performing the methods of the invention) is any nucleic acid sequence encoding a Class I TCP polypeptide, hereinafter also named "Class I TCP nucleic acid sequence" or "Class I TCP gene". A "Class I TCP polypeptide" as defined herein refers to a polypeptide comprising from N-terminus to C-terminus: (i) in increasing order of preference at least 65%, 70%, 75%, 80%, 85%, 90%, 95% or 98% or more sequence identity to the conserved TCP domain (comprising a basic-Helix-Loop-Helix (bHLH)) as represented by SEQ ID NO: 66; and (ii) a consensus C-terminal motif 1 as represented by SEQ ID: 65.

The presence of a conserved TCP domain (comprising a basic-Helix-Loop-Helix (bHLH)) was determined as shown in Examples 2, 3, 4, and 5. The calculation of percentage amino acid identity of SEQ ID NO: 66 with the conserved TCP domain of Class I TCP polypeptides useful in performing the methods of the invention is shown in Example 3 (Table B1).

Within the consensus C-terminal motif 1 as represented by SEQ ID: 65, there may be one or more conservative change at any position, and/or one, two or three non-conservative change(s) at any position. The presence of this motif was determined as shown in Example 2. By "C-terminal" is meant herein the half of the polypeptide sequence comprising the carboxy (C) terminus (the other half comprising the amino (N) terminus). By "consensus C-terminal motif 1" is herein taken to mean that the consensus motif 1 is comprised with the C-terminal half of the polypeptide sequence.

Additionally, the Class I TCP polypeptide may comprise an HQ rich region (H being histidine, Q glutamine), between the conserved C-terminal motif 1 and the C-terminal end of the polypeptide. The HQ rich region comprises at least four, preferably 5, 6, 7, 8, 9, 10, 11, 12, 13, 14, 15, 16, 17, 18, 19, 20 or more either of only H residues, either of only Q residues, or of a combination of H and Q residues (in any proportion). The presence of this motif was determined as described in Examples 2 and 4. By "C-terminal end" of the polypeptide is herein taken to mean the last amino acid residue of the polypeptide sequence.

Alternatively or additionally, a "Class I TCP polypeptide" as defined herein refers to any polypeptide sequence which when used in the construction of a TCP phylogenetic tree, such as the one depicted in FIG. 1, tends to cluster with the clade of TCP polypeptides comprising the polypeptide sequence as represented by SEQ ID NO: 2 (encircled in FIG. 1) rather than with any other TCP clade.

A person skilled in the art could readily determine whether any polypeptide sequence in question falls within the definition of a "Class I TCP polypeptide" using known techniques and software for the making of such a phylogenetic tree, such as a GCG, EBI or CLUSTAL package, using default parameters. Any sequence clustering within the clade comprising SEQ ID NO: 2 (encircled in FIG. 1) would be considered to fall within the aforementioned definition of a Class I TCP polypeptide, and would be considered suitable for use in the methods of the invention.

Examples of polypeptides useful in the methods of the invention and nucleic acid sequences encoding the same are as given below in Table A of Example 1.

Also useful in the methods of the invention are homologues of any one of the polypeptide sequences given in Table A of Example 1, the term "homologue" being as defined in the "Definitions" section herein.

Also useful in the methods of the invention are derivatives of any one of the polypeptides given in Table A of Example 1. The term "Derivatives" is as defined in the "Definitions" section herein.

The invention is illustrated by transforming plants with the *Arabidopsis thaliana* nucleic acid sequence represented by SEQ ID NO: 1, encoding the polypeptide sequence of SEQ ID NO: 2, however performance of the invention is not restricted to these sequences. The methods of the invention may advantageously be performed using any nucleic acid sequence encoding a Class I TCP polypeptide useful in the methods of the invention as defined herein, including orthologues and paralogues, such as any of the nucleic acid sequences given in Table A of Example 1.

The polypeptide sequences given in Table A of Example 1 may be considered to be orthologues and paralogues of the Class I TCP polypeptide represented by SEQ ID NO: 2. The terms "Orthologues" and "paralogues" are as defined herein.

Orthologues and paralogues may easily be found by performing a so-called reciprocal blast search. Typically, this involves a first BLAST involving BLASTing a query sequence (for example using any of the sequences listed in Table A of Example 1) against any sequence database, such as the publicly available NCBI database. BLASTN or TBLASTX (using standard default values) are generally used when starting from a nucleotide sequence, and BLASTP or TBLASTN (using standard default values) when starting from a polypeptide sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against *Arabidopsis thaliana* sequences). The results of the first and second BLASTs are then compared. A paralogue is identified if a high-ranking hit from the first blast is from the same species as from which the query sequence is derived, a BLAST back then ideally results in the query sequence as highest hit; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Table A of Example 1 gives examples of orthologues and paralogues of the Class I TCP polypeptide represented by SEQ ID NO 2. Further orthologues and paralogues may readily be identified using the BLAST procedure described above. The methods of the invention may advantageously be performed using any nucleic acid sequence encoding any one of the Class I TCP polypeptide as given in Table A or orthologues or paralogues of any of the aforementioned SEQ ID NOs.

The polypeptides of the invention are identifiable by the presence of a conserved TCP domain (comprising a basic-Helix-Loop-Helix (bHLH)) (shown in FIG. 3A). The term "domain" is as defined in the "Definitions" section herein.

The term "motif", or "consensus sequence", or "signature" is as defined in the "Definitions" section herein.

Specialist databases also exist for the identification of domains, for example, SMART (Schultz et al. (1998) Proc. Natl. Acad. Sci. USA 95, 5857-5864; Letunic et al. (2002)

Nucleic Acids Res 30, 242-244, InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), or Pfam (Bateman et al., Nucleic Acids Research 30(1): 276-280 (2002). A set of tools for in silico analysis of protein sequences is available on the ExPASY proteomics server (hosted by the Swiss Institute of Bioinformatics (Gasteiger et al., ExPASy: the proteomics server for in-depth protein knowledge and analysis, Nucleic Acids Res. 31:3784-3788 (2003)).

Domains may also be identified using routine techniques, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues, orthologues and paralogues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains (such as the conserved TCP domain, or one of the motifs defined above) may be used as well. The sequence identity values, which are indicated below in Example 3 as a percentage were determined over the entire nucleic acid or polypeptide sequence (Table B), and/or over selected domains or conserved motif(s) (Table B1), using the programs mentioned above using the default parameters.

Furthermore, the presence of regions rich in specific amino acids (such as the HQ region) may identified using computer algorithms or simply by eye inspection. For the former, primary amino acid composition (in %) to determine if a polypeptide region is rich in specific amino acids may be calculated using software programs from the ExPASy server, in particular the ProtParam tool (Gasteiger E et al. (2003) ExPASy: the proteomics server for in-depth protein knowledge and analysis. Nucleic Acids Res 31:3784-3788). The composition of the polypeptide of interest may then be compared to the average amino acid composition (in %) in the Swiss-Prot Protein Sequence data bank. For example, in this databank, the average histidine content is of 2.27%, the average glutamine content is of 3.93%. A polypeptide region is rich in a specific amino acid if the content of that specific amino acid in that domain is above the average amino acid composition (in %) in the Swiss-Prot Protein Sequence data bank. A HQ rich region therefore has either an H content above 2.27%, and/or a G content above 3.93%. For the latter, eye inspection of the multiple sequence alignment of Class I TCP polypeptides of Table A, shows an HQ rich region (H being histidine, Q glutamine), between the conserved C-terminal motif 1 and the C-terminal end of the polypeptides. The HQ rich region comprises at least four, preferably 5, 6, 7, 8, 9, 10, 11, 12, 13, 14, 15, 16, 17, 18, 19, 20 or more either of only H residues, either of only Q residues, or of a combination of H and Q residues (in any proportion). The presence of this motif was determined as shown in Examples 2 and 4.

Furthermore, Class I TCP polypeptides (at least in their native form) typically have DNA activity. Further details on testing for this specific DNA binding activity are provided in Example 6.

Nucleic acid sequences encoding Class I TCP polypeptides useful in the methods of the invention need not be full-length nucleic acid sequences, since performance of the methods of the invention does not rely on the use of full-length nucleic acid sequences. Examples of nucleic acid sequences suitable for use in performing the methods of the invention include the nucleic acid sequences given in Table A of Example 1, but are not limited to those sequences. Nucleic acid variants may also be useful in practising the methods of the invention. Examples of such nucleic acid variants include portions of nucleic acid sequences encoding a Class I TCP polypeptide, nucleic acid sequences hybridising to nucleic acid sequences encoding a Class I TCP, splice variants of nucleic acid sequences encoding a Class I TCP polypeptide, allelic variants of nucleic acid sequences encoding a Class I TCP polypeptide, variants of nucleic acid sequences encoding a Class I TCP polypeptide that are obtained by gene shuffling, or variants of nucleic acid sequences encoding a Class I TCP polypeptide that are obtained by site-directed mutagenesis. The terms portion, hybridising sequence, splice variant, allelic variant, variant obtained by gene shuffling, and variant obtained by site-directed mutagenesis will now be described and are also defined in the "Defintions" section herein.

According to the present invention, there is provided a method for increasing seed yield in plants, comprising introducing and expressing in a plant a portion of any one of the nucleic acid sequences given in Table A of Example 1, or a portion of a nucleic acid sequence encoding an orthologue, paralogue or homologue of any of the polypeptide sequences given in Table A of Example 1.

Portions useful in the methods of the invention, encode a polypeptide falling within the definition of a nucleic acid sequence encoding a Class I TCP polypeptide as defined herein and having substantially the same biological activity as the polypeptide sequences given in Table A of Example 1. Preferably, the portion is a portion of any one of the nucleic acid sequences given in Table A of Example 1. The portion is typically at least 600 consecutive nucleotides in length, preferably at least 700 consecutive nucleotides in length, more preferably at least 800 consecutive nucleotides in length and most preferably at least 900 consecutive nucleotides in length, the consecutive nucleotides being of any one of the nucleic acid sequences given in Table A of Example 1. Preferably, the portion encodes a Class I TCP polypeptide sequence comprising from N-terminus to C-terminus: (i) in increasing order of preference at least 65%, 70%, 75%, 80%, 85%, 90%, 95% or 98% or more sequence identity to the conserved TCP domain (comprising a basic-Helix-Loop-Helix (bHLH)) as represented by SEQ ID NO: 66; and (ii) a consensus C-terminal motif 1 as represented by SEQ ID: 65. Alternatively or additionally, the portion encodes a polypeptide sequence which when used in the construction of a TCP phylogenetic tree, such as the one depicted in FIG. 1, tends to cluster with the clade of TCP polypeptides comprising the polypeptide sequence as represented by SEQ ID NO: 2 (encircled in FIG. 1) rather than with any other TCP clade. Most preferably, the portion is a portion of the nucleic acid sequence of SEQ ID NO: 1.

A portion of a nucleic acid sequence encoding a Class I TCP polypeptide as defined herein may be prepared, for example, by making one or more deletions to the nucleic acid sequence. The portions may be used in isolated form or they may be fused to other coding (or non coding) sequences in order to, for example, produce a polypeptide that combines several activities. When fused to other coding sequences, the resultant polypeptide produced upon translation may be bigger than that predicted for the Class I TCP polypeptide portion.

Another nucleic acid variant useful in the methods of the invention is a nucleic acid sequence capable of hybridising, under reduced stringency conditions, preferably under stringent conditions, with a nucleic acid sequence encoding a Class I TCP polypeptide as defined herein, or with a portion as defined herein.

According to the present invention, there is provided a method for increasing seed yield in plants, comprising introducing and expressing in a plant a nucleic acid sequence capable of hybridising, under reduced stringency conditions, preferably under stringent conditions, with any one of the nucleic acid sequences given in Table A of Example 1, or with a nucleic acid sequence encoding an orthologue, paralogue or homologue of any of the polypeptide sequences given in Table A of Example 1.

Hybridising sequences useful in the methods of the invention, encode a polypeptide having a conserved TCP domain (see the alignment of FIG. 2) and having substantially the same biological activity as the Class I TCP polypeptide represented by any of the polypeptide sequences given in Table A of Example 1. The hybridising sequence is typically at least 600 consecutive nucleotides in length, preferably at least 700 consecutive nucleotides in length, more preferably at least 800 consecutive nucleotides in length and most preferably at least 900 consecutive nucleotides in length, the consecutive nucleotides being of any one of the nucleic acid sequences given in Table A of Example 1. Preferably, the hybridising sequence is one that is capable of hybridising to any of the nucleic acid sequences given in Table A of Example 1, or to a portion of any of these sequences, a portion being as defined above. Further preferably, the hybridising sequence encodes a Class I TCP polypeptide sequence comprising from N-terminus to C-terminus: (i) in increasing order of preference at least 65%, 70%, 75%, 80%, 85%, 90%, 95% or 98% or more sequence identity to the conserved TCP domain (comprising a basic-Helix-Loop-Helix (bHLH)) as represented by SEQ ID NO: 66; and (ii) a consensus C-terminal motif 1 as represented by SEQ ID: 65. Alternatively or additionally, the hybridising sequence encodes a polypeptide sequence which when used in the construction of a TCP phylogenetic tree, such as the one depicted in FIG. 1, tends to cluster with the clade of TCP polypeptides comprising the polypeptide sequence as represented by SEQ ID NO: 2 (encircled in FIG. 1) rather than with any other TCP clade. Most preferably, the hybridising sequence is capable of hybridising to a nucleic acid sequence as represented by SEQ ID NO: 1 or to a portion thereof.

The term "hybridisation" is as defined herein.

Another nucleic acid variant useful in the methods of the invention is a splice variant encoding a Class I TCP polypeptide as defined hereinabove. The term "splice variant" is as defined in the "Definitions" section herein.

According to the present invention, there is provided a method for increasing seed yield in plants, comprising introducing and expressing in a plant a splice variant of any one of the nucleic acid sequences given in Table A of Example 1, or a splice variant of a nucleic acid sequence encoding an orthologue, paralogue or homologue of any of the polypeptide sequences given in Table A of Example 1.

Preferably, the Class I TCP polypeptide sequence encoded by the splice variant comprises from N-terminus to C-terminus: (i) in increasing order of preference at least 65%, 70%, 75%, 80%, 85%, 90%, 95% or 98% or more sequence identity to the conserved TCP domain (comprising a basic-Helix-Loop-Helix (bHLH)) as represented by SEQ ID NO: 66; and (ii) a consensus C-terminal motif 1 as represented by SEQ ID: 65. Alternatively or additionally, the polypeptide sequence encoded by the splice variant encodes a polypeptide sequence which when used in the construction of a TCP phylogenetic tree, such as the one depicted in FIG. 1, tends to cluster with the clade of TCP polypeptides comprising the polypeptide sequence as represented by SEQ ID NO: 2 (encircled in FIG. 1) rather than with any other TCP clade. Most preferred splice variants are splice variants of a nucleic acid sequence represented by SEQ ID NO: 1 or a splice variant of a nucleic acid sequence encoding an orthologue or paralogue of SEQ ID NO: 2.

Another nucleic acid variant useful in performing the methods of the invention is an allelic variant of a nucleic acid sequence encoding a Class I TCP polypeptide as defined hereinabove. The term "allelic variant" is as defined in the "Definitions" section herein. The allelic variants useful in the methods of the present invention have substantially the same biological activity as the Class I TCP polypeptide of SEQ ID NO: 2.

According to the present invention, there is provided a method for increasing seed yield in plants, comprising introducing and expressing in a plant an allelic variant of any one of the nucleic acid sequences given in Table A of Example 1, or comprising introducing and expressing in a plant an allelic variant of a nucleic acid encoding an orthologue, paralogue or homologue of any of the polypeptide sequences given in Table A of Example 1.

Preferably, the Class I TCP polypeptide sequence encoded by the allelic variant comprises from N-terminus to C-terminus: (i) in increasing order of preference at least 65%, 70%, 75%, 80%, 85%, 90%, 95% or 98% or more sequence identity to the conserved TCP domain (comprising a basic-Helix-Loop-Helix (bHLH)) as represented by SEQ ID NO: 66; and (ii) a consensus C-terminal motif 1 as represented by SEQ ID: 65. Alternatively or additionally, the polypeptide sequence encoded by the splice variant, when used in the construction of a TCP phylogenetic tree, such as the one depicted in FIG. 1, tends to cluster with the clade of TCP polypeptides comprising the polypeptide sequence represented by SEQ ID NO: 2 (encircled in FIG. 2) rather than with any other TCP clade. Most preferably, the allelic variant is an allelic variant of SEQ ID NO: 1 or an allelic variant of a nucleic acid sequence encoding an orthologue or paralogue of SEQ ID NO: 2.

A further nucleic acid variant useful in the methods of the invention is a nucleic acid variant obtained by gene shuffling. Gene shuffling or directed evolution is defined in the "Definitions" section herein.

According to the present invention, there is provided a method for increasing seed yield in plants, comprising introducing and expressing in a plant a variant of any one of the nucleic acid sequences given in Table A of Example 1, or comprising introducing and expressing in a plant a variant of a nucleic acid sequence encoding an orthologue, paralogue or homologue of any of the polypeptide sequences given in Table A of Example 1, which variant nucleic acid sequence is obtained by gene shuffling.

Preferably, the variant nucleic acid sequence obtained by gene shuffling encodes a polypeptide sequence comprising comprising from N-terminus to C-terminus: (i) in increasing order of preference at least 65%, 70%, 75%, 80%, 85%, 90%, 95% or 98% or more sequence identity to the conserved TCP domain (comprising a basic-Helix-Loop-Helix (bHLH)) as represented by SEQ ID NO: 66; and (ii) a consensus C-terminal motif 1 as represented by SEQ ID: 65. Alternatively or additionally, the polypeptide encoded sequence by the variant nucleic acid sequence obtained by gene shuffling, when used in the construction of a TCP phylogenetic tree such as the one depicted in FIG. 1, tends to cluster with the clade of TCP polypeptides comprising the polypeptide sequence represented by SEQ ID NO: 2 (encircled in FIG. 2) rather than with any other TCP clade. Most preferably, the variant nucleic acid sequence obtained by gene shuffling is a variant of SEQ ID NO: 1 or a variant of a nucleic acid sequence encoding an orthologue or paralogue of SEQ ID NO: 2, obtained by gene shuffling.

Furthermore, nucleic acid variants may also be obtained by site-directed mutagenesis. Several methods are available to achieve site-directed mutagenesis, the most common being PCR based methods (Current Protocols in Molecular Biology. Wiley Eds.).

According to the present invention, there is provided a method for increasing seed yield in plants, comprising introducing and expressing in a plant a variant of any one of the nucleic acid sequences given in Table A of Example 1, or comprising introducing and expressing in a plant a variant of a nucleic acid sequence encoding an orthologue, paralogue or homologue of any of the polypeptide sequences given in Table A of Example 1, which variant nucleic acid sequence is obtained by site-directed mutagenesis.

Preferably, the variant nucleic acid sequence obtained by site-directed mutagenesis encodes a Class I TCP polypeptide sequence comprising comprising from N-terminus to C-terminus: (i) in increasing order of preference at least 65%, 70%, 75%, 80%, 85%, 90%, 95% or 98% or more sequence identity to the conserved TCP domain (comprising a basic-Helix-Loop-Helix (bHLH)) as represented by SEQ ID NO: 66; and (ii) a consensus C-terminal motif 1 as represented by SEQ ID: 65. Alternatively or additionally, the polypeptide encoded sequence by the variant nucleic acid sequence obtained by site-directed mutagenesis, when used in the construction of a TCP phylogenetic tree such as the one depicted in FIG. 1, tends to cluster with the clade of TCP polypeptides comprising the polypeptide sequence represented by SEQ ID NO: 2 rather than with any other TCP clade. Most preferably, the variant nucleic acid sequence obtained by site-directed mutagenesis is a variant of SEQ ID NO: 1 or a variant of a nucleic acid sequence encoding an orthologue or paralogue of SEQ ID NO: 2, obtained by site-directed mutagenesis.

The following nucleic acid variants encoding a Class I TCP polypeptide are examples of variants suitable in practising the methods of the invention:
 (i) a portion of a nucleic acid sequence encoding a Class I TCP polypeptide;
 (ii) a nucleic acid sequence capable of hybridising with a nucleic acid sequence encoding a Class I TCP polypeptide;
 (iii) a splice variant of a nucleic acid sequence encoding a Class I TCP polypeptide;
 (iv) an allelic variant of a nucleic acid sequence encoding a Class I TCP polypeptide;
 (v) a nucleic acid sequence encoding a Class I TCP polypeptide obtained by gene shuffling;
 (vi) a nucleic acid sequence encoding a Class I TCP polypeptide obtained by site-directed mutagenesis.

Nucleic acid sequences encoding Class I TCP polypeptides may be derived from any natural or artificial source. The nucleic acid sequence may be modified from its native form in composition and/or genomic environment through deliberate human manipulation. Preferably the nucleic acid sequence encoding the Class I TCP polypeptide is from a plant, further preferably from a dicotyledonous plant, more preferably from the Brassicaceae family, most preferably the nucleic acid sequence is from *Arabidopsis thaliana*.

Any reference herein to a Class I TCP polypeptide is therefore taken to mean a Class I TCP polypeptide as defined above. Any nucleic acid sequence encoding such a Class I TCP polypeptide is suitable for use in performing the methods of the invention.

The present invention also encompasses plants or parts thereof (including seeds) obtainable by the methods according to the present invention. The plants or parts thereof comprise a nucleic acid transgene encoding a Class I TCP polypeptide as defined above.

The invention also provides genetic constructs and vectors to facilitate introduction and/or expression of the nucleic acid sequences useful in the methods according to the invention, in a plant. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising
 (a) nucleic acid sequence encoding Class I TCP polypeptide as defined above;
 (b) one or more control sequences capable of driving expression of the nucleic acid sequence of (a); and optionally
 (c) a transcription termination sequence.

A preferred construct is one where the control sequence is a constitutive promoter, preferably a GOS2 promoter.

The invention also provides plants, plant parts, or plant cells transformed with a construct as defined hereinabove.

Plants are transformed with a vector comprising the sequence of interest (i.e., a nucleic acid sequence encoding a Class I TCP polypeptide as defined herein. The skilled artisan is well aware of the genetic elements that must be present on the vector in order to successfully transform, select and propagate host cells containing the sequence of interest. The sequence of interest is operably linked to one or more control sequences (at least to a promoter). The terms "regulatory element", "control sequence" and "promoter" are as defined in the "Definitions" section herein. The term "operably linked" is as defined in the "Definitions" section.

Advantageously, any type of promoter may be used to drive expression of the nucleic acid sequence. The term "promoter" and "Plant Promoter" are defined in the "Definitions" section herein and several examples of promoters are also described.

Preferably the promoter is derived from a plant, more preferably a monocotyledonous plant.

The promoter may be a constitutive promoter. Additionally or alternatively, the promoter may be an organ-specific or tissue-specific promoter.

In one embodiment, the nucleic acid sequence encoding a Class I TCP polypeptide is operably linked to a constitutive promoter, the term "constitutive promoter" is as defined in the "Defintions" section herein. A constitutive promoter is one that is also substantially ubiquitously expressed. Preferably the constitutive promoter is derived from a plant, more preferably a monocotyledonous plant. Further preferably the constitutive promoter is a GOS2 promoter (from rice), for example, as represented by a nucleic acid sequence substantially similar to SEQ ID NO: 67, most preferably the constitutive promoter is as represented by SEQ ID NO: 67. It should be clear that the applicability of the present invention is not restricted to the nucleic acid sequence as represented by SEQ ID NO: 1, nor is the applicability of the invention restricted to expression of a nucleic acid sequence encoding a Class I TCP polypeptide when driven by a GOS2 promoter. Examples of other constitutive promoters which may also be used to drive expression of a nucleic acid sequence encoding a Class I TCP polypeptide are shown in the "Defintions" section herein.

For the identification of functionally equivalent promoters, the promoter strength and/or expression pattern of a candidate promoter may be analysed for example by operably linking the promoter to a reporter gene and assay the expression level and pattern of the reporter gene in various tissues of the plant. Suitable well-known reporter genes include for example beta-glucuronidase or beta galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid sequence used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about $1/10,000$ transcripts to about $1/100,000$ transcripts, to about $1/500,0000$ transcripts per cell. Conversely, a "strong promoter" drives expression of a coding sequence at high level, or at about $1/10$ transcripts to about $1/100$ transcripts to about $1/1,000$ transcripts per cell.

Optionally, one or more terminator sequences may be used in the construct introduced into a plant. The term "terminator" is as defined in the "Definitions" section herein. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5' untranslated region (UTR) or in the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell. biol. 8:4395-4405 (1988); Callis et al., Genes Dev. 1:1183-1200 (1987)). Such intron enhancement of gene expression is typically greatest when placed near the 5' end of the transcription unit. Use of the maize introns Adh1-S intron 1, 2, and 6, the Bronze-1 intron are known in the art. For general information, see The Maize Handbook, Chapter 116, Freeling and Walbot, Eds., Springer, N.Y. (1994).

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acid sequences, it is advantageous to use marker genes (or reporter genes). Therefore, the genetic construct may optionally comprise a selectable marker gene. The terms "selectable marker", "selectable marker gene" or "reporter gene" are defined in the "Defintions" section herein.

The invention also provides a method for the production of transgenic plants having increased seed yield relative to control plants, comprising introduction and expression in a plant of any nucleic acid sequence encoding a Class I TCP polypeptide as defined hereinabove.

The terms "transgenic", "transgene" or "recombinant" are as defined herein

More specifically, the present invention provides a method for the production of transgenic plants having increased seed yield relative to control plants, which method comprises:
 (i) introducing and expressing in a plant or plant cell a nucleic acid sequence encoding a Class I TCP polypeptide; and
 (ii) cultivating the plant cell under conditions promoting plant growth and development.

The nucleic acid sequence may be introduced directly into a plant cell or into the plant itself (including introduction into a tissue, organ or any other part of a plant). According to a preferred feature of the present invention, the nucleic acid sequence is preferably introduced into a plant by transformation.

The term "introduction" or "transformation" is defined in the "Defintions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid sequence encoding a Class I TCP polypeptide as defined hereinabove. Preferred host cells according to the invention are plant cells.

Host plants for the nucleic acid sequences or the vector used in the method according to the invention, the expression cassette or construct or vector are, in principle, advantageously all plants, which are capable of synthesizing the polypeptides used in the inventive method.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

Methods for increasing expression of nucleic acid sequences or genes, or gene products, are well documented in the art and include, for example, overexpression driven by appropriate promoters, the use of transcription enhancers or translation enhancers. Isolated nucleic acid sequences which serve as promoter or enhancer elements may be introduced in an appropriate position (typically upstream) of a non-heterologous form of a polynucleotide so as to upregulate expression. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

The term "expression" or "gene expression" is as defined in the "Defintions" section herein. The term "increasing expression" shall mean an increase of the expression of the nucleic acid sequence encoding a Class I TCP polypeptide, which increase in expression leads to increased seed yield of the plants relative to control plants. Preferably, the increase in expression of the nucleic acid sequence is 1.25, 1.5, 1.75, 2, 5, 7.5, 10, 15, 20, 25, 30, 35, 40, 45, 50, 55, 60, 65, 70, 75, 80, 85, 90, 95, 100 or more fold the expression of the endogenous plant nucleic acid sequence encoding a Class I TCP polypeptide as defined hereinabove.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added as described above.

Other control sequences (besides promoter, enhancer, silencer, intron sequences, 3'UTR and/or 5'UTR regions) may be protein and/or RNA stabilizing elements.

As mentioned above, a preferred method for increasing expression of a nucleic acid sequence encoding a Class I TCP polypeptide is by introducing and expressing in a plant a nucleic acid sequence encoding a Class I TCP polypeptide; however the effects of performing the method, i.e. increasing seed yield may also be achieved using other well known techniques. A description of some of these techniques will now follow.

One such technique is T-DNA activation tagging (Hayashi et al. Science (1992) 1350-1353), which is described in the "Defintions" section herein.

The effects of the invention may also be reproduced using the technique of TILLING (Targeted Induced Local Lesions In Genomes). See the "Defintions" section herein for a description of this technique.

The effects of the invention may also be reproduced using homologous recombination, which is described in the "Defintions" section herein.

Performance of the methods of the invention lead to an increase in seed yield relative to control plants. The term "Seed yield" is defined in the "Defitnions" section herein. The terms "increase", "enhance" or "improve" are also defined in the "Definitions" section.

Increased seed yield may manifest itself as one or more of the following:
  (i) increased total seed yield, which includes an increase in seed biomass (seed weight) and which may be an increase in the seed weight per plant or on an individual seed basis;
  (ii) increased number of panicles per plant
  (iii) increased number of flowers ("florets") per panicle
  (iv) increased seed fill rate
  (v) increased number of (filled) seeds;
  (vi) increased seed size (length, width area, perimeter), which may also influence the composition of seeds;
  (vii) increased seed volume, which may also influence the composition of seeds;
  (viii) increased harvest index, which is expressed as a ratio of the yield of harvestable parts, such as seeds, over the total biomass; and
  (ix) increased Thousand Kernel Weight (TKW), which is extrapolated from the number of filled seeds counted and their total weight. An increased TKW may result from an increased seed size and/or seed weight. An increased TKW may result from an increase in embryo size and/or endosperm size.

An increase in seed size, seed volume, seed area, seed perimeter, seed width or seed length may be due to an increase in specific parts of a seed, for example due to an increase in the size of the embryo and/or endosperm and/or aleurone and/or scutellum, or other parts of a seed.

In particular, increased seed yield is selected from one or more of the following: (i) increased seed weight; (ii) increased harvest index; and (iii) increased TKW.

An increase in seed yield may also be manifested as an increase in seed size and/or seed volume, which may also influence the composition of seeds (including oil, protein and carbohydrate total content and/or composition).

Taking corn as an example, a yield increase may be manifested as one or more of the following: increase in the number of plants established per hectare or acre, an increase in the number of ears per plant, an increase in the number of rows, number of kernels per row, kernel weight, Thousand Kernel Weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in Thousand Kernel Weight, among others.

Since the transgenic plants according to the present invention have increased seed yield, it is likely that these plants exhibit an increased growth rate (during at least part of their life cycle), relative to the growth rate of control plants at a corresponding stage in their life cycle. The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. Increased growth rate may occur during seed development (reproductive growth rate), while the vegetative growth rate is unchanged or even reduced. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species. Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants relative to control plants, which method comprises increasing expression in a plant of a nucleic acid sequence encoding a Class I TCP polypeptide as defined herein. Preferably, the increased growth rate occurs during seed development (reproductive growth rate), the vegetative growth rate being unchanged or even reduced.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol. (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signalling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield relative to suitable control plants grown under comparable conditions. Therefore, according to the present invention, there is provided a method for increasing yield in plants grown under non-stress conditions or under mild drought conditions, which method comprises increasing expression in a plant of a nucleic acid sequence encoding a Class I TCP polypeptide.

The methods of the invention are advantageously applicable to any plant. The term "plant" is as defined in the "Defintions" section herein. Also described are pants that are particularly useful in the methods of the invention.

According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, sorghum and oats.

The present invention also encompasses use of nucleic acid sequences encoding Class I TCP polypeptides as described herein and use of these Class I TCP polypeptides in increasing seed yield in plants. Preferably, increased seed yield is selected from one or more of the following: (i) increased seed weight; (ii) increased harvest index; or (iii) increased Thousand Kernel Weight.

Nucleic acid sequences encoding Class I TCP polypeptides described herein, or the Class I TCP polypeptides themselves, may find use in breeding programmes in which a DNA marker is identified which may be genetically linked to a gene encoding Class I TCP polypeptide. The nucleic acid sequences/genes, or the Class I TCP polypeptides themselves may be used to define a molecular marker. This DNA or protein marker may then be used in breeding programmes to select plants having increased seed yield as defined hereinabove in the methods of the invention.

Allelic variants of a nucleic acid sequence/gene encoding a Class I TCP polypeptide may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acid sequences encoding Class I TCP polypeptides may also be used as probes for genetically and physically mapping the genes that they are a part of, and as markers for traits linked to those genes. Such information may be useful in plant breeding in order to develop lines with desired phenotypes. Such use of nucleic acid sequences encoding Class I TCP polypeptides requires only a nucleic acid sequence of at least 15 nucleotides in length. The nucleic acid sequences encoding Class I TCP polypeptides may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the nucleic acid sequences encoding Class I TCP polypeptides. The resulting banding patterns may then be subjected to genetic analyses using computer programs such as MapMaker (Lander et al. (1987) Genomics 1: 174-181) in order to construct a genetic map. In addition, the nucleic acid sequences may be used to probe Southern blots containing restriction endonuclease-treated genomic DNAs of a set of individuals representing parent and progeny of a defined genetic cross. Segregation of the DNA polymorphisms is noted and used to calculate the position of the nucleic acid sequence encoding a Class I TCP polypeptide in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acid sequences. Examples include allele-specific amplification (Kazazian (1989) J. Lab. Clin. Med. 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased seed yield, as described hereinbefore. These traits may also be combined with other economically advantageous traits, such as yield-enhancing traits, tolerance to other abiotic and biotic stresses, traits modifying various architectural features and/or biochemical and/or physiological features.

DETAILED DESCRIPTION OF THE INVENTION

CAH3

Surprisingly, it has now been found that modulating expression in a plant of a nucleic acid encoding a YEP polypeptide gives plants having enhanced yield-related traits without effects on vegetative biomass, relative to control plants, wherein the YEP is a CAH3. The particular class of CAH3 polypeptides suitable for enhancing yield-related traits in plants is described in detail below.

The present invention provides a method for enhancing yield-related traits in plants relative to control plants, comprising modulating expression in a plant of a nucleic acid encoding a CAH3 polypeptide. The term "control plant" is as defined in the "Defintions" section herein.

In the context of the embodiment relating to CAH3, any reference hereinafter to a "protein useful in the methods of the invention" is taken to mean a CAH3 polypeptide as defined herein. Any reference hereinafter to a "nucleic acid useful in the methods of the invention" is taken to mean a nucleic acid capable of encoding such a CAH3 polypeptide. The terms "polypeptide" and "protein" are as defined in the "Definitions" section herein. The terms "polynucleotide(s)", "nucleic acid sequence(s)", "nucleotide sequence(s)" are as defined in the "Definitions" section herein.

A preferred method for modulating (preferably, increasing) expression of a nucleic acid encoding a protein useful in the methods of the invention is by introducing and expressing in a plant a nucleic acid encoding a protein useful in the methods of the invention as defined below.

The nucleic acid to be introduced into a plant (and therefore useful in performing the methods of the invention) is any nucleic acid encoding the type of protein which will now be described, hereinafter also named "CAH3 nucleic acid" or "CAH3 gene". A "CAH3" polypeptide as defined herein refers to any protein having carbonic anhydrase activity (EC 4.2.1.1). Carbonic anhydrase is also known as carbonate dehydratase (accepted name according to IUBMB Enzyme Nomenclature), anhydrase, carbonate anhydrase, carbonic acid anhydrase, carboxyanhydrase, and carbonic anhydrase A. Methods for assaying enzymatic activity of carbonic anhydrase are known in the art; see the Examples Section for further details.

Preferably, the amino acid sequence of the carbonic anhydrase useful in the methods of the present invention comprises one or more of the following motifs:

```
Motif 1:
                                        (SEQ ID NO: 203)
(S/T)E(H/N)X(L/I/V/M)XXXX(F/Y/L/H)XX(E/D)X(H/Q)

(L/I/V/M/F/A)(L/I/V/M/F/A).
```

Preferably, X on position 4 in motif 1 is one of: T, S, E, F, A, H, L; X on position 6 preferably is one of: N, D, S, H, A, M; X on position 7 preferably is N or G; X on position 8 preferably is one of: K, R, T, Q, E, V, A, K; X on position 9 is preferably one of: R, K, Q, L, H, I, S; X on position 11 preferably is one of: V, A, D, N, P; X on position 12 preferably is on of: L, M, A; X on position 14 is preferably one of Q, E, L, A, V. Further preferably, the residue on position 16 is one of M, L, or V; the residue on position 17 is L or V. Most preferably, the sequence of motif 1 is SEHAMDGRRYAMEAHLV.

```
Motif 2:
                                        (SEQ ID NO: 204)
(L/N/Y/M/T/F/A/R)(A/V/S)V(V/I/L/T)(A/T/G/S)

(F/V/I/L/S/T)(L/F/V/M).
```

Preferably, motif 2 has the sequence (L/F/A/R)(A/V/S)V(V/I/L/T)(A/G/S)(F/V/I/L/T)(L/F/V/M). Most preferably, motif 2 has the sequence LAVLGIM.

```
Motif 3:
                                        (SEQ ID NO: 205)
(Y/F)(Y/F/V/G/A)(R/E/G/T/H)(Y/F)XGS(L/F/Y)T (T/V/A)PPC(S/T/G/D/A)(E/Q)(N/G/D/R)
```

Preferably, X is one of L, I, T, R, M, G, A, D, E, P. Most preferably, motif 3 has the sequence FVHYPGSLTTPPCSEG.

Preferably, the "CAH3" polypeptide as defined herein refers to an amino acid sequence which when used in the construction of a CAH3 phylogenetic tree, such as the one depicted in FIG. 7 A, tends to cluster with the class of alpha CAH3 polypeptides comprising the amino acid sequence represented by SEQ ID NO: 81 rather than with the beta or gamma class.

A person skilled in the art could readily determine whether any amino acid sequence in question falls within the definition of a "CAH3" polypeptide using known techniques and software for the making of such a phylogenetic tree, such as a GCG, EBI or CLUSTAL package, using default parameters. Any sequence clustering within the group comprising SEQ ID NO: 81 would be considered to fall within the aforementioned definition of a CAH3 polypeptide, and would be considered suitable for use in the methods of the invention.

Examples of proteins useful in the methods of the invention and nucleic acids encoding the same are as given below in Table B in the Examples Section.

Also useful in the methods of the invention are homologues of any one of the amino acid sequences given in Table B. "Homologues" of a protein are as defined in the "Definitions" section herein.

Also useful in the methods of the invention are derivatives of any one of the polypeptides given in Table B herein or orthologues or paralogues of any of the aforementioned SEQ ID NOs. "Derivatives" are defined in the "Defintions" section herein.

The invention is illustrated by transforming plants with the Chlamydomonas reinhardtii nucleic acid sequence represented by SEQ ID NO: 80, encoding the polypeptide sequence of SEQ ID NO: 81, however performance of the invention is not restricted to these sequences. The methods of the invention may advantageously be performed using any nucleic acid encoding a protein useful in the methods of the invention as defined herein, including orthologues and paralogues, such as any of the nucleic acid sequences given in Table B herein.

The amino acid sequences given in Table B of Example 14 may be considered to be orthologues and paralogues of the CAH3 polypeptide represented by SEQ ID NO: 81. Orthologues and paralogues are as defined in the "Defintions" section herein.

Orthologues and paralogues may easily be found by performing a so-called reciprocal blast search. Typically, this involves a first BLAST involving BLASTing a query sequence (for example using any of the sequences listed in Table B herein) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 80 or SEQ ID NO: 81, the second BLAST would therefore be against *Chlamydomonas reinhardtii* sequences). The results of the first and second BLASTs are then compared. A paralogue is identified if a high-ranking hit from the first blast is from the same species as from which the query sequence is derived, a BLAST back then ideally results in the query sequence as highest hit; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Table B herein gives examples of orthologues and paralogues of the CAH3 protein represented by SEQ ID NO 81. Further orthologues and paralogues may readily be identified using the BLAST procedure described above.

The proteins of the invention are identifiable by the presence of the conserved carbonic anhydrase domain (Pfam entry PF00194, InterPro IPR001148) (shown in FIG. 6) and/or by one of the motifs listed above. The term "domain" is defined in the "Defintions" section herein. See the "Defintions" section for a definition of the term "motif" or "consensus sequence" or "signature".

Specialist databases also exist for the identification of domains, for example, SMART (Schultz et al. (1998) Proc. Natl. Acad. Sci. USA 95, 5857-5864; Letunic et al. (2002) Nucleic Acids Res 30, 242-244, InterPro (Mulder et al., (2003) Nucl. Acids. Res. 31, 315-318, Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), or Pfam (Bateman et al., Nucleic Acids Research 30(1): 276-280 (2002). A set of tools for in silico analysis of protein sequences is available on the ExPASY proteomics server (hosted by the Swiss Institute of Bioinformatics (Gasteiger et al., ExPASy: the proteomics server for in-depth protein knowledge and analysis, Nucleic Acids Res. 31:3784-3788 (2003)).

Domains may also be identified using routine techniques, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains (such as the carbonic anhydrase domain, or one of the motifs defined above) may be used as well. The sequence identity values, which are indicated below in the Examples Section as a percentage were determined over the entire nucleic acid or amino acid sequence, and/or over selected domains or conserved motif(s), using the programs mentioned above using the default parameters.

Furthermore, CAH3 proteins (at least in their native form) typically have carbonic anhydrase activity. Assays for carbonic anhydrase are well known in the art and include titrimetric assays and spectrophotometric assays, see for example Karlsson et al. (Plant Physiol. 109: 533-539, 1995). Further details are provided in the Examples Section.

Nucleic acids encoding proteins useful in the methods of the invention need not be full-length nucleic acids, since performance of the methods of the invention does not rely on the use of full-length nucleic acid sequences. Examples of nucleic acids suitable for use in performing the methods of the invention include the nucleic acid sequences given in Table B herein, but are not limited to those sequences. Nucleic acid variants may also be useful in practising the methods of the invention. Examples of such nucleic acid variants include portions of nucleic acids encoding a protein useful in the methods of the invention, nucleic acids hybridising to nucleic acids encoding a protein useful in the methods of the invention, splice variants of nucleic acids encoding a protein useful in the methods of the invention, allelic variants of nucleic acids encoding a protein useful in the methods of the invention and variants of nucleic acids encoding a protein useful in the methods of the invention that are obtained by gene shuffling. The terms portion, hybridising sequence, splice variant, allelic variant and gene shuffling will now be described and are also defined in the "Definitions" section herein.

According to the present invention, there is provided a method for enhancing yield-related traits in plants, comprising introducing and expressing in a plant a portion of any one of the nucleic acid sequences given in Table B herein, or a portion of a nucleic acid encoding an orthologue, paralogue or homologue of any of the amino acid sequences given in Table B.

Portions useful in the methods of the invention, encode a polypeptide falling within the definition of a nucleic acid encoding a protein useful in the methods of the invention as defined herein and having substantially the same biological activity as the amino acid sequences given in Table B. Preferably, the portion is a portion of any one of the nucleic acids given in Table B. The portion is typically at least 600 consecutive nucleotides in length, preferably at least 700 consecutive nucleotides in length, more preferably at least 800 consecutive nucleotides in length and most preferably at least 900 consecutive nucleotides in length, the consecutive nucleotides being of any one of the nucleic acid sequences given in Table B. Most preferably the portion is a portion of the nucleic acid of SEQ ID NO: 80. Preferably, the portion encodes an amino acid sequence comprising (any one or more of) carbonic anhydrase domain as defined herein. Preferably, the portion encodes an amino acid sequence which when used in the construction of a CAH3 phylogenetic tree, such as the one depicted in FIG. 7, tends to cluster with the group of alpha CAH3 proteins comprising the amino acid sequence represented by SEQ ID NO: 81 rather than with any other group.

A portion of a nucleic acid encoding a CAH3 protein as defined herein may be prepared, for example, by making one or more deletions to the nucleic acid. The portions may be used in isolated form or they may be fused to other coding (or non coding) sequences in order to, for example, produce a protein that combines several activities. When fused to other coding sequences, the resultant polypeptide produced upon translation may be bigger than that predicted for the CAH3 protein portion.

Another nucleic acid variant useful in the methods of the invention is a nucleic acid capable of hybridising, under reduced stringency conditions, preferably under stringent conditions, with a nucleic acid encoding a CAH3 protein as defined herein, or with a portion as defined herein. The term "hybridisation" is as defined in the "Definiitions" section herein.

Hybridising sequences useful in the methods of the invention, encode a polypeptide having a carbonic anhydrase domain (see the alignment of FIG. 7) and having substantially the same biological activity as the CAH3 protein represented by any of the amino acid sequences given in Table B. The hybridising sequence is typically at least 600 consecutive nucleotides in length, preferably at least 700 consecutive nucleotides in length, more preferably at least 800 consecutive nucleotides in length and most preferably at least 900 consecutive nucleotides in length, the consecutive nucleotides being of any one of the nucleic acid sequences given in Table B. Preferably, the hybridising sequence is one that is capable of hybridising to any of the nucleic acids given in Table B, or to a portion of any of these sequences, a portion being as defined above. Most preferably, the hybridising sequence is capable of hybridising to a nucleic acid as represented by SEQ ID NO: 80 or to a portion thereof. Preferably, the hybridising sequence encodes an amino acid sequence comprising any one or more of the motifs or domains as defined herein. Preferably, the hybridising sequence encodes an amino acid sequence which when used in the construction of a CAH3 phylogenetic tree, such as the one depicted in FIG. 7, tends to cluster with the group of alpha CAH3 proteins comprising the amino acid sequence represented by SEQ ID NO: 81 rather than with any other group.

According to the present invention, there is provided a method for enhancing yield-related traits in plants, comprising introducing and expressing in a plant a nucleic acid capable of hybridizing to any one of the nucleic acids given in the Table B, or comprising introducing and expressing in a plant a nucleic acid capable of hybridising to a nucleic acid encoding an orthologue, paralogue or homologue of any of the nucleic acid sequences given in Table B.

Another nucleic acid variant useful in the methods of the invention is a splice variant encoding a CAH3 protein as defined hereinabove. The term "splice variant" being as defined herein According to the present invention, there is provided a method for enhancing yield-related traits in plants, comprising introducing and expressing in a plant a splice variant of any one of the nucleic acid sequences given in Table B, or a splice variant of a nucleic acid encoding an orthologue, paralogue or homologue of any of the amino acid sequences given in Table B.

Preferred splice variants are splice variants of a nucleic acid represented by SEQ ID NO: 80 or a splice variant of a nucleic acid encoding an orthologue or paralogue of SEQ ID NO: 81. Preferably, the amino acid sequence encoded by the splice variant comprises any one or more of the motifs or domains as defined herein. Preferably, the amino acid sequence encoded by the splice variant, when used in the construction of a CAH3 phylogenetic tree, such as the one depicted in FIG. 7, tends to cluster with the group of alpha CAH3 proteins comprising the amino acid sequence represented by SEQ ID NO: 81 rather than with any other group.

Another nucleic acid variant useful in performing the methods of the invention is an allelic variant of a nucleic acid encoding a CAH3 protein as defined hereinabove. The term "allelic variant" is as defined herein. The allelic variants useful in the methods of the present invention have substantially the same biological activity as the CAH3 protein of SEQ ID NO: 81.

According to the present invention, there is provided a method for enhancing yield-related traits in plants, comprising introducing and expressing in a plant an allelic variant of any one of the nucleic acids given in Table B, or comprising introducing and expressing in a plant an allelic variant of a nucleic acid encoding an orthologue, paralogue or homologue of any of the amino acid sequences given in Table B.

Preferably, the allelic variant is an allelic variant of SEQ ID NO: 80 or an allelic variant of a nucleic acid encoding an orthologue or paralogue of SEQ ID NO: 81. Preferably, the amino acid sequence encoded by the allelic variant comprises any one or more of the motifs or domains as defined herein. Preferably, the amino acid sequence encoded by the allelic variant, when used in the construction of a CAH3 phylogenetic tree, such as the one depicted in FIG. 7, tends to cluster with the group of alpha CAH3 proteins comprising the amino acid sequence represented by SEQ ID NO: 81 rather than with any other group.

A further nucleic acid variant useful in the methods of the invention is a nucleic acid variant obtained by gene shuffling. Gene shuffling or directed evolution is as defined herein According to the present invention, there is provided a method for enhancing yield-related traits in plants, comprising introducing and expressing in a plant a variant of any one of the nucleic acid sequences given in Table B, or comprising introducing and expressing in a plant a variant of a nucleic acid encoding an orthologue, paralogue or homologue of any of the amino acid sequences given in Table B, which variant nucleic acid is obtained by gene shuffling.

Preferably, the variant nucleic acid obtained by gene shuffling encodes an amino acid sequence comprising any one or more of the motifs or domains as defined herein. Preferably, the amino acid encoded sequence by the variant nucleic acid obtained by gene shuffling, when used in the construction of a CAH3 phylogenetic tree such as the one depicted in FIG. 7, tends to cluster with the group of alpha CAH3 proteins comprising the amino acid sequence represented by SEQ ID NO: 81 rather than with any other group.

Furthermore, nucleic acid variants may also be obtained by site-directed mutagenesis. Several methods are available to achieve site-directed mutagenesis, the most common being PCR based methods (Current Protocols in Molecular Biology. Wiley Eds.).

Nucleic acids encoding CAH3 proteins may be derived from any natural or artificial source. The nucleic acid may be modified from its native form in composition and/or genomic environment through deliberate human manipulation. Preferably the CAH3-encoding nucleic acid is from a plant, further preferably from an alga, more preferably from the Chlamydomonadaceae family, most preferably the nucleic acid is from *Chlamydomonas reinhardtii*.

Any reference herein to a CAH3 protein is therefore taken to mean a CAH3 protein as defined above. Any nucleic acid encoding such a CAH3 protein is suitable for use in performing the methods of the invention.

The present invention also encompasses plants or parts thereof (including seeds) obtainable by the methods according to the present invention. The plants or parts thereof comprise a nucleic acid transgene encoding a CAH3 protein as defined above.

The invention also provides genetic constructs and vectors to facilitate introduction and/or expression of the nucleic acid sequences useful in the methods according to the invention, in a plant. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising
 (a) nucleic acid encoding CAH3 protein as defined above;
 (b) one or more control sequences capable of driving expression of the nucleic acid sequence of (a); and optionally
 (c) a transcription termination sequence.

Plants are transformed with a vector comprising the sequence of interest (i.e., a nucleic acid encoding a CAH3 polypeptide as defined herein. The skilled artisan is well aware of the genetic elements that must be present on the vector in order to successfully transform, select and propagate host cells containing the sequence of interest. The sequence of interest is operably linked to one or more control sequences (at least to a promoter). The terms "regulatory element", "control sequence" and "promoter" are as defined in the "Definitions" section herein. The term "operably linked" is also defined herein.

Advantageously, any type of promoter may be used to drive expression of the nucleic acid sequence. The term "promoter" and "plant promoter" are defined in the "Definitions" section herein. The promoter may be a constitutive promoter, as defined herein. Alternatively, the promoter may be an inducible promoter, also defined herein. Additionally or alternatively, the promoter may be an organ-specific or tissue-specific promoter, as defined herein.

Preferably, the CAH3 nucleic acid or variant thereof is operably linked to a young green tissue-specific promoter. A young green tissue-specific promoter as defined herein is a promoter that is transcriptionally active predominantly in young green tissue, substantially to the exclusion of any other parts of a plant, whilst still allowing for any leaky expression in these other plant parts. The young green tissue-specific promoter is preferably a protochlorophyllide reductase (PcR) promoter, more preferably the protochlorophyllide reductase promoter represented by a nucleic acid sequence substantially similar to SEQ ID NO: 206, most preferably the promoter is as represented by SEQ ID NO: 206.

It should be clear that the applicability of the present invention is not restricted to the CAH3-encoding nucleic acid represented by SEQ ID NO: 80, nor is the applicability of the invention restricted to expression of such a CAH3-encoding nucleic acid when driven by a protochlorophyllide reductase promoter. Examples of other young green tissue-specific promoters which may also be used to perform the methods of the invention are shown in Table 2g in the "Definitions" section herein.

For the identification of functionally equivalent promoters, the promoter strength and/or expression pattern of a candidate promoter may be analysed for example by operably linking the promoter to a reporter gene and assay the expression level and pattern of the reporter gene in various tissues of the plant. Suitable well-known reporter genes include for example beta-glucuronidase or beta galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about $1/10,000$ transcripts to about $1/100,000$ transcripts, to about $1/500,0000$ transcripts per cell. Conversely, a "strong promoter" drives expression of a coding sequence at high level, or at about $1/10$ transcripts to about $1/100$ transcripts to about $1/1,000$ transcripts per cell.

Optionally, one or more terminator sequences may be used in the construct introduced into a plant, the term "terminator" being as defined herein. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5' untranslated region (UTR) or in the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell. Biol. 8:4395-4405 (1988); Callis et al., Genes Dev. 1:1183-1200 (1987)). Such intron enhancement of gene expression is typically greatest when placed near the 5' end of the transcription unit. Use of the maize introns Adh1-S intron 1, 2, and 6, the Bronze-1 intron are known in the art. For general information, see The Maize Handbook, Chapter 116, Freeling and Walbot, Eds., Springer, N.Y. (1994).

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. See "Definitions" section herein for a definition of the terms "selectable marker", "selectable marker gene" or "reporter gene".

The invention also provides a method for the production of transgenic plants having enhanced yield-related traits relative to control plants, comprising introduction and expression in a plant of any nucleic acid encoding a CAH3 protein as defined hereinabove.

For the purposes of the invention, "transgenic", "transgene" or "recombinant" are as defined herein in the "Definitions" section. A "transgenic plant" is as defined in the "Definitions" section herein.

More specifically, the present invention provides a method for the production of transgenic plants having increased yield, which method comprises:
  (i) introducing and expressing in a plant or plant cell a CAH3 nucleic acid or variant thereof; and
  (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "introduction" or "transformation" as referred to herein is as defined in the "Definitions" section. The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants.

Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a CAH3 protein as defined hereinabove. Preferred host cells according to the invention are plant cells.

Host plants for the nucleic acids or the vector used in the method according to the invention, the expression cassette or construct or vector are, in principle, advantageously all plants, which are capable of synthesizing the polypeptides used in the inventive method.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression. The terms "increased expression/overexpression" are as defined herein.

As mentioned above, a preferred method for modulating (preferably, increasing) expression of a nucleic acid encoding a CAH3 protein is by introducing and expressing in a plant a nucleic acid encoding a CAH3 protein; however the effects of performing the method, i.e. enhancing yield-related traits may also be achieved using other well known techniques. A description of some of these techniques will now follow.

One such technique is T-DNA activation tagging, which is detailed in the "Definitions" section herein. The effects of the invention may also be reproduced using the technique of TILLING (Targeted Induced Local Lesions In Genomes), also detailed in the "Definitions" section herein. The effects of the invention may also be reproduced using homologous recombination, which is also detailed in the "Definitions" section herein.

Reference herein to enhanced yield-related traits is taken to mean an increase in biomass (weight) of one or more parts of a plant, which may include aboveground (harvestable) parts and/or (harvestable) parts below ground. In particular, such harvestable parts are seeds, and performance of the methods of the invention results in plants having increased seed yield relative to the seed yield of suitable control plants.

The term "yield" and "seed yield" are defined in the "Definitions" section herein. The terms "increase", "enhance" or "improve" are also defined herein.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

Since the transgenic plants according to the present invention have increased yield, it is likely that these plants exhibit an increased growth rate (during at least part of their life cycle), relative to the growth rate of control plants at a corresponding stage in their life cycle. The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding a CAH3 protein as defined herein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield relative to suitable control plants grown under comparable conditions. Therefore, according to the present invention, there is provided a method for increasing yield in plants grown under non-stress conditions or under mild drought conditions, which method comprises increasing expression in a plant of a nucleic acid encoding a CAH3 polypeptide.

In a preferred embodiment of the invention, the increase in yield and/or growth rate occurs according to the methods of the present invention under non-stress conditions.

The methods of the invention are advantageously applicable to any plant, ther term "plant" is defined herein and examples of plants useful in the methods of the invention are also provided.

According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, sorghum and oats.

The present invention also encompasses use of nucleic acids encoding the CAH3 protein described herein and use of these CAH3 proteins in enhancing yield-related traits in plants.

Nucleic acids encoding the CAH3 protein described herein, or the CAH3 proteins themselves, may find use in breeding programmes in which a DNA marker is identified which may be genetically linked to a CAH3-encoding gene. The nucleic acids/genes, or the CAH3 proteins themselves may be used to define a molecular marker. This DNA or protein marker may then be used in breeding programmes to select plants having enhanced yield-related traits as defined hereinabove in the methods of the invention.

Allelic variants of a CAH3 protein-encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acids encoding CAH3 proteins may also be used as probes for genetically and physically mapping the genes that they are a part of, and as markers for traits linked to those genes. Such information may be useful in plant breeding in order to develop lines with desired phenotypes. Such use of CAH3 protein-encoding nucleic acids requires only a nucleic acid sequence of at least 15 nucleotides in length. The CAH3 protein-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the CAH3 protein-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the CAH3 protein-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med. 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

DETAILED DESCRIPTION OF THE INVENTION

Clavata

Surprisingly, it has now been found that increasing expression in a plant of a nucleic acid sequence encoding a YEP, which YEP is a CLV1 polypeptide with a non-functional C-terminal domain, gives plants having enhanced yield-related traits relative to control plants. The particular class of CLV1 polypeptides suitable for disrupting the biological function of the C-terminal domain for the purpose of enhancing yield-related traits in plants relative to control plants is described in detail below.

The present invention provides a method for enhancing yield-related traits in plants relative to control plants, comprising increasing expression in a plant of a nucleic acid sequence encoding a CLV1 polypeptide with a non-functional C-terminal domain. The term "control plant" is as defined in the "Definitions" section herein.

Any reference hereinafter to a "protein useful in the methods of the invention" is taken to mean a CLV1 polypeptide with a non-functional C-terminal domain as defined herein. Any reference hereinafter to a "nucleic acid sequence useful in the methods of the invention" is taken to mean a nucleic acid sequence capable of encoding such a CLV1 polypeptide with a non-functional C-terminal domain. The terms "polypeptide" and "protein" are as defined herein and the terms "polynucleotide(s)", "nucleic acid sequence(s)", "nucleotide sequence(s)" are also defined in the "Definitions" section herein.

A preferred method for increasing expression of a nucleic acid sequence encoding a CLV1 polypeptide with a non-functional C-terminal domain, is by introducing and expressing in a plant a nucleic acid sequence encoding a CLV1 polypeptide with a non-functional C-terminal domain as defined below.

The nucleic acid sequence to be introduced into a plant (and therefore useful in performing the methods of the invention) is any nucleic acid sequence encoding the type of polypeptide which will now be described.

CLV1 polypeptides are well known in the art and are easily identifiable by the presence from N-terminus to C-terminus of: (i) a signal peptide for ER subcellular targeting; (ii) an extracellular LRR domain comprising 20, 21, or 22 LRRs; (iii) a transmembrane domain; and (iv) an intracellular serine/threonine kinase domain (see FIGS. 10a and 11, and Example 28). Furthermore, a CLV1 polypeptide may additionally comprise an amino acid sequence with 50%, 60%, 70%, 80%, 90%, 95%, 98% or more identity to SEQ ID NO: 212 (Example 27).

Additionally, a CLV1 polypeptide may comprise from N-terminus to C-terminus one or both of: (i) Motif 1 as represented by SEQ ID NO: 236; or (ii) Motif 2 as represented by SEQ ID NO: 237. Preferably Motif 1 and Motif 2 are comprised between the signal peptide and the LRR domain. The presence of Motif 1 and Motif 2 was determined as described in Example 26.

The most conserved amino acids within Motif 1 are LXDW, and within Motif 2 XHCXFXGVXCD (where X is a specified subset of amino acids differing for each position, as presented in SEQ ID NO: 236 and SEQ ID NO: 237). Within Motif 1 and Motif 2, are allowed one or more conservative change at any position. Alternatively or additionally, within Motif 1 is allowed one non-conservative change at any position, within Motif 2 are allowed one, two or three non-conservative change(s) at any position.

Alternatively or additionally, a CLV1 polypeptide as defined herein refers to any polypeptide which when used in the construction of a LRR-RLK phylogenetic tree, such as the one depicted in FIG. 10b, tends to cluster with the group of polypeptides comprising the amino acid sequence represented by SEQ ID NO: 212 (represented by a bracket) rather than with any other group of LRR-RLK polypeptides.

A person skilled in the art could readily determine whether any amino acid sequence in question falls within the definition of a "CLV1" polypeptide using known techniques and software for the making of such a phylogenetic tree, such as a GCG, EBI or CLUSTAL package, using default parameters. Any amino acid sequence clustering within the group comprising SEQ ID NO: 212 would be considered to fall within the aforementioned definition of a CLV1 polypeptide, and would be considered suitable for use in the methods of the invention. Such methods are described in Example 25.

Any CLV1 polypeptide is rendered useful in the methods of the invention by disrupting the biological function of the C-terminal domain of this CLV1 polypeptide. Such methods (for disrupting the biological function) are well known in the art and include: removal, substitution and/or insertion of amino acids of the C-terminal domain of the CLV1 polypeptide. Examples of such methods are described in Example 31. One or more amino acid(s) from the C-terminal domain of a CLV1 polypeptide may be removed, substituted and/or inserted.

For the purposes of this application, the C-terminal domain of a CLV1 polypeptide is taken to mean the amino acid sequence following the amino acid sequence encoding the transmembrane domain (from N terminus to C terminus) (see FIGS. 10 and 11), and comprises: (i) the kinase domain; and (ii) one or more phosphorylatable amino acid(s).

An example of a CLV1 polypeptide having a non-functional C-terminal domain is the polypeptide represented by SEQ ID NO: 210, with encoding nucleic acid sequence represented by SEQ ID NO: 209. The amino acid sequence beginning the Arg (R) residue of the RLL motif of kinase subdomain IV (see FIG. 11) and ending at the C-terminus of the full length CLV1 polypeptide (as represented by SEQ ID NO: 212) has been removed.

Examples of CLV1 polypeptides are given in Table C in the Examples Section herein; these sequences may be rendered useful in the methods of the invention by disrupting the biological function of the C-terminal domain of the polypeptide, for example by using any of the methods (for disrupting the biological function) discussed herein.

Also useful in the methods of the invention are homologues of any one of the amino acid sequences given in Table C herein, the term "Homologues" being as defined herein. Also useful in the methods of the invention are derivatives of any one of the polypeptides given in Table C or orthologues or paralogues of any of the SEQ ID NOs given in Table C. "Derivatives" are also defined herein.

The invention is illustrated by transforming plants with the *Arabidopsis thaliana* nucleic acid sequence represented by SEQ ID NO: 209 (comprised in SEQ ID NO: 211), encoding the polypeptide sequence of SEQ ID NO: 210 (comprised in SEQ ID NO: 212), however performance of the invention is not restricted to these sequences. The methods of the invention may advantageously be performed using any nucleic acid sequence encoding a CLV1 polypeptide having a non-functional C-terminal domain as defined herein, including orthologues and paralogues, such as any of the nucleic acid sequences given in Table C of Example 25, having a non-functional C-terminal domain, for example by using any of the methods (for disrupting the biological function) discussed herein.

The amino acid sequences given in Table C herein may be considered to be orthologues and paralogues of the CLV1 polypeptide represented by SEQ ID NO: 212. Orthologues and paralogues being as defined herein.

Orthologues and paralogues may easily be found by performing a so-called reciprocal blast search. Typically, this involves a first BLAST involving BLASTing a query sequence (for example using any of the sequences listed in Table C) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 211 or SEQ ID NO: 212, the second BLAST would therefore be against *Arabidopsis* sequences). The results of the first and second BLASTs are then compared. A paralogue is identified if a high-ranking hit from the first blast is from the same species as from which the query sequence is derived, a BLAST back then ideally results in the query sequence as highest hit; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues. Sequences so identified may subsequently be rendered useful in the methods of the invention by disrupting the biological function of the C-terminal domain of the polypeptide, for example by using any of the methods (for disrupting the biological function) discussed herein.

Table C of Example 25 gives examples of orthologues and paralogues of the CLV1 polypeptide represented by SEQ ID NO 212. Further orthologues and paralogues may readily be identified using the BLAST procedure described above. Sequences so identified are subsequently rendered useful in the methods of the invention by disrupting the biological function of the C-terminal domain of the polypeptide, for example by using any of the methods (for disrupting the biological function) discussed herein.

The proteins of the invention are identifiable by the presence of specific domains, the term "domain" being as defined herein. The term "motif" or "consensus sequence" or "signature" is also defined herein.

Specialist databases also exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), or PFam (Bateman et al., Nucleic Acids Research 30(1): 276-280 (2002). A set of tools for in silico analysis of protein sequences is available on the ExPASY proteomics server (hosted by the Swiss Institute of Bioinformatics (Gasteiger et al., ExPASy: the proteomics server for in-depth protein knowledge and analysis, Nucleic Acids Res. 31:3784-3788 (2003)). In Example 28, are listed the entry accession numbers of the different domains identified by performing such an analysis. For example, a leucine-rich repeat has an InterPro accession number IPR001611, a Prints accession number PR00019, and a PFam accession number PF00560. The LRR domain comprises 20, 21 or 22 such leucine-rich repeats (LRR)s. The kinase domain is identified by InterPro accession number IPR000719, a PFam accession number PF00069, a Prosite accession number PS50011 and a ProDom accession number PD000001. In addition, the kinase domain active site is also identified, as IPR008271. Mutation(s) within this site can be introduced to abolish (or reduce) kinase activity, which is one method of disrupting the biological function the C-terminal domain of a CVL1 polypeptide useful in performing the methods of the invention.

Software algorithms are available to predict subcellular localisation of a polypeptide, or to predict the presence of transmembrane domains. In Example 30, the TargetP1.1 algorithm and the TMHMM2.0 algorithm are respectively used to predict that the CLV1 polypeptide as represented by SEQ ID NO: 212 presents at its N-terminus a signal peptide for ER targeting (endoplasmic reticulum), and comprises a transmembrane domain (across the plasma membrane). Furthermore, the TMHMM2.0 algorithm predicts that the LRR domain is located outside of the cell (to act as an extracellular receptor), whereas the kinase domain is located within the cell (to act a signal transducer).

Domains and motifs may also be identified using routine techniques, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains (such as the LRR domain or the kinase domain, or one of the motifs defined herein) may be used as well. The sequence identity values, which are indicated below in Example 3 as a percentage were determined over the entire nucleic acid or amino acid sequence, and/or over selected domains or conserved motif(s), using the programs mentioned above using the default parameters. Preferably, a CLV1 polypeptide has 50%, 60%, 70%, 80%, 90%, 95%, 98% or more amino acid sequence identity to SEQ ID NO: 212 (Example 27). After its identification, a CLV1 polypeptide is rendered useful in the methods of the invention by disrupting the biological function of the C-terminal domain of the polypeptide as described herein.

In some instances, default parameters may be adjusted to modify the stringency of the search. For example using BLAST, the statistical significance threshold (called "expect" value) for reporting matches against database sequences may be increased to show less stringent matches. In this way, short nearly exact matches may be identified. Motif 1 as represented by SEQ ID NO: 236 and Motif 2 as represented by SEQ ID NO: 237 both comprised in CLV1 polypeptides useful in the methods of the invention can be identified this way (FIG. 11, Example 26). Preferably Motif 1 and Motif 2 are comprised between the signal peptide and the LRR domain.

The most conserved amino acids within Motif 1 are LXDW, and within Motif 2 XHCXFXGVXCD (where X is a specified subset of amino acids differing for each position, as presented in SEQ ID NO: 236 and SEQ ID NO: 237). Within Motif 1 and Motif 2, are allowed one or more conservative change at any position. Alternatively or additionally, within Motif 1 is allowed one non-conservative change at any position, within Motif 2 are allowed one, two or three non-conservative change(s) at any position.

CLV1 polypeptides in their native form typically have kinase activity and are capable of autophosphorylation. Kinase assays are easily performed and are well known in the art. Furthemore, CLV1 polypeptides are capable of interacting with other polypeptides in planta (CLV3, KAPP and more) and in vitro (such as with KAPP in a yeast-two-hybrid assay; Trotochaud et al. (1999) Plant Cell 11, 393-406). After its identification, a CLV1 polypeptide is rendered useful in the methods of the invention by disrupting the biological function of the C-terminal domain of the polypeptide. Further details are provided in Example 31.

Nucleic acid sequences encoding proteins useful in the methods of the invention need not be full-length nucleic acid sequences, since performance of the methods of the invention does not rely on the use of full-length nucleic acid sequences. Examples of nucleic acid sequences suitable for use in performing the methods of the invention include the nucleic acid sequences given in Table C, but are not limited to those sequences. Nucleic acid variants may also be useful in practising the methods of the invention. Examples of such nucleic acid variants include portions of nucleic acid sequences encoding a protein useful in the methods of the invention, nucleic acid sequences hybridising to nucleic acid sequences encoding a protein useful in the methods of the invention, splice variants of nucleic acid sequences encoding a protein useful in the methods of the invention, allelic variants of nucleic acid sequences encoding a protein useful in the methods of the invention and variants of nucleic acid sequences encoding a protein useful in the methods of the invention that are obtained by gene shuffling. The terms portion, hybridising sequence, splice variant, allelic variant, variant obtained by gene shuffling, and variant obtained by site-directed mutagenesis will now be described.

According to the present invention, there is provided a method for enhancing yield-related traits in plants, comprising introducing and expressing in a plant a portion of any one of the nucleic acid sequences given in Table C, or a portion of a nucleic acid sequence encoding an orthologue, paralogue or homologue of any of the amino acid sequences given in Table C of Example 25. After its identification, a CLV1 polypeptide is rendered useful in the methods of the invention by disrupting the biological function of the C-terminal domain of the polypeptide.

Portions useful in the methods of the invention, encode a polypeptide falling within the definition of a nucleic acid sequence encoding a CLV1 polypeptide with a non-functional C-terminal domain as defined herein. The portion typically lacks the nucleic acid sequence encoding the C-terminal domain or parts thereof (from N-terminus to C-terminus, the nucleic acid sequence downstream of the nucleic acid sequence encoding the transmembrane domain). Preferably, the portion is a portion of any one of the nucleic acid sequences given in Table C of Example 25. More preferably, the portion is a portion of the nucleic acid sequence of SEQ ID NO: 211. Most preferably, the portion is as represented by SEQ ID NO: 209.

A portion of a nucleic acid sequence encoding a CLV1 polypeptide with a non-functional C-terminal domain as defined herein may be prepared, for example, by making one or more deletions to the nucleic acid sequence. The portions may be used in isolated form or they may be fused to other coding (or non-coding) sequences in order to, for example, produce a protein that combines several activities. When fused to other coding sequences, the resultant polypeptide produced upon translation may be bigger than that predicted for the CLV1 polypeptide portion.

Another nucleic acid variant useful in the methods of the invention is a nucleic acid sequence capable of hybridising, under reduced stringency conditions, preferably under stringent conditions, with a nucleic acid sequence encoding a CLV1 polypeptide as defined herein, or with a portion as defined herein. The term "hybridisation" is as defined herein.

Hybridising sequences useful in the methods of the invention encode a CLV1 polypeptide as represented by any of the amino acid sequences given in Table C of Example 25. The hybridising sequence is typically at least 500 or 1000 consecutive nucleotides in length, preferably at least 1500 or 2000 consecutive nucleotides in length, more preferably at least 2500 consecutive nucleotides in length and most preferably at least 2900 consecutive nucleotides in length, the consecutive nucleotides being of any one of the nucleic acid sequences given in Table C. Preferably, the hybridising sequence is one that is capable of hybridising to any of the nucleic acid sequences given in Table C, or to a portion of any of these sequences, a portion being as defined above. Most preferably, the hybridising sequence is capable of hybridising to a nucleic acid sequence as represented by SEQ ID NO: 211 or to a portion thereof. Preferably, the hybridising sequence encodes an amino acid sequence comprising any one or more of the motifs or domains as defined herein. Preferably, the hybridising sequence encodes an amino acid sequence which when used in the construction of an LRR-RLK phylogenetic tree, such as the one depicted in FIG. 10b, tends to cluster with the group of polypeptides comprising the amino acid sequence represented by SEQ ID NO: 212 (represented by a bracket) rather than with any other group of LRR-RLK polypeptides. Such hybridising sequences are useful in the methods of the invention by disrupting the biological function of the C-terminal domain of the encoded polypeptide, for example by using any of the methods (for disrupting the biological function) discussed herein.

According to the present invention, there is provided a method for enhancing yield-related traits in plants, comprising introducing and expressing in a plant a nucleic acid sequence capable of hybridizing to any one of the nucleic acid sequences given in the Table C, or comprising introducing and expressing in a plant a nucleic acid sequence capable of hybridising to a nucleic acid sequence encoding an orthologue, paralogue or homologue of any of the nucleic acid sequences given in Table C. Such hybridising sequences are rendered useful in the methods of the invention by disrupting the biological function of the C-terminal domain of the encoded polypeptide, for example by using any of the methods (for disrupting the biological function) discussed herein.

Another nucleic acid variant useful in the methods of the invention is a splice variant encoding a CLV1 polypeptide with a non-functional C-terminal domain. The term "splice variant" being as defined herein.

According to the present invention, there is provided a method for enhancing yield-related traits in plants, comprising introducing and expressing in a plant a splice variant of any one of the nucleic acid sequences given in Table C, or a splice variant of a nucleic acid sequence encoding an orthologue, paralogue or homologue of any of the amino acid sequences given in Table C. Such splice variants are rendered useful in the methods of the invention by disrupting the biological function of the C-terminal domain of the encoded polypeptide, for example by using any of the methods (for disrupting the biological function) discussed herein.

Preferred splice variants are splice variants of a nucleic acid sequence represented by SEQ ID NO: 211 or a splice variant of a nucleic acid sequence encoding an orthologue or paralogue of SEQ ID NO: 212. Preferably, the amino acid sequence encoded by the splice variant, when used in the construction of a LRR-RLK phylogenetic tree, such as the one depicted in FIG. 10b, tends to cluster with the group of polypeptides comprising the amino acid sequence represented by SEQ ID NO: 212 (represented by a bracket) rather than with any other group of LRR-RLK polypeptides. Such splice variants are rendered useful in the methods of the invention by disrupting the biological function of the C-terminal domain of the encoded polypeptide, for example by using any of the methods (for disrupting the biological function) discussed herein.

Another nucleic acid variant useful in performing the methods of the invention is an allelic variant of a nucleic acid sequence encoding a CLV1 polypeptide with a non-functional C-terminal domain. Alleles or allelic variants are alternative forms of a given gene, located at the same chromosomal position. Allelic variants exist in nature, and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

According to the present invention, there is provided a method for enhancing yield-related traits in plants, comprising introducing and expressing in a plant an allelic variant of any one of the nucleic acid sequences given in Table C, or comprising introducing and expressing in a plant an allelic variant of a nucleic acid sequence encoding an orthologue, paralogue or homologue of any of the amino acid sequences given in Table C. Such allelic variants are rendered useful in the methods of the invention by disrupting the biological function of the C-terminal domain of the encoded polypeptide, for example by using any of the methods (for disrupting the biological function) discussed herein.

Preferably, the allelic variant is an allelic variant of SEQ ID NO: 211 or an allelic variant of a nucleic acid sequence encoding an orthologue or paralogue of SEQ ID NO: 212. Preferably, the amino acid sequence encoded by the allelic variant, when used in the construction of a LRR-RLK phylogenetic tree, such as the one depicted in FIG. 10b, tends to cluster with the group of polypeptides comprising the amino acid sequence represented by SEQ ID NO: 212 (represented by a bracket) rather than with any other group of LRR-RLK polypeptides. Such allelic variants are rendered useful in the methods of the invention by disrupting the biological function of the C-terminal domain of the encoded polypeptide, for example by using any of the methods (for disrupting the biological function) discussed herein.

A further nucleic acid variant useful in the methods of the invention is a nucleic acid variant obtained by gene shuffling. Gene shuffling or directed evolution may also be used to generate variants of nucleic acid sequences encoding a CLV1 polypeptide with a non-functional C-terminal domain. This consists of iterations of DNA shuffling followed by appropriate screening and/or selection to generate variants of nucleic acid sequences or portions thereof encoding a CLV1 polypeptide with a non-functional C-terminal domain as defined above (Castle et al., (2004) Science 304(5674): 1151-4; U.S. Pat. Nos. 5,811,238 and 6,395,547).

According to the present invention, there is provided a method for enhancing yield-related traits in plants, comprising introducing and expressing in a plant a variant of any one of the nucleic acid sequences given in Table C, or comprising introducing and expressing in a plant a variant of a nucleic acid sequence encoding an orthologue, paralogue or homologue of any of the amino acid sequences given in Table C, which variant nucleic acid sequence is obtained by gene shuffling.

Preferably, the amino acid sequence encoded by the variant nucleic acid sequence obtained by gene shuffling, when used in the construction a LRR-RLK phylogenetic tree, such as the one depicted in FIG. 10b, tends to cluster with the group of polypeptides comprising the amino acid sequence represented by SEQ ID NO: 212 (represented by a bracket) rather than with any other group of LRR-RLK polypeptides. Such variants obtained by gene shuffling are rendered useful in the methods of the invention by disrupting the biological function of the C-terminal domain of the encoded polypeptide, for example by using any of the methods (for disrupting the biological function) discussed herein.

Furthermore, nucleic acid variants may also be obtained by site-directed mutagenesis. Several methods are available to achieve site-directed mutagenesis, the most common being PCR based methods (Current Protocols in Molecular Biology. Wiley Eds). Targets of site-directed mutagenesis with the aim generate variants of nucleic acid sequence encoding a CLV1 polypeptide with a non-functional C-terminal domain, are described in Example 31.

According to the present invention, there is provided a method for enhancing yield-related traits in plants, comprising introducing and expressing in a plant a variant of any one of the nucleic acid sequences given in Table C, or comprising introducing and expressing in a plant a variant of a nucleic acid sequence encoding an orthologue, paralogue or homologue of any of the amino acid sequences given in Table C, which variant nucleic acid sequence is obtained by site-directed mutagenesis.

Preferably, the amino acid sequence encoded by the variant nucleic acid sequence obtained by site-directed mutagenesis, when used in the construction a LRR-RLK phylogenetic tree, such as the one depicted in FIG. 10b, tends to cluster with the group of polypeptides comprising the amino acid sequence represented by SEQ ID NO: 212 (represented by a bracket) rather than with any other group of LRR-RLK polypeptides. Such variants obtained by site-directed mutagenesis are rendered useful in the methods of the invention by disrupting the biological function of the C-terminal domain of the encoded polypeptide, for example by using any of the methods (for disrupting the biological function) discussed herein.

The following nucleic acid variants encoding a CLV1 polypeptide with a non-functional C-terminal domain, are examples of variants suitable in practising the methods of the invention:

(i) a portion of a nucleic acid sequence encoding a CLV1; or
(ii) a nucleic acid sequence capable of hybridising with a nucleic acid sequence encoding a CLV1 polypeptide; or
(iii) a splice variant of a nucleic acid sequence encoding a CLV1 polypeptide; or
(iv) an allelic variant of a nucleic acid sequence encoding a CLV1; or (v) a nucleic acid sequence encoding a CLV1 polypeptide obtained by gene shuffling; or (vi) a nucleic acid sequence encoding a CLV1 polypeptide obtained by site-directed mutagenesis;

wherein the nucleic acid sequence in (i) to (vi) encodes a CLV1 polypeptide with a non-functional domain.

Nucleic acid sequences encoding a CLV1 polypeptide with a non-functional C-terminal domain may be derived from any natural or artificial source. The nucleic acid sequence may be modified from its native form in composition and/or genomic environment through deliberate human manipulation. Preferably a nucleic acid sequence encoding a CLV1 polypeptide with a non-functional C-terminal domain is from a plant, further preferably from a dicot, more preferably from the Brassicaceae family, most preferably the nucleic acid sequence is from *Arabidopsis thaliana*.

Any reference herein to a CLV1 polypeptide with a non-functional C-terminal domain is therefore taken to mean a CLV1 polypeptide with a non-functional C-terminal domain as defined above. Any nucleic acid sequence encoding such a CLV1 polypeptide with a non-functional C-terminal domain is suitable for use in performing the methods of the invention.

The present invention also encompasses plants or parts thereof (including seeds) obtainable by the methods according to the present invention. The plants or parts thereof comprise a nucleic acid transgene encoding a CLV1 polypeptide with a non-functional C-terminal domain as defined above.

The invention also provides genetic constructs and vectors to facilitate introduction and/or expression of the nucleic acid sequences useful in the methods according to the invention, in a plant. The gene constructs may be inserted into vectors, which may be commercially available, suitable for transforming into plants and suitable for expression of the gene of interest in the transformed cells. The invention also provides use of a construct as defined herein in the methods of the invention.

More specifically, the present invention provides a construct comprising (a) a nucleic acid sequence encoding CLV1 polypeptide with a non-functional C-terminal domain as defined above;

(b) one or more control sequences capable of driving expression of the nucleic acid sequence of (a); and optionally (c) a transcription termination sequence.

In one embodiment, the control sequence of a construct is a tissue-specific promoter for expression in young expanding tissues. An example of a tissue-specific promoter for expression in young expanding tissues is the beta-expansin promoter.

Plants are transformed with a vector comprising the sequence of interest (i.e., a nucleic acid sequence encoding a CLV1 polypeptide with a non-functional C-terminal domain as defined herein. The skilled artisan is well aware of the genetic elements that must be present on the vector in order to successfully transform, select and propagate host cells containing the sequence of interest. The sequence of interest is operably linked to one or more control sequences (at least to a promoter). The terms "regulatory element", "control sequence" and "promoter" are as defined herein. The term "operably linked" is also defined herein.

Advantageously, any type of promoter may be used to drive expression of the nucleic acid sequence. The term "promoter" and "plant promoter" are as defined herein. The promoter may be a constitutive promoter, as defined herein. Alternatively, the promoter may be an inducible promoter, as defined herein. Additionally or alternatively, the promoter may be an organ-specific or tissue-specific promoter, as defined herein.

In one embodiment, a nucleic acid sequence encoding CLV1 polypeptide with a non-functional C-terminal domain as defined above, such as the nucleic acid sequence as represented by SEQ ID NO: 209, is operably linked to a promoter capable of preferentially expressing the nucleic acid sequence in young expanding tissues, or in the apical meristem. Preferably, the promoter capable of preferentially expressing the nucleic acid sequence in young expanding tissues has a comparable expression profile to a beta-expansin promoter. More specifically, the promoter capable of preferentially expressing the nucleic acid sequence in young expanding tissues is a promoter capable of driving expression in the cell expansion zone of a shoot or root. Most preferably, the promoter capable of preferentially expressing the nucleic acid sequence in young expanding tissues is the beta-expansin promoter (SEQ ID NO: 241).

For the identification of functionally equivalent promoters, the promoter strength and/or expression pattern of a candidate promoter may be analysed for example by operably linking the promoter to a reporter gene and assay the expression level and pattern of the reporter gene in various tissues of the plant. Suitable well-known reporter genes include for example beta-glucuronidase or beta galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid sequence used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500,0000 transcripts per cell. Conversely, a "strong promoter" drives expression of a coding sequence at high level, or at about 1/10 transcripts to about 1/100 transcripts to about 1/1,000 transcripts per cell.

Optionally, one or more terminator sequences may be used in the construct introduced into a plant, the term "terminator" being as defined herein. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5' untranslated region (UTR) or in the coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, Mol. Cell. Biol. 8:4395-4405 (1988); Callis et al., Genes Dev. 1:1183-1200 (1987)). Such intron enhancement of gene expression is typically greatest when placed near the 5' end of the transcription unit. Use of the maize introns Adh1-S intron 1, 2, and 6, the Bronze-1 intron are known in the art. For general information, see The Maize Handbook, Chapter 116, Freeling and Walbot, Eds., Springer, N.Y. (1994).

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acid sequences, it is advantageous to use marker genes (or reporter genes). Therefore, the genetic construct may optionally comprise a selectable marker gene. See the "Definitions" section herein for a description of the terms "selectable marker", "selectable marker gene" or "reporter gene".

The invention also provides a method for the production of transgenic plants having enhanced yield-related traits relative to control plants, comprising introduction and expression in a plant of any nucleic acid sequence encoding a CLV1 polypeptide with a non-functional C-terminal domain as defined hereinabove. The terms "transgenic", "transgene" or "recombinant" means are defined herein.

More specifically, the present invention provides a method for the production of transgenic plants having enhanced yield-related traits, which method comprises:
(i) introducing and expressing in a plant or plant cell a nucleic acid sequence encoding a CLV1 polypeptide with a non-functional C-terminal domain, or variant thereof; and
(ii) cultivating the plant cell under conditions promoting plant growth and development.

The nucleic acid sequence may be introduced directly into a plant cell or into the plant itself (including introduction into a tissue, organ or any other part of a plant). According to a preferred feature of the present invention, the nucleic acid sequence is preferably introduced into a plant by transformation. The term "introduction" or "transformation" is as defined herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid sequence encoding a CLV1 polypeptide with a non-functional C-terminal domain as defined hereinabove. Preferred host cells according to the invention are plant cells.

Host plants for the nucleic acid sequences or the vector used in the method according to the invention, the expression cassette or construct or vector are, in principle, advantageously all plants, which are capable of synthesizing the polypeptides used in the inventive method.

A transgenic plant for the purposes of the invention is thus understood as meaning, as above, that the nucleic acid sequences used in the method of the invention are not at their natural locus in the genome of said plant, it being possible for the nucleic acid sequences to be expressed homologously or heterologously. However, as mentioned, transgenic also means that, while the nucleic acid sequences according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acid sequences according to the invention at an unnatural locus in the genome, i.e. homologous or, preferably, heterologous expression of the nucleic acid sequences takes place. Preferred transgenic plants are mentioned herein.

The invention also extends to harvestable parts of a plant such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

Methods for increasing expression of nucleic acid sequences or genes, or gene products, are well documented in the art and include, for example, overexpression driven by appropriate promoters, the use of transcription enhancers or translation enhancers. Isolated nucleic acid sequences which serve as promoter or enhancer elements may be introduced in an appropriate position (typically upstream) of a non-heterologous form of a polynucleotide so as to upregulate expression. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added as described above.

Other control sequences (besides promoter, enhancer, silencer, intron sequences, 3'UTR and/or 5'UTR regions) may be protein and/or RNA stabilizing elements.

As mentioned above, a preferred method for increasing expression of a nucleic acid sequence encoding a CLV1 polypeptide with a non-functional C-terminal domain is by introducing and expressing in a plant a nucleic acid sequence encoding a CLV1 polypeptide with a non-functional C-terminal domain; however the effects of performing the method, i.e. enhancing yield-related traits may also be achieved using other well known techniques. Examples of such techniques include T-DNA activation tagging (Hayashi et al. Science (1992) 1350-1353), as described in the "Definitions" section herein. The effects of the invention may also be reproduced using the technique of TILLING (Targeted Induced Local Lesions In Genomes). The effects of the invention may also be reproduced using homologous recombination. For details of these techniques, see the "Definitions" section herein.

Reference herein to enhanced yield-related traits is taken to mean an increase in biomass (weight) of one or more parts of a plant, which may include aboveground (harvestable) parts and/or (harvestable) parts below ground.

In particular, such harvestable parts are seeds, and performance of the methods of the invention results in plants having increased seed yield relative to the seed yield of suitable control plants.

The terms "yield" and "seed yield" are as defined in the "Definitions" section herein. The terms "increase", "improving" or "improve" are also described herein.

Increased seed yield may manifest itself as one or more of the following:
(i) increased total seed yield, which includes an increase in seed biomass (seed weight) and which may be an increase in the seed weight per plant or on an individual seed basis;
(ii) increased number of panicles per plant
(iii) increased number of flowers ("florets") per panicle
(iv) increased seed fill rate
(v) increased number of (filled) seeds;
(vi) increased seed size (length, width area, perimeter), which may also influence the composition of seeds;
(vii) increased seed volume, which may also influence the composition of seeds;
(viii) increased harvest index, which is expressed as a ratio of the yield of harvestable parts, such as seeds, over the total biomass; and
(ix) increased Thousand Kernel Weight (TKW), which is extrapolated from the number of filled seeds counted and their total weight. An increased TKW may result from an increased seed size and/or seed weight. An increased TKW may result from an increase in embryo size and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased yield may also result in modified architecture, or may occur because of modified architecture.

In particular, enhanced yield-related traits is taken to mean one or more of the following: (i) increase in aboveground biomass; (ii) increase in root biomass; (iii) increase in thin root biomass; (iv) increased number of primary panicles; (v) increased number of flowers per panicle; (vi) increased total seed yield; (vii) increased number of filled seeds; (viii) increased total number of seeds; or (ix) increased harvest index. Therefore, according to the present invention, there is provided a method for enhancing one or more of the following yield-related traits: (i) increase in aboveground biomass; (ii) increase in root biomass; (iii) increase in thin root biomass; (iv) increased number of primary panicles; (v) increased number of flowers per panicle; (vi) increased total seed yield; (vii) increased number of filled seeds; (viii) increased total number of seeds; or (ix) increased harvest index, relative to control plants, which method comprises increasing expression, in a plant of a nucleic acid sequence encoding a CLV1 polypeptide with a non-functional C-terminal domain.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

Since the transgenic plants according to the present invention have enhanced yield-related traits, it is likely that these plants exhibit an increased growth rate (during at least part of their life cycle), relative to the growth rate of control plants at a corresponding stage in their life cycle. The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants relative to control plants, which method comprises increasing expression, in a plant of a nucleic acid sequence encoding a CLV1 polypeptide as defined herein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having enhanced yield related traits relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions enhanced yield-related traits relative to suitable control plants grown under comparable conditions. Therefore, according to the present invention, there is provided a method for increasing yield in plants grown under non-stress conditions or under mild drought conditions, which method comprises increasing expression in a plant of a nucleic acid sequence encoding a CLV1 polypeptide with a non-functional C-terminal domain.

In a preferred embodiment of the invention, the increase in yield and/or growth rate occurs according to the methods of the present invention under non-stress conditions.

The methods of the invention are advantageously applicable to any plant. The term "plant" is defined in the "Definitions" section herein and examples of suitable plants useful in the present invention are also described.

According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, sorghum and oats.

The present invention also encompasses use of nucleic acid sequences encoding a CLV1 polypeptide with a non-functional C-terminal domain as described herein, and use of these CLV1 polypeptides with a non-functional C-terminal domain in enhancing yield-related traits in plants.

Nucleic acid sequences encoding a CLV1 polypeptide with a non-functional C-terminal domain described herein, or the CLV1 polypeptides with a non-functional C-terminal domain themselves, may find use in breeding programmes in which a DNA marker is identified which may be genetically linked to a gene encoding a CLV1 polypeptide with a non-functional C-terminal domain. The genes/nucleic acid sequences, or the CLV1 polypeptides with a non-functional C-terminal domain themselves may be used to define a molecular marker. This DNA or protein marker may then be used in breeding programmes to select plants having enhanced yield-related traits as defined hereinabove in the methods of the invention.

Allelic variants of a gene/nucleic acid sequence encoding a CLV1 polypeptide with a non-functional C-terminal domain, may also find use in marker-assisted breeding programmes.

Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give enhanced yield-related traits. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acid sequences encoding CLV1 polypeptides with a non-functional C-terminal domain may also be used as probes for genetically and physically mapping the genes that they are a part of, and as markers for traits linked to those genes. Such information may be useful in plant breeding in order to develop lines with desired phenotypes. Such use of nucleic acid sequences encoding CLV1 polypeptides requires only a nucleic acid sequence of at least 15 nucleotides in length. The nucleic acids encoding CLV1 polypeptides may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the nucleic acid sequences encoding CLV1 polypeptides. The resulting banding patterns may then be subjected to genetic analyses using computer programs such as MapMaker (Lander et al. (1987) Genomics 1: 174-181) in order to construct a genetic map. In addition, the nucleic acid sequences may be used to probe Southern blots containing restriction endonuclease-treated genomic DNAs of a set of individuals representing parent and progeny of a defined genetic cross. Segregation of the DNA polymorphisms is noted and used to calculate the position of the nucleic acid sequence encoding a CLV1 polypeptide with a non-functional C-terminal domain in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acid sequences. Examples include allele-specific amplification (Kazazian (1989) J. Lab. Clin. Med. 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

DESCRIPTION OF FIGURES

The present invention will now be described with reference to the following figures in which:

FIG. 3 A) shows an alignment of the Class I TCP polypeptide sequences of Table A encoding the basic-Helix-Loop-Helix (bHLH) structure. When considering the polypeptide sequence from N-terminus to C-terminus, the basic residues precede the Helix-Loop-Helix. The sequences shown are: 3B) is a cartoon representing the primary structure of the polypeptide sequences useful in performing the methods of the invention, from N-terminus to C-terminus: a conserved TCP domain comprising the basic-Helix-Loop-Helix (bHLH), a consensus C-terminal motif, and an HQ rich region. The sequences shown are found within the following SEQ ID NOs: Arath_TCP20, SEQ ID NO: 2; Arath_TCP6, SEQ ID NO: 4; Brara_CL I TCP, SEQ ID NO: 44; Braol_CL I TCP, SEQ ID NO: 42; Ociba_CL I TCP, SEQ ID NO: 20; Maldo_CL I TCP, SEQ ID NO: 14; Vitvi_CL I TCP, SEQ ID NO: 32; Poptr_CL I TCP, SEQ ID NO: 24; Nicbe_CL I TCP, SEQ ID NO: 18; Medtr_CL I TCP, SEQ ID NO: 16; Lotco_CL I TCP, SEQ ID NO: 54; Glyma_CL I TCP, SEQ ID NO: 8; Helan_CL I TCP, SEQ ID NO: 48; Aqufo_CL I TCP, SEQ ID NO: 6; Orysa_PCF1, SEQ ID NO: 22; Zeama_CL I TCP, SEQ ID NO: 34; Sacof_CL I TCP, SEQ ID NO: 26; Sorbi_CL I TCP, SEQ ID NO: 30; Bradi_CL I TCP, SEQ ID NO: 40; and Allce_CL I TCP, SEQ ID NO: 38.

FIG. 5 details examples of Class I TCP sequences useful in performing the methods according to the present invention.

FIG. 6 shows the domain structure of the CAH3 polypeptide presented in SEQ ID NO: 81. The carbonic anhydrase domain (Pfam entry PF00194) is indicated in bold underlined.

FIG. 9 details examples of CAH3 sequences useful in performing the methods according to the present invention.

FIG. 10 (B) shows a phylogenetic tree as described in Bommert et al. (2004). Polypeptide sequences useful in performing the methods of the invention should cluster with the clade comprising the CLV1 polypeptide (called "subfamily" A), as delimited in the figure by the bracket. CLV1 is as represented by SEQ ID NO: 212.

FIG. 11 Shows a multiple alignment of several CLV1 polypeptide sequences of Table C (when from full length nucleic acid sequences), using VNTI AlignX multiple alignment program, based on a modified ClustalW algorithm (InforMax, Bethesda, Md., webpage at informaxinc.com), with default settings for gap opening penalty of 10 and a gap extension of 0.05). The signal peptide and the transmembrane domain are boxed in bold. The beginning and the end of the LRR domain (with the 21 LRR numbered and underlined in black), of the kinase domain (with the 11 subdomains numbered and double-underlined), and of the C-terminal domain are marked with a bracket (each). Motif 1 (SEQ ID NO: 236) and Motif 2 (SEQ ID NO: 237) are also boxed. Within Motif 2, the first cysteine pair is marked, as is the second cysteine pair (between the LRR domain and the transmembrane domain). The conserved glycine with subdomain IX (SDIX) of the kinase domain is also marked. The vertical line within subdomain IV (SDIV) of the kinase domain marks the end of the CLV1 polypeptide with a non-functional C-terminal domain as represented by SEQ ID NO: 210. The sequences shown are: Arath_CLAVAT1 FL, SEQ ID NO: 212; Brana_RLK, SEQ ID NO: 214; Eucgr_LRR-RLK, SEQ ID NO: 216; Glyma_CLV1A, SEQ ID NO: 218; Glyma_NARK_CLV1B, SEQ ID NO: 220; Lotja_HAR1, SEQ ID NO: 222; Medtr_SUNN, SEQ ID NO: 224; Orysa_FON1, SEQ ID NO: 226; Pissa_SYM29, SEQ ID NO: 228; Poptr_LRR-RLK II, SEQ ID NO: 230; Poptr_LRR-RLK I, SEQ ID NO: 232; and Zeama_KIN5, SEQ ID NO: 233.

FIG. 13 details examples of CLV1 sequences useful in performing the methods according to the present invention.

Figure 1:
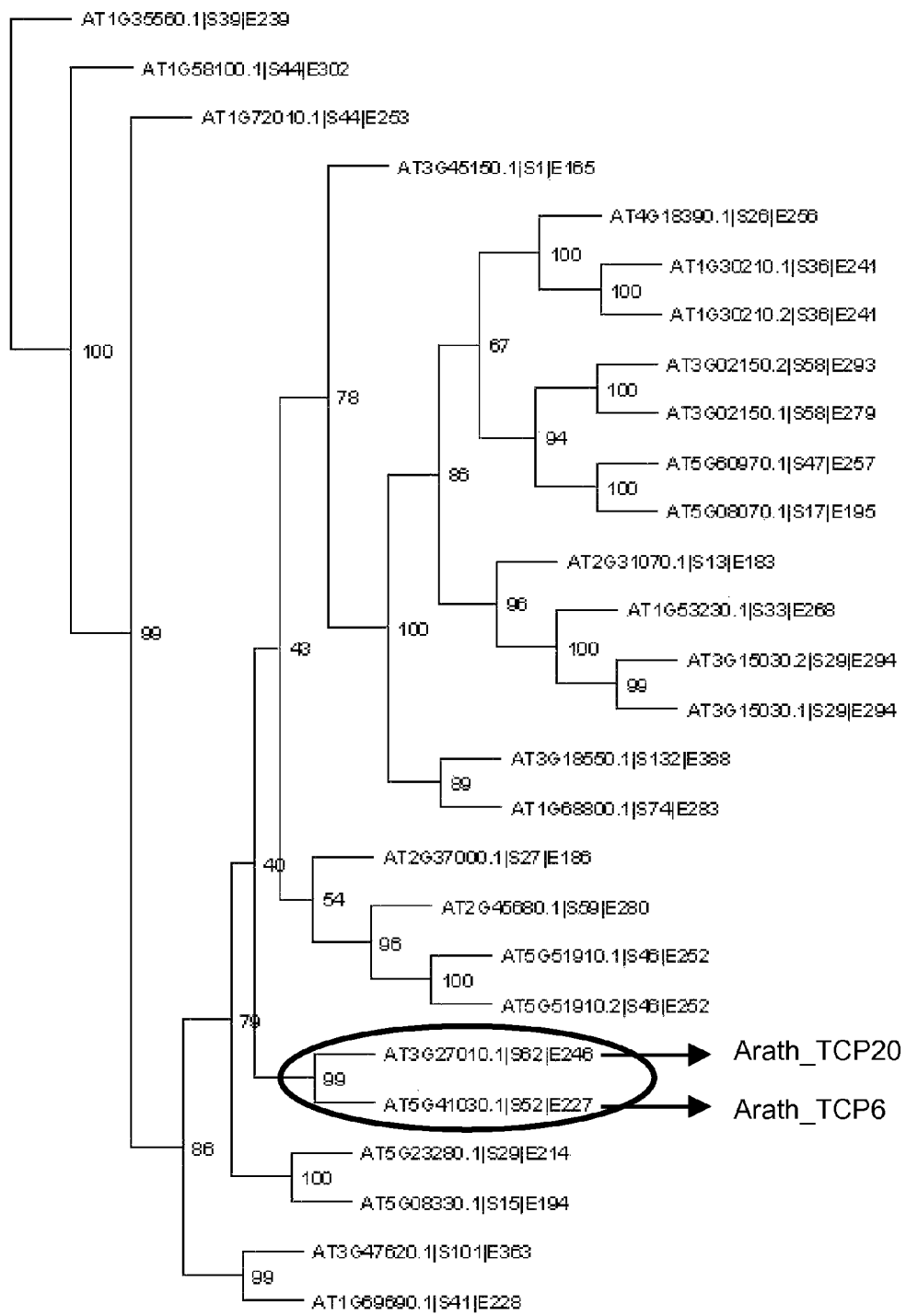
FIG. 1 shows a phylogenetic tree of all the *Arabidopsis thaliana* TCP polypeptides according to the *Arabidopsis* Database for Transcription factors, available at the Center for Bioinformatics (CBI), Peking University, China. The clade of interest, comprising two *Arabidopsis* paralogs At3g27010 (also called AtTCP20 or PCF1) and At5g41030 (also called TCP 6), has been circled.

The present invention will now be described with reference to the following examples, which are by way of illustration alone. The following examples are not intended to completely define or otherwise limit the scope of the invention.

EXAMPLES

PCF1

Example 1

Identification of Sequences Related to SEQ ID NO: 1 and SEQ ID NO: 2

Nucleic acid sequences (full length cDNA, ESTs or genomic) related to SEQ ID NO: 1 and/or polypeptide sequences related to SEQ ID NO: 2 were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. The polypeptide encoded by SEQ ID NO: 1 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search.

In addition to the publicly available nucleic acid sequences available at NCBI, proprietary sequence databases were also searched following the same procedure as described herein above.

Table A provides a list of nucleic acid and polypeptide sequences related to the nucleic acid sequence as represented by SEQ ID NO: 1 and the polypeptide sequence represented by SEQ ID NO: 2.

TABLE A

Nucleic acid sequences related to the nucleic acid sequence (SEQ ID NO: 1) useful in the methods of the present invention, and the corresponding deduced polypeptides.

| Name | Status | Name | Database accession number | Nucleic acid sequence ID number | Polypeptide sequence ID number |
|---|---|---|---|---|---|
| Arath_TCP20 | full length | *Arabidopsis thaliana* | AK118178 At3g27010 | 1 | 2 |
| Arath_TCP6 | full length | *Arabidopsis thaliana* | At5g41030 | 3 | 4 |
| Aqufo_Class I TCP | full length | *Aquilegia formosa* x *Aquilegia pubescens* | DR951658 DT754291 | 5 | 6 |
| Glyma_Class I TCP | full length | *Glycine max* | AI736626.1 BI470329.1 BG044313.1 CA784744.1 BF424472.1 | 7 | 8 |
| Goshi_Class I TCP | full length | *Gossypium hirsutum* | DT574583 DW499958 | 9 | 10 |
| Lyces_Class I TCP | full length | *Lycopersicon esculentum* | BW688913 BP878035.1 BI931745.1 | 11 | 12 |
| Maldo_Class I TCP | full length | *Malus domestica* | EB153444 CN895103 | 13 | 14 |
| Medtr_Class I TCP | full length | *Medicago truncatula* | CG926048.1 CA921765.1 | 15 | 16 |
| Nicbe_Class I TCP | full length | *Nicotiana benthamiana* | CK296978 | 17 | 18 |
| Ociba_Class I TCP | full length | *Ocimum basilicum* | DY322462 | 19 | 20 |
| Orysa_PCF1 | full length | *Oryza sativa* | NM_001051782 Os01g0924400 | 21 | 22 |
| Poptr_Class I TCP | full length | *Populus tremuloides* | CX169560.1 DT515387.1 | 23 | 24 |
| Sacof_Class I TCP | full length | *Saccharum officinarum* | SCJLRT1023A09.g | 25 | 26 |
| Soltu_Class I TCP | full length | *Solanum tuberosum* | CK271473.1 BQ507674.2 | 27 | 28 |
| Sorbi_Class I TCP | full length | *Sorghum bicolor* | CLASS162154.1 ED507285.1 CW333599.1 | 29 | 30 |
| Vitvi_Class I TCP | full length | *Vitis vinifera* | CB972449 EC971921 | 31 | 32 |
| Zeama_Class I TCP_1 | full length | *Zea mays* | DR826915.1 DR794438.1 | 33 | 34 |
| Zeama_Class I TCP_2 | full length | *Zea mays* | DR963477.1 EE022629.1 | 35 | 36 |
| Allce_Class I TCP partial 5' | partial | *Allium cepa* | CF439613 | 37 | 38 |
| Bradi_Class I TCP partial 5' | partial | *Brachypodium distachyon* | DV480032 | 39 | 40 |
| Braol_Class I TCP partial 5' | partial | *Brassica oleracea* | BZ446639.1 BH464032.1 BZ445385.1 | 41 | 42 |
| Brara_Class I TCP partial 3' | partial | *Brassica rapa* | DX909657.1 DU115108.1 | 43 | 44 |
| Cofca_Class I TCP partial middle | partial | *Coffea canephora* | DV701323 | 45 | 46 |
| Helan_Class I TCP partial 3' | partial | *Helianthus annuus* & *petiolaris* | DY906028 DY940311.1 | 47 | 48 |
| Horvu_Class I TCP partial 3' | partial | *Hordeum vulgare* | DN181323 | 49 | 50 |
| Linus_Class I TCP partial middle | partial | *Linum usitatissimum* | Contig LU04MC03342_61667197 | 51 | 52 |
| Lotco_Class I TCP partial 5' | partial | *Lotus corniculatus* | BW630043.1 | 53 | 54 |
| Pethy_Class I TCP partial middle | partial | *Petunia hybrida* | CV296461 CV297628 | 55 | 56 |
| Prupe_Class I TCP partial 3' | partial | *Prunus persica* | BU044166. | 57 | 58 |
| Ricco_Class I TCP partial 3' | partial | *Ricinus communis* | EG685326.1 EG671551 | 59 | 60 |
| Salmi_Class I TCP partial 3' | partial | *Salvia miltiorrhiza* | CV163534 | 61 | 62 |
| Zinel_Class I TCP partial middle | partial | *Zinnia elegans* | AU307217 | 63 | 64 |
| Cicen_Class I TCP partial 3' | partial | *Cichorium endivia*, *Cichorium intybus* | EL361878; EH709336 | 70 | 71 |
| Frave_Class I TCP partial | partial | *Fragaria vesca* | EX657224 | 72 | 73 |
| Jugsp_Class I TCP partial middle | partial | *Juglans hindsii* x *Juglans regia* | EL896093 | 74 | 75 |

TABLE A-continued

Nucleic acid sequences related to the nucleic acid sequence (SEQ ID NO: 1) useful
in the methods of the present invention, and the corresponding deduced polypeptides.

| Name | Status | Name | Database accession number | Nucleic acid sequence ID number | Polypeptide sequence ID number |
|---|---|---|---|---|---|
| Pangi_Class I TCP partial 3' | partial | *Panax ginseng* | CN846083 | 76 | 77 |
| Pontr_Class I TCP partial 3' | partial | *Poncirus trifoliata* | CX644761 | 78 | 79 |

Example 2

Alignment of Relevant Polypeptide Sequences

AlignX from the Vector NTI (Invitrogen) is based on the popular Clustal algorithm of progressive alignment (Thompson et al. (1997) Nucleic Acids Res 25:4876-4882; Chema et al. (2003). Nucleic Acids Res 31:3497-3500). A phylogenetic tree can be constructed using a neighbour-joining clustering algorithm. Default values are for the gap open penalty of 10, for the gap extension penalty of 0.1 and the selected weight matrix is Blosum 62 (if polypeptides are aligned). In some instances, manual adjustment is necessary to better optimize the alignment between the polypeptide sequences, in particular in the case of motif alignment.

In FIG. 1 is provided a TCP phylogenetic tree according to the *Arabidopsis* Database for Transcription factors, available at the Center for Bioinformatics (CBI), Peking University, China. The clade of interest, comprising two *Arabidopsis* paralogs At3g27010 (also called AtTCP20 or PCF1) and At5g41030 (also called TCP 6), has been circled. Any polypeptide falling within this clade (after a new multiple alignment step as described hereinabove) is considered to be useful in performing the methods of the invention as described herein.

Figure 2:
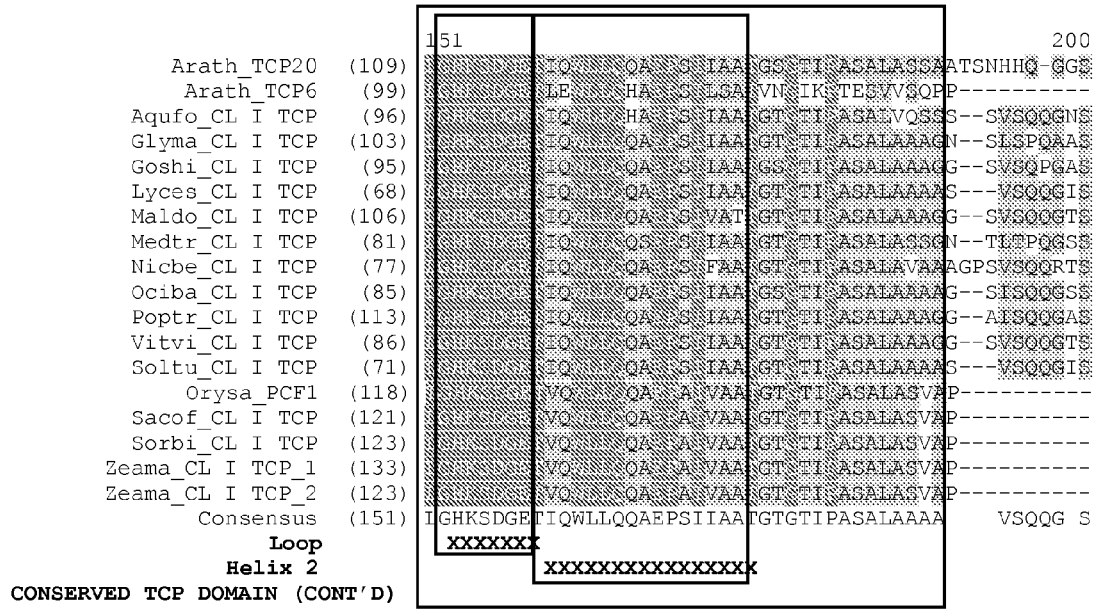
FIG. 2 shows a multiple alignment of several plant Class I TCP polypeptides of Table A (when from full length nucleic acid sequences), using VNTI AlignX multiple alignment program, based on a modified ClustalW algorithm (InforMax, Bethesda, Md., www.informaxinc.com), with default settings for gap opening penalty of 10 and a gap extension of 0.05). The conserved TCP domain (comprising the bHLH) among the polypeptide sequences useful in performing the methods of the invention is heavily boxed. The basic residues (in bold in the consensus line) and the Helix-Loop-Helix (HLH) sequences are lightly boxed, as well as the consensus C-terminal motif PGLEL(G/R/A)LSQX$_{1-5}$G(V/L)L, where X is any amino acid (SEQ ID NO: 65). The HQ rich region (H being histidine, Q glutamine) is equally lightly boxed. The sequences shown are: Arath_TCP20, SEO ID NO: 2; Arath_TCP6, SEO ID NO: 4; Aqufo_CL I TCP, SEQ ID NO: 6; Glyma_CL I TCP, SEQ ID NO: 8; Goshi_CL I TCP, SEQ ID NO: 10; Lyces_CL I TCP, SEQ ID NO: 12; Maldo_CL I TCP, SEQ ID NO: 14; Medtr_CL I TCP, SEQ ID NO: 16; Nicbe_CL I TCP, SEQ ID NO: 18; Ociba_CL I TCP, SEQ ID NO: 20; Poptr_CL I TCP, SEQ ID NO: 24; Vitvi_CL I TCP, SEQ ID NO: 32; Soltu_CL I TCP, SEQ ID NO: 28; Orysa_PCF1, SEQ ID NO: 22; Sacof_CL I TCP, SEQ ID NO: 26; Sorbi_CL I TCP, SEQ ID NO: 30; Zeama_CL I TCP_1, SEQ ID NO: 34; and Zeama_CL I TCP_2, SEQ ID NO: 36.

The result of the multiple sequence alignment of Class I TCP polypeptides of Table A (when from full length nucleic acid sequences) useful in performing the methods of the invention is shown in FIG. 2 of the present application. The conserved TCP domain (comprising the bHLH (basic-Helix-Loop-Helix)) among the polypeptide sequences useful in performing the methods of the invention is heavily boxed. The basic residues (in bold in the consensus line) and the Helix-Loop-Helix (HLH) sequences are lightly boxed, as well as the consensus C-terminal motif PGLEL(G/R/A)LSQX$_{1-5}$G(V/L)L, where X is any amino acid (SEQ ID NO: 65). The HQ rich region (H being histidine, Q glutamine) is equally lightly boxed.

Within this motif, there may be one or more conservative change(s) at any position, and/or one or three non-conservative change(s) at any position.

Example 3

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:
Scoring matrix: Blosum62
First Gap: 12
Extending gap: 2

Results of the software analysis are shown in Table A1 for the global similarity and identity over the full length of the polypeptide sequences (excluding the partial polypeptide sequences). Percentage identity is given above the diagonal and percentage similarity is given below the diagonal.

The percentage identity between the polypeptide sequences useful in performing the methods of the invention can be as low as 29% amino acid identity compared to SEQ ID NO: 2.

TABLE A1

MatGAT results for global similarity and identity over the full length of the polypeptide sequences.

| Full length | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 1. Aqufo CLASS I TCP | | 46.4 | 35.3 | 52.6 | 60.6 | 48.8 | 57 | 50.3 | 47.9 | 56.3 | 39.5 | 55.9 | 38.7 | 48.4 | 38.8 | 64.6 | 37.1 | 39 |
| 2. Arath TCP20 TCP | 62.1 | | 40.4 | 52.1 | 57.4 | 48.4 | 56.2 | 49.2 | 46.9 | 53.7 | 41.6 | 54.1 | 41.3 | 51.2 | 41.6 | 58.8 | 42.6 | 43.1 |
| 3. Arath TCP6 | 48.5 | 52.2 | | 32.1 | 34.8 | 31.3 | 33.4 | 33.7 | 30.9 | 35.4 | 30.2 | 32.6 | 30.3 | 34.2 | 29.8 | 35.5 | 30.4 | 30.8 |
| 4. Glyma CLASS I TCP | 61.2 | 64.1 | 43.8 | | 68 | 52.6 | 68.2 | 54.9 | 55.5 | 61.3 | 40.4 | 64.6 | 37.1 | 56.3 | 39.3 | 73.2 | 38.4 | 39.1 |

TABLE A1-continued

MatGAT results for global similarity and identity over the full length of the polypeptide sequences.

| Full length | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 5. Goshi CLASS I TCP | 70.2 | 68.8 | 50.3 | 73 | | 62.5 | 75.2 | 58.1 | 59.4 | 68.1 | 41.4 | 74.4 | 41.8 | 62.7 | 41.4 | 84.3 | 40.8 | 41.3 |
| 6. Lyces CLASS I TCP | 61.2 | 61.5 | 49.3 | 61.2 | 73.3 | | 57.4 | 50.7 | 69.4 | 56.9 | 37.9 | 54.7 | 37.5 | 91.8 | 37.9 | 63 | 37.8 | 38.4 |
| 7. Maldo CLASS I TCP | 67.3 | 67.9 | 46.4 | 74.5 | 82.9 | 67 | | 55 | 57.6 | 63 | 42.7 | 73.4 | 41.2 | 58.3 | 42.9 | 80.6 | 42.7 | 44.1 |
| 8. Medtr CLASS I TCP | 63.1 | 62.7 | 51.1 | 63.2 | 72 | 67.3 | 66.7 | | 50.8 | 56.3 | 39.4 | 56.1 | 39.3 | 50.7 | 40.5 | 60.4 | 38.5 | 39.8 |
| 9. Nicbe CLASS I TCP | 60.2 | 60.8 | 45.8 | 65.8 | 71.7 | 77.3 | 67.3 | 64.4 | | 56.3 | 37.9 | 54.4 | 35.3 | 71 | 36 | 64.7 | 34.1 | 35.6 |
| 10. Ociba CLASS I TCP | 68.6 | 65.3 | 50.8 | 70.7 | 80 | 71.7 | 73.5 | 70.7 | 70.4 | | 39 | 62.5 | 38.5 | 57.6 | 39.7 | 70.6 | 41 | 41.4 |
| 11. Orysa PCF1 | 52.7 | 57.4 | 46.4 | 53.6 | 54.9 | 49.8 | 53.9 | 52.1 | 52.7 | 51.1 | | 41.1 | 69.6 | 38.2 | 70.6 | 41.8 | 68.4 | 69.3 |
| 12. Poptr CLASS I TCP | 70.6 | 68.1 | 46.6 | 74.8 | 82.8 | 65.9 | 83.2 | 67.5 | 68.8 | 74.4 | 55.3 | | 42.5 | 55.8 | 42.5 | 73.6 | 42.5 | 43 |
| 13. Sacof CLASS I TCP | 53.5 | 53.5 | 45.5 | 50.1 | 55.8 | 52.3 | 53.9 | 53.9 | 52.3 | 54.2 | 79.2 | 55.9 | | 37.5 | 87.5 | 38.9 | 84.9 | 83.9 |
| 14. Soltu CLASS I TCP | 60.5 | 62.4 | 49.5 | 64.3 | 73.7 | 94 | 67 | 66.5 | 79 | 71.4 | 48.9 | 69.7 | 51.9 | | 37.9 | 65.9 | 37.6 | 37 |
| 15. Sorbi CLASS I TCP | 53.2 | 55.4 | 44.3 | 51.6 | 55.4 | 52 | 56.9 | 53.5 | 51.4 | 55.7 | 80 | 56.6 | 90.5 | 51.1 | | 40.9 | 86.1 | 89.4 |
| 16. Vitvi CLASS I TCP | 73.5 | 71 | 50.3 | 76.5 | 92 | 72.6 | 85.4 | 74.3 | 78 | 81.8 | 53.9 | 82.2 | 53.9 | 76.7 | 53.8 | | 40.1 | 41.4 |
| 17. Zeama CLASS I TCP1 | 53.1 | 54 | 43.8 | 55.7 | 54.6 | 51.2 | 55.6 | 52.8 | 52.2 | 56.2 | 78.4 | 57.4 | 88.6 | 49.7 | 90.5 | 53.7 | | 84.9 |
| 18. Zeama CLASS I TCP2 | 54.3 | 57.5 | 43.2 | 53 | 57.1 | 53 | 59.2 | 57.5 | 51.7 | 60.3 | 78.5 | 58.4 | 89.2 | 52.1 | 90.5 | 56.5 | 87.7 | |

The percentage identity can be substantially increased if the identity calculation is performed on the conserved TCP domain (comprising the bHLH, in total 69 contiguous amino acids, for example for SEQ ID NO: 2, the conserved TCP domain is as represented by SEQ ID NO: 66) amongst the polypeptides useful in performing the methods of the invention, as shown in Table A2. Percentage identity over the conserved TCP domain amongst the polypeptide sequences useful in performing the methods of the invention ranges between 65% and 100% amino acid identity.

TABLE A2

MatGAT results for global similarity and identity over the conserved TCP domain (in total 69 contiguous amino acids) amongst of the polypeptide sequences.

| Conserved TCP domain | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 1. Aqufo PCF1 CD | | 91.3 | 68.1 | 91.3 | 89.9 | 91.3 | 88.4 | 91.3 | 89.9 | 89.9 | 88.4 | 91.3 | 88.4 | 91.3 | 88.4 | 91.3 | 88.4 | 88.4 |
| 2. Arath PCF1 CD | 95.7 | | 68.1 | 94.2 | 95.7 | 95.7 | 91.3 | 95.7 | 94.2 | 97.1 | 91.3 | 94.2 | 91.3 | 95.7 | 91.3 | 94.2 | 91.3 | 91.3 |
| 3. Arath TCP6 CD | 84.1 | 84.1 | | 66.7 | 66.7 | 66.7 | 65.2 | 66.7 | 66.7 | 66.7 | 65.2 | 66.7 | 65.2 | 66.7 | 65.2 | 66.7 | 65.2 | 65.2 |
| 4. Glyma PCF1 CD | 94.2 | 98.6 | 82.6 | | 98.6 | 98.6 | 97.1 | 95.7 | 95.7 | 97.1 | 89.9 | 100 | 89.9 | 98.6 | 89.9 | 100 | 89.9 | 89.9 |
| 5. Goshi PCF1 CD | 94.2 | 98.6 | 84.1 | 100 | | 97.1 | 95.7 | 94.2 | 94.2 | 98.6 | 88.4 | 98.6 | 88.4 | 97.1 | 88.4 | 98.6 | 88.4 | 88.4 |
| 6. Lyces PCF1 CD | 95.7 | 100 | 82.6 | 98.6 | 98.6 | | 95.7 | 94.2 | 97.1 | 98.6 | 91.3 | 98.6 | 91.3 | 100 | 91.3 | 98.6 | 91.3 | 91.3 |
| 7. Maldo PCF1 CD | 92.8 | 97.1 | 81.2 | 98.6 | 98.6 | 97.1 | | 92.8 | 94.2 | 94.2 | 89.9 | 97.1 | 89.9 | 95.7 | 89.9 | 97.1 | 89.9 | 89.9 |
| 8. Medtr PCF1 CD | 94.2 | 98.6 | 82.6 | 100 | 100 | 98.6 | 98.6 | | 92.8 | 92.8 | 89.9 | 95.7 | 89.9 | 94.2 | 89.9 | 95.7 | 89.9 | 89.9 |
| 9. Nicbe PCF1 CD | 94.2 | 97.1 | 79.7 | 95.7 | 95.7 | 97.1 | 94.2 | 95.7 | | 95.7 | 91.3 | 95.7 | 91.3 | 97.1 | 91.3 | 95.7 | 91.3 | 91.3 |
| 10. Ociba PCF1 CD | 95.7 | 100 | 84.1 | 98.6 | 98.6 | 100 | 97.1 | 98.6 | 97.1 | | 89.9 | 97.1 | 89.9 | 98.6 | 89.9 | 97.1 | 89.9 | 89.9 |
| 11. Orysa PCF1 | 94.2 | 98.6 | 82.6 | 97.1 | 97.1 | 98.6 | 95.7 | 97.1 | 95.7 | 98.6 | | 89.9 | 100 | 91.3 | 100 | 89.9 | 100 | 100 |
| 12. Poptr PCF1 CD | 94.2 | 98.6 | 82.6 | 100 | 100 | 98.6 | 98.6 | 100 | 95.7 | 98.6 | 97.1 | | 89.9 | 98.6 | 89.9 | 100 | 89.9 | 89.9 |
| 13. Sacof PCF1 CD | 94.2 | 98.6 | 82.6 | 97.1 | 97.1 | 98.6 | 95.7 | 97.1 | 95.7 | 98.6 | 100 | 97.1 | | 91.3 | 100 | 89.9 | 100 | 100 |
| 14. Soltu PCF1 CD | 95.7 | 100 | 82.6 | 98.6 | 98.6 | 100 | 97.1 | 98.6 | 97.1 | 100 | 98.6 | 98.6 | 98.6 | | 91.3 | 98.6 | 91.3 | 91.3 |

TABLE A2-continued

MatGAT results for global similarity and identity over the conserved TCP domain (in total 69 contiguous amino acids) amongst of the polypeptide sequences.

| Conserved TCP domain | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|
| 15. Sorbi PCF1 CD | 94.2 | 98.6 | 82.6 | 97.1 | 97.1 | 98.6 | 95.7 | 97.1 | 95.7 | 98.6 | 100 | 97.1 | 100 | 98.6 |  | 89.9 | 100 | 100 |
| 16. Vitvi PCF1 CD | 94.2 | 98.6 | 82.6 | 100 | 100 | 98.6 | 98.6 | 100 | 95.7 | 98.6 | 97.1 | 100 | 97.1 | 98.6 | 97.1 |  | 89.9 | 89.9 |
| 17. Zeama PCF1 1 CD | 94.2 | 98.6 | 82.6 | 97.1 | 97.1 | 98.6 | 95.7 | 97.1 | 95.7 | 98.6 | 100 | 97.1 | 100 | 98.6 | 100 | 97.1 |  | 100 |
| 18. Zeama PCF1 2 CD | 94.2 | 98.6 | 82.6 | 97.1 | 97.1 | 98.6 | 95.7 | 97.1 | 95.7 | 98.6 | 100 | 97.1 | 100 | 98.6 | 100 | 97.1 | 100 |  |

Example 4

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Interpro is hosted at the European Bioinformatics Institute in the United Kingdom.

The results of the InterPro scan of the polypeptide sequence as represented by SEQ ID NO: 2 are presented in Table A3.

TABLE A3

| InterPro scan results of the polypeptide sequence as represented by SEQ ID NO: 2 | | |
|---|---|---|
| Database | Accession number | Accession name |
| InterPro | IPR005333 | TCP transcription factor |
| PFAM | PF03634 | TCP |

The TCP domain comprises the basic Helix-Loop-Helix (bHLH). The TCP domain of SEQ ID NO: 2 is as represented by SEQ ID NO: 66.

Primary amino acid composition (in %) to determine if a polypeptide region is rich in specific amino acids (for example in an acidic box) may be calculated using software programs from the ExPASy server, in particular the ProtParam tool (Gasteiger E et al. (2003) ExPASy: the proteomics server for in-depth protein knowledge and analysis. Nucleic Acids Res 31:3784-3788). The composition of the polypeptide sequence of interest may then be compared to the average amino acid composition (in %) in the Swiss-Prot Protein Sequence data bank.

Eye inspection of the multiple sequence alignment of the polypeptides useful in performing the methods of the invention shows that, between the conserved C-terminal motif and the C-terminal end of the polypeptide, lies a region rich in histidine (His or H) and glutamine (Gln or Q), the HQ rich region. This low complexity HQ region comprises at least four, preferably 5, 6, 7, 8, 9, 10, 11, 12, 13, 14, 15, 16, 17, 18, 19, 20 or more either of only H residues, either of only Q residues, or of a combination of H and Q residues (in any proportion) The HQ region is boxed in FIG. 2.

Example 5

Prediction of the Secondary Structure of Polypeptide Sequences Useful in Performing the Methods of the Invention A predicted non-canonical basic-Helix-Loop-Helix (bHLH) is found in both classes of TCP transcription factors, as described by Cubas et al. (1999) Plant J 18(2): 215-222. The position of this predicted secondary structure is shown in FIG. 3A. When considering the polypeptide sequence from N-terminus to C-terminus, the basic residues precede the Helix-Loop-Helix.

FIG. 3B is a cartoon representing the primary structure of the polypeptide sequences useful in performing the methods of the invention, from N-terminus to C-terminus: a conserved TCP domain comprising the basic-Helix-Loop-Helix (bHLH), a consensus C-terminal motif 1, and an HQ rich region.

Example 6

Assay Related to the Polypeptide Sequences Useful in Performing the Methods of the Invention The polypeptide sequence as represented by SEQ ID NO: 2 is a transcription factor with DNA binding activity. Consensus DNA binding sequence of these two classes were identified: GGNCCCAC for class 1, and GTGGNCCC for class II. The ability of a transcription factor to bind to a specific DNA sequence can be tested by electrophoretic mobility shift assays (EMSAs; also called gel retarddation assays), which is well known in the art, and reported specifically for TCPs by Kosugi & Ohashi (2002) Plant J 30: 337-348, and by Li et al. (2005) PNAS 102(36): 12978-83. Also reported by Kosugi & Ohashi are methods to detect dimerization partners and specifity, using for example, the yeast two-hybrid system, while Li et al. describe chromatin immunoprecipitation experiments to characterize the promoters to which TCPs bind to. The experiments described in both papers are useful in characterizing TCP class I transcription factors, and are well known in the art.

Example 7

Cloning of Nucleic Acid Sequence as Represented by SEQ ID NO: 1

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The nucleic acid sequence used in the methods of the invention was amplified by PCR using as template an *Arabidopsis thaliana* seedling cDNA library (in pCMV Sport 6.0; Invitrogen, Paisley, UK). PCR was performed using Hifi Taq DNA polymerase in standard conditions, using 200 ng of template in a 50 µl PCR mix. The primers used were prm01501 SEQ ID NO: 68; sense, AttB1 site in lower case:

5'-ggggacaagtttgtacaaaaaagcaggcttcacaATGGATCCCA

AGAACCTAA-3';

and prm01502 (SEQ ID NO: 69; reverse, complementary, AttB2 site in lower case:

5'-ggggaccactttgtacaagaaagctgggtTTTTAACGACCTGAG

CCTT-3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

Example 8

Expression Vector Construction Using the Nucleic Acid Sequence as Represented by SEQ ID NO: 1

The entry clone was subsequently used in an LR reaction with a destination vector used for *Oryza sativa* transformation. This vector contains as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 67) for constitutive expression was located upstream of this Gateway cassette.

Figure 4:
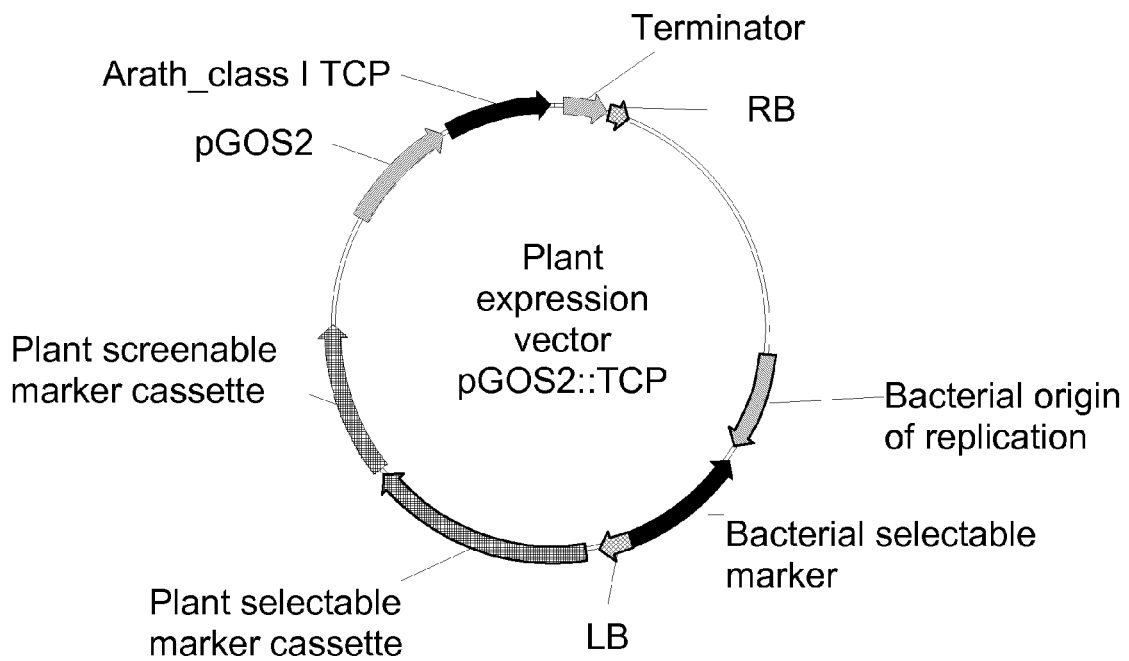
FIG. 4 shows the binary vector for increased expression in *Oryza sativa* of a nucleic acid sequence encoding a Class I TCP polypeptide under the control of a GOS2 promoter.

After the LR recombination step, the resulting expression vector (FIG. 4) was transformed into *Agrobacterium* strain LBA4044 according to methods well known in the art.

Example 9

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for cocultivation. *Agrobacterium* was inoculated on AB medium with the appropriate antibiotics and cultured for 3 days at 28° C. The bacteria were then collected and suspended in liquid co-cultivation medium to a density (OD600) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Example 10

Phenotypic Evaluation Procedure 10.1 Evaluation Setup

Approximately 35 independent T0 rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

From the stage of sowing until the stage of maturity the plants were passed several times through a digital imaging cabinet. At each time point digital images (2048×1536 pixels, 16 million colours) were taken of each plant from at least 6 different angles.

10.2 Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

10.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the time point at which the plant had reached its maximal leafy biomass. The early vigour is the plant (seedling) aboveground area three weeks post-germination. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area (mm$^2$), multiplied by a factor 10$^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 11

Results of the Phenotypic Evaluation of the Transgenic Plants

The results of the evaluation of transgenic rice plants expressing the nucleic acid sequence useful in performing the methods of the invention are presented in Table A4. The percentage difference between the transgenics and the corresponding nullizygotes is also shown, with a P value from the F test below 0.05.

Root/shoot index, seed yield, harvest index and Thousand Kernel Weight (TKW) are significantly increased in the transgenic plants expressing the nucleic acid sequence useful in performing the methods of the invention, compared to the control plants (in this case, the nullizygotes).

TABLE A4

Results of the evaluation of transgenic rice plants expressing the nucleic acid sequence useful in performing the methods of the invention.

| Trait | % Increase in T1 generation |
| --- | --- |
| Aboveground area | −3 |
| Root/shoot index | 4 |
| Total seed yield | 7 |
| Harvest index | 9 |
| TKW | 6 |

Example 12

Transformation of Other Crops

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown DCW and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Cotton Transformation

Cotton is transformed using *Agrobacterium tumefaciens* according to the method described in U.S. Pat. No. 5,159,135. Cotton seeds are surface sterilised in 3% sodium hypochlorite solution during 20 minutes and washed in distilled water with 500 μg/ml cefotaxime. The seeds are then transferred to SH-medium with 50 μg/ml benomyl for germination. Hypocotyls of 4 to 6 days old seedlings are removed, cut into 0.5 cm pieces and are placed on 0.8% agar. An *Agrobacterium* suspension (approx. 108 cells per ml, diluted from an overnight culture transformed with the gene of interest and suitable selection markers) is used for inoculation of the hypocotyl explants. After 3 days at room temperature and lighting, the tissues are transferred to a solid medium (1.6 g/l Gelrite) with Murashige and Skoog salts with B5 vitamins (Gamborg et al., Exp. Cell Res. 50:151-158 (1968)), 0.1 mg/l 2,4-D, 0.1 mg/l 6-furfurylaminopurine and 750 μg/ml MgCL2, and with 50 to 100 μg/ml cefotaxime and 400-500 μg/ml carbenicillin to kill residual bacteria. Individual cell lines are isolated after two to three months (with subcultures every four to six weeks) and are further cultivated on selective medium for tissue amplification (30° C., 16 hr photoperiod). Transformed tissues are subsequently further cultivated on non-selective medium during 2 to 3 months to give rise to somatic embryos. Healthy looking embryos of at least 4 mm length are transferred to tubes with SH medium in fine vermiculite, supplemented with 0.1 mg/l indole acetic acid, 6 furfurylaminopurine and gibberellic acid. The embryos are cultivated at 30° C. with a photoperiod of 16 hrs, and plantlets at the 2 to 3 leaf stage are transferred to pots with vermiculite and nutrients. The plants are hardened and subsequently moved to the greenhouse for further cultivation.

Example 13

Examples of Abiotic Stress Screens

Drought Screen

Plants from a selected number of events are grown in potting soil under normal conditions until they approached the heading stage. They are then transferred to a "dry" section where irrigation is withheld. Humidity probes are inserted in randomly chosen pots to monitor the soil water content (SWC). When SWC go below certain thresholds, the plants are automatically re-watered continuously until a normal level is reached again. The plants are then re-transferred to normal conditions. The rest of the cultivation (plant maturation, seed harvest) is the same as for plants not grown under abiotic stress conditions. Growth and yield parameters are recorded as detailed for growth under normal conditions.

Salt Stress Screen

Plants are grown on a substrate made of coco fibers and argex (3 to 1 ratio). A normal nutrient solution is used during the first two weeks after transplanting the plantlets in the greenhouse. After the first two weeks, 25 mM of salt (NaCl) is added to the nutrient solution, until the plants were harvested. Growth and yield parameters are recorded as detailed for growth under normal conditions.

Reduced Nutrient (Nitrogen) Availability Screen

Plants from six events (T2 seeds) are grown in potting soil under normal conditions except for the nutrient solution. The pots are watered from transplantation to maturation with a specific nutrient solution containing reduced N nitrogen (N) content, usually between 7 to 8 times less. The rest of the cultivation (plant maturation, seed harvest) is the same as for plants not grown under abiotic stress. Growth and yield parameters are recorded as detailed for growth under normal conditions.

EXAMPLES

CAH3

Example 14

Identification of Sequences Related to SEQ ID NO: 80 and SEQ ID NO: 81

Sequences (full length cDNA, ESTs or genomic) related to SEQ ID NO: 80 and/or protein sequences related to SEQ ID NO: 81 were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. The polypeptide encoded by SEQ ID NO: 80 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search.

Table B provides a list of nucleic acid and protein sequences related to the nucleic acid sequence as represented by SEQ ID NO: 80 and the protein sequence represented by SEQ ID NO: 81.

TABLE B

Nucleic acid sequences related to the nucleic acid sequence (SEQ ID NO: 80) useful in the methods of the present invention, and the corresponding deduced polypeptides.

| Name | Source organism | Nucleic acid SEQ ID NO: | Polypeptide SEQ ID NO: | Database accession | Status |
|---|---|---|---|---|---|
| CrCAH3 | Chlamydomonas reinhardtii | 80 | 81 | / | Full length |
| CrCAH3-2 | Chlamydomonas reinhardtii | 82 | 83 | U40871 | Full length |
| AtCAH3 | Arabidopsis thaliana | 84 | 85 | NP_001031206 | Full length |
| MtCAH3 | Medicago truncatula | 86 | 87 | ABE93115 | Full length |
| MtCAH3-2 | Medicago truncatula | 88 | 89 | ABE93118 | Full length |
| AtCAH3-2 | Arabidopsis thaliana | 90 | 91 | At1g70410 | Full length |
| OsCAH3 | Oryza sativa | 92 | 93 | Os09g0464000 | Full length |
| OsCAH3-2 | Oryza sativa | 94 | 95 | NP_001065776 | Full length |
| DsCAH3 | Dunaliella salina | 96 | 97 | AF190735 | Full length |
| DsCAH3-2 | Dunaliella salina | 98 | 99 | AAF22644 | Full length |
| CrCAH3-3 | Chlamydomonas reinhardtii | 100 | 101 | P24258 | Full length |
| CrCAH3-4 | Chlamydomonas reinhardtii | 102 | 103 | BAA14232 | Full length |
| PpCAH3 | Physcomitrella patens | 104 | 105 | CAH58714 | Full length |
| AtCAH3-3 | Arabidopsis thaliana | 106 | 107 | At5g14740 | Full length |
| DsCAH3-3 | Dunaliella salina | 108 | 109 | P54212 | Full length |
| AtCAH3-4 | Arabidopsis thaliana | 110 | 111 | At3g52720 | Full length |
| AtCAH3-5 | Arabidopsis thaliana | 112 | 113 | At5g56330 | Full length |
| AtCAH3-6 | Arabidopsis thaliana | 114 | 115 | At5g04180 | Full length |
| NlCAH3 | Nicotiana langsdorffii x Nicotiana sanderae | 116 | 117 | Q84UV8 | Full length |
| FbCAH3 | Flaveria bidentis | 118 | 119 | P46510 | Full length |
| HvCAH3 | Hordeum vulgare | 120 | 121 | P40880 | Full length |
| CrCAH3-5 | Chlamydomonas reinhardtii | 122 | 123 | AAB19183 | Full length |
| OsCAH3-3 | Oryza sativa | 124 | 125 | Os01g0639900 | Full length |
| AtCAH3-7 | Arabidopsis thaliana | 126 | 127 | At3g01500 | Full length |
| FpCAH3 | Flaveria pringlei | 128 | 129 | P46281 | Full length |
| FlCAH3 | Flaveria linearis | 130 | 131 | P46512 | Full length |
| FbrCAH3 | Flaveria brownii | 132 | 133 | P46511 | Full length |
| NpCAH3 | Nicotiana paniculata | 134 | 135 | BAA25639 | Full length |
| NtCAH3 | Nicotiana tabacum | 136 | 137 | P27141 | Full length |
| PtCAH3 | Populus tremula x Populus tremuloides | 138 | 139 | AAC49785 | Full length |
| PtCAH3-2 | Populus tremula x Populus tremuloides | 140 | 141 | AAB65822 | Full length |
| AtCAH3-8 | Arabidopsis thaliana | 142 | 143 | AT1G23730 | Full length |
| SoCAH3 | Spinacia oleracea | 144 | 145 | P16016 | Full length |
| PsCAH3 | Pisum sativum | 146 | 147 | CAA36792 | Full length |
| MtCAH3-3 | Medicago truncatula | 148 | 149 | ABE84842 | Full length |
| MtCAH3-4 | Medicago truncatula | 150 | 151 | ABE93117 | Full length |

TABLE B-continued

Nucleic acid sequences related to the nucleic acid sequence (SEQ ID NO: 80) useful in the methods of the present invention, and the corresponding deduced polypeptides.

| Name | Source organism | Nucleic acid SEQ ID NO: | Polypeptide SEQ ID NO: | Database accession | Status |
|---|---|---|---|---|---|
| AtCAH3-9 | Arabidopsis thaliana | 152 | 153 | At1g08080 | Full length |
| FpCAH3-2 | Flaveria pringlei | 154 | 155 | ABC41658 | Full length |
| FlCAH3-2 | Flaveria linearis | 156 | 157 | ABC41659 | Full length |
| AtCAH3-10 | Arabidopsis thaliana | 158 | 159 | At1g19580 | Full length |
| GhCAH3 | Gossypium hirsutum | 160 | 161 | DT561379 | Full length |
| LeCAH3 | Lycopersicon esculentum | 162 | 163 | BT014370 | Full length |
| ZmCAH3 | Zea mays | 164 | 165 | U08403 | Full length |
| ZmCAH3-2 | Zea mays | 166 | 167 | U08401 | Full length |
| UpCAH3 | Urochloa panicoides | 168 | 169 | U19741 | Full length |
| UpCAH3-2 | Urochloa panicoides | 170 | 171 | U19739 | Full length |
| CrCAH3-6 | Chlamydomonas reinhardtii | 172 | 173 | AAR82948 | Full length |
| CrCAH3-7 | Chlamydomonas reinhardtii | 174 | 175 | AAS48197 | Full length |
| OsCAH3-4 | Oryza sativa | 176 | 177 | AK103904 | Full length |
| OsCAH3-5 | Oryza sativa | 178 | 179 | Os08g0470200 | Full length |
| DcCAH3 | Dioscorea cayenensis | 180 | 181 | X76187 | Full length |
| DbCAH3 | Dioscorea batatas | 182 | 183 | AB178473 | Full length |
| DaCAH3 | Dioscorea alata | 184 | 185 | AF243526 | Full length |
| OsCAH3-6 | Oryza sativa | 186 | 187 | Os08g0423500 | Full length |
| OsCAH3-7 | Oryza sativa | 188 | 189 | Os12g0153500 | Full length |
| AtCAH3-11 | Arabidopsis thaliana | 190 | 191 | At4g20990 | Full length |
| AtCAH3-12 | Arabidopsis thaliana | 192 | 193 | At1g08065 | Full length |
| AaCAH3 | Adonis aestivalis | | 194 | / | Full length |
| GmCAH3 | Glycine max | | 195 | / | Full length |
| BnCAH3 | Brassica napus | | 196 | / | Full length |
| ZmCAH3-3 | Zea mays | | 197 | / | Full length |
| TaCAH3 | Triticum aestivum | | 198 | / | Full length |
| GmCAH3-2 | Glycine max | | 199 | / | Full length |
| HvCAH3-2 | Hordeum vulgare | | 200 | / | Full length |
| ZmCAH3-4 | Zea mays | | 201 | / | Full length |
| BnCAH3-2 | Brassica napus | | 202 | / | Full length |

Example 15

Alignment of Relevant Polypeptide Sequences

AlignX from the Vector NTI (Invitrogen) is based on the popular Clustal algorithm of progressive alignment (Thompson et al. (1997) Nucleic Acids Res 25:4876-4882; Chenna et al. (2003). Nucleic Acids Res 31:3497-3500). A phylogenetic tree can be constructed using a neighbour-joining clustering algorithm. Default values are for the gap open penalty of 10, for the gap extension penalty of 0.1 and the selected weight matrix is Blosum 62 (if polypeptides are aligned).

Figures 7, 8:
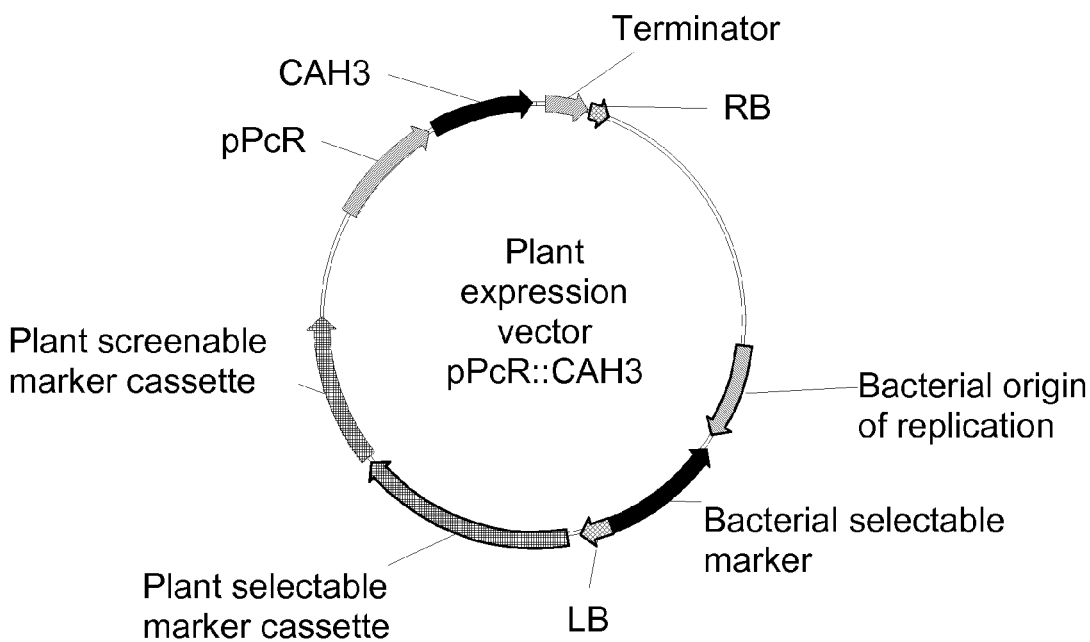
FIG. 7 shows respectively a phylogenetic tree constructed from the sequences listed in FIG. 9 (A), and a multiple alignment of CAH3 protein sequences belonging to the alpha class (B).
FIG. 8 shows the binary vector for increased expression in *Oryza sativa* of a *Chlamydomonas reinhardtii* CAH3 protein-encoding nucleic acid under the control of a protochlorophyllide reductase promoter (PcR).
Figure 10:
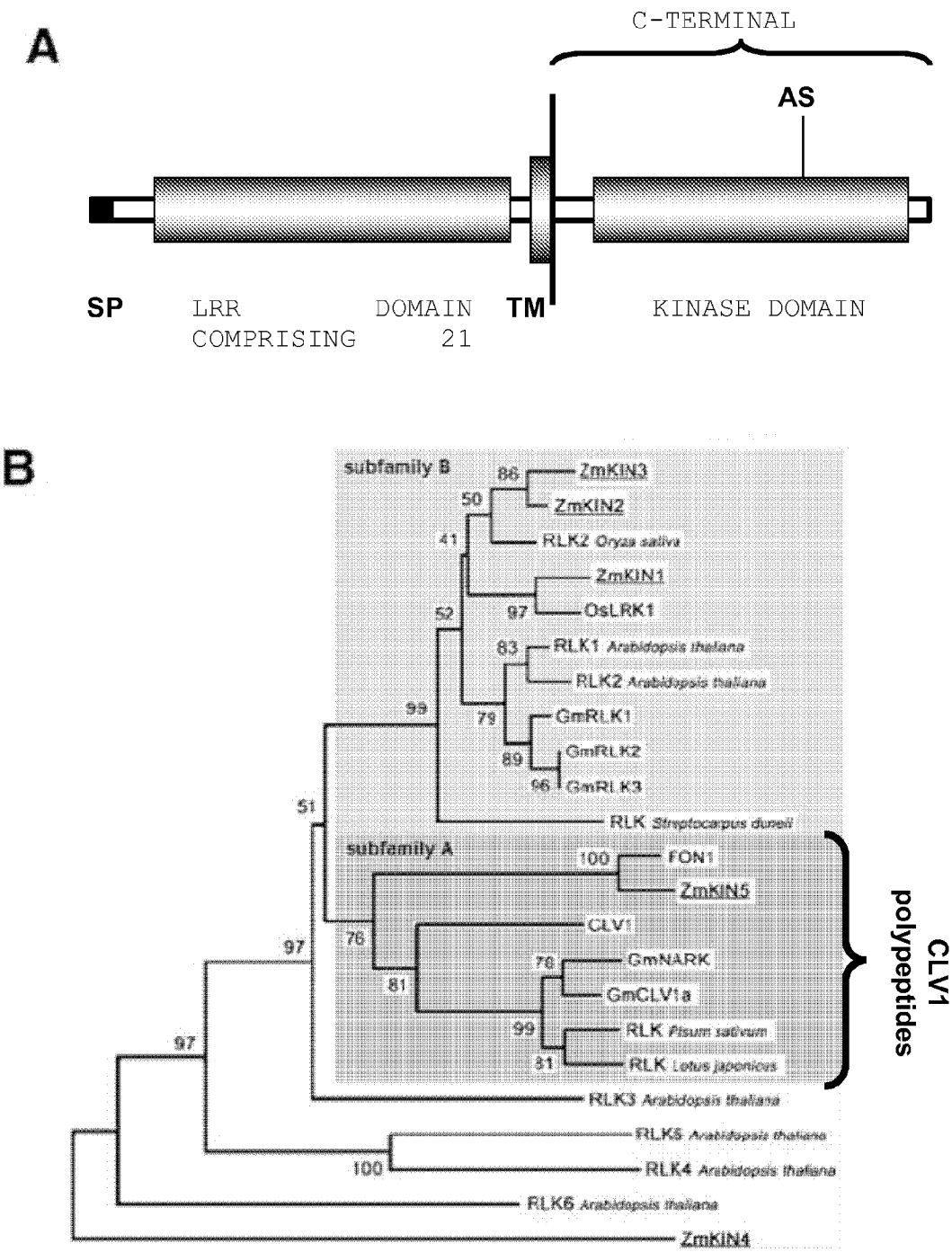
FIG. 10 (A) shows the predicted domain structure of an LRR-RLK polypeptide such as represented by SEQ ID NO: 212; from N-terminus to C-terminus: (i) SP, signal peptide; (ii) 21 LRRs, the 21 leucine-rich repeats; (iii) TM, transmembrane domain; and (iv) the kinase domain. The vertical bold line is placed at the end of the transmembrane domain. According to Bommert et al. (2004) Development 132: 1235-1245.

The result of the multiple sequence alignment using alpha type CAH3 polypeptides relevant in identifying the ones useful in performing the methods of the invention is shown in FIG. 7. Similar multiple alignments may be created for beta- and gamma-type CAH3 polypeptides using the sequences listed in FIG. 9. A multiple alignment of all CAH3 sequences was used as input data for calculating the phylogenetic tree.

Example 16

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table B1 for the global similarity and identity over the full length of the alpha-type CAH3 polypeptide sequences (excluding the partial polypeptide sequences). Percentage identity is given above the diagonal and percentage similarity is given below the diagonal.

The percentage identity between the polypeptide sequences useful in performing the methods of the invention can be as low as 16% amino acid identity compared to SEQ ID NO: 81.

TABLE B1

MatGAT results for global similarity and identity over the full length of the polypeptide sequences.

|  | 1 | 2 | 3 | 4 | 5 | 6 | 7 | 8 | 9 | 10 | 11 |
|---|---|---|---|---|---|---|---|---|---|---|---|
| 1. SEQID81 |  | 28.3 | 27.2 | 25.2 | 29.4 | 24.7 | 25.9 | 25.6 | 26.8 | 28.2 | 27.1 |
| 2. SEQID105 | 43.5 |  | 29.9 | 32.7 | 33.7 | 27.9 | 30.1 | 31.2 | 31.2 | 33.5 | 31.8 |
| 3. SEQID115 | 44.2 | 45.8 |  | 40.4 | 37.5 | 37.7 | 35.2 | 35.7 | 40.4 | 41.3 | 38.8 |
| 4. SEQID179 | 45.5 | 46.5 | 58.5 |  | 56.2 | 42.1 | 44.8 | 44.0 | 46.2 | 44.6 | 49.1 |
| 5. SEQID187 | 44.5 | 50.4 | 54.5 | 74.6 |  | 45.7 | 46.0 | 46.0 | 40.6 | 43.7 | 42.9 |
| 6. SEQID185 | 39.7 | 48.0 | 55.6 | 62.2 | 61.2 |  | 67.5 | 67.8 | 37.8 | 38.3 | 39.4 |
| 7. SEQID181 | 42.3 | 48.7 | 55.6 | 64.4 | 60.1 | 84.2 |  | 91.6 | 36.2 | 42.3 | 42.0 |
| 8. SEQID183 | 41.6 | 49.8 | 55.2 | 62.2 | 60.5 | 83.5 | 93.8 |  | 36.2 | 41.3 | 43.1 |
| 9. SEQID191 | 41.6 | 49.4 | 59.6 | 61.1 | 59.4 | 59.0 | 59.7 | 59.3 |  | 42.1 | 46.2 |
| 10. SEQID117 | 44.2 | 50.7 | 59.2 | 65.8 | 60.9 | 59.1 | 62.4 | 60.9 | 64.6 |  | 46.8 |
| 11. SEQID153 | 43.9 | 48.0 | 58.8 | 69.5 | 62.0 | 64.7 | 64.4 | 65.5 | 64.4 | 69.1 |  |
| 12. SEQID113 | 32.6 | 31.7 | 38.3 | 42.9 | 40.6 | 41.4 | 42.3 | 42.3 | 40.0 | 43.7 | 48.6 |
| 13. SEQID193 | 38.4 | 48.7 | 55.6 | 65.8 | 57.6 | 61.2 | 61.9 | 63.1 | 62.5 | 63.1 | 68.7 |
| 14. SEQID111 | 41.3 | 45.8 | 54.6 | 53.9 | 54.2 | 54.6 | 51.8 | 52.8 | 54.9 | 57.7 | 57.7 |
| 15. SEQID189 | 41.3 | 46.6 | 55.2 | 59.1 | 54.8 | 55.2 | 54.8 | 54.4 | 53.7 | 55.5 | 56.9 |
| 16. SEQID95 | 28.1 | 32.0 | 39.4 | 40.0 | 35.5 | 40.7 | 39.2 | 39.2 | 40.1 | 36.1 | 38.5 |
| 17. SEQID101 | 36.8 | 38.2 | 36.3 | 37.9 | 37.1 | 34.2 | 35.3 | 33.7 | 33.7 | 34.5 | 32.1 |
| 18. SEQID103 | 36.6 | 35.0 | 38.5 | 38.2 | 36.3 | 32.6 | 34.7 | 34.2 | 34.0 | 35.3 | 34.7 |
| 19. SEQID109 | 27.0 | 23.8 | 24.1 | 23.6 | 25.6 | 22.6 | 24.3 | 23.6 | 23.6 | 24.3 | 26.1 |
| 20. SEQID99 | 26.3 | 26.3 | 27.4 | 25.6 | 26.1 | 24.5 | 25.2 | 24.5 | 23.6 | 24.9 | 27.0 |
| 21. SEQID97 | 26.9 | 26.3 | 30.1 | 28.5 | 28.5 | 25.5 | 28.3 | 27.1 | 27.1 | 26.7 | 27.5 |

|  | 12 | 13 | 14 | 15 | 16 | 17 | 18 | 19 | 20 | 21 |
|---|---|---|---|---|---|---|---|---|---|---|
| 1. SEQID81 | 18.7 | 24.9 | 24.0 | 24.8 | 16.0 | 23.5 | 23.0 | 18.6 | 19.1 | 19.1 |
| 2. SEQID105 | 19.4 | 30.3 | 29.4 | 33.7 | 22.0 | 25.6 | 23.8 | 15.7 | 17.4 | 17.4 |
| 3. SEQID115 | 21.6 | 37.6 | 33.4 | 33.7 | 23.3 | 21.5 | 21.9 | 15.9 | 15.4 | 18.4 |
| 4. SEQID179 | 27.5 | 45.7 | 33.1 | 39.2 | 22.5 | 22.7 | 24.0 | 15.8 | 15.9 | 16.7 |
| 5. SEQID187 | 24.3 | 37.9 | 32.6 | 36.1 | 23.2 | 23.3 | 22.3 | 17.7 | 17.4 | 18.2 |
| 6. SEQID185 | 24.9 | 41.7 | 31.6 | 35.8 | 26.1 | 23.2 | 22.3 | 15.9 | 15.2 | 16.2 |
| 7. SEQID181 | 26.5 | 39.9 | 31.7 | 36.5 | 22.9 | 22.1 | 20.7 | 15.1 | 15.7 | 17.0 |
| 8. SEQID183 | 26.0 | 40.7 | 32.5 | 37.3 | 22.9 | 21.7 | 21.9 | 14.8 | 14.6 | 17.0 |
| 9. SEQID191 | 24.8 | 43.5 | 35.3 | 34.3 | 25.4 | 23.9 | 23.8 | 15.6 | 15.8 | 15.0 |
| 10. SEQID117 | 27.4 | 40.3 | 34.1 | 34.7 | 22.4 | 18.8 | 18.5 | 15.2 | 15.8 | 16.8 |
| 11. SEQID153 | 33.8 | 51.8 | 35.3 | 39.0 | 24.7 | 20.9 | 20.7 | 15.6 | 15.9 | 17.0 |
| 12. SEQID113 |  | 36.8 | 20.9 | 24.2 | 14.5 | 14.7 | 11.6 | 15.8 | 15.1 | 12.2 |
| 13. SEQID193 | 48.6 |  | 35.8 | 36.7 | 24.4 | 20.4 | 21.7 | 15.3 | 16.5 | 18.7 |
| 14. SEQID111 | 40.6 | 54.2 |  | 36.7 | 27.0 | 18.7 | 21.1 | 14.4 | 14.0 | 15.5 |
| 15. SEQID189 | 36.6 | 52.7 | 56.7 |  | 41.3 | 22.8 | 22.1 | 16.3 | 17.0 | 20.2 |
| 16. SEQID95 | 23.4 | 38.4 | 39.8 | 48.8 |  | 15.6 | 15.4 | 13.8 | 14.1 | 13.5 |
| 17. SEQID101 | 30.3 | 33.9 | 33.7 | 35.3 | 23.9 |  | 91.9 | 16.7 | 19.3 | 19.1 |
| 18. SEQID103 | 24.9 | 34.2 | 35.0 | 37.7 | 24.9 | 95.0 |  | 16.5 | 19.1 | 19.5 |
| 19. SEQID109 | 25.8 | 24.3 | 23.4 | 25.0 | 19.4 | 27.8 | 28.9 |  | 43.4 | 32.4 |
| 20. SEQID99 | 24.7 | 25.2 | 25.6 | 26.1 | 19.8 | 31.0 | 29.7 | 60.1 |  | 31.3 |
| 21. SEQID97 | 24.3 | 27.7 | 29.5 | 27.7 | 19.5 | 33.7 | 33.5 | 46.2 | 46.5 |  |

Example 17

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Interpro is hosted at the European Bioinformatics Institute in the United Kingdom.

The results of the InterPro scan of the polypeptide sequence as represented by SEQ ID NO: 81 are presented in Table F2.

TABLE B2

InterPro scan results of the polypeptide sequence as represented by SEQ ID NO: 81

| Database | Accession number | Accession name |
|---|---|---|
| PRODOM | PD000865 | Q39588_CHLRE_Q39588 |
| PANTHER | PTHR18952 | CARBONIC ANHYDRASE |
| PFAM | PF00194 | Carb_anhydrase |
| PROFILE | PS00162 | ALPHA_CA_1 |
| PROFILE | PS51144 | ALPHA_CA_2 |
| SUPERFAMILY | SSF51069 | Carbonic anhydrase |

Example 18

Topology Prediction of the Polypeptide Sequences Useful in Performing the Methods of the Invention (Subcellular Localization, Transmembrane . . . )

TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal presequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The results of TargetP 1.1 analysis of the polypeptide sequence as represented by SEQ ID NO: 81 are presented Table B3. The "plant" organism group has been selected, no cutoffs defined, and the predicted length of the transit peptide requested. The subcellular localization of the polypeptide sequence as represented by SEQ ID NO: 81 is predicted to be the mitochondrion, but in *Chlamydomonas reinhardtii* it was shown to be a chloroplastic enzyme. The predicted length of the putative transit peptide is of 13 amino acids starting from the N-terminus (not as reliable as the prediction of the subcellular localization itself, may vary in length of a few amino acids).

TABLE B3

TargetP 1.1 analysis of the polypeptide sequence as represented by SEQ ID NO: 81

| | |
|---|---|
| Length (AA) | 310 |
| Chloroplastic transit peptide | 0.308 |
| Mitochondrial transit peptide | 0.800 |
| Secretory pathway signal peptide | 0.004 |
| Other subcellular targeting | 0.046 |
| Predicted Location | mitochondrion |
| Reliability class | 3 |
| Predicted transit peptide length | 13 |

Many other algorithms can be used to perform such analyses, including:
ChloroP 1.1 hosted on the server of the Technical University of Denmark;
Protein Prowler Subcellular Localisation Predictor version 1.2 hosted on the server of the Institute for Molecular Bioscience, University of Queensland, Brisbane, Australia;
PENCE Proteome Analyst PA-GOSUB 2.5 hosted on the server of the University of Alberta, Edmonton, Alberta, Canada;
TMHMM, hosted on the server of the Technical University of Denmark Example 19

Assay Related to the Polypeptide Sequences Useful in Performing the Methods of the Invention Polypeptide sequence as represented by SEQ ID NO: 81 is an enzyme with as Enzyme Commission (EC; classification of enzymes by the reactions they catalyse) number EC 4.2.2.1 for carbonic anhydrase. The functional assay may be an assay for CA activity based on a titrimetric assay, as described by Karlsson et al. (Plant Physiol. 109: 533-539, 1995). Briefly, CA activity is electrochemically determined by measuring the time for the pH to decrease from 8.0 to 7.2, at 2° C., in a sample of 4 ml of 20 mM veronal buffer, pH 8.3, upon addition of 2 ml of ice-cold $CO_2$-saturated distilled $H_2O$. One WAU (Wilbur-Anderson Unit; Wilbur and Anderson, J Biol Chem 176: 147-154, 1948; Yang et al., Plant Cell Physiol 26: 25-34, 1985) of activity is defined as: $WAU=(t_0-t)/t$, where $t_0$ is the time for the pH change with buffer controls and t is the time obtained when CA-containing samples are added.

Example 20

Cloning of Nucleic Acid Sequence as Represented by SEQ ID NO: 80

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The *Chlamydomonas reinhardtii* CAH3 gene was amplified by PCR using as template an *Chlamydomonas reinhardtii* cDNA library (Invitrogen, Paisley, UK). Primers prm8571 (SEQ ID NO: 207; sense, start codon in bold, AttB1 site in italic: 5'-ggggacaagtttgtacaaaaaag caggcttaaacaatgcgctcagc-cgttc-3') and prm8572 (SEQ ID NO: 208; reverse, complementary, AttB2 site in italic: 5'-ggggaccactttgtacaa-gaaagctgggtctcactg accctagcacactc-3'), which include the AttB sites for Gateway recombination, were used for PCR amplification. PCR was performed using Hifi Taq DNA polymerase in standard conditions. A PCR fragment comprising the CAH3 CDS, including attB sites, was amplified and purified also using standard methods. The first step of the Gateway procedure, the BP reaction, was then performed, during which the PCR fragment recombines in vivo with the pDONR201 plasmid to produce, according to the Gateway terminology, an "entry clone", pCAH3. Plasmid pDONR201 was purchased from Invitrogen, as part of the Gateway® technology.

Example 21

Expression Vector Construction Using the Nucleic Acid Sequence as Represented by SEQ ID NO: 80

The entry clone pCAH3 was subsequently used in an LR reaction with pPCR, a destination vector used for *Oryza sativa* transformation. This vector contains as functional elements within the T-DNA borders: a plant selectable marker; a screenable marker expression cassette; and a Gateway cassette intended for LR in vivo recombination with the nucleic acid sequence of interest already cloned in the entry clone. A rice protochlorophyllide reductase promoter (PcR, SEQ ID NO: 206) for constitutive expression was located upstream of this Gateway cassette.

After the LR recombination step, the resulting expression vector pPCR::CAH3 (FIG. 8) was transformed into *Agrobacterium* strain LBA4044 according to methods well known in the art.

Example 22

Plant Transformation

See Example 9 above for details of rice transformation and see Example 12 above for details of transformation of corn, wheat, soybean, canola/rapeseed, alfalfa and cotton.

Example 23

Phenotypic Evaluation Procedure

See Example 10 above for details.

Example 24

Results of the Phenotypic Evaluation of the Transgenic Plants

The results of the evaluation of transgenic rice plants expressing the nucleic acid sequence useful in performing the methods of the invention are presented in Table B4. The percentage difference between the transgenics and the corresponding nullizygotes is also shown, with a P value from the F test below 0.05.

Total seed yield, number of filled seeds, seed fill rate and harvest index are significantly increased in the transgenic plants expressing the nucleic acid sequence useful in performing the methods of the invention, compared to the control plants (in this case, the nullizygotes).

TABLE B4

Results of the evaluation of transgenic rice plants expressing the nucleic acid sequence useful in performing the methods of the invention.

| Trait | % Increase in T1 generation | % Increase in T2 generation |
|---|---|---|
| Fill rate | 91 | 13 |
| Harvest index | 19.4 | 18.3 |

EXAMPLES

Clavata

Example 25

Identification of Sequences Related to SEQ ID NO: 209, SEQ ID NO: 210, SEQ ID NO: 211 and SEQ ID NO: 212

Nucleic acid sequences (full length cDNA, ESTs or genomic) related to SEQ ID NO: 209 or SEQ ID NO: 211, and/or polypeptide sequences related to SEQ ID NO: 210 and SEQ ID NO: 212 were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. The polypeptide encoded by SEQ ID NO: 209 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search.

In addition to the publicly available nucleic acid sequences available at NCBI, proprietary sequence databases are also searched following the same procedure as described herein above.

Table C provides a list of nucleic acid and amino acid sequences related to the nucleic acid sequence as represented by SEQ ID NO: 211 and the amino acid sequence represented by SEQ ID NO: 212. The nucleic acid sequence as represented by SEQ ID NO: 209 is comprised in SEQ ID NO 211. However, a premature stop codon has been introduced via PCR at position 2251 of the nucleic acid sequence as represented by SEQ ID NO: 211, by substituting the A to a T (changing an AGA codon into a TGA stop codon).

TABLE C

Nucleic acid sequences related to the nucleic acid sequence (SEQ ID NO: 211) useful in the methods of the present invention, and the corresponding deduced polypeptides.

| Name | Source organism | Nucleic acid SEQ ID NO: | Polypeptide SEQ ID NO: | Database accession number | Status |
|---|---|---|---|---|---|
| Arath_CLAVATA1 | Arabidopsis thaliana | 211 | 212 | ATU96879 | Full length |
| Brana_LRR-RLK | Brassica napus | 213 | 214 | AY283519 | Full length |
| Eucgr_LRR-RLK | Eucalyptus grandis | 215 | 216 | AAA79716 | Full length |
| Glyma_CLV1A | Glycine max | 217 | 218 | AF197946 | Full length |
| Glyma_NARK_CLV1B | Glycine max | 219 | 220 | AF197947 | Full length |
| Lotja_HAR1 | Lotus japonicus | 221 | 222 | AB092810.1 | Full length |
| Medtr_SUNN | Medicago truncatula | 223 | 224 | AY769943 | Full length |
| Orysa_FON1 | Oryza sativa | 225 | 226 | AB182388 | Full length |

TABLE C-continued

Nucleic acid sequences related to the nucleic acid sequence (SEQ ID NO: 211) useful in the methods of the present invention, and the corresponding deduced polypeptides.

| Name | Source organism | Nucleic acid SEQ ID NO: | Polypeptide SEQ ID NO: | Database accession number | Status |
|---|---|---|---|---|---|
| Pissa_SYM29 | *Pisum sativa* | 227 | 228 | PSA495759 | Full length |
| Poptr_LRR-RLK I | *Populus tremuloides* | 229 | 230 | scaff_1514.1 | Full length |
| Poptr_LRR-RLK II | *Populus tremuloides* | 231 | 232 | scaff_II.178 | Full length |
| Zeama_KIN5 | *Zea mays* | — | 233 | Bommert et al. | Full length |
| Ipoba_CLV1 like | *Ipomoea batatas* | 234 | 235 | AB162660.1 | Partial |

Example 26

Alignment of Relevant Polypeptide Sequences

AlignX from the Vector NTI (Invitrogen) is based on the popular Clustal algorithm of progressive alignment (Thompson et al. (1997) Nucleic Acids Res 25:4876-4882; Chema et al. (2003). Nucleic Acids Res 31:3497-3500). A phylogenetic tree can be constructed using a neighbour-joining clustering algorithm. Default values are for the gap open penalty of 10, for the gap extension penalty of 0.1 and the selected weight matrix is Blosum 62 (if polypeptides are aligned).

Figure 11:
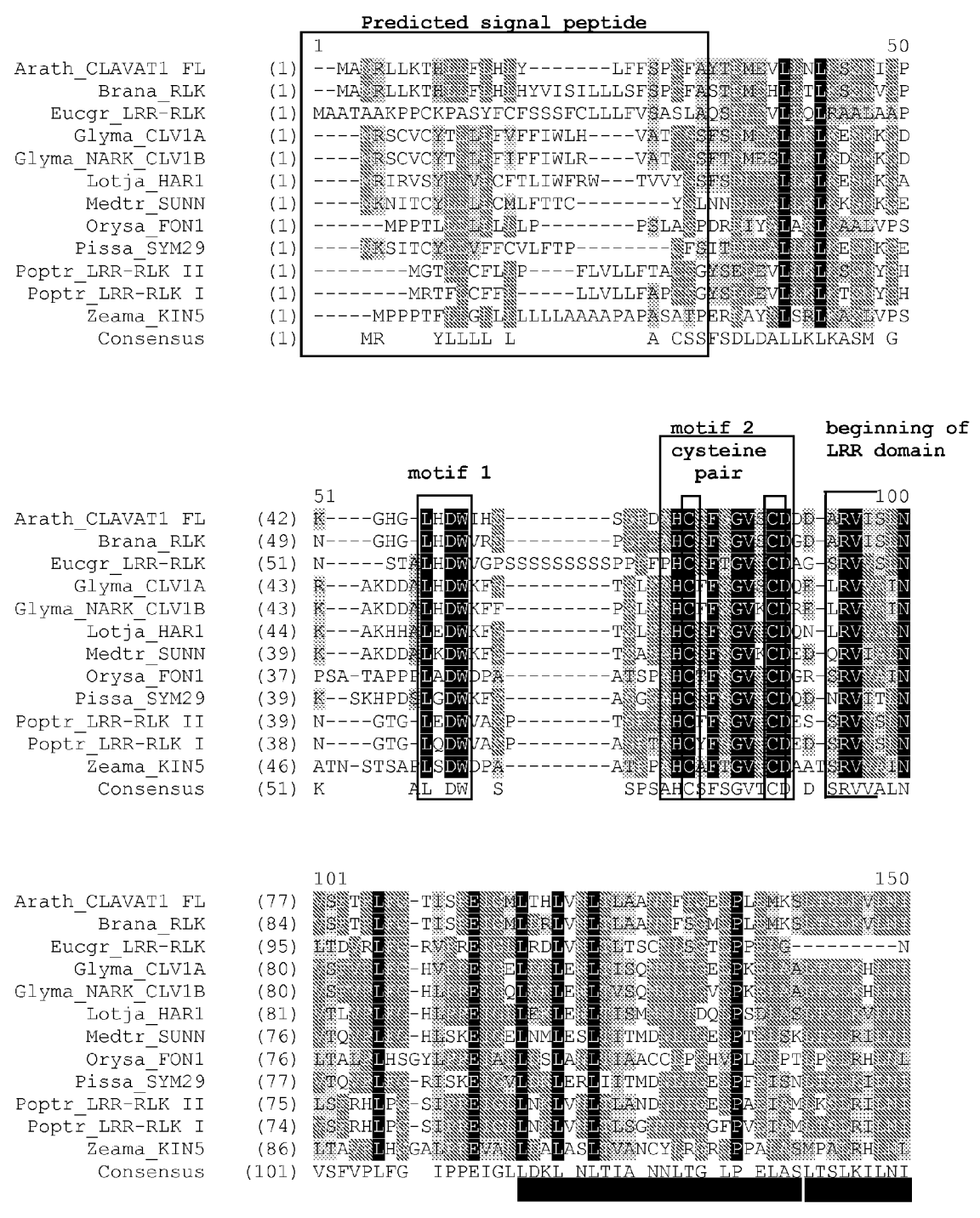
Figure 11:
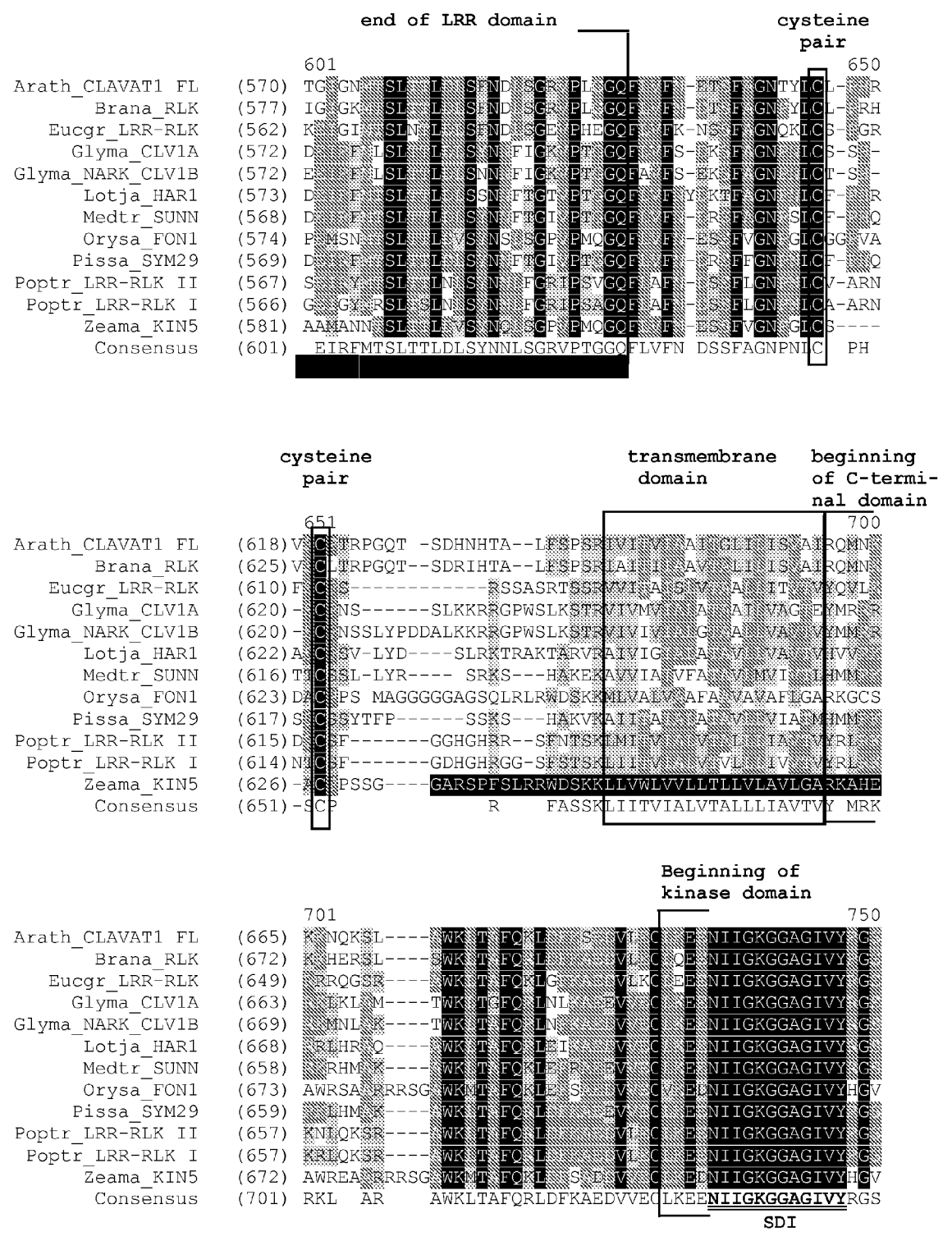

The result of the multiple sequence alignment using polypeptides relevant in identifying the ones useful in performing the methods of the invention is shown in FIG. 11. The following features are identified, from N-terminus to C-terminus:
- a predicted signal peptide (identified as in Example 30);
- Motif 1 as represented by SEQ ID NO: 236
- Motif 2 as represented by SEQ ID NO: 237, comprising a conserved cysteine pair;
- a leucine-rich repeat (LRR) domain, comprising 21 LRRs (see Example 28);
- a second conserved cysteine pair;
- a predicted transmembrane domain (identified as in Example 30);
- a kinase domain, comprising 11 conserved subdomains (see Example 28); within this kinase domain, the predicted kinase active site is identified.

Example 27

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table C1 for the global similarity and identity over the full length of the polypeptide sequences (excluding the partial polypeptide sequences). Percentage identity is given above the diagonal and percentage similarity is given below the diagonal.

The percentage identity between the polypeptide sequences useful in performing the methods of the invention can be as low as 51% amino acid identity compared to SEQ ID NO: 212.

TABLE C1

MatGAT results for global similarity and identity over the full length of the polypeptide sequences.

| | | 1 | 2 | 3 | 4 | 5 | 6 | 7 | 8 | 9 | 10 | 11 | 12 |
|---|---|---|---|---|---|---|---|---|---|---|---|---|---|
| 1. | Arath_CLAVATA1\FL | | 87.1 | 61.8 | 61.6 | 60.3 | 60.2 | 61.2 | 55.9 | 60.9 | 68.2 | 66.7 | 54.2 |
| 2. | Brana_RLK | 92.6 | | 60.8 | 61.2 | 60.4 | 60.8 | 59.9 | 55.6 | 61 | 69.2 | 67.5 | 54.1 |
| 3. | Eucgr_RLK | 76.8 | 75.1 | | 59.7 | 58.8 | 60.8 | 58.6 | 53.4 | 58.8 | 63.2 | 62.7 | 53.3 |
| 4. | Glyma_NARK_CLV1B | 75.3 | 75.9 | 74.5 | | 90.2 | 78 | 75.2 | 53.5 | 74.6 | 64.6 | 63.5 | 53.5 |
| 5. | Glyma_RLK_CLV1A | 75.6 | 75.5 | 73.9 | 94.3 | | 77 | 75.1 | 52.8 | 74.7 | 63.8 | 63 | 52.4 |
| 6. | Lotja_RLK\HAR1 | 76.8 | 77.1 | 74.8 | 88 | 86 | | 79.2 | 52.9 | 78 | 64.9 | 64.9 | 52.8 |
| 7. | Medtr_SUNN | 75.5 | 75.2 | 73.9 | 85.1 | 84.6 | 88.1 | | 52 | 86.2 | 63.5 | 64.2 | 52 |
| 8. | Orysa_FON1 | 70.7 | 71 | 69.5 | 67.8 | 67.9 | 69.1 | 67.7 | | 51.9 | 55.8 | 56.2 | 77.2 |
| 9. | Pissa_LRR-RLK | 75.5 | 74.8 | 74.3 | 85 | 84.5 | 88 | 91.9 | 66.8 | | 64 | 64.2 | 51 |
| 10. | Poptr_RLK\I | 80.9 | 81.3 | 77.1 | 78.9 | 77.9 | 77.8 | 77 | 71.1 | 77.4 | | 86.8 | 54.6 |

TABLE C1-continued

MatGAT results for global similarity and identity over the full length of the polypeptide sequences.

| | 1 | 2 | 3 | 4 | 5 | 6 | 7 | 8 | 9 | 10 | 11 | 12 |
|---|---|---|---|---|---|---|---|---|---|---|---|---|
| 11. Poptr_RLK\II | 79.8 | 80.5 | 76.7 | 77.8 | 77 | 78.2 | 77.1 | 71.3 | 76.5 | 92.2 | | 55.1 |
| 12. Zeama_KIN5 | 69.7 | 68.8 | 68.7 | 67.4 | 66.9 | 68.1 | 66.9 | 85.9 | 66.2 | 71.5 | 70.7 | |

Example 28

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE (PS accessions), TrEMBL, PRINTS (PR accessions), ProDom (PD accessions) and Pfam (PF accessions), Smart (SM accessions), and TIGRFAMs. InterPro is hosted at the European Bioinformatics Institute in the United Kingdom.

The results of the InterPro scan of the polypeptide sequence as represented by SEQ ID NO: 212 are presented in Table C2 and in FIG. 11. The leucine-rich repeat domain comprises a total of 21 tandem copies of 23-25 amino acid residue long leucine-rich repeats (LRRs), and is flanked by pairs of spaced cysteine residues necessary for disulfide bonding with other proteins (for example with Clavata 2). Based on the classification of Shiu and Bleecker (2001) Proc Natl Acad Sc 98(19): 10763-10768), the polypeptide sequence as represented by SEQ ID NO: 212 belongs to the LRR XI subfamily. The LRR domain is followed by a predicted transmembrane domain corresponding to amino acid residues 641 to 659 in the polypeptide sequence as represented by SEQ ID NO: 212 (see Example 30). After the transmembrane domain is the intracellular kinase domain comprising the characteristic 11 subdomains with all invariant amino acid residues conserved in comparison to other eukaryotic protein kinases (Hank and Quinn 1 (1991) Methods Enzymol 200:38-62). A kinase active site is also predicted during the InterPro scan.

TABLE C2

InterPro scan results of the polypeptide sequence as represented by SEQ ID NO: 212

| InterPro accession number | Integrated accession numbers | Accession name |
|---|---|---|
| IPR000719 | PD000001 PF00069 PS50011 | Protein kinase |
| IPR001245 | SM00219 | Tyrosine protein kinase |
| IPR001611 | PR00019 PF00560 | Leucine-rich repeat |
| IPR002290 | SM00220 | Serine/threonine protein kinase |
| IPR003591 | SM00369 | Leucine-rich repeat, typical subtype |
| IPR008271 | PS00108 | Serine/threonine kinase, active site |
| IPR011009 | SSF56112 | Protein kinase-like |
| IPR013210 | PF08263 | Leucine rich repeat, N-terminal |

Example 29

Phosphorylation Prediction Sites Comprised in the Polypeptide Sequences Useful in Performing the Methods of the Invention The phosphorylation/dephosphorylation state of the polypeptide as represented by SEQ ID NO: 212 is directly related to activation/inactivation of the polypeptide (Trotochaud et al., (1999) Plant Cell 11: 393-405). One protein phosphatase, KAPP, binds in a phosphorylation dependent manner to the kinase domain of SEQ ID NO: 212, thereby inactivating the signal transduction. By substituting the phosphorylatable amino acids with the kinase domain of with nonphosphorylatable amino acids, the activity of the polypeptide sequence as represented by SEQ ID NO: 212 is abolished. It is possible to identify serine (S), threonine (T) and tyrosine (Y) phosphorylation prediction sites using algorithms such as NetPhos 2.0, hosted at the server of the Technical University of Denmark. The NetPhos 2.0 server produces neural network predictions for serine, threonine and tyrosine phosphorylation sites in eukaryotic proteins.

The results of NetPhos 2.0 analysis of the polypeptide sequence as represented by SEQ ID NO: 212 are presented below. The kinase domain of SEQ ID NO: 212 has been underlined, and predicted phosphorylation S, T, and Y sites comprised within this domain have been boxed. These can then be mutated to nonphosphorylatable amino acids by techniques well known in the art, such as site-directed mutagenesis.

```
Polypeptide sequence of SEQ ID NO: 212

MAMRLLKTHLLFLHLYLFFSPCFATYDMEVLLNLKSSMIGPKGHGLHDWIHSSSPDAHCSFSGVSCDDDARVISLNVSFT         80
PLFGTISPEIGMLTHLVNLTLAANNFTGELPLEMKSLTSLKVLNISNNGNLTGTFPGEILKAMVDLEVLDTYNNNFNGKL        160
PPEMSELKKLKYLSFGGNFFSGEIPESYGDIQSLEYLGLNGAGLSGKSPAFLSRLKNLREMYIGYYNSYTGGVPREFGGL        240
TKLEILDMASCTLTGEIPTSLSNLKHLHTLFLHINNLTGHIPPELSGLVSLKSLDLSINQLTGEIPQSFINLGNITLINL        320
FRNNLYGQIPEAIGELPKLEVFEVWENNFTLQLPANLGRNGNLIKLDVSDNHLTGLIPKDLCRGEKLEMLILSNNFFFGP        400
IPEELGKCKSLTKIRIVKNLLNGTVPAGLFNLPLVTIIELTDNFFSGELPVTMSGDVLDQIYLSNNWFSGEIPPAIGNFP        480
```

-continued

```
NLQTLFLDRNRFRGNIPREIFELKHLSRINTSANNITGGIPDSISRCSTLISVDLSRNRINGEIPKGINNVKNLGTLNIS    560
GNQLTGSIPTGIGNMTSLTTLDLSFNDLSGRVPLGGQFLVFNETSFAGNTYLCLPHRVSCPTRPGQTSDHNHTALFSPSR    640
IVITVIAAITGLILISVAIRQMNKKKNQKSLAWKLTAFQKLDFKSEDVLECLKEENIIGKGGAGIVYRGSMPNNVDVAIK    720
RLVGRGTGRSDHGFTAEIQTLGRIRHRHIVRLLGYVANKDTNLLLYEYMPNGSLGELLHGSKGGHLQWETRHRVAVEAAK    800
GLCYLHHDCSPLILHRDVKSNNILLDSDFEAHVADFGLAKFLVDGAASECMSSIAGSYGYIAPEYAYTLKVDEKSDVYSF    880
GVVLLELIAGKKPVGEFGEGVDIVRWVRNTEEEITQPSDAAIVVAIVDPRLTGYPLTSVIHVFKIAMMCVEEEAAARPTM    960
REVVHMLTNPPKSVANLIAF                                                               1040
Corresponding predicted phosphorylation sites ...........Y..........S................S..........S..............     80
....................S...........................................    160
........Y.S..........SY............S..S..........................    240
.........S..............................S.......................    320
.....Y...........................................................    400
..............................................S..........Y......    480
....................S...T..........S..S........S................    560
..........S.................................................TS.........S...    640
..........................................................S..........    720
.....T....................Y......................................    800
.................................S..............Y..T......S.....    880
..............T.................T...............................T.    960
...........S.......                                                  1040
```

|  | Ser | Thr | Tyr |
|---|---|---|---|
| Phosphorylation sites predicted | 22 | 7 | 7 |
| Phosphorylation sites predicted comprised in the kinase domain | 3 | 5 | 2 |

Example 30

Topology Prediction of the Polypeptide Sequences Useful in Performing the Methods of the Invention (Subcellular Localization, Transmembrane . . . )

TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal pre-sequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The results of TargetP 1.1 analysis of the polypeptide sequence as represented by SEQ ID NO: 212 are presented Table C3. The "plant" organism group has been selected, no cutoffs defined, and the predicted length of the transit peptide requested. The subcellular localization of the polypeptide sequence as represented by SEQ ID NO: 210 is the secretory pathway (endoplasmic reticulum or ER), and the predicted length of the signal peptide is of 24 amino acids starting from the N-terminus (not as reliable as the prediction of the subcellular localization itself, may vary in length of a few amino acids).

TABLE C3

TargetP 1.1 analysis of the polypeptide sequence as represented by SEQ ID NO: 210

| | |
|---|---|
| Length (AA) | 980 |
| Chloroplastic transit peptide | 0.001 |
| Mitochondrial transit peptide | 0.113 |
| Secretory pathway signal peptide | 0.973 |
| Other subcellular targeting | 0.018 |
| Predicted Location | Secretory (endoplasmic reticulum or ER) |
| Reliability class | 1 |
| Predicted signal peptide length | 24 |

Many other algorithms can be used to perform such analyses, including:

ChloroP 1.1 hosted on the server of the Technical University of Denmark;

Protein Prowler Subcellular Localisation Predictor version 1.2 hosted on the server of the Institute for Molecular Bioscience, University of Queensland, Brisbane, Australia;

PENCE Proteome Analyst PA-GOSUB 2.5 hosted on the server of the University of Alberta, Edmonton, Alberta, Canada;

TMHMM, hosted on the server of the Technical University of Denmark. The output of TMHMM2.0 algorithm on the polypeptide sequence of SEQ ID NO: 212 is given in the Table C4 below. Two hydrophobic regions are identified, which correspond to: (i) a signal peptide for ER subcellular targeting; and (ii) a transmembrane domain.

TABLE C4 output of TMHMM2.0 algorithm on the polypeptide sequence of SEQ ID NO: 212

| Position relative to plasma membrane | Amino acids from N-terminus to C-terminus of SEQ ID NO: 212 | Corresponding domain on the polypeptide sequence of SEQ ID NO: 212 |
| --- | --- | --- |
| Sequence outside cell | 1-640 | Extracellular LRR domain |
| Transmembrane helix | 641-659 | Transmembrane domain |
| Sequence inside cell | 660-980 | Intracellular kinase domain |

Example 31

Assay Related to the Polypeptide Sequences Useful in Performing the Methods of the Invention, and Methods of Disrupting the Biological Function of the C-Terminal Domain In a first step, activity of the polypeptides useful in performing the methods of the invention is identified by their capacity to bind to their natural interactors, such as in Trotochaud et al. (1999; Plant Cell 11: 393-406), using the methods described therein. One assay of CLV1 activity is by testing the physical interaction of KAPP with the kinase domain of the CLV1 polypeptide using the yeast two-hybrid system.

In a second step, the identified CLV1 polypeptides are rendered useful for the methods of the invention by disrupting the biological function of the C-terminal domain. Such methods (for disrupting the biological function) are well known in the art and include: removal, substitution and/or insertion of amino acids of the C-terminal domain. One or more amino acid(s) from the C-terminal domain may be removed, substituted and/or inserted, usually using PCR-based techniques, for example:
  (i) Removal, substitution and/or insertion of amino acids comprising all or part of the C-terminal domain (in this particular (i) example, taken to mean the amino acid sequence following the amino acid sequence encoding the transmembrane domain (from N terminus to C terminus)); or
  (ii) substituting conserved amino acids (such as the kinase active site as shown in FIG. 2 and Example 28 (involved substrate ATP binding site), or the conserved G in kinase subdomain IX (involved in autophosphorylation), or the conserved cysteines in the second pair (involved in homo- and heterodimerization)) by alanine, etc.; or
  (iii) inserting amino acids in the kinase active site, for example, to disrupt substrate binding;
  (iv) substituting phosphorylatable amino acids (such as serine, threonine or tyrosine) by non-phosphorylatable amino acids (for interaction with other proteins, for example);
  (v) or any other method for disrupting the biological function known in the art.

One example of disruption of the biological function of the C-terminal domain of a CLV1 polypeptide comprises introducing a premature stop codon (on the reverse primer, SEQ ID NO: 239) via PCR at position 2251 of the nucleic acid sequence as represented by SEQ ID NO: 211, by substituting the A to a T (changing an AGA codon into a TGA stop codon).

Example 32

Cloning of Nucleic Acid Sequence as Represented by SEQ ID NO: 209

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The *Arabidopsis thaliana* nucleic acid sequence encoding the CLV1 polypeptide with a non-functional domain of SEQ ID NO: 210 was amplified by PCR using as template an *Arabidopsis thaliana* seedling cDNA library (Invitrogen, Paisley, UK). The following primers which include the AttB sites for Gateway recombination, were used for PCR amplification:

1) prm8591 (SEQ ID NO: 238; sense, start codon in bold, AttB1 site in italic):

5'-*ggggacaagtttgtacaaaaaagcaggct taaaca*atggcgatg agactttgaag-3';

and 2) prm8592 (SEQ ID NO: 239; reverse, complementary, AttB2 site in italic):

5'-*ggggaccactttgtacaagaaagctgggt*cgctacgtaaccaag aagtcac-3').

PCR was performed using Hifi Taq DNA polymerase in standard conditions. A PCR fragment was amplified and purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

Example 33

Expression Vector Construction Using the Nucleic Acid Sequence as Represented by SEQ ID NO: 209

The entry clone containing the nucleic acid sequence encoding the CLV1 polypeptide of SEQ ID NO: 210 was subsequently used in an LR reaction with a destination vector used for *Oryza sativa* transformation. This vector contains as functional elements within the T-DNA borders: a plant selectable marker; a screenable marker expression cassette; and a Gateway cassette intended for LR in vivo recombination with the nucleic acid sequence of interest already cloned in the entry clone. A rice beta-expansin promoter (SEQ ID NO: 240) for expression in young expanding tissues, was located upstream of this Gateway cassette.

Figure 12:
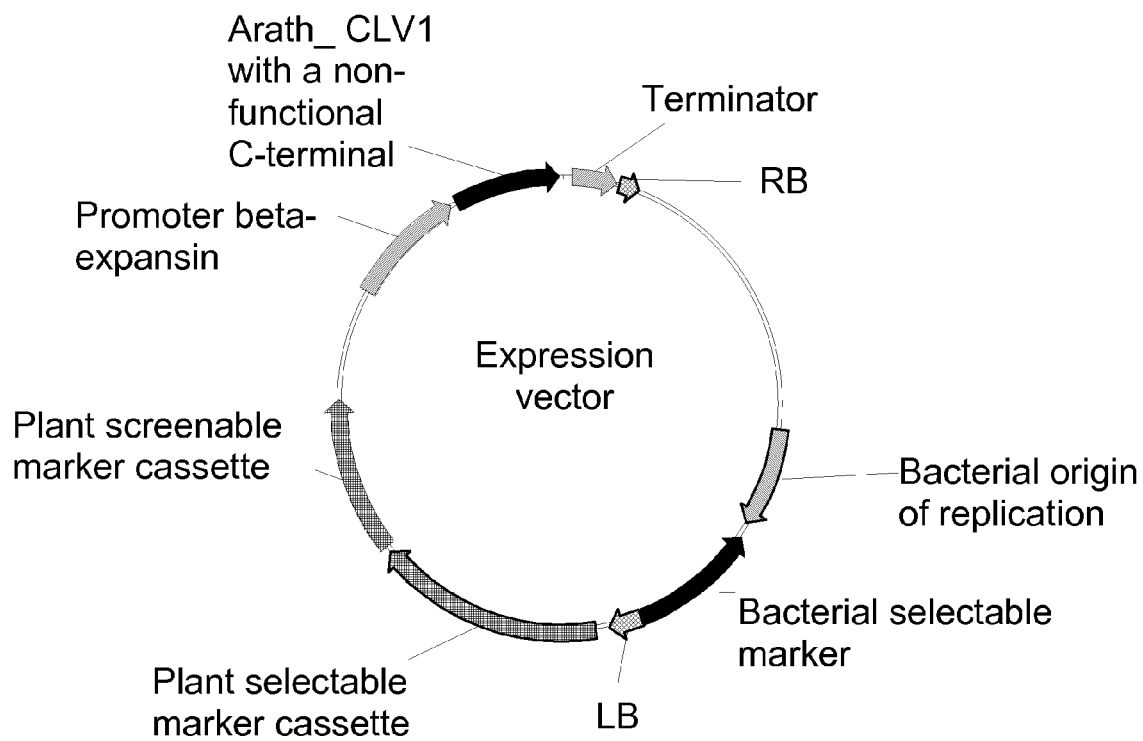
FIG. 12 shows the binary vector for increased expression in *Oryza sativa* of an *Arabidopsis thaliana* nucleic acid sequence encoding CLV1 polypeptide with a non-functional C-terminal domain, under the control of a beta-expansin promoter (for expression in young expanding tissues).

After the LR recombination step, the resulting expression vector comprising the nucleic acid sequence for the beta-expansin promoter upstream of the nucleic acid sequence encoding Arath_CLV1 with a non-functional C-terminal domain (FIG. 12) was transformed into *Agrobacterium* strain LBA4044 according to methods well known in the art.

Example 34

Plant Transformation

See Example 9 above for details of rice transformation and see Example 12 above for details of transformation of corn, wheat, soybean, canola/rapeseed, alfalfa and cotton.

Example 35

Phenotypic Evaluation Procedure

See Example 10 above for details.

Example 36

Results of the Phenotypic Evaluation of the Transgenic Plants

The results of the evaluation of transgenic rice plants expressing the nucleic acid sequence useful in performing the methods of the invention are presented in Table C5. The percentage difference between the transgenics and the corresponding nullizygotes is also shown, with a P value from the F test below 0.05.

Aboveground biomass, total root biomass, thin root biomass, number of primary panicles, number of flowers per panicle, total seed yield, number of filled seeds, total number of seeds, and harvest index are significantly increased in the transgenic plants expressing the nucleic acid sequence useful in performing the methods of the invention, compared to the control plants (in this case, the nullizygotes).

TABLE C5

Results of the evaluation of transgenic rice plants expressing the nucleic acid sequence useful in performing the methods of the invention.

| Trait | % Increase in T1 generation |
| --- | --- |
| Aboveground biomass | 5 |
| Total root biomass | 2 |
| Thin root biomass | 2 |
| Number of primary panicles | 8 |
| Number of flowers per panicle | 6 |
| Total seed yield | 9 |
| Number of filled seeds | 12 |
| Total number of seeds | 14 |
| Harvest index | 5 |
| TKW | −3 |

The invention claimed is:

1. A method for increasing seed yield in a plant relative to a corresponding control plant, comprising
   (a) introducing in a plant or plant cell an isolated nucleic acid sequence encoding a Class I TCP polypeptide, and
   (b) selecting for a plant having increased seed yield,
   wherein said Class I TCP polypeptide comprises from N-terminus to C-terminus:
   (i) an amino acid sequence having at least 80% or more sequence identity to the conserved TCP domain of SEQ ID NO: 66, wherein the conserved TCP domain comprises a basic-Helix-Loop-Helix (bHLH); and
   (ii) the consensus C-terminal motif 1 amino acid sequence of SEQ ID NO: 65.

2. The method of claim 1, wherein said Class I TCP polypeptide additionally comprises an HQ rich region, where H is histidine, and Q is glutamine, between the conserved C-terminal motif 1 and the C-terminal end of the polypeptide.

3. The method of claim 1, wherein said nucleic acid sequence is operably linked to a constitutive promoter.

4. The method of claim 1, wherein said nucleic acid sequence encoding a Class I TCP polypeptide is of plant origin.

5. The method of claim 1, wherein the increased seed yield is one or more of the following: (i) increased seed weight; (ii) increased harvest index; or (iii) increased Thousand Kernel Weight.

6. The method of claim 1, wherein the amino acid sequence has at least 95% sequence identity to the conserved TCP domain of SEQ ID NO: 66.

7. The method of claim 1, wherein the amino acid sequence comprises the conserved TCP domain of SEQ ID NO: 66.

8. The method of claim 3, wherein the constitutive promoter is a GOS2 promoter.

9. A method for the production of a transgenic plant or part thereof having increased seed yield relative to a corresponding control plant, comprising:
 (a) introducing in a plant or plant cell an isolated nucleic acid sequence encoding a Class I TCP polypeptide;
 (b) cultivating the plant or plant cell under conditions promoting plant growth and development; and
 (c) selecting for a plant or part thereof having increased seed yield relative to a corresponding control plant or part thereof;

wherein said Class I TCP polypeptide comprises from N-terminus to C-terminus:
 (i) an amino acid sequence having at least 80% or more sequence identity to the conserved TCP domain of SEQ ID NO: 66, wherein the conserved TCP domain comprises a basic-Helix-Loop-Helix (bHLH); and
 (ii) the consensus C-terminal motif 1 amino acid sequence of SEQ ID NO: 65.

10. The method of claim 9, wherein said increased seed yield is selected from one or more of the following: (i) increased seed weight; (ii) increased harvest index; or (iii) increased Thousand Kernel Weight.

11. The method of claim 1, further comprising obtaining a plant cell or progeny, wherein the plant cell or progeny comprise said isolated nucleic acid.

12. The method of claim 9, further comprising obtaining a plant cell or progeny, wherein the plant cell or progeny comprise said isolated nucleic acid.

* * * * *